(12) United States Patent  (10) Patent No.: US 8,449,898 B2
Gregory et al.  (45) Date of Patent: *May 28, 2013

(54) FUNGICIDAL MIXTURES

(75) Inventors: Vann Gregory, Newark, DE (US); Robert James Pasteris, Newark, DE (US); Mary Ann Hanagan, Newark, DE (US)

(73) Assignee: E I du Pont de Nemours and Company, Wilmington, DC (US)

( * ) Notice: Subject to any disclaimer, the term of this patent is extended or adjusted under 35 U.S.C. 154(b) by 121 days.

This patent is subject to a terminal disclaimer.

(21) Appl. No.: 12/679,361

(22) PCT Filed: Oct. 23, 2008

(86) PCT No.: PCT/US2008/080850
§ 371 (c)(1),
(2), (4) Date: Mar. 22, 2010

(87) PCT Pub. No.: WO2009/055514
PCT Pub. Date: Apr. 30, 2009

(65) Prior Publication Data
US 2010/0240619 A1  Sep. 23, 2010

Related U.S. Application Data

(60) Provisional application No. 61/000,002, filed on Oct. 23, 2007, provisional application No. 61/062,400, filed on Jan. 25, 2008.

(51) Int. Cl.
A01N 43/40 (2006.01)
A01N 43/78 (2006.01)
A01N 43/80 (2006.01)
A01N 43/56 (2006.01)
A01N 43/653 (2006.01)
A01N 43/90 (2006.01)
A01P 3/00 (2006.01)
C07D 211/00 (2006.01)
C07D 239/00 (2006.01)

(52) U.S. Cl.
USPC .......... 424/405; 514/241; 514/326; 544/369; 546/209

(58) Field of Classification Search
USPC ................. 514/241, 326; 544/369; 546/209
See application file for complete search history.

(56) References Cited

U.S. PATENT DOCUMENTS

| | | | | |
|---|---|---|---|---|
| 5,001,115 A | * | 3/1991 | Sloan | 514/34 |
| 7,851,473 B2 | | 12/2010 | Matsumoto et al. | |
| 2005/0069965 A1 | * | 3/2005 | Kitamura et al. | 435/7.31 |
| 2005/0255048 A1 | * | 11/2005 | Hirsh et al. | 424/44 |
| 2007/0004750 A1 | | 1/2007 | Lorsbach et al. | |

FOREIGN PATENT DOCUMENTS

| | | |
|---|---|---|
| WO | 01/34150 A1 | 5/2001 |
| WO | 2004/058751 A1 | 7/2004 |
| WO | 2005/003128 A1 | 1/2005 |
| WO | 2005/074934 A1 | 8/2005 |
| WO | 2005/087765 A1 | 9/2005 |
| WO | 2005/116653 A2 | 12/2005 |
| WO | 2006/032322 A1 | 3/2006 |
| WO | 2006/034279 A1 | 3/2006 |
| WO | 2006/054652 A1 | 5/2006 |
| WO | 2007/014290 A2 | 2/2007 |

(Continued)

*Primary Examiner* — Kortney L Klinkel

(57) ABSTRACT

Disclosed is a fungicidal composition comprising (a) at least one compound selected from the compounds of Formula 1 N-oxides, and salts thereof,

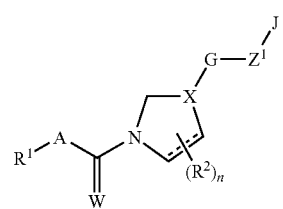

wherein $R^1$, $R^2$, A, G, W, $Z^1$, X, J, and n are as defined in the disclosure, and (b) at least one additional fungicidal compound.

Also disclosed is a method for controlling plant diseases caused by fungal plant pathogens comprising applying to the plant or portion thereof, or to the plant seed, a fungicidally effective amount of the aforesaid composition.

Also disclosed is a composition comprising component (a) of aforesaid composition and at least one insecticide.

Also disclosed are compounds of Formula 1A, 1B and 1C,

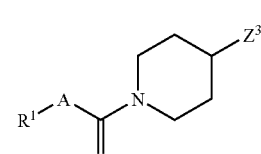

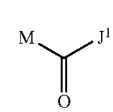

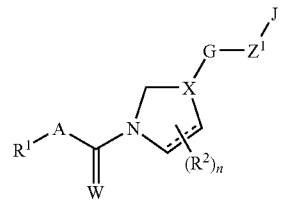

wherein
$R^1$, $R^2$, A, G, W, $Z^1$, X, J, n, $Z^3$, M and $J^1$ are as defined in the disclosure.

14 Claims, No Drawings

FOREIGN PATENT DOCUMENTS

| WO | 2007/064553 | A2 | 6/2007 |
| WO | 2007/070433 | A2 | 6/2007 |
| WO | 2008/013622 | A2 | 1/2008 |
| WO | 2008/013925 | A2 | 1/2008 |
| WO | 2008/091580 | A2 | 7/2008 |
| WO | 2008/091594 | A2 | 7/2008 |
| WO | 2009/094407 | A2 | 7/2009 |

* cited by examiner

FUNGICIDAL MIXTURES

FIELD OF THE INVENTION

This invention relates to fungicidal mixtures of certain carboxamide derivatives, their N-oxides and salts, and to compositions comprising such mixtures and methods for using such mixtures as fungicides.

BACKGROUND OF THE INVENTION

The control of plant diseases caused by fungal plant pathogens is extremely important in achieving high crop efficiency. Plant disease damage to ornamental, vegetable, field, cereal and fruit crops can cause significant reduction in productivity and thereby result in increased costs to the consumer. In addition to often being highly destructive, plant diseases can be difficult to control and may develop resistance to commercial fungicides. Combinations of fungicides are often used to facilitate disease control, to broaden spectrum of control and to retard resistance development. Furthermore, certain rare combinations of fungicides demonstrate a greater-than-additive (i.e. synergistic) effect to provide commercially important levels of plant disease control. The advantages of particular fungicide combinations are recognized in the art to vary, depending on such factors as the particular plant species and plant disease to be treated, and whether the plants are treated before or after infection with the fungal plant pathogen. Accordingly new advantageous combinations are needed to provide a variety of options to best satisfy particular plant disease control needs. Remarkably advantageous combinations have now been discovered.

SUMMARY OF THE INVENTION

This invention relates to a fungicidal combination (e.g., composition) comprising
(a) at least one compound selected from the compounds of Formula 1 (including all geometric and stereoisomers), N-oxides, and salts thereof,

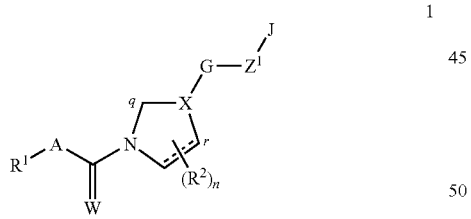

wherein
$R^1$ is an optionally substituted phenyl, naphthalenyl or 5- or 6-membered heteroaromatic ring;
A is $CHR^{15}$ or $NR^{16}$;
$R^{15}$ is H, halogen, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_3$-$C_5$ alkoxycarbonylalkyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl or $C_1$-$C_4$ haloalkylsulfonyl; or $R^{15}$ is —SH, amino, $C_1$-$C_6$ hydroxyalkyl, $C_2$-$C_4$ alkenyloxy, $C_2$-$C_4$ alkynyloxy, $C_2$-$C_4$ haloalkenyloxy, $C_2$-$C_4$ haloalkynyloxy, $C_2$-$C_5$ alkylcarbonyloxy, $C_2$-$C_5$ alkoxycarbonyloxy, $C_2$-$C_5$ haloalkylcarbonyloxy, $C_2$-$C_5$ haloalkoxycarbonyloxy, $C_2$-$C_5$ alkylaminocarbonyloxy, $C_3$-$C_6$ dialkylaminocarbonyloxy, $C_2$-$C_5$ haloalkylaminocarbonyloxy, $C_3$-$C_6$ halodialkylaminocarbonyloxy, $C_2$-$C_5$ alkoxyalkoxy, $C_2$-$C_5$ haloalkoxyalkoxy, $C_1$-$C_4$ alkylsulfonyloxy, $C_1$-$C_4$ haloalkylsulfonyloxy, $C_3$-$C_{10}$ trialkylsilyloxy, $C_2$-$C_4$ alkenylthio, $C_2$-$C_4$ alkynylthio, $C_2$-$C_4$ haloalkenylthio, $C_2$-$C_4$ haloalkynylthio, $C_2$-$C_5$ alkylcarbonylthio, $C_2$-$C_5$ alkoxycarbonylthio, $C_2$-$C_5$ haloalkylcarbonylthio, $C_2$-$C_5$ haloalkoxycarbonylthio, $C_2$-$C_5$ alkylaminocarbonylthio, $C_3$-$C_6$ dialkylaminocarbonylthio, $C_2$-$C_5$ haloalkylaminocarbonylthio, $C_3$-$C_6$ halodialkylaminocarbonylthio, $C_2$-$C_5$ alkoxyalkylthio, $C_2$-$C_5$ haloalkoxyalkylthio, $C_1$-$C_4$ alkylsulfonylthio, $C_1$-$C_4$ haloalkylsulfonylthio, $C_3$-$C_{10}$ trialkylsilylthio, $C_1$-$C_4$ alkylamino, $C_2$-$C_4$ alkenylamino, $C_2$-$C_4$ alkynylamino, $C_2$-$C_4$ dialkylamino, $C_1$-$C_4$ haloalkylamino, $C_2$-$C_4$ haloalkenylamino, $C_2$-$C_4$ haloalkynylamino, $C_2$-$C_4$ halodialkylamino, $C_2$-$C_5$ alkylcarbonylamino, $C_2$-$C_5$ haloalkylcarbonylamino, $C_2$-$C_5$ alkoxycarbonylamino, $C_2$-$C_5$ haloalkoxycarbonylamino, $C_2$-$C_5$ alkylaminocarbonylamino, $C_3$-$C_6$ dialkylaminocarbonylamino, $C_2$-$C_5$ haloalkylaminocarbonylamino, $C_3$-$C_6$ halodialkylaminocarbonylamino, $C_2$-$C_5$ alkoxyalkylamino, $C_2$-$C_5$ haloalkoxyalkylamino, $C_1$-$C_4$ alkylsulfonylamino or $C_1$-$C_4$ halo alkylsulfonylamino;
$R^{16}$ is H, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_2$-$C_5$ alkoxycarbonyl, $C_3$-$C_5$ alkoxycarbonylalkyl, $C_2$-$C_5$ alkylaminocarbonyl, $C_3$-$C_5$ dialkylaminocarbonyl, $C_1$-$C_4$ alkylsulfonyl or $C_1$-$C_4$ haloalkylsulfonyl;
W is O or S;
X is a radical selected from

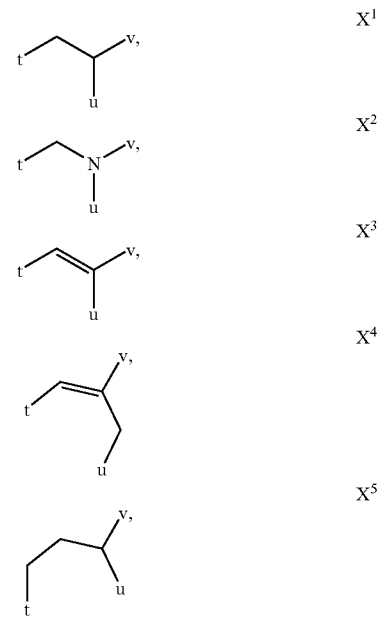

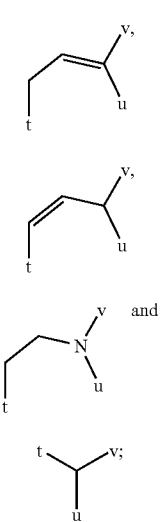

wherein the bond of $X^1$, $X^2$, $X^3$, $X^4$, $X^5$, $X^6$, $X^7$, $X^8$ or $X^9$ which is identified is connected to the carbon atom identified with "q" of Formula 1, the bond which is identified with "u" is connected to the carbon atom identified with "r" of Formula 1, and the bond which is identified with "v" is connected to G;

each $R^2$ is independently halogen, cyano, hydroxy, $C_1$-$C_4$ alkyl, $C_1$-$C_4$ alkenyl, $C_1$-$C_4$ haloalkyl or $C_1$-$C_4$ alkoxy; or two $R^2$ are taken together as $C_1$-$C_4$ alkylene or $C_2$-$C_4$ alkenylene to form a bridged bicyclic or fused bicyclic ring system; or two $R^2$ attached to adjacent ring carbon atoms joined by a double bond are taken together as —CH=CH—CH=CH— optionally substituted with 1 to 3 substituents selected from halogen, hydroxy, amino, cyano, nitro, $C_1$-$C_4$ alkyl, $C_1$-$C_4$ haloalkyl, $C_1$-$C_4$ alkoxy and $C_1$-$C_4$ haloalkoxy;

G is an optionally substituted 5-membered heteroaromatic ring or 5-membered saturated or partially saturated heterocyclic ring;

J is a 5-, 6- or 7-membered ring, an 8- to 11-membered bicyclic ring system or a 7- to 11-membered spirocyclic ring system, each ring or ring system containing ring members selected from carbon and optionally 1 to 4 heteroatoms selected from up to 2 O, up to 2 S and up to 4 N, and optionally including 1 to 3 ring members selected from the group consisting of C(=O), C(=S), S(O), S(O)$_2$ and SiR$^{17}$R$^{18}$, each ring or ring system optionally substituted with 1 to 5 substituents independently selected from $R^5$;

each $R^5$ is independently H, halogen, cyano, hydroxy, amino, nitro, —CHO, —C(=O)OH, —C(=O)NH$_2$, —NR$^{25}$R$^{26}$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{10}$ alkylcycloalkylalkyl, $C_3$-$C_8$ cycloalkenyl, $C_3$-$C_8$ halocycloalkenyl, $C_2$-$C_6$ alkoxyalkyl, $C_2$-$C_6$ haloalkoxyalkyl, $C_1$-$C_6$ hydroxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_2$-$C_6$ haloalkylaminoalkyl, $C_3$-$C_8$ dialkylaminoalkyl, $C_4$-$C_{10}$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_4$-$C_8$ cycloalkoxycarbonyl, $C_5$-$C_{10}$ cycloalkylalkoxycarbonyl, $C_2$-$C_6$ alkylaminocarbonyl, $C_3$-$C_8$ dialkylaminocarbonyl, $C_4$-$C_8$ cycloalkylaminocarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_{10}$ trialkylsilyl, $C_1$-$C_6$ alkylsulfonylamino, $C_1$-$C_6$ haloalkylsulfonylamino or —Z$^2$Q;

each $R^{25}$ is independently H, $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

each $R^{26}$ is independently $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl, $C_2$-$C_6$ haloalkoxycarbonyl or —Z$^4$Q;

each $R^{17}$ and $R^{18}$ is independently $C_1$-$C_5$ alkyl, $C_2$-$C_5$ alkenyl, $C_2$-$C_5$ alkynyl, $C_3$-$C_5$ cycloalkyl, $C_3$-$C_6$ halocycloalkyl, $C_4$-$C_{10}$ cycloalkylalkyl, $C_4$-$C_7$ alkylcycloalkyl, $C_5$-$C_7$ alkylcycloalkylalkyl, $C_1$-$C_5$ haloalkyl, $C_1$-$C_5$ alkoxy or $C_1$-$C_5$ haloalkoxy;

each Q is independently a phenyl, a benzyl, a naphthalenyl, a 5- or 6-membered heteroaromatic ring or an 8- to 11-membered heteroaromatic bicyclic ring system, each ring or ring system optionally substituted with 1 to 5 substituents independently selected from $R^7$ on carbon atom ring members and $R^{12}$ on nitrogen atom ring members; or each Q is independently a 3- to 7-membered nonaromatic carbocyclic ring, a 5-, 6- or 7-membered nonaromatic heterocyclic ring or an 8- to 11-membered nonaromatic bicyclic ring system, each ring or ring system optionally including ring members selected from the group consisting of C(=O), C(=S), S(O), S(O)$_2$ and SiR$^{17}$R$^{18}$, and optionally substituted with 1 to 5 substituents independently selected from $R^7$ on carbon atom ring members and $R^{12}$ on nitrogen atom ring members;

each $R^7$ is independently halogen, hydroxy, amino, cyano, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_2$-$C_4$ alkoxyalkyl, $C_1$-$C_4$ hydroxyalkyl, $C_1$-$C_4$ alkoxy, $C_1$-$C_4$ haloalkoxy, $C_2$-$C_6$ alkylcarbonyloxy, $C_1$-$C_4$ alkylthio, $C_1$-$C_4$ haloalkylthio, $C_2$-$C_6$ alkylcarbonylthio, $C_1$-$C_4$ alkylsulfinyl, $C_1$-$C_4$ alkylsulfonyl, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; or $R^5$ and $R^7$ are taken together with the atoms linking $R^5$ and $R^7$ to form an optionally substituted 5- to 7-membered ring containing ring members selected from carbon and optionally 1 to 3 heteroatoms selected from up to 1 O, up to 1 S and up to 1 N and optionally including 1 to 3 ring members selected from the group consisting of C(=O), C(=S), S(O), S(O)$_2$ and SiR$^{17}$R$^{18}$;

each R$^{12}$ is independently H, C$_1$-C$_3$ alkyl, C$_1$-C$_3$ alkylcarbonyl, C$_1$-C$_3$ alkoxycarbonyl or C$_1$-C$_3$ alkoxy;

each Z$^1$ and Z$^2$ is independently a direct bond, O, C(=O), S(O)$_m$, CHR$^{20}$ or NR$^{21}$;

each Z$^4$ is independently O, C(=O), S(O)$_m$ or CHR$^{20}$;

each R$^{20}$ is independently H, C$_1$-C$_4$ alkyl or C$_1$-C$_4$ haloalkyl;

each R$^{21}$ is independently H, C$_1$-C$_6$ alkyl, C$_1$-C$_6$ haloalkyl, C$_3$-C$_8$ cycloalkyl, C$_2$-C$_6$ alkylcarbonyl, C$_2$-C$_6$ haloalkylcarbonyl, C$_2$-C$_6$ alkoxycarbonyl or C$_2$-C$_6$ haloalkoxycarbonyl;

each m is independently 0, 1 or 2; and n is 0, 1 or 2; and (b) at least one additional fungicidal compound.

This invention also relates to a method for controlling plant diseases caused by fungal plant pathogens comprising applying to the plant or portion thereof, or to the plant seed, a fungicidally effective amount of the aforesaid composition.

This invention also relates to a composition comprising: (a) at least one compound selected from the compounds of Formula 1 described above, N-oxides, and salts thereof; and at least one insecticide.

This invention also relates to compounds of Formula 1C (including all geometric and stereoisomers), N-oxides, and salts thereof, agricultural compositions containing them and their use as fungicides:

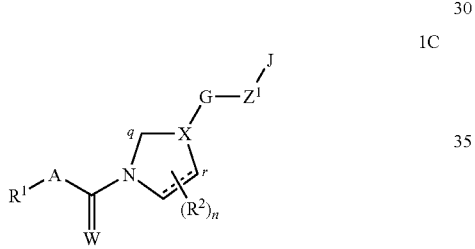

1C wherein
R$^1$ is an optionally substituted phenyl, naphthalenyl or 5- or 6-membered heteroaromatic ring;
A is CHR$^{15}$ or NR$^{16}$;
R$^{15}$ is —SH, amino, C$_1$-C$_6$ hydroxyalkyl, C$_2$-C$_4$ alkenyloxy, C$_2$-C$_4$ alkynyloxy, C$_2$-C$_4$ haloalkenyloxy, C$_2$-C$_4$ haloalkynyloxy, C$_2$-C$_5$ alkylcarbonyloxy, C$_2$-C$_5$ alkoxycarbonyloxy, C$_2$-C$_5$ haloalkylcarbonyloxy, C$_2$-C$_5$ haloalkoxycarbonyloxy, C$_2$-C$_5$ alkylaminocarbonyloxy, C$_3$-C$_6$ dialkylaminocarbonyloxy, C$_2$-C$_5$ haloalkylaminocarbonyloxy, C$_3$-C$_6$ halodialkylaminocarbonyloxy, C$_2$-C$_5$ alkoxyalkoxy, C$_2$-C$_5$ haloalkoxyalkoxy, C$_1$-C$_4$ alkylsulfonyloxy, C$_1$-C$_4$ haloalkylsulfonyloxy, C$_3$-C$_{10}$ trialkylsilyloxy, C$_2$-C$_4$ alkenylthio, C$_2$-C$_4$ alkynylthio, C$_2$-C$_4$ haloalkenylthio, C$_2$-C$_4$ haloalkynylthio, C$_2$-C$_5$ alkylcarbonylthio, C$_2$-C$_5$ alkoxycarbonylthio, C$_2$-C$_5$ haloalkylcarbonylthio, C$_2$-C$_5$ haloalkoxycarbonylthio, C$_2$-C$_5$ alkylaminocarbonylthio, C$_3$-C$_6$ dialkylaminocarbonylthio, C$_2$-C$_5$ haloalkylaminocarbonylthio, C$_3$-C$_6$ halodialkylaminocarbonylthio, C$_2$-C$_5$ alkoxyalkylthio, C$_2$-C$_5$ haloalkoxyalkylthio, C$_1$-C$_4$ alkylsulfonylthio, C$_1$-C$_4$ haloalkylsulfonylthio, C$_3$-C$_{10}$ trialkylsilylthio, C$_1$-C$_4$ alkylamino, C$_2$-C$_4$ alkenylamino, C$_2$-C$_4$ alkynylamino, C$_1$-C$_4$ dialkylamino, C$_1$-C$_4$ haloalkylamino, C$_2$-C$_4$ haloalkenylamino, C$_2$-C$_4$ haloalkynylamino, C$_2$-C$_4$ halodialkylamino, C$_2$-C$_5$ alkylcarbonylamino, C$_2$-C$_5$ haloalkylcarbonylamino, C$_2$-C$_5$ alkoxycarbonylamino, C$_2$-C$_5$ haloalkoxycarbonylamino, C$_2$-C$_5$ alkylaminocarbonylamino, C$_3$-C$_6$ dialkylaminocarbonylamino, C$_2$-C$_5$ haloalkylaminocarbonylamino, C$_3$-C$_6$ halodialkylaminocarbonylamino, C$_2$-C$_5$ alkoxyalkylamino, C$_2$-C$_5$ haloalkoxyalkylamino, C$_1$-C$_4$ alkylsulfonylamino or C$_1$-C$_4$ halo alkylsulfonylamino;

R$^{16}$ is halogen, hydroxy, C$_1$-C$_4$ alkyloxy, C$_2$-C$_4$ alkenyloxy, C$_2$-C$_4$ alkynyloxy, C$_2$-C$_4$ haloalkenyloxy, C$_2$-C$_4$ haloalkynyloxy, C$_2$-C$_5$ alkylcarbonyloxy, C$_2$-C$_5$ alkoxycarbonyloxy, C$_2$-C$_5$ haloalkylcarbonyloxy, C$_2$-C$_5$ haloalkoxycarbonyloxy, C$_2$-C$_5$ alkylaminocarbonyloxy, C$_3$-C$_6$ dialkylaminocarbonyloxy, C$_2$-C$_5$ haloalkylaminocarbonyloxy, C$_3$-C$_6$ halodialkylaminocarbonyloxy, C$_2$-C$_5$ alkoxyalkoxy, C$_2$-C$_5$ haloalkoxyalkoxy, C$_1$-C$_4$ alkylsulfonyloxy, C$_1$-C$_4$ haloalkylsulfonyloxy or C$_3$-C$_{10}$ trialkylsilyloxy;

W is O or S;

X is a radical selected from

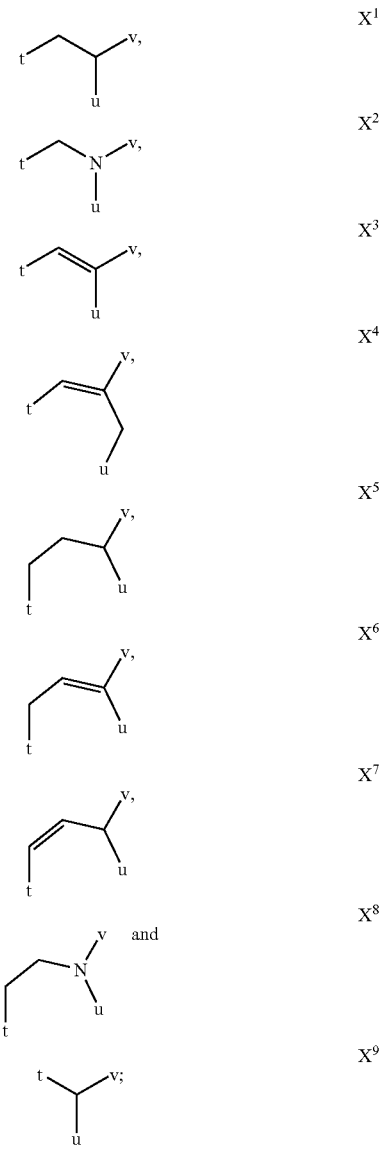

wherein the bond of X$^1$, X$^2$, X$^3$, X$^4$, X$^5$, X$^6$, X$^7$, X$^8$ or X$^9$ which is identified is connected to the carbon atom identified with "q" of Formula 1, the bond which is identified with "u" is connected to the carbon atom identified with "r" of Formula 1, and the bond which is identified with "v" is connected to G;

each $R^2$ is independently halogen, cyano, hydroxy, $C_1$-$C_4$ alkyl, $C_1$-$C_4$ alkenyl, $C_1$-$C_4$ haloalkyl, or $C_1$-$C_4$ alkoxy; or two $R^2$ are taken together as $C_1$-$C_4$ alkylene or $C_2$-$C_4$ alkenylene to form a bridged bicyclic or fused bicyclic ring system; or two $R^2$ attached to adjacent ring carbon atoms joined by a double bond are taken together as —CH=CH—CH=CH— optionally substituted with 1 to 3 substituents selected from halogen, hydroxy, amino, cyano, nitro, $C_1$-$C_4$ alkyl, $C_1$-$C_4$ haloalkyl, $C_1$-$C_4$ alkoxy and $C_1$-$C_4$ haloalkoxy;

G is an optionally substituted 5-membered heteroaromatic ring or 5-membered saturated or partially saturated heterocyclic ring;

J is a 5-, 6- or 7-membered ring, an 8- to 11-membered bicyclic ring system or a 7- to 11-membered spirocyclic ring system, each ring or ring system containing ring members selected from carbon and optionally 1 to 4 heteroatoms selected from up to 2 O, up to 2 S and up to 4 N, and optionally including 1 to 3 ring members selected from the group consisting of C(=O), C(=S), S(O), S(O)$_2$ and SiR$^{17}$R$^{18}$, each ring or ring system optionally substituted with 1 to 5 substituents independently selected from $R^5$;

each $R^5$ is independently H, halogen, cyano, hydroxy, amino, nitro, —CHO, —C(=O)OH, —C(=O)NH$_2$, —NR$^{25}$R$^{26}$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_4$-$C_{10}$ halocycloalkylalkyl, $C_5$-$C_{10}$ alkylcycloalkylalkyl, $C_3$-$C_8$ cycloalkenyl, $C_3$-$C_8$ halocycloalkenyl, $C_2$-$C_6$ alkoxyalkyl, $C_2$-$C_6$ haloalkoxyalkyl, $C_1$-$C_6$ hydroxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_3$-$C_8$ dialkylaminoalkyl, $C_2$-$C_6$ haloalkylaminoalkyl, $C_4$-$C_{10}$ cycloalkylaminoalkyl, $C_2$-$C_6$ alkylcarbonyl, $C_2$-$C_6$ haloalkylcarbonyl, $C_4$-$C_8$ cycloalkylcarbonyl, $C_2$-$C_6$ alkoxycarbonyl, $C_4$-$C_8$ cycloalkoxycarbonyl, $C_5$-$C_{10}$ cycloalkylalkoxycarbonyl, $C_2$-$C_6$ alkylaminocarbonyl, $C_3$-$C_8$ dialkylaminocarbonyl, $C_4$-$C_8$ cycloalkylaminocarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_{10}$ trialkylsilyl, $C_1$-$C_6$ alkylsulfonylamino, $C_1$-$C_6$ haloalkylsulfonylamino or —Z$^2$Q;

each $R^{25}$ is indepently H, $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

each $R^{26}$ is indepently $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl, $C_2$-$C_6$ haloalkoxycarbonyl or —Z$^4$Q;

each $R^{17}$ and $R^{18}$ is independently $C_1$-$C_5$ alkyl, $C_2$-$C_5$ alkenyl, $C_2$-$C_5$ alkynyl, $C_3$-$C_5$ cycloalkyl, $C_3$-$C_6$ halocycloalkyl, $C_4$-$C_{10}$ cycloalkylalkyl, $C_4$-$C_7$ alkylcycloalkyl, $C_5$-$C_7$ alkylcycloalkylalkyl, $C_1$-$C_5$ haloalkyl, $C_1$-$C_5$ alkoxy or $C_1$-$C_5$ haloalkoxy;

each Q is independently a phenyl, a benzyl, a naphthalenyl, a 5- or 6-membered heteroaromatic ring or an 8- to 11-membered heteroaromatic bicyclic ring system, each ring or ring system optionally substituted with 1 to 5 substituents independently selected from $R^7$ on carbon atom ring members and $R^{12}$ on nitrogen atom ring members; or each Q is independently a 3- to 7-membered nonaromatic carbocyclic ring, a 5-, 6- or 7-membered nonaromatic heterocyclic ring or an 8- to 11-membered nonaromatic bicyclic ring system, each ring or ring system optionally including ring members selected from the group consisting of C(=O), C(=S), S(O), S(O)$_2$ and SiR$^{17}$R$^{18}$, and optionally substituted with 1 to 5 substituents independently selected from $R^7$ on carbon atom ring members and $R^{12}$ on nitrogen atom ring members;

each $R^7$ is independently halogen, hydroxy, amino, cyano, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_2$-$C_4$ alkoxyalkyl, $C_1$-$C_4$ hydroxyalkyl, $C_1$-$C_4$ alkoxy, $C_1$-$C_4$ haloalkoxy, $C_2$-$C_6$ alkylcarbonyloxy, $C_1$-$C_4$ alkylthio, $C_2$-$C_6$ alkylcarbonylthio $C_1$-$C_4$ haloalkylthio, $C_1$-$C_4$ alkylsulfinyl, $C_1$-$C_4$ alkylsulfonyl, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; or $R^5$ and $R^7$ are taken together with the atoms linking $R^5$ and $R^7$ to form an optionally substituted 5- to 7-membered ring containing ring members selected from carbon and optionally 1 to 3 heteroatoms selected from up to 1 O up to 1 S and up to 1 N and optionally including 1 to 3 ring members selected from the group consisting of C(=O), C(=S), S(O), S(O)$_2$ and SiR$^{17}$R$^{18}$;

each $R^{12}$ is independently H, $C_1$-$C_3$ alkyl, $C_1$-$C_3$ alkylcarbonyl, $C_1$-$C_3$ alkoxycarbonyl or $C_1$-$C_3$ alkoxy;

each $Z^1$ and $Z^2$ is independently a direct bond, O, C(=O), S(O)$_m$, CHR$^{20}$ or NR$^{21}$;

each $Z^4$ is independently O, C(=O), S(O)$_m$ or CHR$^{20}$;

each $R^{20}$ is independently H, $C_1$-$C_4$ alkyl or $C_1$-$C_4$ haloalkyl;

each $R^{21}$ is independently H, $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

each m is independently 0, 1 or 2; and n is 0, 1 or 2.

More particularly, this invention pertains to a compound of Formula 1C (including all geometric and stereoisomers), an N-oxide or a salt thereof This invention also relates to a fungicidal composition comprising a fungicidally effective amount of a compound of Formula 1C and at least one additional component selected from the group consisting of surfactants, solid diluents and liquid diluents.

This invention further relates to a method for controlling plant diseases caused by fungal plant pathogens comprising applying to the plant or portion thereof, or to the plant seed, a fungicidally effective amount of a compound of Formula 1C (e.g., as a composition described herein).

This invention also relates to a compound of Formula 1A

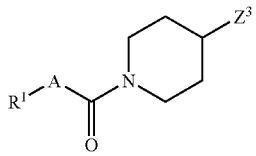

1A wherein
R¹ is U-1, U-20 or U-50 as depicted in Exhibit 1 below;
A is CH$_2$ or NH; or
A is CHOH or NOH;
each R$^{4a}$ is independently halogen, cyano, nitro, C$_1$-C$_3$ alkyl, C$_2$-C$_3$ alkenyl, C$_2$-C$_3$ alkynyl, cyclopropyl, C$_1$-C$_3$ haloalkyl, C$_2$-C$_3$ haloalkenyl, C$_2$-C$_3$ haloalkynyl, halocyclopropyl, C$_1$-C$_2$ alkoxy, C$_1$-C$_2$ haloalkoxy, C$_2$-C$_3$ alkoxyalkyl, C$_1$-C$_2$ alkylthio, C$_1$-C$_2$ haloalkylthio, C$_2$-C$_3$ alkylcarbonyl, C$_2$-C$_3$ alkoxycarbonyl, C$_2$-C$_3$ alkylaminocarbonyl or C$_3$-C$_4$ dialkylaminocarbonyl;
Z³ is CN or C(=S)NH$_2$; and
k is 0, 1 or 2;
provided that when R¹ is U-1, then A is NH.

This invention also relates to a compound of Formula 1B

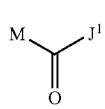

1B wherein
M is hydroxy, C$_1$-C$_3$ alkyl, C$_1$-C$_3$ haloalkyl, C$_1$-C$_4$ alkoxy, C$_1$-C$_2$ haloalkoxy, C$_1$-C$_4$ alkylamino, C$_2$-C$_8$ dialkylamino, 1-piperidinyl, 1-pyrrolidinyl or 4-morpholinyl; and
J¹ is J-29-59 or J-29-60 as depicted in Exhibit A below.

This invention pertains to compounds of Formulae 1A and 1B (including all geometric and stereoisomers), an N-oxide or a salt thereof, except that the compounds of Formula 1B of this invention are limited to those stereoisomer embodiments depicted for J¹ in the Summary of the Invention above.

DETAILS OF THE INVENTION

As used herein, the terms "comprises," "comprising," "includes," "including," "has," "having", "contains" or "containing" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed or bud of a vegetative propagation unit such as tuber, corm or rhizome.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include CH$_2$, CH$_2$CH$_2$, CH(CH$_3$), CH$_2$CH$_2$CH$_2$, CH$_2$CH(CH$_3$) and the different butylene isomers. "Alkenylene" denotes a straight-chain or branched alkenediyl containing one olefinic bond. Examples of "alkenylene" include CH=CH, CH$_2$CH=CH, CH=C(CH$_3$), CH$_2$CH=CH and CH$_2$CH=CHCH$_2$.

"Alkoxy" includes, for example, methoxy, ethoxy, n-propyloxy, isopropyloxy and the different butoxy, pentoxy and hexyloxy isomers. "Alkenyloxy" includes straight-chain or branched alkenyl attached to and linked through an oxygen atom. Examples of "alkenyloxy" include H$_2$C=CHCH$_2$O, (CH$_3$)$_2$C=CHCH$_2$O, CH$_3$CH=CHCH$_2$O, CH$_3$CH=C(CH$_3$)CH$_2$O and CH$_2$=CHCH$_2$CH$_2$O. "Alkynyloxy" includes straight-chain or branched alkynyl ttached to and linked through an oxygen atom. Examples of "alkynyloxy" include HC≡CCH$_2$O, CH$_3$C≡CCH$_2$O and CH$_3$C≡CCH$_2$CH$_2$O. The term "alkylthio" includes straight-chain or branched alkylthio moieties such as methylthio, ethylthio, and the different propylthio, butylthio, pentylthio and hexylthio isomers. "Alkenylthio" denotes straight-chain or branched alkenyl attached to and linked through a sulfur atom such as CH$_2$=CHS, CH$_2$=CHCH$_2$S and CH$_3$CH=CHS. "Alkynylthio" denotes straight-chain or branched alkynyl attached to and linked through a sulfur atom such as CH≡CCH$_2$S and CH$_3$C≡CCH$_2$S. "Alkylsulfinyl" includes both enantiomers of an alkylsulfinyl group. Examples of "alkylsulfinyl" include CH$_3$S(O), CH$_3$CH$_2$S(O), CH$_3$CH$_2$CH$_2$S(O), (CH$_3$)$_2$CHS(O) and the different butylsulfinyl, pentylsulfinyl and hexylsulfinyl isomers. Examples of "alkylsulfonyl" include CH$_3$S(O)$_2$, CH$_3$CH$_2$S(O)$_2$, CH$_3$CH$_2$CH$_2$S(O)$_2$, (CH$_3$)$_2$CHS(O)$_2$ and the different butylsulfonyl, pentylsulfonyl and hexylsulfonyl isomers. "Alkylamino includes an NH radical substituted with straight-chain or branched alkyl. Examples of "alkylamino" include $CH_3CH_2NH$, $CH_3CH_2CH_2NH$, and $(CH_3)_2CHCH_2NH$. Examples of "dialkylamino" include $(CH_3)_2N$, $(CH_3CH_2CH_2)_2N$ and $CH_3CH_2(CH_3)N$. "Alkenylamino" includes an NH radical substituted with straight-chain or branched alkenyl. Examples of "alkenylamino" include $CH_2=CHNH$, $CH_2=CHCH_2NH$ and $CH_3CH=CH_2NH$.

"Alkynylamino" includes an NH radical substituted with straight-chain or branched alkynyl. Examples of "alkynylamino" include $CH\equiv CNH$, $CH\equiv CCH_2NH$ and $CH_3C\equiv CNH$.

The term "alkylcarbonyl" denotes straight-chain or branched alkyl bonded to a $C(=O)$ moiety. Examples of "alkylcarbonyl" include $CH_3C(O)$, $CH_3CH_2CH_2C(O)$ and $(CH_3)_2CHC(O)$.

"Trialkylsilyl" includes 3 branched and/or straight-chain alkyl radicals attached to and linked through a silicon atom, such as trimethylsilyl, triethylsilyl and tert-butyldimethylsilyl. The term "trialkylsilyloxy" denotes trialkylsilyl attached to and linked through an oxygen atom, such as triethylsilyloxy and tert-butyldimethylsilyloxy. "Trialkylsilylthio" is defined analogously to the above examples.

"Hydroxyalkyl" denotes an alkyl group substituted with one hydroxy group. Examples of "hydroxyalkyl" include $HOCH_2CH_2$, $CH_3CH_2(OH)CH$ and $HOCH_2CH_2CH_2$.

"Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on another alkoxy moiety. "Alkoxyalkoxyalkyl" denotes alkoxyalkoxy substitution on alkyl. Examples of "alkoxyalkoxyalkyl" include $CH_3OCH_2OCH_2$, $CH_3OCH_2OCH_2CH_2$, $CH_3CH_2OCH_2OCH_2$ and $CH_3OCH_3CH_2OCH_2CH_2$. "Alkoxycarbonylthio" denotes straight-chain or branched alkyloxy attached to a $C(=O)S$ moiety. Examples of "alkyloxycarbonylthio" include $CH_3CH_2CH_2OC(=O)S$, and $(CH_3)_2CHCH_2OC(=O)S$.

"Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$; "alkylsulfinylalkyl" and "alkylsulfonylalkyl" include the corresponding sulfoxides and sulfones, respectively. "Alkylcarbonylthio" denotes straight-chain or branched alkylcarbonyl attached to and linked through a sulfur atom. Examples of "alkylcarbonylthio" include $CH_3C(=O)S$, $CH_3CH_2CH_2C(=O)S$ and $(CH_3)_2CHC(=O)S$.

"Alkylaminoalkyl" denotes alkylamino substitution on alkyl. Examples of "alkylaminoalkyl" include $CH_3NHCH_2$, $CH_3NHCH_2CH_2$, $CH_3CH_2NHCH_2$, $CH_3CH_2CH_2CH_2NHCH_2$ and $CH_3CH_2NHCH_2CH_2$. Examples of "dialkylaminoalkyl" include $(CH_3)_2CH(CH_3)N$, $(CH_3CH_2CH_2)_2N$ and $CH_3CH_2(CH_3)N$. The term "alkylcarbonylamino" denotes alkyl bonded to a $C(=O)NH$ moiety. Examples of "alkylcarbonylamino" include $CH_3CH_2C(=O)NH$ and $CH_3CH_2CH_2C(=O)NH$. The term "alkoxycarbonylamino" denotes alkoxy bonded to a $C(=O)NH$ moiety. Examples of "alkoxycarbonylamino" include $CH_3OC(=O)NH$ and $CH_3CH_2OC(=O)NH$. The term "alkoxyalkylamino" denotes alkoxyalkyl bonded to NH. Examples of "alkoxyalkylamino" include $CH_3OCH_2NH$, $CH_3OCH_2CH_2NH$, $CH_3CH_2OCH_2NH$, $CH_3CH_2CH_2OCH_2NH$ and $CH_3CH_2OCH_2NH$. Examples of "alkoxyalkylthio" include $CH_3OCH_2S$, $CH_3OCH_2CH_2S$, $CH_3CH_2OCH_2S$, $(CH_3)_2CHCH_2OCH_2S$ and $CH_3CH_2OCH_2CH_2S$.

Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino- or pentylaminocarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $(CH_3)_2CH(CH_3)NC(=O)$ and $CH_3CH_2CH_2(CH_3)NC(=O)$. The term "alkylcarbonyloxy" denotes straight-chain or branched alkyl bonded to a $C(=O)O$ moiety. Examples of "alkylcarbonyloxy" include $CH_3CH_2C(=O)O$ and $(CH_3)_2CHC(=O)O$. "Alkoxycarbonylalkyl" denotes alkoxycarbonyl substitution on straight-chain or branched alkyl. Examples of "alkoxycarbonylalkyl" include $CH_3OC(=O)CH_2CH(CH_3)$, $CH_3CH_2OC(=O)CH_2CH_2$, $(CH_3)_2CHOC(=O)CH_2$. The term "alkylcarbonylalkoxy" denotes alkylcarbonyl bonded to an alkoxy moiety. Examples of "alkylcarbonylalkoxy" include $CH_3C(=O)CH_2CH_2O$ and $CH_3CH_2C(=O)CH_2O$. Examples of "alkoxycarbonyloxy" include $CH_3CH_2CH_2OC(=O)O$ and $(CH_3)_2CHOC(=O)O$.

The term "alkylsulfonyloxy" denotes alkylsulfonyl attached to and linked through an oxygen atom. Examples of "alkylsulfonyloxy" include $CH_3S(=O)_2O$ and $CH_3CH_2S(=O)_2O$. The term "alkylsulfonylthio" denotes alkylsulfonyl attached to and linked through a sulfur atom. Examples of "alkylsulfonylthio" include $(CH_3)_2CHS(=O)_2S$ and $CH_3CH_2S(=O)_2S$. "Alkylsulfonylamino" denotes an NH radical substituted with an alkylsulfonyl. Examples of "alkylsulfonylamino" include $CH_3CH_2S(=O)_2NH$ and $(CH_3)_2CHS(=O)_2NH$.

The term "alkylaminocarbonylamino" denotes straight-chain or branched alkylaminocarbonyl bonded to NH. Examples of "alkylaminocarbonylamino" include $CH_3NHC(=O)NH$ and $CH_3CH_2NHC(=O)NH$. Examples of "dialkylaminocarbonylamino" include $(CH_3)_2NC(=O)NH$ and $CH_3CH_2(CH_3)NC(=O)NH$. The term "alkylaminocarbonyloxy" denotes straight-chain or branched alkylaminocarbonyl attached to and linked through an oxygen atom. Examples of "alkylaminocarbonyloxy" include $(CH_3)_2CHCH_2NHC(=O)O$ and $CH_3CH_2NHC(=O)O$. Examples of "dialkylaminocarbonyloxy" include $CH_3CH_2CH_2(CH_3)NC(=O)O$ and $(CH_3)_2NC(=O)O$. The term "alkylaminocarbonylthio" denotes straight-chain or branched alkylaminocarbonyl attached to and linked through an oxygen atom. Examples of "alkylaminocarbonylthio" include $CH_3CH_2CH_2NHC(=O)S$ and $(CH_3)_2CHNHC(=O)S$. Examples of "dialkylaminocarbonylthio" include $(CH_3)_2NC(=O)S$ and $(CH_3)_2CH(CH_3)NC(=O)S$.

"Cycloalkyl" includes, for example, cyclopropyl, cyclobutyl, cyclopentyl, and cyclohexyl. The term "cycloalkylalkyl" denotes cycloalkyl substitution on an alkyl group. Examples of "cycloalkylalkyl" include cyclopropylmethyl, cyclopentylethyl, and other cycloalkyl moieties bonded to straight-chain or branched alkyl groups. "Alkylcycloalkyl" denotes alkyl substitution on a cycloalkyl moiety. Examples include 4-methylcyclohexyl and 3-ethylcyclopentyl. "Cycloalkenyl" includes groups such as cyclopentenyl and cyclohexenyl as well as groups with more than one double bond such as 1,3- and 1,4-cyclohexadienyl.

The term "cycloalkoxy" denotes cycloalkyl attached to and linked through an oxygen atom such as cyclopentyloxy and cyclohexyloxy. The term "cycloalkoxyalkyl" denotes cycloalkoxy substitution on an alkyl moiety. Examples of "cycloalkoxyalkyl" include cyclopropyloxymethyl, cyclopentyloxyethyl, and other cycloalkoxy moieties bonded to straight-chain or branched alkyl groups. "Cycloalkylalkoxy" denotes cycloalkylalkyl attached to and linked through an oxygen atom. Examples of "cycloalkylalkoxy" include cyclopropylmethoxy, cyclopentylethoxy, and other cycloalkyl moieties bonded to straight-chain or branched alkoxy groups.

The term "cycloalkylthio" denotes cycloalkyl attached to and linked through a sulfur atom such as cyclopropylthio and cyclopentylthio; "cycloalkylsulfonyl" includes the corresponding sulfones.

"Alkylcycloalkylalkyl" denotes an alkyl group substituted with alkylcycloalkyl. Examples of "alkylcycloalkylalkyl" include 1-, 2-, 3-, or 4-methyl or ethyl cyclohexylmethyl. The term "cycloalkylcycloalkyl" denotes cycloalkyl substitution on another cycloalkyl ring, wherein each cycloalkyl ring independently has from 3 to 7 carbon ring members. Examples of cycloalkylcycloalkyl include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1'-bicyclohexyl-1-yl), and the different cis- and trans-cycloalkylcycloalkyl isomers, (such as (1R,2S)-1,1'-bicyclopropyl-2-yl and (1R, 2R)-1,1'-bicyclopropyl-2-yl).

"Cycloalkylamino" denotes an NH radical substituted with cycloalkyl. Examples of "cycloalkylamino" include cyclopropylamino and cyclohexylamino. The term "cycloalkylaminoalkyl" denotes cycloalkylamino substitution on an alkyl group. Examples of "cycloalkylaminoalkyl" include cyclopropylaminomethyl, cyclopentylaminoethyl, and other cycloalkylamino moieties bonded to straight-chain or branched alkyl groups.

"Cycloalkylcarbonyl" denotes cycloalkyl bonded to a $C(=O)$ group including, for example, cyclopropylcarbonyl and cyclopentylcarbonyl. "Cycloalkylcarbonyloxy" denotes cycloalkylcarbonyl attached to and linked through an oxygen, for example, cyclopentylcarbonyloxy and cyclohexylcarbonyloxy. The term "cycloalkoxycarbonyl" means cycloalkoxy bonded to a $C(=O)$ group. "Cycloalkylaminocarbonyl" denotes cycloalkylamino bonded to a $C(=O)$ group, for example, cyclopentylaminocarbonyl and cyclohexylaminocarbonyl. The term "cycloalkoxycarbonyl" means cycloalkoxy bonded to a $C(=O)$ group, for example, cyclopropyloxycarbonyl and cyclopentyloxycarbonyl. "Cycloalkylalkoxycarbonyl" denotes cycloalkylalkoxy bonded to a $C(=O)$ group. Examples of "cycloalkylalkoxycarbonyl" include cyclopropylethoxycarbonyl and cyclopentylmethoxycarbonyl. "Cycloalkylcarbonyloxy" denotes cycloalkylcarbonyl attached to and linked through an oxygen atom. Examples of "cycloalkylcarbonyloxy" include cyclohexylcarbonyloxy and cyclopentylcarbonyloxy.

The term "halogen", either alone or in compound words such as "haloalkyl", includes fluorine, chlorine, bromine or iodine. Furthermore, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The term halodialkyl, either alone or in compound words such as "halodialkylamino", means two separate alkyl groups each of which may independently be partially or fully substituted with halogen atoms which may be the same or different. The terms "haloalkenyl", "haloalkynyl", "haloalkoxy", "haloalkylthio", "haloalkylamino", "halodialkylamino", "haloalkylsulfonyl", "haloalkylsulfinyl", "halocycloalkyl", and the like, are defined analogously to the term "haloalkyl". Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylamino" include $CF_3(CH_3)CHNH$, $(CF_3)_2CHNH$ and $CH_2ClCH_2NH$. Examples of "halodialkylamino" include $(BrCH_2CH_2)_2N$ and $BrCH_2CH_2(ClCH_2CH_2)N$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$. Examples of "halocycloalkyl" include $CF_3OCH_2O$, $ClCH_2CH_2OCH_2CH_2O$, $Cl_3CCH_2OCH_2O$ as well as branched alkyl derivatives.

Unless otherwise indicated, a "ring" or "ring system" as a component of Formula 1 or Formula 1C (e.g., substituent J and Q) is carbocyclic or heterocyclic. The term "ring system" denotes two or more connected rings. The term "spirocyclic ring system" denotes a ring system consisting of two rings connected at a single atom (so the rings have a single atom in common). Illustrative of a $J^1$ moiety that is a spirocyclic ring system is J-29-59 specified in the definition of Formula 1B and shown in Exhibit A below. The term "bicyclic ring system" denotes a ring system consisting of two rings sharing two or more common atoms. In a "fused bicyclic ring system" the common atoms are adjacent, and therefore the rings share two adjacent atoms and a bond connecting them. In a "bridged bicyclic ring system" the common atoms are not adjacent (i.e. there is no bond between the bridgehead atoms). A "bridged bicyclic ring system" is conceptually formed by bonding a segment of one or more atoms to nonadjacent ring members of a ring.

A ring, a bicyclic ring system or a spirocyclic ring system can be part of an extended ring system containing more than two rings wherein substituents on the ring, bicyclic ring system or spirocyclic ring system are taken together to form the additional rings, which may be in bicyclic and/or spirocyclic relationships with other rings in the extended ring system. For example, the J moiety J-29-26 depicted in Exhibit A below consists of a dihydro isoxazoline ring having one $R^5$ substituent as $Z^2Q$, which is a cyclobutyl ring substituted with two methyl groups as $R^7$ and also one $R^7$ group taken together with another $R^5$ substituent on the dihydro isoxazoline ring as —$CH_2CH_2$— to form the additional six-membered ring component in the ring system.

The term "ring member" refers to an atom (e.g., C, O, N or S) or other moiety (e.g., $C(=O)$, $C(=S)$, $S(O)$ or $S(O)_2$) forming the backbone of a ring or ring system. The term "carbocyclic ring" denotes a ring wherein the atoms forming the ring backbone are selected only from carbon. "Aromatic" indicates that each of the ring atoms is essentially in the same plane and has a p-orbital perpendicular to the ring plane, and in which (4n +2) π electrons, where n is a positive integer, are associated with the ring to comply with Hückel's rule.

The term "carbocyclic ring system" denotes two or more connected rings wherein the atoms forming the backbone of the rings are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

The terms "heterocyclic ring" or "heterocycle" denotes a ring wherein at least one of the atoms forming the ring backbone is other than carbon. The term "heterocyclic ring system" denotes two or more connected rings wherein at least one of the atoms forming the backbone of the rings is other than carbon. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or aromatic heterocyclic ring. "Saturated heterocyclic ring" refers a heterocyclic ring containing only single bonds between ring members. "Partially saturated heterocyclic ring" refers a heterocyclic ring containing at least one double bond but which is not aromatic.

The dotted line in Formula 1, Formula 1C, and in other rings depicted in the present description (e.g., J-44, J-45, J-48 and J-49 in Exhibit 3) indicates that the bond can be a single bond or double bond. Unless otherwise indicated, heterocyclic rings and ring systems are attached to the remainder of Formula 1 or Formula 1C through any available carbon or nitrogen by replacement of a hydrogen on said carbon or nitrogen, and all substituents on the heterocyclic rings and ring systems are attached through any available carbon or nitrogen by replacement of a hydrogen on said carbon or nitrogen.

As already described, J is a 5-, 6- or 7-membered ring, an 8- to 11-membered bicyclic ring system or a 7- to 11-membered spirocyclic ring system, each ring or ring system containing ring members selected from carbon and optionally 1 to 4 heteroatoms selected from up to 2 O, up to 2 S and up to 4 N, and optionally including 1 to 3 ring members selected from the group consisting of $C(=O)$, $C(=S)$, $S(O)$, $S(O)_2$ and $SiR^{17}R^{18}$, each ring or ring system optionally substituted with 1 to 5 substituents independently selected from $R^5$. As the heteroatoms are optional, 0 to 4 heteroatoms may be present. In this description the heteroatoms selected from up to 2 S are atoms and not the moieties $S(O)$ or $S(O)_2$. The heteroatoms selected from up to 4 N may be oxidized as N-oxides, because compounds of Formula 1 and Formula 1C also relates to N-oxide derivatives. Therefore the optional 1 to 3 ring members selected from the group consisting of $C(=O)$, $C(=S)$, $S(O)$, $S(O)_2$ and $SiR^{17}R^{18}$ are in addition to the optional 1 to 4 heteroatoms selected from up to 2 O, up to 2 S and up to 4 N. Of note is when the total number of unoxidized sulfur atoms (i.e. S) and oxidized sulfur moieties (i.e. $S(O)$ and $S(O)_2$) does not exceed 2, so that at most two ring members selected from S, $S(O)$ and $S(O)_2$ are present in the ring or ring system. When none of the optional heteroatoms and none of the optional ring members selected from $S(O)$, $S(O)_2$ and $SiR^{17}R^{18}$ are present, the ring or ring system is carbocyclic. The $R^5$ substituents may be attached to carbon atom ring members and to nitrogen atom ring members having an available point of attachment. The carbon-based ring members $C(=O)$ and $C(=S)$ do not have available points of attachment. Furthermore in $SiR^{17}R^{18}$ ring members, the substituents $R^{17}$ and $R^{18}$ are otherwise separately defined, and these ring members cannot be further substituted with $R^5$. As the $R^5$ substituents are optional, 0 to 5 substituents may be present, limited by the number of available points of attachment.

Similarly, $R^5$ and $R^7$ may be taken together with the atoms linking $R^5$ and $R^7$ to form an optionally substituted 5- to 7-membered ring containing ring members selected from carbon and optionally 1 to 3 heteroatoms selected from up to 1 O, up to 1 S and up to 1 N and optionally including 1 to 3 ring members selected from the group consisting of $C(=O)$, $C(=S)$, $S(O)$, $S(O)_2$ and $SiR^{17}R^{18}$. As the heteroatoms are optional, 0 to 3 heteroatoms may be present. In this description the heteroatom selected from up to 1 S is an atom and not the moieties $S(O)$ or $S(O)_2$. The heteroatom selected from up to 1 N may be oxidized as an N-oxide, because compounds of Formula 1 and Formula 1C also relates to N-oxide derivatives derivatives. Therefore the optional 1 to 3 ring members selected from the group consisting of $C(=O)$, $C(=S)$, $S(O)$, $S(O)_2$ and $SiR^{17}R^{18}$ are in addition to the optional 1 to 3 heteroatoms selected from up to 1 O, up to 1 S and up to 1 N. Of note is when the total number of unoxidized sulfur atoms (i.e. S) and oxidized sulfur moieties (i.e. $S(O)$ and $S(O)_2$) does not exceed 1, so that at most one ring member selected from S, $S(O)$ and $S(O)_2$ is present in the ring. When none of the optional heteroatoms and none of the optional ring members selected from $S(O)$, $S(O)_2$ and $SiR^{17}R^{18}$ are present, the ring is carbocyclic. The 5- to 7-membered ring is optionally substituted. The substituents on the atoms linking $R^5$ and $R^7$ are described in the definition of the components linking $R^5$ and $R^7$. For example, when linking component $Z^2$ is $CHR^{20}$, the substituent $R^{20}$ is defined to be H, $C_1$-$C_4$ alkyl or $C_1$-$C_4$ haloalkyl. Regarding optional substituents attached to the portion of the ring consisting of $R^5$ and $R^7$ taken together, an optional substituent is a non-hydrogen substituent that does not extinguish fungicidal activity. Optional substituents may be attached to carbon atom ring members and to nitrogen atom ring members having an available point of attachment. The carbon-based ring members $C(=O)$ and $C(=S)$ do not have available points of attachment. Furthermore in $SiR^{17}R^{18}$ ring members, the substituents $R^{17}$ and $R^{18}$ are otherwise separately defined, and these ring members cannot be further substituted.

The total number of carbon atoms in a substituent group is indicated by the "$C_i$-$C_j$" prefix where i and j are numbers from 1 to 14. For example, $C_1$-$C_4$ alkylsulfonyl designates methylsulfonyl through butylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

When a compound is substituted with a substituent bearing a subscript that indicates the number of said substituents can vary, then when the number of said substituents is greater than 1, said substituents are independently selected from the group of defined substituents. Furthermore when a range is indicated (e.g., i-j substituents), then the number of substituents may be selected from the integers between i and j inclusive. When a group (e.g., J) contains a substituent (e.g., $R^5$) which can be hydrogen, then when this substituent is taken as hydrogen, it is recognized that this is equivalent to said group being unsubstituted. When a variable group is shown to be optionally attached to a position, for example $(R^2)_n$ wherein n may be 0, or as a further example $(R^4)_k$ wherein k may be 0 in Exhibit 1, then hydrogen may be at the position even if not recited in the definition of the variable group (e.g., $R^2$ and $R^4$). When a position on a group is said to be "not substituted" or "unsubstituted", then hydrogen atoms are attached to take up any free valency. The term "optionally substituted" in connection with groups $R^1$, $R^2$, $R^5$, $R^7$, G, J and Q refers to groups that are unsubstituted or have at least 1 non-hydrogen substituent. Unless otherwise indicated, these groups may be substituted with as many optional substituents as can be accommodated by replacing a hydrogen atom with a non-hydrogen substituent on any available carbon or nitrogen atom. Commonly, the number of optional substituents (when present) ranges from 1 to 3. When a range specified for the number of substituents (e.g., x being an integer from 0 to 5 in Exhibit 3) exceeds the number of positions available for substituents on a ring (e.g., 2 positions available for $(R^5)_x$ on J-1 in Exhibit 3), the actual higher end of the range is recognized to be the number of available positions. The term "optionally substituted" means that the number of substituents can be zero. For example, the phrase "optionally substituted with up to 2 substituents selected from $R^3$ on carbon ring members and selected from $R^{11}$ on nitrogen ring members" means that 0, 1 or 2 substituents can be present (if the number of potential connection points allows), and thus the number of $R^3$ and $R^{11}$ substituents can be zero. Similarly, the phrase "optionally substituted with 1 to 5 substituents" means that 0, 1, 2, 3, 4 or 5 substituents can be present if the number of available connection points allows. The term "unsubstituted" in connection with a group such as a ring or ring system means the group does not have any substituents other than its one or more attachments to the remainder of Formula 1 or Formula 1C. The term "meta-substituted phenyl" means a phenyl ring substituted with a non-hydrogen substituent at a meta position relative to attachment of the phenyl ring to the remainder of Formula 1 or Formula 1C.

As noted above, $R^1$ is an optionally substituted phenyl, naphthalenyl or 5- or 6-membered heteroaromatic ring; G is an optionally substituted 5-membered heteroaromatic ring or 5-membered saturated or partially saturated heterocyclic ring; and $R^5$ and $R^7$ may be taken together with the atoms linking $R^5$ and $R^7$ to form an optionally substituted 5- to 7-membered ring containing ring members selected from carbon and optionally 1 to 3 heteroatoms selected from up to 1 O, up to 1 S and up to 1 N and optionally including 1 to 3 ring members selected from the group consisting of C(=O), C(=S), S(O), S(O)$_2$ and SiR$^{17}$R$^{18}$. The term "substituted" in connection with the definitions of $R^1$, G, $R^5$ and $R^7$ refers to groups that have at least one non-hydrogen substituent that does not extinguish fungicidal activity. Since these groups are optionally substituted, they need not have any non-hydrogen substituents. As these groups are "optionally substituted" without the number of substituents indicated, these groups may be substituted with as many optional substituents as can be accommodated by replacing a hydrogen atom with a non-hydrogen substituent on any available carbon or nitrogen atom.

Naming of substituents in the present disclosure uses recognized terminology providing conciseness in precisely conveying to those skilled in the art the chemical structure. For sake of conciseness, locant descriptors may be omitted; "pyrazol-1-yl" means "1H-pyrazol-1-yl" according to the Chemical Abstracts system of nomenclature. The term "pyridyl" is synonymous with "pyridinyl". The order of listing substituents may be different from the Chemical Abstracts system if the difference does not affect the meaning Compounds of Formula 1 and Formula 1C can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Compounds of Formula 1 and Formula 1C may be present as a mixture of stereoisomers, individual stereoisomers, or as an optically active form. For example, when J is J-29 (see Exhibit 3) bonded at the 3-position to the remainder of Formula 1 and J-29 has one $R^5$ substituent other than H at the 5-position, then Formula 1 possesses a chiral center at the carbon atom to which $R^5$ is bonded. The two enantiomers are depicted as Formula 1' and Formula 1" with the chiral center identified with an asterisk (*).

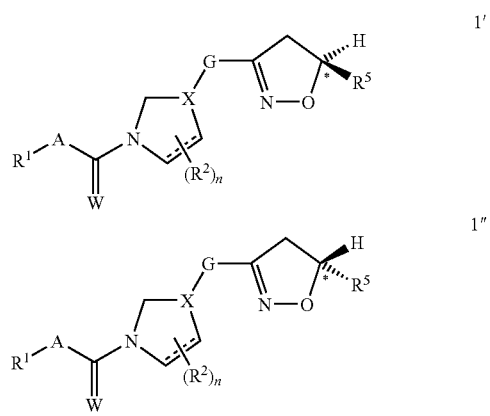

Compounds of Formula 1 and Formula 1C comprise racemic mixtures, for example, equal amounts of the enantiomers of Formulae 1' and 1". In addition, compounds of Formula 1 and Formula 1C include compounds that are enriched compared to the racemic mixture in an enantiomer of Formula 1 or Formula 1C. Also included are the essentially pure enantiomers of compounds of Formula 1, for example, Formula 1' and Formula 1".

When enantiomerically enriched, one enantiomer is present in greater amounts than the other, and the extent of enrichment can be defined by an expression of enantiomeric excess ("ee"), which is defined as $(2x-1)\cdot 100\%$, where x is the mole fraction of the dominant enantiomer in the mixture (e.g., an ee of 20% corresponds to a 60:40 ratio of enantiomers).

Preferably the compositions of this invention of Formula 1 or Formula 1C have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 and Formula 1C can comprise additional chiral centers. For example, substituents and other molecular constituents such as $R^4$, $R^5$, $R^7$, G, J, Q, $X^1$ through $X^9$ $Z^2$, $Z^3$ and $Z^4$ may themselves contain chiral centers. Compounds of Formula 1 and Formula 1C comprise racemic mixtures as well as enriched and essentially pure stereoconfigurations at these additional chiral centers.

Compounds of Formula 1 and Formula 1C can exist as one or more conformational isomers due to restricted rotation about the amide bond (e.g., C(W)—N) in Formula 1 and Formula 1C. Compounds of Formula 1 and Formula 1C comprise mixtures of conformational isomers. In addition, compounds of Formula 1 and Formula 1C include compounds that are enriched in one conformer relative to others.

Some of the unsaturated rings and ring systems depicted in Exhibits 1, 2, 3 and 4 can have an arrangement of single and double bonds between ring members different from that depicted. Such differing arrangements of bonds for a particular arrangement of ring atoms correspond to different tautomers. For these unsaturated rings and ring systems, the particular tautomer depicted is to be considered representative of all the tautomers possible for the arrangement of ring atoms shown. The tables listing particular compounds incorporating the ring and ring systems depicted in the Exhibits may involve a tautomer different from the tautomer depicted in the Exhibits.

Compounds of Formula 1 and Formula 1C typically exist in more than one form, and Formula 1 and Formula 1C thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 and Formula 1C can exhibit beneficial effects (e.g., suitability for preparation of useful formulations, improved biological performance) relative to another polymorph or a mixture of polymorphs of the same compound of Formula 1 and Formula 1C. Preparation and isolation of a particular polymorph of a compound of Formula 1 and Formula 1C can be achieved by methods known to those skilled in the art including, for example, crystallization using selected solvents and temperatures.

Compounds of Formula 1 and Formula 1C include N-oxide derivatives. One skilled in the art will appreciate that not all nitrogen-containing heterocycles can form N-oxides since the nitrogen requires an available lone pair of electrons for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as tent-butyl hydroperoxide, sodium perborate, and dioxiranes such as dimethyldioxirane. These methods for the preparation of N-oxides have been extensively described and reviewed in the literature, see for example: T. L. Gilchrist in Comprehensive Organic Synthesis, vol. 7, pp 748-750, S. V. Ley, Ed., Pergamon Press; M. Tisler and B. Stanovnik in Comprehensive Heterocyclic Chemistry, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding non-salt forms, salts share the biological utility of the nonsalt forms. When the compounds forming the present mixtures and compositions contain acidic or basic moieties, a wide variety of salts can be formed, and these salts are useful in the present mixtures and compositions for controlling plant diseases caused by fungal plant pathogens (i.e. are agriculturally suitable). When a compound contains a basic moiety such as an amine function, salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound contains an acidic moiety such as a carboxylic acid or phenol, salts include those formed with organic or inorganic bases such as pyridine, triethylamine or ammonia, or amides, hydrides, hyroxides or carbonates of sodium, potassium, lithium, calcium, magnesium or barium.

Component (b) is selected from the group consisting of
- (b1) methyl benzimidazole carbamate (MBC) fungicides;
- (b2) dicarboximide fungicides;
- (b3) demethylation inhibitor (DMI) fungicides;
- (b4) phenylamide fungicides;
- (b5) amine/morpholine fungicides;
- (b6) phospholipid biosynthesis inhibitor fungicides;
- (b7) carboxamide fungicides;
- (b8) hydroxy(2-amino-)pyrimidine fungicides;
- (b9) anilinopyrimidine fungicides;
- (b10) N-phenyl carbamate fungicides;
- (b11) quinone outside inhibitor (QoI) fungicides;
- (b12) phenylpyrrole fungicides;
- (b13) quinoline fungicides;
- (b14) lipid peroxidation inhibitor fungicides;
- (b15) melanin biosynthesis inhibitors-reductase (MBI-R) fungicides;
- (b16) melanin biosynthesis inhibitors-dehydratase (MBI-D) fungicides;
- (b17) hydroxyanilide fungicides;
- (b18) squalene-epoxidase inhibitor fungicides;
- (b19) polyoxin fungicides;
- (b20) phenylurea fungicides;
- (b21) quinone inside inhibitor (QiI) fungicides;
- (b22) benzamide fungicides;
- (b23) enopyranuronic acid antibiotic fungicides;
- (b24) hexopyranosyl antibiotic fungicides;
- (b25) glucopyranosyl antibiotic: protein synthesis fungicides;
- (b26) glucopyranosyl antibiotic: trehalase and inositol biosynthesis fungicides;
- (b27) cyanoacetamideoxime fungicides;
- (b28) carbamate fungicides;
- (b29) oxidative phosphorylation uncoupling fungicides;
- (b30) organo tin fungicides;
- (b31) carboxylic acid fungicides;
- (b32) heteroaromatic fungicides;
- (b33) phosphonate fungicides;
- (b34) phthalamic acid fungicides;
- (b35) benzotriazine fungicides;
- (b36) benzene-sulfonamide fungicides;
- (b37) pyridazinone fungicides;
- (b38) thiophene-carboxamide fungicides;
- (b39) pyrimidinamide fungicides;
- (b40) carboxylic acid amide (CAA) fungicides;
- (b41) tetracycline antibiotic fungicides;
- (b42) thiocarbamate fungicides;
- (b43) benzamide fungicides;
- (b44) host plant defense induction fungicides;
- (b45) multi-site contact activity fungicides;
- (b46) fungicides other than fungicides of component (a) and components (b1) through (b45); and salts of compounds of (b1) through (b46).

Of note are embodiments wherein component (b) comprises at least one fungicide from each of two different groups selected from (b1) through (b46).

Also of note are embodiments wherein component (a) is 4-[4-[(5R)-4,5-dihydro-5-phenyl-3-isoxazolyl]-2-thiazolyl]-1-[[5-methyl-3-(trifluoromethyl)-1H-pyrazol-1-yl]acetyl]piperidine, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[[5-methyl-3-(trifluoromethyl)-1H-pyrazol-1-yl]acetyl]-4-[4-(5-phenyl-3-isoxazolyl)-2-thiazolyl]piperidine. In these embodiments, component (b) comprises a fungicide selected from (b1) through (b46). These embodiments include, but not limited to, compositions wherein component (b) comprises at least one fungicide from each of two different groups selected from (b1) through (b46).

Also of note are embodiments wherein component (a) is 1-[4-[4-[(5R)-4,5-dihydro-5-methyl-5-phenyl-3-isoxazolyl]-2-thiazolyl]-1-piperidinyl]-2-[5-methyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 2-[5-methyl-3-(trifluoromethyl)-1H-pyrazol-1-yl]-1-[4-[4-[(3aS,9bR),3a,4,5 ,9b-tetrahydronaphth[2,1-d]isoxazol-3-yl]-2-thiazolyl]-1-piperidinyl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (3aS,9bR)-enantiomer or its racemic mixture.

Also of note are embodiments wherein component (a) is 1-[4-[4-[(5R)-4,5-dihydro-5-phenyl-3-isoxazolyl]-2-thiazolyl]-1-piperidinyl]-2-[5-ethyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 2-[3,5- bis(trifluoromethyl)-1H-pyrazol-1-yl]-1-[4-[4-[(5R)-4,5-dihydro-5-phenyl-3-isoxazolyl]-2-thiazolyl]-1-piperidinyl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[4-[4-[(5R)-3',4'-dihydrospiro [isoxazole-5(4H),1',(2'H)-naphthalen]-3-yl]-2-thiazolyl]-1-piperidinyl]-2-[5-methyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[4-[4-[(5R)-2,3-dihydrospiro[1H-indene-1,5'(4'H)-isoxazol]-3'-yl]-2-thiazolyl]-1-piperidinyl]-2-[5-methyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 2-[5-chloro-3-(trifluoromethyl)-1H-pyrazol-1-yl]-1-[4-[4-[(5R)-4,5-dihydro-5-phenyl-3-isoxazoly]-2-thiazolyl]-1-piperidinyl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 2-[(5R)-4,5-dihydro-3-[2-[1-[2-[5-methyl-3-(trifluoromethyl)-1H-pyrazol-1-yl]acetyl]-4-piperidinyl]-4-thiazolyl-5-isoxazolyl]-1H-isoindole-1,3(2H)-dione, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 2-[5-chloro-3-(trifluoromethyl)-1H-pyrazol-1-yl]-1-[4-[4-[(1R)-2,3-dihydrospiro[1H-indene-1,5'(4'H) -isoxazol]-3'-yl]-2-thiazolyl]-1-piperidinyl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (1R)-enantiomer or its racemic mixture.

Also of note are embodiments wherein component (a) is 2-[5-chloro-3-(trifluoromethyl)-1H-pyrazol-1-yl]-1-[4-[4-[(1'R)-3',4'-dihydrospiro[isoxazole-5(4H),1'(2'H)-naphthalen]-3-yl]-2-thiazolyl]-1-piperidinyl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (1'R)-enantiomer or its racemic mixture.

Also of note are embodiments wherein component (a) is 2-[5-methyl-3-(trifluoromethyl)-1H-pyrazol-1-yl]-1-[4-[4-(3R)-spiro[benzofuran-3(2H),5'(4'H)-isoxazol-3'-yl-2-thiazolyl]-1-piperidinyl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (3R)-enantiomer or its racemic mixture.

Also of note are embodiments wherein component (a) is 1-[4-[4-[(1R)-2,3-dihydrospiro[1H-indene-1,5'(4'H)-isoxazol]-3'-yl]-2-thiazolyl]-1-piperidinyl]-2-(3,5-dimethyl-1H-pyrazol-1-yl)ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (1R)-enantiomer or its racemic mixture.

Also of note are embodiments wherein component (a) is 2-[3,5-bis(trifluoromethyl)-1H-pyrazol-1-yl]-1-[4-[4-[(1'R)-3',4'-dihydrospiro[isoxazole-5(4H),1'(2'H)-naphthalen]-3-yl]-2-thiazolyl]-1-piperidinyl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (1'R)-enantiomer or its racemic mixture.

Also of note are embodiments wherein component (a) is 2-[3,5-bis(trifluoromethyl)-1H-pyrazol-1-yl]-1-[4-[4-[(1R)-2,3-dihydrospiro[1H-indene-1,5'(4'H)-isoxazol]-3'-yl]-2-thiazolyl]-1-piperidinyl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (1R)-enantiomer or its racemic mixture.

Also of note are embodiments wherein component (a) is 1-[4-[4-[(5R)-5-(2,6-dichlorophenyl)-4,5-dihydro-3-isoxazolyl]-2-thiazolyl]-1-piperidinyl]-2-[5-methyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[4-[4-[(5R)-4,5-dihydro-5-(2-fluorophenyl)-3-isoxazolyl]-2-thiazolyl]-1-piperidinyl]-2-[5-methyl-3-trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[4-[4-[(5R)-4,5-dihydro-5-(2-methylphenyl)-3-isoxazolyl]-2-thiazolyl]-1-piperidinyl]-2-[5-methyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[4-[4-[(5R)-5-(2,6-dimethylphenyl)-4,5-dihydro-3-isoxazolyl]-2-thiazolyl]-1-piperidinyl]-2-[5-methyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[4-[4-[(5R)-4,5-dihydro-5-(2,4,6-trimethylphenyl)-3-isoxazolyl]-2-thiazolyl]-1-piperidinyl]-2-[5-methyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[4-[4-[(1'R)-3',4'-dihydrospiro[isoxazole-5(4H),1'(2'H)-naphthalen]-3-yl]-2-thiazolyl]-1-piperidinyl]-2-(3,5-dimethyl-1H-pyrazol-1-yl)ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (1'R)-enantiomer or its racemic mixture.

Also of note are embodiments wherein component (a) is 1-[4-[4-[(5R)-4,5-dihydro-5-(2,4,6-trimethoxyphenyl)-3-isoxazolyl]-2-thiazolyl]-1-piperidinyl]-2-[5-methyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 3-[(5R)-4,5-dihydro-3-[2-[1-[2-[5-methyl-3-(trifluoromethyl)-1H-pyrazol-1-yl]acetyl]-4-piperidinyl]-4-thiazolyl-5-isoxazolyl]-2(3H)-benzoxazolone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[4-[4-[(5R)-5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 2-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]benzonitrile, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 2-[5-chloro-3-(trifluoromethyl)-1H-pyrazol-1-yl]-1-[4-[4-[(5R)-4,5-dihydro-5-methyl-5-phenyl-3-isoxazolyl]-2-thiazolyl]-1-piperidinyl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 2-[3,5-bis(trifluoromethyl)-1H-pyrazol-1-yl]-1-[4-[4-[(5R)-4,5-dihydro-5-methyl-5-phenyl-3-isoxazolyl]-2-thiazolyl]-1-piperidinyl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[4-[4-[(5R)-5-(2-chlorophenyl)-4,5-dihydro-3-isoxazolyl]-2-thiazolyl]-1-piperidinyl]-2-[5-methyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[4-[4-[(5R)-4,5-dihydro-5-phenyl-3-isoxazolyl]-2-thiazolyl]-1-piperidinyl]-2-[3-methyl-5-(trifluoromethyl-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[4-[4-[(4S)-2,3-dihydrospiro[4H-1-benzopyran-4,5'(4'H)-isoxazol]-3'-yl]-2-thiazolyl]-1-piperidinyl]-2-[5-methyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (4S)-enantiomer or its racemic mixture.

Also of note are embodiments wherein component (a) is (5R)-4,5-dihydro-3-[2-[1-[2-[5-methyl-3-(trifluoromethyl)-1H-pyrazol-1-yl]acetyl]-4-piperidinyl]-4-thiazolyl]-5-phenyl-5-isoxazolecarbonitrile, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[4-[4-[(5R)-4,5-dihydro-5-phenyl-3-isoxazolyl]-2-thiazolyl]-1-piperidinyl]-2-[5-methyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[(5R)-4,5-dihydro-3-[2-[1-[2-[5-methyl-3-(trifluoromethyl)-1H-pyrazol-1-yl]acetyl]-4-piperidinyl]-4-thizolyl]-5-isoxazolyl]-1,3-dihydro-3-methyl-2H-benzimidazol-2-one, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is N-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-N-phenylacetamide, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 4-[4-[(5R)-4,5-dihydro-5-phenyl-3-isoxazolyl]-2-thiazolyl]-N-(2,5-dimethylphenyl)-1-piperidinecarboxamide, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 3-[(5R)-4,5-dihydro-3-[2-[1-[2-[5-methyl-3-(trifluoromethyl)-1H-pyrazol-1-yl]acetyl]-4-piperidinyl]-4-thizolyl]-5-isoxazolyl]-2(3H)-benzothiazolone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-acetyl-3-[(5R)-4,5-dihydro-3-[2-[1-[2-[5-methyl-3-(trifluoromethyl)-1H-pyrazol-1-yl]acetyl]-4-piperidinyl]-4-thizolyl]-5-isoxazolyl]-1,3-dihydro-2H-benzimidazol-2-one, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 4-[4-[(5R)-4,5-dihydro-5-phenyl-3-isoxazolyl]-2-thiazolyl]-N-[5-methyl-3-(trifluoromethyl)-1H-pyrazolyl-1-yl]-1-piperidinecarboxamide, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[4-[4-[(5R)-5-(2-bromophenyl)-4,5-dihydro-3-isoxazolyl]-2-thiazolyl]-1-piperidinyl]-2-[5-methyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 4-[4-[(5R)-5-(2,6-difluorophenyl)-4,5-dihydro-3-isoxazolyl]-2-thiazolyl]-N-(2,5-dimethylphenyl)-1-piperidinecarboxamide, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 2-(3,5-dimethyl-1H-pyrazol-1-yl)-1-[4-[4-[(5R)-5-(2,6-difluorophenyl)-4,5-dihydro-3-isoxazolyl]-2-thizolyl]-1-piperidinyl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 2-(2,5-dimethylphenyl)-1-[4-[4-[(5R)-5-(2,6-difluorophenyl)-4,5-dihydro-3-isoxazolyl]-2-thiazolyl]-1-piperidinyl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

Also of note are embodiments wherein component (a) is 1-[4-[4-[(5R)-4,5-dihydro-5-[2-(trifluoromethyl)phenyl]-3-isoxazolyl]-2-thiazolyl]-1-piperidinyl]-2-[5-methyl-3-(trifluoromethyl)-1H-pyrazol-1-yl]ethanone, its enantiomer or a mixture thereof (e.g., a racemic mixture). In these embodiments, component (b) comprises a fungicide selected from (b1) through (b46). These embodiments include, but not limited to, compositions wherein component (b) comprises at least one fungicide from each of two different groups selected from (b1) through (b46). Preferably component (a) is the (5R)-enantiomer or its racemic mixture.

"Methyl benzimidazole carbamate (MBC) fungicides (b1)" (Fungicide Resistance Action Committee (FRAC) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

"Dicarboximide fungicides (b2)" (Fungicide Resistance Action Committee (FRAC) code 2) are proposed to inhibit a lipid peroxidation in fungi through interference with NADH cytochrome c reductase. Examples include chlozolinate, iprodione, procymidone and vinclozolin.

"Demethylation inhibitor (DMI) fungicides (b3)" (Fungicide Resistance Action Committee (FRAC) code 3) inhibit C14-demethylase which plays a role in sterol production. Sterols, such as ergosterol, are needed for membrane structure and function, making them essential for the development of functional cell walls. Therefore, exposure to these fungicides result in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz, pefurazoate and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

"Phenylamide fungicides (b4)" (Fungicide Resistance Action Committee (FRAC) code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl, metalaxyl-M/mefenoxam. The oxazolidinones include oxadixyl. The butyrolactones include ofurace.

"Amine/morpholine fungicides (b5)" (Fungicide Resistance Action Committee (FRAC) code 5) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

"Phospholipid biosynthesis inhibitor fungicides (b6)" (Fungicide Resistance Action Committee (FRAC) code 6) inhibit growth of fungi by affecting phospholipid biosynthesis. Phospholipid biosynthesis fungicides include phophorothiolate and dithiolane fungicides. The phosphorothiolates include edifenphos, iprobenfos and pyrazophos. The dithiolanes include isoprothiolane.

"Carboxamide fungicides (b7)" (Fungicide Resistance Action Committee (FRAC) code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include benzamide, furan carboxamide, oxathiin carboxamide, thiazole carboxamide, pyrazole carboxamide and pyridine carboxamide. The Benzamides include benodanil, flutolanil and mepronil. The furan carboxamides include fenfuram. The oxathiin carboxamide include carboxin and oxycarboxin. The thiazole carboxamides include thifluzamide. The pyrazole carboxamides include furametpyr, penthiopyrad, bixafen, N-[2-(1S,2R)-[1, 1'-bicyclopropyl]-2-ylphenyl]-3-(difluoromethyl)-1-methyl-1H-pyrazole-4-carboxamide and N-[2-(1,3-dimethylbutyl)phenyl]-5-fluoro-1,3-dimethyl-1H-pyrazole-4-carboxamide (PCT Patent Publication WO 2003/010149). The pyridine carboxamide include boscalid.

"Hydroxy(2-amino-)pyrimidine fungicides (b8)" (Fungicide Resistance Action Committee (FRAC) code 8) inhibit nucleic acid synthesis by interfering with adenosine deaminase. Examples include bupirimate, dimethirimol and ethirimol.

"Anilinopyrimidine fungicides (b9)" (Fungicide Resistance Action Committee (FRAC) code 9) are proposed to inhibit biosynthesis of the amino acid methionine and to disrupt the secretion of hydrolytic enzymes that lyse plant cells during infection. Examples include cyprodinil, mepanipyrim and pyrimethanil.

"N-Phenyl carbamate fungicides (b10)" (Fungicide Resistance Action Committee (FRAC) code 10) inhibit mitosis by binding to β-tubulin and disrupting microtubule assembly. Inhibition of microtubule assembly can disrupt cell division, transport within the cell and cell structure. Examples include diethofencarb.

"Quinone outside inhibitor (QoI) fungicides (b11)" (Fungicide Resistance Action Committee (FRAC) code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi. Inhibiting mitochondrial respiration prevents normal fungal growth and development. Quinone outside inhibitor fungicides (also known as strobilurin fungicides) include methoxyacrylate, methoxycarbamate, oximinoacetate, oximinoacetamide, oxazolidinedione, dihydrodioxazine, imidazolinone and benzylcarbamate fungicides. The methoxyacrylates include azoxystrobin, enestroburin (SYP-Z071) and picoxystrobin. The methoxycarbamates include pyraclostrobin. The oximinoacetates include kresoxim-methyl and trifloxystrobin. The oximinoacetamides include dimoxystrobin, metominostrobin, orysastrobin and α-(methoxyimino)-N-methyl-2-[[[1-[3-(trifluoromethyl)phenyl]-ethoxy]imino]methyl]benzeneacetamide. The oxazolidinediones include famoxadone. The dihydrodioxazines include fluoxastrobin. The imidazolinones include fenamidone. The benzylcarbamates include pyribencarb.

"Phenylpyrrole fungicides (b12)" (Fungicide Resistance Action Committee (FRAC) code 12) inhibit a MAP protein kinase associated with osmotic signal transduction in fungi. Fenpiclonil and fludioxonil are examples of this fungicide class.

"Quinoline fungicides (b13)" (Fungicide Resistance Action Committee (FRAC) code 13) are proposed to inhibit signal transduction by affecting G-proteins in early cell signaling. They have been shown to interfere with germination and/or appressorium formation in fungi that cause powder mildew diseases. Quinoxyfen is an example of this class of fungicide.

"Lipid peroxidation inhibitor fungicides (b14)" (Fungicide Resistance Action Committee (FRAC) code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbons include biphenyl, chloroneb, dicloran, quintozene, tecnazene and tolclofos-methyl. The 1,2,4-thiadiazoles include etridiazole.

"Melanin biosynthesis inhibitors-reductase (MBI-R) fungicides (b15)" (Fungicide Resistance Action Committee (FRAC) code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

"Melanin biosynthesis inhibitors-dehydratase (MBI-D) fungicides (b16)" (Fungicide Resistance Action Committee (FRAC) code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

"Hydroxyanilide fungicides (b17)" (Fungicide Resistance Action Committee (FRAC) code 17) inhibit C4-demethylase which plays a role in sterol production. Examples include fenhexamid.

"Squalene-epoxidase inhibitor fungicides (b18)" (Fungicide Resistance Action Committee (FRAC) code 18) inhibit squalene-epoxidase in ergosterol biosynthesis pathway. Sterols such as ergosterol are needed for membrane structure and function making them essential for the development of functional cell walls. Therefore exposure to these fungicides result in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

"Polyoxin fungicides (b19)" (Fungicide Resistance Action Committee (FRAC) code 19) inhibit chitin synthase. Examples include polyoxin.

"Phenylurea fungicides (b20)" (Fungicide Resistance Action Committee (FRAC) code 20) are proposed to affect cell division. Examples include pencycuron.

"Quinone inside inhibitor (QiI) fungicides (b21)" (Fungicide Resistance Action Committee (FRAC) code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

"Benzamide fungicides (b22)" (Fungicide Resistance Action Committee (FRAC) code 22) inhibit mitosis by binding to β-tubulin and disrupting microtubule assembly Inhibition of microtubule assembly can disrupt cell division, transport within the cell and cell structure. Examples include zoxamide.

"Enopyranuronic acid antibiotic fungicides (b23)" (Fungicide Resistance Action Committee (FRAC) code 23) inhibit growth of fungi by affecting protein biosynthesis. Examples include blasticidin-S.

"Hexopyranosyl antibiotic fungicides (b24)" (Fungicide Resistance Action Committee (FRAC) code 24) inhibit growth of fungi by affecting protein biosynthesis. Examples include kasugamycin.

"Glucopyranosyl antibiotic: protein synthesis fungicides (b25)" (Fungicide Resistance Action Committee (FRAC) code 25) inhibit growth of fungi by affecting protein biosynthesis. Examples include streptomycin.

"Glucopyranosyl antibiotic: trehalase and inositol biosynthesis fungicides (b26)" (Fungicide Resistance Action Committee (FRAC) code 26) inhibit trehalase in inositol biosynthesis pathway. Examples include validamycin.

"Cyanoacetamideoxime fungicides (b27) (Fungicide Resistance Action Committee (FRAC) code 27) include cymoxanil.

"Carbamate fungicides (b28)" (Fungicide Resistance Action Committee (FRAC) code 28) are considered multi-site inhibitors of fungal growth. They are proposed to interfere with the synthesis of fatty acids in cell membranes, which then disrupts cell membrane permeability. Propamacarb, iodocarb, and prothiocarb are examples of this fungicide class.

"Oxidative phosphorylation uncoupling fungicides (b29)" (Fungicide Resistance Action Committee (FRAC) code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

"Organo tin fungicides (b30)" (Fungicide Resistance Action Committee (FRAC) code 30) inhibit adenosine triphosphate (ATP) synthase in oxidative phosphorylation pathway. Examples include fentin acetate, fentin chloride and fentin hydroxide.

"Carboxylic acid fungicides (b31)" (Fungicide Resistance Action Committee (FRAC) code 31) inhibit growth of fungi by affecting deoxyribonucleic acid (DNA) topoisomerase type II (gyrase). Examples include oxolinic acid.

"Heteroaromatic fungicides (b32)" (Fungicide Resistance Action Committee (FRAC) code 32) are proposed to affect DNA/ribonucleic acid (RNA) synthesis. Heteroaromatic fungicides include isoxazole and isothiazolone fungicides. The isoxazoles include hymexazole and the isothiazolones include octhilinone.

"Phosphonate fungicides (b33)" (Fungicide Resistance Action Committee (FRAC) code 33) include phosphorous acid and its various salts, including fosetyl-aluminum.

"Phthalamic acid fungicides (b34)" (Fungicide Resistance Action Committee (FRAC) code 34) include teclofthalam.

"Benzotriazine fungicides (b35)" (Fungicide Resistance Action Committee (FRAC) code 35) include triazoxide.

"Benzene-sulfonamide fungicides (b36)" (Fungicide Resistance Action Committee (FRAC) code 36) include flusulfamide.

"Pyridazinone fungicides (b37)" (Fungicide Resistance Action Committee (FRAC) code 37) include diclomezine.

"Thiophene-carboxamide fungicides (b38)" (Fungicide Resistance Action Committee (FRAC) code 38) are proposed to affect ATP production. Examples include silthiofam.

"Pyrimidinamide fungicides (b39)" (Fungicide Resistance Action Committee (FRAC) code 39) inhibit growth of fungi by affecting phospholipid biosynthesis and include diflumetorim.

"Carboxylic acid amide (CAA) fungicides (b40)" (Fungicide Resistance Action Committee (FRAC) code 40) are proposed to inhibit phospholipid biosynthesis and cell wall deposition. Inhibition of these processes prevents growth and leads to death of the target fungus. Carboxylic acid amide fungicides include cinnamic acid amide, valinamide carbamate and mandelic acid amide fungicides. The cinnamic acid amides include dimethomorph and flumorph. The valinamide carbamates include benthiavalicarb, benthiavalicarb-isopropyl, iprovalicarb and valiphenal. The mandelic acid amides include mandipropamid, N-[2-[4-[[3-(4-chlorophenyl)-2-propyn-1-yl]oxy]-3-methoxyphenyl]-ethyl]-3-methyl-2-[(methylsulfonyl)amino]butanamide and N-[2-[4-[[3-(4-chlorophenyl)-2-propyn-1-yl]oxy]-3-methoxyphenyl]ethyl]-3-methyl-2-[(ethylsulfonyl)amino]-butanamide.

"Tetracycline antibiotic fungicides (b41)" (Fungicide Resistance Action Committee (FRAC) code 41) inhibit growth of fungi by affecting complex 1 nicotinamide adenine dinucleotide (NADH) oxidoreductase. Examples include oxytetracycline.

"Thiocarbamate fungicides (b42)" (Fungicide Resistance Action Committee (FRAC) code 42) include methasulfocarb.

"Benzamide fungicides (b43)" (Fungicide Resistance Action Committee (FRAC) code 43) inhibit growth of fungi by delocalization of spectrin-like proteins. Examples include acylpicolide fungicides such as fluopicolide and fluopyram.

"Host plant defense induction fungicides (b44)" (Fungicide Resistance Action Committee (FRAC) code P) induce host plant defense mechanisms. Host plant defense induction fungicides include benzo-thiadiazole, benzisothiazole and thiadiazole-carboxamide fungicides. The benzo-thiadiazoles include acibenzolar-S-methyl. The benzisothiazoles include probenazole. The thiadiazole-carboxamides include tiadinil and isotianil.

"Multi-site contact fungicides (b45)" inhibit fungal growth through multiple sites of action and have contact/preventive activity. This class of fungicides includes: "copper fungicides (b45.1) (Fungicide Resistance Action Committee (FRAC) code Ml)", "sulfur fungicides (b45.2) (Fungicide Resistance Action Committee (FRAC) code M2)", "dithiocarbamate fungicides (b45.3) (Fungicide Resistance Action Committee (FRAC) code M3)", "phthalimide fungicides (b45.4) (Fungicide Resistance Action Committee (FRAC) code M4)", "chloronitrile fungicides (b45.5) (Fungicide Resistance Action Committee (FRAC) code M5)", "sulfamide fungicides (b45.6) (Fungicide Resistance Action Committee (FRAC) code M6)", "guanidine fungicides (b45.7) (Fungicide Resistance Action Committee (FRAC) code M7)" "triazines fungicides (b45.8) (Fungicide Resistance Action Committee (FRAC) code M8)" and "quinone fungicides (b45.9) (Fungicide Resistance Action Committee (FRAC) code M9)". "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolylfluanid. "Guanidine fungicides" include dodine, guazatine and iminoctadine. "Triazines fungicides" include anilazine. "Quinone fungicides" include dithianon.

"Fungicides other than fungicides of component (a) and components (b1) through (b45); (b46)" include certain fungicides considered to have an unknown mode of action. These include: "thiazole carboxamide fungicide (b46.1) (Fungicide Resistance Action Committee (FRAC) code U5)", "phenyl-acetamide fungicide (b46.2) (Fungicide Resistance Action Committee (FRAC) code U6)", "quinazolinone fungicide (b46.3) (Fungicide Resistance Action Committee (FRAC) code U7)" and "benzophenone fungicide (b46.4) (Fungicide Resistance Action Committee (FRAC) code U8)". The thiazole carboxamides include ethaboxam. The phenyl-acetamides include cyflufenamid and N-[[(cyclopropylmethoxy)amino][6-(difluoromethoxy)-2,3-difluorophenyl]-methylene]benzeneacetamide. The quinazolinones include proquinazid, 6-bromo-3-propyl-2-propyloxy-4(3H)-quinazolinone, 6,8-diiodo-3-propyl-2-propyloxy-4-(3H)-quinazolinone, 6-chloro-2-propoxy-3-propylthieno [2,3-d]pyrimidin-4(3H)-one, 2,3-dibutyl-6-chlorothieno [2,3-d]pyrimidin-4(3H)-one, 6-bromo-2-propoxy-3-propylthieno [2,3-d]pyrimidin-4(3H)-one, 7-bromo-2-propoxy-3-propylthieno [3 ,2-d]pyrimidin-4(3H)-one, 6-bromo-2-propoxy-3-propylpyrido [2,3-d]pyrimidin-4(3H)-one, 6,7-dibromo-2-propoxy-3-propylthieno[3,2-d]pyrimidin-4(3H)-one, 3-(cyclopropylmethyl)-6-iodo-2-(propylthio)pyrido[2,3-d]pyrimidin-4(3H)-one, 2-butoxy-6-iodo-3-propyl-4H-1-benzopyran-4-one, 2-ethoxy-6-iodo-3-propyl-4H-1-benzopyran-4-one, 6-iodo-2-propoxy-3-propyl-4H-1-benzopyran-4-one, 2-(2-butynyloxy)-6-iodo-3-propyl-4H-1-benzopyran-4-one, 6-iodo-2-(1-methylbutoxy)-3-propyl-4H-1-benzopyran-4-one, 2-(3-butenyloxy)-6-iodo-3-propyl-4H-1-benzopyran-4-one, 3-butyl-6-iodo-2-(1-methylethoxy)-4H-1-benzopyran-4-one, and 6-iodo-3-propyl-2H-1,3-benzoxazine-2,4(3H)-dione 2-(O-methyloxime). The benzophenones include metrafenone. The (b46) group also includes 5-chloro-6-(2,4,6-trifluorophenyl)-7-(4-methylpiperidin-1-yl)[1,2,4]triazolo[1,5-a]pyrimidine (BAS600), 3-[5-(4-chlorophenyl)-2,3-dimethyl-3-isoxazolidinyl]pyridine (SYP-Z 048), 4-fluorophenyl N-[1-[[[1-(4-cyanophenyl)ethyl]sulfonyl]methyl]propyl] carbamate (XR-539), N-[4-[4-chloro-3-(trifluoromethyl)phenoxy]-2,5-dimethylphenyl]-N-ethyl-N-methylmethanimidamide, 2-[[2-fluoro-5-(trifluoromethyl)phenyl]thio]-2-[3-(2-methoxyphenyl)-2-thiazolidinylidene]acetonitrile (OK-5203) and N-(4-chloro-2-nitrophenyl)-N-ethyl-4-methylbenzenesulfonamide (TF-991).

Accordingly, the present invention comprises compositions of one or more compounds selected from Formula 1, N-oxides and salts thereof, with one or more compounds or salts thereof selected from (b) as described in the Summary of the Invention.

In the embodiments of the present invention, including those described below, reference to Formula 1 includes N-oxides and salts thereof, and reference to "a compound of Formula 1" includes the definitions of substituents specified in the Summary of the Invention unless further defined in the Embodiments.

Embodiment 1. The composition described in the Summary of the Invention wherein component (a) is a compound of Formula 1 wherein A is CHR$^{15}$.

Embodiment 1a. The composition described in the Summary of the Invention or Embodiment 1 wherein R$^{15}$ is H, halogen, cyano, hydroxy, —CHO, $C_1$-$C_4$ alkyl, $C_1$-$C_4$ haloalkyl or $C_2$-$C_5$ alkoxycarbonyl.

Embodiment 1b. The composition of Embodiment 1a wherein R$^{15}$ is H, cyano, hydroxy, methyl or methoxycarbonyl.

Embodiment 1c. The composition of Embodiment 1b wherein R$^{15}$ is H.

Embodiment 1d. The composition of Embodiment 1 wherein R$^{15}$ is $C_2$-$C_4$ alkenyloxy, $C_2$-$C_4$ alkynyloxy, $C_2$-$C_4$ haloalkenyloxy, $C_2$-$C_4$ haloalkynyloxy, $C_2$-$C_5$ alkylcarbonyloxy, $C_2$-$C_5$ alkoxycarbonyloxy, $C_2$-$C_5$ haloalkylcarbonyloxy, $C_2$-$C_5$ haloalkoxycarbonyloxy, $C_2$-$C_5$ alkylaminocarbonyloxy, $C_3$-$C_6$ dialkylaminocarbonyloxy, $C_2$-$C_5$ haloalkylaminocarbonyloxy, $C_3$-$C_6$ halodialkylaminocarbonyloxy, $C_2$-$C_5$ alkoxyalkoxy, $C_2$-$C_5$ haloalkoxyalkoxy, $C_1$-$C_4$ alkylsulfonyloxy, $C_1$-$C_4$ haloalkylsulfonyloxy or $C_3$-$C_{10}$ trialkylsilyloxy.

Embodiment 1e. The composition of Embodiment 1d wherein R$^{15}$ is $C_2$-$C_3$ alkenyloxy, $C_2$-$C_3$ alkynyloxy, $C_2$-$C_3$ alkylcarbonyloxy, $C_2$-$C_3$ alkoxycarbonyloxy, $C_2$-$C_3$ haloalkylcarbonyloxy, $C_2$-$C_3$ haloalkoxycarbonyloxy, $C_2$-$C_3$ alkylaminocarbonyloxy, $C_3$-$C_4$ dialkylaminocarbonyloxy, $C_2$-$C_3$ haloalkylaminocarbonyloxy, $C_3$-$C_4$ halodialkylaminocarbonyloxy, $C_2$-$C_3$ alkoxyalkoxy, $C_2$-$C_3$ haloalkoxyalkoxy, $C_1$-$C_3$ alkylsulfonyloxy, $C_1$-$C_3$ halo alkylsulfonyloxy or $C_3$-$C_6$ trialkylsilyloxy.

Embodiment 1f. The composition of Embodiment 1e wherein R$^{15}$ is $C_2$-$C_3$ alkylcarbonyloxy, $C_2$-$C_3$ alkoxycarbonyloxy, $C_2$-$C_3$ haloalkylcarbonyloxy, $C_2$-$C_3$ haloalkoxycarbonyloxy, $C_2$-$C_3$ alkoxyalkoxy, $C_2$-$C_3$ haloalkoxyalkoxy, or $C_3$-$C_6$ trialkylsilyloxy.

Embodiment 1g. The composition described in the Summary of the Invention or Embodiment 1 where R$^{15}$ is as described in Embodiment 1a or Embodiment 1d.

Embodiment 1h. The composition described in the Summary of the Invention or Embodiment 1 where R$^{15}$ is as described in Embodiment 1b or Embodiment 1e.

Embodiment 1i. The composition described in the Summary of the Invention or Embodiment 1 where R$^{15}$ is as described in Embodiment 1c or Embodiment 1f.

Embodiment 2. The composition described in the Summary of the Invention wherein component (a) is a compound of Formula 1 wherein A is NR$^{16}$.

Embodiment 2a. The composition of Embodiment 2 wherein $R^{16}$ is H, $C_1$-$C_4$ alkyl, $C_1$-$C_4$ haloalkyl, $C_2$-$C_4$ alkylcarbonyl, $C_2$-$C_4$ haloalkylcarbonyl or $C_2$-$C_4$ alkoxycarbonyl.

Embodiment 2b. The composition of Embodiment 2a wherein $R^{16}$ is H, methyl, methylcarbonyl or methoxycarbonyl.

Embodiment 2c. The composition of Embodiment 2b wherein $R^{16}$ is H.

Embodiment 3. The composition described in the Summary of the Invention wherein component (a) is a compound of Formula 1 wherein W is O.

Embodiment 4. The composition described in the Summary of the Invention wherein component (a) is a compound of Formula 1 wherein W is S.

Embodiment 5. The composition described in the Summary of the Invention wherein component (a) is a compound of Formula 1 wherein each $R^2$ is independently halogen, cyano, hydroxy, $C_1$-$C_2$ alkyl, $C_1$-$C_2$ haloalkyl or $C_1$-$C_2$ alkoxy.

Embodiment 5a. The composition of Embodiment 5 wherein each $R^2$ is independently cyano, hydroxy, methyl or methoxy.

Embodiment 5b. The composition of Embodiment 5a wherein each $R^2$ is methyl.

Embodiment 6. The composition described in the Summary of the Invention wherein component (a) is a compound of Formula 1 wherein n is 0 or 1.

Embodiment 7. The composition of Embodiment 6 wherein n is 0.

Embodiment 7a. The composition of Embodiment 6 wherein n is 1.

Embodiment 8. The composition described in the Summary of the Invention wherein component (a) is a compound of Formula 1 wherein X is $X^1$, $X^2$ or $X^3$.

Embodiment 9. The composition of Embodiment 8 wherein X is $X^1$ or $X^2$.

Embodiment 10. The composition of Embodiment 9 wherein X is $X^1$.

Embodiment 11. The composition described in the Summary of the Invention wherein component (a) is a compound of Formula 1 wherein the ring comprising X is saturated (i.e. contains only single bonds).

Embodiment 12. The composition described in the Summary of the Invention wherein component (a) is a compound of Formula 1 wherein $R^1$ is a phenyl or a 5- or 6-membered heteroaromatic ring optionally substituted with substituents that do not link together to make $R^1$ a fused ring system.

Embodiment 12a. The composition of Embodiment 12 wherein $R^1$ is a phenyl or a 5- or 6-membered heteroaromatic ring optionally substituted with 1-3 substituents independently selected from $R^{4a}$ on carbon ring members and $R^{4b}$ on nitrogen ring members;
each $R^{4a}$ is independently halogen, hydroxy, amino, cyano, nitro, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ alkylsulfonyl, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; and
each $R^{4b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl.

Embodiment 12b. The composition of Embodiment 12a wherein $R^1$ is a phenyl or a 5- or 6-membered heteroaromatic ring optionally substituted with 1 to 2 substituents independently selected from $R^{4a}$ on carbon ring members and $R^{4b}$ on nitrogen ring members.

Embodiment 13. The composition of Embodiment 12b wherein $R^1$ is one of U-1 through U-50 depicted in Exhibit 1;

Exhibit 1

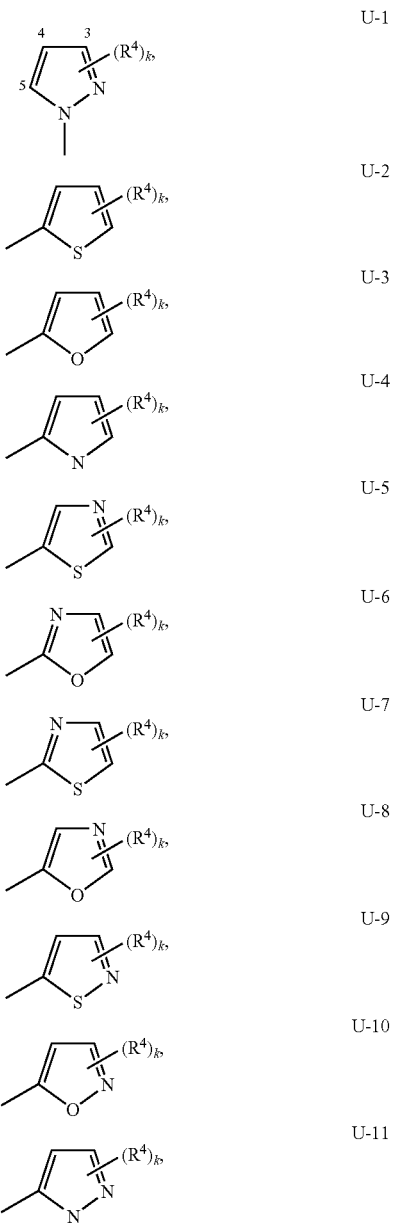

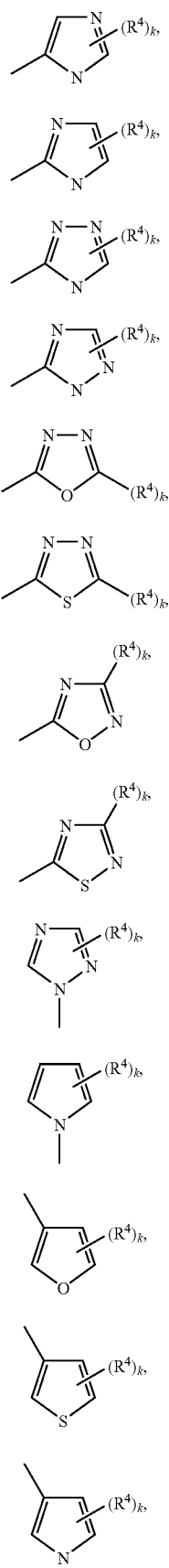
U-12 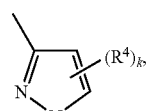 U-25
U-13 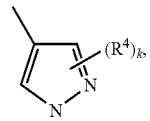 U-26
U-14 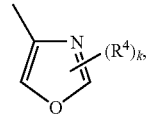 U-27
U-15 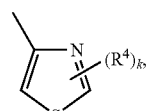 U-28
U-16 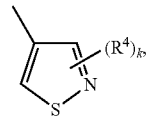 U-29
U-17 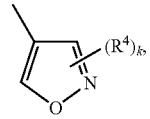 U-30
U-18 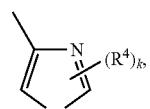 U-31
U-19 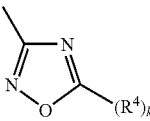 U-32
U-20 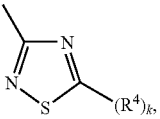 U-33
U-21 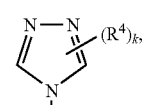 U-34
U-22 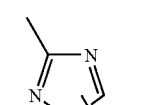 U-35
U-23 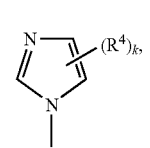 U-36
U-24

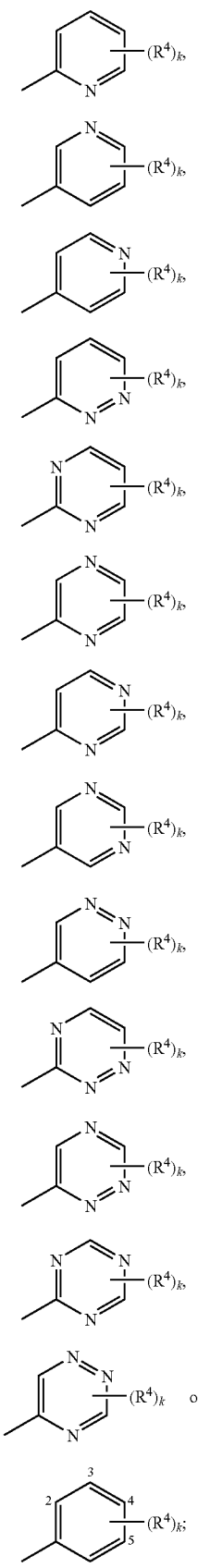

wherein
when R⁴ is attached to a carbon ring member, said R⁴ is selected from R$^{4a}$, and when R⁴ is attached to a nitrogen ring member (e.g., in U-4, U-11 through U-15, U-24 through U-26, U-31 or U-35), said R⁴ is selected from Rob; and k is 0, 1 or 2.

Embodiment 14. The composition of Embodiment 13 wherein R¹ is selected from U-1 through U-5, U-8, U-11, U-13, U-15, U-20 through U-28, U-31, U-36 through U-39 and U-50.

Embodiment 15. The composition of Embodiment 14 wherein R¹ is selected from U-1 through U-3, U-5, U-8, U-11, U-13, U-20, U-22, U-23, U-25 through U-28, U-36 through U-39 and U-50.

Embodiment 16. The composition of Embodiment 15 wherein R¹ is selected from U-1 through U-3, U-11, U-13, U-20, U-22, U-23, U-36 through U-39 and U-50.

Embodiment 17. The composition of Embodiment 16 wherein R¹ is U-1, U-20 or U-50.

Embodiment 17a. The composition of Embodiment 17 wherein R¹ is U-1 or U-50.

Embodiment 18. The composition of Embodiment 17 or 17a wherein R¹ is U-1.

Embodiment 18a. The composition of Embodiment 17 wherein R¹ is U-20.

Embodiment 19. The composition of Embodiment 17 or 17a wherein R¹ is U-50.

Embodiment 20. The composition of any one of Embodiments 12a through 19 wherein each R$^{4a}$ is independently halogen, cyano, nitro, $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, $C_1$-$C_2$ alkoxy, $C_1$-$C_2$ haloalkoxy, $C_1$-$C_2$ alkylthio, $C_1$-$C_2$ haloalkylthio, $C_2$-$C_3$ alkoxyalkyl, $C_2$-$C_3$ alkylcarbonyl, $C_2$-$C_3$ alkoxycarbonyl, $C_2$-$C_3$ alkylaminocarbonyl or $C_3$-$C_4$ dialkylaminocarbonyl.

Embodiment 21. The composition of Embodiment 20 wherein each R$^{4a}$ is independently halogen, cyano, nitro, $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, halocyclopropyl, $C_1$-$C_2$ alkoxy or $C_1$-$C_2$ haloalkoxy.

Embodiment 22. The composition of Embodiment 21 wherein each R$^{4a}$ is independently halogen, $C_1$-$C_3$ alkyl, $C_1$-$C_3$ haloalkyl, $C_1$-$C_2$ alkoxy or $C_1$-$C_2$ haloalkoxy.

Embodiment 23. The composition of Embodiment 22 wherein each R$^{4a}$ is independently halogen, $C_1$-$C_2$ alkyl, $C_1$-$C_2$ haloalkyl or $C_1$-$C_2$ alkoxy.

Embodiment 24. The composition of Embodiment 23 wherein each R$^{4a}$ is independently Cl, Br, I, $C_1$-$C_2$ alkyl, trifluoromethyl or methoxy.

Embodiment 25. The composition of Embodiment 24 wherein each R$^{4a}$ is independently Cl, Br, $C_1$-$C_2$ alkyl or trifluoromethyl.

Embodiment 26. The composition of any one of any one of Embodiments 12a through wherein each R$^{4b}$ is independently $C_1$-$C_3$ alkyl, $C_3$ alkenyl (e.g., allyl), $C_3$ alkynyl (e.g., propargyl), cyclopropyl, $C_1$-$C_3$ haloalkyl, $C_3$ haloalkenyl, $C_3$ haloalkynyl, halocyclopropyl or $C_2$-$C_3$ alkoxyalkyl.

Embodiment 27. The composition of Embodiment 26 wherein each R$^{4b}$ is independently $C_1$-$C_3$ alkyl, $C_3$ alkenyl, $C_3$ alkynyl, cyclopropyl, $C_1$-$C_3$ haloalkyl, $C_3$ haloalkenyl or halocyclopropyl.

Embodiment 28. The composition of Embodiment 27 wherein each $R^{4b}$ is independently $C_1$-$C_2$ alkyl or $C_1$-$C_2$ haloalkyl.

Embodiment 29. The composition of Embodiment 28 wherein each $R^{4b}$ is independently $C_1$-$C_2$ alkyl or trifluoromethyl.

Embodiment 30. The composition of Embodiment 29 wherein each $R^{4b}$ is independently $C_1$-$C_2$ alkyl.

Embodiment 31. The composition of Embodiment 13 wherein k is 1 or 2 and at least one $R^4$ is Cl.

Embodiment 32. The composition of Embodiment 13 wherein k is 1 or 2 and at least one $R^4$ is Br.

Embodiment 33. The composition of Embodiment 13 wherein k is 1 or 2 and at least one $R^4$ is methyl.

Embodiment 34. The composition of Embodiment 13 wherein k is 1 or 2 and at least one $R^4$ is ethyl.

Embodiment 35. The composition of Embodiment 13 wherein k is 1 or 2 and at least one $R^4$ is trifluoromethyl.

Embodiment 36. The composition of Embodiment 13 wherein k is 1 or 2 and at least one $R^4$ is methoxy.

Embodiment 37. The composition of Embodiment 18 wherein k is 1 and $R^4$ is connected to the 3- or 5-position of U-1.

Embodiment 37a. The composition of Embodiment 18 wherein k is 2 and one $R^4$ is connected to the 3-position and the other $R^4$ is connected to the 5-position of U-1.

Embodiment 38. The composition of Embodiment 18a wherein k is 1 and $R^4$ is connected to the 3- or 5-position of U-20.

Embodiment 38a. The composition of Embodiment 18a wherein k is 2 and one $R^4$ is connected to the 3-position and the other $R^4$ is connected to the 5-position of U-20.

Embodiment 39. The composition of Embodiment 19 wherein k is 1 and $R^4$ is connected to the 2- or 3-position of U-50.

Embodiment 40. The composition of Embodiment 19 wherein k is 2 and one $R^4$ is connected to the 2-position and the other $R^4$ is connected to the 5-position of U-50.

Embodiment 41. The composition described in the Summary of the Invention wherein component (a) is a compound of Formula 1 wherein G is a 5-membered heteroaromatic ring or 5-membered saturated or partially saturated heterocyclic ring, each ring optionally substituted with up to 2 substituents selected from $R^3$ on carbon ring members and selected from $R^{11}$ on nitrogen ring members;

each $R^3$ is independently halogen, $C_1$-$C_3$ alkyl or $C_1$-$C_3$ haloalkyl; and each $R^{11}$ is independently $C_1$-$C_3$ alkyl.

Embodiment 42. The composition of Embodiment 41 wherein G is one of G-1 through G-59 depicted in Exhibit 2;

Exhibit 2

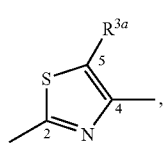
G-1

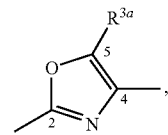
G-2

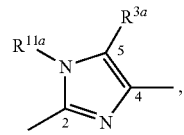
G-3

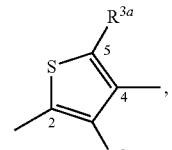
G-4

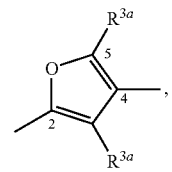
G-5

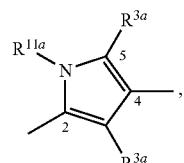
G-6

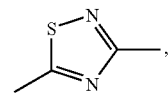
G-7

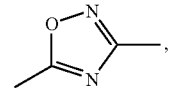
G-8

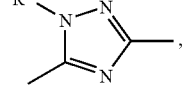
G-9

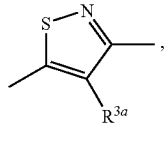
G-10

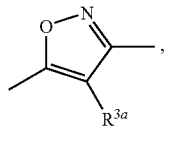
G-11

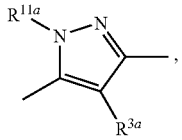
G-12

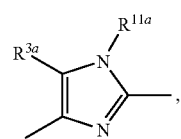 G-13
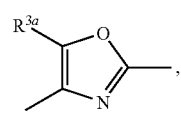 G-14
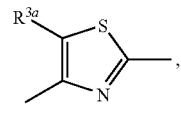 G-15
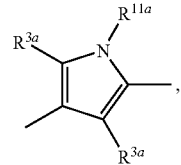 G-16
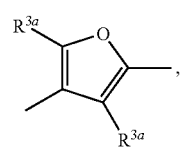 G-17
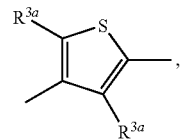 G-18
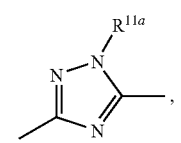 G-19
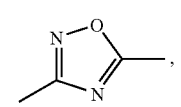 G-20
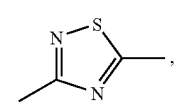 G-21
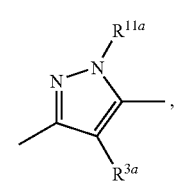 G-22
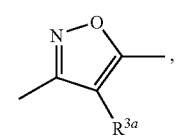 G-23
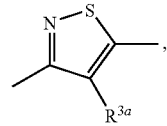 G-24
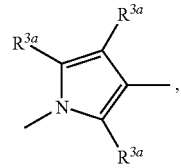 G-25
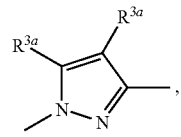 G-26
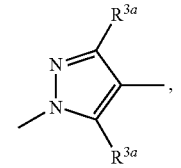 G-27
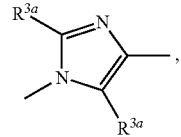 G-28
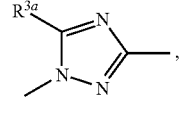 G-29
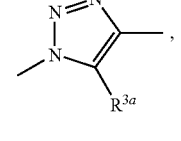 G-30
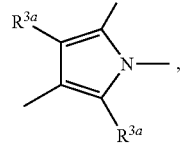 G-31
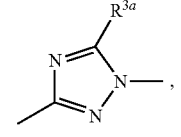 G-32
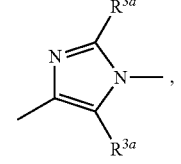 G-33

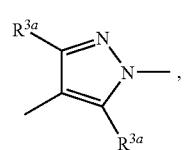 G-34
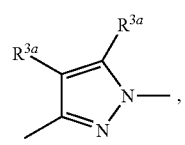 G-35
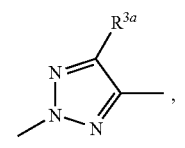 G-36
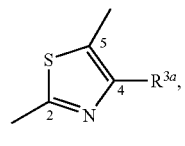 G-37
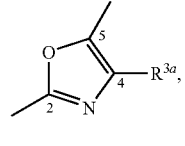 G-38
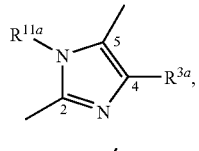 G-39
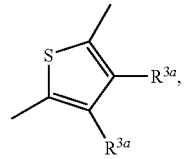 G-40
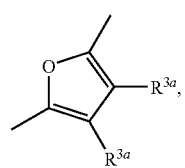 G-41
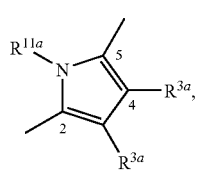 G-42
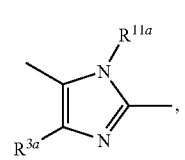 G-43
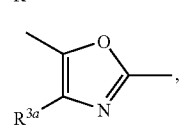 G-44
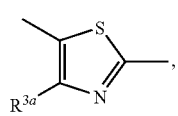 G-45
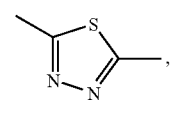 G-46
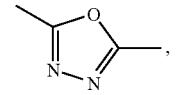 G-47
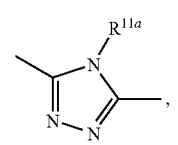 G-48
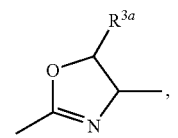 G-49
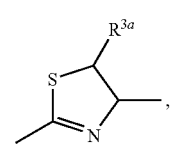 G-50
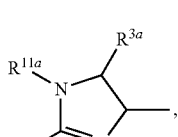 G-51
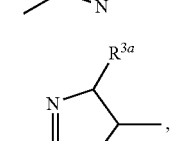 G-52
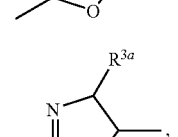 G-53
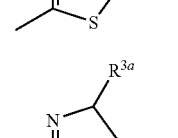 G-54
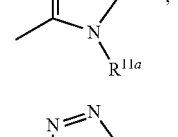 G-55
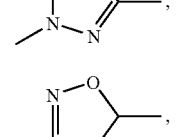 G-56

-continued

G-57

G-58

G-59 wherein the bond projecting to the left is bonded to X, and the bond projecting to the right is bonded to $Z^1$; each $R^{3a}$ is independently selected from H or $R^3$; and $R^{11a}$ is selected from H and $R^{11}$;
provided that:
when G is G-6, G-16 or G-42, and each $R^{3a}$ is other than H, then $R^{11a}$ is H;
when G is G-25 or G-31, then at least one $R^{3a}$ is H; and
when G is one of G-31 through G-35, then $Z^1$ is a direct bond or $CHR^{20}$.

Embodiment 43. The composition of Embodiment 42 wherein G is selected from G-1 through G-3, G-7, G-8, G-10, G-11, G-14, G-15, G-23, G-24, G-26 through G-28, G-30, G-36 through G-38 and G-49 through G-55.

Embodiment 44. The composition of Embodiment 43 wherein G is selected from G-1, G-2, G-7, G-8, G-14, G-15, G-23, G-24, G-26, G-27, G-36, G-37, G-38, G-49, G-50 and G-55.

Embodiment 45. The composition of Embodiment 44 wherein G is selected from G-1, G-2, G-15, G-26, G-27, G-36, G-37 and G-38.

Embodiment 46. The composition of Embodiment 45 wherein G is selected from G-1, G-2, G-15, G-26 and G-36.

Embodiment 47. The composition of Embodiment 46 wherein G is G-1. Of note are embodiments of these compounds within Embodiments 1 through 40, Embodiments 52 through 83, and Embodiments A1 through A5.

Embodiment 48. The composition of Embodiment 46 wherein G is G-2. Of note are embodiments of these compounds within Embodiments 1 through 40, Embodiments 52 through 83, and Embodiments A1 through A5.

Embodiment 49. The composition of Embodiment 46 wherein G is G-15. Of note are embodiments of these compounds within Embodiments 1 through 40, Embodiments 52 through 83, and Embodiments A1 through A5.

Embodiment 50. The composition of Embodiment 46 wherein G is G-26. Of note are embodiments of these compounds within Embodiments 1 through 40, Embodiments 52 through 83, and Embodiments A1 through A5.

Embodiment 51. The composition of Embodiment 46 wherein G is G-36. Of note are embodiments of these compounds within Embodiments 1 through 40, Embodiments 52 through 83, and Embodiments A1 through A5.

Embodiment 52. The composition of any one of Embodiments 42 through 51 wherein each $R^{3a}$ is independently H, $C_1$-$C_3$ alkyl or halogen.

Embodiment 53. The composition of Embodiment 52 wherein each $R^{3a}$ is independently H or methyl.

Embodiment 54. The composition of any one of Embodiments 42 through 51 wherein $R^{3a}$ is H and $R^{11a}$ is H or methyl.

Embodiment 55. The composition described in the Summary of the Invention wherein component (a) is a compound of Formula 1 wherein G is unsubstituted.

Embodiment 55a. The composition of any one of Embodiments 41 through 51 wherein G is unsubstituted.

Embodiment 56. The composition described in the Summary of the Invention wherein component (a) is a compound of Formula 1 wherein J is one of J-1 through J-82 depicted in Exhibit 3;

Exhibit 3

J-1

J-2

J-3

J-4

J-5

J-6

J-7

J-8

J-9

-continued
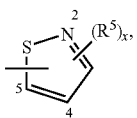 J-10
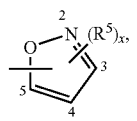 J-11
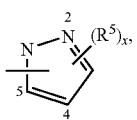 J-12
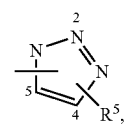 J-13
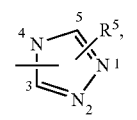 J-14
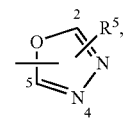 J-15
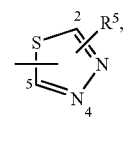 J-16
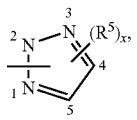 J-17
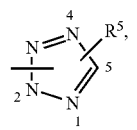 J-18
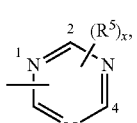 J-19
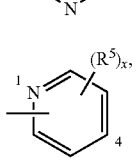 J-20
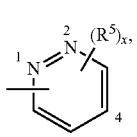 J-21
-continued
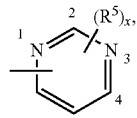 J-22
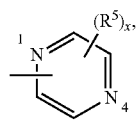 J-23
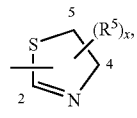 J-24
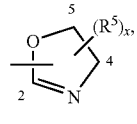 J-25
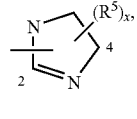 J-26
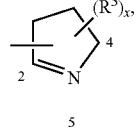 J-27
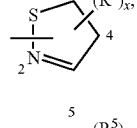 J-28
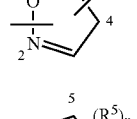 J-29
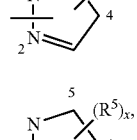 J-30
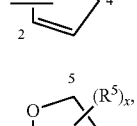 J-31
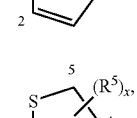 J-32
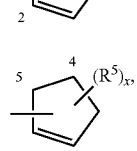 J-33
J-34

-continued
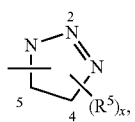 J-35
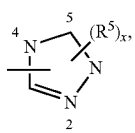 J-36
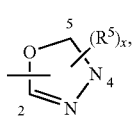 J-37
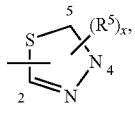 J-38
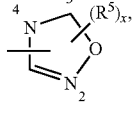 J-39
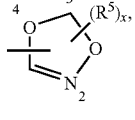 J-40
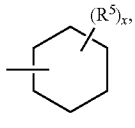 J-41
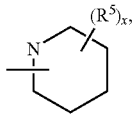 J-42
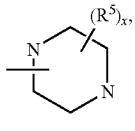 J-43
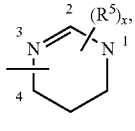 J-44
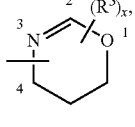 J-45
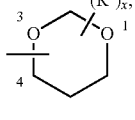 J-46
-continued
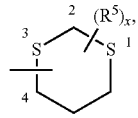 J-47
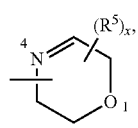 J-48
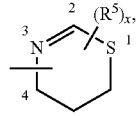 J-49
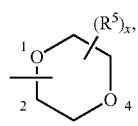 J-50
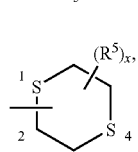 J-51
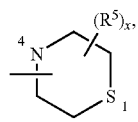 J-52
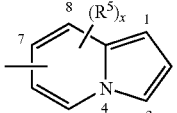 J-53
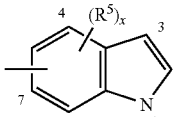 J-54
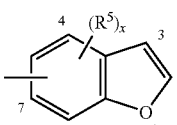 J-55
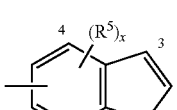 J-56
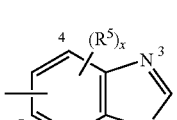 J-57

-continued
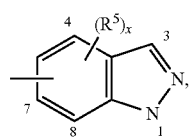 J-58
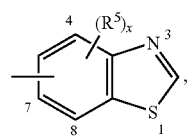 J-59
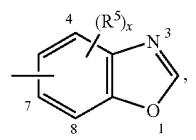 J-60
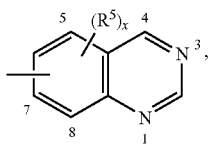 J-61
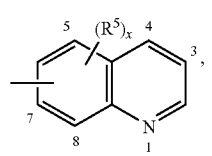 J-62
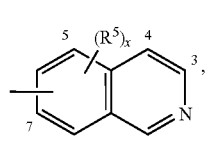 J-63
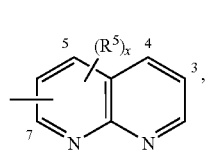 J-64
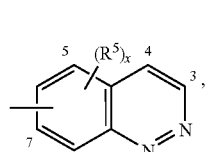 J-65
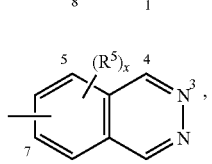 J-66
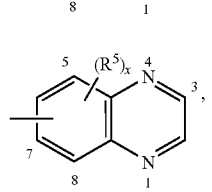 J-67
-continued
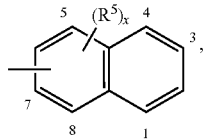 J-68
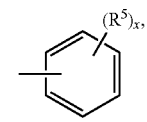 J-69
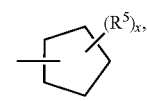 J-70
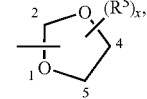 J-71
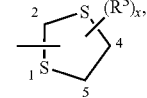 J-72
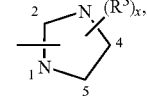 J-73
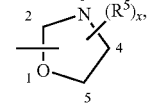 J-74
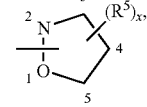 J-75
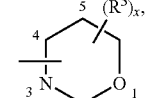 J-76
 J-77
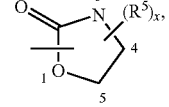 J-77
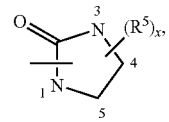 J-78

-continued
J-79
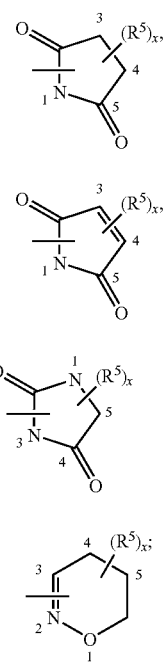
J-80
J-81
J-82
wherein the bond shown projecting to the left is bonded to $Z^1$; and x is an integer from 0 to 5.
Embodiment 56a. The composition of Embodiment 56 wherein J is one of J-29-1 through J-29-60 depicted in Exhibit A;
Exhibit A
J-29-1
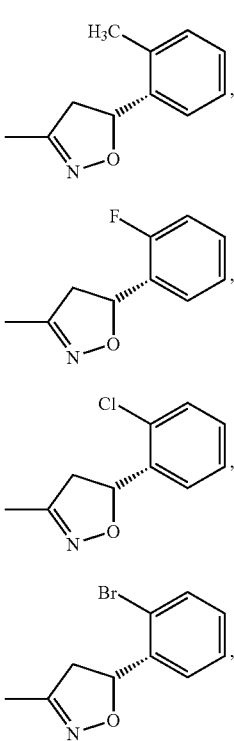
J-29-2
J-29-3
J-29-4
-continued
J-29-5
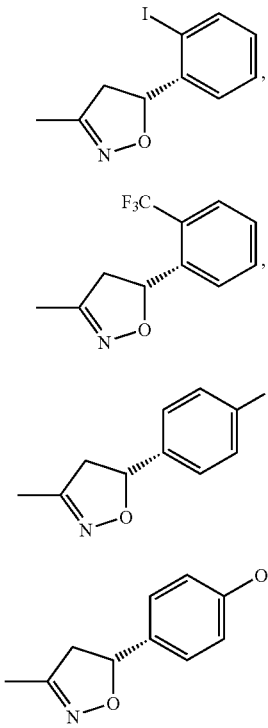
J-29-6
J-29-7
J-29-8
J-29-9
J-29-10
J-29-11
J-29-12
J-29-13
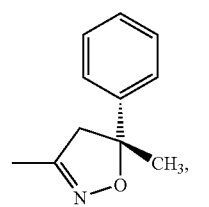

-continued
| | |
|---|---|
| 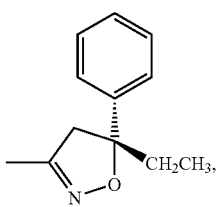 | J-29-14 |
| 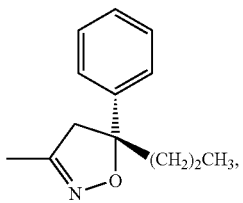 | J-29-15 |
| 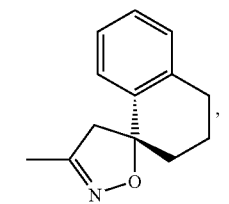 | J-29-16 |
| 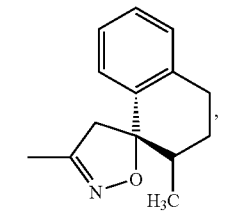 | J-29-17 |
| 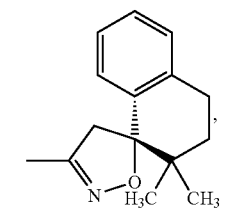 | J-29-18 |
| 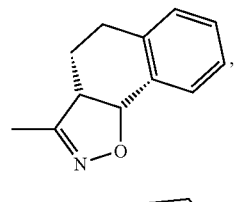 | J-29-19 |
| 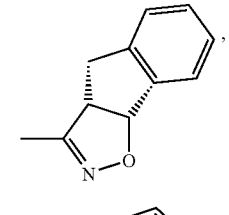 | J-29-20 |
| 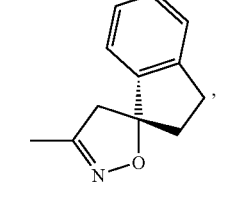 | J-29-21 |
| | |
|---|---|
| 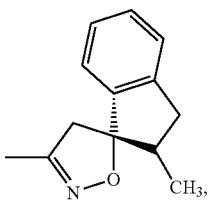 | J-29-22 |
| 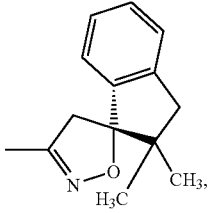 | J-29-23 |
| 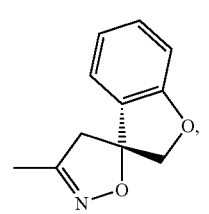 | J-29-24 |
| 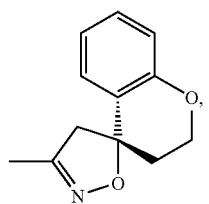 | J-29-25 |
| 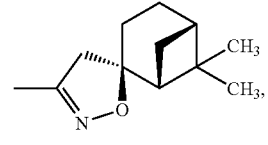 | J-29-26 |
| 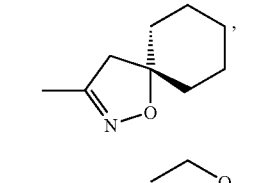 | J-29-27 |
| 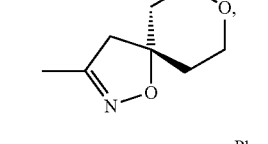 | J-29-28 |
| 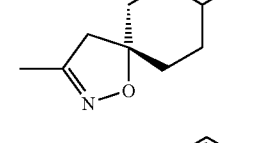 | J-29-29 |
| 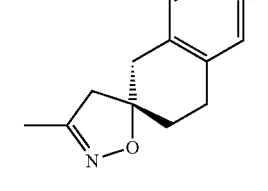 | J-29-30 |

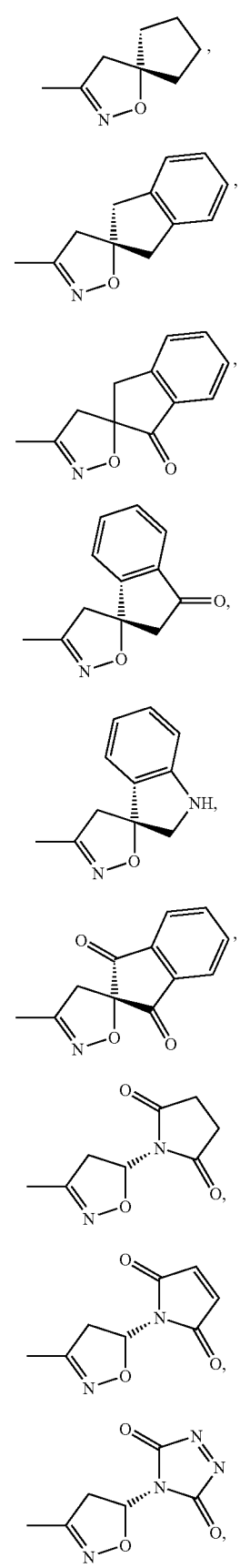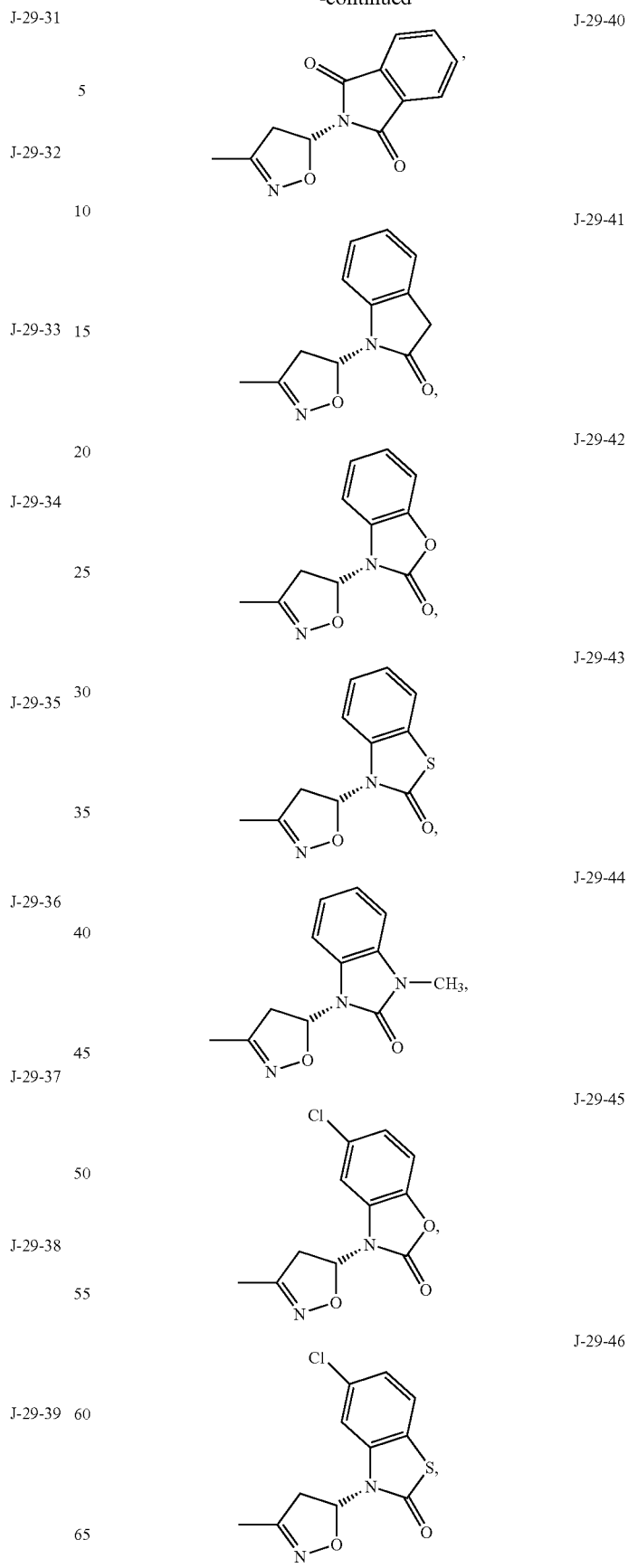

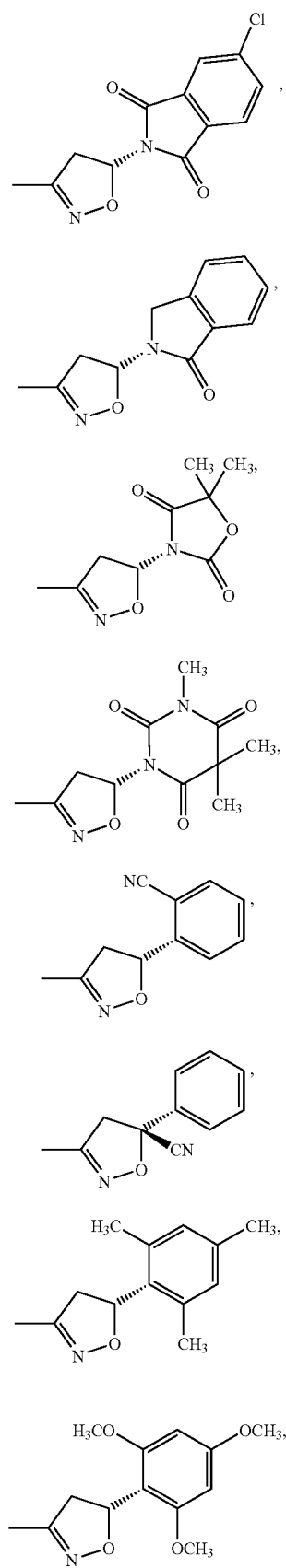

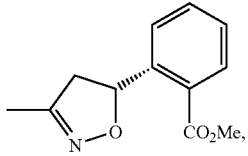

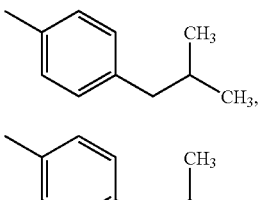

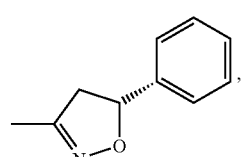

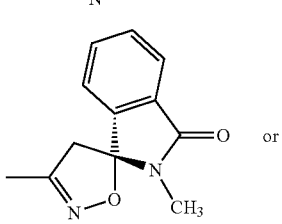

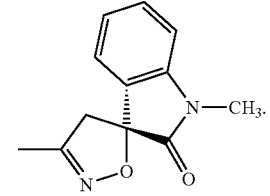

Embodiment 57. The composition of Embodiment 56 wherein J is selected from J-1, J-2, J-3, J-4, J-5, J-7, J-8, J-9, J-10, J-11, J-12, J-14, J-15, J-16, J-20, J-24, J-25, J-26, J-29, J-30, J-37, J-38, J-45 and J-69.

Embodiment 58. The composition of Embodiment 57 wherein J is selected from J-4, J-5, J-8, J-11, J-15, J-16, J-20, J-29, J-30, J-37, J-38 and J-69.

Embodiment 59. The composition of Embodiment 58 wherein J is selected from J-4, J-5, J-11, J-20, J-29, J-37, J-38 and J-69.

Embodiment 60. The composition of Embodiment 59 wherein J is J-11.

Embodiment 61. The composition of Embodiment 59 wherein J is J-29.

Embodiment 61a. The composition of Embodiment 61 wherein J is any one of J-29-1 to J-29-60 (depicted in Exhibit A).

Embodiment 61b. The composition of Embodiment 61 wherein J is any one of J-29-1 to J-29-58 (depicted in Exhibit A).

Embodiment 62. The composition of Embodiment 59 wherein J is J-69.

Embodiment 63. The composition of Embodiment 60 wherein the 3-position of J-11 is connected to $Z^1$ and the 5-position of J-11 is connected to $R^5$ other than H.

Embodiment 63a. The composition of Embodiment 63 wherein the 3-position of J-11 is connected to $Z^1$ and the 5-position of J-11 is connected to $Z^2Q$.

Embodiment 64. The composition of Embodiment 61 wherein the 3-position of J-29 is connected to $Z^1$ and the 5-position of J-29 is connected to $R^5$ other than H.

Embodiment 64a. The composition of Embodiment 64 wherein the 3-position of J-29 is connected to $Z^1$ and the 5-position of J-29 is connected to $Z^2Q$.

Embodiment 65. The composition described in the Summary of the Invention wherein component (a) is a compound of Formula 1 or Embodiment 56-wherein each $R^5$ is independently H, cyano, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_3$-$C_{10}$ trialkylsilyl, —NR$^{25}$R$^{26}$ or $Z^2Q$.

Embodiment 66. The composition of Embodiment 65 or Embodiment 65a wherein each $R^5$ is independently H, cyano, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxyalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyalkoxy, $C_2$-$C_6$ alkylcarbonyloxy, $C_2$-$C_6$ haloalkylcarbonyloxy, $C_1$-$C_6$ alkylthio, $C_1$-$C_6$ haloalkylthio, $C_3$-$C_{10}$ trialkylsilyl, —NR$^{25}$R$^{26}$ or $Z^2Q$.

Embodiment 67. The composition of Embodiment 66 wherein each $R^5$ is independently H, cyano, $C_1$-$C_6$ alkyl, $C_1$-$C_6$ haloalkyl, $C_1$-$C_6$ alkoxy, $C_1$-$C_6$ haloalkoxy, —NR$^{25}$R$^{26}$ or $Z^2Q$.

Embodiment 68. The composition described in the Summary of the Invention wherein component (a) is a compound of Formula 1 or Embodiment 56-wherein one instance of $R^5$ is $Z^2Q$ and other instances of $R^5$ are independently selected from H, cyano, $C_1$-$C_4$ alkyl, $C_1$-$C_4$ haloalkyl, $C_1$-$C_4$ alkylcarbonyl and halogen.

Embodiment 69. The composition of Embodiment 68 or Embodiment 68a wherein the other instances of $R^5$ are independently selected from H, CN and $C_1$-$C_3$ alkyl.

Embodiment 69a. The composition of Embodiment 68 or Embodiment 68a wherein the other instances of $R^5$ are independently selected from H and $C_1$-$C_3$ alkyl.

Embodiment 70. The composition of Embodiment 56 wherein x is 1 or 2.

Embodiment 71. The composition of Embodiment 70 wherein x is 1.

Embodiment 72. The composition of Embodiment 70 wherein $R^5$ is $Z^2Q$.

Embodiment 73. The composition described in the Summary of the Invention wherein component (a) is a compound of Formula 1 wherein $Z^1$ is a direct bond.

Embodiment 74. The composition described in the Summary of the Invention wherein component (a) is a compound of Formula 1-wherein $Z^2$ is a direct bond.

Embodiment 75. The composition described in the Summary of the Invention wherein component (a) is a compound of Formula 1 wherein Q is one of Q-1 through Q-102 depicted in Exhibit 4;

Exhibit 4

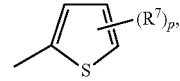
Q-1

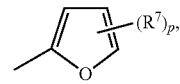
Q-2

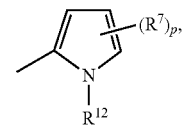
Q-3

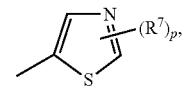
Q-4

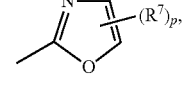
Q-5

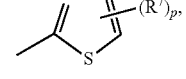
Q-6

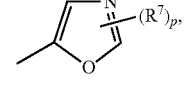
Q-7

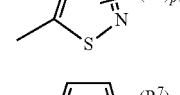
Q-8

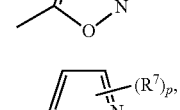
Q-9

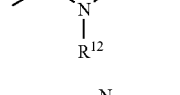
Q-10

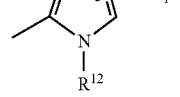
Q-11

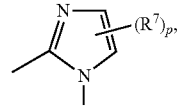
Q-12

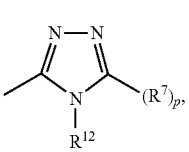
Q-13

-continued
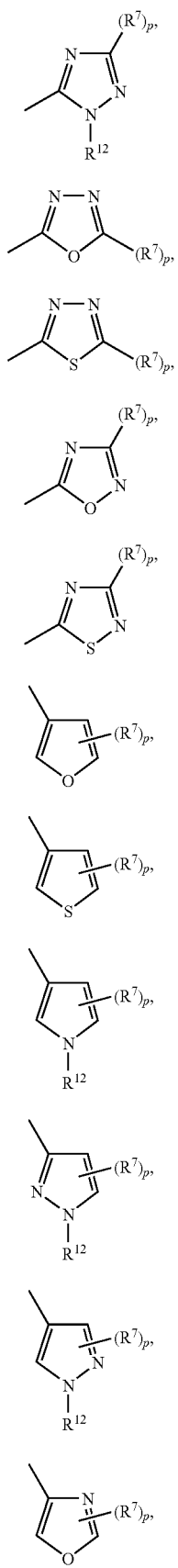
Q-14
Q-15
Q-16
Q-17
Q-18
Q-19
Q-20
Q-21
Q-22
Q-23
Q-24
-continued
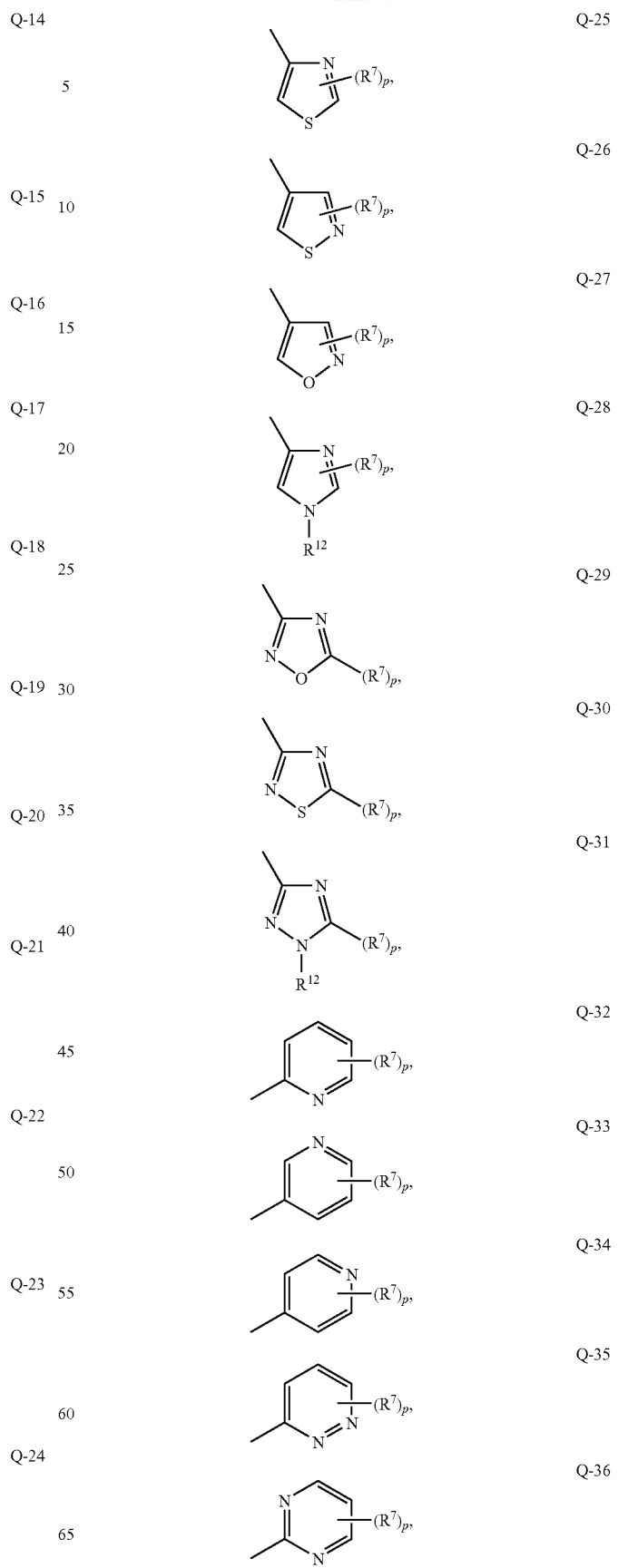
Q-25
Q-26
Q-27
Q-28
Q-29
Q-30
Q-31
Q-32
Q-33
Q-34
Q-35
Q-36

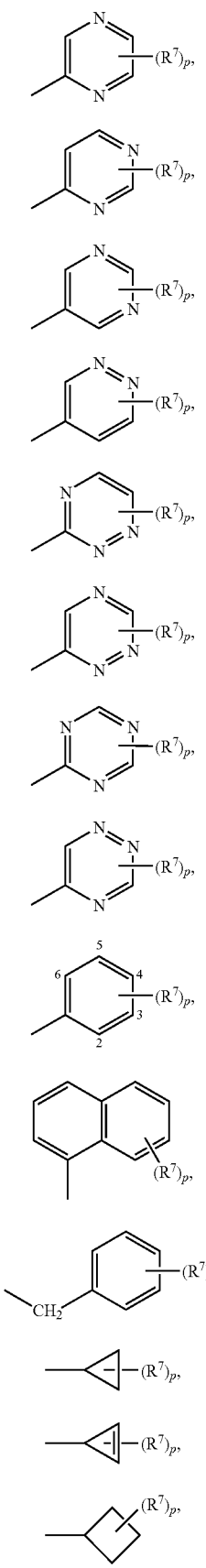
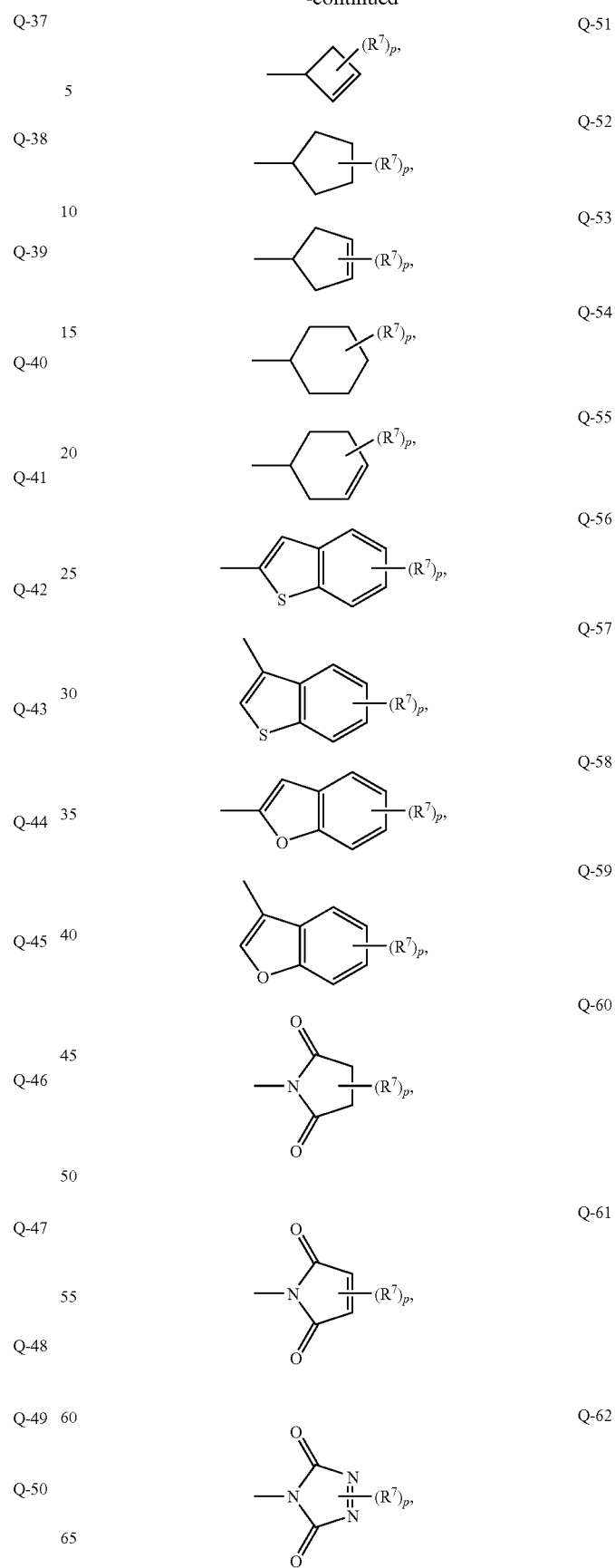

Q-63 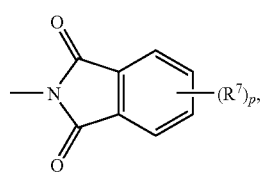
Q-64 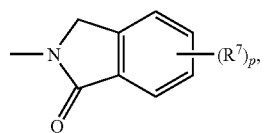
Q-65 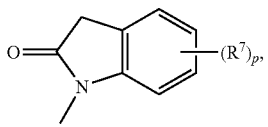
Q-66 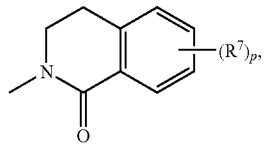
Q-67 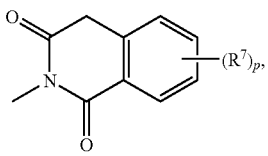
Q-68 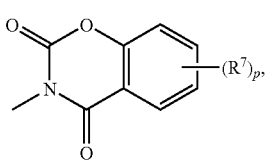
Q-69 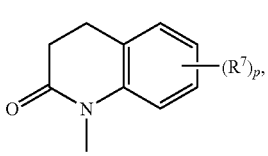
Q-70 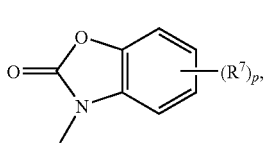
Q-71 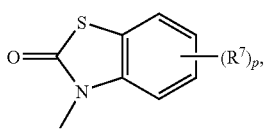
Q-72 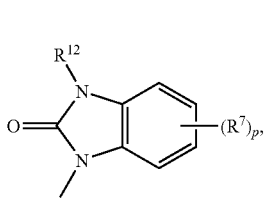
Q-73 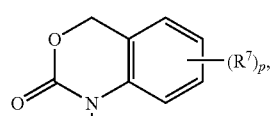
Q-74 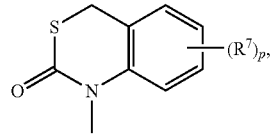
Q-75 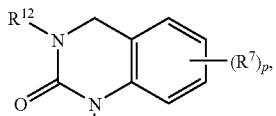
Q-76 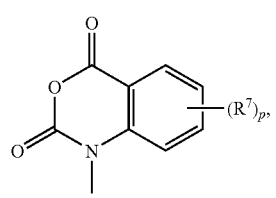
Q-77 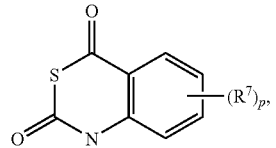
Q-78 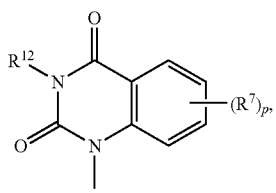
Q-79 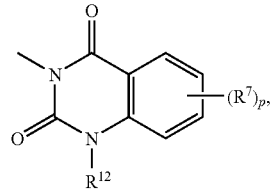
Q-80 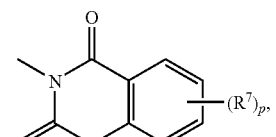
Q-81 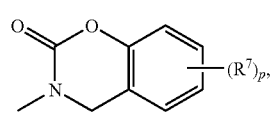

-continued
Q-82 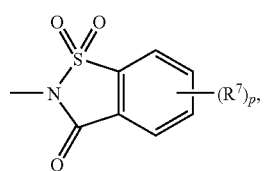
Q-83 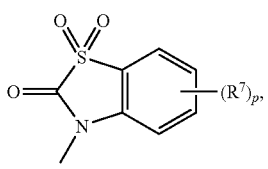
Q-84 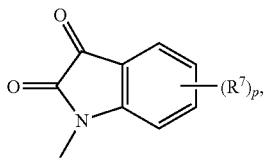
Q-85 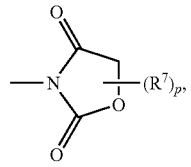
Q-86 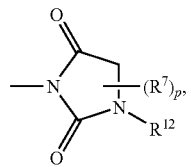
Q-87 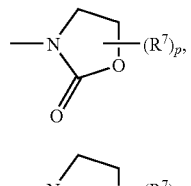
Q-88 
Q-89 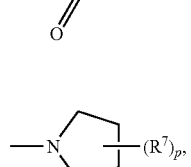
Q-90 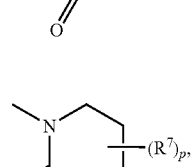
Q-91
-continued
Q-92 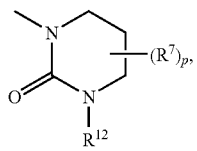
Q-93 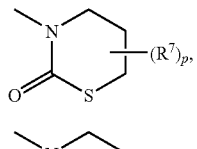
Q-94 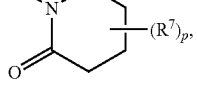
Q-95 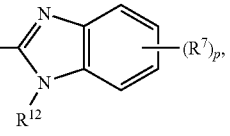
Q-96 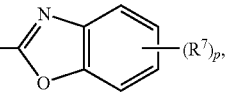
Q-97 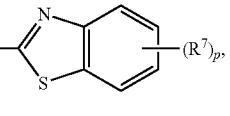
Q-98 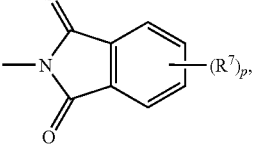
Q-99 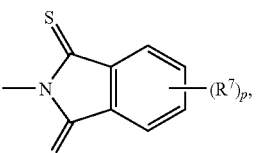
Q-100 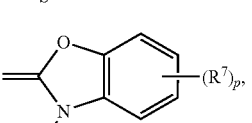
Q-101 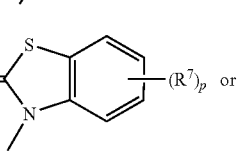 or
Q-102 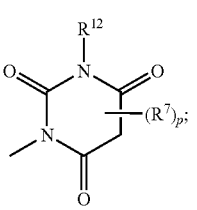
wherein p is 0, 1, 2, 3, 4 or 5.

Embodiment 76. The composition of Embodiment 75 wherein Q is selected from Q-1, Q-20, Q-32 through Q-34, Q-45 through Q-47, Q-60 through Q-73, Q-76 through Q-79, Q-84 through Q-94 and Q-98 through Q-102.

Embodiment 77. The composition of Embodiment 76 wherein Q is Q-1, Q-45, Q-63, Q64, Q-65, Q-68, Q-69, Q-70, Q-71, Q-72, Q-73, Q-76, Q-78, Q-79, Q-84, Q-85, Q-98, Q-99, Q-100, Q-101 or Q-102.

Embodiment 78. The composition of Embodiment 77 wherein Q is Q-45, Q-63, Q-64, Q-65, Q-68, Q-69, Q-70, Q-71, Q-72, Q-84 or Q-85.

Embodiment 78a. The composition of Embodiment 77 wherein Q is Q-45, Q-63, Q-64, Q-65, Q-68, Q-69, Q-70, Q-71, Q-72 or Q-85.

Embodiment 78b. The composition of Embodiment 78 wherein Q is Q-45, Q-63, Q-65, Q-70, Q-71, Q-72, Q-84 or Q-85.

Embodiment 78c. The composition of Embodiment 78a wherein Q is Q-45, Q-63, Q-65, Q-70, Q-71, Q-72 or Q-85.

Embodiment 78c. The composition of Embodiment 78b wherein Q is Q-45, Q-63, Q-65, Q-70, Q-71, Q-72 or Q-84.

Embodiment 78d. The composition of Embodiment 78c wherein Q is Q-45, Q-63, Q-65 or Q-70.

Embodiment 79. The composition described in the Summary of the Invention wherein component (a) is a compound of Formula 1 or Embodiment 75 wherein each $R^7$ is independently $C_1$-$C_3$ alkyl, $C_1$-$C_3$ haloalkyl, halogen, hydroxy, amino, cyano, nitro, $C_1$-$C_2$ alkoxy or $C_1$-$C_2$ haloalkoxy.

Embodiment 80. The composition of Embodiment 79 wherein each $R^7$ is independently $C_1$-$C_3$ alkyl, halogen, hydroxy, cyano or $C_1$-$C_2$ alkoxy.

Embodiment 81. The composition of Embodiment 80 wherein each $R^7$ is independently methyl, F, Cl, Br, hydroxy, cyano or methoxy.

Embodiment 82. The composition described in the Summary of the Invention wherein component (a) is a compound of Formula 1 wherein when $R^5$ and $R^7$ are taken together with the atoms linking $R^5$ and $R^7$ to form an optionally substituted 5- to 7-membered ring, the ring members are selected from carbon and optionally 1 to 3 heteroatoms selected from up to 1 O, up to 1 S and up to 1 N and optionally include 1 to 3 ring members selected from the group consisting of C(=O), C(=S), S(O), $S(O)_2$ and $SiR^{17}R^{18}$.

Embodiment 82a. The composition of Embodiment 82 wherein when $R^5$ and $R^7$ are taken together with the atoms linking $R^5$ and $R^7$ to form an optionally substituted 5- to 7-membered ring, then $R^5$ and $R^7$ are taken together with the atoms linking $R^5$ and $R^7$ to form a 5- to 7-membered ring containing as ring members carbon atoms and optionally 1 to 3 heteroatoms selected from up to 1 O, up to 1 S and up to 1 N, and optionally including 1 to 3 ring members selected from the group consisting of C(=O), C(=S), S(O), $S(O)_2$ and $SiR^{17}R^{18}$, optionally substituted with up to 2 substituents selected from $R^8$; and each $R^8$ is independently $C_1$-$C_3$ alkyl.

Embodiment 82b. The composition described in the Summary of the Invention wherein component (a) is a compound of Formula 1 wherein when $R^5$ and $R^7$ are taken together with the atoms linking $R^5$ and $R^7$ to form an optionally substituted 5- to 7-membered ring, then $R^5$ and $R^7$ are taken together with the atoms linking $R^5$ and $R^7$ to form a 5- to 7-membered ring containing ring members selected from carbon and optionally 1 to 3 heteroatoms selected from up to 1 O, up to 1 S and up to 1 N, and optionally including 1 to 3 ring members selected from the group consisting of C(=O), C(=S), S(O), $S(O)_2$ and $SiR^{17}R^{18}$, the ring optionally substituted on ring members other than the atoms linking $R^5$ and $R^7$ with substituents selected from $R^8$; and each $R^8$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl.

Embodiment 82c. The composition described in the Summary of the Invention wherein component (a) is a compound of Formula 1 wherein when $R^5$ and $R^7$ are taken together with the atoms linking $R^5$ and $R^7$ to form an optionally substituted 5- to 7-membered ring, then $R^5$ and $R^7$ are taken together with the atoms linking $R^5$ and $R^7$ to form a 5- to 7-membered ring containing as ring members 2 to 7 carbon atoms and optionally 1 to 3 heteroatoms selected from up to 1 O, up to 1 S, up to 1 Si and up to 1 N, the ring optionally substituted on ring members other than the atoms linking $R^5$ and $R^7$ with substituents selected from $R^8$; and each $R^8$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl.

Embodiment 82d. The composition of Embodiment 82b or 82c wherein the ring is optionally substituted on ring members other than the atoms linking $R^5$ and $R^7$ with up to 4 substituents selected from $R^8$.

Embodiment 82e. The composition of Embodiment 82d wherein the ring is optionally substituted on ring members other than the atoms linking $R^5$ and $R^7$ with up to 2 substituents selected from $R^8$.

Embodiment 82f. The composition of Embodiment 82b or 82c wherein each $R^8$ is independently $C_1$-$C_3$ alkyl.

Embodiment 82g. The composition of Embodiment 82b wherein when $R^5$ and $R^7$ are taken together with the atoms linking $R^5$ and $R^7$ to form an optionally substituted 5- to 7-membered ring, then $R^5$ and $R^7$ are taken together with the atoms linking $R^5$ and $R^7$ to form a 5- to 7-membered ring containing ring members selected from carbon and optionally 1 to 3 heteroatoms selected from up to 1 O, up to 1 S and up to 1 N, and optionally including 1 to 3 ring members selected from the group consisting of C(=O), C(=S), S(O), S(O)$_2$ and SiR$^{17}$R$^{18}$, optionally substituted with up to 2 substituents selected from R$^8$; and each R$^8$ is C$_1$-C$_3$ alkyl.

Embodiment 82h. The composition of Embodiment 82c wherein when R$^5$ and R$^7$ are taken together with the atoms linking R$^5$ and R$^7$ to form an optionally substituted 5- to 7-membered ring, then R$^5$ and R$^7$ are taken together with the atoms linking R$^5$ and R$^7$ to form a 5- to 7-membered ring containing as ring members 2 to 7 carbon atoms and optionally 1 to 3 heteroatoms selected from up to 1 O, up to 1 S and up to 1 N, optionally substituted with up to 2 substituents selected from R$^8$; and each R$^8$ is C$_1$-C$_3$ alkyl.

Embodiment 83. The composition described in the Summary of the Invention wherein component (a) is a compound of Formula 1 or Embodiment 75 wherein p is 0, 1, 2 or 3.

Embodiment 84. The composition described in the Summary of the Invention wherein component (a) is a compound of Formula 1 wherein R$^1$ is an optionally substituted phenyl or 5- or 6-membered heteroaromatic ring.

Embodiment 85. The composition described in the Summary of the Invention wherein component (a) is a compound of Formula 1 wherein A is CH$_2$ or NH.

Embodiment 86. The composition described in the Summary of the Invention wherein component (a) is a compound of Formula 1 wherein X is selected from X$^1$, X$^2$, X$^3$, X$^4$, X$^5$, X$^6$, X$^7$ and X$^8$.

Embodiment 87. The composition described in the Summary of the Invention wherein component (a) is a compound of Formula 1 wherein J is a 5- or 6-membered ring, a 8- to 11-membered bicyclic ring system or a 7- to 11-membered spirocyclic ring system, each ring or ring system containing ring members selected from carbon and optionally 1 to 3 heteroatoms selected from up to 1 O, up to 1 S and up to 3 N, and optionally including 1 to 3 ring members selected from the group consisting of C(=O), C(=S), S(O) and S(O)$_2$, each ring or ring system optionally substituted with 1 to 5 substituents independently selected from R$^5$.

Embodiment 88. The composition described in the Summary of the Invention wherein component (a) is a compound of Formula 1 wherein J is a phenyl or 5- or 6-membered heteroaromatic ring, or a naphthalenyl or 8- to 11-membered heteroaromatic bicyclic ring system, each ring or ring system optionally substituted with 1 to 5 substituents independently selected from R$^5$; or J is a 5-, 6- or 7-membered nonaromatic ring, an 8- to 11-membered nonaromatic bicyclic or a 7- to 11-membered spirocyclic ring system, each ring or ring system optionally including 1 to 3 ring members selected from the group consisting of C(=O), C(=S), S(O), S(O)$_2$ and SiR$^{17}$R$^{18}$, and optionally substituted with 1 to 5 substituents independently selected from R$^5$.

Embodiment 89. The composition described in the Summary of the Invention wherein component (a) is a compound of Formula 1 wherein each R$^5$ is independently H, halogen, hydroxy, amino, cyano, nitro, C$_1$-C$_6$ alkyl, C$_2$-C$_6$ alkenyl, C$_2$-C$_6$ alkynyl, C$_3$-C$_6$ cycloalkyl, C$_4$-C$_{10}$ cycloalkylalkyl, C$_4$-C$_{10}$ alkylcycloalkyl, C$_5$-C$_{10}$ alkylcycloalkylalkyl, C$_1$-C$_6$ haloalkyl, C$_2$-C$_6$ haloalkenyl, C$_2$-C$_6$ haloalkynyl, C$_3$-C$_6$ halocycloalkyl, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ alkylsulfonyl, C$_1$-C$_6$ haloalkylsulfinyl, C$_1$-C$_6$ haloalkylsulfonyl, C$_1$-C$_6$ alkylamino, C$_2$-C$_8$ dialkylamino, C$_3$-C$_6$ cycloalkylamino, C$_2$-C$_6$ alkoxyalkyl, C$_2$-C$_6$ haloalkoxyalkyl, C$_1$-C$_6$ hydroxyalkyl, C$_2$-C$_6$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl, C$_3$-C$_6$ trialkylsilyl or —Z$^2$Q; each R$^7$ is independently halogen, hydroxy, amino, cyano, nitro, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, C$_3$-C$_6$ cycloalkyl, C$_4$-C$_{10}$ cycloalkylalkyl, C$_4$-C$_{10}$ alkylcycloalkyl, C$_5$-C$_{10}$ alkylcycloalkylalkyl, C$_3$-C$_6$ halocycloalkyl, C$_1$-C$_4$ alkoxy, C$_1$-C$_4$ haloalkoxy, C$_1$-C$_4$ alkylthio, C$_1$-C$_4$ haloalkylthio, C$_1$-C$_4$ alkylsulfinyl, C$_1$-C$_4$ alkylsulfonyl, C$_1$-C$_4$ haloalkylsulfinyl, C$_1$-C$_4$ haloalkylsulfonyl, C$_1$-C$_4$ alkylamino, C$_2$-C$_8$ dialkylamino, C$_3$-C$_6$ cycloalkylamino, C$_2$-C$_4$ alkoxyalkyl, C$_1$-C$_4$ hydroxyalkyl, C$_2$-C$_4$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl or C$_3$-C$_6$ trialkylsilyl; or R$^5$ and R$^7$ are taken together with the atoms linking R$^5$ and R$^7$ to form an optionally substituted 5- to 7-membered ring containing as ring members 2 to 7 carbon atoms and optionally 1 to 3 heteroatoms selected from up to 1 O, up to 1 S and up to 1 N.

Embodiment 90. The composition described in the Summary of the Invention wherein component (a) is a compound of Formula 1 wherein each Q is independently an optionally substituted phenyl, benzyl, naphthalenyl, C$_3$-C$_6$ cycloalkyl, C$_3$-C$_6$ cycloalkenyl or 5- or 6-membered heteroaromatic ring, each optionally substituted with 1 to 3 substituents selected from R$^7$ on carbon ring members and R$^{12}$ on nitrogen ring members.

Embodiment 90a. The composition described in the Summary of the Invention wherein component (a) is a compound of Formula 1 wherein each Q is independently a 3- to 7-membered nonaromatic carbocyclic ring, a 5-, 6- or 7-membered nonaromatic heterocyclic ring or an 8- to 11-membered nonaromatic bicyclic ring system, each optionally including ring members selected from the group consisting of C(=O), C(=S), S(O), S(O)$_2$ and SiR$^{17}$R$^{18}$, and optionally substituted with 1 to 5 substituents independently selected from R$^7$ on carbon atom ring members and R$^{12}$ on nitrogen atom ring members;

Embodiment 91. The composition described in the Summary of the Invention wherein component (a) is a compound of Formula 1 wherein each Z$^1$ and Z$^2$ is independently a direct bond, O, C(=O), S(O)$_m$, CHR$^{20}$ or NR$^{21}$;

Embodiment 92. The composition described in the Summary of the Invention wherein component (a) is a compound of Formula 1 wherein R$^{21}$ is H, C$_1$-C$_3$ alkyl, C$_1$-C$_3$ alkylcarbonyl or C$_2$-C$_3$ alkoxycarbonyl.

Embodiment 93. The composition described in the Summary of the Invention wherein component (a) is a compound of Formula 1 wherein when G is an optionally substituted thiazole ring connected at its 2-position to X and at its 4-position to Z$^1$ in Formula 1, A is CHR$^{15}$, and J is an optionally substituted isoxazole ring connected at its 4-position to Z$^1$, then Z$^1$ is O, C(=O), S(O)$_m$, CHR$^{20}$ or NR$^{21}$.

Embodiment 94. The composition described in the Summary of the Invention wherein component (a) is a compound of Formula 1 wherein when G is an optionally substituted thiazole ring connected at its 2-position to X and at its 4-position to Z$^1$ in Formula 1, and J is an optionally substituted isoxazole ring connected at its 4-position to Z$^1$, then Z$^1$ is O, C(=O), S(O)$_m$, CHR$^{20}$ or NR$^{21}$.

Embodiment 95. The composition described in the Summary of the Invention wherein component (a) is a compound of Formula 1 wherein when G is an optionally substituted thiazole ring connected at its 2-position to X and at its 4-position to $Z^1$ in Formula 1, A is $CHR^{15}$, $Z^1$ is a direct bond, and J is an optionally substituted isoxazole ring, then J is connected to the remainder of the Formula 1 at the 3- or 5-position of the isoxazole ring.

Embodiment 96. The composition described in the Summary of the Invention wherein component (a) is a compound of Formula 1 wherein when G is an optionally substituted thiazole ring connected at its 2-position to X and at its 4-position to $Z^1$ in Formula 1, A is $CHR^{15}$, $Z^1$ is a direct bond, and J is an optionally substituted isoxazole ring, then J is connected to the remainder of the Formula 1 at the 3-position of the isoxazole ring.

Embodiment 97. The composition described in the Summary of the Invention wherein component (a) is a compound of Formula 1 wherein when G is an optionally substituted thiazole ring connected at its 2-position to X and at its 4-position to $Z^1$ in Formula 1, $Z^1$ is a direct bond, and J is an optionally substituted isoxazole ring, then J is connected to the remainder of the Formula 1 at the 3-position of the isoxazole ring.

Embodiment 98. The composition described in the Summary of the Invention wherein component (a) is a compound of Formula 1 wherein when X is $X^2$ and the ring containing X is saturated, A is $CHR^{15}$, G is an optionally substituted 5-membered heteroaromatic ring, $Z^1$ is a direct bond, and J is a phenyl or 5- or 6-membered heteroaromatic ring or a naphthalenyl or 8- to 11-membered heteroaromatic bicyclic ring system, then the J ring or ring system is substituted with at least one $R^5$ that is other than H.

Embodiment 99. The composition described in the Summary of the Invention wherein component (a) is a compound of Formula 1 wherein when X is $X^2$ and the ring containing X is saturated, A is $CHR^{15}$, G is an optionally substituted 5-membered heteroaromatic ring, $Z^1$ is a direct bond, and J is a phenyl or 5- or 6-membered heteroaromatic ring or a naphthalenyl or 8- to 11-membered heteroaromatic bicyclic ring system, then the J ring or ring system is substituted with at least one $R^5$ that is $Z^2Q$.

Embodiment 100. The composition described in the Summary of the Invention wherein component (a) is a compound of Formula 1 wherein when X is $X^1$ and the ring containing X is saturated, A is NH, G is an optionally substituted thiazole ring connected at its 2-position to X and at its 4-position to $Z^1$ in Formula 1, and J is an optionally substituted imidazole ring connected at its 2-position to the remainder of Formula 1, then $Z^1$ is O, C(=O), S(O)$_m$, $CHR^{20}$ or $NR^{21}$.

Embodiment 101. The composition described in the Summary of the Invention wherein component (a) is a compound of Formula 1 wherein when X is $X^1$ and the ring containing X is saturated, A is $NR^{16}$, G is an optionally substituted thiazole ring connected at its 2-position to X and at its 4-position to $Z^1$ in Formula 1, and J is an optionally substituted imidazole ring connected at its 2-position to the remainder of Formula 1, then $Z^1$ is O, C(=O), S(O)$_m$, $CHR^{20}$ or $NR^{21}$.

Embodiment 102. The composition described in the Summary of the Invention wherein component (a) is a compound of Formula 1 wherein when G is an optionally substituted thiazole ring connected at its 2-position to X and at its 4-position to $Z^1$ in Formula 1, then J is other than optionally substituted imidazolyl.

Embodiment 103. The composition described in the Summary of the Invention wherein component (a) is a compound of Formula 1 wherein each $Z^4$ is independently C(=O) or S(O)$_2$.

Embodiment 104. The composition of Embodiment 103 wherein each $Z^4$ is C(=O).

Embodiment 105. The composition described in the Summary of the Invention wherein component (a) is a compound of Formula 1 wherein
each $R^2$ is independently $C_1$-$C_4$ alkyl, $C_1$-$C_4$ alkenyl, $C_1$-$C_4$ haloalkyl, $C_1$-$C_4$ alkoxy, halogen, cyano or hydroxy; or
two $R^2$ are taken together as $C_1$-$C_3$ alkylene or $C_2$-$C_3$ alkenylene to form a bridged bicyclic ring system; or
two $R^2$ attached to adjacent ring carbon atoms joined by a double bond are taken together as —CH=CH—CH=CH— optionally substituted with 1 to 3 substituents selected from $C_1$-$C_4$ alkyl, $C_1$-$C_4$ haloalkyl, $C_1$-$C_4$ alkoxy, $C_1$-$C_4$ haloalkoxy, halogen, hydroxy, amino, cyano and nitro.

Embodiments of this invention, including Embodiments 1-105 above as well as any other embodiments described herein, can be combined in any manner, and the descriptions of variables in the embodiments pertain not only to the compositions comprising the compounds of Formula 1 but also to the compounds of Formula 1, the starting compounds and intermediate compounds useful for preparing the compounds of Formula 1 unless further defined in the Embodiments. In addition, embodiments of this invention, including Embodiments 1-105 above as well as any other embodiments described herein, and any combination thereof, pertain to the compounds, compositions and methods of the present invention. Combinations of Embodiments 1-105 are illustrated by:

Embodiment A1. The composition described in the Summary of the Invention wherein component (a) is a compound of Formula 1 or salt thereof, wherein
G is a 5-membered heteroaromatic ring or a 5-membered saturated or partially saturated heterocyclic ring, each ring optionally substituted with up to 2 substituents selected from $R^3$ on carbon ring members and selected from $R^{11}$ on nitrogen ring members;
$R^1$ is a phenyl or a 5- or 6-membered heteroaromatic ring optionally substituted with 1 to 2 substituents independently selected from $R^{4a}$ on carbon ring members and $R^{4b}$ on nitrogen ring members;
each $R^2$ is independently halogen, cyano, hydroxy, $C_1$-$C_2$ alkyl, $C_1$-$C_2$ haloalkyl or $C_1$-$C_2$ alkoxy;
each $R^3$ is independently halogen, $C_1$-$C_3$ alkyl or $C_1$-$C_3$ haloalkyl;
each $R^{4a}$ is independently halogen, hydroxy, amino, cyano, nitro, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_3$-$C_6$ halocycloalkyl, $C_2$-$C_4$ alkoxyalkyl, $C_1$-$C_4$ hydroxyalkyl, $C_1$-$C_4$ alkoxy, $C_1$-$C_4$ haloalkoxy, $C_2$-$C_6$ alkylcarbonyloxy, $C_1$-$C_4$ alkylthio, $C_1$-$C_4$ haloalkylthio, $C_2$-$C_6$ alkylcarbonylthio, $C_1$-$C_4$ alkylsulfinyl, $C_1$-$C_4$ alkylsulfonyl, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl;

each $R^{4b}$ is independently $C_1$-$C_6$ alkyl, $C_3$-$C_6$ alkenyl, $C_3$-$C_6$ alkynyl, $C_3$-$C_6$ cycloalkyl, $C_1$-$C_6$ haloalkyl, $C_3$-$C_6$ haloalkenyl, $C_3$-$C_6$ haloalkynyl, $C_3$-$C_6$ halocycloalkyl or $C_2$-$C_4$ alkoxyalkyl;

each $R^{11}$ is independently $C_1$-$C_3$ alkyl;

$R^{15}$ is H, halogen, cyano, hydroxy, —CHO, $C_1$-$C_4$ alkyl, $C_1$-$C_4$ haloalkyl or $C_2$-$C_5$ alkoxycarbonyl; or $R^{15}$ is $C_2$-$C_4$ alkenyloxy, $C_2$-$C_4$ alkynyloxy, $C_2$-$C_4$ haloalkenyloxy, $C_2$-$C_4$ haloalkynyloxy, $C_2$-$C_5$ alkylcarbonyloxy, $C_2$-$C_5$ alkoxycarbonyloxy, $C_2$-$C_5$ haloalkylcarbonyloxy, $C_2$-$C_5$ haloalkoxycarbonyloxy, $C_2$-$C_5$ alkylaminocarbonyloxy, $C_3$-$C_6$ dialkylaminocarbonyloxy, $C_2$-$C_5$ haloalkylaminocarbonyloxy, $C_3$-$C_6$ halodialkylaminocarbonyloxy, $C_2$-$C_5$ alkoxyalkoxy, $C_2$-$C_5$ haloalkoxyalkoxy, $C_1$-$C_4$ alkylsulfonyloxy, $C_1$-$C_4$ haloalkylsulfonyloxy or $C_3$-$C_{10}$ trialkylsilyloxy;

$R^{16}$ is H, $C_1$-$C_4$ alkyl, $C_1$-$C_4$ haloalkyl, $C_2$-$C_4$ alkylcarbonyl, $C_2$-$C_4$ haloalkylcarbonyl or $C_2$-$C_4$ alkoxycarbonyl;

when $R^5$ and $R^7$ are taken together with the atoms linking $R^5$ and $R^7$ to form an optionally substituted 5- to 7-membered ring, then $R^5$ and $R^7$ are taken together with the atoms linking $R^5$ and $R^7$ to form a 5- to 7-membered ring containing ring members selected from carbon and optionally 1 to 3 heteroatoms selected from up to 1 O, up to 1 S and up to 1 N, and optionally including 1 to 3 ring members selected from the group consisting of C(=O), C(=S), S(O), S(O)$_2$ and SiR$^{17}$R$^{18}$, the ring optionally substituted on ring members other than the atoms linking $R^5$ and $R^7$ with up to 4 substituents selected from $R^8$;

each $R^8$ is independently halogen, hydroxy, amino, cyano, nitro, $C_1$-$C_6$ alkyl, $C_2$-$C_6$ alkenyl, $C_1$-$C_6$ haloalkyl, $C_2$-$C_6$ haloalkenyl, $C_2$-$C_6$ haloalkynyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_3$-$C_6$ halocycloalkyl, $C_2$-$C_4$ alkoxyalkyl, $C_1$-$C_4$ hydroxyalkyl, $C_1$-$C_4$ alkoxy, $C_1$-$C_4$ haloalkoxy, $C_2$-$C_6$ alkylcarbonyloxy, $C_1$-$C_4$ alkylthio, $C_1$-$C_4$ haloalkylthio, $C_2$-$C_6$ alkylcarbonylthio, $C_1$-$C_4$ alkylsulfinyl, $C_1$-$C_4$ alkylsulfonyl, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkylcarbonyl, $C_2$-$C_6$ alkoxycarbonyl, $C_2$-$C_6$ alkylaminocarbonyl, $C_3$-$C_8$ dialkylaminocarbonyl or $C_3$-$C_6$ trialkylsilyl; and each $Z^4$ is independently C(=O) or S(O)$_2$.

Embodiment A2. The composition of Embodiment A1 wherein

G is one of G-1 through G-59 (as depicted in Exhibit 2) wherein the bond projecting to the left is bonded to X, and bond projecting to the right is bonded to $Z^1$;

J is one of J-1 through J-82 (as depicted in Exhibit 3) wherein the bond shown projecting to the left is bonded to $Z^1$;

Q is one of Q-1 through Q-102 (as depicted in Exhibit 4);

$R^1$ is one of U-1 through U-50 (as depicted in Exhibit 1);

each $R^2$ is independently methyl, methoxy, cyano or hydroxy;

each $R^{3a}$ is independently selected from H and $R^3$;

each $R^5$ is independently H, cyano, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_2$-$C_6$ alkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkoxycarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_2$-$C_6$ haloalkynyloxy, $C_2$-$C_6$ alkoxyalkoxy, $C_2$-$C_6$ alkylcarbonyloxy, $C_2$-$C_6$ haloalkylcarbonyloxy, $C_4$-$C_8$ cycloalkylcarbonyloxy, $C_3$-$C_6$ alkylcarbonylalkoxy, $C_1$-$C_6$ alkylthio, $C_1$-$C_6$ haloalkylthio, $C_3$-$C_8$ cycloalkylthio, $C_3$-$C_{10}$ trialkylsilyl, —NR$^{25}$R$^{26}$ or $Z^2$Q;

$R^{11a}$ is selected from H and $R^{11}$;

$R^{15}$ is H, cyano, hydroxy, methyl or methoxycarbonyl; or $R^{15}$ is $C_2$-$C_3$ alkenyloxy, $C_2$-$C_3$ alkynyloxy, $C_2$-$C_3$ alkylcarbonyloxy, $C_2$-$C_3$ alkoxycarbonyloxy, $C_2$-$C_3$ haloalkylcarbonyloxy, $C_2$-$C_3$ haloalkoxycarbonyloxy, $C_2$-$C_3$ alkylaminocarbonyloxy, $C_3$-$C_4$ dialkylaminocarbonyloxy, $C_2$-$C_3$ haloalkylaminocarbonyloxy, $C_3$-$C_4$ halodialkylaminocarbonyloxy, $C_2$-$C_3$ alkoxyalkoxy, $C_2$-$C_3$ haloalkoxyalkoxy, $C_1$-$C_3$ alkylsulfonyloxy, $C_1$-$C_3$ haloalkylsulfonyloxy or $C_3$-$C_6$ trialkylsilyloxy;

$R^{16}$ is H, methyl, methylcarbonyl or methoxycarbonyl;

each $Z^4$ is C(=O);

k is 0, 1 or 2;

p is 0, 1, 2 or 3; and x is an integer from 0 to 5;

provided that:

(i) when $R^4$ is attached to a carbon ring member, said $R^4$ is selected from $R^{4a}$;

(ii) when $R^4$ is attached to a nitrogen ring member (e.g., in U-4, U-11 through U-15, U-24 through U-26, U-31 or U-35), said $R^4$ is selected from $R^{4b}$;

(iii) when G is G-6, G-16 or G-42, and each $R^{3a}$ is other than H, then $R^{11a}$ is H;

(iv) when G is G-25 or G-31, then at least one $R^{3a}$ is H; and (v) when G is one of G-31 through G-35, then $Z^1$ is a direct bond or CHR$^{20}$.

Embodiment A3. The composition of Embodiment A2 wherein

G is selected from G-1, G-2, G-7, G-8, G-14, G-15, G-23, G-24, G-26, G-27, G-36, G-37, G-38, G-49, G-50 and G-55;

J is selected from J-1, J-2, J-3, J-4, J-5, J-7, J-8, J-9, J-10, J-11, J-12, J-14, J-15, J-16, J-20, J-24, J-25, J-26, J-29, J-30, J-37, J-38, J-45 and J-69;

each Q is independently Q-1, Q-20, Q-32 through Q-34, Q-45 through Q-47, Q-60 through Q-73, Q-76 through Q-79, Q-84 through Q-94 and Q-98 through Q-102;

A is CH$_2$ or NH;

W is O;

X is $X^1$, $X^2$ or $X^3$;

each $R^5$ is independently H, cyano, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxyalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyalkoxy, $C_2$-$C_6$ alkylcarbonyloxy, $C_2$-$C_6$ halo alkylcarbonyloxy, $C_1$-$C_6$ alkylthio, $C_1$-$C_6$ haloalkylthio, $C_3$-$C_{10}$ trialkylsilyl, —NR$^{25}$R$^{26}$ or $Z^2$Q;

$Z^1$ is a direct bond;

$Z^2$ is a direct bond or NR$^{21}$;

$R^1$ is selected from U-1 through U-3, U-11, U-13, U-20, U-22, U-23, U-36 through U-39 and U-50;

each $R^3$ is independently methyl or halogen;

each $R^{4a}$ is independently $C_1$-$C_2$ alkyl, $C_1$-$C_2$ haloalkyl, halogen, $C_1$-$C_2$ alkoxy or $C_1$-$C_2$ haloalkoxy;

each $R^{4b}$ is independently $C_1$-$C_2$ alkyl or $C_1$-$C_2$ haloalkyl;

each $R^7$ is independently halogen, cyano, $C_1$-$C_3$ alkyl, $C_1$-$C_3$ haloalkyl, hydroxy, $C_1$-$C_2$ alkoxy or $C_1$-$C_2$ haloalkoxy;

k is 1 or 2; and n is 0.

Embodiment A4. The composition of Embodiment A3 wherein

A is $CH_2$;

G is selected from G-1, G-2, G-15, G-26, G-27, G-36, G-37 and G-38; and G is unsubstituted;

J is selected from J-4, J-5, J-8, J-11, J-15, J-16, J-20, J-29, J-30, J-37, J-38, and J-69;

Q is selected from Q-1, Q-45, Q-63, Q-64, Q-65, Q-68, Q-69, Q-70, Q-71, Q-72, Q-73, Q-76, Q-78, Q-79, Q-84, Q-85, Q-98, Q-99, Q-100, Q-101 and Q-102;

X is $X^1$ or $X^2$; and the ring comprising X is saturated;

$R^1$ is U-1 or U-50;

each $R^{4a}$ is independently $C_1$-$C_2$ alkyl, trifluoromethyl, Cl, Br, I or methoxy;

each $R^{4b}$ is independently $C_1$-$C_2$ alkyl or trifluoromethyl; and each $R^5$ is independently H, cyano, $C_1$-$C_6$ alkyl, $C_1$-$C_6$ haloalkyl, $C_1$-$C_6$ alkoxy, $C_1$-$C_6$ haloalkoxy, -$NR^{25}R^{26}$ or $Z^2Q$.

Embodiment A4a. The composition of Embodiment A3 wherein

G is selected from G-1, G-2, G-15, G-26, G-27, G-36, G-37 and G-38; and G is unsubstituted;

J is selected from J-4, J-5, J-8, J-11, J-15, J-16, J-20, J-29, J-30, J-37, J-38, and J-69;

Q is selected from Q-1, Q-45, Q-63, Q-64, Q-65, Q-68, Q-69, Q-70, Q-71, Q-72, Q-73, Q-76, Q-78, Q-79, Q-84, Q-85, Q-98, Q-99, Q-100, Q-101 and Q-102;

X is $X^1$ or $X^2$; and the ring comprising X is saturated;

$R^1$ is U-1, U-20 or U-50;

each $R^{4a}$ is independently $C_1$-$C_2$ alkyl, trifluoromethyl, Cl, Br, I or methoxy;

each $R^{4b}$ is independently $C_1$-$C_2$ alkyl or trifluoromethyl; and each $R^5$ is independently H, cyano, $C_1$-$C_6$ alkyl, $C_1$-$C_6$ haloalkyl, $C_1$-$C_6$ alkoxy, $C_1$-$C_6$ haloalkoxy, —$NR^{25}R^{26}$ or $Z^2Q$.

Embodiment A5. The composition of Embodiment A4 wherein

G is selected from G-1, G-2, G-15, G-26 and G-36;

J is selected from J-4, J-5, J-11, J-20, J-29, J-37, J-38, and J-69;

Q is selected from Q-45, Q-63, Q-64, Q-65, Q-68, Q-69, Q-70, Q-71, Q-72 and Q-85; and X is $X^1$.

Embodiment A6. The composition described in the Summary of the Invention wherein component (a) is a compound of Formula 1 or a salt thereof, wherein $R^1$ is an optionally substituted phenyl or 5- or 6-membered heteroaromatic ring;

A is $CH_2$ or NH;

X is $X^1$, $X^2$, $X^3$, $X^4$, $X^5$, $X^6$, $X^7$ or $X^8$;

each $R^2$ is independently $C_1$-$C_4$ alkyl, $C_1$-$C_4$ alkenyl, $C_1$-$C_4$ haloalkyl, $C_1$-$C_4$ alkoxy, halogen, cyano or hydroxy; or two $R^2$ are taken together as $C_1$-$C_3$ alkylene or $C_2$-$C_3$ alkenylene to form a bridged bicyclic ring system; or two $R^2$ attached to adjacent ring carbon atoms joined by a double bond are taken together as —CH=CH— CH=CH— optionally substituted with 1 to 3 substituents selected from $C_1$-$C_4$ alkyl, $C_1$-$C_4$ haloalkyl, $C_1$-$C_4$ alkoxy, $C_1$-$C_4$ haloalkoxy, halogen, hydroxy, amino, cyano and nitro;

G is an optionally substituted 5-membered heteroaromatic ring or 5-membered saturated or partially saturated heterocyclic ring;

J is a 5- or 6-membered ring or a 8- to 11-membered bicyclic ring system, each ring or ring system containing ring members selected from carbon and optionally 1 to 3 heteroatoms selected from up to 1 O, up to 1 S and up to 3 N, and optionally including 1 to 3 ring members selected from the group consisting of C(=O), C(=S), S(O), or S(O)$_2$, each ring or ring system optionally substituted with 1 to 5 substituents independently selected from $R^5$;

each $R^5$ is independently H, $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_6$ alkoxy, $C_1$-$C_6$ haloalkoxy, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, $C_1$-$C_6$ alkylamino, $C_2$-$C_8$ dialkylamino, $C_3$-$C_6$ cycloalkylamino, $C_2$-$C_6$ alkoxyalkyl, $C_2$-$C_6$ haloalkoxyalkyl, $C_1$-$C_6$ hydroxyalkyl, $C_2$-$C_6$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl, $C_3$-$C_6$ trialkylsilyl, or —$Z^2Q$;

each Q is independently an optionally substituted phenyl, benzyl, naphthalenyl, $C_3$-$C_6$ cycloalkyl, $C_3$-$C_6$ cycloalkenyl or 5- or 6-membered heteroaromatic ring, each optionally substituted with 1 to 3 substituents selected from $R^7$ on carbon ring members and $R^{12}$ on nitrogen ring members;

each $R^7$ is independently $C_1$-$C_6$ alkyl, $C_2$-$C_6$ alkenyl, $C_2$-$C_6$ alkynyl, $C_3$-$C_6$ cycloalkyl, $C_4$-$C_{10}$ cycloalkylalkyl, $C_4$-$C_{10}$ alkylcycloalkyl, $C_5$-$C_{10}$ alkylcycloalkylalkyl, $C_1$-$C_6$ haloalkyl, $C_2$-$C_6$ haloalkenyl, $C_2$-$C_6$ haloalkynyl, $C_3$-$C_6$ halocycloalkyl, halogen, hydroxy, amino, cyano, nitro, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_1$-$C_4$ alkylamino, $C_2$-$C_8$ dialkylamino, $C_3$-$C_6$ cycloalkylamino, $C_2$-$C_4$ alkoxyalkyl, $C_1$-$C_4$ hydroxyalkyl, $C_2$-$C_4$ alkylcarbonyl, $C_2$-$C_6$ alkoxycarbonyl, $C_2$-$C_6$ alkylcarbonyloxy, $C_2$-$C_6$ alkylcarbonylthio, $C_2$-$C_6$ alkylaminocarbonyl, $C_3$-$C_8$ dialkylaminocarbonyl or $C_3$-$C_6$ trialkylsilyl; or $R^5$ and $R^7$ are taken together with the atoms linking $R^5$ and $R^7$ to form an optionally substituted 5- to 7-membered ring containing as ring members 2 to 7 carbon atoms and optionally 1 to 3 heteroatoms selected from up to 1 O, up to 1 S and up to 1 N;

$R^{12}$ is $C_1$-$C_3$ alkyl;

each $Z^1$ and $Z^2$ are independently a direct bond, O, S(O)$_m$, $CHR^{20}$ or $NR^{21}$; and $R^{21}$ is H or $C_1$-$C_3$ alkyl.

Embodiment A7. The composition of Embodiment A6 wherein

G is a 5-membered heteroaromatic ring or 5-membered saturated or partially saturated heterocyclic ring, each ring optionally substituted with up to 2 substituents selected from $R^3$ on carbon ring members and selected from $R^{11}$ on nitrogen ring members;

R$^1$ is a phenyl or 5- or 6-membered heteroaromatic ring optionally substituted with 1 to 2 substituents independently selected from R$^{4a}$ on carbon ring members and R$^{4b}$ on nitrogen ring members;

each R$^3$ is independently C$_1$-C$_3$ alkyl, C$_1$-C$_3$ haloalkyl or halogen;

each R$^{4a}$ is independently C$_1$-C$_6$ alkyl, C$_2$-C$_6$ alkenyl, C$_2$-C$_6$ alkynyl, C$_3$-C$_6$ cycloalkyl, C$_4$-C$_{10}$ cycloalkylalkyl, C$_4$-C$_{10}$ alkylcycloalkyl, C$_5$-C$_{10}$ alkylcycloalkylalkyl, C$_1$-C$_6$ haloalkyl, C$_2$-C$_6$ haloalkenyl, C$_2$-C$_6$ haloalkynyl, C$_3$-C$_6$ halocycloalkyl, halogen, hydroxy, amino, cyano, nitro, C$_1$-C$_4$ alkoxy, C$_1$-C$_4$ haloalkoxy, C$_1$-C$_4$ alkylthio, C$_1$-C$_4$ alkylsulfinyl, C$_1$-C$_4$ alkylsulfonyl, C$_1$-C$_4$ haloalkylthio, C$_1$-C$_4$ haloalkylsulfinyl, C$_1$-C$_4$ haloalkylsulfonyl, C$_1$-C$_4$ alkylamino, C$_2$-C$_g$ dialkylamino, C$_3$-C$_6$ cycloalkylamino, C$_2$-C$_4$ alkoxyalkyl, C$_1$-C$_4$ hydroxyalkyl, C$_2$-C$_4$ alkylcarbonyl, C$_2$-C$_6$ alkoxycarbonyl, C$_2$-C$_6$ alkylcarbonyloxy, C$_2$-C$_6$ alkylcarbonylthio, C$_2$-C$_6$ alkylaminocarbonyl, C$_3$-C$_8$ dialkylaminocarbonyl or C$_3$-C$_6$ trialkylsilyl;

each R$^{4b}$ is independently C$_1$-C$_6$ alkyl, C$_3$-C$_6$ alkenyl, C$_3$-C$_6$ alkynyl, C$_3$-C$_6$ cycloalkyl, C$_1$-C$_6$ haloalkyl, C$_3$-C$_6$ haloalkenyl, C$_3$-C$_6$ haloalkynyl, C$_3$-C$_6$ halocycloalkyl or C$_2$-C$_4$ alkoxyalkyl;

each R$^{11}$ is independently C$_1$-C$_3$ alkyl; and when R$^5$ and R$^7$ are taken together with the atoms linking R$^5$ and R$^7$ to form an optionally substituted 5- to 7-membered ring, then R$^5$ and R$^7$ are taken together with the atoms linking R$^5$ and R$^7$ to form a 5- to 7-membered ring containing as ring members 2 to 7 carbon atoms and optionally 1 to 3 heteroatoms selected from up to 1 O, up to 1 S and up to 1 N, optionally substituted with up to 2 substituents selected from R$^8$; and each R$^8$ is independently C$_1$-C$_3$ alkyl.

Embodiment A8. The composition of Embodiment A7 wherein

G is one of G-1 through G-55 (as depicted in Exhibit 2) wherein the bond projecting to the left is bonded to X, and bond projecting to the right is bonded to Z$^1$;

J is one of J-1 through J-82 (as depicted in Exhibit 3) wherein the bond shown projecting to the left is bonded to Z$^1$;

Q is one of Q-1 through Q-55 (as depicted in Exhibit 4);

R$^1$ is one of U-1 through U-50 (as depicted in Exhibit 1);

each R$^{3a}$ is independently selected from H and R$^3$;

R$^{11a}$ is selected from H and R$^{11}$;

k is 0, 1 or 2;

p is 0, 1 or 2; and x is an integer from 0 to 5;

provided that:
  (i) when R$^4$ is attached to a carbon ring member, said R$^4$ is selected from R$^{4a}$;
  (ii) when R$^4$ is attached to a nitrogen ring member (e.g., in U-4, U-11 through U-15, U-24 through U-26, U-31 or U-35), said R$^4$ is selected from R$^{4b}$;
  (iii) when G is G-6, G-16 or G-42, and each R$^{3a}$ is other than H, then R$^{11a}$ is H;
  (iv) when G is G-25 or G-31, then at least one R$^{3a}$ is H; and
  (v) when G is one of G-31 through G-35, then Z$^1$ is a direct bond or CHR$^{20}$.

Embodiment A9. The composition of Embodiment A8 wherein

G is selected from G-1, G-2, G-15, G-26, G-27, G-36, G-37 and G-38;

J is selected from J-1, J-2, J-3, J-4, J-5, J-7, J-8, J-9, J-10, J-11, J-12, J-14, J-15, J-16, J-20, J-24, J-25, J-26, J-29, J-30, J-45 and J-69;

each Q is independently Q-1, Q-20, Q-32 to 34, Q-45 Q-46 or Q-47;

W is O;

X is X$^1$, X$^2$ or X$^3$;

each Z$^1$ and Z$^2$ is a direct bond;

R$^1$ is selected from U-1 through U-3, U-11, U-13, U-20, U-22, U-23, U-36 through U-39 and U-50;

each R$^3$ is independently methyl or halogen;

each R$^{4a}$ is independently C$_1$-C$_2$ alkyl, C$_1$-C$_2$ haloalkyl, halogen or C$_1$-C$_2$ alkoxy;

each R$^{4b}$ is independently C$_1$-C$_2$ alkyl or C$_1$-C$_2$ haloalkyl;

one instance of R$^5$ is Z$^2$Q and other instances of R$^5$ are independently selected from H, C$_1$-C$_4$ alkyl, C$_1$-C$_4$ haloalkyl and halogen;

each R$^7$ is independently halogen, C$_1$-C$_3$ alkyl, C$_1$-C$_3$ haloalkyl, hydroxy, C$_1$-C$_2$ alkoxy or C$_1$-C$_2$ haloalkoxy;

k is 1 or 2; and n is 0.

Embodiment A10. The composition of Embodiment A9 wherein

A is CH$_2$;

G is selected from G-1, G-2, G-15, G-26, and G-36; and G is unsubstituted;

J is selected from J-11, J-25, J-26, J-29 and J-30;

Q is selected from Q-1 and Q-45;

X is X$^1$ or X$^2$; and the ring comprising X is saturated;

R$^1$ is U-1 or U-50;

each R$^{4a}$ is independently C$_1$-C$_2$ alkyl, trifluoromethyl, Cl, Br, I or methoxy; and each R$^{4b}$ is independently C$_1$-C$_2$ alkyl or trifluoromethyl.

Embodiment A11. The composition of Embodiment A10 wherein

J is selected from J-11 and J-29;

X is X$^1$; and each R$^{4a}$ is independently C$_1$-C$_2$ alkyl, trifluoromethyl or Cl.

Embodiment A12. The composition of Embodiment A1 wherein component (a) is selected from the group consisting of:

4-[4-[(5R)-4,5-dihydro-5-phenyl-3-isoxazolyl]-2-thiazolyl]-1-[[5-methyl-3-(trifluoromethyl)-1H-pyrazol-1-yl]acetyl]piperidine and its enantiomer (Compound 1), 1-[[5-methyl-3-(trifluoromethyl)-1H-pyrazol-1-yl]acetyl]-4-[4-(5-phenyl-3-isoxazolyl)-2-thiazolyl]piperidine (Compound 2), 1-[4-[4-[(5R)-4,5-dihydro-5-methyl-5-phenyl-3-isoxazolyl]-2-thiazolyl]-1-piperidinyl]-2-[5-methyl-3-(trifluoromethyl)-1H-pyrazol-1-yl]ethanone and its enantiomer (Compound 15), 2-[5-methyl-3-(trifluoromethyl)-1H-pyrazol-1-yl]-1-[4-[4-[(3aS,9bR),3a2,5,9b-tetrahydronaphth[2,1-d]isoxazol-3-yl]-2-thiazolyl]-1-piperidinyl]ethanone and its enantiomer (Compound 16), 1-[4-[4-[(5R)-4,5-dihydro-5-phenyl-3-isoxazolyl]-2-thiazolyl]-1-piperidinyl]-2-[5-ethyl-3-(trifluoromethyl)-1H-pyrazol-1-yl]ethanone and its enantiomer (Compound 19), 2-[3,5-bis(trifluoromethyl)-1H-pyrazol-1-yl]-14444-[(5R)-4,5-dihydro-5-phenyl-3-isoxazolyl]-2-thiazolyl]-1-piperidinyl]ethanone and its enantiomer (Compound 22), 1-[4-[4-[(5R)-3',4'-dihydrospiro [isoxazole-5(4H),1',(2'H)-naphthalen]-3-yl]-2-thiazolyl]-1-piperidinyl]-2-[5-methyl-3-(trifluoromethyl)-1H-pyrazol-1-yl]ethanone and its enantiomer (Compound 37), 1-[4-[4-[(5R)-2,3-dihydrospiro [1H-indene-1,5'(4'H)-isoxazol]-3'-yl]-2-thiazolyl]-1-piperidinyl]-2-[5-methyl-3-(trifluoromethyl)-1H-pyrazol-1-yl]ethanone and its enantiomer (Compound 44), 2-[5-chloro-3-(trifluoromethyl)-1H-pyrazol-1-yl]-1-[4-[4-[(5R)-4,5-dihydro-5-phenyl-3-isoxazoly]-2-thiazolyl]-1-piperidinyl]ethanone and its enantiomer (Compound 107), 2-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-1H-isoindole-1,3(2H)-dione and its enantiomer (Compound 129), 2-[5-chloro-3-(trifluoromethyl)-1H-pyrazol-1-yl]-1-[4-[4-[(1R)-2,3-dihydrospiro[1H-indene-1,5'(4'H)-isoxazol]-3'-yl]-2-thiazolyl]-1-piperidinyl]ethanone and its enantiomer (Compound 232), 2-[5-chloro-3-(trifluoromethyl)-1H-pyrazol-1-yl]-1-[4-[4-[(1'R)-3',4'-dihydrospiro[isoxazole-5(4H),1'(2'H)-naphthalen]-3-yl]-2-thiazolyl]-1-piperidinyl]ethanone and its enantiomer (Compound 230), 2-[5-methyl-3-(trifluoromethyl)-1H-pyrazol-1-yl]-1-[4-[4-(3R)-spiro[benzofuran-3(2H),5'(4'H)-isoxazol]-3'-yl-2-thiazolyl]-1-piperidinyl]ethanone and it (Compound 185), 1-[4-[4-[(1R)-2,3-dihydrospiro[1H-indene-1,5'(4'H)-isoxazol]-3'-yl]-2-thizolyl]-1-piperidinyl-2-(3,5-dimethyl-1H-pyrazol-1-yl)ethanone and its enantiomer (Compound 165), 2-[3,5-bis(trifluoromethyl)-1H-pyrazol-1-yl]-1-[4-[4-[(1'R)-3',4'-dihydrospiro[isoxazole-5(4H),1'(2'H)-naphthalen]-3-yl]-2-thiazolyl]-1-piperidinyl]ethanone and its enantiomer (Compound 229), 2-[3,5-bis(trifluoromethyl)-1H-pyrazol-1-yl]-1-[4-[4-[(1R)-2,3-dihydrospiro[1H-indene-1,5'(4'H)-isoxazol]-3'-yl]-2-thiazolyl]-1-piperidinyl]ethanone and its enantiomer (Compound 231), 1-[4-[4-[(5R)-5-(2,6-dichlorophenyl)-4,5-dihydro-3-isoxazolyl]-2-thiazolyl]-1-piperidinyl]-2-[5-methyl-3-(trifluoromethyl)-1H-pyrazol-1-yl]ethanone and its enantiomer (Compound 135), 1-[4-[4-[(5R)-4,5-dihydro-5-(2-fluorophenyl)-3-isoxazolyl]-2-thiazolyl]-1-piperidinyl]-2-[5-methyl-3-(trifluoromethyl)-1H-pyrazol-1-yl]ethanone and its enantiomer (Compound 79), 1-[4-[4-[(5R)-4,5-dihydro-5-(2-methylphenyl)-3-isoxazolyl]-2-thiazolyl]-1-piperidinyl]-2-[5-methyl-3-(trifluoromethyl)-1H-pyrazol-1-yl]ethanone and its enantiomer (Compound 161), 1-[4-[4-[(5R)-5-(2,6-dimethylphenyl)-4,5-dihydro-3-isoxazolyl]-2-thiazolyl]-1-piperidinyl]-2-[5-methyl-3-(trifluoromethyl)-1H-pyrazol-1-yl]ethanone and its enantiomer (Compound 178), 1-[4-[4-[(5R)-4,5-dihydro-5-(2,4,6-trimethylphenyl)-3-isoxazolyl]-2-thiazolyl]-1-piperidinyl]-2-[5-methyl-3-(trifluoromethyl)-1H-pyrazol-1-yl]ethanone and its enantiomer (Compound 179), 1-[4-[4-[(1'R)-3',4'-dihydrospiro[isoxazole-5(4H),1'(2'H)-naphthalen]-3-yl]-2-thiazolyl]-1-piperidinyl]-2-(3,5-dimethyl-1H-pyrazol-1-yl)ethanone and its enantiomer (Compound 164), 1-[4-[4-[(5R)-4,5-dihydro-5-(2,4,6-trimethoxyphenyl)-3-isoxazolyl]-2-thiazolyl]-1-piperidinyl]-2-[5-methyl-3-(trifluoromethyl)-1H-pyrazol-1-yl]ethanone and its enantiomer (Compound 155), 3-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-2(3H)-benzoxazolone and its enantiomer (Compound 225), 1-[4-[4-[(5R)-5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone and its enantiomer (Compound 214), 2-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]benzonitrile and its enantiomer (Compound 220), 2-[5-chloro-3-(trifluoromethyl)-1H-pyrazol-1-yl]-1-[4-[4-[(5R)-4,5-dihydro-5-methyl-5-phenyl-3-isoxazolyl]-2-thiazolyl]-1-piperidinyl]ethanone and its enantiomer (Compound 261), 2-[3,5-bis(trifluoromethyl)-1H-pyrazol-1-yl]-1-[4-[4-[(5R)-4,5-dihydro-5-methyl-5-phenyl-3-isoxazolyl]-2-thiazolyl]-1-piperidinyl]ethanone and its enantiomer (Compound 260), 1-[4-[4-[(5R)-5-(2-chlorophenyl)-4,5-dihydro-3-isoxazolyl]-2-thiazolyl]-1-piperidinyl]-2-[5-methyl-3-(trifluoromethyl)-1H-pyrazol-1-yl]ethanone and its enantiomer (Compound 8), 1-[4-[4-[(5R)-4,5-dihydro-5-phenyl-3-isoxazolyl]-2-thiazolyl]-1-piperidinyl]-2-[3-methyl-5-(trifluoromethyl)-1H-pyrazol-1-yl]ethanone and its enantiomer (Compound 128), 1-[4-[4-[(4S)-2,3-dihydrospiro[4H-1-benzopyran-4,5'(4'H)-isoxazol]-3'-yl)-2-thiazolyl]-1-piperidinyl]-2-[5-methyl-3-(trifluoromethyl)-1H-pyrazol-1-yl]ethanone and its enantiomer (Compound 137), (5R)-4,5-dihydro-3-[2-[1-[2-[5-methyl-3-(trifluoromethyl)-1H-pyrazol-1-yl]acetyl]-4-piperidinyl]-4-thiazolyl]-5-phenyl-5-isoxazolecarbonitrile and its enantiomer (Compound 265), 1-[4-[4-[(5R)-4,5-dihydro-5-phenyl-3-isoxazolyl]-2-thiazolyl]-1-piperidinyl]-2-[5-methyl-3-(trifluoromethyl)-1H-pyrazol-1-yl]ethanone (Compound 3) and its enantiomer, 1-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-1,3-dihydro-3-methyl-2H-benzimidazol-2-one and its enantiomer (Compound 275), N-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-N-phenylacetamide and its enantiomer (Compound 285), 4-[4-[(5R)-4,5-dihydro-5-phenyl-3-isoxazolyl]-2-thiazolyl]-N-(2,5-dimethylphenyl)-1-piperidinecarboxamide and its enantiomer (Compound 292), 3-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-2(3H)-benzothiazolone and its enantiomer (Compound 297), 1-acetyl-3-[(5R)-4,5-dihydro-3-[2-[142-[5-methyl-3-(trifluoromethyl)-1H-pyrazol-1-yl]acetyl]-4-piperidinyl]-4-thiazolyl]-5-isoxazolyl]-1,3-dihydro-2H-benzimidazol-2-one and its enantiomer (Compound 298), 4-[4-[(5R)-4,5-dihydro-5-phenyl-3-isoxazolyl]-2-thia-zolyl]-N-[5-methyl-3-(trifluoromethyl)-1H-pyra-zolyl-1-yl]-1-piperidinecarboxamide and its enantiomer (Compound 300), and 1-[4-[4-[(5R)-5-(2-bromophenyl)-4,5-dihydro-3-isox-azolyl]-2-thiazolyl]-1-piperidinyl]-2-[5-methyl-3-(trifluoromethyl)-1H-pyrazol-1-yl]ethanone and its enantiomer (Compound 189).

Embodiment A12a. The composition of Embodiment A1 wherein component (a) is selected from the group consisting of:

4-[4-[(5R)-5-(2,6-difluorophenyl)-4,5-dihydro-3-isox-azolyl]-2-thiazolyl]-N-(2,5-dimethylphenyl)-1-piperidinecarboxamide and its enantiomer (Compound 391), 2-(3,5-dimethyl-1H-pyrazol-1-yl)-1-[4-[4-[(5R)-5-(2,6-difluorophenyl)-4,5-dihydro-3-isoxazolyl]-2-thiazolyl]-1-piperidinyl]ethanone and its enantiomer (Compound 342), 2-(2,5-dimethylphenyl)-1-[4-[4-[(5R)-5-(2,6-difluorophenyl)-4,5-dihydro-3-isoxazolyl]-2-thiazolyl]-1-piperidinyl]ethanone and its enantiomer (Compound 425), and 1-[4-[4-[(5R)-4,5-dihydro-5-[2-(trifluoromethyl)phenyl]-3-isoxazolyl]-2-thiazolyl]-1-piperidinyl]-2-[5-methyl-3-(trifluoromethyl)-1H-pyrazol-1-yl]ethanone and its enantiomer (Compound 114).

Embodiment B1. The composition described in the Summary of the Invention (including but not limited to the composition of any one of Embodiments 1 through 105 and A1 through A12a) wherein component (b) includes at least one compound selected from (b1) methyl benzimidazole carbamate fungicides such as benomyl, carbendazim and thiophanate-methyl.

Embodiment B2. The composition described in the Summary of the Invention (including but not limited to the composition of any one of Embodiments 1 through 105 and A1 through A12a) wherein component (b) includes at least one compound selected from (b2) dicarboximide fungicides such as procymidone, iprodione and vinclozolin.

Embodiment B3. The composition described in the Summary of the Invention (including but not limited to the composition of any one of Embodiments 1 through 105 and A1 through A12a) wherein component (b) includes at least one compound selected from (b3) demethylation inhibitor fungicides such as epoxiconazole, fluquinconazole, triadimenol, simeconazole, ipconazole, triforine, cyproconazole, difenconazole, flusilazole, flutriafol, metconazole, myclobutanil, prochloraz, propiconazole, prothioconazole, tebuconazole and tetraconazole.

Embodiment B4. The composition described in the Summary of the Invention (including but not limited to the composition of any one of Embodiments 1 through 105 and A1 through A12a) wherein component (b) includes at least one compound selected from (b4) phenylamide fungicides such as mefenoxam, metalaxyl, metalaxyl-M, benalaxyl, benalaxyl-M, furalaxyl, ofurace and oxadixyl.

Embodiment B5. The composition described in the Summary of the Invention (including but not limited to the composition of any one of Embodiments 1 through 105 and A1 through A12a) wherein component (b) includes at least one compound selected from (b5) amine/morpholine fungicides such as aldimorph, dodemorph, fenpropimorph, tridemorph, trimorphamide, fenpropidin, piperalin and spiroxamine.

Embodiment B6. The composition described in the Summary of the Invention (including but not limited to the composition of any one of Embodiments 1 through 105 and A1 through A12a) wherein component (b) includes at least one compound selected from (b6) phospholipid biosynthesis inhibitor fungicides such as edifenphos and isoprothiolane.

Embodiment B7. The composition described in the Summary of the Invention (including but not limited to the composition of any one of Embodiments 1 through 105 and A1 through A12a) wherein component (b) includes at least one compound selected from (b7) carboxamide fungicides such as boscalid, penthiopyrad, bixafen, carboxin and oxycarboxin.

Embodiment B8. The composition described in the Summary of the Invention (including but not limited to the composition of any one of Embodiments 1 through 105 and A1 through A12a) wherein component (b) includes at least one compound selected from (b8) hydroxy(2-amino-)pyrimidine fungicides such as ethirimol.

Embodiment B9. The composition described in the Summary of the Invention (including but not limited to the composition of any one of Embodiments 1 through 105 and A1 through A12a) wherein component (b) includes at least one compound selected from (b9) anilinopyrimidine fungicides such as cyprodinil.

Embodiment B10. The composition described in the Summary of the Invention (including but not limited to the composition of any one of Embodiments 1 through 105 and A1 through A12a) wherein component (b) includes at least one compound selected from (b10) N-phenyl carbamate fungicides such as diethofencarb.

Embodiment B11. The composition described in the Summary of the Invention (including but not limited to the composition of any one of Embodiments 1 through 105 and A1 through A12a) wherein component (b) includes at least one compound selected from (1)11) quinone outside inhibitor fungicides such as azoxystrobin, pyraclostrobin, kresoxim-methyl, trifloxystrobin, picoxystrobin, pyribencarb, famoxadone, fenamidone, discostrobin, enestrobin, dimoxystrobin, metominostrobin, orysastrobin and fluoxastrobin.

Embodiment B12. The composition described in the Summary of the Invention (including but not limited to the composition of any one of Embodiments 1 through 105 and A1 through A12a) wherein component (b) includes at least one compound selected from (b12) phenylpyrrole fungicides compound such as fenpiclonil and fludioxonil.

Embodiment B13. The composition described in the Summary of the Invention (including but not limited to the composition of any one of Embodiments 1 through 105 and A1 through A12a) wherein component (b) includes at least one compound selected from (b13) quinoline fungicides such as quinoxyfen.

Embodiment B14. The composition described in the Summary of the Invention (including but not limited to the composition of any one of Embodiments 1 through 105 and A1 through A12a) wherein component (b) includes at least one compound selected from (b14) lipid peroxidation inhibitor fungicides such as chloroneb.

Embodiment B15. The composition described in the Summary of the Invention (including but not limited to the composition of any one of Embodiments 1 through 105 and A1 through A12a) wherein component (b) includes at least one compound selected from (b15) melanin biosynthesis inhibitors-reductase fungicides such as pyroquilon and tricyclazole.

Embodiment B16. The composition described in the Summary of the Invention (including but not limited to the composition of any one of Embodiments 1 through 105 and A1 through A12a) wherein component (b) includes at least one compound selected from (b16) melanin biosynthesis inhibitors-dehydratase fungicides such as carpropamid.

Embodiment B17. The composition described in the Summary of the Invention (including but not limited to the composition of any one of Embodiments 1 through 105 and A1 through A12a) wherein component (b) includes at least one compound selected from (b17) hydroxyanilide fungicides such as fenhexamid.

Embodiment B18. The composition described in the Summary of the Invention (including but not limited to the composition of any one of Embodiments 1 through 105 and A1 through A12a) wherein component (b) includes at least one compound selected from (b18) squalene-epoxidase inhibitor fungicides such as pyributicarb.

Embodiment B19. The composition described in the Summary of the Invention (including but not limited to the composition of any one of Embodiments 1 through 105 and A1 through A12a) wherein component (b) includes at least one compound selected from (b19) polyoxin fungicides such as polyoxin.

Embodiment B20. The composition described in the Summary of the Invention (including but not limited to the composition of any one of Embodiments 1 through 105 and A1 through A12a) wherein component (b) includes at least one compound selected from (b20) phenylurea fungicides such as pencycuron.

Embodiment B21. The composition described in the Summary of the Invention (including but not limited to the composition of any one of Embodiments 1 through 105 and A1 through A12a) wherein component (b) includes at least one compound selected from (b21) quinone inside inhibitor fungicides such as cyazofamid and amisulbrom.

Embodiment B22. The composition described in the Summary of the Invention (including but not limited to the composition of any one of Embodiments 1 through 105 and A1 through A12a) wherein component (b) includes at least one compound selected from (b22) benzamide fungicides such as zoxamide.

Embodiment B23. The composition described in the Summary of the Invention (including but not limited to the composition of any one of Embodiments 1 through 105 and A1 through A12a) wherein component (b) includes at least one compound selected from (b23) enopyranuronic acid antibiotic fungicides such as blasticidin-S.

Embodiment B24. The composition described in the Summary of the Invention (including but not limited to the composition of any one of Embodiments 1 through 105 and A1 through A12a) wherein component (b) includes at least one compound selected from (b24) hexopyranosyl antibiotic fungicides such as kasugamycin.

Embodiment B25. The composition described in the Summary of the Invention (including but not limited to the composition of any one of Embodiments 1 through 105 and A1 through A12a) wherein component (b) includes at least one compound selected from (b25) glucopyranosyl antibiotic: protein synthesis fungicides such as streptomycin.

Embodiment B26. The composition described in the Summary of the Invention (including but not limited to the composition of any one of Embodiments 1 through 105 and A1 through A12a) wherein component (b) includes at least one compound selected from (b26) glucopyranosyl antibiotic: trehalase and inositol biosynthesis fungicides such as validamycin.

Embodiment B27. The composition described in the Summary of the Invention (including but not limited to the composition of any one of Embodiments 1 through 105 and A1 through A12a) wherein component (b) includes at least one compound selected from (b27) cyanoacetylamideoxime fungicides such as cymoxanil.

Embodiment B28. The composition described in the Summary of the Invention (including but not limited to the composition of any one of Embodiments 1 through 105 and A1 through A12a) wherein component (b) includes at least one compound selected from (b28) carbamate fungicides such as propamacarb, prothiocarb and iodocarb.

Embodiment B29. The composition described in the Summary of the Invention (including but not limited to the composition of any one of Embodiments 1 through 105 and A1 through A12a) wherein component (b) includes at least one compound selected from (b29) oxidative phosphorylation uncoupling fungicides such as fluazinam, binapacryl, ferimzone, meptyldinocap and dinocap.

Embodiment B30. The composition described in the Summary of the Invention (including but not limited to the composition of any one of Embodiments 1 through 105 and A1 through A12a) wherein component (b) includes at least one compound selected from (b30) organo tin fungicides such as fentin acetate.

Embodiment B31. The composition described in the Summary of the Invention (including but not limited to the composition of any one of Embodiments 1 through 105 and A1 through A12a) wherein component (b) includes at least one compound selected from (b31) carboxylic acid fungicides such as oxolinic acid.

Embodiment B32. The composition described in the Summary of the Invention (including but not limited to the composition of any one of Embodiments 1 through 105 and A1 through A12a) wherein component (b) includes at least one compound selected from (b32) heteroaromatic fungicides such as hymexazole.

Embodiment B33. The composition described in the Summary of the Invention (including but not limited to the composition of any one of Embodiments 1 through 105 and A1 through A12a) wherein component (b) includes at least one compound selected from (b33) phosphonate fungicides such as phosphorous acid and its various salts, including fosetyl-aluminum.

Embodiment B34. The composition described in the Summary of the Invention (including but not limited to the composition of any one of Embodiments 1 through 105 and A1 through A12a) wherein component (b) includes at least one compound selected from (b34) phthalamic acid fungicides such as teclofthalam.

Embodiment B35. The composition described in the Summary of the Invention (including but not limited to the composition of any one of Embodiments 1 through 105 and A1 through A12a) wherein component (b) includes at least one compound selected from (b35) benzotriazine fungicides such as triazoxide.

Embodiment B36. The composition described in the Summary of the Invention (including but not limited to the composition of any one of Embodiments 1 through 105 and A1 through A12a) wherein component (b) includes at least one compound selected from (b36) benzenesulfonamide fungicides such as flusulfamide.

Embodiment B37. The composition described in the Summary of the Invention (including but not limited to the composition of any one of Embodiments 1 through 105 and A1 through A12a) wherein component (b) includes at least one compound selected from (b37) pyridazinone fungicides such as diclomezine.

Embodiment B38. The composition described in the Summary of the Invention (including but not limited to the composition of any one of Embodiments 1 through 105 and A1 through A12a) wherein component (b) includes at least one compound selected from (b38) thiophene-carboxamide fungicides such as silthiofam.

Embodiment B39. The composition described in the Summary of the Invention (including but not limited to the composition of any one of Embodiments 1 through 105 and A1 through A12a) wherein component (b) includes at least one compound selected from (b39) pyrimidinamide fungicides such as diflumetorim.

Embodiment B40. The composition described in the Summary of the Invention (including but not limited to the composition of any one of Embodiments 1 through 105 and A1 through A12a) wherein component (b) includes at least one compound selected from (b40) carboxylic acid amide fungicides such as dimethomorph, benthiavalicarb, benthiavalicarb-isopropyl, iprovalicarb, valiphenal, mandipropamid and flumorph.

Embodiment B41. The composition described in the Summary of the Invention (including but not limited to the composition of any one of Embodiments 1 through 105 and A1 through A12a) wherein component (b) includes at least one compound selected from (b41) tetracycline antibiotic fungicides such as oxytetracycline.

Embodiment B42. The composition described in the Summary of the Invention (including but not limited to the composition of any one of Embodiments 1 through 105 and A1 through A12a) wherein component (b) includes at least one compound selected from (b42) thiocarbamate fungicides such as methasulfocarb.

Embodiment B43. The composition described in the Summary of the Invention (including but not limited to the composition of any one of Embodiments 1 through 105 and A1 through A12a) wherein component (b) includes at least one compound selected from (b43) benzamide fungicides such as fluopicolide and fluopyram.

Embodiment B44. The composition described in the Summary of the Invention (including but not limited to the composition of any one of Embodiments 1 through 105 and A1 through A12a) wherein component (b) includes at least one compound selected from (b44) host plant defense induction fungicides such as acibenzolar-S-methyl.

Embodiment B45. The composition described in the Summary of the Invention (including but not limited to the composition of any one of Embodiments 1 through 105 and A1 through A12a) wherein component (b) includes at least one compound selected from (b45) multi-site contact fungicides such as copper oxychloride, copper sulfate, copper hydroxide, Bordeaux composition (tribasic copper sulfide), elemental sulfur, mancozeb, metiram, propineb, ferbam, maneb, thiram, zineb, ziram, folpet, captan, captafol and chlorothalonil.

Embodiment B46. The composition described in the Summary of the Invention (including but not limited to the composition of any one of Embodiments 1 through 105 and A1 through A12a) wherein component (b) includes at least one compound selected from (b46) fungicides other than fungicides of component (a) and components (b1) through (b45) such as ethaboxam, cyflufenamid, proquinazid, metrafenone, 5-chloro-6-(2,4,6-trifluorophenyl)-7-(4-methylpiperidin-1-yl)[1,2,4]triazolo[1,5-a]pyrimidine (BAS600), 2-butoxy-6-iodo-3-propyl-4H-1-benzopyran-4-one, 3-[5-(4-chlorophenyl)-2,3-dimethyl-3-isoxazolidinyl]pyridine (SYP-Z048), 4-fluorophenyl N-[1-[[[1-(4-cyanophenyl)ethyl]sulfonyl]methyl]propyl]carbamate (XR-539), N-[[(cyclopropylmethoxy)amino][6-(difluoromethoxy)-2,3-difluorophenyl]methylene]benzeneacetamide, N'-[4-[4-chloro-3-(trifluoromethyl)phenoxy]-2,5-dimethylphenyl]-N-ethyl-N-methylmethanimidamide, 2-[[2-fluoro-5-(trifluoromethyl)phenyl]thio]-2-[3-(2-methoxyphenyl)-2-thiazolidinylidene]acetonitrile (OK-5203) and N-(4-chloro-2-nitrophenyl)-N-ethyl-4-methylbenzenesulfonamide (TF-991).

Of note is the composition of any one of the embodiments described herein, including Embodiments 1 through 105, A1 through A11, and B1 through B46, wherein reference to Formula 1 includes salts thereof but not N-oxides thereof therefore the phrase "a compound of Formula 1" can be replaced by the phrase "a compound of Formula 1 or a salt thereof".

Of note is the composition of any one of the embodiments described herein, including Embodiments 1 through 105 and B1 through B46, wherein reference to Formula 1 includes salts thereof but not N-oxides thereof therefore the phrase "a compound of Formula 1" can be replaced by the phrase "a compound of Formula 1 or salt thereof."

Embodiments of the present invention also include:

Embodiment C1. A compound of Formula 1A wherein each $R^{4a}$ is independently halogen, cyano, $C_1$-$C_3$ alkyl, $C_1$-$C_3$ haloalkyl, $C_1$-$C_2$ alkoxy or $C_1$-$C_2$ haloalkoxy.

Embodiment C2. A compound of Formula 1A wherein $R^1$ is U-1, k is 2 and one $R^{4a}$ is connected to the 3-position and the other $R^{4a}$ is connected to the 5-position of U-1.

Embodiment C3. A compound of Formula 1A wherein $R^1$ is U-20, k is 2 and one $R^{4a}$ is connected to the 3-position and the other $R^{4a}$ is connected to the 5-position of U-20.

Embodiment C4. A compound of Formula 1A wherein $R^1$ is U-50, k is 2 and one $R^{4a}$ is connected to the 2-position and the other $R^{4a}$ is connected to the 5-position of U-50.

Specific embodiments also include compounds of Formula 1A selected from the group consisting of:

1-[2-(3,5-dichloro-1H-1,2,4-triazol-1-yl)acetyl]-4-piperidinecarbonitrile,

1-[2-(3,5-dibromo-1H-1,2,4-triazol-1-yl)acetyl]-4-piperidinecarbonitrile,

1-[2-(3,5-dichloro-1H-1,2,4-triazol-1-yl)acetyl]-4-piperidinecarbothioamide,

1-[2-(3,5-dibromo-1H-1,2,4-triazol-1yl)acetyl]-4-piperidinecarbothioamide, 4-cyano-N-(3,5-dimethyl-1H-pyrazol-1-yl)-1-piperidinecarboxamide, 4-cyano-N-[5-methyl-3-(trifluoromethyl)-1H-pyrazol-1-yl]-1-piperidinecarboxamide, 4-cyano-N-(2,5-dimethylphenyl)-1-piperidinecarboxamide, 4-cyano-N-(5-chloro-2-methylphenyl)-1-piperidinecarboxamide, 4-cyano-N-(2-chloro-5-methylphenyl)-1-piperidinecarboxamide, 4-thiocarbamoyl-N-(3,5-dimethyl-1H-pyrazol-1-yl)-1-piperidinecarboxamide, 4-thiocarbamoyl-N-[5-methyl-3-(trifluoromethyl)-1H-pyrazol-1-yl]-1-piperidinecarboxamide,
4-thiocarbamoyl-N-(2,5-dimethylphenyl)-1-piperidinecarboxamide,
4-thiocarbamoyl-N-(5-chloro-2-methylphenyl)-1-piperidinecarboxamide,
4-thiocarbamoyl-N-(2-chloro-5-methylphenyl)-1-piperidinecarboxamide,
1-[2-(2,5-dimethylphenyl)acetyl]-4-piperidinecarbonitrile,
1-[2-(2,5-dichlorophenyl)acetyl]-4-piperidinecarbonitrile,
1-[2-(5-chloro-2-methylphenyl)acetyl]-4-piperidinecarbonitrile,
1-[2-(2-chloro-5-methyl phenyl)acetyl]-4-piperidinecarbonitrile,
1-[2-(2,5-dimethylphenyl)acetyl]-4-piperidinecarbothioamide,
1-[2-(2,5-dichlorophenyl)acetyl]-4-piperidinecarbothioamide,
1-[2-(5-chloro-2-methylphenyl)acetyl]-4-piperidinecarbothioamide, and
1-[2-(2-chloro-5-methyl phenyl)acetyl]-4-piperidinecarbothioamide.

Embodiments of the present invention include Embodiments 1, 1d through 1f, 3 through 84 and 86 through 105 where reference to the composition described in the Summary of the Invention wherein the phrase "component (a) is a compound of Formula 1" is replaced with the phrase "a compound of Formula 1C" (including all geometric and stereoisomers), N-oxides and salts thereof. In these embodiments the definitions of substituents are as specified in the Summary of the Invention for Formula 1C unless further defined in the Embodiments 1d through 1f, Embodiments 3 through 84 and Embodiments 86 through 105.

Of particular note is the composition described in the Summary of the Invention of any one of Embodiments 1, 2 through 105, A1 through A12a and B1 through B46 wherein component (a) is a compound or compounds of Formula 1 as defined in the Summary of the Inventions wherein $R^{15}$ is H, halogen, cyano, hydroxy, —CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_4$ alkoxyalkyl, $C_2$-$C_4$ alkylthioalkyl, $C_2$-$C_4$ alkylsulfinylalkyl, $C_2$-$C_4$ alkylsulfonylalkyl, $C_3$-$C_5$ alkoxycarbonylalkyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl, $C_3$-$C_5$ dialkylaminocarbonyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl or $C_1$-$C_4$ haloalkylsulfonyl.

Of further note is the composition described in the Summary of the Invention of any one of Embodiments 1, 2 through 105, A1 through A12a and B1 through B46 wherein component (a) is a compound or compounds of Formula 1 as defined in the Summary of the Inventions wherein $R^{15}$ is —SH, amino, $C_1$-$C_6$ hydroxyalkyl, $C_2$-$C_4$ alkenyloxy, $C_2$-$C_4$ alkynyloxy, $C_2$-$C_4$ haloalkenyloxy, $C_2$-$C_4$ haloalkynyloxy, $C_2$-$C_5$ alkylcarbonyloxy, $C_2$-$C_5$ alkoxycarbonyloxy, $C_2$-$C_5$ haloalkylcarbonyloxy, $C_2$-$C_5$ haloalkoxycarbonyloxy, $C_2$-$C_5$ alkylaminocarbonyloxy, $C_3$-$C_6$ dialkylaminocarbonyloxy, $C_2$-$C_5$ haloalkylaminocarbonyloxy, $C_3$-$C_6$ halodialkylaminocarbonyloxy, $C_2$-$C_5$ alkoxyalkoxy, $C_2$-$C_5$ haloalkoxyalkoxy, $C_1$-$C_4$ alkylsulfonyloxy, $C_1$-$C_4$ haloalkylsulfonyloxy, $C_3$-$C_{10}$ trialkylsilyloxy, $C_2$-$C_4$ alkenylthio, $C_2$-$C_4$ haloalkenylthio, $C_2$-$C_4$ haloalkynylthio, $C_2$-$C_5$ alkylcarbonylthio, $C_2$-$C_5$ alkoxycarbonylthio, $C_2$-$C_5$ haloalkylcarbonylthio, $C_2$-$C_5$ haloalkoxycarbonylthio, $C_2$-$C_5$ alkylaminocarbonylthio, $C_3$-$C_6$ dialkylaminocarbonylthio, $C_2$-$C_5$ haloalkylaminocarbonylthio, $C_3$-$C_6$ halodialkylaminocarbonylthio, $C_2$-$C_5$ alkoxyalkylthio, $C_2$-$C_5$ haloalkoxyalkylthio, $C_1$-$C_4$ alkylsulfonylthio, $C_1$-$C_4$ haloalkylsulfonylthio, $C_3$-$C_{10}$ trialkylsilylthio, $C_1$-$C_4$ alkylamino, $C_2$-$C_4$ alkenylamino, $C_2$-$C_4$ alkynylamino, $C_2$-$C_4$ dialkylamino, $C_1$-$C_4$ haloalkylamino, $C_2$-$C_4$ haloalkenylamino, $C_2$-$C_4$ haloalkynylamino, $C_2$-$C_4$ halodialkylamino, $C_2$-$C_5$ alkylcarbonylamino, $C_2$-$C_5$ haloalkylcarbonylamino, $C_2$-$C_5$ alkoxycarbonylamino, $C_2$-$C_5$ haloalkoxycarbonylamino, $C_2$-$C_5$ alkylaminocarbonylamino, $C_3$-$C_6$ dialkylaminocarbonylamino, $C_2$-$C_5$ haloalkylaminocarbonylamino, $C_3$-$C_6$ halodialkylaminocarbonylamino, $C_2$-$C_5$ alkoxyalkylamino, $C_2$-$C_5$ haloalkoxyalkylamino, $C_1$-$C_4$ alkylsulfonylamino or $C_1$-$C_4$ haloalkylsulfonylamino.

Also of note is a compound of Formula 1A (including all geometric and stereoisomers), an N-oxide or a salt thereof, as described in the Summary of the Invention or any one of Embodiments C1 through C4 wherein A is $CH_2$ or NH.

Also noteworthy as embodiments are fungicidal compositions of the present invention comprising a fungicidally effective amount of a composition of Embodiments 1 to 105, A1 to A12a, and B1 to B46 and at least one additional component selected from the group consisting of surfactants, solid diluents and liquid diluents. Embodiments of the invention further include methods for controlling plant diseases caused by fungal plant pathogens comprising applying to the plant or portion thereof, or to the plant seed or seedling, a fungicidally effective amount of a composition of Embodiments 1 to 105, A1 to A12a, and B1 to B46 (e.g., as a composition described herein). The preferred methods of use include those involving the above preferred compositions; and the diseases controlled with particular effectiveness include plant diseases caused by Oomycete fungal plant pathogens. Combinations of fungicides used in accordance with this invention can facilitate disease control and retard resistance development.

Compositions include those where component (a) and component (b) are present in a fungicidally effective amount and the weight ratio of component (a) to component (b) is from about 125:1 to 1:125. These compositions are particularly effective for controlling plant diseases caused by Oomycete fungal plant pathogens. Of note are compositions where the weight ratio of component (a) to component (b) is from about 25:1 to 1:25. Of particular note are compositions where the weight ratio of component (a) to component (b) is from about 5:1 to 1:5. Compositions also include those where component (a) and component (b) are present in a fungicidally effective amount and the weight ratio of component (a) to component (b) is outside the range of 125:1 to 1:125; see, for example, Table A1 below, which lists specific combinations of a component (a) compound with component (b) illustrative of the mixtures, compositions and methods of the present invention.

Compounds of Formula 1 can be prepared by one or more of the following methods and variations as described in Schemes 1-20. The definitions of A, G, J, W, X, Q, $Z^1$, $R^1$, $R^2$, $R^{15}$, $R^{16}$ and n in the compounds of Formulae 1-37 below are as defined above in the Summary of the Invention unless otherwise noted. Formulae 1a-1e are various subsets of Formula 1.

As shown in Scheme 1, compounds of Formula 1a (Formula 1 wherein A is $CHR^{15}$) wherein W is O can be prepared by coupling an acid chloride of Formula 2 with an amine of Formula 3 in the presence of an acid scavenger. Typical acid scavengers include amine bases such as triethylamine, N,N-diisopropylethylamine and pyridine. Other scavengers include hydroxides such as sodium and potassium hydroxide and carbonates such as sodium carbonate and potassium carbonate. In certain instances it is useful to use polymer-supported acid scavengers such as polymer-bound N,N-diisopropylethylamine and polymer-bound 4-(dimethylamino)pyridine. Acid salts of the Formula 3 amines can also be used in this reaction, provided that at least 2 equivalents of the acid scavenger is present. Typical acids used to form salts with amines include hydrochloric acid, oxalic acid and trifluoroacetic acid. In a subsequent step, amides of Formula 1a wherein W is O can be converted to thioamides of Formula 1a wherein W is S using a variety of standard thiating reagents such as phosphorus pentasulfide or 2,4-bis(4-methoxyphenyl)-1,3-dithia-2,4-diphosphetane-2,4-disulfide (Lawesson's reagent).

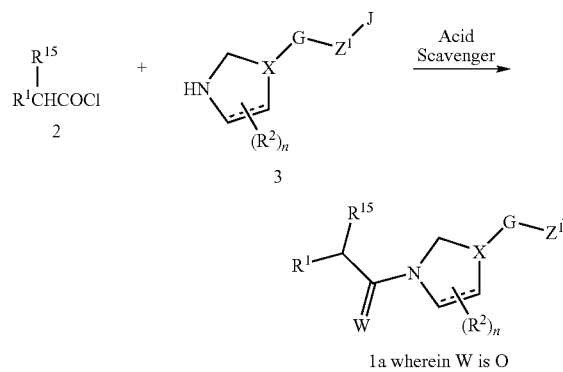

Scheme 1

1a wherein W is O

An alternate procedure for the preparation of compounds of Formula 1a wherein W is O is depicted in Scheme 2 and involves coupling of an acid of Formula 4 with an amine of Formula 3 (or its acid salt) in the presence of a dehydrative coupling reagent such as dicyclohexylcarbodiimide (DCC), 1-(3-dimethylaminopropyl)-3-ethylcarbodiimide hydrochloride (EDC) or O-benzotriazol-1-yl-N,N,N',N'-tetramethyluronium hexafluoro-phosphate (HBTU). Polymer-supported reagents are again useful here, such as polymer-bound cyclohexylcarbodiimide. These reactions are typically run at 0-40° C. in a solvent such as dichloromethane or acetonitrile in the presence of a base such as triethylamine or N,N-diisopropylethylamine. The acids of Formula 4 are known or can be prepared by methods known to one skilled in the art. For example, $R^1CH_2COOH$ where $R^1$ is a heteroaromatic ring linked through nitrogen can be prepared by reacting the corresponding $R^1H$ compound with a haloacetic acid or ester in the presence of base; see, for example, U.S. Pat. No. 4,084,955. $R^1CH_2COOH$ wherein $R^1$ is a phenyl or a heteroaromatic ring linked through carbon can be prepared from the corresponding $R^1CH_2$-halogen compounds by displacement of the halogen with cyanide followed by hydrolysis; see, for example, K. Adachi, *Yuki Gosei Kagaku Kyokaishi* 1969, 27, 875-876; or from $R^1C(=O)CH_3$ by the Willgerodt-Kindler reaction; see, for example, H. R. Darabi et al., *Tetrahedron Letters* 1999, 40, 7549-7552 and M. M. Alam and S. R. Adapa, *Synthetic Communications* 2003, 33, 59-63 and references cited therein; or from $R^1Br$ or $R^1I$ by palladium-catalyzed coupling with tent-butyl acetate or diethyl malonate followed by ester hydrolysis; see, for example, W. A. Moradi and S. L. Buchwald, *J. Am. Chem. Soc.* 2001, 123, 7996-8002 and J. F. Hartwig et al., *J. Am. Chem. Soc.* 2002, 124, 12557-12565.

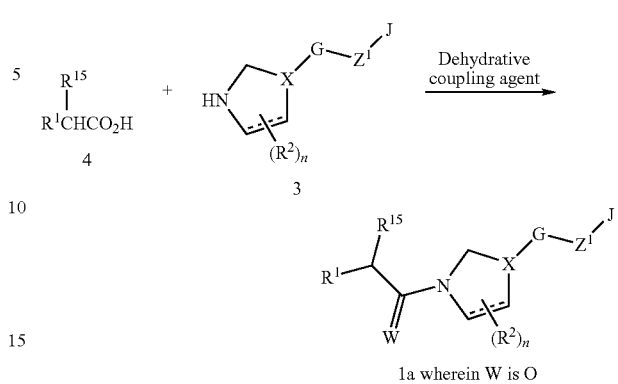

Scheme 2

1a wherein W is O

As the synthetic literature includes many amide-forming methods, the synthetic procedures of Schemes 1 and 2 are simply representative examples of an wide variety of methods useful for the preparation of Formula 1 compounds. One skilled in the art also realizes that acid chlorides of Formula 2 can be prepared from acids of Formula 4 by numerous well-known methods.

Certain compounds of Formula 1b (Formula 1 wherein A is $CHR^{15}$ and W is O) wherein $R^1$ is a 5-membered nitrogen-containing heteroaromatic ring linked through the nitrogen atom can be prepared by reaction of the parent heterocycle of Formula 5 and a haloacetamide of Formula 6 as shown in Scheme 3. The reaction is carried out in the presence of a base such as sodium hydride or potassium carbonate in a solvent such as tetrahydrofuran, N,N-dimethylformamide or acetonitrile at 0 to 80° C. The haloacetamide of Formula 6 can be prepared by the reaction of an amine of Formula 3 with an α-halo carboxylic acid halide or an α-halo carboxylic acid or its anhydride, analogous to the amide-forming reactions described in Schemes 1 and 2, respectively.

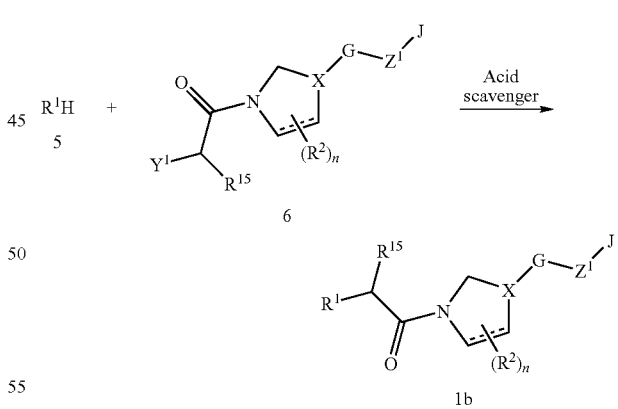

Scheme 3

1b wherein $R^1$ is a 5-membered nitrogen-containing heteroaromatic ring unsubstituted on N; and $Y^1$ is Cl, Br or I.

Compounds of Formula 1c (Formula 1 wherein A is $NR^{16}$), wherein $R^{16}$ is H, $R^1$ is phenyl, naphthalenyl or a 5- or 6-membered heteroaromatic ring and W is O or S, can be prepared by reaction of an amine of Formula 3 with an isocyanate or isothiocyanate, respectively, of Formula 7 as depicted in Scheme 4. This reaction is typically carried out at ambient temperature in an aprotic solvent such as dichloromethane or acetonitrile.

Scheme 4

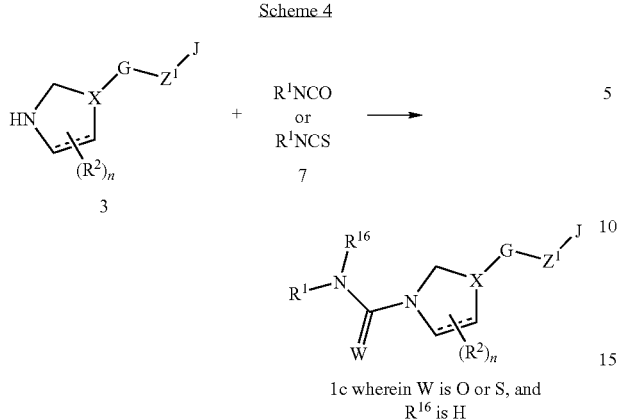

1c wherein W is O or S, and R[16] is H

Compounds of Formula 1c can also be prepared by the reaction of an amine of Formula 8 with a carbamoyl or thiocarbamoyl chloride or imidazole of Formula 9 as shown in Scheme 5. When Y is chlorine, the reaction is typically carried out in the presence of an acid scavenger. Typical acid scavengers include amine bases such as triethylamine, N,N-diisopropylethylamine and pyridine. Other scavengers include hydroxides such as sodium and potassium hydroxide and carbonates such as sodium carbonate and potassium carbonate. The carbamoyl or thiocarbamoyl chlorides of Formula 9 (wherein Y is Cl) can be prepared from amines of Formula 3 by treatment with phosgene or thiophosgene, respectively, or their equivalents, while carbamoyl or thiocarbamoyl imidazoles of Formula 9 (wherein Y is imidazol-1-yl) can be prepared from amines of Formula 3 by treatment with 1,1'-carbonyldiimidazole or 1,1'-thiocarbonyldiimidazole, respectively, according to general methods known to one skilled in the art.

Scheme 5

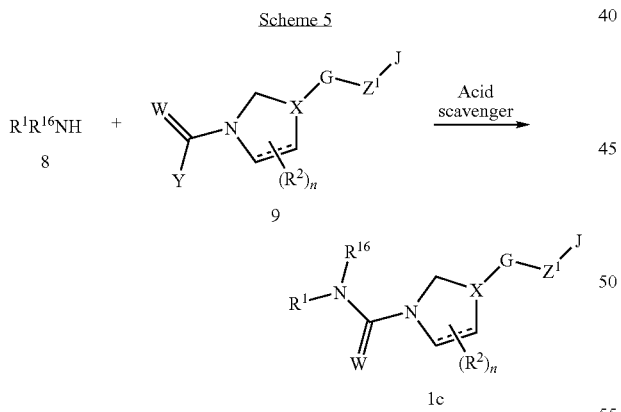

wherein W is O or S; and Y is Cl or imidazol-1-yl.

Certain compounds of Formula 1d (i.e. Formula 1 in which the ring containing X is saturated) can be prepared from compounds of Formula 1e where the ring containing X is unsaturated by catalytic hydrogenation as shown in Scheme 6. Typical conditions involve exposing a compound of Formula 1e to hydrogen gas at a pressure of 70 to 700 kPa, preferably 270 to 350 kPa, in the presence of a metal catalyst such as palladium supported on an inert carrier such as activated carbon, in a weight ratio of 5 to 20% of metal to carrier, suspended in a solvent such as ethanol at ambient temperature. This type of reduction is very well known; see, for example, Catalytic Hydrogenation, L. Cerveny, Ed., Elsevier Science, Amsterdam, 1986. One skilled in the art will recognize that certain other functionalities that may be present in compounds of Formula 1e can also be reduced under catalytic hydrogenation conditions, thus requiring a suitable choice of catalyst and conditions.

Scheme 6

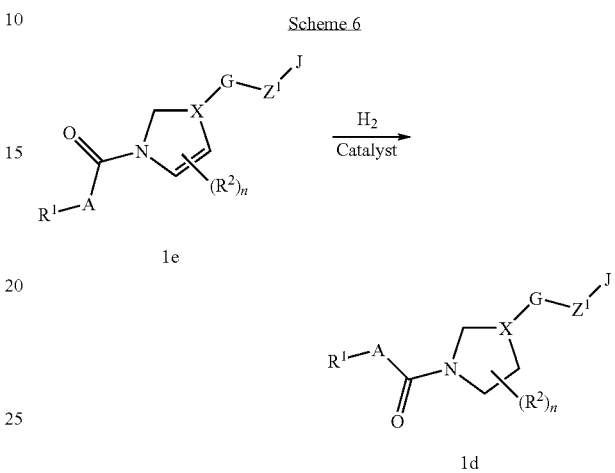

wherein X is $X^1$, $X^2$, $X^5$, $X^8$ or $X^9$.

Certain compounds of Formula 1 wherein X is $X^1$, $X^5$, $X^7$ or $X^9$, and G is linked to the ring containing X via a nitrogen atom, can be prepared by displacement of an appropriate leaving group $Y^2$ on the ring containing the X of Formula 10 with a nitrogen-containing heterocycle of Formula 11 in the presence of a base as depicted in Scheme 7. Suitable bases include sodium hydride or potassium carbonate, and the reaction is carried out in a solvent such as N,N-dimethylformamide or acetonitrile at 0 to 80° C. Suitable leaving groups in the compounds of Formula 10 include bromide, iodide, mesylate ($OS(O)_2CH_3$), triflate ($OS(O)_2CF_3$) and the like, and compounds of Formula 10 can be prepared from the corresponding compounds wherein $Y^2$ is OH, using general methods known in the art.

Scheme 7

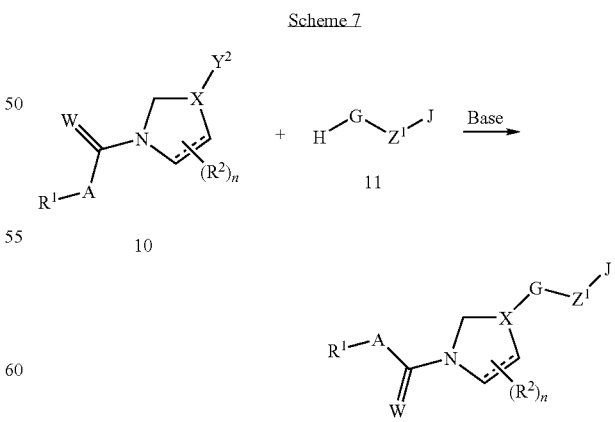

wherein W is O or S; X is $X^1$, $X^5$, $X^7$ or $X^9$; and $Y^2$ is a leaving group such as Br, I, $OS(O)_2Me$ or $OS(O)_2CF_3$.

Compounds of Formula 1 wherein X is $X^2$ or $X^8$ can be prepared by reaction of a compound of Formula 12 with a heterocyclic halide or triflate $(OS(O)_2CF_3)$ of Formula 13 as shown in Scheme 8. The reaction is carried out in the presence of a base such as potassium carbonate in a solvent such as dimethylsulfoxide, N,N-dimethylformamide or acetonitrile at 0 to 80° C. Compounds of Formula 13 wherein $Y^2$ is triflate can be prepared from corresponding compounds wherein $Y^2$ is OH by methods known to one skilled in the art Scheme 8

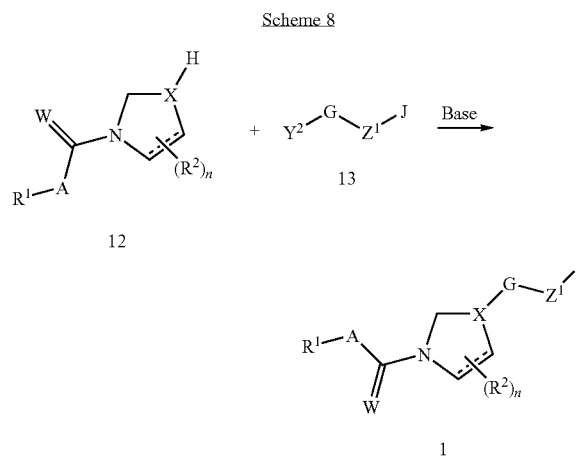

wherein W is O or S; X is $X^2$ or $X^8$; and $Y^2$ is a leaving group such as Br, I $OS(O)_2Me$ or $OS(O)_2CF_3$.

The amine compounds of Formula 3 can be prepared from the protected amine compounds of Formula 14 where $Y^3$ is an amine-protecting group as shown in Scheme 9. A wide array of amine-protecting groups are available (see, for example, T. W. Greene and P. G. M. Wuts, *Protective Groups in Organic Synthesis,* 2nd ed.; Wiley: New York, 1991), and the use and choice of the appropriate protecting groups will be apparent to one skilled in chemical synthesis. The protecting group can be removed and the amine isolated as its acid salt or the free amine by general methods known in the art. One skilled in the art will also recognize that the protected amines of Formula 14 can be prepared by methods analogous to those described in Schemes 6, 7, and 8 above where the group $R^1AC(=W)$ is replaced by $Y^3$ to give useful intermediates of Formula 14 for the preparation of compounds of Formula 1.

Scheme 9

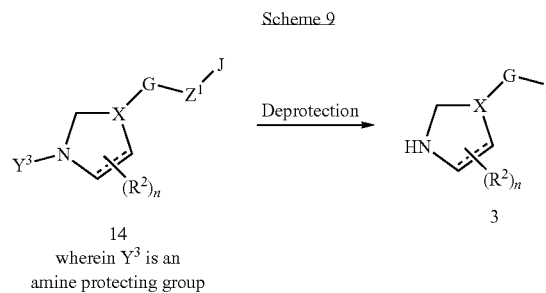

wherein $Y^3$ is an amine protecting group

The compounds of Formula 14 can also be prepared by reaction of a suitably functionalized compound of Formula 15 with a suitably functionalized compound of Formula 16 as shown in Scheme 10. The functional groups $Y^4$ and $Y^5$ are selected from, but not limited to, moieties such as aldehydes, ketones, esters, acids, amides, thioamides, nitriles, amines, alcohols, thiols, hydrazines, oximes, amidines, amideoximes, olefins, acetylenes, halides, alkyl halides, methanesulfonates, trifluoromethanesulfonates, boronic acids, boronates, and the like, which under the appropriate reaction conditions, will allow the construction of the various heterocyclic rings G. As an example, reaction of a compound of Formula 15 where $Y^4$ is a thioamide group with a compound of Formula 16 where $Y^5$ is a bromoacetyl group will give a compound of Formula 14 where G is a thiazole ring. The synthetic literature describes many general methods for forming 5-membered heteroaromatic rings and 5-membered partially saturated heterocyclic rings (e.g., G-1 through G-59); see, for example, *Comprehensive Heterocyclic Chemistry*, Vol. 4-6, A. R. Katritzky and C. W. Rees editors, Pergamon Press, New York, 1984; *Comprehensive Heterocyclic Chemistry II*, Vol. 2-4, A. R. Katritzky, C. W. Rees, and E. F. Scriven editors, Pergamon Press, New York, 1996; and the series, *The Chemistry of Heterocyclic Compounds*, E. C. Taylor, editor, Wiley, New York. The use of intermediates of Formula 15 where X is $X^1$ and $Y^4$ is Br, I, methanesulfonate or trifluoromethanesulfonate to prepare organozinc reagents for use in cross-coupling reactions with aromatic rings has been described; see, for example, S. Bellotte, *Synlett* 1998, 379-380, and M. Nakamura et al., *Synlett* 2005, 1794-1798. One skilled in the art knows how to select the appropriate functional groups to construct the desired heterocyclic rings such as G. Compounds of Formula 15 and 16 are known or can be prepared by one skilled in the art.

Scheme 10

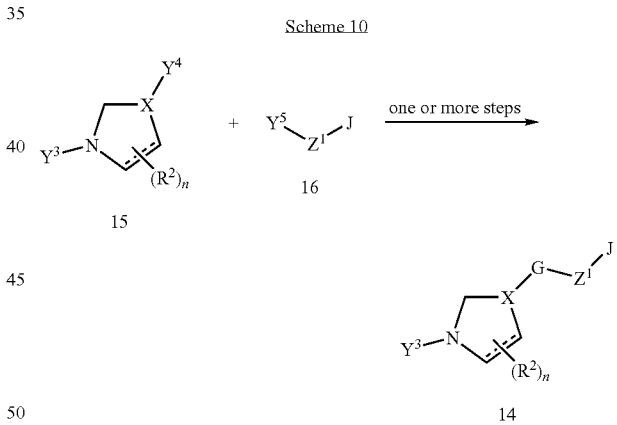

wherein $Y^4$ and $Y^5$ are functional groups suitable for construction of the desired heterocycle G.

Certain compounds of Formula 14 where $Z^1$ is O, S, or $NR^{21}$ can be prepared by displacement of an appropriate leaving group $Y^2$ on G of Formula 17 with a compound of Formula 18 in the presence of a base as depicted in Scheme 11. Suitable bases include sodium hydride or potassium carbonate, and the reaction is carried out in a solvent such as N,N-dimethylformamide or acetonitrile at 0 to 80° C. Suitable leaving groups in the compounds of Formula 17 include bromide, iodide, mesylate $(OS(O)_2CH_3)$, triflate $(OS(O)_2CF_3)$ and the like. Compounds of Formula 17 can be prepared from corresponding compounds wherein $Y^2$ is OH by general methods known in the art. Many of the compounds of Formula 18 are known or can be prepared by general methods known in the art.

Scheme 11

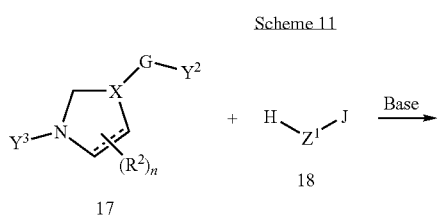

wherein $Y^2$ is a leaving group such as Br, I, $OS(O)_2Me$ or $OS(O)_2CF_3$; and $Z^1$ is O, S or $NR^{21}$.

Certain compounds of Formula 14 where $Z^1$ is O, S, or $NR^{21}$ can also be prepared by displacement of an appropriate leaving group $Y^2$ on J of Formula 20 with a compound of Formula 19 in the presence of a base as depicted in Scheme 12. Suitable bases include sodium hydride or potassium carbonate, and the reaction is carried out in a solvent such as N,N-dimethylformamide or acetonitrile at 0 to 80° C. Suitable leaving groups in the compounds of Formula 20 include bromide, iodide, mesylate ($OS(O)_2CH_3$), triflate ($OS(O)_2CF_3$) and the like. Compounds of Formula 20 can be prepared from corresponding compounds wherein $Y^2$ is OH using general methods known in the art.

Scheme 12

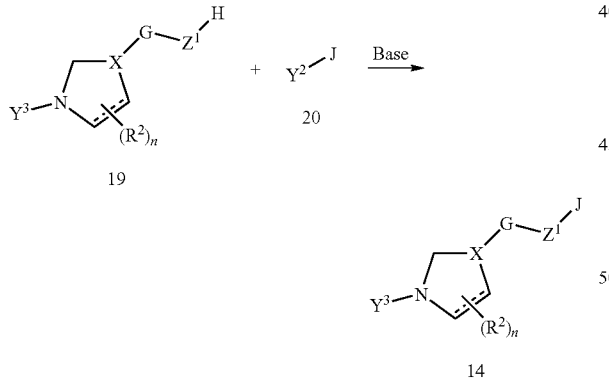

wherein $Y^2$ is a leaving group such as Br, I, $OS(O)_2Me$ or $OS(O)_2CF_3$; and $Z^1$ is O, S or $NR^{21}$.

Compounds of Formula 14 can also be prepared by reaction of a suitably functionalized compound of Formula 21 with a suitably functionalized compound of Formula 22 as shown in Scheme 13. The functional groups $Y^6$ and $Y^7$ are selected from, but not limited to, moieties such as aldehydes, ketones, esters, acids, amides, thioamides, nitriles, amines, alcohols, thiols, hydrazines, oximes, amidines, amide oximes, olefins, acetylenes, halides, alkyl halides, methanesulfonates, trifluoromethanesulfonates, boronic acids, boronates, and the like, which, under the appropriate reaction conditions will allow the construction of the various heterocyclic rings J. As an example, reaction of a compound of Formula 21 where $Y^6$ is a chloro oxime moiety with a compound of Formula 22 where $Y^7$ is a vinyl or acetylene group in the presence of base will give a compound of Formula 14 where J is an isoxazoline or isoxazole, respectively. The synthetic literature includes many general methods for the formation of carbocyclic and heterocyclic rings and ring systems (for example, J-1 through J-82); see, for example, *Comprehensive Heterocyclic Chemistry*, Vol. 4-6, A. R. Katritzky and C. W. Rees editors, Pergamon Press, New York, 1984; *Comprehensive Heterocyclic Chemistry II*, Vol. 2-4, A. R. Katritzky, C. W. Rees, and E. F. Scriven editors, Pergamon Press, New York, 1996; the series, *The Chemistry of Heterocyclic Compounds*, E. C. Taylor, editor, Wiley, New York, and *Rodd's Chemistry of Carbon Compounds*, Vol. 2-4, Elsevier, New York. General procedures for cycloaddition of nitrile oxides with olefins are well documented in the chemical literature. For relevant references see Lee, *Synthesis* 1982, 6, 508-509 and Kanemasa et al., *Tetrahedron* 2000, 56, 1057-1064 as well as references cited within. One skilled in the art knows how to select the appropriate functional groups to construct the desired heterocyclic ring J. Compounds of Formula 22 are known or can be prepared by general methods known in the art.

Scheme 13

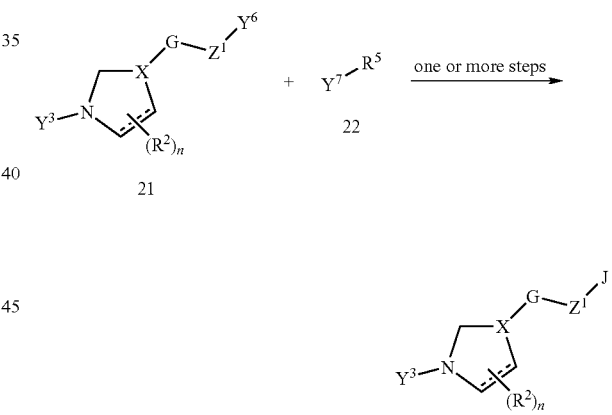

wherein $Y^6$ and $Y^7$ are functional groups suitable for construction of the desired heterocycle J.

An alternate preparation for the compounds of Formula 14 where $Z^1$ is a bond includes the well known Suzuki reaction involving Pd-catalyzed cross-coupling of an iodide or bromide of Formula 23 or 26 with a boronic acid of Formula 24 or 25, respectively, as shown in Scheme 14. Many catalysts are useful for this type of transformation; a typical catalyst is tetrakis(triphenylphosphine)palladium. Solvents such as tetrahydrofuran, acetonitrile, diethyl ether and dioxane are suitable. The Suzuki reaction and related coupling procedures offer many alternatives for creation of the G-J bond. For leading references see for example C. A. Zificsak and D. J. Hlasta, *Tetrahedron* 2004, 60, 8991-9016. For a thorough review of palladium chemistry applicable to the synthesis of G-J bonds see J. J. Li and G. W. Gribble, editors, *Palladium in Heterocyclic Chemistry: A Guide for the Synthetic Chemist*, Elsevier: Oxford, UK, 2000. Many variations of catalyst type, base and reaction conditions are known in the art for this general method.

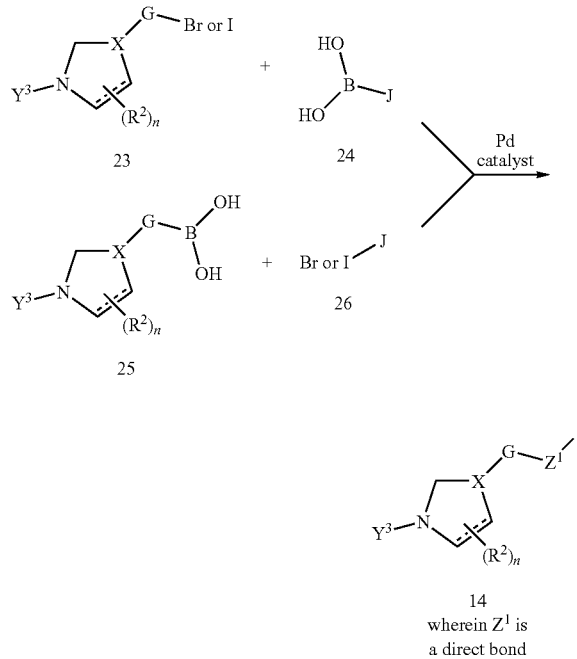

Scheme 14

One skilled in the art will recognize that many compounds of Formula 1 can be prepared directly by methods analogous to those described in Schemes 10 through 14 above where the group $Y^3$ is replaced by $R^1AC(=W)$. Thus, compounds corresponding to Formulae 15, 17, 19, 21, 23 and 25 in which $Y^3$ is replaced by $R^1AC(=W)$ are useful intermediates for the preparation of compounds of Formula 1.

Thioamides of Formula 1Ab are particularly useful intermediates for preparing compounds of Formula 1 wherein X is $X^1$. A thioamide of Formula 1Ab can be prepared by the addition of hydrogen sulfide to the corresponding nitrile of Formula 1Aa as shown in Scheme 15.

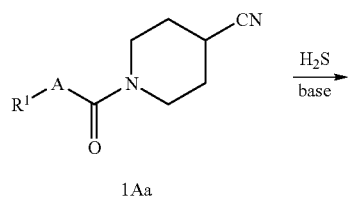

Scheme 15

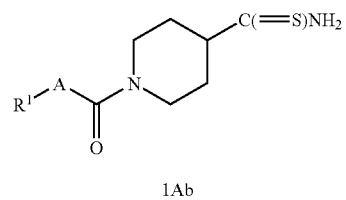

1Ab wherein $R^1$ as defined for Formula 1.

The method of Scheme 15 can be carried out by contacting a compound of Formula 1Aa with hydrogen sulfide in the presence of an amine such as pyridine, diethylamine or diethanolamine. Alternatively, hydrogen sulfide can be used in the form of its bisulfide salt with an alkali metal or ammonia. This type of reaction is well documented in the literature (e.g., A. Jackson et al., EP 696,581 (1996)).

Certain compounds of Formula 1Aa wherein A is NH can be prepared by treating 4-cyanopiperidine with the corresponding isocyanate $R^1NCO$ in a solvent such as dichloromethane, tetrahydrofuran, N,N-dimethylformamide or acetonitrile at 0 to 80° C. Many $R^1NCO$ are known or can be prepared by one skilled in the art.

Certain compounds of Formula 1Aa wherein A is $CH_2$ and $R^1$ is a 5-membered nitrogen-containing heteroaromatic ring linked through a nitrogen atom can be prepared by reaction of the parent heterocycle of Formula 5 and a haloacetamide of Formula 27 as shown in Scheme 16. The reaction is carried out in the presence of a base such as sodium hydride or potassium carbonate in a solvent such as tetrahydrofuran, N,N-dimethylformamide or acetonitrile at 0 to 80° C.

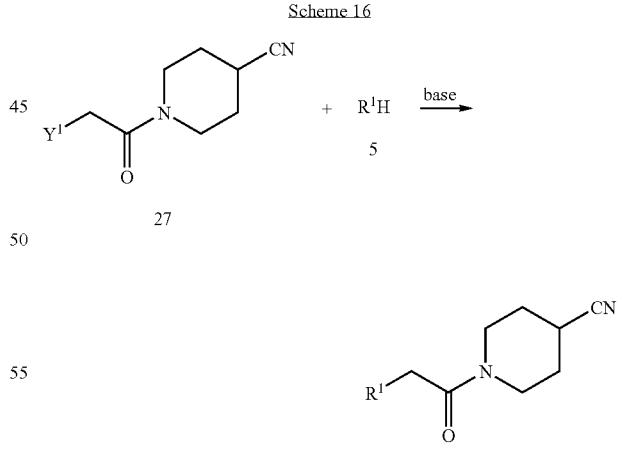

Scheme 16 wherein $R^1$ is a 5-membered nitrogen-containing heteroaromatic ring unsubstituted on N (i.e. a 5-membered heteroaromatic ring comprising a ring member of the formula —(NH)—); and $Y^1$ is Cl, Br or I.

The haloacetamides of Formula 27 can be prepared by the two methods shown in Scheme 17.

Scheme 17

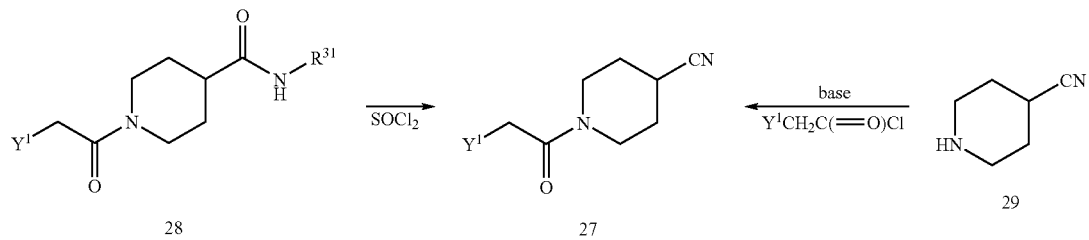

wherein $Y^1$ is Cl, Br, or I; and $R^{31}$ is a tertiary alkyl group such as —C(Me)$_3$.

In one method, 4-cyanopiperidine of Formula 29 is haloacetylated by contact with the appropriate haloacetyl chloride typically in the presence of a base according to standard methods. Preferred conditions involve use of an aqueous solution of an inorganic base such as an alkali metal or alkaline-earth carbonate, bicarbonate, or phosphate, and a non-water-miscible organic solvent such as toluene, ethyl acetate or 1,2-dichloroethane. In the second method depicted in Scheme 17, a 1-(haloacetyl)-N-substituted isonipecotamide derivative of Formula 28, wherein $R^{31}$ is tertiary alkyl such as C(Me)$_3$, is dehydrated using a standard amide dehydrating agent such as thionyl chloride or phosphorus oxychloride in a suitable solvent. A particularly preferred solvent for this transformation is an N,N-dialkylamide such as N,N-dimethylformamide. The reaction is typically carried out by adding 0.9 to 2 equivalents, preferably 1.1 equivalents, of phosphorus oxychloride or thionyl chloride, to a mixture of a compound of Formula 28 and 0.5 to 10 parts by weight of solvent, at a temperature at which the reaction rapidly proceeds during the addition. The addition time for this reaction is typically around 20 to 90 minutes at typical temperatures of around 35 to 55° C.

As shown in Scheme 18, compounds of Formula 28 can be prepared from compounds of Formula 30 by a method analogous to the haloacetylation reaction described for Scheme 17.

Scheme 18

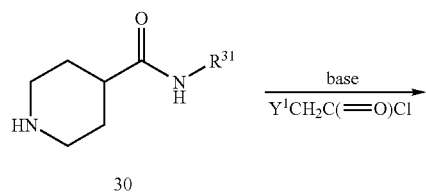

-continued

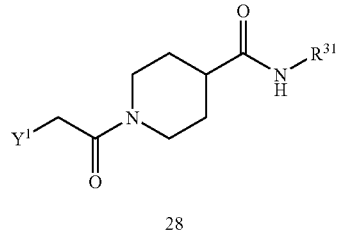

The compounds of Formula 30 are known or can be prepared from 4-cyanopyridine or isonicotinic acid using methods well-known in the art; see, for example, German patent application DE 3,537,762 (1986) for preparation of N-t-butyl pyridinecarboxamides from cyanopyridines and t-butanol and S. F. Nelsen, et al., *J. Org. Chem.*, 1990, 55, 3825 for hydrogenation of N-methylisonicotinamide with a platinum catalyst.

Halomethyl isoxazoline ketones of Formula 35 are particularly useful intermediates for preparing certain chiral compounds of Formula 1 wherein J is, for example, selected from J-29-1 through J-29-12 as depicted in Exhibit A. Halomethyl isoxazoline ketones of Formula 35 can be prepared by the multi-step reaction sequences shown in Scheme 19.

One skilled in the art will recognize that Scheme 19 can also be practiced without the use of a resolving agent, so that a compound of Formula 32 is converted directly to a racemic analog of Formula 31a, which can then be used to prepare racemic analogs of Formulae 34, 35 and certain racemic compounds of Formula 1 (e.g., compounds containing racemic analogs of J-29-1 through J-29-12).

Scheme 19

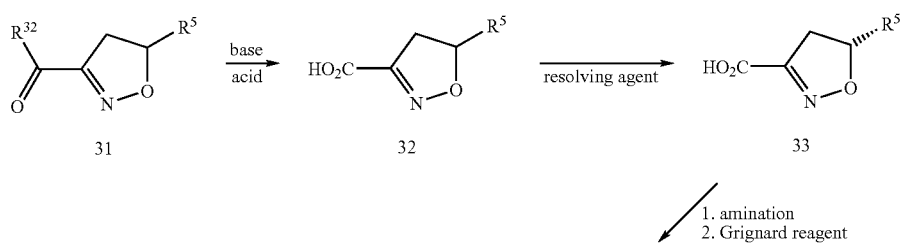

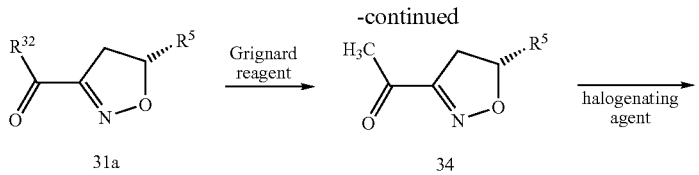

wherein $R^{32}$ is $C_2$-$C_8$ dialkylamino, $C_2$-$C_6$ haloalkylamino, 1-piperidinyl, 1-pyrrolidinyl or 4-morpholinyl; and $R^5$ is as defined above in the Summary of the Invention.

The preparation of racemic carboxylic acids of Formula 32 can be accomplished according to the well-known methods of basic or acidic hydrolysis of the corresponding compounds of Formula 31, preferably using a slight excess of sodium hydroxide in a water-miscible co-solvent such as methanol or tetrahydrofuran at about 25 to 45° C. The product can be isolated by adjusting the pH of the reaction mixture to about 1 to 3 and then filtration or extraction, optionally after removal of the organic solvent by evaporation. The racemic carboxylic acids of Formula 32 can be resolved by classical fractional crystallization of diastereomeric salts of suitable chiral amine bases such as cinchonine, dihydrocinchonine or a mixture thereof. A cinchonine-dihydrocinchonine mixture in about a 85:15 ratio is particularly useful, as it provides, for example, the (R)-configured carboxylic acids of Formula 33, wherein $R^5$ is a substituted phenyl group, as the less soluble salt. Furthermore, these chiral amine bases are readily available on a commercial scale. The halomethyl ketones of Formula 35 can be prepared by first reacting the corresponding amides of Formula 31, either as pure enantiomers (i.e. Formula 31a) or in enantiomerically enriched or racemic mixtures, with one molar equivalent of a methylmagnesium halide (Grignard reagent) in a suitable solvent or solvent mixture such as tetrahydrofuran and toluene at about 0 to 20° C., and the crude ketone products of Formula 34 can be isolated by quenching with aqueous acid, extraction, and concentration. Then the crude ketones of Formula 34 are halogenated with a reagent such as sulfuryl chloride to afford the chloromethyl ketones of Formula 35 wherein $Y^1$ is Cl or molecular bromine to afford the corresponding bromomethyl ketones of Formula 35 wherein $Y^1$ is Br. The halomethyl ketones of Formula 35 can be purified by crystallization from a solvent such as hexanes or methanol, or can be used without further purification in the condensation reaction with thioamides.

The isoxazoline carboxamides of Formula 31 can be prepared by cycloaddition of the corresponding hydroxamoyl chlorides of Formula 36 with olefin derivatives of Formula 37, as shown in Scheme 20.

Scheme 20

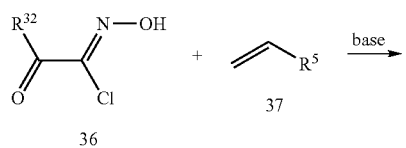

-continued

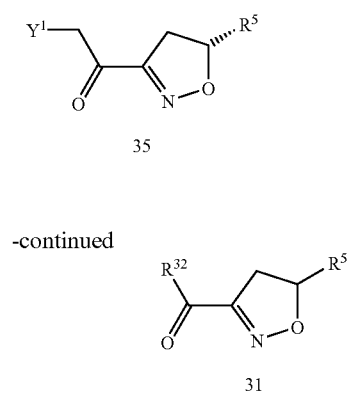

wherein $R^{32}$ is $C_2$-$C_8$ dialkylamino, $C_2$-$C_6$ haloalkylamino, 1-piperidinyl, 1-pyrrolidinyl or 4-morpholinyl; and $R^5$ is as defined above in the Summary of the Invention.

In this method, all three reacting components (the compounds of Formulae 36 and 37, and the base) are contacted so as to minimize hydrolysis or dimerization of the hydroxamoyl chloride of Formula 36. In one typical procedure, the base, which can either be a tertiary amine base such as triethylamine or an inorganic base such as an alkali metal or alkaline-earth carbonate, bicarbonate or phosphate, is mixed with the olefin derivative of Formula 37, and the hydroxamoyl chloride of Formula 36 is added gradually at a temperature at which the cycloaddition proceeds at a relatively rapid rate, typically between 5 and 25° C. Alternatively, the base can be added gradually to the other two components (the compounds of Formulae 36 and 37). This alternative procedure is preferable when the hydroxamoyl chloride of Formula 36 is substantially insoluble in the reaction medium. The solvent in the reaction medium can be water or an inert organic solvent such as toluene, hexane or even the olefin derivative used in excess. The product can be separated from the salt co-product by filtration or washing with water, followed by evaporation of the solvent. The crude product can be purified by crystallization, or the crude product can be used directly in the methods of Scheme 19. Compounds of Formula 31 are useful precursors to the corresponding methyl ketones of Formula 34 and halomethyl ketones of Formula 35, and are also useful for preparing the resolved enantiomers of the compounds of Formulae 34 and 35 by hydrolysis, resolution, methyl ketone synthesis and halogenation, as shown in Scheme 19.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, T. W. Greene and P. G. M. Wuts, *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "m" means multiplet, "q" means quartet, "dd" means doublet of doublet, "br s" means broad singlet, "br d" means broad doublet, "br t" means broad triplet, "br m" means broad multiplet.

EXAMPLE 1

Preparation of 4-[4-[4,5-dihydro-5-phenyl-3-isoxazolyl]-2-thiazolyl]-1-[[5-methyl-3-(trifluoromethyl)-1H-pyrazol-1-yl]acetyl]piperidine (Compound 1)

Step A: Preparation of 1,1-dimethylethyl 4-[4-(4,5-dihydro-5-phenyl-3-isoxazolyl)-2-thiazolyl]-1-piperidinecarboxylate To a suspension of 1,1-dimethylethyl 4-(4-formyl-2-thiazolyl)-1-piperidinecarboxylate (1.0 g, 3.4 mmol) in ethanol (5 mL) was added an aqueous solution of hydroxylamine (50 wt. %, 0.25 mL, 4.0 mmol). The reaction mixture was heated at 60° C. for 1 h, during which time the reaction mixture became homogeneous. The resulting solution was cooled to room temperature and diluted with tetrahydrofuran (10 mL). To the reaction mixture was added styrene (0.57 mL, 5 mmol), followed by portionwise addition of Clorox® aqueous sodium hypochlorite solution (10.5 mL) over 3 h. The reaction mixture was stirred overnight at room temperature, and the resulting solid was filtered, washed with water and diethyl ether, and air dried to give the title compound as a white powder (610 mg). The filtrate was diluted with saturated aqueous sodium bicarbonate solution and extracted with diethyl ether. The extract was dried (MgSO$_4$) and concentrated under reduced pressure to give 850 mg of the title compound as a yellow oil. The oil was diluted with diethyl ether (4 mL) and allowed to stand to give an additional 233 mg of the product as a white solid.

$^1$H NMR (CDCl$_3$): δ 1.47 (s, 9H), 1.7 (m, 2H), 2.1 (m, 2H), 2.85 (m, 2H), 3.2 (m, 1H), 3.45 (m, 1H), 3.84 (m, 1H) 4.2 (br s, 2H), 5.75 (m, 1H), 7.25-7.40 (m, 5H), 7.61 (s, 1H).

Step B: Preparation of 4-[4-[4,5-dihydro-5-phenyl-3-isoxazolyl]-2-thiazolyl]-1-[[5-methyl-3-(trifluoromethyl)-1H-pyrazol-1-yl]acetyl]piperidine To a solution of 1,1-dimethylethyl 4-[4-(4,5-dihydro-5-phenyl-3-isoxazolyl]-2-thiazolyl]-1-piperidinecarboxylate (i.e. the product of Example 1, Step A) (0.815 g, 1.97 mmol) in dichloromethane (50 mL) was added a solution of hydrogen chloride in diethyl ether (2 M, 10 mL, 20 mmol). The reaction mixture was stirred at room temperature for 1 h to give a gummy precipitate. Methanol was added to dissolve the precipitate, and the reaction mixture was stirred for an additional 1 h. The reaction mixture was concentrated under reduced pressure and partitioned between ethyl acetate and saturated aqueous sodium bicarbonate solution, and the organic layer was dried (MgSO$_4$) and concentrated to give the free amine as a clear oil (0.31 g), which solidified on standing. A mixture of the resulting free amine (0.31 g, 1.0 mmol), 5-methyl-3-(trifluoromethyl)-1H-pyrazole-1-acetic acid (0.208 g, 1.0 mmol), 1-[3-(dimethylamino)propyl]-3-ethylcarbodiimide hydrochloride (0.25 g, 1.3 mmol), triethylamine (150 μL, 1.08 mmol) and a catalytic amount of 1-hydroxy-benzotriazole hydrate (~1 mg) in dichloromethane (5 mL) was swirled to form a vortex and held at room temperature for 16 h. The reaction mixture was diluted with dichloromethane (10 mL), and washed with 1 N aqueous hydrochloric acid and saturated aqueous sodium bicarbonate solution. The organic layer was dried (MgSO$_4$) and concentrated under reduced pressure to give 0.47 g of the title product as a white foam.

$^1$H NMR (CDCl$_3$): δ 1.8 (m, 2H), 2.2 (m, 2H), 2.32 (s, 3H), 2.9 (m, 1H), 3.3 (m, 2H), 3.42 (m, 1H), 3.85 (m, 1H), 4.05 (m, 1H), 4.55 (m, 1H), 4.98 (m, 2H), 5.75 (m, 1H), 6.33 (s, 1H), 7.25-7.42 (m, 5H), 7.63 (s, 1H).

The following compounds were prepared by procedures analogous to Step B of Example 1:

1-[4-[4-(4,5-dihydro-5-phenyl-3-isoxazolyl)-2-thiazolyl]-1-piperidinyl]-2-[3-methyl-5-(trifluoromethyl)-1H-pyrazol-1-yl]ethanone (Compound 128); $^1$H NMR (CDCl$_3$): δ 1.7-1.9 (m, 2H), 2.16 (m, 1H), 2.24 (m, 1H), 2.29 (s, 3H), 2.84-2.92 (br t, 1H), 3.30 (m, 2H), 3.43 (m, 1H), 3.86 (m, 2H), 4.59 (br d, 1H), 5.04 (s, 2H), 5.75 (m, 1H), 6.47 (s, 1H), 7.29-7.39 (m, 5H), 7.64 (s, 1H).

1-[4-[4-(4,5-dihydro-5-phenyl-3-isoxazolyl)-2-thiazolyl]-1-piperidinyl]-2-[5-ethyl-3-(trifluoromethyl)-1H-pyrazol-1-yl]ethanone (Compound 19); m.p. 128-133° C. (crystallized from methyl acetate/petroleum ether); $^1$H NMR (CDCl$_3$): δ 1.28 (t, 3H), 1.8 (m, 2H), 2.2 (m, 2H), 2.62 (q, 2H), 2.9 (m, 1H), 3.3 (m, 2H), 3.42 (m, 1H), 3.85 (m, 1H), 4.05 (m, 1H), 4.55 (m, 1H), 4.98 (m, 2H), 5.75 (m, 1H), 6.33 (s, 1H), 7.25-7.42 (m, 5H), 7.63 (s, 1H).

2-[3,5-bis(trifluoromethyl)-1H-pyrazol-1-yl]-1-[4-[4-(4,5-dihydro-5-phenyl-3-isoxazolyl)-2-thiazolyl]-1-piperidinyl]ethanone (Compound 22); m.p. 130-133° C. (crystallized from methyl acetate/petroleum ether); $^1$H NMR (CDCl$_3$): δ 1.8 (m, 2H), 2.2 (m, 2H), 2.9 (m, 1H), 3.3 (m, 2H), 3.42 (m, 1H), 3.85 (m, 2H), 4.55 (m, 1H), 5.10 (s, 2H), 5.77 (m, 1H), 6.95 (s, 1H), 7.25-7.42 (m, 5H), 7.64 (s, 1H).

1-[4-[4-(2,3-dihydrospiro[4H-1-benzopyran-4,5'(4'H)-isoxazol]-3'-yl)-2-thiazolyl]-1-piperidinyl]-2-[5-methyl-3-(trifluoromethyl)-1H-pyrazol-1-yl]ethanone (Compound 137); $^1$H NMR (CDCl$_3$): δ 1.83 (m, 2H), 2.18 (m, 3H), 2.33 (s, 3H), 2.42 (m, 1H), 2.90 (m, 1H), 3.31 (m, 2H), 3.47 (d, 1H), 3.83 (d, 1H), 4.05 (m, 1H), 4.27 (m, 1H), 4.40 (m, 1H), 4.58 (d, 1H), 4.97 (m, 2H), 6.33 (s, 1H), 6.87 (d, 1H), 6.95 (dd, 1H), 7.21 (dd, 1H), 7.38 (d, 1H), 7.67 (s, 1H).

1-[4-[4-(2,3-dihydrospiro[4H-1-benzothiopyran-4,5'(4'H)-isoxazol]-3'-yl)-2-thiazolyl]-1-piperidinyl]-2-[5-methyl-3-(trifluoromethyl)-1H-pyrazol-1-yl]ethanone (Compound 102); $^1$H NMR (CDCl$_3$): δ 1.82 (m, 2H), 2.23 (m, 2H), 2.31 (s, 3H), 2.37 (m, 1H), 2.50 (m, 1H), 2.90 (m, 1H), 3.14 (m, 1H), 3.17 (m, 1H), 3.27 (m, 2H), 3.48 (d, 1H), 3.66 (d, 1H), 4.05 (m, 1H), 4.57 (d, 1H), 4.97 (m, 2H), 6.33 (s, 1H), 7.06 (m, 3H), 7.45 (d, 1H), 7.65 (s, 1H).

EXAMPLE 2

Preparation of 1-[[5-methyl-3-(trifluoromethyl)-1H-pyrazol-1-yl]acetyl]-4-[4-(5-phenyl-3-isoxazolyl)-2-thiazolyl]piperidine (Compound 2)

Step A: Preparation of 2-(4-piperidinyl)-4-thiazolecarboxaldehyde mono-hydrochloride To a solution of 1,1-dimethylethyl 4-(4-formyl-2-thiazolyl)-1-piperidinecarboxylate (1.0 g, 3.4 mmol) in dichloromethane (20 mL) was added a solution of hydrogen chloride in diethyl ether (2.0 mL, 15 ml, 30 mmol). The reaction mixture was stirred under nitrogen at room temperature for 2 h and then evaporated under reduced pressure to give 1.2 g of the title compound as a white solid.

$^1$H NMR (CDCl$_3$): δ 2.31-2.38 (m, 2H), 2.44-2.50 (m, 2H), 3.11-3.20 (m, 2H), 3.36-3.44 (m, 1H), 3.57-3.65 (m, 2H), 8.14 (s, 1H), 10.01 (s, 1H).

Step B: Preparation of 4-(4-formyl-2-thiazolyl)-1-[[5-methyl-3-(trifluoromethyl)-1H-pyrazol-1-yl]acetyl]piperidine (also known as 2-[1-[2-[5-methyl-3-(trifluoromethyl)-1H-pyrazol-1-yl]acetyl]-4-piperidinyl]-4-thiazolecarboxaldehyde)

To a solution of 5-methyl-3-(trifluoromethyl)-1H-pyrazole-1-acetic acid (0.8 g, 3.8 mmol) in dichloromethane (10 mL) was added oxalyl chloride (2.4 g, 19.2 mmol) and two drops of N,N-dimethylformamide, resulting in slight exothermicity. The reaction mixture was then heated at reflux for 15 minutes. The reaction mixture was concentrated under reduced pressure, and the residue was suspended in tetrahydrofuran (10 mL) and treated with a solution of 2-(4-piperidinyl)-4-thiazolecarboxaldehyde monohydrochloride (i.e. the product of Example 2, Step A) (1.1 g, 5.1 mmol) in tetrahydrofuran (10 mL), followed by dropwise addition of triethylamine (1.2 g, 11.9 mmol). The reaction mixture was stirred overnight at room temperature and then partitioned between 1 N aqueous hydrochloric acid and ethyl acetate. The organic layer was separated, and the aqueous layer was extracted with additional ethyl acetate (2×30 mL). The combined organic layers were washed with 1 N aqueous hydrochloric acid, saturated aqueous sodium bicarbonate solution, and brine. The organic layer was dried (MgSO$_4$) and evaporated under reduced pressure to give 0.8 g of the title compound as a yellow oil.

$^1$H NMR (CDCl$_3$): δ 1.79-1.90 (m, 2H), 2.18-2.29 (m, 2H), 2.33 (s, 3H), 2.87-2.94 (m, 1H), 3.28-3.40 (m, 2H), 4.05-4.15 (m, 1H), 4.56-4.64 (m, 1H), 4.99-5.02 (m, 2H), 6.35 (s, 1H), 8.12 (s, 1H), 10.01 (s, 1H).

Step C: Preparation of 4-[4-[(hydroxyimino)methyl]-2-thiazolyl]-1-[[5-methyl-3-(trifluoromethyl)-1H-pyrazol-1-yl]acetyl]piperidine (also known as 2-[1-[2-[5-methyl-3-(trifluoromethyl)-1H-pyrazolyl-1-yl]-4-piperidinyl]-4-thiazolecarboxaldehyde 4-oxime)

To a solution of 4-(4-formyl-2-thiazolyl)-1-[[5-methyl-3-(trifluoromethyl)-1H-pyrazol-1-yl]acetyl]piperidine (i.e. the product of Example 2, Step B) (0.8 g, 2.07 mmol) in ethyl alcohol (15 mL) was added hydroxylamine (50% aqueous solution, 0.136 g, 4.1 mmol), and the reaction mixture was stirred at room temperature for 10 minutes. The reaction mixture was concentrated under reduced pressure to give a yellow oil, which was purified by flash column chromatography on silica gel using 50% ethyl acetate in hexanes as eluant to give 0.7 g of the title compound as a white solid.

$^1$H NMR (CDCl$_3$): δ 1.72-1.85 (m, 2H), 2.17-2.27 (m, 2H), 2.32 (s, 3H), 2.82-2.91 (m, 1H), 3.25-3.37 (m, 2H), 4.02-4.09 (m, 1H), 4.58-4.63 (m, 1H), 4.95-5.03 (m, 2H), 6.35 (s, 1H), 7.43 (s, 1H), 7.71 (s, 1H), 8.19 (s, 1H).

Step D: Preparation of 1-[[5-methyl-3-(trifluoromethyl)-1H-pyrazol-1-yl]acetyl]-4-[4-(5-phenyl-3-isoxazolyl)-2-thiazolyl]piperidine 4-[4-[(Hydroxyimino)methyl]-2-thiazolyl]-1-[[5-methyl-3-(trifluoromethyl)-1H-pyrazol-1-yl]acetyl]piperidine (i.e. the product of Example 2, Step C) (0.2 g, 0.5 mmol) was suspended in tetrahydrofuran (20 mL), and phenylacetylene (1.1 mL, 1 mmol) was added, followed by a slow dropwise addition of Clorox® bleach solution (6.15 wt. % sodium hypochlorite, 10 mL) over 1 h. The reaction mixture was partitioned between saturated aqueous sodium bicarbonate solution and ethyl acetate. The organic layer was separated, and the aqueous layer was extracted with ethyl acetate (3×30 mL). The combined organic layers were washed with brine, dried (MgSO$_4$) and concentrated under reduced pressure to give an oil, which was purified by flash column chromatography on silica gel using 10% methanol in ethyl acetate as eluant to give to give 70 mg of the title product as a clear yellow oil.

$^1$H NMR (CDCl$_3$): δ 1.80-1.92 (m, 2H), 2.22-2.32 (m, 2H), 2.34 (s, 3H), 2.90-2.98 (m, 1H), 3.31-3.41 (m, 2H), 4.05-4.11 (m, 1H), 4.58-4.65 (m, 1H), 4.97-5.07 (m, 2H), 6.36 (s, 1H), 6.98 (s, 1H), 7.47-7.53 (m, 3H), 7.84 (s, 2H), 7.88 (m, 1H).

EXAMPLE 3

Preparation of 4-[4-(4,5-dihydro-1-methyl-5-phenyl-1H-imidazol-2-yl)-2-thiazolyl]-1-[[5-methyl-3-(trifluoromethyl)-1H-pyrazol-1-yl]acetyl]piperidine (Compound 7)

To a solution of 4-(4-formyl-2-thiazolyl)-1-[[5-methyl-3-(trifluoromethyl)-1H-pyrazol-1-yl]acetyl]piperidine (i.e. the product of Example 2, Step B) (0.8 g, 2.07 mmol) in tert-butanol (5 mL) was added N1-methyl-1-phenyl-1,2-ethanediamine (43.57 mg, 0.29 mmol). The reaction mixture was stirred at room temperature under a nitrogen atmosphere for 30 minutes, and then potassium carbonate (107.8 mg, 0.78 mmol) and iodine (43.57 mg, 0.33 mmol) were added. The reaction mixture was stirred at 70° C. for 3 h and then quenched by addition of saturated aqueous sodium sulfite solution until the iodine color almost disappeared. The reaction mixture was extracted with chloroform, and the organic layer was washed with saturated aqueous sodium bicarbonate solution and brine, dried (Na$_2$SO$_4$), filtered and concentrated. The residue was purified by preparative thin-layer chromatography on silica gel using a mixture of 94% ethyl acetate, 5% methanol and 1% triethylamine as eluant to give 64 mg of the title product as an oil.

$^1$H NMR (CDCl$_3$): δ 1.72-1.87 (m, 2H), 2.15-2.28 (m, 2H), 2.31 (s, 3H), 2.86-2.92 (m, 1H), 2.97 (s, 3H), 3.26-3.37 (m, 2H), 3.62-4.39 (m, 2H), 4.0-4.6 (m, 2H), 4.93-5.05 (m, 2H), 6.31 (s, 1H), 7.30-7.41 (m, 5H), 7.88 (s, 1H).

EXAMPLE 4

Preparation of 4-]4-(4,5-dihydro-3-phenyl-5-isoxazolyl)-2-thiazolyl]-1-[(5-methyl-3-(trifluoromethyl)-1H-pyrazol-1-yl)acetyl]piperidine (Compound 6)

Step A: Preparation of 1,1-dimethylethyl 4-(4-ethenyl-2-thiazolyl)-1-piperidinecarboxylate To a cold (−50° C.) suspension of methyltriphenylphosphonium bromide (1.2 g, 3.3 mmol) in tetrahydrofuran (5 mL) was added a solution of sodium bis(trimethyl-silyl)amide (3.4 mL, 3.4 mmol), and the mixture was stirred for 1 h at room temperature. The resulting cloudy yellow solution was re-cooled to −30° C., and 1,1-dimethylethyl 4-(4-formyl-2-thiazolyl)-1-piperidinecarboxylate (0.5 g, 1.68 mmol) was added. The resulting slightly yellow solution was stirred at room temperature for 3 h, then diluted with water, and extracted with ethyl acetate. The organic layer was washed with brine, dried ($MgSO_4$), filtered, and purified by column chromatography on silica gel using 15-30% ethyl acetate in hexanes as eluant to give 471 mg of the title compound as a colorless oil.

$^1$H NMR ($CDCl_3$): δ 1.47 (s, 9H), 1.68 (m, 2H), 2.10 (m, 2H), 2.88 (m, 2H), 3.15 (m, 1H), 4.18 (m, 2H), 5.34 (d, 1H), 6.02 (d, 1H), 6.68 (dd, 1H), 6.99 (s, 1H).

Step B: Preparation of 4-(4-ethenyl-2-thiazolyl)piperidine

To a solution of 1,1-dimethylethyl 4-(4-ethenyl-2-thiazolyl)-1-piperidinecarboxylate (i.e. the product of Example 4, Step A) (471 mg, 1.6 mmol) in dichloromethane (5 mL) was added a solution of hydrogen chloride in diethyl ether (2.0 M, 7 mL, 14 mmol). The reaction mixture was stirred under nitrogen at room temperature for 4 h, and then 1 N aqueous sodium hydroxide solution was added until pH of the reaction mixture increased to about 10. The resulting mixture was extracted with dichloromethane (2×). The organic layers were combined, washed with brine, dried ($MgSO_4$), filtered and concentrated under reduced pressure to give 302 mg of the title compound as an oil.

$^1$H NMR ($CDCl_3$): δ 1.70 (m, 2H), 1.82 (br s, 1H), 2.12 (br d, 2H), 2.76 (br t, 2H), 3.11 (m, 1H), 3.18 (m, 2H), 5.32 (d, 1H), 6.02 (d, 1H), 6.70 (dd, 1H), 6.99 (s, 1H).

Step C: Preparation of 4-(4-ethenyl-2-thiazolyl)-1-[[5-methyl-3-(trifluoromethyl)-1H-pyrazol-1-yl]acetyl]piperidine To a solution of 5-methyl-3-(trifluoromethyl)-1H-pyrazole-1-acetic acid (0.5 g, 2.4 mmol) in dichloromethane (4 mL) was added oxalyl chloride (0.3 mL, 3.6 mmol) and one drop of N,N-dimethylformamide, resulting in slight exothermicity. The reaction mixture was then heated at reflux for 15 minutes. The reaction mixture was evaporated, and the resulting residue was suspended in dichloromethane (4 mL) and treated with a solution of 4-(4-ethenyl-2-thiazolyl)piperidine (i.e. the product of Example 4, Step B) (302 mg, 1.5 mmol) in dichloromethane (2 mL), followed by addition of triethylamine (0.32 mL, 2.3 mmol). The reaction mixture was stirred overnight at room temperature, then concentrated, and purified by column chromatography on silica gel using 30-40% ethyl acetate in hexanes as eluant to give 414 mg of the title compound as a white solid.

$^1$H NMR ($CDCl_3$): δ 1.78 (m, 2H), 2.18 (m, 2H), 2.32 (s, 3H), 2.90 (br t, 1H), 3.30 (m, 2H), 4.03 (d, 1H), 4.55 (d, 1H), 5.00 (m, 2H), 5.35 (d, 1H), 6.02 (d, 1H), 6.33 (s, 1H), 6.68 (dd, 1H), 7.01 (s, 1H).

Step D: Preparation of 4-[4-(4,5-dihydro-3-phenyl-5-isoxazolyl)-2-thiazolyl]-1-[(5-methyl-3-(trifluoromethyl)-1H-pyrazol-1-yl)acetyl]piperidine To a solution of benzaldehyde oxime (49 mg, 0.4 mmol) in N,N-dimethylformamide (3 mL) was added N-chlorosuccinimide (54 mg, 0.4 mmol), followed by addition of 4-(4-ethenyl-2-thiazolyl)-1-[[5-methyl-3-(trifluoromethyl)-1H-pyrazol-1-yl]acetyl]piperidine (i.e. the product of Example 4, Step C) (103 mg, 0.27 mmol) and triethylamine (41 mg, 0.4 mmol). The resulting mixture was stirred at room temperature for 5 h, then diluted with water, and extracted with dichloromethane (2×). The organic layers were combined and dried ($MgSO_4$), and filtered. The filtrate was concentrated, and the residue was purified by column chromatography on silica gel using 55-70% ethyl acetate in hexanes as eluant to give 90 mg of the title product as a white solid.

$^1$H NMR ($CDCl_3$): δ 1.76 (m, 2H), 2.17 (m, 2H), 2.31 (s, 3H), 2.88 (br t, 1H), 3.25 (m, 2H), 3.65 (m, 1H), 3.78 (m, 1H), 4.02 (br d, 1H), 4.56 (br d, 1H), 4.99 (m, 2H), 5.84 (dd, 1H), 6.32 (s, 1H), 7.28 (s, 1H), 7.40-7.42 (m, 3H), 7.69-7.71 (m, 2H).

EXAMPLE 5

Preparation of 1-[4-[4-[5-(2-chlorophenyl)-4,5-dihydro-3-isoxazolyl]-2-thiazolyl]-1-piperidinyl]-2-[5-methyl-3-(trifluoromethyl)-1H-pyrazol-1-yl]ethanone (Compound 8)

To a solution of 1-chloro-2-ethenylbenzene (0.035 g, 0.25 mmol), triethylamine (2.5 mg, 0.025 mmol) and Clorox® aqueous sodium hypochlorite solution (1 mL, 16.1 mmol) in dichloromethane (5 mL) was added 4-[4-[(hydroxyimino)methyl]-2-thiazolyl]-1-[[5-methyl-3-(trifluoromethyl)-1H-pyrazol-1-yl]acetyl]piperidine (i.e. the product of Example 2, Step C) (0.10 g, 0.25 mmol) in dichloromethane (5 mL) dropwise over 1 h at 0° C. The reaction mixture was allowed to stir for 1 h, then filtered through Celite® diatomaceous filter aid, and concentrated under reduced pressure to give an oil, which was purified by column chromatography on silica gel using 50% ethyl acetate in hexane as eluant to give 73 mg of the title compound as a white foam, melting at 115-122° C. (crystallized from methyl acetate/petroleum ether).

$^1$H NMR ($CDCl_3$): δ 1.74-1.80 (m, 2H), 2.14-2.22 (m, 2H), 2.32 (s, 3H), 2.85-2.91 (m, 1H), 3.26-3.30 (m, 2H), 3.31-3.32 (m, 1H), 4.05-4.07 (m, 1H), 4.55-4.58 (m, 1H), 4.93-5.03 (q, 2H), 6.01-6.06 (m, 1H), 6.331 (s, 1H), 7.25-7.29 (m, 2H), 7.38-7.40 (m, 1H), 7.56-7.58 (m, 1H), 7.62 (s, 1H).

EXAMPLE 6

Preparation of 1-[4-[4-(4,5-dihydro-5-phenyl-3-isoxazolyl)-2-thiazolyl]-1-piperidinyl]-2-[5-methyl-3-(trifluoromethyl)-1H-pyrazol-1-yl]ethanethione (Compound 130)

A solution of 4-[4-[4,5-dihydro-5-phenyl-3-isoxazolyl]-2-thiazolyl]-1-[[5-methyl-3-(trifluoromethyl)-1H-pyrazol-1-yl]acetyl]piperidine (i.e. the product of Example 1, Step B) (235 mg, 0.47 mmol) and phosphorus pentasulfide (104.5 mg, 0.235 mmol) in pyridine (5 ml) was heated at reflux for 2 h.

The reaction mixture was then concentrated under reduced pressure, and the residue was portioned between dichloromethane (10 mL) and water (10 mL). The organic layer was washed with 1 N hydrochloric acid, water, saturated aqueous sodium bicarbonate solution and brine, dried (MgSO$_4$), and concentrated under reduced pressure to give 240 mg of the title product as a white foam.

$^1$H NMR (CDCl$_3$): δ 1.80-2.00 (m, 2H), 2.20-2.28 (m, 2H), 2.45 (s, 3H), 3.35-3.46 (3H, m), 3.50-3.61 (m, 1H), 3.80-3.88 (m, 1H), 4.70-4.80 (m, 1H), 5.30-5.33 (m, 2H), 5.35-5.40 (m, 1H), 5.74-5.80 (m, 1H), 6.32 (s, 1H), 7.30-7.40 (m, 5H), 7.65 (s, 1H).

EXAMPLE 7

Preparation of 1-[4-[4-(4,5-dihydro-5-phenyl-3-isoxazolyl)-2-thiazolyl]-1-piperazinyl]-2-[5-methyl-3-(trifluoromethyl)-1H-pyrazol-1-yl]ethanone (Compound 154)

Step A: Preparation of 1,1-dimethylethyl 4-(aminothioxomethyl)-1-piperazine-carboxylate To a solution of thiocarbonyldiimidazole (2.1 g, 11.8 mmol) in tetrahydrofuran (30 mL) at room temperature, was added 1,1-dimethylethyl 1-piperazinecarboxylate (2 g, 10.75 mmol). The reaction mixture was stirred at room temperature for 2 h and then heated to 55° C. for additional 2 h. The reaction mixture was cooled to room temperature and concentrated under reduced pressure until approximately 20 mL of tetrahydrofuran remained. The residue was then treated with a 2 M solution of ammonia in methanol (10 mL) and stirred at room temperature for 24 h. The reaction mixture was concentrated under reduced pressure, and the residue was triturated with diethyl ether (25 mL) to give a white precipitate. The precipitate was filtered and dried to give 1.5 g of the title compound as a white solid.

$^1$H NMR (CDCl$_3$): δ 1.39 (s, 9H), 3.32 (m, 4H), 3.73 (m, 4H), 7.49 (br s, 2H).

Step B: Preparation of 3-chloro-N-hydroxy-2-oxopropanimidoyl chloride

To a solution of 1,3-dichloroacetone (100 g, 0.79 mol) in 2 M solution of hydrogen chloride in diethyl ether (400 mL) at 15° C. was added t-butyl nitrite (55 g, 0.534 mol) over 10 minutes. The reaction progress was monitored by $^1$H NMR to obtain ~85% conversion with no more than 3% of the bis-nitrosation side product. The reaction mixture was concentrated under reduced pressure to leave a semi-solid, which was then thoroughly rinsed with n-BuCl. The resulting solid was collected under filtration to give a 77 g of the title compound as a white solid. The filtrate was further concentrated under reduced pressure to give a semi-solid residue, which was rinsed with additional n-BuCl. The resulting solid was collected under filtration to give additional 15 g of the title compound as a white solid.

$^1$H NMR (DMSO-d$_6$) δ 4.96 (s, 2H), 13.76 (s, 1H).

Step C: Preparation of 2-chloro-1-(4,5-dihydro-5-phenyl-3-isoxazolyl)ethanone

To a mixture of styrene (6.79 g, 65.3 mmol) and sodium bicarbonate (32.1 g, powder) in acetonitrile (100 mL), 3-chloro-N-hydroxy-2-oxopropanimidoyl chloride (i.e. the product of Example 7, Step B) (10 g, 64.1 mmol) was added in 10 portions over 20 minutes. The reaction mixture was then stirred for an additional 1 h and filtered. The filtered solid was rinsed with acetonitrile, and the combined filtrates were concentrated under reduced pressure to leave an oil, which was triturated first with hexanes and then with 1-chlorobutane to give 13.6 g of the title compound as a white solid.

$^1$H NMR (CDCl$_3$): δ 3.13 (m, 1H), 3.66 (m, 1H), 4.96 (s, 2H), 5.83 (m, 1H), 7.34-7.44 (m, 5H).

Step D: Preparation of 1,1-dimethylethyl 4-[4-(4,5-dihydro-5-phenyl-3-isoxazolyl)-2-thiazolyl]-1-piperazineacetate To a solution of 2-chloro-1-(4,5-dihydro-5-phenyl-3-isoxazolyl)ethanone (i.e. the product of Example 7, Step C) (0.450 g, 2.018 mmol) and 1,1-dimethylethyl 4-(aminothioxomethyl)-1-piperazinecarboxylate (i.e. the product of Example 7, Step A) (0.5 g, 2.04 mmol) in ethanol (10 mL) was added triethylamine (0.204 g, 2.013 mmol), and the reaction mixture was stirred at room temperature for 12 h. The reaction mixture was concentrated under reduced pressure, and the residue was partitioned between ethyl acetate (30 mL) and water (30 mL). The organic layer was separated and washed with brine (25 mL), dried (Na$_2$SO$_4$), and concentrated under reduced pressure. The crude residue was purified by column chromatography using 20% ethyl acetate in petroleum ether as eluant to give 700 mg of the title compound as a white solid.

$^1$H NMR (CDCl$_3$): δ 1.48 (s, 9H), 3.30 (m, 1H), 3.54 (m, 8H), 3.74 (m, 1H), 5.71 (m, 1H), 6.91 (s, 1H), 7.40-7.29 (m, 5H).

Step E: Preparation of 1-[4-(4,5-dihydro-5-phenyl-3-isoxazolyl)-2-thiazolyl]-piperazine hydrochloride To a solution of 1,1-dimethylethyl 4-[4-(4,5-dihydro-5-phenyl-3-isoxazolyl)-2-thiazolyl]-1-piperazineacetate (i.e. the product of Example 7, Step D) (0.7 g, 1.686 mmol) in diethyl ether (10 mL) was added a 2 M solution of hydrogen chloride in methanol (10 mL) at room temperature. The reaction mixture was stirred at room temperature for 8 h. The resulting white precipitate was filtered and dried to give 500 mg of the title compound as a white solid.

$^1$H NMR (CDCl$_3$): δ 3.21 (m, 4H), 3.27 (m, 1H), 3.68 (m, 4H), 3.79 (m, 1H), 5.68 (m, 1H), 7.41-7.29 (m, 6H), 9.49 (br s, 2H).

Step F: Preparation of 1-[4-[4-(4,5-dihydro-5-phenyl-3-isoxazolyl)-2-thiazolyl]-1-piperazinyl]-2-[5-methyl-3-(trifluoromethyl)-1H-pyrazol-1-yl]ethanone To a solution of 1-[4-(4,5-dihydro-5-phenyl-3-isoxazolyl)-2-thiazolyl]piperazine hydrochloride (i.e. the product of Example 7, Step E) (200 mg, 0.57 mmol) and 5-methyl-3-(trifluoromethyl)-1H-pyrazole-1-acetic acid (0.120 g, 0.57 mmol) in dichloromethane (10 mL) at room temperature was added 1-[3-(dimethylamino)propyl]-3-ethylcarbodiimide hydrochloride (0.110 g, 0.57 mmol), triethylamine (0.086 g, 0.85 mmol) and 1-hydroxy-benzotriazole hydrate (0.020 g, 0.14 mmol). The reaction mixture was stirred at room temperature for 24 h. The reaction mixture was diluted with dichloromethane (30 mL) and washed with water (20 mL) and brine (20 mL). The organic layer was dried (Na$_2$SO$_4$) and concentrated under reduced pressure. The crude residue was purified by column chromatography using 3% methanol in chloroform as eluant to give 180 mg of the title product as a white solid.

¹H NMR (CDCl₃): δ 2.32 (s, 3H), 3.29 (m, 1H), 3.52 (m, 2H), 3.61 (m, 2H), 3.79-3.72 (m, 5H), 4.98 (m, 2H), 5.69 (m,1H), 6.33 (s, 1H), 6.93 (s, 1H), 7.38-7.28 (m, 5H).

Mass spectrum at 505.5 (M+1).

EXAMPLE 8

Preparation of 1-[4-[4-(3',4'-dihydrospiro[isoxazole-5(4H),1',(2'H)-naphthalen]-3-yl)-2-thiazolyl]-1-piperidinyl]-2-[5-methyl-3-(trifluoromethyl)-1H-pyrazol-1-yl]ethanone (Compound 37)

Step A: Preparation of 1-(2-chloroacetyl)-4-piperidinecarbonitrile

A mixture of 4-piperidinecarbonitrile (200 g, 1.80 mol) and 40% aqueous potassium carbonate solution (342 g, 0.99 mol) in dichloromethane (1 L) was cooled to −10° C., and a solution of chloroacetyl chloride (210 g, 1.86 mol) in dichloromethane (300 mL) was added over about 75 minutes while maintaining the reaction mixture at −10 to 0° C. After the addition was complete, the reaction mixture was separated, the upper aqueous phase was extracted with dichloromethane (2×300 mL), and the combined organic phases were concentrated under reduced pressure to give 312 g of the title compound as a liquid which slowly crystallized on standing. This compound was of sufficient purity to use in subsequent reactions.

¹H NMR (CDCl₃): δ 1.8-2.1 (m, 4H), 2.95 (m, 1H), 3.5-3.8 (m, 4H), 4.08 (q, 2H).

Step A1: Alternative preparation of 1-(2-chloroacetyl)-4-piperidinecarbonitrile

A solution of N-(1,1-dimethylethyl)-4-piperidinecarboxamide (201 g, 1.0 mol) in dichloromethane (1 L) was cooled under nitrogen to −5° C., and chloroacetyl chloride (124 g, 1.1 mol) in 300 mL of dichloromethane was added dropwise over 30 minutes while maintaining the reaction mixture at 0 to 5° C. Then 20% aqueous potassium carbonate solution (450 g, 0.65 mol) was added dropwise over 30 minutes while keeping reaction temperature between 0 and 5° C. The reaction mixture was stirred for an additional 30 minutes at 0° C., and then allowed to warm to room temperature. The layers were separated, and the aqueous layer was extracted with dichloromethane (200 mL). The combined dichloromethane layers were concentrated under reduced pressure to yield a solid, which was triturated with 400 mL of hexanes. The slurry was filtered, and the filter cake was washed with 100 mL of hexanes and dried in a vacuum oven overnight at 50° C. to give 185.5 g of 1-(2-chloroacetyl)-N-(1,1-dimethylethyl)-4-piperidinecarboxamide as a solid, melting at 140.5-141.5° C.

¹H NMR (CDCl₃): δ 1.35 (s, 9H), 1.6-2.0 (m, 4H), 2.25 (m, 1H), 2.8 (t, 1H), 3.2 (t, 1H), 3.9 (d, 1H), 4.07 (s, 2H), 4.5 (d, 1H), 5.3 (br s, 1H).

To a solution of 1-(2-chloroacetyl)-N-(1,1-dimethylethyl)-4-piperidinecarboxamide (26.1 g, 0.10 mol) in N,N-dimethylformamide (35 mL) was added phosphorus oxychloride (18.8 g, 0.123 mol) dropwise over 30 minutes while allowing the temperature of the reaction mixture to rise to 37° C. The reaction mixture was heated at 55° C. for 1 h and then was slowly added to water (about 150 g) cooled with ice to maintain a temperature of about 10° C. The pH of the reaction mixture was adjusted to 5.5 with 50% NaOH aqueous solution. The mixture was extracted with dichloromethane (4×100 mL), and the combined extract was concentrated under reduced pressure to give 18.1 g of the title compound as a solid. This compound was of sufficient purity to use in subsequent reactions.

Step B: Preparation of 1-[2-[5-methyl-3-(trifluoromethyl)-1H-pyrazol-1-yl]acetyl]-4-piperidinecarbonitrile A solution of 3-methyl-5-trifluoromethylpyrazole (9.3 g, 62 mmol) and 45% aqueous potassium hydroxide solution (7.79 g, 62 mmol) in N,N-dimethylformamide (25 mL) was cooled to 5° C., and 1-(2-chloroacetyl)-4-piperidinecarbonitrile (i.e. the product of Example 8, Step A or A1) (11.2 g, 60 mmol) was added. The reaction mixture was stirred for 8 h at 5-10° C., then diluted with water (100 mL), and filtered. The filter cake was washed with water and dried at 50° C. in a vacuum-oven to give 15 g of the title compound as a solid containing 3% of its regioisomer, i.e. 1-[2-[3-methyl-5-(trifluoromethyl)-1H-pyrazol-1-yl]acetyl]-4-piperidinecarbonitrile.

¹H NMR (CDCl₃): δ 1.88 (m, 4H), 2.32 (s, 3H), 2.95 (m, 1H), 3.7 (m, 4H), 5.0 (q, 2H), 6.34 (s, 1H).

Step C: Preparation of 1-[2-[5-methyl-3-(trifluoromethyl)-1H-pyrazol-1-yl]acetyl]-4-piperidinecarbothioamide Hydrogen sulfide gas was passed into a solution of 1-[2-[5-methyl-3-(trifluoromethyl)-1H-pyrazol-1-yl]acetyl]-4-piperidinecarbonitrile (i.e. the product of Example 8, Step B) (9.0 g, 30 mmol) and diethanolamine (3.15 g, 30 mmol) in N,N-dimethylformamide (15 mL) at 50° C. in a flask equipped with dry-ice condenser. The hydrogen sulfide feed was stopped when the reaction mixture became saturated with hydrogen sulfide, as indicated by condensation on the cold-finger. The reaction mixture was stirred for an additional 30 minutes at 50° C. Then excess hydrogen sulfide gas was sparged into the scrubber by a subsurface nitrogen flow, and water (70 mL) was gradually added. The reaction mixture was cooled to 5° C., filtered, and washed with water (2×30 mL). The filter cake was dried at 50° C. in a vacuum-oven to give 8.0 g of the title compound as a solid, melting at 185-186° C.

¹H NMR (CDCl₃): δ 1.7 (m, 2H), 2.0 (m, 2H), 2.29 (s, 3H), 2.65 (t, 1H), 3.0 (m, 1H), 3.2 (t, 1H), 4.0 (d, 1H), 4.6 (d, 1H), 4.96 (d, 1H), 5.4 (d, 1H), 6.35 (s, 1H), 7.4 (br s, 1H), 7.5 (br s, 1H).

Step D: Preparation of 1-[4-[4-(3',4'-dihydrospiro[isoxazole-5(4H),1',(2'H)-naphthalen]-3-yl)-2-thiazolyl]-1-piperidinyl]-2-[5-methyl-3-(trifluoromethyl)-1H-pyrazol-1-yl]ethanone A solution of 1-[2-[5-methyl-3-(trifluoromethyl)-1H-pyrazol-1-yl]acetyl]-4-piperidine-carbothioamide (i.e. the product of Example 8, Step C) (0.5 g, 1.5 mmol), 2-chloro-1-(3',4'-dihydrospiro[isoxazole-5(4H),1',(2'H)-naphthalen]-3-yl)ethanone (prepared by a method analogous to Example 7, Step C) (0.4 g, 1.5 mmol) and tetrabutylammonium bromide (0.030 g, 0.10 mmol) in tetrahydrofuran (15 mL) was stirred overnight at room temperature and then heated at 55-60° C. for 3 h. The reaction mixture was diluted with water and extracted with dichloromethane. The extract was washed with brine, dried (MgSO₄), and concentrated under reduced pressure. The crude product was further purified by medium-pressure liquid chromatography using 50% ethyl acetate in hexanes as eluant to give 260 mg of the title product as an off-white solid, melting at 81-84° C.

¹H NMR (CDCl₃): δ 1.76-1.86 (m, 3H), 2.04-2.08 (m, 2H), 2.16-2.26 (m, 2H), 2.32 (s, 3H), 2.83-2.87 (m, 2H), 2.88-2.93 (m, 1H), 3.27-3.35 (m, 2H), 3.48-3.65 (m, 2H), 4.02-4.06 (m, 1H), 4.55-4.59 (m, 1H), 4.94-5.04 (q, 2H), 6.33 (s, 1H), 7.10-7.12 (m, 1H), 7.19-7.21 (m, 2H), 7.40-7.43 (m, 1H), 7.62 (s, 1H).

The following compounds were prepared by procedures analogous to Step D of Example 8:

1-[4-[4-(4,5-dihydro-5-methyl-5-phenyl-3-isoxazolyl)-2-thiazolyl]-1-piperidinyl]-2-[5-methyl-3-(trifluoromethyl)-1H-pyrazol-1-yl]ethanone (Compound 15); m.p. 97-100° C. (crystallized from methyl acetate/petroleum ether); ¹H NMR (CDCl₃): δ 1.74-1.80 (m, 1H), 1.81 (s, 3H), 2.14-2.20 (m, 2H), 2.32 (s, 3H), 2.85-2.91 (m, 1H), 3.26-3.32 (m, 2H), 3.52-3.62 (m, 2H), 4.01-4.05 (m, 1H), 4.54-4.58 (m, 1H), 4.94-5.04 (q, 2H), 6.33 (s, 1H), 7.26-7.29 (m, 1H), 7.35-7.38 (m, 2H), 7.48-7.50 (m, 2H), 7.58 (s, 1H).

2-[5-methyl-3-(trifluoromethyl)-1H-pyrazol-1-yl]-1-[4-[4-(3a,4,5,9b-tetrahydro-naphth[2,1-d]isoxazol-3-yl)-2-thiazolyl]-1-piperidinyl]ethanone (Compound 16); m.p. 162-165° C. (crystallized from methyl acetate/petroleum ether); ¹H NMR (CDCl₃): δ 1.79-1.85 (m, 2H), 2.00-2.05 (m, 2H), 2.20-2.26 (m, 2H), 2.33 (s, 3H), 2.68-2.72 (m, 2H), 2.88-2.94 (m, 1H), 3.30-3.35 (m, 2H), 3.92-3.98 (m, 1H), 4.06-4.10 (m, 1H), 4.58-4.60 (m, 1H), 4.94-5.06 (m, 2H), 5.58-5.60 (d, 1H), 6.34 (s, 1H), 7.17-7.20 (m, 1H), 7.28-7.30 (m, 2H), 7.47-7.49 (m, 1H), 7.72 (s, 1H).

1-[4-[4-(2,3-dihydrospiro[1H-indene-1,5'(4'H)-isoxazol]-3'-yl)-2-thiazolyl]-1-piperidinyl]-2-[5-methyl-3-(trifluoromethyl)-1H-pyrazol-1-yl]ethanone (Compound 44); ¹H NMR (CDCl₃): δ 1.77-1.84 (m, 2H), 2.17-2.25 (m, 2H), 2.33 (s, 3H), 2.61-2.68 (m, 1H), 2.90-2.96 (m, 2H), 3.12-3.20 (m, 1H), 3.31-3.35 (m, 2H), 3.54-3.75 (m, 2H), 4.04-4.10 (m, 1H), 4.56-4.60 (m, 1H), 4.94-5.04 (q, 2H), 6.34 (s, 1H), 7.28-7.30 (m, 3H), 7.37-7.38 (m, 1H), 7.64 (s, 1H).

1-[4-[4-[4,5-dihydro-5-(4-methoxyphenyl)-3-isoxazolyl]-2-thiazolyl]-1-piperidinyl]-2-[5-methyl-3-(trifluoromethyl)-1H-pyrazol-1-yl]ethanone (Compound 18); m.p.t 119-124° C. (crystallized from methyl acetate/petroleum ether); ¹H NMR (CDCl₃): δ 1.76-1.82 (m, 2H), 2.16-2.24 (m, 2H), 2.32 (s, 3H), 2.86-2.92 (m, 1H), 3.28-3.34 (m, 2H), 3.37-3.43 (m, 1H), 3.76-3.83 (m, 1H), 3.81 (s, 3H), 4.03-4.06 (m, 1H), 4.56-459 (m, 1H), 4.94-5.04 (q, 2H), 5.67-5.72 (m, 1H), 6.33 (s, 1H), 6.89-6.91 (d, 2H), 7.31-7.33 (d, 2H), 7.62 (s, 1H).

EXAMPLE 9

Preparation of 1-[4-[4-(4,5-dihydro-5-(2-pyridinyl)-3-isoxazolyl]-2-thiazolyl]-1-piperidinyl]-2-[5-methyl-3-(trifluoromethyl)-1H-pyrazol-1-yl]ethanone (Compound 98)

To a solution of 1-[2-[5-methyl-3-(trifluoromethyl)-1H-pyrazol-1-yl]acetyl]-4-piperidinecarbothioamide (i.e. the product of Example 8, Step C) (200 mg, 0.6 mmol) in tetrahydrofuran (8 mL) was added 3-chloro-N-hydroxy-2-oxopropanimidoyl chloride (i.e. the product of Example 7, Step B) (93 mg, 0.6 mmol), followed by tetrabutylammonium bromide (15 mg, 0.05 mmol). The reaction mixture was heated at 50° C. for 4 h. The reaction mixture was cooled and concentrated under reduced pressure. To the resulting residue, acetonitrile (8 mL) and finely powdered sodium bicarbonate (151 mg, 1.0 mmol) were added followed by 2-ethenylpyridine (63 mg, 0.6 mmol), and the resulting mixture was stirred at room temperature overnight. The reaction mixture was concentrated under reduced pressure and purified by flash chromatography on a silica gel (20 g) Varian Bond Elute SI® column using 0 to 75% ethyl acetate in hexanes as eluant to give 80 mg of the title product as a yellow semi-solid.

¹H NMR (CDCl₃): δ 1.47-1.62 (m, 1H), 1.70-1.85 (m, 1H), 2.01-2.18 (m, 2H), 2.49 (s. 3H), 2.82 (t, 1H), 3.20-3.42 (m, 2H), 3.73 (dd, 1H), 3.82 (dd, 1H), 3.98 (d, 1H), 4.38 (d, 1H), 5.26 (m, 2H), 5.80 (dd, 1H), 6.50 (s, 1H), 7.38 (dd, 1H), 7.50 (d, 1H), 7.82 (t, 1H), 8.05 (s, 1H), 8.60 (d, 1H).

EXAMPLE 10

Preparation of 2-[5-chloro-3-(trifluoromethyl)-1H-pyrazol-1-yl]-1-[4-[4-(4,5-dihydro-5-phenyl-3-isoxazolyl]-2-thiazolyl]-1-piperidinyl]ethanone (Compound 107)

Step A: Preparation of N,N-dimethyl-3-(trifluoromethyl)-1H-pyrazole-1-sulfonamide To a solution of 3-trifluoromethylpyrazole (5.0 g, 36 mmol), triethylamine (7.0 mL, 50 mmol) in dichloromethane (40 mL) was added dimethylsulfamoyl chloride (5.5 mL, 51 mmol), and the reaction mixture was heated at reflux for 2 days. The resulting mixture was cooled to ambient temperature and filtered through a pad of silica gel using dichloromethane as eluent. The filtrate was then concentrated under reduced pressure to give an amber residue. The resulting residue was dissolved in diethyl ether. The ether solution was washed with water, dried (MgSO₄), and concentrated under reduced pressure to give 8.71 g of the title compound.

¹H NMR (CDCl₃): δ 3.01 (s, 6H), 6.65 (s, 1H), 8.03 (s, 1H).

Step B: Preparation of 5-chloro-N,N-dimethyl-3-(trifluoromethyl)-1H-pyrazole-1-sulfonamide A stirred solution of N,N-dimethyl-3-(trifluoromethyl)-1H-pyrazole-1-sulfonamide (i.e. the product of Example 10, Step A) (4.0 g, 16 mmol) in tetrahydrofuran (25 mL) was cooled to −78° C., and then treated dropwise with 2 M n-butyllithium in cyclohexane (8.6 mL, 17.2 mmol). The reaction mixture was stirred for a further 30 minutes, and then a solution of hexachloroethane (4.2 g, 18 mmol) in tetrahydrofuran (15 mL) was added dropwise. The reaction mixture was stirred for 1 h, warmed to room temperature, and quenched with water (50 mL). The resulting solution was extracted with dichloromethane, dried (MgSO₄), and concentrated under reduced pressure to give 4.38 g of title compound. This compound was of sufficient purity to use in subsequent reactions.

¹H NMR (CDCl₃): δ 3.15 (s, 6H), 6.58 (s, 1H).

Step C: Preparation 5-chloro-3-(trifluoromethyl)-1H-pyrazole

A solution of 5-chloro-N,N-dimethyl-3-(trifluoromethyl)-1H-pyrazole-1-sulfonamide (i.e. the product of Example 10, Step B) (4.38 g, 15.8 mmol) and trifluoroacetic acid (2.7 mL, 35 mmol) was stirred at 0° C. for 1.5 h. The reaction mixture was diluted with water (15 mL), and sodium carbonate was added to raise the pH to 12. The solution was extracted with diethyl ether, dried (MgSO₄), and concentrated under reduced pressure to give 2.1 g of the title compound. This compound was of sufficient purity to use in subsequent reactions.

¹H NMR (CDCl₃): δ 6.57 (m, 1 H).

Step D: Preparation of ethyl 5-chloro-3-(trifluoromethyl)-1H-pyrazole-1-acetate

To a suspension of 5-chloro-3-(trifluoromethyl)-1H-pyrazole (i.e. the product of Example 10, Step C) (2.1 g, 12.3 mmol) and potassium carbonate (3.6 g, 26.0 mmol) in 20 mL of N,N-dimethylformamide was added ethyl bromoacetate (2.1 mL, 18.8 mmol), and the resulting mixture was stirred at room temperature for 12 h. The resulting mixture was diluted with ethyl acetate, washed with water, and dried ($MgSO_4$). The reaction mixture was concentrated under reduced pressure and further purified by medium-pressure liquid chromatography using 0-50% of ethyl acetate in hexanes as eluant to give 940 mg of the title compound as an oil.

$^1$H NMR ($CDCl_3$): δ 1.29 (m, 3 H), 4.27 (q, 2 H), 4.96 (m, 2 H), 6.55 (s, 1 H).

Step D1: Alternative preparation of ethyl 5-chloro-3-(trifluoromethyl)-1H-pyrazole-1-acetate To a solution of aluminum chloride (3.0 g, 22.5 mmol) in dichloromethane (100 mL) was added dropwise a solution of trifluoroacetyl chloride (3 g, 22.6 mmol) in dichloro-methane (5 mL) while keeping the temperature of the reaction mixture below −30° C. The reaction mixture was stirred for 15 minutes at −50° C. Then a solution of vinylidene chloride (2.2 g, 22.7 mmol) in dichloromethane (10 mL) was added dropwise over 2 h to the reaction mixture. The reaction mixture was stirred an additional 2 h at −50° C. and then warmed gradually to room temperature. The reaction mixture was diluted with water, and the aqueous layer was extracted with dichloromethane. The organic layers were combined, dried ($MgSO_4$), and concentrated under reduced pressure to give 4,4-dichloro-1,1,1-trifluoro-3-buten-2-one as an oil which was used for the next step without further purification.

$^1$H NMR ($CDCl_3$): δ 5.30 (s, 1H).

$^{19}$F NMR ($CDCl_3$): δ −63.6.

To a mixture of ethyl hydrazinoacetate hydrochloride (2.8 g, 18.1 mmol) and triethylamine (9.2 g, 91 mmol) in a solution of ethanol (20 mL) and N,N-dimethylformamide (1 mL), a solution of crude 4,4-dichloro-1,1,1-trifluoro-3-buten-2-one in dichloromethane (20 mL) was added dropwise while keeping the temperature of the reaction mixture below 10° C. After stirring a further 2 h at below 10° C., the reaction mixture was concentrated under reduced pressure. The residue was diluted with diethyl ether, and the mixture was filtered. The resulting filtrate was concentrated to give 4.34 g of the title compound as a solid. This compound was of sufficient purity to use in subsequent reactions.

$^1$H NMR ($CDCl_3$): δ 1.29 (t, 3H), 4.27 (q, 2H), 4.97 (s, 1H), 6.55 (s, 1H).

$^{19}$F NMR ($CDCl_3$) δ −63.4.

Step E: Preparation of 5-chloro-3-(trifluoromethyl)-1H-pyrazole-1-acetic acid A solution of ethyl 5-chloro-3-(trifluoromethyl)-1H-pyrazole-1-acetate (i.e. the product of Example 10, Step D or D1) (218 mg, 0.85 mmol) in tetrahydrofuran (1 mL) was treated with a 50 wt. % aqueous solution of sodium hydroxide (0.2 mL) in water (0.6 mL). The reaction mixture was stirred at room temperature for 4 h. The reaction mixture was treated with concentrated aqueous hydrochloric acid to lower the pH to 1 and then extracted with ethyl acetate. The extract was dried ($MgSO_4$) and concentrated under pressure to give 140 mg of the title compound. This compound was of sufficient purity to use in subsequent reactions.

$^1$H NMR (DMSO-$d_6$): δ 5.41 (s, 2H), 7.09 (s, 1H).

Step F: Preparation of 2-[5-chloro-3-(trifluoromethyl)-1H-pyrazol-1-yl]-1-[4-[4-(4,5-dihydro-5-phenyl-3-isoxazolyl)-2-thiazolyl]-1-piperidinyl]ethanone To a solution of 1,1-dimethylethyl 4-[4-(4,5-dihydro-5-phenyl-3-isoxazolyl)-2-thiazolyl]-1-piperidinecarboxylate (i.e. the product of Example 1, Step A) (1.026 g, 2.48 mmol) in ethanol (10 mL) was added a 2 M solution of hydrogen chloride in diethyl ether (4.2 mL, 12.6 mmol). The reaction mixture was stirred at room temperature overnight. Then the reaction mixture was heated at 60° C. for 2 h. The reaction mixture was cooled to room temperature and concentrated under reduced pressure to give 0.710 g of 4-[4-(4,5-dihydro-5-phenyl-3-isoxazolyl)-2-thiazolyl]-1-piperidine hydrochloride as a white solid.

To 5-chloro-3-(trifluoromethyl)-1H-pyrazole-1-acetic acid (i.e. the product of Example 10, Step E) (0.14 g, 0.61 mmol) in dichloromethane (5 mL) was added N,N-dimethylformamide (1 drop) followed by oxalyl chloride (0.07 mL, 0.80 mmol) at room temperature. The reaction mixture was stirred at room temperature for 1 h and then concentrated under reduced pressure. The resulting crude 5-chloro-3-(trifluoromethyl)-1H-pyrazole-1-acetyl chloride was taken up in 5 mL of dichloromethane, and the resulting solution was added dropwise to a mixture of 4-[4-(4,5-dihydro-5-phenyl-3-isoxazolyl)-2-thiazolyl]-1-piperidine hydrochloride (0.20 g, 0.57 mmol) prepared above and triethylamine (0.40 mL, 2.85 mmol) in 10 mL of dichloromethane at 0° C. The reaction mixture was stirred overnight at room temperature and then diluted with 1 N aqueous hydrochloric acid solution. The organic layer was separated, washed with water, dried ($MgSO_4$), and concentrated under reduced pressure and purified by medium-pressure liquid chromatography using ethyl acetate in hexanes as eluant to give 40 mg of the title product as a solid, melting at 128-131° C.

$^1$H NMR ($CDCl_3$): δ 1.81 (m, 2H), 2.20 (m, 2H), 2.89 (m, 1H), 3.31 (m, 2H), 3.46 (m, 1H), 3.87 (m, 2H), 4.55 (m, 1H), 5.08 (M, 2H), 5.75 (m, 1H), 6.54 (s, 1H), 7.25-7.42 (m, 5H), 7.63 (s, 1H).

EXAMPLE 11

Preparation of 2-[5-bromo-3-(trifluoromethyl)-1H-pyrazol-1-yl]-1-[4-[4-(4,5-dihydro-5-phenyl-3-isoxazolyl)-2-thiazolyl]-1-piperidinyl]ethanone (Compound 126)

Step A: Preparation of 5-bromo-N,N-dimethyl-3-(trifluoromethyl)-1H-pyrazole-1-sulfonamide A stirred solution of N,N-dimethyl-3-(trifluoromethyl)-1H-pyrazole-1-sulfonamide (i.e. the product of Example 10, Step A) (4.25 g, 17.5 mmol) in tetrahydrofuran (50 mL) was cooled to −78° C., and then 2 M n-butyllithium in cyclohexane (10.0 mL, 20.0 mmol) was added dropwise. The reaction mixture was stirred a further 30 minutes, and then bromine (1.0 mL, 3.1 g, 18.7 mmol) was added dropwise. The reaction mixture was stirred for 10 minutes, warmed to room temperature, and quenched with brine (50 mL). The resulting mixture was extracted with diethyl ether, and the extract was dried ($MgSO_4$), and concentrated under reduced pressure to give 6.77 g of title compound as a light yellow oil. This compound was of sufficient purity to use in subsequent reactions.

$^1$H NMR (CDCl$_3$): δ 3.15 (s, 6H), 6.69 (s, 1H).

Step B: Preparation 5-bromo-3-(trifluoromethyl)-1H-pyrazole

A solution of 5-bromo-N,N-dimethyl-3-(trifluoromethyl)-1H-pyrazole-1-sulfonamide (i.e. the product of Example 11, Step A) (4.50 g, 14.0 mmol) and trifluoroacetic acid (2.0 mL, 26 mmol) was stirred at 25° C. for 4 h. The reaction mixture was diluted with water (20 mL), and sodium hydroxide was added to raise the pH to 12. The solution was extracted with chloroform, dried (MgSO$_4$), and concentrated under reduced pressure to give 2.73 g of the title compound as a yellow light oil. This compound was of sufficient purity to use in subsequent reactions.

$^1$H NMR (CDCl$_3$): δ 6.63 (m, 1H).

Step C: Preparation of ethyl 5-bromo-3-(trifluoromethyl)-1H-pyrazole-1-acetate A suspension of 5-bromo-3-(trifluoromethyl)-1H-pyrazole (i.e. the product of Example 11, Step B) (2.73 g, 12.7 mmol) and potassium carbonate (2.0 g, 14.5 mmol) in N,N-dimethylformamide (20 mL) was treated with ethyl iodoacetate (3.0 ml, 25.3 mmol), and the resulting mixture was stirred at 95° C. for 3 h. The resulting mixture was diluted with ethyl acetate, washed with water, and dried (MgSO$_4$). The reaction mixture was concentrated under reduced pressure and further purified by medium-pressure liquid chromatography using 0-50% of ethyl acetate in hexanes as eluant to give 2.84 g of the title compound as a brown oil.

$^1$H NMR (CDCl$_3$): δ 1.29 (m, 3H), 4.26 (q, 2H), 5.00 (m, 2H), 6.64 (s, 1H).

Step D: Preparation of 5-bromo-3-(trifluoromethyl)-1H-pyrazole-1-acetic acid A solution of ethyl 5-bromo-3-(trifluoromethyl)-1H-pyrazole-1-acetate (i.e. the product of Example 11, Step C) (2.84 g, 9.4 mmol) in tetrahydrofuran (10 mL) was treated with a 50 wt. % aqueous sodium hydroxide solution (1.0 mL). The reaction mixture was stirred at room temperature for 2 h. The reaction mixture was treated with concentrated aqueous hydrochloric acid to lower the pH to 1 and then extracted with ethyl acetate. The extract was dried (MgSO$_4$) and concentrated under pressure to give 2.26 g of the title compound as a light brown solid. Recrystallization from 1-chlorobutane (20 mL) gave 0.68 g of the title compound as lustrous light pink plates.

$^1$H NMR (CDCl$_3$): δ 5.08 (s, 2H), 6.65 (s, 1H).

Step E: Preparation of 2-[5-bromo-3-(trifluoromethyl)-1H-pyrazol-1-yl]-1-[4-[4-(4,5-dihydro-5-phenyl-3-isoxazolyl)-2-thiazolyl]-1-piperidinyl]ethanone To a solution of 5-bromo-3-(trifluoromethyl)-1H-pyrazole-1-acetic acid (i.e. the product of Example 11, Step D) (0.12 g, 0.61 mmol) in dichloromethane (5 mL) was added N,N-dimethylformamide (1 drop) followed by oxalyl chloride (0.25 mL, 2.86 mmol). The reaction mixture was stirred at room temperature for 1 h and then concentrated under reduced pressure. The residue containing crude acid chloride was taken up in dichloromethane (5 mL), and the solution was added dropwise to a mixture of 4-[4-(4,5-dihydro-5-phenyl-3-isoxazolyl)-2-thiazolyl]-1-piperidine hydrochloride (i.e. the intermediate of Example 10, Step F) (0.15 g, 0.43 mmol) and triethylamine (0.25 mL, 1.8 mmol) in dichloromethane (5 mL) at 0° C. The reaction mixture was allowed to warm to room temperature and then stirred overnight at room temperature. The mixture was then partitioned between 1.0 N aqueous hydrochloric acid solution and dichloromethane. The organic layer was washed with water, dried (MgSO$_4$), concentrated under reduced pressure, and purified by medium-pressure liquid chromatography using ethyl acetate in hexanes as eluant to give 90 mg of the title product as an amorphous solid.

$^1$H NMR (CDCl$_3$): δ 1.84 (m, 2H), 2.20 (m, 2H), 2.89 (m, 1H), 3.31 (m, 2H), 3.46 (m, 1H), 3.89 (m, 2H), 4.58 (m, 1H), 5.11 (m, 2H), 5.75 (m, 1H), 6.63 (s, 1H), 7.25-7.42 (m, 5H), 7.66 (s, 1H).

EXAMPLE 12

Preparation of 1-[4-[4-[(5R)-4,5-dihydro-5-phenyl-3-isoxazolyl]-2-thiazolyl]-1-piperidinyl]-2-[5-methyl-3-(trifluoromethyl)-1H-pyrazol-1-yl]ethanone (Compound 3)

Step A: Preparation of 4,5-dihydro-N,N-dimethyl-5-phenyl-3-isoxazolecarboxamide To a solution of 2-(dimethylamino)-N-hydroxy-2-oxoethanimidoyl chloride (prepared according to the procedure of E. Raleigh, U.S. Pat. No. 3,557,089) (6.0 g, 40 mmol) and styrene (6.0 g, 60 mmol) in toluene (15 mL) was added a solution of potassium hydrogen carbonate (5.0 g, 50 mmol) in water (25 mL) over 1 h, while keeping the reaction temperature between 7 and 10° C. The reaction mixture was diluted with 10 mL of toluene and stirred for an additional 10 minutes. The organic layer was separated and washed with water. The organic layer was concentrated under reduced pressure until no styrene remained to give 8.7 g of the title compound as a light yellow oil. This compound was of sufficient purity to use in subsequent reactions.

$^1$H NMR (CDCl$_3$): δ 3.08 (s, 3H), 3.32 (s, 3H), 3.35 (dd, 1H), 3.71 (dd, 1H), 5.65 (dd, 1H), 7.35 (m, 5H).

Step B: Preparation of 4,5-dihydro-5-phenyl-3-isoxazolecarboxylic acid

To a solution of 4,5-dihydro-N,N-dimethyl-5-phenyl-3-isoxazolecarboxamide (i.e. the product of Example 12, Step A) (60.0 g, 275 mmol) in methanol (300 mL) was added an aqueous sodium hydroxide solution (44 g of 50 wt. % aqueous NaOH in 50 mL of water) dropwise over 30 minutes while maintaining the temperature of the reaction mixture at 45° C. The reaction mixture was allowed to cool to room temperature and stirred overnight. The resulting mixture was concentrated under reduced pressure and treated with 200 mL of water. The pH of the reaction mixture was adjusted using concentrated hydrochloric acid to about 1.0. The crude product was extracted into ethyl acetate (200 mL). The ethyl acetate solution was concentrated under reduced pressure, and the residue was triturated with hexanes. The resulting precipitate was filtered, washed with hexanes (2×20 mL), and dried under vacuum to give 46.5 g of the title compound as a solid.

$^1$H NMR (CDCl$_3$): δ 3.25 (dd, 1H), 3.75 (dd, 1H), 5.85 (dd, 1H), 7.35 (m, 5H), 8.1 (br s, 1H).

Step C: Preparation of the cinchonine salt of (5R)-4,5-dihydro-5-phenyl-3-isoxazole-carboxylic acid A mixture of racemic 4,5-dihydro-5-phenyl-3-isoxazole-carboxylic acid (i.e. the product of Example 12, Step B) (9.5 g, 50 mmol) in methanol (70 mL) was heated to 55° C., and cinchonine (containing about 15% dihydrocinchonine, 14.5 g, 50 mmol) was added over 20 minutes while keeping the temperature of the reaction mixture between 53 and 57° C. The reaction mixture was allowed to cool to room temperature over 60 minutes, and then water (35 mL) was added dropwise over 30 minutes. The resulting slurry was cooled to 10° C. and filtered. The filter cake was washed twice with 10 mL of 25% methanol in water, and air dried to give 8.52 g of the title compound as a solid. The diastereomeric ratio of the product was determined using chiral high performance liquid chromatography (HPLC) analysis on a Daicel Chiralcel® OD HPLC column to be about 99:1.

$^1$H NMR (CDCl$_3$): δ 3.25 (dd, 1H), 3.75 (dd, 1H), 5.85 (dd, 1H), 7.35 (m, 5H), 8.1 (br s, 1H).

Step D: Preparation of (5R)-4,5-dihydro-N,N-dimethyl-5-phenyl-3-isoxazole-carboxamide The cinchonine salt of (5R)-4,5-dihydro-5-phenyl-3-isoxazolecarboxylic acid (i.e. the product of Example 12, Step C) (98% diastereomeric excess, 16.5 g, 34.3 mmol) was slurried in a mixture of 1 N hydrochloric acid (90 mL), cyclohexane (100 mL) and ethyl acetate (40 mL). After all the solids dissolved, the phases were separated, and the organic layer was washed with brine (20 mL) and concentrated under reduced pressure to give 5.6 g of white solid. To a solution of the resulting free acid (5.0 g, 26.2 mmol) in ethyl acetate (100 mL) at room temperature was added N,N-dimethylformamide (1 drop) followed by thionyl chloride (4.25 g, 35.7 mmol). The reaction mixture was then heated under reflux for 3 h. The resulting mixture was cooled and concentrated under reduced pressure. The residue containing crude acid chloride was dissolved in ethyl acetate (25 mL), and this solution was added in portions to a pre-cooled (5° C.) mixture of dimethylamine in tetrahydrofuran (29 mL, of a 2.0 M solution), while maintaining the temperature of the mixture at 5-10° C. When the addition was complete, the reaction mixture was concentrated under reduced pressure, and diluted with water (50 mL). The resulting precipitate was filtered, washed with water and suction-dried overnight to give 4.1 g of the title compound as a light tan solid, melting at 59-61° C. This compound was of sufficient purity to use in subsequent reactions.

Step E: Preparation of 2-bromo-1-[(5R)-4,5-dihydro-5-phenyl-3-isoxazolyl]ethanone A solution of (5R)-4,5-dihydro-N,N-dimethyl-5-phenyl-3-isoxazole-carboxamide (i.e. the product of Example 12, Step D) (3.5 g, 16.0 mmol) in a mixture of tetrahydrofuran (5 mL) and toluene (10 mL) was cooled to −15° C., and methyl magnesium bromide (3.0 M solution in tetrahydrofuran, 8.8 mL, 26.4 mmol) was added over 1 h at −15° C. Then the reaction mixture was poured over a mixture of 20 g of concentrated hydrochloric acid and 80 g of ice, and the organic phase was separated. The aqueous phase was extracted with ethyl acetate (100 mL), and the combined extract was washed with brine (40 mL) and concentrated under reduced pressure to give 3.2 g of 1-[(5R)-4,5-dihydro-5-phenyl-3-isoxazoyl]ethanone.

$^1$H NMR (CDCl$_3$): δ 2.55 (s, 3H), 3.17 (dd, 1H), 3.54 (dd, 1H), 5.75 (dd, 1H), 7.35 (m, 5H).

1-[(5R)-4,5-dihydro-5-phenyl-3-isoxazoyl]ethanone (3.2 g, 16.7 mmol) was dissolved in 1,2-dichloroethane (15 mL), and a solution of bromine (2.13 g, 13.3 mmol) in dichloroethane (5 mL) was added over 30 minutes while maintaining the temperature of the reaction mixture at about 30° C. The reaction mixture was diluted with water (10 mL), and the organic layer was concentrated under reduced pressure and purified by medium-pressure liquid chromatography using 35% of dichloromethane in hexanes as eluant to give 2.6 g of the title compound as a white solid, melting at 31-33° C.

$^1$H NMR (CDCl$_3$): δ 3.20 (dd, 1H), 3.60 (dd, 1H), 4.49 (s, 2H), 5.80 (dd, 1H), 7.35 (m, 5H).

Step E1: Preparation of 2-bromo-1-(4,5-dihydro-5-phenyl-3-isoxazolyl)ethanone (racemate)

To a solution of 4,5-dihydro-N,N-dimethyl-5-phenyl-3-isoxazolecarboxamide (i.e. the product of Example 12, Step A) (17 g, 78.0 mmol) in a mixture of tetrahydrofuran (20 mL) and toluene (80 mL) was added methyl magnesium bromide (3.0 M solution in tetrahydrofuran, 28 mL, 84 mmol) over 1 h, while keeping the reaction temperature between −10 and −15° C. The reaction mixture was poured over a mixture of concentrated hydrochloric acid (20 g) and ice (80 g), and the organic phase was separated. The aqueous phase was extracted with ethyl acetate (100 mL), and the combined organic extracts were washed with brine (40 mL) and concentrated under reduced pressure to give 14.4 g of 1-(4,5-dihydro-5-phenyl-3-isoxazoyl)ethanone as a light yellow oil.

$^1$H NMR (CDCl$_3$): δ 2.55 (s, 3H), 3.17 (dd, 1H), 3.54 (dd, 1H), 5.75 (dd, 1H), 7.35 (m, 5H).

1-(4,5-Dihydro-5-phenyl-3-isoxazoyl)ethanone (11.5 g, 60 mmol) was dissolved in ethyl acetate (45 mL), and a solution of bromine (9.6 g, 60.0 mmol) in ethyl acetate (30 mL) was added over 30 minutes while maintaining the temperature of the reaction mixture at about 30° C. After 1 h, the reaction mixture was diluted with water (10 mL), and the organic layer was concentrated under reduced pressure to give 16.7 g of reddish oil which contained about 10% starting methyl ketone and ~10% dibrominated ketone.

$^1$H NMR (CDCl$_3$) δ 3.20 (dd, 1H), 3.60 (dd, 1H), 4.49 (s, 2H), 5.80 (dd, 1H), 7.35 (m, 5H).

Step F: Preparation of 1-[4-[4-[(5R)-4,5-dihydro-5-phenyl-3-isoxazolyl]-2-thiazolyl]-1-piperidinyl]-2-[5-methyl-3-(trifluoromethyl)-1H-pyrazol-1-yl]ethanone A mixture of 1-[2-[5-methyl-3-(trifluoromethyl)-1H-pyrazol-1-yl]acetyl]-4-piperidine-carbothioamide (i.e. the product of Example 8, Step C) (1.7 g, 5.0 mmol) and 2-bromo-1-[(5R)-4,5-dihydro-5-phenyl-3-isoxazolyl]ethanone (i.e. the product of Example 12, Step E) (1.35 g, 5 mmol) in ethanol (15 mL) was heated at 50° C. for 30 minutes. The reaction mixture was diluted with water and extracted with dichloromethane. The extract was washed with brine, dried (MgSO$_4$), and concentrated under reduced pressure to give the title product as a pale-yellow gum. High performance liquid chromatography (HPLC) analysis showed that the title product was about 95% pure and contained the (R)-enantiomer in about 98% enantiomeric excess.

$^1$H NMR (CDCl$_3$): δ 1.8 (m, 2H), 2.2 (m, 2H), 2.32 (s, 3H), 2.9 (m, 1H), 3.3 (m, 2H), 3.42 (dd, 1H), 3.82 (dd, 1H), 4.05 (m, 1H), 4.6 (m, 1H), 5.0 (q, 2H), 5.78 (dd, 1H), 6.35 (s, 1H), 7.4 (m, 5H), 7.62 (s, 1H).

EXAMPLE 13

Preparation of 1-[4-[4-(4,5-dihydro-5-phenyl-3-isoxazolyl)-2-thiazolyl]-3,6-dihydro-1(2H)-pyridinyl]-2-[5-methyl-3-(trifluoromethyl)-1H-pyrazol-1-yl]ethanone (Compound 217)

Step A: Preparation of 4-[4-(4,5-dihydro-5-phenyl-3-isoxazolyl)-2-thiazolyl]pyridine To a solution of thioisonicotinamide (0.5 g, 3.6 mmol) in 1-methyl-2-pyrrolidinone (25 mL) was added 2-chloro-1-(4,5-dihydro-5-phenyl-3-isoxazolyl)ethanone (0.807 g, 3.6 mmol), at room temperature. The reaction mixture was then heated to 100° C. for 3 h. Then the reaction mixture was cooled to room temperature, quenched with water (100 mL) and extracted with ethyl acetate (50 mL×2). The reaction mixture was diluted with water (50 mL) and brine (50 mL), and the organic layer was concentrated under reduced pressure and purified by medium-pressure liquid chromatography using 2% of methanol in chloroform as eluant to give 0.7 g of the title compound as a brown solid.

$^1$H NMR (CDCl$_3$): δ 3.5 (m, 1H), 3.9 (m, 1H), 5.8 (m, 1H), 7.35 (m, 5H), 8.16 (s, 1H), 8.3 (d, 2H), 8.8 (d, 2H).

Step B: Preparation of 4-[4-(4,5-dihydro-5-phenyl-3-isoxazolyl)-2-thiazolyl]-1,2,3,6-tetrahydro-1-(phenylmethyl)pyridine To a solution of 4-[4-(4,5-dihydro-5-phenyl-3-isoxazolyl)-2-thiazolyl]pyridine (i.e. the product of Example 13, Step A) (0.60 g, 1.95 mmol) in toluene (10 mL) was added benzyl bromide (0.670 g, 3.90 mmol), and the reaction mixture was heated to 100° C. for 12 h. Then the reaction mixture was cooled to room temperature. The solid that precipitated out was filtered and dried. The solid was dissolved in methanol (10 mL), and sodium borohydride (0.072 g, 1.95 mmol) was added in portions. The reaction mixture was stirred at room temperature for 2 h, diluted with water (50 mL), neutralized with 1.5 N aqueous hydrochloric acid solution, and extracted with ethyl acetate (50 mL). The organic layer was separated, washed with brine (25 mL), and concentrated under reduced pressure. The residue was purified by medium-pressure liquid chromatography using 3% of methanol in chloroform as eluant to give 0.4 g of the title compound as a white solid.

$^1$H NMR (CDCl$_3$): δ 3.03-3.1 (m, 2H), 3.4-3.6 (m, 4H), 3.8-4.0 (m, 2H), 4.25-4.32 (m, 2H), 5.76-5.79 (m, 1H), 6.47 (s, 1H), 7.34-7.48 (m, 10H), 7.72 (s, 1H).

Step C: Preparation of 4-[4-(4,5-dihydro-5-phenyl-3-isoxazolyl)-2-thiazolyl]-1,2,3,6-tetrahydropyridine hydrochloride To a solution of 4-[4-(4,5-dihydro-5-phenyl-3-isoxazolyl)-2-thiazolyl]-1,2,3,6-tetrahydro-1-(phenylmethyl)pyridine (i.e. the product of Example 13, Step B) (0.400 g, 0.99 mmol) in dichloroethane (10 mL) was added 1-chloroethyl chloroformate (0.286 g, 1.99 mmol), and the reaction mixture was heated to 80° C. for 5 h. The reaction mixture was cooled to room temperature and concentrated under reduced pressure. Methanol (10 mL) was added to the residue, and the resulting mixture was heated to 60° C. for 1 h, cooled to room temperature, and concentrated under reduced pressure. The residue was triturated with 50% of petroleum ether in ethyl acetate, and the solid formed was filtered and dried to give 0.25 g of the title compound as a white solid.

$^1$H NMR (DMSO-d$_6$): δ 2.50-2.55 (m, 2H), 3.31-3.39 (m, 3H), 3.86-3.91 (m, 3H), 5.73-5.78 (m, 1H), 6.67 (s, 1H), 7.34-7.39 (m, 5H), 7.68 (s, 1H), 9.47 (s, 2H).

Step D: Preparation of 1-[4-[4-(4,5-dihydro-5-phenyl-3-isoxazolyl)-2-thiazolyl]-3,6-dihydro-1(2H)-pyridinyl]-2-[5-methyl-3-(trifluoromethyl)-1H-pyrazol-1-yl]ethanone To a solution of 4-[4-(4,5-dihydro-5-phenyl-3-isoxazolyl)-2-thiazolyl]-1,2,3,6-tetrahydropyridine hydrochloride (i.e. the product of Example 13, Step C) (0.250 g, 0.720 mmol) and 5-methyl-3-(trifluoromethyl)-1H-pyrazole-1-acetic acid (0.150 g, 0.720 mmol) in dichloromethane (10 mL) was added N-(3-dimethylaminopropyl)-N'-ethylcarbodiimide (0.138 g, 0.720 mmol), 1-hydroxybenzotriazole (0.024 g, 0.177 mmol), and triethylamine (0.145 g, 1.44 mmol) at room temperature. The reaction mixture was stirred at room temperature for 24 h. The reaction mixture was diluted with dichloromethane (30 mL) and washed with water (20 mL) and brine (20 mL). The organic layer was separated, washed with water, dried (Na$_2$SO$_4$), and concentrated under reduced pressure and purified by medium-pressure liquid chromatography using 3% methanol in chloroform as eluant to give 200 mg of the title product as a white solid.

$^1$H NMR (CDCl$_3$): δ 2.3 (s, 3H), 2.71-2.75 (m, 2H), 3.42-3.46 (m, 1H), 3.74-3.88 (m, 3H), 4.24-4.27 (m, 2H), 5.02 (s, 2H), 5.71-5.76 (m, 1H), 6.32 (s, 1H), 6.57 (s, 1H), 7.3-7.38 (m, 5H), 7.64 (s, 1H).

EXAMPLE 14

Preparation of 1-[4-[4-[(5R)-4,5-dihydro-5-phenyl-3-isoxazolyl]-2-thiazolyl]-1-piperidinyl]-N-[2,5-dimethylphenyl]carboxamide (Compound 343)

Step A: Preparation of 4-cyano-N-(2,5-dimethylphenyl)piperidinecarboxamide

A solution of 4-cyanopiperidine (11.0 g, 100 mmol) in diethyl ether (350 mL) was cooled to 0° C. with an ice-water bath. A solution of 2,5-dimethylphenyl isocyanate (14.7 g, 100 mmol) in diethyl ether (50 mL) was added into the reaction mixture over 30 minutes to give a thick precipitate. The reaction mixture was warmed to room temperature, and the resulting solids were filtered, washed with diethyl ether and air-dried to give 25.3 g of the title compound as a white powder, melting at 187-190° C.

$^1$H NMR (CDCl$_3$): δ 1.95 (m, 4H), 2.19 (s, 3H), 2.30 (s, 3H), 2.90 (m, 1H), 3.45 (m, 2H), 3.70 (m, 2H), 6.10 (br s, 1H), 6.85 (m, 1H), 7.04 (m, 1H), 7.37 (m, 1H).

Step B: Preparation of N-(2,5-dimethylphenyl)-4-thiocarbamoylpiperidine-carboxamide A mixture of 4-cyano-N-(2,5-dimethylphenyl)piperidinecarboxamide (i.e. the product of Example 14, Step A) (12.75 g, 49.6 mmol), sodium hydrosulfide hydrate (11.1 g, 150 mmol) and diethylamine hydrochloride (10.9 g, 100 mmol) in N,N-dimethylformamide (50 mL) was stirred at room temperature for 3 days. The resulting thick, green suspension was added dropwise into ice water (600 mL). The resulting solid was filtered, washed with water and air-dried to give 12.5 g of the title compound as a tan solid decomposing at 155-156° C.

$^1$H NMR (DMSO-d$_6$): δ 1.67 (m, 4H), 2.10 (s, 3H), 2.23 (s, 3H), 2.75 (m, 3H), 4.15 (m, 2H), 6.85 (m, 1H), 7.0 (m, 1H), 7.05 (m, 1H), 7.95 (br s, 1H), 9.15 (br s, 1H), 9.22 (br s, 1H).

Step C: Preparation of 1-[4-[4-[(5R)-4,5-dihydro-5-phenyl-3-isoxazolyl]-2-thiazolyl]-1-piperidinyl]-N-[2,5-dimethylphenyl]carboxamide A mixture of N-(2,5-dimethylphenyl)-4-thiocarbamoylpiperidine carboxamide (i.e. the product of Example 14, Step B) (291 mg, 1.0 mmol) and 409 (i.e. the product of Example 12, Step E) (268 mg, 1.0 mmol) in acetone (10 mL) was vortexed for 16 h and then heated at 45° C. for 1 h. The reaction mixture was allowed to cool to room temperature, treated with solid sodium bicarbonate (168 mg, 2.0 mmol), and stirred for 1 h. The reaction mixture was then concentrated under reduced pressure, diluted with ethyl acetate, washed with water and brine, dried (MgSO$_4$), and concentrated under reduced pressure to give the title product as a pale-yellow foam. The sample was dissolved in methyl acetate (2 mL) and allowed to sit at room temperature and then at 0° C. to give 220 mg of colorless crystals melting at 120-125° C. A second preparation was crystallized from methanol to give large prisms melting at 121-124° C.

$^1$H NMR (CDCl$_3$): δ 1.85 (m, 2H), 1.99 (m, 2H), 2.21 (s, 3H), 2.31 (s, 3H), 3.08 (m, 2H), 3.25 (m, 1H), 3.42 (dd, 1H), 3.82 (dd, 1H), 4.15 (m, 2H), 5.78 (dd, 1H), 6.12 (br s, 1H), 6.82 (m, 1H), 7.02 (m, 1H), 7.2-7.4 (m, 5H), 7.46 (m, 1H), 7.62 (s, 1H).

EXAMPLE 15

Preparation of 2-(3,5-dibromo-1H-1,2,4-triazol-1-yl)-1-[4-[4-[5-(2,6-difluorophenyl)-4,5-dihydro-3-isoxazolyl]-2-thiazolyl]-1-piperidinyl]ethanone (Compound 409)

Step A: Preparation of 3,5-dibromo-1H-1,2,4-triazole

To a solution of 13.8 g (200 mmol) of 1,2,4-triazole in a mixture of water (150 mL) and dichloromethane (20 mL) was added simultaneously sodium hydroxide (48 g of 50% aqueous solution, 600 mmol) in water (50 mL) and bromine (65.0 g, 406 mmol) in dichloromethane (20 mL) cooled with an ice-bath over a period of 30 minutes. The reaction mixture was allowed to warm to room temperature and stirred overnight. The resulting thick white suspension was acidified with 6 N hydrochloric acid (40 mL, 240 mmol) with cooling in an ice-bath, and stirring was continued for 1 h. The reaction mixture was filtered on a Buchner funnel, and the collected solid was air dried for 5 days to give 41.92 g of the title compound as a pure white solid melting at 213-217° C.

Step B: Preparation of 3,5-dibromo-1H-1,2,4-triazole-1-acetic acid

A solution of 3,5-dibromo-1H-1,2,4-triazole (i.e. the product of Example 15, Step A) (4.54 g, 20.0 mmol) in acetonitrile (20 mL) was treated with potassium carbonate (5.0 g) and ethyl bromoacetate (4.52 g, 27.0 mmol). The reaction mixture was heated at reflux for 4 h and then cooled to room temperature. The reaction mixture was diluted with ethyl acetate (150 mL), filtered, washed with water, 1 N hydrochloric acid and saturated aqueous sodium bicarbonate, and dried (MgSO$_4$). The resulting mixture was filtered and concentrated under reduced pressure to give 6.19 g of ester compound as a pale yellow oil. The ester compound in tetrahydrofuran (40 mL) was treated with 2 N aqueous sodium hydroxide (20 mL) and stirred at room temperature for 3 h. The reaction mixture was cooled in an ice bath and acidified with 6 N hydrochloric acid (10 mL). The resulting mixture was extracted with ether (200 mL), and the separated organic layer was washed with saturated aqueous sodium chloride, dried (MgSO$_4$), filtered and concentrated to give 6.38 g of the title compound as a pale yellow oil. The crude product was triturated with hot n-butyl chloride (100 mL). The mixture was cooled to room temperature and filtered to give 3.77 g of the title compound as a white solid melting at 147-152° C.

$^1$H NMR (CDCl$_3$): δ 5.00 (s, 2 H).

Step C: Preparation of 2-(3,5-dibromo-1H-1,2,4-triazol-1-yl)-1-[4-[4-[5-(2,6-difluorophenyl)-4,5-dihydro-3-isoxazolyl]-2-thiazolyl]-1-piperidinyl] ethanone A mixture of 3,5-dibromo-1H-1,2,4-triazole-1-acetic acid (i.e. the product of Example 15, Step B) (430 mg, 1.51 mmol) in thionyl chloride (10 mL) was heated at reflux for 1 h. The reaction mixture was then cooled to room temperature and concentrated under reduced pressure. The resulting crude acid chloride was dissolved in dichloromethane (5 mL) and added to a solution of 4-[4-[4,5-dihydro-5-(2,6-difluorophenyl)-3-isoxazolyl]-2-thiazolyl]piperidine hydrochloride (prepared by a method analogous to Example 10, Step F) (585 mg, 1.52 mmol) and triethylamine (1 mL) in dichloromethane (10 mL). The reaction mixture was stirred at room temperature for 2 h, diluted with dichloromethane, washed with 1 N hydrochloric acid, aqueous sodium chloride, and dried (MgSO4). The reaction mixture was concentrated under reduced pressure and further purified by medium-pressure liquid chromatography to give 338 mg of the title product as a white solid melting at 185-189° C.

$^1$H NMR (CDCl$_3$): δ 1.90 (m, 2H), 2.27 (m, 2H), 2.97 (m, 1H), 3.33 (m, 2H), 3.64 (m, 1H), 3.81 (m, 2H), 4.57 (m, 1H), 5.03 (s, 2H), 6.09 (m, 1H), 6.92 (m, 2H), 7.31 (m, 1H), 7.68 (s, 1H).

EXAMPLE 16

Preparation of 2-(3,5-dichloro-1H-1,2,4-triazol-1-yl)-1-[4-[4-[5-(2,6-difluorophenyl)-4,5-dihydro-3-isoxazolyl]-2-thiazolyl]-1-piperidinyl]ethanone (Compound 410)

Step A: Preparation of 3,5-dichloro-1H-1,2,4-triazole

To a solution of concentrated aqueous hydrochloric acid (50 mL) in an ice (50 mL) was added 3,5-diamino-1,2,4-triazole (2.10 g, 21.2 mmol) and sodium nitrite (4.4 g, 63.7 mmol) sequentially over a period of 15 minutes. The reaction mixture was stirred for 1 h and warmed to room temperature. The reaction mixture was extracted with ether (300 mL). The combined organic layers were washed with saturated aqueous sodium chloride, dried (MgSO$_4$), filtered, and concentrated to give 2.75 g of the title compound as a light yellow solid suitable for use in subsequent reactions.

Step B: Preparation of 3,5-dichloro-1H-1,2,4-triazole-1-acetic acid

A solution of 3,5-dichloro-1H-1,2,4-triazole (i.e. the product of Example 16, Step A), (2.75 g, 19.6 mmol) in ethanol (25 mL) was treated with potassium carbonate (2.0 g) and ethyl bromoacetate (4.52 g, 27.0 mmol). The reaction mixture was heated at reflux for 1 h and then cooled to room temperature. The reaction mixture was diluted with water (100 mL) and extracted with ether (150 mL). The combined organic layers were washed with saturated aqueous sodium chloride and dried (MgSO₄). The resulting mixture was filtered and concentrated under reduced pressure to give 3.69 g of ester compound as a pale yellow oil. The ester compound in tetrahydrofuran (75 mL) was treated with 2 N aqueous sodium hydroxide (20 mL) and stirred at room temperature for 2 h. The reaction mixture was cooled in an ice bath and acidified with 1 N hydrochloric acid (35 mL). The resulting mixture was extracted with ether (200 mL), and the separated organic layer was washed with saturated aqueous sodium chloride, dried (MgSO₄), filtered and concentrated to give 2.51 g of the title compound a colorless oil.

$^1$H NMR (CDCl$_3$): δ 4.96 (s, 2 H).

Step C: Preparation of 2-(3,5-dichloro-1H-1,2,4-triazol-1-yl)-1-[4-[4-[5-(2,6-difluorophenyl)-4,5-dihydro-3-isoxazolyl]-2-thiazolyl]-1-piperidinyl]-ethanone A mixture of 3,5-dichloro-1H-1,2,4-triazole-1-acetic acid (i.e. the product of Example 16, Step B), (114 mg, 0.58 mmol) in thionyl chloride (5 mL) was heated at reflux for 1 h. The reaction mixture was then cooled to room temperature and concentrated under reduced pressure. The resulting crude acid chloride was dissolved in dichloromethane (5 mL) and added to a solution of 4-[4-[4,5-dihydro-5-(2,6-difluorophenyl)-3-isoxazolyl]-2-thiazolyl]piperidine hydrochloride (196 mg, 0.51 mmol) and triethylamine (0.5 mL) in dichloromethane (5 mL). The reaction mixture was stirred at room temperature for 3 h, diluted with dichloromethane, washed with 1 N hydrochloric acid, aqueous sodium chloride, and dried (MgSO₄). The reaction mixture was concentrated under reduced pressure and further purified by medium-pressure liquid chromatography to give 80 mg of the title product as a white solid melting at 147-150° C.

$^1$H NMR (CDCl$_3$): δ 1.89 (m, 2H), 2.26 (m, 2H), 2.95 (m, 1H), 3.34 (m, 2H), 3.62 (m, 1H), 3.80 (m, 2H), 4.57 (m, 1H), 4.98 (s, 2H), 6.08 (m, 1H), 6.92 (m, 2H), 7.32 (m, 1H), 7.67 (s, 1H).

By the procedures described herein, together with methods known in the art, the following compounds of Tables 1A to 7 can be prepared. The following abbreviations are used in the Tables which follow: t means tertiary, s means secondary, n means normal, i means iso, c means cyclo, Ac means acetyl, Me means methyl, Et means ethyl, Pr means propyl (i.e. n-propyl), i-Pr means isopropyl, c-Pr means cyclopropyl, Bu means butyl, Pen means pentyl, Hex means hexyl, Am means amyl, CN means cyano. A dash (-) indicates no substituents.

The invention includes but is not limited to the following exemplary species of component (a) compounds.

TABLE 1A

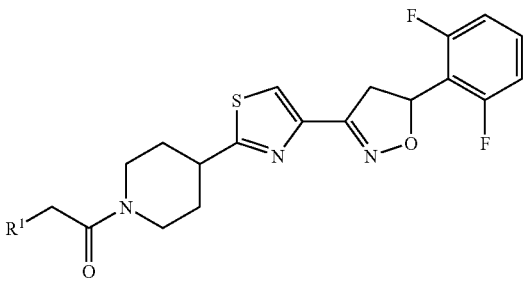

R¹ phenyl
2-methylphenyl
2-methoxyphenyl
2-chlorophenyl
2-bromophenyl
2-ethylphenyl
2-ethoxyphenyl
2-(methylthio)phenyl
2-(ethylthio)phenyl
2-(trifluoromethoxy)phenyl
3-chlorophenyl
3-bromophenyl
3-iodophenyl
3-methylphenyl
2-chloro-5-(trifluoromethyl)phenyl
2-chloro-5-(2,2,2-trifluoroethyl)phenyl
2-chloro-5-(pentafluoroethyl)phenyl
2-chloro-5-cyanophenyl
2-chloro-5-nitrophenyl
2-bromo-5-chlorophenyl
2,5-dibromophenyl
2-bromo-5-iodophenyl
2-bromo-5-methylphenyl
2-bromo-5-ethylphenyl
2-bromo-5-propylphenyl
2-bromo-5-isopropylphenyl
2-bromo-5-(trifluoromethyl)phenyl
2-bromo-5-(2,2,2-trifluoroethyl)phenyl
2-bromo-5-(pentafluoroethyl)phenyl
2-bromo-5-cyanophenyl
2-bromo-5-nitrophenyl
5-chloro-2-methylphenyl
5-bromo-2-methylphenyl
5-iodo-2-methylphenyl
2,5-dimethylphenyl
5-ethyl-2-methylphenyl
2-methyl-5-propylphenyl
5-isopropyl-2-methylphenyl
2-methyl-5-(trifluoromethyl)phenyl
2-methyl-5-(2,2,2-trifluoroethyl)phenyl
2-methyl-5-(pentafluoroethyl)phenyl
5-cyano-2-methylphenyl
2-methyl-5-nitrophenyl
5-chloro-2-methoxyphenyl
5-bromo-2-methoxyphenyl
5-iodo-2-methoxyphenyl
2-methoxy-5-methylphenyl
3-iodo-5-methylpyrazol-1-yl
3-ethyl-5-methylpyrazol-1-yl
5-methyl-3-propylpyrazol-1-yl
3-isopropyl-5-methylpyrazol-1-yl
5-methyl-3-(trifluoromethyl)pyrazol-1-yl
5-methyl-3-(2,2,2-trifluoroethyl)pyrazol-1-yl
5-methyl-3-(pentafluoroethyl)pyrazol-1-yl
3-cyano-5-methylpyrazol-1-yl
5-methyl-3-nitropyrazol-1-yl
5-chloro-3-methylpyrazol-1-yl
3,5-dichloropyrazol-1-yl
5-chloro-3-bromopyrazol-1-yl
5-chloro-3-iodopyrazol-1-yl
5-chloro-3-ethylpyrazol-1-yl
5-chloro-3-propylpyrazol-1-yl
5-chloro-3-isopropylpyrazol-1-yl
5-chloro-3-(trifluoromethyl)pyrazol-1-yl TABLE 1A-continued

[Structure: 2,6-difluorophenyl-dihydroisoxazole-thiazole-piperidine-C(O)-CH2-R1]

R1

5-chloro-3-(2,2,2-trifluoroethyl)pyrazol-1-yl
5-chloro-3-(pentafluoroethyl)pyrazol-1-yl
5-chloro-3-cyanopyrazol-1-yl
5-chloro-3-nitropyrazol-1-yl
5-bromo-3-methylpyrazol-1-yl
5-bromo-3-chloropyrazol-1-yl
3,5-dibromopyrazol-1-yl
5-bromo-3-iodopyrazol-1-yl
5-bromo-3-ethylpyrazol-1-yl
5-bromo-3-propylpyrazol-1-yl
5-bromo-3-isopropylpyrazol-1-yl
5-bromo-3-(trifluoromethyl)pyrazol-1-yl
5-bromo-3-(2,2,2-trifluoroethyl)pyrazol-1-yl
5-bromo-3-(pentafluoroethyl)pyrazol-1-yl
5-bromo-3-cyanopyrazol-1-yl
5-bromo-3-nitropyrazol-1-yl
2-chloro-5-(dimethylamino)phenyl
2-chloro-5-(diethylamino)phenyl
2-chloro-5-(cyclopropylamino)phenyl
3-(methoxymethyl)phenyl
2-chloro-5-(ethoxymethyl)phenyl
2-chloro-5-(hyroxymethyl)phenyl
2-chloro-5-(methoxycarbonyl)phenyl
2-chloro-5-(ethylcarbonyl)phenyl
2-chloro-5-(methylcarbonyloxy)phenyl
2-chloro-5-(metylaminocarbonyl)phenyl
2-chloro-5-(dimethylaminocarbonyl)phenyl
2-methyl-5-(trimethylsilyl)phenyl
3,5-dimethyl-2-thienyl
3,5-dichloro-2-thienyl
3,5-dimethyl-2-furyl
1-methyl-2-pyrrolyl
4-methyl-2-(trifluoromethyl)-5-thiazolyl
4-(trifluoromethyl)-2-thiazolyl
4-(trifluoromethyl)-2-oxazolyl
4-methyl-2-(trifluoromethyl)-5-oxazolyl
4-bromo-5-isothiazolyl
4-bromo-5-isoxazolyl
1-methyl-5-pyrazolyl
1-methyl-5-imidazolyl
1-methyl-4-(trifluoromethyl)-2-imidazolyl
4-methyl-3-(1,3,4-triazolyl)
2-methyl-3-(1,2,4-triazolyl)
5-(trifluoromethyl)-2-(1,3,4-thiadiazolyl)
5-(trifluoromethyl)-2-(1,3,4-oxadiazolyl)
3-(trifluoromethyl)-5-(1,2,4-thiadiazolyl)
3-(trifluoromethyl)-5-(1,2,4-oxadiazolyl)
3-(trifluoromethyl)-1-(1,2,4-triazolyl)
2,5-dimethyl-1-pyrrolyl
1-methyl-3-(trifluoromethyl)pyrazol-5-yl
3-bromo-5-(trifluoromethyl)pyrazol-1-yl
3-iodo-5-(trifluoromethyl)pyrazol-1-yl
3-ethyl-5-(trifluoromethyl)-pyrazol-1-yl
3-propyl-5-(trifluoromethyl)pyrazol-1-yl
3-isopropyl-5-(trifluoromethyl)pyrazol-1-yl
3-methyl-5-(trifluoromethyl))-pyrazol-1-yl
3-methoxy-5-(trifluoromethyl)-pyrazol-1-yl
5-difluoromethoxy-3-methylpyrazol-1-yl
5-difluoromethoxy-3-chloropyrazol-1-yl
3,5-dibromopyrazol-1-yl
5-difluoromethoxy-3-iodopyrazol-1-yl
5-difluoromethoxy-3-ethylpyrazol-1-yl
5-difluoromethoxy-3-propylpyrazol-1-yl
5-difluoromethoxy-3-isopropylpyrazol-1-yl TABLE 1A-continued

[Structure: 2,6-difluorophenyl-dihydroisoxazole-thiazole-piperidine-C(O)-CH2-R1]

R1

5-difluoromethoxy-3-(trifluoromethyl)pyrazol-1-yl
5-difluoromethoxy-3-(2,2,2-trifluoroethyl)pyrazol-1-yl
5-difluoromethoxy-3-(pentafluoroethyl)pyrazol-1-yl
5-difluoromethoxy-3-cyanopyrazol-1-yl
5-difluoromethoxy-3-nitropyrazol-1-yl
3-carbomethoxy-5-(trifluoromethyl)pyrazol-1-yl
5-methoxy-3-methylpyrazol-1-yl
5-methoxy-3-bromopyrazol-1-yl
5-methoxy-3-iodopyrazol-1-yl
5-methoxy-3-ethylpyrazol-1-yl
5-methoxy-3-propylpyrazol-1-yl
5-methoxy-3-isopropylpyrazol-1-yl
5-methoxy-3-(trifluoromethyl)pyrazol-1-yl
5-methoxy-3-(2,2,2-trifluoroethyl)pyrazol-1-yl
5-methoxy-3-(pentafluoroethyl)pyrazol-1-yl
5-methoxy-3-cyanopyrazol-1-yl
5-methoxy-3-nitropyrazol-1-yl
3,5-dichlorotriazol-1-yl
3-methyl-5-chlorotriazol-1-yl
3-methyl-5-bromo triazol-1-yl
3-chloro-5-trifluoromethyl triazol-1-yl
3-bromo-5-trifluoromethyl triazol-1-yl
3,5-bistrifluoromethyl triazol-1-yl
3-ethylphenyl
3-propylphenyl
3-isopropylphenyl
3-(trifluoromethyl)phenyl
3-(2,2,2-trifluoroethyl)phenyl
3-(pentafluoroethyl)phenyl
3-cyanophenyl
3-nitrophenyl
2,5-dichlorophenyl
5-bromo-2-chlorophenyl
2-chloro-5-iodophenyl
2-chloro-5-methylphenyl
2-chloro-5-ethylphenyl
2-chloro-5-propylphenyl
2-chloro-5-isopropylphenyl
5-ethyl-2-methoxyphenyl
2-methoxy-5-propylphenyl
5-isopropyl-2-methoxyphenyl
2-methoxy-5-(trifluoromethyl)phenyl
2-methoxy-5-(2,2,2-trifluoroethyl)phenyl
2-methoxy-5-(pentafluoroethyl)phenyl
5-cyano-2-methoxyphenyl
2-methoxy-5-nitrophenyl
5-chloro-2-ethylphenyl
5-bromo-2-ethylphenyl
2-ethyl-5-iodophenyl
2-ethyl-5-methylphenyl
2,5-diethylphenyl
2-ethyl-5-propylphenyl
2-ethyl-5-isopropylphenyl
2-ethyl-5-(trifluoromethyl)phenyl
2-ethyl-5-(2,2,2-trifluoroethyl)phenyl
2-ethyl-5-(pentafluoroethyl)phenyl
5-cyano-2-ethylphenyl
2-ethyl-5-nitrophenyl
3-methylpyrazol-1-yl
3-chloropyrazol-1-yl
3-bromopyrazol-1-yl
3-iodopyrazol-1-yl
3-ethylpyrazol-1-yl
3-(trifluoromethyl)pyrazol-1-yl

TABLE 1A-continued

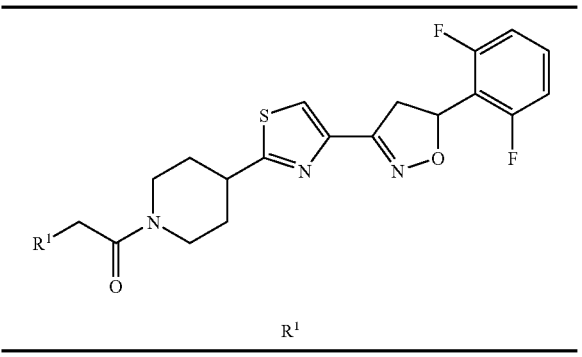

R¹

3-(2,2,2-trifluoroethyl)pyrazol-1-yl
3-(pentafluoroethyl)pyrazol-1-yl
3-cyanopyrazol-1-yl
3-nitropyrazol-1-yl
3,5-dimethylpyrazol-1-yl
3-chloro-5-methylpyrazol-1-yl
3-bromo-5-methylpyrazol-1-yl
5-methoxy-3-methylpyrazol-1-yl
3-chloro-5-methoxypyrazol-1-yl
5-ethyl-3-methylpyrazol-1-yl
3-chloro-5-ethylpyrazol-1-yl
3-bromo-5-ethylpyrazol-1-yl
5-ethyl-3-iodopyrazol-1-yl
3,5-diethylpyrazol-1-yl
5-ethyl-3-propylpyrazol-1-yl
5-ethyl-3-isopropylpyrazol-1-yl
5-ethyl-3-(trifluoromethyl)pyrazol-1-yl
5-ethyl-3-(2,2,2-trifluoroethyl)pyrazol-1-yl
5-ethyl-3-(pentafluoroethyl)pyrazol-1-yl
3-cyano-5-ethylpyrazol-1-yl
5-ethyl-3-nitropyrazol-1-yl
5-butyl-2-methylphenyl
5-hexyl-2-methylphenyl
5-allyl-2-methylphenyl
2-methyl-5-(4-methyl-3-pentenyl)phenyl
2-methyl-5-propargylphenyl
2-methyl-5-(3-methylpropargyl)phenyl
5-cyclopropyl-2-methylphenyl
5-cyclohexyl-2-methylphenyl
2-methyl-5-(pentafluoroisopropyl)phenyl
5-(3,3-dichloro-2-propen-1-yl)-2-methylphenyl
2-methyl-5-(4,4,4-trifluoro-2-butyn-1-yl)phenyl
5-(2,2-dichlorocyclopropan-1-yl)-2-methylphenyl
2-methyl-5-(trifluoromethoxy)phenyl
2-chloro-5-(isobutylthio)phenyl
2-chloro-5-(ethylsulfonyl)phenyl
2-chloro-5-(trifluoromethylthio)phenyl
2-chloro-5-(trifluoromethylsulfonyl)phenyl
2-chloro-5-(methylamino)phenyl
2-chloro-5-(tert-butylamino)phenyl
2,5-dimethyl-3-furyl
2,5-dimethyl-3-thienyl
2,5-dichloro-3-thienyl
1,4-dimethyl-3-pyrrolyl
1,4-dimethyl-3-pyrazolyl
1,3-dimethyl-4-pyrazolyl
2,5-dimethyl-4-oxazolyl
2,5-dimethyl-4-thiazolyl
3-bromo-4-isothiazolyl
3-bromo-4-isooxazolyl
1-methyl-4-imidazolyl
5-(trifluoromethyl)-3-(1,2,4-oxadiazolyl)
5-(trifluoromethyl)-3-(1,2,4-thiadiazolyl)
2-bromo-1-(1,3,4-triazolyl)
5-(trifluoromethyl)-3-(1,2,4-triazolyl)
2-bromo-1-imidazolyl
3,6-dimethyl-2-pyridyl
2,5-dimethyl-3-pyridyl
2,5-dimethyl-4-pyridyl
3,6-dichloro-2-pyridyl
2,5-dichloro-3-pyridyl
2,5-dichloro-4-pyridyl
4-bromo-3-pyridazinyl
4-(trifluoromethyl)-2-pyrimidinyl

TABLE 1A-continued

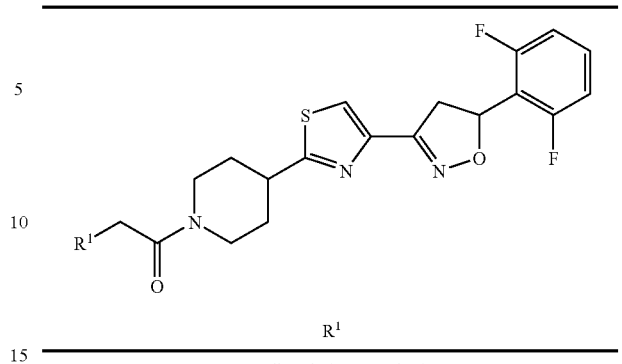

R¹

3,6-dimethyl-2-pyrazinyl
2,5-dimethyl-4-pyrimidinyl
4-methoxy-5-pyrimidinyl
3,6-dimethyl-4-pyridazinyl
5-(trifluoromethyl)-3-(1,2,4-triazinyl)
5-methoxy-6-(1,2,4-triazinyl)
4-(trifluoromethyl)-2-(1,3,5-triazinyl)
3,6-dimethyl-5-(1,2,4-triazinyl)
1-methyl-4-(trifluoromethyl)imidazol-2-yl
3,5-bis-(trifluoromethyl)pyrazol-1-yl
3-(2,2,2-trifluoroethyl)-5-(trifluoromethyl)pyrazol-1-yl
3-(pentafluoroethyl)-5-(trifluoromethyl)pyrazol-1-yl
3-cyano-5-(trifluoromethyl)pyrazol-1-yl
3-nitro-5-(trifluoromethyl)pyrazol-1-yl
3-chloro-5-(trifluoromethyl)-pyrazol-1-yl
3,5-bis-(trichloromethyl)pyrazol-1-yl
3-difluoromethoxy-5-methylpyrazol-1-yl
3-difluoromethoxy-5-chloropyrazol-1-yl
3-difluoromethoxy-5-bromopyrazol-1-yl
3-difluoromethoxy-5-iodopyrazol-1-yl
3-difluoromethoxy-5-ethylpyrazol-1-yl
3-difluoromethoxy-5-(trifluoromethyl)pyrazol-1-yl
3-difluoromethoxy-5-(2,2,2-trifluoroethyl)pyrazol-1-yl
3-difluoromethoxy-5-(pentafluoroethyl)pyrazol-1-yl
3-difluoromethoxy-5-cyanopyrazol-1-yl
3-difluoromethoxy-5-nitropyrazol-1-yl
3,5-bis-(difluoromethoxy)pyrazol-1-yl
5-carbomethoxy-3-(trifluoromethyl)pyrazol-1-yl
3,5-dimethoxypyrazol-1-yl
5-ethoxy-3-methylpyrazol-1-yl
5-ethoxy-3-bromopyrazol-1-yl
5-ethoxy-3-iodopyrazol-1-yl
5-ethoxy-3-ethylpyrazol-1-yl
5-ethoxy-3-propylpyrazol-1-yl
5-ethoxy-3-isopropylpyrazol-1-yl
5-ethoxy-3-(trifluoromethyl)pyrazol-1-yl
5-ethoxy-3-(2,2,2-trifluoroethyl)pyrazol-1-yl
5-ethoxy-3-(pentafluoroethyl)pyrazol-1-yl
5-ethoxy-3-cyanopyrazol-1-yl
5-ethoxy-3-nitropyrazol-1-yl
3,5-dibromotriazol-1-yl
3-chloro-5-methyl triazol-1-yl
3-bromo-5-methyl triazol-1-yl
3-trifluoromethyl-5-chloro triazol-1-yl
3-trifluoromethyl-5-bromo triazol-1-yl In the structure shown above Table 1A the 4,5-dihydro-5-(2,6-difluorophenyl)-3-isoxazolyl moiety is J-29 as defined in Exhibit 3 in the above Embodiments wherein J-29 is connected at the 3-position to G and is substituted at the 5-position with one $R^5$ group, which is —$Z^2Q$ (i.e. 2,6-difluorophenyl). As defined in the Summary of the Invention and above Embodiments, the present invention also includes but is not limited to component (a) compounds (i.e. compounds of Formula 1) wherein the 4,5-dihydro-5-(2,6-difluorophenyl)-3-isoxazolyl moiety (i.e. J-29) in the structure above Table 1A is replaced with a different J group. As such, the present invention also includes Table 1A¹ wherein the 4,5-dihydro-5-(2,6-difluorophenyl)-3-isoxazolyl moiety (i.e. J-29) in the structure above Table 1A is replaced with J-29-1 (defined in Exhibit A in the above Embodiments) and the remaining substituents are as defined in Table 1A. Thus, for example, Table 1A$^1$ specifically discloses 1-[4-[4-[(5R)-4,5-dihydro-5-(2-methylphenyl)-3-isoxazolyl]-2-thiazolyl]-1-piperidinyl]-2-[5-methyl-3-(trifluoromethyl)-1H-pyrazol-1-yl]ethanone, 2-(2,5-dimethylphenyl)-1-[4-[4-[(5R)-5-(2-methylphenyl)-4,5-dihydro-3-isoxazolyl]-2-thiazolyl]-1-piperidinyl]ethanone, and 1-[4-[4-[(5R)-4,5-dihydro-5-(2-methylphenyl)-3-isoxazolyl]-2-thiazolyl]-1-piperidinyl]-2-[3,5-dibromo-1H-triazol-1-yl]ethanone). Also, the present invention includes Tables 1A$^2$ through 1A$^{60}$ wherein the 4,5-dihydro-5-(2,6-difluorophenyl)-3-isoxazolyl moiety (i.e. J-29) in the structure above Table 1A is replaced with J-29-2 through J-29-60 (defined in Exhibit A in the above Embodiments) and the remaining substituents are as defined in Table 1A. Tables 1A$^2$ through 1A$^{60}$ are constructed similar to Table 1A$^1$, and include, for example, the compounds 1-[4-[4-[(5R)-4,5-dihydro-5-(2,6-dimethylphenyl)-3-isoxazolyl]-2-thiazolyl]-1-piperidinyl]-2-[5-methyl-3-(trifluoromethyl)-1H-pyrazol-1-yl]ethanone (Table 1A$^{11}$), 1-[4-[4-[(5R)-2,3-dihydrospiro[1H-indene-1,5'(4'H)-isoxazol]-3'-yl]-2-thiazolyl]-1-piperidinyl]-2-[5-methyl-3-(trifluoromethyl)-1H-pyrazol-1-yl]ethanone (Table 1A$^{21}$), 2-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-1H-isoindole-1,3(2H)-dione (Table 1A$^{40}$), 3-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-2(3H)-benzoxazolone (Table 1A$^{42}$) and (5R)-4,5-dihydro-3-[2-[1-[2-[5-methyl-3-(trifluoromethyl)-1H-pyrazol-1-yl]acetyl]-4-piperidinyl]-4-thiazolyl]-5-phenyl-5-isoxazolecarbonitrile (Table 1A$^{52}$).

The present invention also includes Tables 1A$^{1a}$ through 1A$^{60a}$ which correspond to Tables 1A$^1$ through 1A$^{60}$ respectively, except that J is not limited to the specific enantiomers disclosed in Exhibit A. Accordingly, the compounds included in Tables 1A$^{1a}$ through 1A$^{60a}$ include all enantiomers as well as mixtures thereof (e.g., racemic mixtures). Thus, for example, Table 1A$^{1a}$ specifically discloses 1-[4-[4-[4,5-dihydro-5-(2-methylphenyl)-3-isoxazolyl]-2-thiazolyl]-1-piperidinyl]-2-[5-methyl-3-(trifluoromethyl)-1H-pyrazol-1-yl]ethanone, 2-(2,5-dimethylphenyl)-1-[4-[4-[5-(2-methylphenyl)-4,5-dihydro-3-isoxazolyl]-2-thiazolyl]-1-piperidinyl]ethanone, and 1-[4-[4-[4,5-dihydro-5-(2-methylphenyl)-3-isoxazolyl]-2-thiazolyl]-1-piperidinyl]-2-[3,5-dibromo-1H-triazol-1-yl]ethanone). Tables 1A$^{2a}$ through 1A$^{60a}$ are constructed similar to Table 1A$^{1a}$, and include, for example, the compounds 1-[4-[4-[4,5-dihydro-5-(2,6-dimethylphenyl)-3-isoxazolyl]-2-thiazolyl]-1-piperidinyl]-2-[5-methyl-3-(trifluoromethyl)-1H-pyrazol-1-yl]ethanone (Table 1A$^{11a}$), 1-[4-[4-[2,3-dihydrospiro[1H-indene-1,5'(4'H)-isoxazol]-3'-yl]-2-thiazolyl]-1-piperidinyl]-2-[5-methyl-3-(trifluoromethyl)-1H-pyrazol-1-yl]ethanone (Table 1A$^{21a}$), 2-[4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-1H-isoindole-1,3(2H)-dione (Table 1A$^{40a}$), 3-[4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-2(3H)-benzoxazolone (Table 1A$^{42a}$) and 4,5-dihydro-3-[2-[1-[2-[5-methyl-3-(trifluoromethyl)-1H-pyrazol-1-yl]acetyl]-4-piperidinyl]-4-thiazolyl]-5-phenyl-5-isoxazolecarbonitrile (Table 1A$^{52a}$).

As disclosed in Scheme 13 above, compounds of Formula 21, wherein Y$^3$ is replaced by R$^1$AC(=W) and Y$^6$ is a functional group suitable for construction of the desired heterocycle J (e.g., —CHO, —CH(=N)OH, —C(Cl)=NOH or —C(=O)CH$_3$), are useful intermediates for the preparation of compounds of Formula 1 (e.g., the compounds of Formula 1 disclosed in Table 1A) The present invention includes but is not limited to the following exemplary species of compounds of Formula 21: Table 1A$^a$ wherein Y$^3$ in Formula 21 is replaced by R$^1$AC(=W), and A is CH$_2$, W is O, X is X$^1$, n is 0, G is G-1, Z$^1$ is a direct bond, Y$^6$ is —CHO, and R$^1$ is as defined in Table 1A. Thus, the compounds disclosed in Table 1A$^a$ include the compounds disclosed in Table 1A where the 4,5-dihydro-5-(2,6-difluorophenyl)-3-isoxazolyl moiety (i.e. J-29) in the structure above Table 1A is replaced with Z$^1$—Y$^6$ and Z$^1$ is a direct bond and Y$^6$ is —CHO. For example, Table 1A$^a$ specifically discloses 2-[1-[2-[5-methyl-3-(trifluoromethyl)-1H-pyrazol-1-yl]acetyl]-4-piperidinyl]-4-thiazolecarboxaldehyde. Also, the present invention includes Table 1A$^b$ wherein the 4,5-dihydro-5-(2,6-difluorophenyl)-3-isoxazolyl moiety (i.e. J-29) in the structure above Table 1A is replaced with Z$^1$—Y$^6$ and Z$^1$ is a direct bond, Y$^6$ is —CH(=N)OH, and the remaining substituents are as defined in Table 1A$^a$. For example, Table 1A$^b$ specifically discloses 2-[1-[2-[5-methyl-3-(trifluoromethyl)-1H-pyrazol-1-yl]acetyl]-4-piperidinyl]-4-thiazolecarboxaldehyde 4-oxime. Also, the present invention includes Table 1A$^c$ wherein the 4,5-dihydro-5-(2,6-difluorophenyl)-3-isoxazolyl moiety (i.e. J-29) in the structure above Table 1A is replaced with Z$^1$—Y$^6$ and Z$^1$ is a direct bond, Y$^6$ is —C(Cl)=NOH, and the remaining substituents are as defined in Table 1A$^a$. For example, Table 1A$^c$ specifically discloses N-hydroxy-2-[1-[2-[5-methyl-3-(trifluoromethyl)-1H-pyrazol-1-yl]acetyl-4-piperidinyl]-4-thiazolecarboximidoyl chloride. Also, the present invention includes Table 1A$^d$ wherein the 4,5-dihydro-5-(2,6-difluorophenyl)-3-isoxazolyl moiety (i.e. J-29) in the structure above Table 1A is replaced with Z$^1$—Y$^6$ and Z$^1$ is a direct bond, Y$^6$ is —C(=O)CH$_3$, and the remaining substituents are as defined in Table 1A$^a$. For example, Table 1A$^d$ specifically discloses 1-[4-(4-acetyl-2-thiazolyl)-1-piperidinyl]-2-[5-methyl-3-(trifluoromethyl)-1H-pyrazol-1-yl]ethanone.

TABLE 1B

| R$^1$ | A | W |
|---|---|---|
| 2-methoxyphenyl | NH | O |
| 2,5-dichlorophenyl | NH | O |
| 5-bromo-2-chlorophenyl | NH | O |
| 2-chloro-5-methylphenyl | NH | O |
| 2-chloro-5-(trifluoromethyl)phenyl | NH | O |
| 2,5-dibromophenyl | NH | O |
| 2-bromo-5-methylphenyl | NH | O |
| 2-bromo-5-(trifluoromethyl)phenyl | NH | O |
| 5-chloro-2-methylphenyl | NH | O |
| 5-bromo-2-methylphenyl | NH | O |
| 2,5-dimethylphenyl | NH | O |
| 5-ethyl-2-methylphenyl | NH | O |
| 2-methyl-5-(trifluoromethyl)phenyl | NH | O |
| 5-bromo-2-methoxyphenyl | NH | O |
| 2-methoxy-5-methylphenyl | NH | O |
| 2-methoxy-5-(trifluoromethyl)phenyl | NH | O |
| 3-ethyl-5-methylpyrazol-1-yl | CH$_2$ | S |
| 5-methyl-3-(trifluoromethyl)pyrazol-1-yl | CH$_2$ | S |

TABLE 1B-continued

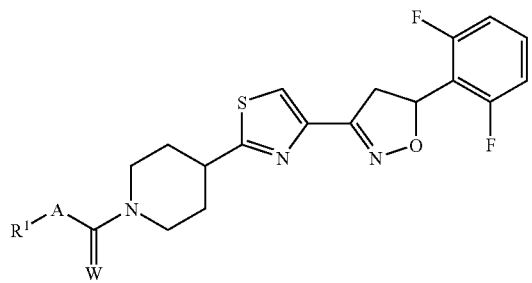

| R¹ | A | W |
|---|---|---|
| 3,5-dichloropyrazol-1-yl | CH₂ | S |
| 5-chloro-3-(trifluoromethyl)pyrazol-1-yl | CH₂ | S |
| 3,5-bis-(trifluoromethyl)pyrazol-1-yl | CH₂ | S |
| 3,5-dimethylpyrazol-1-yl | CH₂ | S |
| 3,5-dibromopyrazol-1-yl | CH₂ | S |
| 5-bromo-3-(trifluoromethyl)pyrazol-1-yl | CH₂ | S |
| 3,5-diethylpyrazol-1-yl | CH₂ | S |
| 5-ethyl-3-(trifluoromethyl)pyrazol-1-yl | CH₂ | S |
| 2-methoxyphenyl | NH | S |
| 2,5-dichlorophenyl | NH | S |
| 5-bromo-2-chlorophenyl | NH | S |
| 2-chloro-5-methylphenyl | NH | S |
| 2-chloro-5-(trifluoromethyl)phenyl | NH | S |
| 2,5-dibromophenyl | NH | S |
| 2-bromo-5-methylphenyl | NH | S |
| 2-bromo-5-(trifluoromethyl)phenyl | NH | S |
| 5-chloro-2-methylphenyl | NH | S |
| 5-bromo-2-methylphenyl | NH | S |
| 2,5-dimethylphenyl | NH | S |
| 5-ethyl-2-methylphenyl | NH | S |
| 2-methyl-5-(trifluoromethyl)phenyl | NH | S |
| 5-bromo-2-methoxyphenyl | NH | S |
| 2-methoxy-5-methylphenyl | NH | S |
| 2-methoxy-5-(trifluoromethyl)phenyl | NH | S |
| 5-methyl-3-(trifluoromethyl)pyrazol-1-yl | NCH₃ | O |
| 5-methyl-3-(trifluoromethyl)pyrazol-1-yl | NAc | O |
| 3-methyl-5-(trifluoromethyl)pyrazol-1-yl | CH₂ | S |
| 5-methyl-3-(trifluoromethyl)pyrazol-1-yl | CHCH₃ | O |
| 5-methyl-3-(trifluoromethyl)pyrazol-1-yl | CHCOOCH₃ | O |
| 5-methyl-3-(trifluoromethyl)pyrazol-1-yl | CHCl | O |
| 5-methyl-3-(trifluoromethyl)pyrazol-1-yl | NCOOCH₃ | O |
| 5-methyl-3-(trifluoromethyl)pyrazol-1-yl | NH | S |
| 3,5-dimethylpyrazol-1-yl | NH | O |
| 3,5-dichloropyrazol-1-yl | NH | O |
| 3,5-dibromopyrazol-1-yl | NH | O |
| 5-methyl-3-(trifluoromethyl)pyrazol-1-yl | NH | O |
| 5-chloro-3-(trifluoromethyl)pyrazol-1-yl | NH | O |
| 5-bromo-3-(trifluoromethyl)pyrazol-1-yl | NH | O |
| 5-ethyl-3-(trifluoromethyl)pyrazol-1-yl | NH | O |
| 3,5-bis-(trifluoromethyl)pyrazol-1-yl | NH | O |
| 3-methyl-5-(trifluoromethyl)pyrazol-1-yl | NH | O |
| 3-chloro-5-(trifluoromethyl)pyrazol-1-yl | NH | O |
| 3-bromo-5-(trifluoromethyl)pyrazol-1-yl | NH | O |
| 5-methoxy-3-(trifluoromethyl)pyrazol-1-yl | NH | O |
| 5-difluoromethoxy-3-(trifluoromethyl)pyrazol-1-yl | NH | O |
| 2-methoxyphenyl | CHOH | O |
| 2,5-dichlorophenyl | CHOH | O |
| 5-bromo-2-chlorophenyl | CHOH | O |
| 2-chloro-5-methylphenyl | CHOH | O |
| 2-chloro-5-(trifluoromethyl)phenyl | CHOH | O |
| 2,5-dibromophenyl | CHOH | O |
| 2-bromo-5-methylphenyl | CHOH | O |
| 2-bromo-5-(trifluoromethyl)phenyl | CHOH | O |
| 5-chloro-2-methylphenyl | CHOH | O |
| 5-bromo-2-methylphenyl | CHOH | O |
| 2,5-dimethylphenyl | CHOH | O |
| 5-ethyl-2-methylphenyl | CHOH | O |
| 2-methyl-5-(trifluoromethyl)phenyl | CHOH | O |
| 5-bromo-2-methoxyphenyl | CHOH | O |
| 2-methoxy-5-methylphenyl | CHOH | O |
| 2-methoxy-5-(trifluoromethyl)phenyl | CHOH | O |
| 3-ethyl-5-methylpyrazol-1-yl | CHOH | O |
| 5-methyl-3-(trifluoromethyl)pyrazol-1-yl | CHOH | O |

TABLE 1B-continued

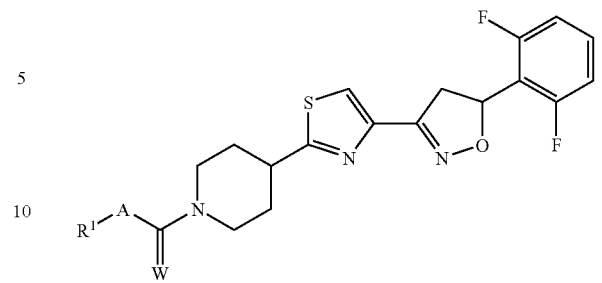

| R¹ | A | W |
|---|---|---|
| 3,5-dichloropyrazol-1-yl | CHOH | O |
| 5-chloro-3-(trifluoromethyl)pyrazol-1-yl | CHOH | O |
| 3,5-bis-(trifluoromethyl)pyrazol-1-yl | CHOH | O |
| 3,5-dimethylpyrazol-1-yl | CHOH | O |
| 3,5-dibromopyrazol-1-yl | CHOH | O |
| 5-bromo-3-(trifluoromethyl)pyrazol-1-yl | CHOH | O |
| 3,5-diethylpyrazol-1-yl | CHOH | O |
| 5-ethyl-3-(trifluoromethyl)pyrazol-1-yl | CHOH | O |
| 2-methoxyphenyl | CHOMe | O |
| 2,5-dichlorophenyl | CHOMe | O |
| 5-bromo-2-chlorophenyl | CHOMe | O |
| 2-chloro-5-methylphenyl | CHOMe | O |
| 2-chloro-5-(trifluoromethyl)phenyl | CHOMe | O |
| 2,5-dibromophenyl | CHOMe | O |
| 2-bromo-5-methylphenyl | CHOMe | O |
| 2-bromo-5-(trifluoromethyl)phenyl | CHOMe | O |
| 5-chloro-2-methylphenyl | CHOMe | O |
| 5-bromo-2-methylphenyl | CHOMe | O |
| 2,5-dimethylphenyl | CHOMe | O |
| 5-ethyl-2-methylphenyl | CHOMe | O |
| 2-methyl-5-(trifluoromethyl)phenyl | CHOMe | O |
| 5-bromo-2-methoxyphenyl | CHOMe | O |
| 2-methoxy-5-methylphenyl | CHOMe | O |
| 2-methoxy-5-(trifluoromethyl)phenyl | CHOMe | O |
| 3-ethyl-5-methylpyrazol-1-yl | CHOMe | O |
| 5-methyl-3-(trifluoromethyl)pyrazol-1-yl | CHOMe | O |
| 3,5-dichloropyrazol-1-yl | CHOMe | O |
| 5-chloro-3-(trifluoromethyl)pyrazol-1-yl | CHOMe | O |
| 3,5-bis-(trifluoromethyl)pyrazol-1-yl | CHOMe | O |
| 3,5-dimethylpyrazol-1-yl | CHOMe | O |
| 3,5-dibromopyrazol-1-yl | CHOMe | O |
| 5-bromo-3-(trifluoromethyl)pyrazol-1-yl | CHOMe | O |
| 3,5-diethylpyrazol-1-yl | CHOMe | O |
| 5-ethyl-3-(trifluoromethyl)pyrazol-1-yl | CHOMe | O |
| 2-methoxyphenyl | CHOAc | O |
| 2,5-dichlorophenyl | CHOAc | O |
| 5-bromo-2-chlorophenyl | CHOAc | O |
| 2-chloro-5-methylphenyl | CHOAc | O |
| 2-chloro-5-(trifluoromethyl)phenyl | CHOAc | O |
| 2,5-dibromophenyl | CHOAc | O |
| 2-bromo-5-methylphenyl | CHOAc | O |
| 2-bromo-5-(trifluoromethyl)phenyl | CHOAc | O |
| 5-chloro-2-methylphenyl | CHOAc | O |
| 5-bromo-2-methylphenyl | CHOAc | O |
| 2,5-dimethylphenyl | CHOAc | O |
| 5-ethyl-2-methylphenyl | CHOAc | O |
| 2-methyl-5-(trifluoromethyl)phenyl | CHOAc | O |
| 5-bromo-2-methoxyphenyl | CHOAc | O |
| 2-methoxy-5-methylphenyl | CHOAc | O |
| 2-methoxy-5-(trifluoromethyl)phenyl | CHOAc | O |
| 3-ethyl-5-methylpyrazol-1-yl | CHOAc | O |
| 5-methyl-3-(trifluoromethyl)pyrazol-1-yl | CHOAc | O |
| 3,5-dichloropyrazol-1-yl | CHOAc | O |
| 5-chloro-3-(trifluoromethyl)pyrazol-1-yl | CHOAc | O |
| 3,5-bis-(trifluoromethyl)pyrazol-1-yl | CHOAc | O |
| 3,5-dimethylpyrazol-1-yl | CHOAc | O |
| 3,5-dibromopyrazol-1-yl | CHOAc | O |
| 5-bromo-3-(trifluoromethyl)pyrazol-1-yl | CHOAc | O |
| 3,5-diethylpyrazol-1-yl | CHOAc | O |
| 5-ethyl-3-(trifluoromethyl)pyrazol-1-yl | CHOAc | O |
| 2,5-dimethylphenyl | CHOEt | O |
| 2,5-dimethylphenyl | CHO—i-Pr | O |
| 2,5-dimethylphenyl | CHO—t-Bu | O |
| 2,5-dimethylphenyl | CHO-allyl | O |

TABLE 1B-continued

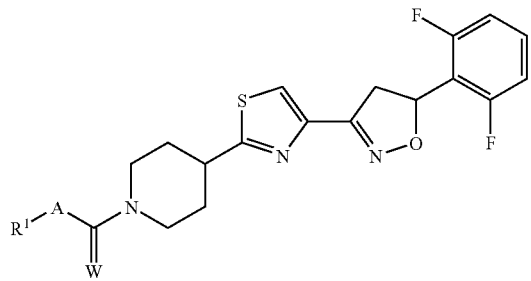

| R$^1$ | A | W |
|---|---|---|
| 2,5-dimethylphenyl | CHO-propargyl | O |
| 2,5-dimethylphenyl | CHOCHF$_2$ | O |
| 2,5-dimethylphenyl | CHOC(=O)Et | O |
| 2,5-dimethylphenyl | CHOC(=O)—t-Bu | O |
| 2,5-dimethylphenyl | CHOC(=O)CF$_3$ | O |
| 2,5-dimethylphenyl | CHOCOOMe | O |
| 2,5-dimethylphenyl | CHOCOO—t-Bu | O |
| 2,5-dimethylphenyl | CHOCOOCH$_2$CF$_3$ | O |
| 2,5-dimethylphenyl | CHOC(=O)NHMe | O |
| 2,5-dimethylphenyl | CHOC(=O)NMe$_2$ | O |
| 2,5-dimethylphenyl | CHOCH$_2$OMe | O |
| 2,5-dimethylphenyl | CHOCH$_2$OEt | O |
| 2,5-dimethylphenyl | CHOCH$_2$CH$_2$OMe | O |
| 2,5-dimethylphenyl | CHOSO$_2$Me | O |
| 2,5-dimethylphenyl | CHOSO$_2$CF$_3$ | O |
| 2,5-dimethylphenyl | CHOSiMe$_3$ | O |
| 2,5-dimethylphenyl | CHOSi(i-Pr)$_3$ | O |
| 2,5-dimethylphenyl | CHOSi(Me)$_2$—t-Bu | O |
| 2,5-dimethylphenyl | CHSH | O |
| 2,5-dimethylphenyl | CHSMe | O |
| 2,5-dimethylphenyl | CHSEt | O |
| 2,5-dimethylphenyl | CHSAc | O |
| 2,5-dimethylphenyl | CHSCOOMe | O |
| 2,5-dimethylphenyl | CHSC(=O)NHMe | O |
| 2,5-dimethylphenyl | CHNH$_2$ | O |
| 2,5-dimethylphenyl | CHNHMe | O |
| 2,5-dimethylphenyl | CHNHEt | O |
| 2,5-dimethylphenyl | CHNMe$_2$ | O |
| 2,5-dimethylphenyl | CHNHAc | O |
| 2,5-dimethylphenyl | CHNHCOOMe | O |
| 2,5-dimethylphenyl | CHNHC(=O)NHMe | O |
| 2,5-dimethylphenyl | NOH | O |

In the structure shown above Table 1B the 4,5-dihydro-5-(2,6-difluorophenyl)-3-isoxazolyl moiety is J-29 as defined in Exhibit 3 in the above Embodiments wherein J-29 is connected at the 3-position to G and is substituted at the 5-position with one R$^5$ group, which is —Z$^2$Q (i.e. 2,6-difluorophenyl). As defined in the Summary of the Invention and above Embodiments, the present invention also includes but is not limited to component (a) compounds (i.e. compounds of Formula 1) wherein the 4,5-dihydro-5-(2,6-difluorophenyl)-3-isoxazolyl moiety (i.e. J-29) in the structure above Table 1B is replaced with a different J group. As such, the present invention also includes Table 1B$^1$ wherein the 4,5-dihydro-5-(2,6-difluorophenyl)-3-isoxazolyl moiety (i.e. J-29) in the structure above Table 1B is replaced with J-29-1 (defined in Exhibit A in the above Embodiments) and the remaining substituents are as defined in Table 1B. Thus, for example, Table 1B$^1$ specifically discloses 4- [4- [(5R)-4,5-dihydro-5-(2-methylphenyl)-3-isoxazolyl]-2-thiazolyl]-N-(2,5-dimethylphenyl)-1-piperidinecarboxamide, 1-[4-[4-[(5R)-4,5-dihydro-5-(2-methylphenyl)-3-isoxazolyl]-2-thiazolyl]-1-piperidinyl]-2-(2,5-dimethylphenyl)-2-methyoxyethanone, 1-[4-[4-[(5R)-4,5-dihydro-5-(2-methylphenyl)-3-isoxazolyl]-2-thiazolyl]-1-piperidinyl]-2-(2,5- dimethylphenyl)-2-hydroxyethanone, and 2-(acetyloxy)-1-[4-[4-[(5R)-4,5-dihydro-5-(2-methylphenyl)-3-isoxazolyl]-2-thiazole]-1-piperidinyl]-2-(2,5-dimethylphenyl)ethanone. Also, the present invention includes Tables 1B$^2$ through 1B$^{60}$ wherein the 4,5-dihydro-5-(2,6-difluorophenyl)-3-isoxazolyl moiety (i.e. J-29) in the structure above Table 1B is replaced with J-29-2 through J-29-60 (defined in Exhibit A in the above Embodiments) and the remaining substituents are as defined in Table 1B. Tables 1B$^2$ through 1B$^{60}$ are constructed similar to Table 1B$^1$, and include, for example, the compounds 4-[4-[(5R)-5-(2,6-dichlorophenyl)-4,5-dihydro-3-isoxazolyl]-2-thiazolyl]-N-(2,5-dimethylphenyl)-1-piperidinecarboxamide, and 1-[4-[4-[(5R)-5-(2,6-dichlorophenyl)-4,5-dihydro-3-isoxazolyl]-2-thiazolyl]-1-piperidinyl]-2-(2,5 -dimethylphenyl)-2-hydroxyethanone (Table1B$^{10}$), 4-[4-[(5R)-5-(2-cyanophenyl)-4,5 -dihydro-3-isoxazolyl]-2-thiazolyl]-N-(2, 5-dimethylphenyl)-1-piperidinecarboxamide, and 2-[3-[2-[1-[2-(2,5-dimethylphenyl)-2-hydroxyacetyl]-4-piperidinyl]-4-thiazolyl]-(5R)-[4,5-dihydro-5-isoxazolyl] benznitrile (Table1B$^{51}$).

The present invention also includes Tables 1B$^{1a}$ through 1B$^{60a}$ which correspond to Tables 1B$^1$ through 1B$^{60}$ respectively, except that J is not limited to the specific enantiomers disclosed in Exhibit A. Accordingly, the compounds included in Tables 1B$^{1a}$ through 1B$^{60a}$ include all enantiomers as well as mixtures thereof (e.g., racemic mixtures). Thus, for example, Table 1B$^{1a}$ specifically discloses 4-[-4-[4,5-dihydro-5-(2-methylphenyl)-3-isoxazolyl]-2-thiazolyl]-N-(2,5-dimethylphenyl)-1-piperidinecarboxamide, 1-[4-[4-[4,5-dihydro-5-(2-methylphenyl)-3-isoxazolyl]-2-thiazolyl]-1-piperidinyl]-2-(2,5-dimethylphenyl)-2-methyoxyethanone, 1-[4-[4-[4,5-dihydro-5-(2-methylphenyl)-3-isoxazolyl]-2-thiazolyl]-1-piperidinyl]-2-(2,5-dimethylphenyl)-2-hydroxyethanone, and 2-(acetyloxy)-1-[4-[4-[4,5-dihydro-5-(2-methylphenyl)-3-isoxazolyl]-2-thiazole]-1-piperidinyl]-2-(2,5-dimethylphenyl)ethanone. Tables 1B$^{2a}$ through 1B$^{60a}$ are constructed similar to Table 1B$^{1a}$ and include, for example, the compounds 4-[4-[5-(2,6-dichlorophenyl)-4,5-dihydro-3-isoxazolyl]-2-thiazolyl]-N-(2,5-dimethylphenyl)-1-piperidinecarboxamide, and 1-[4-[4-[5-(2,6-dichlorophenyl)-4,5-dihydro-3-isoxazolyl]-2-thiazolyl]-1-piperidinyl]-2-(2,5-dimethylphenyl)-2-hydroxyethanone (Table1B$^{10a}$), 4-[4-[5-(2-cyanophenyl)-4,5-dihydro-3-isoxazolyl]-2-thiazolyl]-N-(2,5 -dimethylphenyl)-1-piperidinecarboxamide, and 2-[3-[2-[1-[2-(2,5-dimethylphenyl)-2-hydroxyacetyl]-4-piperidinyl]-4-thiazolyl]-[4,5-dihydro-5-isoxazolyl]benznitrile (Table1B$^{51a}$).

As disclosed in Scheme 13 above, compounds of Formula 21, wherein Y$^3$ is replaced by R$^1$AC(=W) and Y$^6$ is a functional group suitable for construction of the desired heterocycle J (e.g., —CHO, —CH(=N)OH, —C(Cl)=NOH or —C(=O)CH$_3$), are useful intermediates for the preparation of compounds of Formula 1 (i.e. such as the compounds of Formula 1 disclosed in Table 1B) The present invention includes but is not limited to the following exemplary species of compounds Formula 21: Table 1B$^a$ wherein Y$^3$ in Formula 21 is replaced by R$^1$AC(=W), X is X$^1$, n is 0, G is G-1, Z$^1$ is a direct bond, Y$^6$ is —CHO, and R$^1$, A and W are as defined in Table 1B. Thus, the compounds disclosed in Table 1B$^a$ include the compounds disclosed in Table 1B where the 4,5-dihydro-5-(2,6-difluorophenyl)-3-isoxazolyl moiety (i.e. J-29) in the structure above Table 1B is replaced with Z$^1$-Y$^6$ and Z$^1$ is a direct bond and Y$^6$ is —CHO. For example, Table 1B$^a$ specifically discloses N-(2,5-dimethylphenyl)-4-(4-formyl-2-thiazolyl)-1-piperidinecarboxamide. Also, the present invention includes Tables 1B$^b$ wherein the 4,5-dihydro-5-(2,6-difluorophenyl)-3-isoxazolyl moiety (i.e. J-29) in the structure above Table 1B is replaced with Z$^1$-Y$^6$ and Z$^1$ is a direct bond, Y$^6$ is —CH(=N)OH, and the remaining substituents are as defined in Table 1B$^a$. For example, Table 1B$^b$ specifically discloses N-(2,5-dimethylphenyl)-4-[4-[(hydroxyimino)methyl]-2-thiazolyl]-1-piperidinecarboxamide. Also, the present invention includes Tables 1B$^c$ wherein the 4,5-dihydro-5-(2,6-difluorophenyl)-3-isoxazolyl moiety (i.e. J-29) in the structure above Table 1B is replaced is replaced with Z$^1$-Y$^6$ and Z$^1$ is a direct bond, Y$^6$ is —C(Cl)=NOH, and the remaining substituents are as defined in Table 1B$^a$. For example, Table 1B$^c$ specifically discloses 2-[1-[[(2,5-dimethylphenyl)amino]carbonyl]-4-piperidinyl]-N-hydroxy-4-thiazolecarboximidoyl chloride. Also, the present invention includes Tables 1B$^d$ wherein the 4,5-dihydro-5-(2,6-difluorophenyl)-3-isoxazolyl moiety (i.e. J-29) in the structure above Table 1B is replaced with Z$^1$-Y$^6$ and Z$^1$ is a direct bond, Y$^6$ is —C(=O)CH$_3$, and the remaining substituents are as defined in Table 1B$^a$. For example, Table 1B$^d$ specifically discloses 4-(4-acetyl-2-thiazolyl]-N-(2,5-dimethylphenyl)-1-piperidinecarboxamide.

TABLE 2*

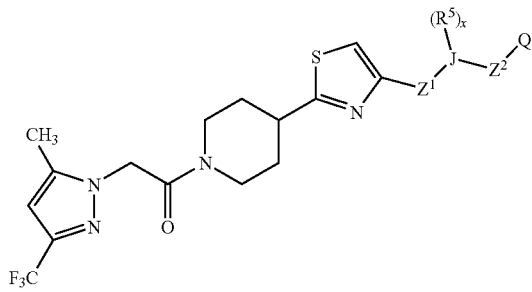

| Z$^1$ | J | (R$^5$)$_x$ | Z$^2$ | Q | (R$^7$)$_p$ | R$^{12}$ | J-orientation** |
|---|---|---|---|---|---|---|---|
| bond | J-1 | — | bond | Q-45 | — | — | 2/4 |
| bond | J-1 | — | bond | Q-45 | — | — | 2/5 |
| bond | J-1 | — | bond | Q-45 | — | — | 4/2 |
| bond | J-1 | — | bond | Q-45 | — | — | 5/2 |
| bond | J-2 | — | bond | Q-45 | — | — | 2/4 |
| bond | J-2 | — | bond | Q-45 | — | — | 2/5 |
| bond | J-2 | — | bond | Q-45 | — | — | 4/2 |
| bond | J-2 | — | bond | Q-45 | — | — | 5/2 |
| bond | J-3 | 1-Me | bond | Q-45 | — | — | 2/4 |
| bond | J-3 | 1-Me | bond | Q-45 | — | — | 2/5 |
| bond | J-3 | 1-Me | bond | Q-45 | — | — | 4/2 |
| bond | J-3 | 1-Me | bond | Q-45 | — | — | 5/2 |
| CH$_2$ | J-3 | — | bond | Q-45 | — | — | 1/4 |
| bond | J-3 | — | bond | Q-45 | — | — | 4/1 |
| bond | J-4 | — | bond | Q-45 | — | — | 2/4 |
| bond | J-4 | — | bond | Q-45 | — | — | 2/5 |
| bond | J-4 | — | bond | Q-45 | — | — | 4/2 |
| bond | J-4 | — | bond | Q-45 | — | — | 5/2 |
| bond | J-4 | — | bond | Q-45 | — | — | 3/5 |
| bond | J-4 | — | bond | Q-45 | — | — | 5/3 |
| bond | J-5 | — | bond | Q-45 | — | — | 2/4 |
| bond | J-5 | — | bond | Q-45 | — | — | 2/5 |
| bond | J-5 | — | bond | Q-45 | — | — | 4/2 |
| bond | J-5 | — | bond | Q-45 | — | — | 5/2 |
| bond | J-5 | — | bond | Q-45 | — | — | 3/5 |
| bond | J-5 | — | bond | Q-45 | — | — | 5/3 |
| bond | J-6 | — | bond | Q-45 | — | — | 2/4 |
| bond | J-6 | — | bond | Q-45 | — | — | 2/5 |
| bond | J-6 | — | bond | Q-45 | — | — | 4/2 |
| bond | J-6 | — | bond | Q-45 | — | — | 5/2 |
| bond | J-6 | — | bond | Q-45 | — | — | 3/5 |
| bond | J-6 | — | bond | Q-45 | — | — | 5/3 |
| CH$_2$ | J-6 | — | bond | Q-45 | — | — | 1/3 |
| bond | J-6 | — | bond | Q-45 | — | — | 3/1 |
| bond | J-7 | — | bond | Q-45 | — | — | 5/3 |
| bond | J-7 | — | bond | Q-45 | — | — | 3/5 |
| bond | J-8 | — | bond | Q-45 | — | — | 5/3 |
| bond | J-8 | — | bond | Q-45 | — | — | 3/5 |
| bond | J-9 | 1-Me | bond | Q-45 | — | — | 5/3 |
| bond | J-9 | 1-Me | bond | Q-45 | — | — | 3/5 |
| CH$_2$ | J-9 | — | bond | Q-45 | — | — | 1/4 |
| bond | J-9 | — | bond | Q-45 | — | — | 4/1 |
| bond | J-10 | — | bond | Q-45 | — | — | 3/5 |
| bond | J-10 | — | bond | Q-45 | — | — | 5/3 |
| bond | J-11 | — | bond | Q-45 | — | — | 3/5 |
| bond | J-11 | — | bond | Q-45 | — | — | 5/3 |
| bond | J-12 | 1-Me | bond | Q-45 | — | — | 3/5 |
| bond | J-12 | 1-Me | bond | Q-45 | — | — | 5/3 |
| CH$_2$ | J-12 | — | bond | Q-45 | — | — | 1/3 |
| bond | J-12 | — | bond | Q-45 | — | — | 3/1 |
| bond | J-13 | — | bond | Q-45 | — | — | 1/4 |

TABLE 2*-continued

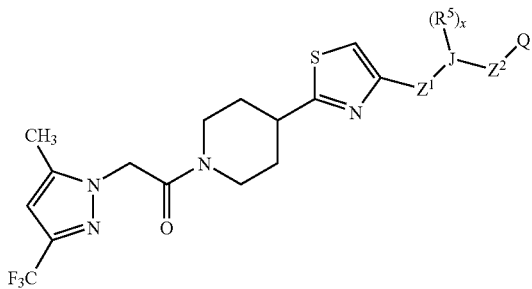

| $Z^1$ | J | $(R^5)_x$ | $Z^2$ | Q | $(R^7)_p$ | $R^{12}$ | J-orientation** |
|---|---|---|---|---|---|---|---|
| bond | J-13 | — | bond | Q-45 | — | — | 4/1 |
| bond | J-14 | 1-Me | bond | Q-45 | — | — | 3/5 |
| bond | J-14 | — | bond | Q-45 | — | — | 5/3 |
| bond | J-15 | — | bond | Q-45 | — | — | 2/5 |
| bond | J-16 | — | bond | Q-45 | — | — | 2/5 |
| $CH_2$ | J-17 | — | bond | Q-45 | — | — | 2/4 |
| bond | J-17 | — | bond | Q-45 | — | — | 4/2 |
| $CH_2$ | J-18 | — | bond | Q-45 | — | — | 2/5 |
| bond | J-18 | — | bond | Q-45 | — | — | 5/2 |
| bond | J-19 | — | bond | Q-45 | — | — | 2/4 |
| bond | J-19 | — | bond | Q-45 | — | — | 4/2 |
| bond | J-20 | — | bond | Q-45 | — | — | 2/4 |
| bond | J-20 | — | bond | Q-45 | — | — | 2/5 |
| bond | J-20 | — | bond | Q-45 | — | — | 2/6 |
| bond | J-20 | — | bond | Q-45 | — | — | 3/5 |
| bond | J-20 | — | bond | Q-45 | — | — | 4/2 |
| bond | J-20 | — | bond | Q-45 | — | — | 5/2 |
| bond | J-21 | — | bond | Q-45 | — | — | 3/5 |
| bond | J-21 | — | bond | Q-45 | — | — | 3/6 |
| bond | J-21 | — | bond | Q-45 | — | — | 5/3 |
| bond | J-22 | — | bond | Q-45 | — | — | 2/4 |
| bond | J-22 | — | bond | Q-45 | — | — | 2/5 |
| bond | J-22 | — | bond | Q-45 | — | — | 4/6 |
| bond | J-22 | — | bond | Q-45 | — | — | 4/2 |
| bond | J-22 | — | bond | Q-45 | — | — | 5/2 |
| bond | J-23 | — | bond | Q-45 | — | — | 2/5 |
| bond | J-23 | — | bond | Q-45 | — | — | 2/6 |
| bond | J-24 | — | bond | Q-45 | — | — | 2/4 |
| bond | J-24 | — | bond | Q-45 | — | — | 2/5 |
| bond | J-24 | — | bond | Q-45 | — | — | 4/2 |
| bond | J-24 | — | bond | Q-45 | — | — | 5/2 |
| bond | J-25 | — | bond | Q-45 | — | — | 2/4 |
| bond | J-25 | — | bond | Q-45 | — | — | 2/5 |
| bond | J-25 | — | bond | Q-45 | — | — | 4/2 |
| bond | J-25 | — | bond | Q-45 | — | — | 5/2 |
| bond | J-26 | — | bond | Q-45 | — | — | 2/4 |
| bond | J-26 | — | bond | Q-45 | — | — | 2/5 |
| bond | J-26 | — | bond | Q-45 | — | — | 4/2 |
| bond | J-26 | — | bond | Q-45 | — | — | 5/2 |
| $CH_2$ | J-26 | — | bond | Q-45 | — | — | 1/4 |
| bond | J-26 | — | bond | Q-45 | — | — | 4/1 |
| bond | J-27 | — | bond | Q-45 | — | — | 2/4 |
| bond | J-27 | — | bond | Q-45 | — | — | 2/5 |
| bond | J-27 | — | bond | Q-45 | — | — | 3/5 |
| bond | J-27 | — | bond | Q-45 | — | — | 4/2 |
| bond | J-27 | — | bond | Q-45 | — | — | 5/2 |
| bond | J-27 | — | bond | Q-45 | — | — | 5/3 |
| bond | J-28 | — | bond | Q-45 | — | — | 3/5 |
| bond | J-28 | — | bond | Q-45 | — | — | 5/3 |
| bond | J-29 | — | bond | Q-45 | — | — | 3/5 |
| bond | J-29 | — | bond | Q-45 | — | — | 5/3 |
| bond | J-30 | — | bond | Q-45 | — | — | 3/5 |
| bond | J-30 | — | bond | Q-45 | — | — | 5/3 |
| $CH_2$ | J-30 | — | bond | Q-45 | — | — | 1/3 |
| bond | J-30 | — | bond | Q-45 | — | — | 3/1 |
| $CH_2$ | J-30 | — | bond | Q-45 | — | — | 1/4 |
| bond | J-30 | — | bond | Q-45 | — | — | 4/1 |
| $CH_2$ | J-31 | — | bond | Q-45 | — | — | 1/3 |
| $CH_2$ | J-31 | — | bond | Q-45 | — | — | 1/4 |
| bond | J-31 | — | bond | Q-45 | — | — | 2/4 |
| bond | J-31 | — | bond | Q-45 | — | — | 2/5 |
| bond | J-31 | — | bond | Q-45 | — | — | 3/5 |
| bond | J-31 | — | bond | Q-45 | — | — | 3/1 |

TABLE 2*-continued

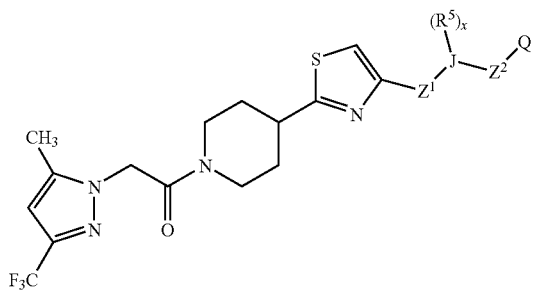

| $Z^1$ | J | $(R^5)_x$ | $Z^2$ | Q | $(R^7)_p$ | $R^{12}$ | J-orientation** |
|---|---|---|---|---|---|---|---|
| bond | J-31 | — | bond | Q-45 | — | — | 4/1 |
| bond | J-31 | — | bond | Q-45 | — | — | 4/2 |
| bond | J-31 | — | bond | Q-45 | — | — | 5/2 |
| bond | J-32 | — | bond | Q-45 | — | — | 2/4 |
| bond | J-32 | — | bond | Q-45 | — | — | 2/5 |
| bond | J-32 | — | bond | Q-45 | — | — | 3/5 |
| bond | J-32 | — | bond | Q-45 | — | — | 5/3 |
| bond | J-32 | — | bond | Q-45 | — | — | 5/2 |
| bond | J-32 | — | bond | Q-45 | — | — | 4/2 |
| bond | J-33 | — | bond | Q-45 | — | — | 2/4 |
| bond | J-33 | — | bond | Q-45 | — | — | 2/5 |
| bond | J-33 | — | bond | Q-45 | — | — | 3/5 |
| bond | J-33 | — | bond | Q-45 | — | — | 5/3 |
| bond | J-33 | — | bond | Q-45 | — | — | 5/2 |
| bond | J-33 | — | bond | Q-45 | — | — | 4/2 |
| bond | J-34 | — | bond | Q-45 | — | — | 1/3 |
| bond | J-34 | — | bond | Q-45 | — | — | 1/4 |
| bond | J-34 | — | bond | Q-45 | — | — | 3/5 |
| bond | J-34 | — | bond | Q-45 | — | — | 3/1 |
| bond | J-34 | — | bond | Q-45 | — | — | 4/1 |
| $CH_2$ | J-35 | — | bond | Q-45 | — | — | 1/4 |
| bond | J-35 | — | bond | Q-45 | — | — | 4/1 |
| $CH_2$ | J-36 | — | bond | Q-45 | — | — | 1/3 |
| bond | J-36 | — | bond | Q-45 | — | — | 3/1 |
| bond | J-36 | — | bond | Q-45 | — | — | 3/5 |
| bond | J-36 | — | bond | Q-45 | — | — | 5/3 |
| bond | J-37 | — | bond | Q-45 | — | — | 2/5 |
| bond | J-37 | — | bond | Q-45 | — | — | 5/2 |
| bond | J-37 | — | bond | Q-45 | — | — | 2/4 |
| bond | J-37 | — | bond | Q-45 | — | — | 4/2 |
| bond | J-38 | — | bond | Q-45 | — | — | 2/5 |
| bond | J-38 | — | bond | Q-45 | — | — | 5/2 |
| bond | J-38 | — | bond | Q-45 | — | — | 2/4 |
| bond | J-38 | — | bond | Q-45 | — | — | 4/2 |
| bond | J-39 | 4-Me | bond | Q-45 | — | — | 3/5 |
| bond | J-39 | 4-Me | bond | Q-45 | — | — | 5/3 |
| bond | J-40 | — | bond | Q-45 | — | — | 3/5 |
| bond | J-40 | — | bond | Q-45 | — | — | 5/3 |
| bond | J-41 | — | bond | Q-45 | — | — | 1/3 |
| bond | J-41 | — | bond | Q-45 | — | — | 1/4 |
| $CH_2$ | J-42 | — | bond | Q-45 | — | — | 1/3 |
| $CH_2$ | J-42 | — | bond | Q-45 | — | — | 1/4 |
| $CH_2$ | J-43 | — | bond | Q-45 | — | — | 1/4 |
| bond | J-44 | — | bond | Q-45 | — | — | 1/3 |
| bond | J-44 | — | bond | Q-45 | — | — | 2/4 |
| bond | J-44 | — | bond | Q-45 | — | — | 2/5 |
| bond | J-44 | — | bond | Q-45 | — | — | 2/6 |
| bond | J-45 | — | bond | Q-45 | — | — | 2/4 |
| bond | J-45 | — | bond | Q-45 | — | — | 2/5 |
| bond | J-45 | — | bond | Q-45 | — | — | 2/6 |
| bond | J-46 | — | bond | Q-45 | — | — | 2/4 |
| bond | J-46 | — | bond | Q-45 | — | — | 2/5 |
| bond | J-46 | — | bond | Q-45 | — | — | 4/2 |
| bond | J-46 | — | bond | Q-45 | — | — | 5/2 |
| bond | J-47 | — | bond | Q-45 | — | — | 2/4 |
| bond | J-47 | — | bond | Q-45 | — | — | 2/5 |
| bond | J-47 | — | bond | Q-45 | — | — | 4/2 |
| bond | J-47 | — | bond | Q-45 | — | — | 5/2 |
| bond | J-48 | — | bond | Q-45 | — | — | 3/5 |
| bond | J-49 | — | bond | Q-45 | — | — | 2/4 |
| bond | J-49 | — | bond | Q-45 | — | — | 2/5 |
| bond | J-49 | — | bond | Q-45 | — | — | 4/2 |
| bond | J-49 | — | bond | Q-45 | — | — | 5/2 |

TABLE 2*-continued

| $Z^1$ | J | $(R^5)_x$ | $Z^2$ | Q | $(R^7)_p$ | $R^{12}$ | J-orientation** |
|---|---|---|---|---|---|---|---|
| bond | J-50 | — | bond | Q-45 | — | — | 2/6 |
| bond | J-51 | — | bond | Q-45 | — | — | 2/6 |
| bond | J-52 | — | bond | Q-45 | — | — | 2/6 |
| bond | J-53 | — | — | — | — | — | 2/3 |
| bond | J-54 | — | — | — | — | — | 2/3 |
| bond | J-55 | — | — | — | — | — | 2/3 |
| bond | J-56 | — | — | — | — | — | 2/3 |
| bond | J-57 | 1-Me | — | — | — | — | 2/4 |
| bond | J-58 | 1-Me | — | — | — | — | 3/4 |
| bond | J-59 | — | — | — | — | — | 2/4 |
| bond | J-60 | — | — | — | — | — | 2/4 |
| bond | J-61 | — | — | — | — | — | 2/4 |
| bond | J-62 | — | — | — | — | — | 2/4 |
| bond | J-63 | — | — | — | — | — | 3/4 |
| bond | J-64 | — | — | — | — | — | 2/3 |
| bond | J-65 | — | — | — | — | — | 3/4 |
| bond | J-66 | — | — | — | — | — | 6/7 |
| bond | J-67 | — | — | — | — | — | 2/3 |
| bond | J-68 | — | — | — | — | — | 2/3 |
| bond | J-69 | — | bond | Q-45 | — | — | 1/3 |
| bond | J-69 | — | bond | Q-45 | — | — | 1/4 |
| bond | J-70 | — | bond | Q-45 | — | — | 1/3 |
| bond | J-71 | — | bond | Q-45 | — | — | 2/4 |
| bond | J-71 | — | bond | Q-45 | — | — | 4/2 |
| bond | J-72 | — | bond | Q-45 | — | — | 2/4 |
| bond | J-72 | — | bond | Q-45 | — | — | 4/2 |
| bond | J-73 | — | bond | Q-45 | — | — | 2/4 |
| bond | J-73 | — | bond | Q-45 | — | — | 4/2 |
| bond | J-73 | — | bond | Q-45 | — | — | 1/3 |
| bond | J-73 | — | bond | Q-45 | — | — | 1/4 |
| bond | J-73 | — | bond | Q-45 | — | — | 4/1 |
| bond | J-74 | 3-Me | bond | Q-45 | — | — | 2/4 |
| bond | J-74 | 3-Me | bond | Q-45 | — | — | 2/5 |
| bond | J-74 | 3-Me | bond | Q-45 | — | — | 4/2 |
| bond | J-74 | 3-Me | bond | Q-45 | — | — | 5/2 |
| bond | J-74 | — | bond | Q-45 | — | — | 3/5 |
| bond | J-74 | — | bond | Q-45 | — | — | 5/3 |
| bond | J-75 | — | bond | Q-45 | — | — | 3/5 |
| bond | J-75 | — | bond | Q-45 | — | — | 5/3 |
| bond | J-75 | — | bond | Q-45 | — | — | 2/4 |
| bond | J-75 | — | bond | Q-45 | — | — | 2/5 |
| bond | J-75 | 2-Me | bond | Q-45 | — | — | 3/5 |
| bond | J-75 | 2-Me | bond | Q-45 | — | — | 5/3 |
| bond | J-76 | — | bond | Q-45 | — | — | 3/6 |
| bond | J-76 | — | bond | Q-45 | — | — | 6/3 |
| bond | J-77 | — | bond | Q-45 | — | — | 3/5 |
| bond | J-77 | — | bond | Q-45 | — | — | 5/3 |
| bond | J-78 | — | bond | Q-45 | — | — | 1/3 |
| bond | J-79 | — | bond | Q-45 | — | — | 1/3 |
| bond | J-79 | — | bond | Q-45 | — | — | 3/1 |
| bond | J-80 | — | bond | Q-45 | — | — | 1/3 |
| bond | J-80 | — | bond | Q-45 | — | — | 3/1 |
| bond | J-81 | — | bond | Q-45 | — | — | 3/5 |
| bond | J-81 | — | bond | Q-45 | — | — | 5/3 |
| bond | J-82 | — | bond | Q-45 | — | — | 3/5 |
| bond | J-82 | — | bond | Q-45 | — | — | 3/6 |
| bond | J-82 | — | bond | Q-45 | — | — | 5/3 |
| bond | J-82 | — | bond | Q-45 | — | — | 6/3 |
| $CH_2$ | J-83 | — | — | — | — | — | 2/6 |
| O | J-29 | — | bond | Q-45 | — | — | 3/5 |
| S | J-29 | — | bond | Q-45 | — | — | 3/5 |
| SO | J-29 | — | bond | Q-45 | — | — | 3/5 |
| $SO_2$ | J-29 | — | bond | Q-45 | — | — | 3/5 |

TABLE 2*-continued

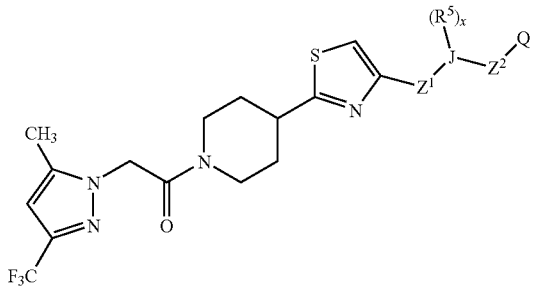

| $Z^1$ | J | $(R^5)_x$ | $Z^2$ | Q | $(R^7)_p$ | $R^{12}$ | J-orientation** |
|---|---|---|---|---|---|---|---|
| NH | J-29 | — | bond | Q-45 | — | — | 3/5 |
| NMe | J-29 | — | bond | Q-45 | — | — | 3/5 |
| NPr | J-29 | — | bond | Q-45 | — | — | 3/5 |
| CH$_2$ | J-29 | — | bond | Q-45 | — | — | 3/5 |
| CH—i-Bu | J-29 | — | bond | Q-45 | — | — | 3/5 |
| bond | J-29 | 4-Me | bond | Q-45 | — | — | 3/5 |
| bond | J-29 | 5-Me | bond | Q-45 | — | — | 3/5 |
| bond | J-29 | 4,5-di-Me | bond | Q-45 | — | — | 3/5 |
| bond | J-29 | 4,4-di-Me | bond | Q-45 | — | — | 3/5 |
| bond | J-29 | [Note 1] | bond | Q-45 | 6-Me, [Note 1] | — | 3/5 |
| bond | J-29 | [Note 2] | bond | Q-45 | 6-Me, [Note 2] | — | 3/5 |
| bond | J-29 | 5-Et | bond | Q-45 | — | — | 3/5 |
| bond | J-29 | 5-t-Bu | — | — | — | — | 3/5 |
| bond | J-29 | 5-t-amyl | — | — | — | — | 3/5 |
| bond | J-29 | 5-(4-Me-3-penten-1-yl) | — | — | — | — | 3/5 |
| bond | J-29 | 5-(3,3-di-Me-1-butyn-1-yl) | — | — | — | — | 3/5 |
| bond | J-29 | 5-c-Pr | bond | Q-45 | — | — | 3/5 |
| bond | J-29 | 5-(4-Me-cyclohexyl) | — | — | — | — | 3/5 |
| bond | J-29 | 5-CF$_3$ | bond | Q-45 | — | — | 3/5 |
| bond | J-29 | 5-perfluoropropyl | — | — | — | — | 3/5 |
| bond | J-29 | 5-(3,3-di-Cl-2-propen-1-yl) | — | — | — | — | 3/5 |
| bond | J-29 | 5-OMe | bond | Q-45 | — | — | 3/5 |
| bond | J-29 | 5-SiMe$_3$ | — | — | — | — | 3/5 |
| bond | J-69 | 4-F | bond | Q-45 | — | — | 1/3 |
| bond | J-69 | 4-Cl | bond | Q-45 | — | — | 1/3 |
| bond | J-69 | 4-OH | bond | Q-45 | — | — | 1/3 |
| bond | J-69 | 4-NH$_2$ | bond | Q-45 | — | — | 1/3 |
| bond | J-69 | 4-CN | O | Q-45 | — | — | 1/3 |
| bond | J-69 | 4-NO$_2$ | NH | Q-45 | — | — | 1/3 |
| bond | J-69 | 4-CF$_3$ | S | Q-45 | — | — | 1/3 |
| bond | J-69 | — | O | Q-45 | — | — | 1/3 |
| bond | J-69 | — | S | Q-45 | — | — | 1/3 |
| bond | J-69 | — | SO | Q-45 | — | — | 1/3 |
| bond | J-69 | — | SO$_2$ | Q-45 | — | — | 1/3 |
| bond | J-69 | — | NH | Q-45 | — | — | 1/3 |
| bond | J-69 | — | N-Me | Q-45 | — | — | 1/3 |
| bond | J-69 | — | CH$_2$ | Q-45 | — | — | 1/3 |
| bond | J-69 | 4-OEt | bond | Q-45 | — | — | 1/3 |
| bond | J-69 | 4-OCF$_3$ | bond | Q-45 | — | — | 1/3 |
| bond | J-69 | 4-SMe | bond | Q-45 | — | — | 1/3 |
| bond | J-69 | 4-SOMe | bond | Q-45 | — | — | 1/3 |
| bond | J-69 | 4-SO$_2$Me | bond | Q-45 | — | — | 1/3 |
| bond | J-69 | 4-SO$_2$—t-Bu | — | — | — | — | 1/3 |
| bond | J-69 | 4-SCF$_3$ | bond | Q-45 | — | — | 1/3 |
| bond | J-69 | 4-SO$_2$CH$_2$CF$_3$ | — | — | — | — | 1/4 |
| bond | J-22 | 4-NH—i-Bu | — | — | — | — | 2/4 |
| bond | J-22 | 4-di-EtN | — | — | — | — | 2/4 |
| bond | J-22 | 4-NH-cyclohexyl | — | — | — | — | 2/4 |
| bond | J-69 | 4-CH$_2$O—i-Pr | — | — | — | — | 1/4 |
| bond | J-69 | 4-CH$_2$OCHF$_2$ | bond | Q-45 | — | — | 1/3 |
| bond | J-69 | 4-CH$_2$OH | bond | Q-45 | — | — | 1/3 |
| bond | J-74 | 3-acetyl | bond | Q-45 | — | — | 2/5 |
| bond | J-69 | 4-CO$_2$—i-Pr | — | — | — | — | 1/4 |
| bond | J-69 | 4-O-acetyl | bond | Q-45 | — | — | 1/3 |
| bond | J-69 | 4-S-acetyl | bond | Q-45 | — | — | 1/3 |
| bond | J-69 | 4-CONHMe | bond | Q-45 | — | — | 1/3 |
| bond | J-69 | 4-CONEt$_2$ | — | — | — | — | 1/4 |
| bond | J-69 | — | O | Q-45 | — | — | 1/4 |
| bond | J-29 | — | bond | Q-1 | — | — | 3/5 |
| bond | J-29 | — | bond | Q-2 | — | — | 3/5 |
| bond | J-29 | — | bond | Q-3 | — | Me | 3/5 |
| bond | J-29 | — | bond | Q-4 | — | — | 3/5 |
| bond | J-29 | — | bond | Q-5 | — | — | 3/5 |

TABLE 2*-continued

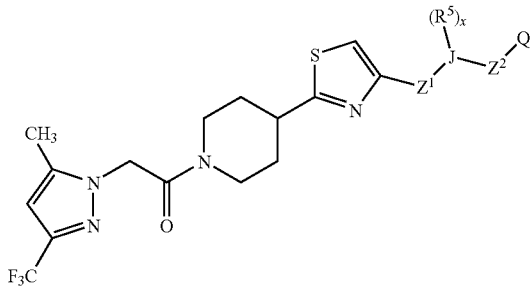

| $Z^1$ | J | $(R^5)_x$ | $Z^2$ | Q | $(R^7)_p$ | $R^{12}$ | J-orientation** |
|---|---|---|---|---|---|---|---|
| bond | J-29 | — | bond | Q-6 | — | — | 3/5 |
| bond | J-29 | — | bond | Q-7 | — | — | 3/5 |
| bond | J-29 | — | bond | Q-8 | — | — | 3/5 |
| bond | J-29 | — | bond | Q-9 | — | — | 3/5 |
| bond | J-29 | — | bond | Q-10 | — | Me | 3/5 |
| bond | J-29 | — | bond | Q-11 | — | Me | 3/5 |
| bond | J-29 | — | bond | Q-12 | — | Me | 3/5 |
| bond | J-29 | — | bond | Q-13 | — | Me | 3/5 |
| bond | J-29 | — | bond | Q-14 | — | Me | 3/5 |
| bond | J-29 | — | bond | Q-15 | — | — | 3/5 |
| bond | J-29 | — | bond | Q-16 | — | — | 3/5 |
| bond | J-29 | — | bond | Q-17 | — | — | 3/5 |
| bond | J-29 | — | bond | Q-18 | — | — | 3/5 |
| bond | J-29 | — | bond | Q-19 | — | — | 3/5 |
| bond | J-29 | — | bond | Q-20 | — | — | 3/5 |
| bond | J-29 | — | bond | Q-21 | — | Me | 3/5 |
| bond | J-29 | — | bond | Q-22 | — | Me | 3/5 |
| bond | J-29 | — | bond | Q-23 | — | Me | 3/5 |
| bond | J-29 | — | bond | Q-24 | — | — | 3/5 |
| bond | J-29 | — | bond | Q-25 | — | — | 3/5 |
| bond | J-29 | — | bond | Q-26 | — | — | 3/5 |
| bond | J-29 | — | bond | Q-27 | — | — | 3/5 |
| bond | J-29 | — | bond | Q-28 | — | Me | 3/5 |
| bond | J-29 | — | bond | Q-29 | — | — | 3/5 |
| bond | J-29 | — | bond | Q-30 | — | — | 3/5 |
| bond | J-29 | — | bond | Q-31 | — | Me | 3/5 |
| bond | J-29 | — | bond | Q-32 | — | — | 3/5 |
| bond | J-29 | — | bond | Q-33 | — | — | 3/5 |
| bond | J-29 | — | bond | Q-34 | — | — | 3/5 |
| bond | J-29 | — | bond | Q-35 | — | — | 3/5 |
| bond | J-29 | — | bond | Q-36 | — | — | 3/5 |
| bond | J-29 | — | bond | Q-37 | — | — | 3/5 |
| bond | J-29 | — | bond | Q-38 | — | — | 3/5 |
| bond | J-29 | — | bond | Q-39 | — | — | 3/5 |
| bond | J-29 | — | bond | Q-40 | — | — | 3/5 |
| bond | J-29 | — | bond | Q-41 | — | — | 3/5 |
| bond | J-29 | — | bond | Q-42 | — | — | 3/5 |
| bond | J-29 | — | bond | Q-43 | — | — | 3/5 |
| bond | J-29 | — | bond | Q-44 | — | — | 3/5 |
| bond | J-29 | — | bond | Q-46 | — | — | 3/5 |
| bond | J-29 | — | $CH_2$ | Q-47 | — | — | 3/5 |
| bond | J-29 | — | bond | Q-48 | — | — | 3/5 |
| bond | J-29 | — | bond | Q-49 | — | — | 3/5 |
| bond | J-29 | — | bond | Q-50 | — | — | 3/5 |
| bond | J-29 | — | bond | Q-51 | — | — | 3/5 |
| bond | J-29 | — | bond | Q-52 | — | — | 3/5 |
| bond | J-29 | — | bond | Q-53 | — | — | 3/5 |
| bond | J-29 | — | bond | Q-54 | — | — | 3/5 |
| bond | J-29 | — | bond | Q-55 | — | — | 3/5 |
| bond | J-29 | — | bond | Q-56 | — | — | 3/5 |
| bond | J-29 | — | bond | Q-57 | — | — | 3/5 |
| bond | J-29 | — | bond | Q-58 | — | — | 3/5 |
| bond | J-29 | — | bond | Q-59 | — | — | 3/5 |
| bond | J-29 | — | bond | Q-60 | — | — | 3/5 |
| bond | J-29 | — | bond | Q-61 | — | — | 3/5 |
| bond | J-29 | — | bond | Q-62 | — | — | 3/5 |
| bond | J-29 | — | bond | Q-63 | — | — | 3/5 |
| bond | J-29 | — | bond | Q-64 | — | — | 3/5 |
| bond | J-29 | — | bond | Q-65 | — | — | 3/5 |
| bond | J-29 | — | bond | Q-66 | — | — | 3/5 |
| bond | J-29 | — | bond | Q-67 | — | — | 3/5 |
| bond | J-29 | — | bond | Q-68 | — | — | 3/5 |
| bond | J-29 | — | bond | Q-69 | — | — | 3/5 |

TABLE 2*-continued

| $Z^1$ | J | $(R^5)_x$ | $Z^2$ | Q | $(R^7)_p$ | $R^{12}$ | J-orientation** |
|---|---|---|---|---|---|---|---|
| bond | J-29 | — | bond | Q-45 | 2-Me | — | 3/5 |
| bond | J-29 | — | bond | Q-45 | 3-Me | — | 3/5 |
| bond | J-29 | — | bond | Q-45 | 4-Me | — | 3/5 |
| bond | J-29 | — | bond | Q-45 | 2-Cl | — | 3/5 |
| bond | J-29 | — | bond | Q-45 | 3-Cl | — | 3/5 |
| bond | J-29 | — | bond | Q-45 | 4-Cl | — | 3/5 |
| bond | J-29 | — | bond | Q-45 | 2-OMe | — | 3/5 |
| bond | J-29 | — | bond | Q-45 | 3-OMe | — | 3/5 |
| bond | J-29 | — | bond | Q-45 | 4-OMe | — | 3/5 |
| bond | J-29 | — | bond | Q-45 | 2-Et | — | 3/5 |
| bond | J-29 | — | bond | Q-45 | 3-i-Pr | — | 3/5 |
| bond | J-29 | — | bond | Q-45 | 2,6-di-Me | — | 3/5 |
| bond | J-29 | — | bond | Q-45 | 4-vinyl | — | 3/5 |
| bond | J-29 | — | bond | Q-45 | 4-ethynyl | — | 3/5 |
| bond | J-29 | — | bond | Q-45 | 4-c-Pr | — | 3/5 |
| bond | J-29 | — | bond | Q-45 | 3-$CF_3$ | — | 3/5 |
| bond | J-29 | — | bond | Q-45 | 3-$OCF_3$ | — | 3/5 |
| bond | J-29 | — | bond | Q-45 | 4-Br | — | 3/5 |
| bond | J-29 | — | bond | Q-45 | 3-OH | — | 3/5 |
| bond | J-29 | — | bond | Q-45 | 3-$NH_2$ | — | 3/5 |
| bond | J-29 | — | bond | Q-45 | 2-CN | — | 3/5 |
| bond | J-29 | — | bond | Q-45 | 2-$NO_2$ | — | 3/5 |
| bond | J-29 | — | bond | Q-45 | 4-O—t-Bu | — | 3/5 |
| bond | J-29 | — | bond | Q-45 | 4-SMe | — | 3/5 |
| bond | J-29 | — | bond | Q-45 | 4-$SCF_3$ | — | 3/5 |
| bond | J-29 | — | bond | Q-45 | 3-$SO_2$Me | — | 3/5 |
| bond | J-29 | — | bond | Q-45 | 3-NHMe | — | 3/5 |
| bond | J-29 | — | bond | Q-45 | 4-$NMe_2$ | — | 3/5 |
| bond | J-29 | — | bond | Q-45 | 2-$CH_2$OMe | — | 3/5 |
| bond | J-29 | — | bond | Q-45 | 3-COMe | — | 3/5 |
| bond | J-29 | — | bond | Q-45 | 3-$CO_2$Me | — | 3/5 |
| bond | J-29 | — | bond | Q-45 | 3-CONHMe | — | 3/5 |
| bond | J-29 | — | bond | Q-45 | 4-OCOMe | — | 3/5 |
| bond | J-29 | — | bond | Q-45 | 4-SCOMe | — | 3/5 |
| bond | J-29 | — | bond | Q-45 | 3-$CONMe_2$ | — | 3/5 |
| bond | J-29 | — | bond | Q-45 | 4-$SiMe_3$ | — | 3/5 |
| bond | J-29 | — | bond | Q-45 | 2,6-di-F | — | 3/5 |
| bond | J-29 | — | bond | Q-45 | 2,6-di-Cl | — | 3/5 |
| bond | J-29 | — | bond | Q-45 | 2-OH | — | 3/5 |
| bond | J-29 | — | bond | Q-45 | 4-$OCHF_2$ | — | 3/5 |
| bond | J-26 | 1-Me | bond | Q-45 | — | — | 2/5 |
| bond | J-26 | [Note 3] | bond | Q-45 | [Note 3] | — | 2/5 |
| bond | J-26 | 1-Me, [Note 3] | bond | Q-45 | [Note 3] | — | 2/5 |
| bond | J-26 | — | bond | Q-45 | 4-OH | — | 2/5 |
| bond | J-26 | — | bond | Q-45 | 4-OMe | — | 2/5 |
| bond | J-26 | — | $CH_2$ | Q-45 | 4-OH | — | 2/5 |
| bond | J-26 | — | $CH_2$ | Q-45 | 4-OMe | — | 2/5 |
| bond | J-26 | — | bond | Q-45 | 4-OH | — | 2/4 |
| bond | J-26 | — | bond | Q-45 | 4-OMe | — | 2/4 |
| bond | J-26 | — | $CH_2$ | Q-45 | 4-OH | — | 2/4 |
| bond | J-26 | — | $CH_2$ | Q-45 | 4-OMe | — | 2/4 |
| bond | J-25 | — | bond | Q-45 | 4-OH | — | 2/4 |
| bond | J-25 | — | bond | Q-45 | 4-OMe | — | 2/4 |
| bond | J-25 | — | $CH_2$ | Q-45 | 4-OH | — | 2/4 |
| bond | J-25 | — | $CH_2$ | Q-45 | 4-OMe | — | 2/4 |
| bond | J-1 | 5-Me | bond | Q-45 | — | — | 2/4 |
| bond | J-3 | — | bond | Q-45 | — | — | 2/4 |
| bond | J-3 | [Note 4] | bond | Q-45 | [Note 4] | — | 2/5 |
| bond | J-29 | 5-$CO_2$Me | bond | Q-45 | — | — | 3/5 |
| bond | J-29 | 5-$CO_2$Et | bond | Q-45 | — | — | 3/5 |
| bond | J-29 | 4,4-di-Me-5-$CO_2$Me | bond | Q-45 | — | — | 3/5 |
| bond | J-29 | 5-$CONEt_2$ | bond | Q-45 | — | — | 3/5 |
| bond | J-29 | — | NH | Q-45 | — | — | 3/5 |

TABLE 2*-continued

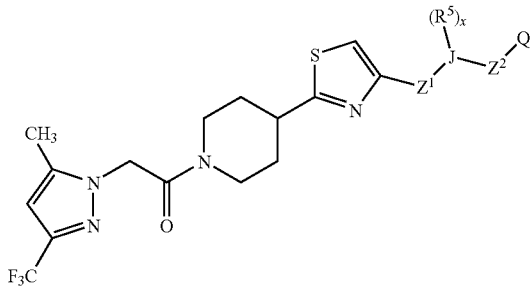

| $Z^1$ | J | $(R^5)_x$ | $Z^2$ | Q | $(R^7)_p$ | $R^{12}$ | J-orientation** |
|---|---|---|---|---|---|---|---|
| bond | J-29 | — | NMe | Q-45 | — | — | 3/5 |
| bond | J-29 | — | NEt | Q-45 | — | — | 3/5 |
| bond | J-29 | — | NPr | Q-45 | — | — | 3/5 |
| bond | J-29 | 5-NHAc | — | — | — | — | 3/5 |
| bond | J-29 | 5-NAc$_2$ | — | — | — | — | 3/5 |
| bond | J-29 | 5-N(Me)Ac | — | — | — | — | 3/5 |
| bond | J-29 | 5-N(Me)C(=O)Ph | — | — | — | — | 3/5 |
| bond | J-29 | 5-N(Et)Ac | — | — | — | — | 3/5 |
| bond | J-29 | 5-N(Et)C(=O)Ph | — | — | — | — | 3/5 |
| bond | J-29 | 5-NHC(=O)OMe | — | — | — | — | 3/5 |
| bond | J-29 | 5-N(Me)C(=O)OMe | — | — | — | — | 3/5 |
| bond | J-29 | 5-NHC(=O)OEt | — | — | — | — | 3/5 |
| bond | J-29 | 5-N(Me)C(=O)OEt | — | — | — | — | 3/5 |
| bond | J-69 | 3-Cl | — | — | — | — | 1/3 |
| bond | J-69 | 3-Br | — | — | — | — | 1/3 |
| bond | J-69 | 3-I | — | — | — | — | 1/3 |
| bond | J-69 | 3-Me | — | — | — | — | 1/3 |
| bond | J-69 | 3-Et | — | — | — | — | 1/3 |
| bond | J-69 | 3-Pr | — | — | — | — | 1/3 |
| bond | J-69 | 3-i-Pr | — | — | — | — | 1/3 |
| bond | J-69 | 3-Bu | — | — | — | — | 1/3 |
| bond | J-69 | 3-i-Bu | — | — | — | — | 1/3 |
| bond | J-69 | 3-s-Bu | — | — | — | — | 1/3 |
| bond | J-69 | 3-t-Bu | — | — | — | — | 1/3 |
| bond | J-69 | 3-Am | — | — | — | — | 1/3 |
| bond | J-69 | 3-i-Am | — | — | — | — | 1/3 |
| bond | J-69 | 3-t-Am | — | — | — | — | 1/3 |
| bond | J-69 | 3-cyclopropyl | — | — | — | — | 1/3 |
| bond | J-69 | 3-cyclobutyl | — | — | — | — | 1/3 |
| bond | J-69 | 3-cyclopentyl | — | — | — | — | 1/3 |
| bond | J-69 | 3-cyclohexyl | — | — | — | — | 1/3 |
| bond | J-69 | 3-trifluoromethoxy | — | — | — | — | 1/3 |
| bond | J-69 | 3-isopropyloxy | — | — | — | — | 1/3 |
| bond | J-69 | 3-isobutoxy | — | — | — | — | 1/3 |
| bond | J-69 | 4-Cl | — | — | — | — | 1/4 |
| bond | J-69 | 4-Br | — | — | — | — | 1/4 |
| bond | J-69 | 4-I | — | — | — | — | 1/4 |
| bond | J-69 | 4-Me | — | — | — | — | 1/4 |
| bond | J-69 | 4-Et | — | — | — | — | 1/4 |
| bond | J-69 | 4-Pr | — | — | — | — | 1/4 |
| bond | J-69 | 4-i-Pr | — | — | — | — | 1/4 |
| bond | J-69 | 4-Bu | — | — | — | — | 1/4 |
| bond | J-69 | 4-i-Bu | — | — | — | — | 1/4 |
| bond | J-69 | 4-s-Bu | — | — | — | — | 1/4 |
| bond | J-69 | 4-t-Bu | — | — | — | — | 1/4 |
| bond | J-69 | 4-Am | — | — | — | — | 1/4 |
| bond | J-69 | 4-i-Am | — | — | — | — | 1/4 |
| bond | J-69 | 4-t-Am | — | — | — | — | 1/4 |
| bond | J-69 | 4-cyclopropyl | — | — | — | — | 1/4 |
| bond | J-69 | 4-cyclobutyl | — | — | — | — | 1/4 |
| bond | J-69 | 4-cyclopentyl | — | — | — | — | 1/4 |
| bond | J-69 | 4-cyclohexyl | — | — | — | — | 1/4 |
| bond | J-69 | 4-trifluoromethoxy | — | — | — | — | 1/4 |
| bond | J-69 | 4-isopropyloxy | — | — | — | — | 1/4 |
| bond | J-69 | 4-isobutoxy | — | — | — | — | 1/4 |
| bond | J-69 | 3,4-di-Cl | — | — | — | — | 1/4 |
| bond | J-69 | 3,4-di-Br | — | — | — | — | 1/4 |
| bond | J-69 | 3,4-di-Me | — | — | — | — | 1/4 |
| bond | J-69 | 3,4-di-Et | — | — | — | — | 1/4 |
| bond | J-69 | 3,4-di-OMe | — | — | — | — | 1/4 |
| bond | J-69 | 3,4-di-OEt | — | — | — | — | 1/4 |
| bond | J-69 | 3-OMe-4-O-propargyl | — | — | — | — | 1/4 |
| bond | J-4 | 5-i-Bu | — | — | — | — | 2/5 |

TABLE 2*-continued

| Z¹ | J | (R⁵)ₓ | Z² | Q | (R⁷)ₚ | R¹² | J-orientation** |
|---|---|---|---|---|---|---|---|
| bond | J-4 | 5-i-Am | — | — | — | — | 2/5 |
| bond | J-5 | 5-i-Bu | — | — | — | — | 2/5 |
| bond | J-5 | 5-i-Am | — | — | — | — | 2/5 |
| bond | J-11 | 5-i-Bu | — | — | — | — | 3/5 |
| bond | J-11 | 5-i-Am | — | — | — | — | 3/5 |
| bond | J-29 | — | bond | Q-70 | — | — | 3/5 |
| bond | J-29 | — | bond | Q-71 | — | — | 3/5 |
| bond | J-29 | — | bond | Q-72 | — | Me | 3/5 |
| bond | J-29 | — | bond | Q-73 | — | — | 3/5 |
| bond | J-29 | — | bond | Q-74 | — | — | 3/5 |
| bond | J-29 | — | bond | Q-75 | — | Me | 3/5 |
| bond | J-29 | — | bond | Q-76 | — | — | 3/5 |
| bond | J-29 | — | bond | Q-77 | — | — | 3/5 |
| bond | J-29 | — | bond | Q-78 | — | Me | 3/5 |
| bond | J-29 | — | bond | Q-79 | — | Me | 3/5 |
| bond | J-29 | — | bond | Q-80 | — | — | 3/5 |
| bond | J-29 | — | bond | Q-81 | — | — | 3/5 |
| bond | J-29 | — | bond | Q-82 | — | — | 3/5 |
| bond | J-29 | — | bond | Q-83 | — | — | 3/5 |
| bond | J-29 | — | bond | Q-84 | — | — | 3/5 |
| bond | J-29 | — | bond | Q-85 | — | — | 3/5 |
| bond | J-29 | — | bond | Q-86 | — | Me | 3/5 |
| bond | J-29 | — | bond | Q-87 | — | — | 3/5 |
| bond | J-29 | — | bond | Q-88 | — | Me | 3/5 |
| bond | J-29 | — | bond | Q-89 | — | — | 3/5 |
| bond | J-29 | — | bond | Q-90 | — | — | 3/5 |
| bond | J-29 | — | bond | Q-91 | — | — | 3/5 |
| bond | J-29 | — | bond | Q-92 | — | Me | 3/5 |
| bond | J-29 | — | bond | Q-93 | — | — | 3/5 |
| bond | J-29 | — | bond | Q-94 | — | — | 3/5 |
| bond | J-29 | — | bond | Q-95 | — | Me | 3/5 |
| bond | J-29 | — | bond | Q-96 | — | — | 3/5 |
| bond | J-29 | — | bond | Q-97 | — | — | 3/5 |
| bond | J-29 | — | bond | Q-98 | — | — | 3/5 |
| bond | J-29 | — | bond | Q-99 | — | — | 3/5 |
| bond | J-29 | — | bond | Q-100 | — | — | 3/5 |
| bond | J-29 | — | bond | Q-101 | — | — | 3/5 |
| bond | J-29 | — | bond | Q-102 | — | Me | 3/5 |
| bond | J-29 | — | bond | Q-87 | 4-phenyl | — | 3/5 |
| bond | J-29 | — | bond | Q-72 | — | acetyl | 3/5 |
| bond | J-29 | — | bond | Q-72 | — | methoxycarbonyl | 3/5 |
| bond | J-29 | — | bond | Q-72 | — | methoxy | 3/5 |
| bond | J-29 | — | bond | Q-71 | 4-Cl | — | 3/5 |
| bond | J-29 | — | bond | Q-71 | 5-Cl | — | 3/5 |
| bond | J-29 | — | bond | Q-71 | 6-Cl | — | 3/5 |
| bond | J-29 | — | bond | Q-71 | 7-Cl | — | 3/5 |
| bond | J-29 | — | bond | Q-71 | 4-Me | — | 3/5 |
| bond | J-29 | — | bond | Q-71 | 5-Me | — | 3/5 |
| bond | J-29 | — | bond | Q-71 | 6-Me | — | 3/5 |
| bond | J-29 | — | bond | Q-71 | 5-CF₃ | — | 3/5 |
| bond | J-29 | — | bond | Q-71 | 5-NO₂ | — | 3/5 |
| bond | J-29 | — | bond | Q-71 | 6-Br | — | 3/5 |
| bond | J-29 | — | bond | Q-71 | 6-NO₂ | — | 3/5 |
| bond | J-29 | — | bond | Q-71 | 6-NH₂ | — | 3/5 |
| bond | J-29 | — | bond | Q-71 | 6-OMe | — | 2/5 |
| bond | J-29 | — | bond | Q-71 | 5,6-di-OMe | — | 3/5 |
| bond | J-29 | — | bond | Q-71 | 5,6-di-Cl | — | 3/5 |
| bond | J-29 | — | bond | Q-70 | 5-Cl | — | 3/5 |
| bond | J-29 | — | bond | Q-70 | 5-Me | — | 3/5 |
| bond | J-29 | — | bond | Q-70 | 5-NO₂ | — | 3/5 |
| bond | J-29 | — | bond | Q-70 | 5-NH₂ | — | 3/5 |
| bond | J-29 | — | bond | Q-70 | 6-Cl | — | 3/5 |
| bond | J-29 | — | bond | Q-70 | 6-Me | — | 3/5 |

TABLE 2*-continued

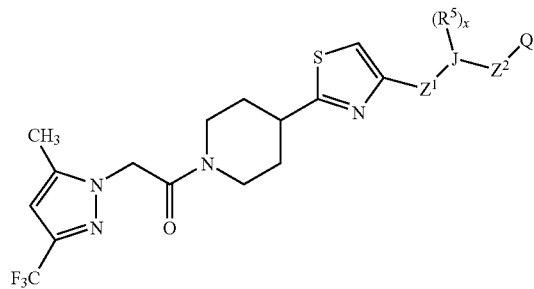

| $Z^1$ | J | $(R^5)_x$ | $Z^2$ | Q | $(R^7)_p$ | $R^{12}$ | J-orientation** |
|---|---|---|---|---|---|---|---|
| bond | J-29 | — | bond | Q-70 | 6-NO$_2$ | — | 3/5 |
| bond | J-29 | — | bond | Q-70 | 6-NH$_2$ | — | 3/5 |
| bond | J-29 | — | bond | Q-70 | 5,6-di-Cl | — | 3/5 |
| bond | J-29 | — | bond | Q-70 | 5-Cl-6-OH | — | 3/5 |
| bond | J-29 | — | bond | Q-72 | 5-Cl | Me | 3/5 |
| bond | J-29 | — | bond | Q-72 | 5-Me | Me | 3/5 |
| bond | J-29 | — | bond | Q-72 | 5-NO$_2$ | Me | 3/5 |
| bond | J-29 | — | bond | Q-72 | 5-NH$_2$ | Me | 3/5 |
| bond | J-29 | — | bond | Q-72 | 6-Cl | Me | 3/5 |
| bond | J-29 | — | bond | Q-72 | 6-Me | Me | 3/5 |
| bond | J-29 | — | bond | Q-72 | 6-NO$_2$ | Me | 3/5 |
| bond | J-29 | — | bond | Q-72 | 6-NH$_2$ | Me | 3/5 |
| bond | J-29 | — | bond | Q-72 | 5,6-di-Cl | Me | 3/5 |
| bond | J-29 | — | bond | Q-63 | 4-Me | — | 3/5 |
| bond | J-29 | — | bond | Q-63 | 4-NO$_2$ | — | 3/5 |
| bond | J-29 | — | bond | Q-63 | 4-NH$_2$ | — | 3/5 |
| bond | J-29 | — | bond | Q-63 | 5-Cl | — | 3/5 |
| bond | J-29 | — | bond | Q-63 | 5-Me | — | 3/5 |
| bond | J-29 | — | bond | Q-63 | 5-CN | — | 3/5 |
| bond | J-29 | — | bond | Q-63 | 5-NO$_2$ | — | 3/5 |
| bond | J-29 | — | bond | Q-63 | 5-NH$_2$ | — | 3/5 |
| bond | J-29 | — | bond | Q-63 | 5-COOMe | — | 3/5 |
| bond | J-29 | — | bond | Q-63 | 5,6-di-Cl | — | 3/5 |
| bond | J-29 | 5-N(Ac)C(=O)Ph | bond | — | — | — | 3/5 |
| bond | J-29 | 5-N(Ac)C(=O)(2-carbomethoxy-Ph) | bond | — | — | — | 3/5 |

*The definitions of J and Q in the compounds of this table are as defined in Exhibits 3 and 4 in the above Embodiments. A dash "—" in the $(R^5)_x$ column indicates no substitution on J. A dash in both the $Z^2$ and Q columns indicates that no $Z^2Q$ substituent is attached as $R^5$ to J. A dash in the $(R^7)_p$ and/or $R^{12}$ columns indicates no substitution on Q.
**J-orientation refers to the attachment points of ring J to $Z^1$ and $Z^2$ (or another $R^5$ when $Z^2$ is not present) on ring J. The first number refers to the ring position on J where $Z^1$ is attached, and the second number refers to the ring position on J where $Z^2$ is attached or, when $Z^2$ is not present, the ring position on J where the substituent listed under $(R^3)_x$ is attached.
[Note 1]: $R^5$ and $R^7$ taken together to form a CH$_2$CH$_2$ bridge between position 4 of J-29 and position 2 of Q-45.
[Note 2]: $R^5$ and $R^7$ taken together to form a CH$_2$ bridge between position 4 of J-29 and position 2 of Q-45.
[Note 3]: $R^5$ and $R^7$ taken together to form a CH$_2$CH$_2$ bridge between position 4 of J-26 and position 2 of Q-45.
[Note 4]: $R^5$ and $R^7$ taken together to form a CH$_2$CH$_2$ bridge between position 1 of J-3 and position 2 of Q-45.

In the structure shown above Table 2 the 2-[5-methyl-3-(trifluoromethyl)-1H-pyrazol-1-yl]acetyl moiety is L-1 as defined in Index Table A below. As defined in the Summary of the Invention and above Embodiments, the present invention also includes but is not limited to component (a) compounds (i.e. compounds of Formula 1) wherein the 2-[5-methyl-3-(trifluoromethyl)-1H-pyrazol-1-yl]acetyl moiety (i.e. L-1) in the structure above Table 2 is other than 2-[5-methyl-3-(trifluoromethyl)-1H-pyrazol-1-yl]acetyl. As such, the present invention also includes Table 2² wherein the 2-[5-methyl-3-(trifluoromethyl)-1H-pyrazol-1-yl]acetyl moiety (i.e. L-1) in the structure above Table 2 is replaced with L-2 (defined in Index Table A below) and the remaining substituents are as defined in Table 2. Thus, for example, Table 2² specifically discloses 1-[4-[4-[5-(2,6-difluorophenyl)-4,5-dihydro-3-isoxazolyl]-2-thiazolyl]-1-piperidinyl]-2-[5-ethyl-3-(trifluoromethyl)-1H-pyrazol-1-yl]ethanone and 2-[3-[2-[1-[2-[5-ethyl-3-(trifluoromethyl)-1H-pyrazol-1-yl]acetyl]-4-piperidinyl]-4-thiazolyl]-4,5-dihydro-5-isoxazolyl]benzonitrile. Also, the present invention includes Tables 2³ through 2⁹⁷ wherein the 2-[5-methyl-3-(trifluoromethyl)-1H-pyrazol-1-ylacetyl moiety (i.e. L-1) in the structure above Table 2 is replaced with L-3 through L-97 (wherein the L groups are as defined Index Table A below) and the remaining substituents are as defined in Table 2. Tables 2³ through 2⁹⁷ are constructed similar to Table 2², and include, for example, the compounds 1-[4-[4-[5-(2,6-difluorophenyl)-4,5-dihydro-3-isoxazolyl]-2-thiazolyl]-1-piperidinyl]-2-(2,5-dimethylphenyl)ethanone (in Table2⁶), 4-[4-[5-(2,6-difluorophenyl)-4,5-dihydro-3-isoxazolyl]-2-thiazolyl]-N-(2,5-dimethylphenyl)-1-piperdinecarboxamide (in Table2³⁵) and 1-[4-[4-[5-(2,6-difluorophenyl)-4,5-dihydro-3-isoxazolyl]-2-thiazolyl]-1-piperidinyl]-2-(2,5-dimethylphenyl)-2-hydroxyethanone (Table2⁹⁴).

As disclosed in Scheme 2 above, compounds of Formula 3 are useful intermediates for the preparation of compounds of Formula 1a wherein W is O (e.g., the compounds of Formula 1a disclosed in Table 2). The present invention includes but is not limited to the following exemplary species of the compounds Formula 3: Table 2ᵃ wherein X in the structure of Formula 3 is X¹, n is 0, and G, Z¹ and J are as defined in Table 2. Thus, the compounds disclosed in Table 2ᵃ include the compounds disclosed in Table 2 wherein the 2-[5-methyl-3-(trifluoromethyl)-1H-pyrazol-1-yl]acetyl moiety in the structure above Table 2 is replaced with H. For example, Table 2a specifically discloses 2-[4,5-dihydro-3-[2-(4-piperidinyl)-4-thiazolyl]-5-isoxazolyl]benzonitrile, 4-[4-(5-phenyl-3-isoxazolyl)-2-thiazolyl]piperidine and 4-[4-[4,5-dihydro-5-phenyl-3-isothiazolyl)-2-thiazolyl]piperidine.

TABLE 3*

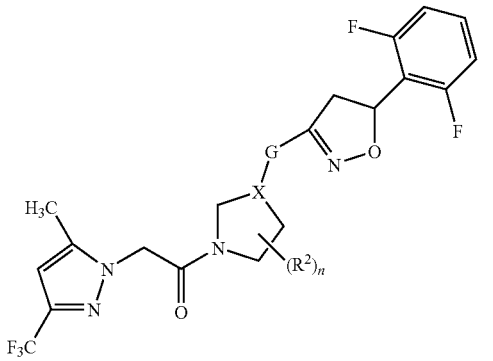

| X | $(R^2)_n$ | G | $R^{3a}$ | $R^{11a}$ |
|---|---|---|---|---|
| $X^1$ | — | G-1 | H | — |
| $X^1$ | — | G-2 | H | — |
| $X^1$ | — | G-3 | H | H |
| $X^1$ | — | G-4 | H | — |
| $X^1$ | — | G-5 | H | — |
| $X^1$ | — | G-6 | H | H |
| $X^1$ | — | G-7 | H | — |
| $X^1$ | — | G-8 | H | — |
| $X^1$ | — | G-9 | H | H |
| $X^1$ | — | G-10 | H | — |
| $X^1$ | — | G-11 | H | — |
| $X^1$ | — | G-12 | H | H |
| $X^1$ | — | G-13 | H | H |
| $X^1$ | — | G-14 | H | — |
| $X^1$ | — | G-15 | H | — |
| $X^1$ | — | G-16 | H | H |
| $X^1$ | — | G-17 | H | — |
| $X^1$ | — | G-18 | H | — |
| $X^1$ | — | G-19 | H | H |
| $X^1$ | — | G-20 | H | — |
| $X^1$ | — | G-21 | H | — |
| $X^1$ | — | G-22 | H | H |
| $X^1$ | — | G-23 | H | — |
| $X^1$ | — | G-24 | H | — |
| $X^1$ | — | G-25 | H | — |
| $X^1$ | — | G-26 | H | — |
| $X^1$ | — | G-27 | H | — |
| $X^1$ | — | G-28 | H | — |
| $X^1$ | — | G-29 | H | — |
| $X^1$ | — | G-30 | H | — |
| $X^1$ | — | G-31 | H | — |
| $X^1$ | — | G-32 | H | — |
| $X^1$ | — | G-33 | H | — |
| $X^1$ | — | G-34 | H | — |
| $X^1$ | — | G-35 | H | — |
| $X^1$ | — | G-36 | H | — |
| $X^1$ | — | G-37 | H | — |
| $X^1$ | — | G-38 | H | — |
| $X^1$ | — | G-39 | H | H |
| $X^1$ | — | G-40 | H | — |
| $X^1$ | — | G-41 | H | — |
| $X^1$ | — | G-42 | H | H |
| $X^1$ | — | G-43 | H | H |
| $X^1$ | — | G-44 | H | — |
| $X^1$ | — | G-45 | H | — |
| $X^1$ | — | G-46 | H | — |
| $X^1$ | — | G-47 | H | — |
| $X^1$ | — | G-48 | H | H |
| $X^1$ | — | G-49 | H | — |
| $X^1$ | — | G-50 | H | — |
| $X^1$ | — | G-51 | H | H |
| $X^1$ | — | G-52 | H | — |
| $X^1$ | — | G-53 | H | — |
| $X^1$ | — | G-54 | H | H |
| $X^1$ | — | G-55 | H | — |
| $X^1$ | — | G-56 | H | — |
| $X^1$ | — | G-57 | H | — |
| $X^1$ | — | G-58 | H | H |
| $X^1$ | — | G-59 | H | H |
| $X^1$ | — | G-2 | Me | — |
| $X^1$ | — | G-2 | Cl | — |
| $X^1$ | — | G-2 | F | — |
| $X^1$ | — | G-2 | $CF_3$ | — |
| $X^1$ | — | G-14 | n-Pr | — |
| $X^1$ | — | G-3 | H | Me |
| $X^1$ | — | G-3 | H | n-Pr |
| $X^1$ | — | G-26 | 5-Me | — |
| $X^1$ | 2-Me | G-1 | H | — |
| $X^1$ | 3-Me | G-1 | H | — |
| $X^1$ | 2,6-di-Me | G-1 | H | — |
| $X^1$ | 3,5-di-Me | G-1 | H | — |
| $X^1$ | 3-n-Bu | G-1 | H | — |
| $X^1$ | 4-MeO | G-1 | H | — |
| $X^1$ | 4-OH | G-1 | H | — |
| $X^1$ | 4-Cl | G-1 | H | — |
| $X^1$ | 4-Br | G-1 | H | — |
| $X^1$ | 4-CN | G-1 | H | — |
| $X^2$ | — | G-1 | H | — |
| $X^2$ | — | G-2 | H | — |
| $X^2$ | — | G-3 | H | H |
| $X^2$ | — | G-4 | H | — |
| $X^2$ | — | G-5 | H | — |
| $X^2$ | — | G-6 | H | H |
| $X^2$ | — | G-7 | H | — |
| $X^2$ | — | G-8 | H | — |
| $X^2$ | — | G-9 | H | H |
| $X^2$ | — | G-10 | H | — |
| $X^2$ | — | G-11 | H | — |
| $X^2$ | — | G-12 | H | H |
| $X^2$ | — | G-13 | H | H |
| $X^2$ | — | G-14 | H | — |
| $X^2$ | — | G-15 | H | — |
| $X^2$ | — | G-16 | H | H |
| $X^2$ | — | G-17 | H | — |
| $X^2$ | — | G-18 | H | — |
| $X^2$ | — | G-19 | H | H |
| $X^2$ | — | G-20 | H | — |
| $X^2$ | — | G-21 | H | — |
| $X^2$ | — | G-22 | H | H |
| $X^2$ | — | G-23 | H | — |
| $X^2$ | — | G-24 | H | — |
| $X^2$ | — | G-31 | H | — |
| $X^2$ | — | G-32 | H | — |
| $X^2$ | — | G-33 | H | — |
| $X^2$ | — | G-34 | H | — |
| $X^2$ | — | G-35 | H | — |
| $X^2$ | — | G-37 | H | — |
| $X^2$ | — | G-38 | H | — |
| $X^2$ | — | G-39 | H | H |
| $X^2$ | — | G-40 | H | — |

TABLE 3*-continued

| X | (R²)ₙ | G | R³ᵃ | R¹¹ᵃ |
|---|---|---|---|---|
| X² | — | G-41 | H | — |
| X² | — | G-42 | H | H |
| X² | — | G-43 | H | H |
| X² | — | G-44 | H | — |
| X² | — | G-45 | H | — |
| X² | — | G-46 | H | — |
| X² | — | G-47 | H | — |
| X² | — | G-48 | H | H |
| X² | — | G-49 | H | — |
| X² | — | G-50 | H | — |
| X² | — | G-51 | H | H |
| X² | — | G-52 | H | — |
| X² | — | G-53 | H | — |
| X² | — | G-54 | H | H |
| X² | — | G-2 | Me | — |
| X² | — | G-2 | Cl | — |
| X² | — | G-2 | F | — |
| X² | — | G-2 | CF₃ | — |
| X² | — | G-14 | n-Pr | — |
| X² | — | G-3 | H | Me |
| X² | — | G-3 | H | n-Pr |
| X² | 2-Me | G-1 | H | — |
| X² | 3-Me | G-1 | H | — |
| X² | 2,6-di-Me | G-1 | H | — |
| X² | 3,5-di-Me | G-1 | H | — |
| X² | 3-n-Bu | G-1 | H | — |
| X³ | — | G-1 | H | — |
| X³ | — | G-2 | H | — |
| X³ | — | G-3 | H | H |
| X³ | — | G-4 | H | — |
| X³ | — | G-5 | H | — |
| X³ | — | G-6 | H | H |
| X³ | — | G-7 | H | — |
| X³ | — | G-8 | H | — |
| X³ | — | G-9 | H | H |
| X³ | — | G-10 | H | — |
| X³ | — | G-11 | H | — |
| X³ | — | G-12 | H | H |
| X³ | — | G-13 | H | H |
| X³ | — | G-14 | H | — |
| X³ | — | G-15 | H | — |
| X³ | — | G-16 | H | H |
| X³ | — | G-17 | H | — |
| X³ | — | G-18 | H | — |
| X³ | — | G-19 | H | H |
| X³ | — | G-20 | H | — |
| X³ | — | G-21 | H | — |
| X³ | — | G-22 | H | H |
| X³ | — | G-23 | H | — |
| X³ | — | G-24 | H | — |
| X³ | — | G-31 | H | — |
| X³ | — | G-32 | H | — |
| X³ | — | G-33 | H | — |
| X³ | — | G-34 | H | — |
| X³ | — | G-35 | H | — |
| X³ | — | G-37 | H | — |
| X³ | — | G-38 | H | — |
| X³ | — | G-39 | H | H |
| X³ | — | G-40 | H | — |
| X³ | — | G-41 | H | — |
| X³ | — | G-42 | H | H |
| X³ | — | G-43 | H | H |
| X³ | — | G-44 | H | — |
| X³ | — | G-45 | H | — |
| X³ | — | G-46 | H | — |
| X³ | — | G-47 | H | — |
| X³ | — | G-48 | H | H |
| X³ | — | G-49 | H | — |
| X³ | — | G-50 | H | — |
| X³ | — | G-51 | H | H |
| X³ | — | G-52 | H | — |
| X³ | — | G-53 | H | — |
| X³ | — | G-54 | H | H |
| X³ | — | G-2 | Me | — |
| X³ | — | G-2 | Cl | — |
| X³ | — | G-2 | F | — |
| X³ | — | G-2 | CF₃ | — |
| X³ | — | G-14 | n-Pr | — |
| X³ | — | G-3 | H | Me |
| X³ | — | G-3 | H | n-Pr |
| X³ | 2-Me | G-1 | H | — |
| X³ | 3-Me | G-1 | H | — |
| X³ | 2,6-di-Me | G-1 | H | — |
| X³ | 3,5-di-Me | G-1 | H | — |
| X³ | 3-n-Bu | G-1 | H | — |
| X³ | 5-Me | G-1 | H | — |
| X³ | 6-Me | G-1 | H | — |
| X⁴ | — | G-1 | H | — |
| X⁵ | — | G-1 | H | — |
| X⁶ | — | G-1 | H | — |
| X⁷ | — | G-1 | H | — |
| X⁸ | — | G-1 | H | — |
| X⁹ | — | G-1 | H | — |

*X¹, X², X³, X⁴, X⁵, X⁶, X⁷, X⁸ and X⁹ in the compounds of this table are as defined in the Summary of the Invention. The definitions of G, R³ᵃ and R¹¹ᵃ are as defined in Exhibit 2 in the above Embodiments.
A dash "—" in the (R²)ₙ column indicates no substituents.

As disclosed in Scheme 2 above, compounds of Formula 3 are useful intermediates for the preparation of compounds of Formula 1a wherein W is O (e.g., the compounds of Formula 1a disclosed in Table 3). The present invention includes but is not limited to the following exemplary species of the compounds Formula 3: Table 3ᵃ wherein X, R², G, Z¹ and J are as defined in Table 3. Thus, the compounds disclosed in Table 3ᵃ include the compounds disclosed in Table 3 where the 2-[5-methyl-3-(trifluoromethyl)-1H-pyrazol-1-yl]acetyl moiety in the structure above Table 3 is replaced with H. For example, Table 3ᵃ specifically discloses 4-[4-[5-(2,6-difluorophenyl)-4,5-dihydro-3-isoxazolyl]-2-oxazolyl]piperidine, 4-[5-[5-(2,6-difluorophenyl)-4,5-dihydro-3-isoxazolyl]-2-thiazolyl]piperidine, 4-[2-[5-(2,6-difluorophenyl)-4,5-dihydro-3-isoxazolyl]-4-thiazolyl]piperidine and 4-[3-[5-(2,6-difluorophenyl)-4,5-dihydro-3-isoxazolyl]-1H-pyrazol-1-yl]piperidine.

TABLE 4*

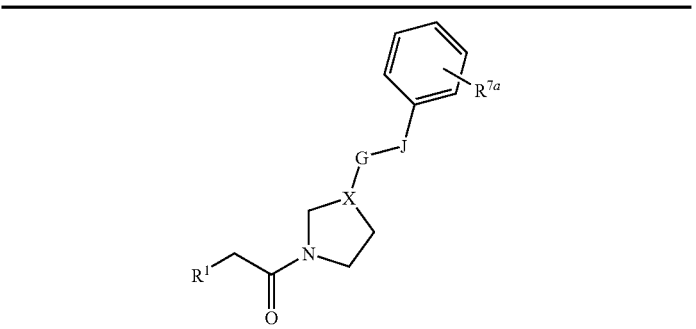

| R¹ | X | G | J* | (R⁵)ᵧ | R⁷ᵃ |
|---|---|---|---|---|---|
| 2,5-dichlorophenyl | X¹ | G-1 | J-1 (2/4) | — | H |
| 2-chloro-5-(trifluoromethyl)phenyl | X¹ | G-1 | J-1 (2/4) | — | H |
| 2,5-dimethylphenyl | X¹ | G-1 | J-1 (2/4) | — | H |
| 2-methyl-5-(trifluoromethyl)phenyl | X¹ | G-1 | J-1 (2/4) | — | H |
| 3,5-dimethylpyrazol-1-yl | X¹ | G-1 | J-1 (2/4) | — | H |
| 5-methyl-3-(trifluoromethyl)pyrazol-1-yl | X¹ | G-1 | J-1 (2/4) | — | H |
| 5-chloro-3-(trifluoromethyl)pyrazol-1-yl | X¹ | G-1 | J-1 (2/4) | — | H |
| 5-bromo-3-(trifluoromethyl)pyrazol-1-yl | X¹ | G-1 | J-1 (2/4) | — | H |
| 5-ethyl-3-(trifluoromethyl)pyrazol-1-yl | X¹ | G-1 | J-1 (2/4) | — | H |
| 3,5-bis-(trifluoromethyl)pyrazol-1-yl | X¹ | G-1 | J-1 (2/4) | — | H |
| 1-methyl-3-(trifluoromethyl)pyrazol-5-yl | X¹ | G-1 | J-1 (2/4) | — | H |
| 1-methyl-4-(trifluoromethyl)imidazol-2-yl | X¹ | G-1 | J-1 (2/4) | — | H |
| 2,5-dichlorophenyl | X¹ | G-1 | J-2 (2/4) | — | H |
| 2-chloro-5-(trifluoromethyl)phenyl | X¹ | G-1 | J-2 (2/4) | — | H |
| 2,5-dimethylphenyl | X¹ | G-1 | J-2 (2/4) | — | H |
| 2-methyl-5-(trifluoromethyl)phenyl | X¹ | G-1 | J-2 (2/4) | — | H |
| 3,5-dimethylpyrazol-1-yl | X¹ | G-1 | J-2 (2/4) | — | H |
| 5-methyl-3-(trifluoromethyl)pyrazol-1-yl | X¹ | G-1 | J-2 (2/4) | — | H |
| 5-chloro-3-(trifluoromethyl)pyrazol-1-yl | X¹ | G-1 | J-2 (2/4) | — | H |
| 5-bromo-3-(trifluoromethyl)pyrazol-1-yl | X¹ | G-1 | J-2 (2/4) | — | H |
| 5-ethyl-3-(trifluoromethyl)pyrazol-1-yl | X¹ | G-1 | J-2 (2/4) | — | H |
| 3,5-bis-(trifluoromethyl)pyrazol-1-yl | X¹ | G-1 | J-2 (2/4) | — | H |
| 1-methyl-3-(trifluoromethyl)pyrazol-5-yl | X¹ | G-1 | J-2 (2/4) | — | H |
| 1-methyl-4-(trifluoromethyl)imidazol-2-yl | X¹ | G-1 | J-2 (2/4) | — | H |
| 2,5-dichlorophenyl | X¹ | G-1 | J-3 (2/4) | 1-Me | H |
| 2-chloro-5-(trifluoromethyl)phenyl | X¹ | G-1 | J-3 (2/4) | 1-Me | H |
| 2,5-dimethylphenyl | X¹ | G-1 | J-3 (2/4) | 1-Me | H |
| 2-methyl-5-(trifluoromethyl)phenyl | X¹ | G-1 | J-3 (2/4) | 1-Me | H |
| 3,5-dimethylpyrazol-1-yl | X¹ | G-1 | J-3 (2/4) | 1-Me | H |
| 5-methyl-3-(trifluoromethyl)pyrazol-1-yl | X¹ | G-1 | J-3 (2/4) | 1-Me | H |
| 5-chloro-3-(trifluoromethyl)pyrazol-1-yl | X¹ | G-1 | J-3 (2/4) | 1-Me | H |
| 5-bromo-3-(trifluoromethyl)pyrazol-1-yl | X¹ | G-1 | J-3 (2/4) | 1-Me | H |
| 5-ethyl-3-(trifluoromethyl)pyrazol-1-yl | X¹ | G-1 | J-3 (2/4) | 1-Me | H |
| 3,5-bis-(trifluoromethyl)pyrazol-1-yl | X¹ | G-1 | J-3 (2/4) | 1-Me | H |
| 1-methyl-3-(trifluoromethyl)pyrazol-5-yl | X¹ | G-1 | J-3 (2/4) | 1-Me | H |
| 1-methyl-4-(trifluoromethyl)imidazol-2-yl | X¹ | G-1 | J-3 (2/4) | 1-Me | H |
| 2,5-dichlorophenyl | X¹ | G-1 | J-4 (2/5) | — | H |
| 2-chloro-5-(trifluoromethyl)phenyl | X¹ | G-1 | J-4 (2/5) | — | H |
| 2,5-dimethylphenyl | X¹ | G-1 | J-4 (2/5) | — | H |
| 2-methyl-5-(trifluoromethyl)phenyl | X¹ | G-1 | J-4 (2/5) | — | H |
| 3,5-dimethylpyrazol-1-yl | X¹ | G-1 | J-4 (2/5) | — | H |
| 5-methyl-3-(trifluoromethyl)pyrazol-1-yl | X¹ | G-1 | J-4 (2/5) | — | H |
| 5-chloro-3-(trifluoromethyl)pyrazol-1-yl | X¹ | G-1 | J-4 (2/5) | — | H |
| 5-bromo-3-(trifluoromethyl)pyrazol-1-yl | X¹ | G-1 | J-4 (2/5) | — | H |
| 5-ethyl-3-(trifluoromethyl)pyrazol-1-yl | X¹ | G-1 | J-4 (2/5) | — | H |
| 3,5-bis-(trifluoromethyl)pyrazol-1-yl | X¹ | G-1 | J-4 (2/5) | — | H |
| 1-methyl-3-(trifluoromethyl)pyrazol-5-yl | X¹ | G-1 | J-4 (2/5) | — | H |
| 1-methyl-4-(trifluoromethyl)imidazol-2-yl | X¹ | G-1 | J-4 (2/5) | — | H |
| 2,5-dichlorophenyl | X¹ | G-1 | J-8 (5/3) | — | H |
| 2-chloro-5-(trifluoromethyl)phenyl | X¹ | G-1 | J-8 (5/3) | — | H |
| 2,5-dimethylphenyl | X¹ | G-1 | J-8 (5/3) | — | H |
| 2-methyl-5-(trifluoromethyl)phenyl | X¹ | G-1 | J-8 (5/3) | — | H |
| 3,5-dimethylpyrazol-1-yl | X¹ | G-1 | J-8 (5/3) | — | H |
| 5-methyl-3-(trifluoromethyl)pyrazol-1-yl | X¹ | G-1 | J-8 (5/3) | — | H |
| 5-chloro-3-(trifluoromethyl)pyrazol-1-yl | X¹ | G-1 | J-8 (5/3) | — | H |
| 5-bromo-3-(trifluoromethyl)pyrazol-1-yl | X¹ | G-1 | J-8 (5/3) | — | H |
| 5-ethyl-3-(trifluoromethyl)pyrazol-1-yl | X¹ | G-1 | J-8 (5/3) | — | H |
| 3,5-bis-(trifluoromethyl)pyrazol-1-yl | X¹ | G-1 | J-8 (5/3) | — | H |
| 1-methyl-3-(trifluoromethyl)pyrazol-5-yl | X¹ | G-1 | J-8 (5/3) | — | H |
| 1-methyl-4-(trifluoromethyl)imidazol-2-yl | X¹ | G-1 | J-8 (5/3) | — | H |
| 2,5-dichlorophenyl | X¹ | G-1 | J-9 (5/3) | — | H |
| 2-chloro-5-(trifluoromethyl)phenyl | X¹ | G-1 | J-9 (5/3) | — | H |

TABLE 4*-continued

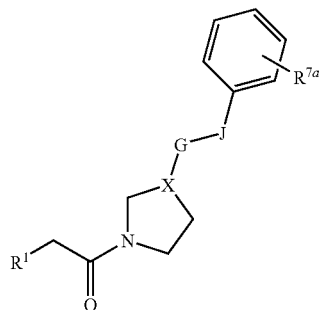

| R¹ | X | G | J* | (R⁵)_y | R⁷ᵃ |
|---|---|---|---|---|---|
| 2,5-dimethylphenyl | X¹ | G-1 | J-9 (5/3) | — | H |
| 2-methyl-5-(trifluoromethyl)phenyl | X¹ | G-1 | J-9 (5/3) | — | H |
| 3,5-dimethylpyrazol-1-yl | X¹ | G-1 | J-9 (5/3) | — | H |
| 5-methyl-3-(trifluoromethyl)pyrazol-1-yl | X¹ | G-1 | J-9 (5/3) | — | H |
| 5-chloro-3-(trifluoromethyl)pyrazol-1-yl | X¹ | G-1 | J-9 (5/3) | — | H |
| 5-bromo-3-(trifluoromethyl)pyrazol-1-yl | X¹ | G-1 | J-9 (5/3) | — | H |
| 5-ethyl-3-(trifluoromethyl)pyrazol-1-yl | X¹ | G-1 | J-9 (5/3) | — | H |
| 3,5-bis-(trifluoromethyl)pyrazol-1-yl | X¹ | G-1 | J-9 (5/3) | — | H |
| 1-methyl-3-(trifluoromethyl)pyrazol-5-yl | X¹ | G-1 | J-9 (5/3) | — | H |
| 1-methyl-4-(trifluoromethyl)imidazol-2-yl | X¹ | G-1 | J-9 (5/3) | — | H |
| 2,5-dichlorophenyl | X¹ | G-1 | J-11 (3/5) | — | H |
| 2-chloro-5-(trifluoromethyl)phenyl | X¹ | G-1 | J-11 (3/5) | — | H |
| 2,5-dimethylphenyl | X¹ | G-1 | J-11 (3/5) | — | H |
| 2-methyl-5-(trifluoromethyl)phenyl | X¹ | G-1 | J-11 (3/5) | — | H |
| 3,5-dimethylpyrazol-1-yl | X¹ | G-1 | J-11 (3/5) | — | H |
| 5-methyl-3-(trifluoromethyl)pyrazol-1-yl | X¹ | G-1 | J-11 (3/5) | — | H |
| 5-chloro-3-(trifluoromethyl)pyrazol-1-yl | X¹ | G-1 | J-11 (3/5) | — | H |
| 5-bromo-3-(trifluoromethyl)pyrazol-1-yl | X¹ | G-1 | J-11 (3/5) | — | H |
| 5-ethyl-3-(trifluoromethyl)pyrazol-1-yl | X¹ | G-1 | J-11 (3/5) | — | H |
| 3,5-bis-(trifluoromethyl)pyrazol-1-yl | X¹ | G-1 | J-11 (3/5) | — | H |
| 1-methyl-3-(trifluoromethyl)pyrazol-5-yl | X¹ | G-1 | J-11 (3/5) | — | H |
| 1-methyl-4-(trifluoromethyl)imidazol-2-yl | X¹ | G-1 | J-11 (3/5) | — | H |
| 2,5-dichlorophenyl | X¹ | G-1 | J-12 (3/5) | — | H |
| 2-chloro-5-(trifluoromethyl)phenyl | X¹ | G-1 | J-12 (3/5) | — | H |
| 2,5-dimethylphenyl | X¹ | G-1 | J-12 (3/5) | — | H |
| 2-methyl-5-(trifluoromethyl)phenyl | X¹ | G-1 | J-12 (3/5) | — | H |
| 3,5-dimethylpyrazol-1-yl | X¹ | G-1 | J-12 (3/5) | — | H |
| 5-methyl-3-(trifluoromethyl)pyrazol-1-yl | X¹ | G-1 | J-12 (3/5) | — | H |
| 5-chloro-3-(trifluoromethyl)pyrazol-1-yl | X¹ | G-1 | J-12 (3/5) | — | H |
| 5-bromo-3-(trifluoromethyl)pyrazol-1-yl | X¹ | G-1 | J-12 (3/5) | — | H |
| 5-ethyl-3-(trifluoromethyl)pyrazol-1-yl | X¹ | G-1 | J-12 (3/5) | — | H |
| 3,5-bis-(trifluoromethyl)pyrazol-1-yl | X¹ | G-1 | J-12 (3/5) | — | H |
| 1-methyl-3-(trifluoromethyl)pyrazol-5-yl | X¹ | G-1 | J-12 (3/5) | — | H |
| 1-methyl-4-(trifluoromethyl)imidazol-2-yl | X¹ | G-1 | J-12 (3/5) | — | H |
| 2,5-dichlorophenyl | X¹ | G-1 | J-12 (3/5) | 1-Me | H |
| 2-chloro-5-(trifluoromethyl)phenyl | X¹ | G-1 | J-12 (3/5) | 1-Me | H |
| 2,5-dimethylphenyl | X¹ | G-1 | J-12 (3/5) | 1-Me | H |
| 2-methyl-5-(trifluoromethyl)phenyl | X¹ | G-1 | J-12 (3/5) | 1-Me | H |
| 3,5-dimethylpyrazol-1-yl | X¹ | G-1 | J-12 (3/5) | 1-Me | H |
| 5-methyl-3-(trifluoromethyl)pyrazol-1-yl | X¹ | G-1 | J-12 (3/5) | 1-Me | H |
| 5-chloro-3-(trifluoromethyl)pyrazol-1-yl | X¹ | G-1 | J-12 (3/5) | 1-Me | H |
| 5-bromo-3-(trifluoromethyl)pyrazol-1-yl | X¹ | G-1 | J-12 (3/5) | 1-Me | H |
| 5-ethyl-3-(trifluoromethyl)pyrazol-1-yl | X¹ | G-1 | J-12 (3/5) | 1-Me | H |
| 3,5-bis-(trifluoromethyl)pyrazol-1-yl | X¹ | G-1 | J-12 (3/5) | 1-Me | H |
| 1-methyl-3-(trifluoromethyl)pyrazol-5-yl | X¹ | G-1 | J-12 (3/5) | 1-Me | H |
| 1-methyl-4-(trifluoromethyl)imidazol-2-yl | X¹ | G-1 | J-12 (3/5) | 1-Me | H |
| 2,5-dichlorophenyl | X¹ | G-1 | J-14 (3/5) | — | H |
| 2-chloro-5-(trifluoromethyl)phenyl | X¹ | G-1 | J-14 (3/5) | — | H |
| 2,5-dimethylphenyl | X¹ | G-1 | J-14 (3/5) | — | H |
| 2-methyl-5-(trifluoromethyl)phenyl | X¹ | G-1 | J-14 (3/5) | — | H |
| 3,5-dimethylpyrazol-1-yl | X¹ | G-1 | J-14 (3/5) | — | H |
| 5-methyl-3-(trifluoromethyl)pyrazol-1-yl | X¹ | G-1 | J-14 (3/5) | — | H |
| 5-chloro-3-(trifluoromethyl)pyrazol-1-yl | X¹ | G-1 | J-14 (3/5) | — | H |
| 5-bromo-3-(trifluoromethyl)pyrazol-1-yl | X¹ | G-1 | J-14 (3/5) | — | H |
| 5-ethyl-3-(trifluoromethyl)pyrazol-1-yl | X¹ | G-1 | J-14 (3/5) | — | H |
| 3,5-bis-(trifluoromethyl)pyrazol-1-yl | X¹ | G-1 | J-14 (3/5) | — | H |
| 1-methyl-3-(trifluoromethyl)pyrazol-5-yl | X¹ | G-1 | J-14 (3/5) | — | H |
| 1-methyl-4-(trifluoromethyl)imidazol-2-yl | X¹ | G-1 | J-14 (3/5) | — | H |
| 2,5-dichlorophenyl | X¹ | G-1 | J-15 (2/5) | — | H |
| 2-chloro-5-(trifluoromethyl)phenyl | X¹ | G-1 | J-15 (2/5) | — | H |
| 2,5-dimethylphenyl | X¹ | G-1 | J-15 (2/5) | — | H |
| 2-methyl-5-(trifluoromethyl)phenyl | X¹ | G-1 | J-15 (2/5) | — | H |

TABLE 4*-continued

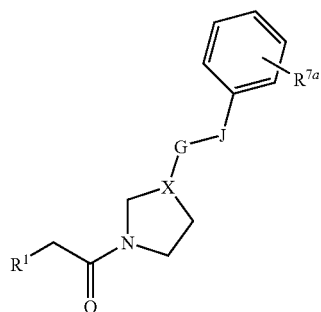

| R¹ | X | G | J* | (R⁵)_y | R⁷ᵃ |
|---|---|---|---|---|---|
| 3,5-dimethylpyrazol-1-yl | X¹ | G-1 | J-15 (2/5) | — | H |
| 5-methyl-3-(trifluoromethyl)pyrazol-1-yl | X¹ | G-1 | J-15 (2/5) | — | H |
| 5-chloro-3-(trifluoromethyl)pyrazol-1-yl | X¹ | G-1 | J-15 (2/5) | — | H |
| 5-bromo-3-(trifluoromethyl)pyrazol-1-yl | X¹ | G-1 | J-15 (2/5) | — | H |
| 5-ethyl-3-(trifluoromethyl)pyrazol-1-yl | X¹ | G-1 | J-15 (2/5) | — | H |
| 3,5-bis-(trifluoromethyl)pyrazol-1-yl | X¹ | G-1 | J-15 (2/5) | — | H |
| 1-methyl-3-(trifluoromethyl)pyrazol-5-yl | X¹ | G-1 | J-15 (2/5) | — | H |
| 1-methyl-4-(trifluoromethyl)imidazol-2-yl | X¹ | G-1 | J-15 (2/5) | — | H |
| 2,5-dichlorophenyl | X¹ | G-1 | J-16 (2/5) | — | H |
| 2-chloro-5-(trifluoromethyl)phenyl | X¹ | G-1 | J-16 (2/5) | — | H |
| 2,5-dimethylphenyl | X¹ | G-1 | J-16 (2/5) | — | H |
| 2-methyl-5-(trifluoromethyl)phenyl | X¹ | G-1 | J-16 (2/5) | — | H |
| 3,5-dimethylpyrazol-1-yl | X¹ | G-1 | J-16 (2/5) | — | H |
| 5-methyl-3-(trifluoromethyl)pyrazol-1-yl | X¹ | G-1 | J-16 (2/5) | — | H |
| 5-chloro-3-(trifluoromethyl)pyrazol-1-yl | X¹ | G-1 | J-16 (2/5) | — | H |
| 5-bromo-3-(trifluoromethyl)pyrazol-1-yl | X¹ | G-1 | J-16 (2/5) | — | H |
| 5-ethyl-3-(trifluoromethyl)pyrazol-1-yl | X¹ | G-1 | J-16 (2/5) | — | H |
| 3,5-bis-(trifluoromethyl)pyrazol-1-yl | X¹ | G-1 | J-16 (2/5) | — | H |
| 1-methyl-3-(trifluoromethyl)pyrazol-5-yl | X¹ | G-1 | J-16 (2/5) | — | H |
| 1-methyl-4-(trifluoromethyl)imidazol-2-yl | X¹ | G-1 | J-16 (2/5) | — | H |
| 2,5-dichlorophenyl | X¹ | G-1 | J-22 (2/4) | — | H |
| 2-chloro-5-(trifluoromethyl)phenyl | X¹ | G-1 | J-22 (2/4) | — | H |
| 2,5-dimethylphenyl | X¹ | G-1 | J-22 (2/4) | — | H |
| 2-methyl-5-(trifluoromethyl)phenyl | X¹ | G-1 | J-22 (2/4) | — | H |
| 3,5-dimethylpyrazol-1-yl | X¹ | G-1 | J-22 (2/4) | — | H |
| 5-methyl-3-(trifluoromethyl)pyrazol-1-yl | X¹ | G-1 | J-22 (2/4) | — | H |
| 5-chloro-3-(trifluoromethyl)pyrazol-1-yl | X¹ | G-1 | J-22 (2/4) | — | H |
| 5-bromo-3-(trifluoromethyl)pyrazol-1-yl | X¹ | G-1 | J-22 (2/4) | — | H |
| 5-ethyl-3-(trifluoromethyl)pyrazol-1-yl | X¹ | G-1 | J-22 (2/4) | — | H |
| 3,5-bis-(trifluoromethyl)pyrazol-1-yl | X¹ | G-1 | J-22 (2/4) | — | H |
| 1-methyl-3-(trifluoromethyl)pyrazol-5-yl | X¹ | G-1 | J-22 (2/4) | — | H |
| 1-methyl-4-(trifluoromethyl)imidazol-2-yl | X¹ | G-1 | J-22 (2/4) | — | H |
| 2,5-dichlorophenyl | X¹ | G-1 | J-24 (2/4) | — | H |
| 2-chloro-5-(trifluoromethyl)phenyl | X¹ | G-1 | J-24 (2/4) | — | H |
| 2,5-dimethylphenyl | X¹ | G-1 | J-24 (2/4) | — | H |
| 2-methyl-5-(trifluoromethyl)phenyl | X¹ | G-1 | J-24 (2/4) | — | H |
| 3,5-dimethylpyrazol-1-yl | X¹ | G-1 | J-24 (2/4) | — | H |
| 5-methyl-3-(trifluoromethyl)pyrazol-1-yl | X¹ | G-1 | J-24 (2/4) | — | H |
| 5-chloro-3-(trifluoromethyl)pyrazol-1-yl | X¹ | G-1 | J-24 (2/4) | — | H |
| 5-bromo-3-(trifluoromethyl)pyrazol-1-yl | X¹ | G-1 | J-24 (2/4) | — | H |
| 5-ethyl-3-(trifluoromethyl)pyrazol-1-yl | X¹ | G-1 | J-24 (2/4) | — | H |
| 3,5-bis-(trifluoromethyl)pyrazol-1-yl | X¹ | G-1 | J-24 (2/4) | — | H |
| 1-methyl-3-(trifluoromethyl)pyrazol-5-yl | X¹ | G-1 | J-24 (2/4) | — | H |
| 1-methyl-4-(trifluoromethyl)imidazol-2-yl | X¹ | G-1 | J-24 (2/4) | — | H |
| 2,5-dichlorophenyl | X¹ | G-1 | J-25 (2/4) | — | H |
| 2-chloro-5-(trifluoromethyl)phenyl | X¹ | G-1 | J-25 (2/4) | — | H |
| 2,5-dimethylphenyl | X¹ | G-1 | J-25 (2/4) | — | H |
| 2-methyl-5-(trifluoromethyl)phenyl | X¹ | G-1 | J-25 (2/4) | — | H |
| 3,5-dimethylpyrazol-1-yl | X¹ | G-1 | J-25 (2/4) | — | H |
| 5-methyl-3-(trifluoromethyl)pyrazol-1-yl | X¹ | G-1 | J-25 (2/4) | — | H |
| 5-chloro-3-(trifluoromethyl)pyrazol-1-yl | X¹ | G-1 | J-25 (2/4) | — | H |
| 5-bromo-3-(trifluoromethyl)pyrazol-1-yl | X¹ | G-1 | J-25 (2/4) | — | H |
| 5-ethyl-3-(trifluoromethyl)pyrazol-1-yl | X¹ | G-1 | J-25 (2/4) | — | H |
| 3,5-bis-(trifluoromethyl)pyrazol-1-yl | X¹ | G-1 | J-25 (2/4) | — | H |
| 1-methyl-3-(trifluoromethyl)pyrazol-5-yl | X¹ | G-1 | J-25 (2/4) | — | H |
| 1-methyl-4-(trifluoromethyl)imidazol-2-yl | X¹ | G-1 | J-25 (2/4) | — | H |
| 2,5-dichlorophenyl | X¹ | G-1 | J-26 (2/4) | — | H |
| 2-chloro-5-(trifluoromethyl)phenyl | X¹ | G-1 | J-26 (2/4) | — | H |
| 2,5-dimethylphenyl | X¹ | G-1 | J-26 (2/4) | — | H |
| 2-methyl-5-(trifluoromethyl)phenyl | X¹ | G-1 | J-26 (2/4) | — | H |
| 3,5-dimethylpyrazol-1-yl | X¹ | G-1 | J-26 (2/4) | — | H |
| 5-methyl-3-(trifluoromethyl)pyrazol-1-yl | X¹ | G-1 | J-26 (2/4) | — | H |

TABLE 4*-continued

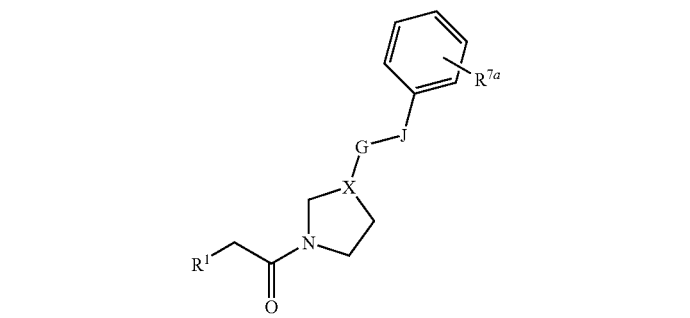

| R¹ | X | G | J* | (R⁵)ᵧ | R⁷ᵃ |
|---|---|---|---|---|---|
| 5-chloro-3-(trifluoromethyl)pyrazol-1-yl | X¹ | G-1 | J-26 (2/4) | — | H |
| 5-bromo-3-(trifluoromethyl)pyrazol-1-yl | X¹ | G-1 | J-26 (2/4) | — | H |
| 5-ethyl-3-(trifluoromethyl)pyrazol-1-yl | X¹ | G-1 | J-26 (2/4) | — | H |
| 3,5-bis-(trifluoromethyl)pyrazol-1-yl | X¹ | G-1 | J-26 (2/4) | — | H |
| 1-methyl-3-(trifluoromethyl)pyrazol-5-yl | X¹ | G-1 | J-26 (2/4) | — | H |
| 1-methyl-4-(trifluoromethyl)imidazol-2-yl | X¹ | G-1 | J-26 (2/4) | — | H |
| 2,5-dichlorophenyl | X¹ | G-1 | J-26 (2/4) | 1-Me | H |
| 2-chloro-5-(trifluoromethyl)phenyl | X¹ | G-1 | J-26 (2/4) | 1-Me | H |
| 2,5-dimethylphenyl | X¹ | G-1 | J-26 (2/4) | 1-Me | H |
| 2-methyl-5-(trifluoromethyl)phenyl | X¹ | G-1 | J-26 (2/4) | 1-Me | H |
| 3,5-dimethylpyrazol-1-yl | X¹ | G-1 | J-26 (2/4) | 1-Me | H |
| 5-methyl-3-(trifluoromethyl)pyrazol-1-yl | X¹ | G-1 | J-26 (2/4) | 1-Me | H |
| 5-chloro-3-(trifluoromethyl)pyrazol-1-yl | X¹ | G-1 | J-26 (2/4) | 1-Me | H |
| 5-bromo-3-(trifluoromethyl)pyrazol-1-yl | X¹ | G-1 | J-26 (2/4) | 1-Me | H |
| 5-ethyl-3-(trifluoromethyl)pyrazol-1-yl | X¹ | G-1 | J-26 (2/4) | 1-Me | H |
| 3,5-bis-(trifluoromethyl)pyrazol-1-yl | X¹ | G-1 | J-26 (2/4) | 1-Me | H |
| 1-methyl-3-(trifluoromethyl)pyrazol-5-yl | X¹ | G-1 | J-26 (2/4) | 1-Me | H |
| 1-methyl-4-(trifluoromethyl)imidazol-2-yl | X¹ | G-1 | J-26 (2/4) | 1-Me | H |
| 2,5-dichlorophenyl | X¹ | G-1 | J-26 (2/5) | 1-Me | H |
| 2-chloro-5-(trifluoromethyl)phenyl | X¹ | G-1 | J-26 (2/5) | 1-Me | H |
| 2,5-dimethylphenyl | X¹ | G-1 | J-26 (2/5) | 1-Me | H |
| 2-methyl-5-(trifluoromethyl)phenyl | X¹ | G-1 | J-26 (2/5) | 1-Me | H |
| 3,5-dimethylpyrazol-1-yl | X¹ | G-1 | J-26 (2/5) | 1-Me | H |
| 5-methyl-3-(trifluoromethyl)pyrazol-1-yl | X¹ | G-1 | J-26 (2/5) | 1-Me | H |
| 5-chloro-3-(trifluoromethyl)pyrazol-1-yl | X¹ | G-1 | J-26 (2/5) | 1-Me | H |
| 5-bromo-3-(trifluoromethyl)pyrazol-1-yl | X¹ | G-1 | J-26 (2/5) | 1-Me | H |
| 5-ethyl-3-(trifluoromethyl)pyrazol-1-yl | X¹ | G-1 | J-26 (2/5) | 1-Me | H |
| 3,5-bis-(trifluoromethyl)pyrazol-1-yl | X¹ | G-1 | J-26 (2/5) | 1-Me | H |
| 1-methyl-3-(trifluoromethyl)pyrazol-5-yl | X¹ | G-1 | J-26 (2/5) | 1-Me | H |
| 1-methyl-4-(trifluoromethyl)imidazol-2-yl | X¹ | G-1 | J-26 (2/5) | 1-Me | H |
| 2,5-dichlorophenyl | X¹ | G-1 | J-28 (3/5) | — | H |
| 2-chloro-5-(trifluoromethyl)phenyl | X¹ | G-1 | J-28 (3/5) | — | H |
| 2,5-dimethylphenyl | X¹ | G-1 | J-28 (3/5) | — | H |
| 2-methyl-5-(trifluoromethyl)phenyl | X¹ | G-1 | J-28 (3/5) | — | H |
| 3,5-dimethylpyrazol-1-yl | X¹ | G-1 | J-28 (3/5) | — | H |
| 5-methyl-3-(trifluoromethyl)pyrazol-1-yl | X¹ | G-1 | J-28 (3/5) | — | H |
| 5-chloro-3-(trifluoromethyl)pyrazol-1-yl | X¹ | G-1 | J-28 (3/5) | — | H |
| 5-bromo-3-(trifluoromethyl)pyrazol-1-yl | X¹ | G-1 | J-28 (3/5) | — | H |
| 5-ethyl-3-(trifluoromethyl)pyrazol-1-yl | X¹ | G-1 | J-28 (3/5) | — | H |
| 3,5-bis-(trifluoromethyl)pyrazol-1-yl | X¹ | G-1 | J-28 (3/5) | — | H |
| 1-methyl-3-(trifluoromethyl)pyrazol-5-yl | X¹ | G-1 | J-28 (3/5) | — | H |
| 1-methyl-4-(trifluoromethyl)imidazol-2-yl | X¹ | G-1 | J-28 (3/5) | — | H |
| 2,5-dichlorophenyl | X¹ | G-1 | J-30 (3/5) | — | H |
| 2-chloro-5-(trifluoromethyl)phenyl | X¹ | G-1 | J-30 (3/5) | — | H |
| 2,5-dimethylphenyl | X¹ | G-1 | J-30 (3/5) | — | H |
| 2-methyl-5-(trifluoromethyl)phenyl | X¹ | G-1 | J-30 (3/5) | — | H |
| 3,5-dimethylpyrazol-1-yl | X¹ | G-1 | J-30 (3/5) | — | H |
| 5-methyl-3-(trifluoromethyl)pyrazol-1-yl | X¹ | G-1 | J-30 (3/5) | — | H |
| 5-chloro-3-(trifluoromethyl)pyrazol-1-yl | X¹ | G-1 | J-30 (3/5) | — | H |
| 5-bromo-3-(trifluoromethyl)pyrazol-1-yl | X¹ | G-1 | J-30 (3/5) | — | H |
| 5-ethyl-3-(trifluoromethyl)pyrazol-1-yl | X¹ | G-1 | J-30 (3/5) | — | H |
| 3,5-bis-(trifluoromethyl)pyrazol-1-yl | X¹ | G-1 | J-30 (3/5) | — | H |
| 1-methyl-3-(trifluoromethyl)pyrazol-5-yl | X¹ | G-1 | J-30 (3/5) | — | H |
| 1-methyl-4-(trifluoromethyl)imidazol-2-yl | X¹ | G-1 | J-30 (3/5) | — | H |
| 2,5-dichlorophenyl | X¹ | G-1 | J-30 (3/5) | 1-Me | H |
| 2-chloro-5-(trifluoromethyl)phenyl | X¹ | G-1 | J-30 (3/5) | 1-Me | H |
| 2,5-dimethylphenyl | X¹ | G-1 | J-30 (3/5) | 1-Me | H |
| 2-methyl-5-(trifluoromethyl)phenyl | X¹ | G-1 | J-30 (3/5) | 1-Me | H |
| 3,5-dimethylpyrazol-1-yl | X¹ | G-1 | J-30 (3/5) | 1-Me | H |
| 5-methyl-3-(trifluoromethyl)pyrazol-1-yl | X¹ | G-1 | J-30 (3/5) | 1-Me | H |
| 5-chloro-3-(trifluoromethyl)pyrazol-1-yl | X¹ | G-1 | J-30 (3/5) | 1-Me | H |
| 5-bromo-3-(trifluoromethyl)pyrazol-1-yl | X¹ | G-1 | J-30 (3/5) | 1-Me | H |

TABLE 4*-continued

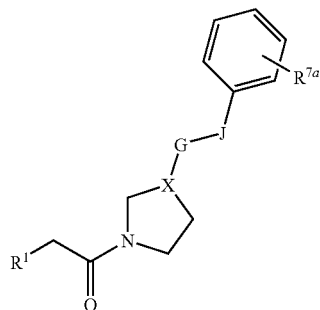

| R¹ | X | G | J* | (R⁵)ᵧ | R⁷ᵃ |
|---|---|---|---|---|---|
| 5-ethyl-3-(trifluoromethyl)pyrazol-1-yl | X¹ | G-1 | J-30 (3/5) | 1-Me | H |
| 3,5-bis-(trifluoromethyl)pyrazol-1-yl | X¹ | G-1 | J-30 (3/5) | 1-Me | H |
| 1-methyl-3-(trifluoromethyl)pyrazol-5-yl | X¹ | G-1 | J-30 (3/5) | 1-Me | H |
| 1-methyl-4-(trifluoromethyl)imidazol-2-yl | X¹ | G-1 | J-30 (3/5) | 1-Me | H |
| 2,5-dichlorophenyl | X¹ | G-1 | J-36 (3/5) | 1-Me | H |
| 2-chloro-5-(trifluoromethyl)phenyl | X¹ | G-1 | J-36 (3/5) | 1-Me | H |
| 2,5-dimethylphenyl | X¹ | G-1 | J-36 (3/5) | 1-Me | H |
| 2-methyl-5-(trifluoromethyl)phenyl | X¹ | G-1 | J-36 (3/5) | 1-Me | H |
| 3,5-dimethylpyrazol-1-yl | X¹ | G-1 | J-36 (3/5) | 1-Me | H |
| 5-methyl-3-(trifluoromethyl)pyrazol-1-yl | X¹ | G-1 | J-36 (3/5) | 1-Me | H |
| 5-chloro-3-(trifluoromethyl)pyrazol-1-yl | X¹ | G-1 | J-36 (3/5) | 1-Me | H |
| 5-bromo-3-(trifluoromethyl)pyrazol-1-yl | X¹ | G-1 | J-36 (3/5) | 1-Me | H |
| 5-ethyl-3-(trifluoromethyl)pyrazol-1-yl | X¹ | G-1 | J-36 (3/5) | 1-Me | H |
| 3,5-bis-(trifluoromethyl)pyrazol-1-yl | X¹ | G-1 | J-36 (3/5) | 1-Me | H |
| 1-methyl-3-(trifluoromethyl)pyrazol-5-yl | X¹ | G-1 | J-36 (3/5) | 1-Me | H |
| 1-methyl-4-(trifluoromethyl)imidazol-2-yl | X¹ | G-1 | J-36 (3/5) | 1-Me | H |
| 2,5-dichlorophenyl | X¹ | G-1 | J-37 (2/5) | — | H |
| 2-chloro-5-(trifluoromethyl)phenyl | X¹ | G-1 | J-37 (2/5) | — | H |
| 2,5-dimethylphenyl | X¹ | G-1 | J-37 (2/5) | — | H |
| 2-methyl-5-(trifluoromethyl)phenyl | X¹ | G-1 | J-37 (2/5) | — | H |
| 3,5-dimethylpyrazol-1-yl | X¹ | G-1 | J-37 (2/5) | — | H |
| 5-methyl-3-(trifluoromethyl)pyrazol-1-yl | X¹ | G-1 | J-37 (2/5) | — | H |
| 5-chloro-3-(trifluoromethyl)pyrazol-1-yl | X¹ | G-1 | J-37 (2/5) | — | H |
| 5-bromo-3-(trifluoromethyl)pyrazol-1-yl | X¹ | G-1 | J-37 (2/5) | — | H |
| 5-ethyl-3-(trifluoromethyl)pyrazol-1-yl | X¹ | G-1 | J-37 (2/5) | — | H |
| 3,5-bis-(trifluoromethyl)pyrazol-1-yl | X¹ | G-1 | J-37 (2/5) | — | H |
| 1-methyl-3-(trifluoromethyl)pyrazol-5-yl | X¹ | G-1 | J-37 (2/5) | — | H |
| 1-methyl-4-(trifluoromethyl)imidazol-2-yl | X¹ | G-1 | J-37 (2/5) | — | H |
| 2,5-dichlorophenyl | X¹ | G-1 | J-38 (2/5) | — | H |
| 2-chloro-5-(trifluoromethyl)phenyl | X¹ | G-1 | J-38 (2/5) | — | H |
| 2,5-dimethylphenyl | X¹ | G-1 | J-38 (2/5) | — | H |
| 2-methyl-5-(trifluoromethyl)phenyl | X¹ | G-1 | J-38 (2/5) | — | H |
| 3,5-dimethylpyrazol-1-yl | X¹ | G-1 | J-38 (2/5) | — | H |
| 5-methyl-3-(trifluoromethyl)pyrazol-1-yl | X¹ | G-1 | J-38 (2/5) | — | H |
| 5-chloro-3-(trifluoromethyl)pyrazol-1-yl | X¹ | G-1 | J-38 (2/5) | — | H |
| 5-bromo-3-(trifluoromethyl)pyrazol-1-yl | X¹ | G-1 | J-38 (2/5) | — | H |
| 5-ethyl-3-(trifluoromethyl)pyrazol-1-yl | X¹ | G-1 | J-38 (2/5) | — | H |
| 3,5-bis-(trifluoromethyl)pyrazol-1-yl | X¹ | G-1 | J-38 (2/5) | — | H |
| 1-methyl-3-(trifluoromethyl)pyrazol-5-yl | X¹ | G-1 | J-38 (2/5) | — | H |
| 1-methyl-4-(trifluoromethyl)imidazol-2-yl | X¹ | G-1 | J-38 (2/5) | — | H |
| 2,5-dichlorophenyl | X¹ | G-1 | J-39 (3/5) | — | H |
| 2-chloro-5-(trifluoromethyl)phenyl | X¹ | G-1 | J-39 (3/5) | — | H |
| 2,5-dimethylphenyl | X¹ | G-1 | J-39 (3/5) | — | H |
| 2-methyl-5-(trifluoromethyl)phenyl | X¹ | G-1 | J-39 (3/5) | — | H |
| 3,5-dimethylpyrazol-1-yl | X¹ | G-1 | J-39 (3/5) | — | H |
| 5-methyl-3-(trifluoromethyl)pyrazol-1-yl | X¹ | G-1 | J-39 (3/5) | — | H |
| 5-chloro-3-(trifluoromethyl)pyrazol-1-yl | X¹ | G-1 | J-39 (3/5) | — | H |
| 5-bromo-3-(trifluoromethyl)pyrazol-1-yl | X¹ | G-1 | J-39 (3/5) | — | H |
| 5-ethyl-3-(trifluoromethyl)pyrazol-1-yl | X¹ | G-1 | J-39 (3/5) | — | H |
| 3,5-bis-(trifluoromethyl)pyrazol-1-yl | X¹ | G-1 | J-39 (3/5) | — | H |
| 1-methyl-3-(trifluoromethyl)pyrazol-5-yl | X¹ | G-1 | J-39 (3/5) | — | H |
| 1-methyl-4-(trifluoromethyl)imidazol-2-yl | X¹ | G-1 | J-39 (3/5) | — | H |
| 2,5-dichlorophenyl | X¹ | G-1 | J-40 (3/5) | — | H |
| 2-chloro-5-(trifluoromethyl)phenyl | X¹ | G-1 | J-40 (3/5) | — | H |
| 2,5-dimethylphenyl | X¹ | G-1 | J-40 (3/5) | — | H |
| 2-methyl-5-(trifluoromethyl)phenyl | X¹ | G-1 | J-40 (3/5) | — | H |
| 3,5-dimethylpyrazol-1-yl | X¹ | G-1 | J-40 (3/5) | — | H |
| 5-methyl-3-(trifluoromethyl)pyrazol-1-yl | X¹ | G-1 | J-40 (3/5) | — | H |
| 5-chloro-3-(trifluoromethyl)pyrazol-1-yl | X¹ | G-1 | J-40 (3/5) | — | H |
| 5-bromo-3-(trifluoromethyl)pyrazol-1-yl | X¹ | G-1 | J-40 (3/5) | — | H |
| 5-ethyl-3-(trifluoromethyl)pyrazol-1-yl | X¹ | G-1 | J-40 (3/5) | — | H |
| 3,5-bis-(trifluoromethyl)pyrazol-1-yl | X¹ | G-1 | J-40 (3/5) | — | H |

TABLE 4*-continued

| R¹ | X | G | J* | (R⁵)ᵧ | R⁷ᵃ |
|---|---|---|---|---|---|
| 1-methyl-3-(trifluoromethyl)pyrazol-5-yl | X¹ | G-1 | J-40 (3/5) | — | H |
| 1-methyl-4-(trifluoromethyl)imidazol-2-yl | X¹ | G-1 | J-40 (3/5) | — | H |
| 2,5-dichlorophenyl | X¹ | G-1 | J-69 (1/3) | — | H |
| 2-chloro-5-(trifluoromethyl)phenyl | X¹ | G-1 | J-69 (1/3) | — | H |
| 2,5-dimethylphenyl | X¹ | G-1 | J-69 (1/3) | — | H |
| 2-methyl-5-(trifluoromethyl)phenyl | X¹ | G-1 | J-69 (1/3) | — | H |
| 3,5-dimethylpyrazol-1-yl | X¹ | G-1 | J-69 (1/3) | — | H |
| 5-methyl-3-(trifluoromethyl)pyrazol-1-yl | X¹ | G-1 | J-69 (1/3) | — | H |
| 5-chloro-3-(trifluoromethyl)pyrazol-1-yl | X¹ | G-1 | J-69 (1/3) | — | H |
| 5-bromo-3-(trifluoromethyl)pyrazol-1-yl | X¹ | G-1 | J-69 (1/3) | — | H |
| 5-ethyl-3-(trifluoromethyl)pyrazol-1-yl | X¹ | G-1 | J-69 (1/3) | — | H |
| 3,5-bis-(trifluoromethyl)pyrazol-1-yl | X¹ | G-1 | J-69 (1/3) | — | H |
| 1-methyl-3-(trifluoromethyl)pyrazol-5-yl | X¹ | G-1 | J-69 (1/3) | — | H |
| 1-methyl-4-(trifluoromethyl)imidazol-2-yl | X¹ | G-1 | J-69 (1/3) | — | H |
| 2,5-dichlorophenyl | X¹ | G-1 | J-69 (1/4) | — | H |
| 2-chloro-5-(trifluoromethyl)phenyl | X¹ | G-1 | J-69 (1/4) | — | H |
| 2,5-dimethylphenyl | X¹ | G-1 | J-69 (1/4) | — | H |
| 2-methyl-5-(trifluoromethyl)phenyl | X¹ | G-1 | J-69 (1/4) | — | H |
| 3,5-dimethylpyrazol-1-yl | X¹ | G-1 | J-69 (1/4) | — | H |
| 5-methyl-3-(trifluoromethyl)pyrazol-1-yl | X¹ | G-1 | J-69 (1/4) | — | H |
| 5-chloro-3-(trifluoromethyl)pyrazol-1-yl | X¹ | G-1 | J-69 (1/4) | — | H |
| 5-bromo-3-(trifluoromethyl)pyrazol-1-yl | X¹ | G-1 | J-69 (1/4) | — | H |
| 5-ethyl-3-(trifluoromethyl)pyrazol-1-yl | X¹ | G-1 | J-69 (1/4) | — | H |
| 3,5-bis-(trifluoromethyl)pyrazol-1-yl | X¹ | G-1 | J-69 (1/4) | — | H |
| 1-methyl-3-(trifluoromethyl)pyrazol-5-yl | X¹ | G-1 | J-69 (1/4) | — | H |
| 1-methyl-4-(trifluoromethyl)imidazol-2-yl | X¹ | G-1 | J-69 (1/4) | — | H |
| 2,5-dichlorophenyl | X¹ | G-1 | J-11 (3/5) | — | 2-Me |
| 2-chloro-5-(trifluoromethyl)phenyl | X¹ | G-1 | J-11 (3/5) | — | 2-Me |
| 2,5-dimethylphenyl | X¹ | G-1 | J-11 (3/5) | — | 2-Me |
| 2-methyl-5-(trifluoromethyl)phenyl | X¹ | G-1 | J-11 (3/5) | — | 2-Me |
| 3,5-dimethylpyrazol-1-yl | X¹ | G-1 | J-11 (3/5) | — | 2-Me |
| 5-methyl-3-(trifluoromethyl)pyrazol-1-yl | X¹ | G-1 | J-11 (3/5) | — | 2-Me |
| 5-chloro-3-(trifluoromethyl)pyrazol-1-yl | X¹ | G-1 | J-11 (3/5) | — | 2-Me |
| 5-bromo-3-(trifluoromethyl)pyrazol-1-yl | X¹ | G-1 | J-11 (3/5) | — | 2-Me |
| 5-ethyl-3-(trifluoromethyl)pyrazol-1-yl | X¹ | G-1 | J-11 (3/5) | — | 2-Me |
| 3,5-bis-(trifluoromethyl)pyrazol-1-yl | X¹ | G-1 | J-11 (3/5) | — | 2-Me |
| 1-methyl-3-(trifluoromethyl)pyrazol-5-yl | X¹ | G-1 | J-11 (3/5) | — | 2-Me |
| 1-methyl-4-(trifluoromethyl)imidazol-2-yl | X¹ | G-1 | J-11 (3/5) | — | 2-Me |
| 2,5-dichlorophenyl | X¹ | G-1 | J-11 (3/5) | — | 3-Me |
| 2-chloro-5-(trifluoromethyl)phenyl | X¹ | G-1 | J-11 (3/5) | — | 3-Me |
| 2,5-dimethylphenyl | X¹ | G-1 | J-11 (3/5) | — | 3-Me |
| 2-methyl-5-(trifluoromethyl)phenyl | X¹ | G-1 | J-11 (3/5) | — | 3-Me |
| 3,5-dimethylpyrazol-1-yl | X¹ | G-1 | J-11 (3/5) | — | 3-Me |
| 5-methyl-3-(trifluoromethyl)pyrazol-1-yl | X¹ | G-1 | J-11 (3/5) | — | 3-Me |
| 5-chloro-3-(trifluoromethyl)pyrazol-1-yl | X¹ | G-1 | J-11 (3/5) | — | 3-Me |
| 5-bromo-3-(trifluoromethyl)pyrazol-1-yl | X¹ | G-1 | J-11 (3/5) | — | 3-Me |
| 5-ethyl-3-(trifluoromethyl)pyrazol-1-yl | X¹ | G-1 | J-11 (3/5) | — | 3-Me |
| 3,5-bis-(trifluoromethyl)pyrazol-1-yl | X¹ | G-1 | J-11 (3/5) | — | 3-Me |
| 1-methyl-3-(trifluoromethyl)pyrazol-5-yl | X¹ | G-1 | J-11 (3/5) | — | 3-Me |
| 1-methyl-4-(trifluoromethyl)imidazol-2-yl | X¹ | G-1 | J-11 (3/5) | — | 3-Me |
| 2,5-dichlorophenyl | X¹ | G-1 | J-11 (3/5) | — | 4-Me |
| 2-chloro-5-(trifluoromethyl)phenyl | X¹ | G-1 | J-11 (3/5) | — | 4-Me |
| 2,5-dimethylphenyl | X¹ | G-1 | J-11 (3/5) | — | 4-Me |
| 2-methyl-5-(trifluoromethyl)phenyl | X¹ | G-1 | J-11 (3/5) | — | 4-Me |
| 3,5-dimethylpyrazol-1-yl | X¹ | G-1 | J-11 (3/5) | — | 4-Me |
| 5-methyl-3-(trifluoromethyl)pyrazol-1-yl | X¹ | G-1 | J-11 (3/5) | — | 4-Me |
| 5-chloro-3-(trifluoromethyl)pyrazol-1-yl | X¹ | G-1 | J-11 (3/5) | — | 4-Me |
| 5-bromo-3-(trifluoromethyl)pyrazol-1-yl | X¹ | G-1 | J-11 (3/5) | — | 4-Me |
| 5-ethyl-3-(trifluoromethyl)pyrazol-1-yl | X¹ | G-1 | J-11 (3/5) | — | 4-Me |
| 3,5-bis-(trifluoromethyl)pyrazol-1-yl | X¹ | G-1 | J-11 (3/5) | — | 4-Me |
| 1-methyl-3-(trifluoromethyl)pyrazol-5-yl | X¹ | G-1 | J-11 (3/5) | — | 4-Me |
| 1-methyl-4-(trifluoromethyl)imidazol-2-yl | X¹ | G-1 | J-11 (3/5) | — | 4-Me |

TABLE 4*-continued

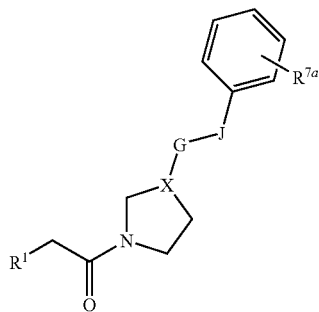

| R¹ | X | G | J* | (R⁵)ᵧ | R⁷ᵃ |
|---|---|---|---|---|---|
| 2,5-dichlorophenyl | X¹ | G-1 | J-11 (3/5) | — | 2-Cl |
| 2-chloro-5-(trifluoromethyl)phenyl | X¹ | G-1 | J-11 (3/5) | — | 2-Cl |
| 2,5-dimethylphenyl | X¹ | G-1 | J-11 (3/5) | — | 2-Cl |
| 2-methyl-5-(trifluoromethyl)phenyl | X¹ | G-1 | J-11 (3/5) | — | 2-Cl |
| 3,5-dimethylpyrazol-1-yl | X¹ | G-1 | J-11 (3/5) | — | 2-Cl |
| 5-methyl-3-(trifluoromethyl)pyrazol-1-yl | X¹ | G-1 | J-11 (3/5) | — | 2-Cl |
| 5-chloro-3-(trifluoromethyl)pyrazol-1-yl | X¹ | G-1 | J-11 (3/5) | — | 2-Cl |
| 5-bromo-3-(trifluoromethyl)pyrazol-1-yl | X¹ | G-1 | J-11 (3/5) | — | 2-Cl |
| 5-ethyl-3-(trifluoromethyl)pyrazol-1-yl | X¹ | G-1 | J-11 (3/5) | — | 2-Cl |
| 3,5-bis-(trifluoromethyl)pyrazol-1-yl | X¹ | G-1 | J-11 (3/5) | — | 2-Cl |
| 1-methyl-3-(trifluoromethyl)pyrazol-5-yl | X¹ | G-1 | J-11 (3/5) | — | 2-Cl |
| 1-methyl-4-(trifluoromethyl)imidazol-2-yl | X¹ | G-1 | J-11 (3/5) | — | 2-Cl |
| 2,5-dichlorophenyl | X¹ | G-1 | J-11 (3/5) | — | 4-Cl |
| 2-chloro-5-(trifluoromethyl)phenyl | X¹ | G-1 | J-11 (3/5) | — | 4-Cl |
| 2,5-dimethylphenyl | X¹ | G-1 | J-11 (3/5) | — | 4-Cl |
| 2-methyl-5-(trifluoromethyl)phenyl | X¹ | G-1 | J-11 (3/5) | — | 4-Cl |
| 3,5-dimethylpyrazol-1-yl | X¹ | G-1 | J-11 (3/5) | — | 4-Cl |
| 5-methyl-3-(trifluoromethyl)pyrazol-1-yl | X¹ | G-1 | J-11 (3/5) | — | 4-Cl |
| 5-chloro-3-(trifluoromethyl)pyrazol-1-yl | X¹ | G-1 | J-11 (3/5) | — | 4-Cl |
| 5-bromo-3-(trifluoromethyl)pyrazol-1-yl | X¹ | G-1 | J-11 (3/5) | — | 4-Cl |
| 5-ethyl-3-(trifluoromethyl)pyrazol-1-yl | X¹ | G-1 | J-11 (3/5) | — | 4-Cl |
| 3,5-bis-(trifluoromethyl)pyrazol-1-yl | X¹ | G-1 | J-11 (3/5) | — | 4-Cl |
| 1-methyl-3-(trifluoromethyl)pyrazol-5-yl | X¹ | G-1 | J-11 (3/5) | — | 4-Cl |
| 1-methyl-4-(trifluoromethyl)imidazol-2-yl | X¹ | G-1 | J-11 (3/5) | — | 4-Cl |
| 2,5-dichlorophenyl | X¹ | G-1 | J-29 (3/5) | 5-Me | 2-Me |
| 2-chloro-5-(trifluoromethyl)phenyl | X¹ | G-1 | J-29 (3/5) | 5-Me | 2-Me |
| 2,5-dimethylphenyl | X¹ | G-1 | J-29 (3/5) | 5-Me | 2-Me |
| 2-methyl-5-(trifluoromethyl)phenyl | X¹ | G-1 | J-29 (3/5) | 5-Me | 2-Me |
| 3,5-dimethylpyrazol-1-yl | X¹ | G-1 | J-29 (3/5) | 5-Me | 2-Me |
| 5-methyl-3-(trifluoromethyl)pyrazol-1-yl | X¹ | G-1 | J-29 (3/5) | 5-Me | 2-Me |
| 5-chloro-3-(trifluoromethyl)pyrazol-1-yl | X¹ | G-1 | J-29 (3/5) | 5-Me | 2-Me |
| 5-bromo-3-(trifluoromethyl)pyrazol-1-yl | X¹ | G-1 | J-29 (3/5) | 5-Me | 2-Me |
| 5-ethyl-3-(trifluoromethyl)pyrazol-1-yl | X¹ | G-1 | J-29 (3/5) | 5-Me | 2-Me |
| 3,5-bis-(trifluoromethyl)pyrazol-1-yl | X¹ | G-1 | J-29 (3/5) | 5-Me | 2-Me |
| 1-methyl-3-(trifluoromethyl)pyrazol-5-yl | X¹ | G-1 | J-29 (3/5) | 5-Me | 2-Me |
| 1-methyl-4-(trifluoromethyl)imidazol-2-yl | X¹ | G-1 | J-29 (3/5) | 5-Me | 2-Me |
| 2,5-dichlorophenyl | X¹ | G-1 | J-29 (3/5) | — | 3-Me |
| 2-chloro-5-(trifluoromethyl)phenyl | X¹ | G-1 | J-29 (3/5) | — | 3-Me |
| 2,5-dimethylphenyl | X¹ | G-1 | J-29 (3/5) | — | 3-Me |
| 2-methyl-5-(trifluoromethyl)phenyl | X¹ | G-1 | J-29 (3/5) | — | 3-Me |
| 3,5-dimethylpyrazol-1-yl | X¹ | G-1 | J-29 (3/5) | — | 3-Me |
| 5-methyl-3-(trifluoromethyl)pyrazol-1-yl | X¹ | G-1 | J-29 (3/5) | — | 3-Me |
| 5-chloro-3-(trifluoromethyl)pyrazol-1-yl | X¹ | G-1 | J-29 (3/5) | — | 3-Me |
| 5-bromo-3-(trifluoromethyl)pyrazol-1-yl | X¹ | G-1 | J-29 (3/5) | — | 3-Me |
| 5-ethyl-3-(trifluoromethyl)pyrazol-1-yl | X¹ | G-1 | J-29 (3/5) | — | 3-Me |
| 3,5-bis-(trifluoromethyl)pyrazol-1-yl | X¹ | G-1 | J-29 (3/5) | — | 3-Me |
| 1-methyl-3-(trifluoromethyl)pyrazol-5-yl | X¹ | G-1 | J-29 (3/5) | — | 3-Me |
| 1-methyl-4-(trifluoromethyl)imidazol-2-yl | X¹ | G-1 | J-29 (3/5) | — | 3-Me |
| 2,5-dichlorophenyl | X¹ | G-1 | J-29 (3/5) | — | 4-Me |
| 2-chloro-5-(trifluoromethyl)phenyl | X¹ | G-1 | J-29 (3/5) | — | 4-Me |
| 2,5-dimethylphenyl | X¹ | G-1 | J-29 (3/5) | — | 4-Me |
| 2-methyl-5-(trifluoromethyl)phenyl | X¹ | G-1 | J-29 (3/5) | — | 4-Me |
| 3,5-dimethylpyrazol-1-yl | X¹ | G-1 | J-29 (3/5) | — | 4-Me |
| 5-methyl-3-(trifluoromethyl)pyrazol-1-yl | X¹ | G-1 | J-29 (3/5) | — | 4-Me |
| 5-chloro-3-(trifluoromethyl)pyrazol-1-yl | X¹ | G-1 | J-29 (3/5) | — | 4-Me |
| 5-bromo-3-(trifluoromethyl)pyrazol-1-yl | X¹ | G-1 | J-29 (3/5) | — | 4-Me |
| 5-ethyl-3-(trifluoromethyl)pyrazol-1-yl | X¹ | G-1 | J-29 (3/5) | — | 4-Me |
| 3,5-bis-(trifluoromethyl)pyrazol-1-yl | X¹ | G-1 | J-29 (3/5) | — | 4-Me |
| 1-methyl-3-(trifluoromethyl)pyrazol-5-yl | X¹ | G-1 | J-29 (3/5) | — | 4-Me |
| 1-methyl-4-(trifluoromethyl)imidazol-2-yl | X¹ | G-1 | J-29 (3/5) | — | 4-Me |
| 2,5-dichlorophenyl | X¹ | G-1 | J-29 (3/5) | 5-Me | 2-Cl |
| 2-chloro-5-(trifluoromethyl)phenyl | X¹ | G-1 | J-29 (3/5) | 5-Me | 2-Cl |

TABLE 4*-continued

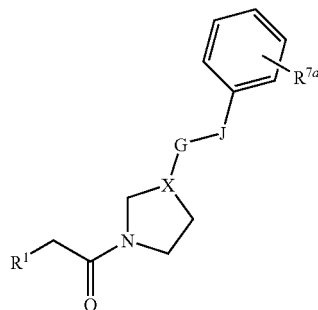

| R¹ | X | G | J* | (R⁵)ᵧ | R⁷ᵃ |
|---|---|---|---|---|---|
| 2,5-dimethylphenyl | X¹ | G-1 | J-29 (3/5) | 5-Me | 2-Cl |
| 2-methyl-5-(trifluoromethyl)phenyl | X¹ | G-1 | J-29 (3/5) | 5-Me | 2-Cl |
| 3,5-dimethylpyrazol-1-yl | X¹ | G-1 | J-29 (3/5) | 5-Me | 2-Cl |
| 5-methyl-3-(trifluoromethyl)pyrazol-1-yl | X¹ | G-1 | J-29 (3/5) | 5-Me | 2-Cl |
| 5-chloro-3-(trifluoromethyl)pyrazol-1-yl | X¹ | G-1 | J-29 (3/5) | 5-Me | 2-Cl |
| 5-bromo-3-(trifluoromethyl)pyrazol-1-yl | X¹ | G-1 | J-29 (3/5) | 5-Me | 2-Cl |
| 5-ethyl-3-(trifluoromethyl)pyrazol-1-yl | X¹ | G-1 | J-29 (3/5) | 5-Me | 2-Cl |
| 3,5-bis-(trifluoromethyl)pyrazol-1-yl | X¹ | G-1 | J-29 (3/5) | 5-Me | 2-Cl |
| 1-methyl-3-(trifluoromethyl)pyrazol-5-yl | X¹ | G-1 | J-29 (3/5) | 5-Me | 2-Cl |
| 1-methyl-4-(trifluoromethyl)imidazol-2-yl | X¹ | G-1 | J-29 (3/5) | 5-Me | 2-Cl |
| 2,5-dichlorophenyl | X¹ | G-1 | J-29 (3/5) | — | 4-Cl |
| 2-chloro-5-(trifluoromethyl)phenyl | X¹ | G-1 | J-29 (3/5) | — | 4-Cl |
| 2,5-dimethylphenyl | X¹ | G-1 | J-29 (3/5) | — | 4-Cl |
| 2-methyl-5-(trifluoromethyl)phenyl | X¹ | G-1 | J-29 (3/5) | — | 4-Cl |
| 3,5-dimethylpyrazol-1-yl | X¹ | G-1 | J-29 (3/5) | — | 4-Cl |
| 5-methyl-3-(trifluoromethyl)pyrazol-1-yl | X¹ | G-1 | J-29 (3/5) | — | 4-Cl |
| 5-chloro-3-(trifluoromethyl)pyrazol-1-yl | X¹ | G-1 | J-29 (3/5) | — | 4-Cl |
| 5-bromo-3-(trifluoromethyl)pyrazol-1-yl | X¹ | G-1 | J-29 (3/5) | — | 4-Cl |
| 5-ethyl-3-(trifluoromethyl)pyrazol-1-yl | X¹ | G-1 | J-29 (3/5) | — | 4-Cl |
| 3,5-bis-(trifluoromethyl)pyrazol-1-yl | X¹ | G-1 | J-29 (3/5) | — | 4-Cl |
| 1-methyl-3-(trifluoromethyl)pyrazol-5-yl | X¹ | G-1 | J-29 (3/5) | — | 4-Cl |
| 1-methyl-4-(trifluoromethyl)imidazol-2-yl | X¹ | G-1 | J-29 (3/5) | — | 4-Cl |
| 2,5-dichlorophenyl | X¹ | G-1 | J-29 (3/5) | 5-Me | H |
| 2-chloro-5-(trifluoromethyl)phenyl | X¹ | G-1 | J-29 (3/5) | 5-Me | H |
| 2,5-dimethylphenyl | X¹ | G-1 | J-29 (3/5) | 5-Me | H |
| 2-methyl-5-(trifluoromethyl)phenyl | X¹ | G-1 | J-29 (3/5) | 5-Me | H |
| 3,5-dimethylpyrazol-1-yl | X¹ | G-1 | J-29 (3/5) | 5-Me | H |
| 5-methyl-3-(trifluoromethyl)pyrazol-1-yl | X¹ | G-1 | J-29 (3/5) | 5-Me | H |
| 5-chloro-3-(trifluoromethyl)pyrazol-1-yl | X¹ | G-1 | J-29 (3/5) | 5-Me | H |
| 5-bromo-3-(trifluoromethyl)pyrazol-1-yl | X¹ | G-1 | J-29 (3/5) | 5-Me | H |
| 5-ethyl-3-(trifluoromethyl)pyrazol-1-yl | X¹ | G-1 | J-29 (3/5) | 5-Me | H |
| 3,5-bis-(trifluoromethyl)pyrazol-1-yl | X¹ | G-1 | J-29 (3/5) | 5-Me | H |
| 1-methyl-3-(trifluoromethyl)pyrazol-5-yl | X¹ | G-1 | J-29 (3/5) | 5-Me | H |
| 1-methyl-4-(trifluoromethyl)imidazol-2-yl | X¹ | G-1 | J-29 (3/5) | 5-Me | H |
| 2,5-dichlorophenyl | X¹ | G-1 | J-29 (3/5) | 4-Me | H |
| 2-chloro-5-(trifluoromethyl)phenyl | X¹ | G-1 | J-29 (3/5) | 4-Me | H |
| 2,5-dimethylphenyl | X¹ | G-1 | J-29 (3/5) | 4-Me | H |
| 2-methyl-5-(trifluoromethyl)phenyl | X¹ | G-1 | J-29 (3/5) | 4-Me | H |
| 3,5-dimethylpyrazol-1-yl | X¹ | G-1 | J-29 (3/5) | 4-Me | H |
| 5-methyl-3-(trifluoromethyl)pyrazol-1-yl | X¹ | G-1 | J-29 (3/5) | 4-Me | H |
| 5-chloro-3-(trifluoromethyl)pyrazol-1-yl | X¹ | G-1 | J-29 (3/5) | 4-Me | H |
| 5-bromo-3-(trifluoromethyl)pyrazol-1-yl | X¹ | G-1 | J-29 (3/5) | 4-Me | H |
| 5-ethyl-3-(trifluoromethyl)pyrazol-1-yl | X¹ | G-1 | J-29 (3/5) | 4-Me | H |
| 3,5-bis-(trifluoromethyl)pyrazol-1-yl | X¹ | G-1 | J-29 (3/5) | 4-Me | H |
| 1-methyl-3-(trifluoromethyl)pyrazol-5-yl | X¹ | G-1 | J-29 (3/5) | 4-Me | H |
| 1-methyl-4-(trifluoromethyl)imidazol-2-yl | X¹ | G-1 | J-29 (3/5) | 4-Me | H |
| 2,5-dichlorophenyl | X¹ | G-1 | J-29 (3/5) | 4,4-di-Me | H |
| 2-chloro-5-(trifluoromethyl)phenyl | X¹ | G-1 | J-29 (3/5) | 4,4-di-Me | H |
| 2,5-dimethylphenyl | X¹ | G-1 | J-29 (3/5) | 4,4-di-Me | H |
| 2-methyl-5-(trifluoromethyl)phenyl | X¹ | G-1 | J-29 (3/5) | 4,4-di-Me | H |
| 3,5-dimethylpyrazol-1-yl | X¹ | G-1 | J-29 (3/5) | 4,4-di-Me | H |
| 5-methyl-3-(trifluoromethyl)pyrazol-1-yl | X¹ | G-1 | J-29 (3/5) | 4,4-di-Me | H |
| 5-chloro-3-(trifluoromethyl)pyrazol-1-yl | X¹ | G-1 | J-29 (3/5) | 4,4-di-Me | H |
| 5-bromo-3-(trifluoromethyl)pyrazol-1-yl | X¹ | G-1 | J-29 (3/5) | 4,4-di-Me | H |
| 5-ethyl-3-(trifluoromethyl)pyrazol-1-yl | X¹ | G-1 | J-29 (3/5) | 4,4-di-Me | H |
| 3,5-bis-(trifluoromethyl)pyrazol-1-yl | X¹ | G-1 | J-29 (3/5) | 4,4-di-Me | H |
| 1-methyl-3-(trifluoromethyl)pyrazol-5-yl | X¹ | G-1 | J-29 (3/5) | 4,4-di-Me | H |
| 1-methyl-4-(trifluoromethyl)imidazol-2-yl | X¹ | G-1 | J-29 (3/5) | 4,4-di-Me | H |
| 2,5-dichlorophenyl | X¹ | G-2 | J-1 (2/4) | — | H |
| 2-chloro-5-(trifluoromethyl)phenyl | X¹ | G-2 | J-1 (2/4) | — | H |
| 2,5-dimethylphenyl | X¹ | G-2 | J-1 (2/4) | — | H |
| 2-methyl-5-(trifluoromethyl)phenyl | X¹ | G-2 | J-1 (2/4) | — | H |

TABLE 4*-continued

| R¹ | X | G | J* | (R⁵)ᵧ | R⁷ᵃ |
|---|---|---|---|---|---|
| 3,5-dimethylpyrazol-1-yl | X¹ | G-2 | J-1 (2/4) | — | H |
| 5-methyl-3-(trifluoromethyl)pyrazol-1-yl | X¹ | G-2 | J-1 (2/4) | — | H |
| 5-chloro-3-(trifluoromethyl)pyrazol-1-yl | X¹ | G-2 | J-1 (2/4) | — | H |
| 5-bromo-3-(trifluoromethyl)pyrazol-1-yl | X¹ | G-2 | J-1 (2/4) | — | H |
| 5-ethyl-3-(trifluoromethyl)pyrazol-1-yl | X¹ | G-2 | J-1 (2/4) | — | H |
| 3,5-bis-(trifluoromethyl)pyrazol-1-yl | X¹ | G-2 | J-1 (2/4) | — | H |
| 1-methyl-3-(trifluoromethyl)pyrazol-5-yl | X¹ | G-2 | J-1 (2/4) | — | H |
| 1-methyl-4-(trifluoromethyl)imidazol-2-yl | X¹ | G-2 | J-1 (2/4) | — | H |
| 2,5-dichlorophenyl | X¹ | G-2 | J-2 (2/4) | — | H |
| 2-chloro-5-(trifluoromethyl)phenyl | X¹ | G-2 | J-2 (2/4) | — | H |
| 2,5-dimethylphenyl | X¹ | G-2 | J-2 (2/4) | — | H |
| 2-methyl-5-(trifluoromethyl)phenyl | X¹ | G-2 | J-2 (2/4) | — | H |
| 3,5-dimethylpyrazol-1-yl | X¹ | G-2 | J-2 (2/4) | — | H |
| 5-methyl-3-(trifluoromethyl)pyrazol-1-yl | X¹ | G-2 | J-2 (2/4) | — | H |
| 5-chloro-3-(trifluoromethyl)pyrazol-1-yl | X¹ | G-2 | J-2 (2/4) | — | H |
| 5-bromo-3-(trifluoromethyl)pyrazol-1-yl | X¹ | G-2 | J-2 (2/4) | — | H |
| 5-ethyl-3-(trifluoromethyl)pyrazol-1-yl | X¹ | G-2 | J-2 (2/4) | — | H |
| 3,5-bis-(trifluoromethyl)pyrazol-1-yl | X¹ | G-2 | J-2 (2/4) | — | H |
| 1-methyl-3-(trifluoromethyl)pyrazol-5-yl | X¹ | G-2 | J-2 (2/4) | — | H |
| 1-methyl-4-(trifluoromethyl)imidazol-2-yl | X¹ | G-2 | J-2 (2/4) | — | H |
| 2,5-dichlorophenyl | X¹ | G-2 | J-3 (2/4) | 1-Me | H |
| 2-chloro-5-(trifluoromethyl)phenyl | X¹ | G-2 | J-3 (2/4) | 1-Me | H |
| 2,5-dimethylphenyl | X¹ | G-2 | J-3 (2/4) | 1-Me | H |
| 2-methyl-5-(trifluoromethyl)phenyl | X¹ | G-2 | J-3 (2/4) | 1-Me | H |
| 3,5-dimethylpyrazol-1-yl | X¹ | G-2 | J-3 (2/4) | 1-Me | H |
| 5-methyl-3-(trifluoromethyl)pyrazol-1-yl | X¹ | G-2 | J-3 (2/4) | 1-Me | H |
| 5-chloro-3-(trifluoromethyl)pyrazol-1-yl | X¹ | G-2 | J-3 (2/4) | 1-Me | H |
| 5-bromo-3-(trifluoromethyl)pyrazol-1-yl | X¹ | G-2 | J-3 (2/4) | 1-Me | H |
| 5-ethyl-3-(trifluoromethyl)pyrazol-1-yl | X¹ | G-2 | J-3 (2/4) | 1-Me | H |
| 3,5-bis-(trifluoromethyl)pyrazol-1-yl | X¹ | G-2 | J-3 (2/4) | 1-Me | H |
| 1-methyl-3-(trifluoromethyl)pyrazol-5-yl | X¹ | G-2 | J-3 (2/4) | 1-Me | H |
| 1-methyl-4-(trifluoromethyl)imidazol-2-yl | X¹ | G-2 | J-3 (2/4) | 1-Me | H |
| 2,5-dichlorophenyl | X¹ | G-2 | J-4 (2/5) | — | H |
| 2-chloro-5-(trifluoromethyl)phenyl | X¹ | G-2 | J-4 (2/5) | — | H |
| 2,5-dimethylphenyl | X¹ | G-2 | J-4 (2/5) | — | H |
| 2-methyl-5-(trifluoromethyl)phenyl | X¹ | G-2 | J-4 (2/5) | — | H |
| 3,5-dimethylpyrazol-1-yl | X¹ | G-2 | J-4 (2/5) | — | H |
| 5-methyl-3-(trifluoromethyl)pyrazol-1-yl | X¹ | G-2 | J-4 (2/5) | — | H |
| 5-chloro-3-(trifluoromethyl)pyrazol-1-yl | X¹ | G-2 | J-4 (2/5) | — | H |
| 5-bromo-3-(trifluoromethyl)pyrazol-1-yl | X¹ | G-2 | J-4 (2/5) | — | H |
| 5-ethyl-3-(trifluoromethyl)pyrazol-1-yl | X¹ | G-2 | J-4 (2/5) | — | H |
| 3,5-bis-(trifluoromethyl)pyrazol-1-yl | X¹ | G-2 | J-4 (2/5) | — | H |
| 1-methyl-3-(trifluoromethyl)pyrazol-5-yl | X¹ | G-2 | J-4 (2/5) | — | H |
| 1-methyl-4-(trifluoromethyl)imidazol-2-yl | X¹ | G-2 | J-4 (2/5) | — | H |
| 2,5-dichlorophenyl | X¹ | G-2 | J-8 (5/3) | — | H |
| 2-chloro-5-(trifluoromethyl)phenyl | X¹ | G-2 | J-8 (5/3) | — | H |
| 2,5-dimethylphenyl | X¹ | G-2 | J-8 (5/3) | — | H |
| 2-methyl-5-(trifluoromethyl)phenyl | X¹ | G-2 | J-8 (5/3) | — | H |
| 3,5-dimethylpyrazol-1-yl | X¹ | G-2 | J-8 (5/3) | — | H |
| 5-methyl-3-(trifluoromethyl)pyrazol-1-yl | X¹ | G-2 | J-8 (5/3) | — | H |
| 5-chloro-3-(trifluoromethyl)pyrazol-1-yl | X¹ | G-2 | J-8 (5/3) | — | H |
| 5-bromo-3-(trifluoromethyl)pyrazol-1-yl | X¹ | G-2 | J-8 (5/3) | — | H |
| 5-ethyl-3-(trifluoromethyl)pyrazol-1-yl | X¹ | G-2 | J-8 (5/3) | — | H |
| 3,5-bis-(trifluoromethyl)pyrazol-1-yl | X¹ | G-2 | J-8 (5/3) | — | H |
| 1-methyl-3-(trifluoromethyl)pyrazol-5-yl | X¹ | G-2 | J-8 (5/3) | — | H |
| 1-methyl-4-(trifluoromethyl)imidazol-2-yl | X¹ | G-2 | J-8 (5/3) | — | H |
| 2,5-dichlorophenyl | X¹ | G-2 | J-9 (5/3) | — | H |
| 2-chloro-5-(trifluoromethyl)phenyl | X¹ | G-2 | J-9 (5/3) | — | H |
| 2,5-dimethylphenyl | X¹ | G-2 | J-9 (5/3) | — | H |
| 2-methyl-5-(trifluoromethyl)phenyl | X¹ | G-2 | J-9 (5/3) | — | H |
| 3,5-dimethylpyrazol-1-yl | X¹ | G-2 | J-9 (5/3) | — | H |
| 5-methyl-3-(trifluoromethyl)pyrazol-1-yl | X¹ | G-2 | J-9 (5/3) | — | H |

TABLE 4*-continued

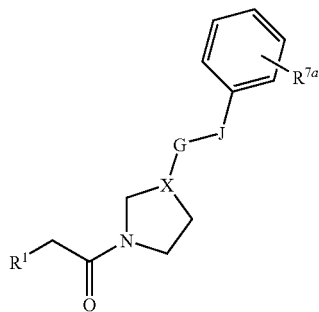

| R¹ | X | G | J* | (R⁵)ᵧ | R⁷ᵃ |
|---|---|---|---|---|---|
| 5-chloro-3-(trifluoromethyl)pyrazol-1-yl | X¹ | G-2 | J-9 (5/3) | — | H |
| 5-bromo-3-(trifluoromethyl)pyrazol-1-yl | X¹ | G-2 | J-9 (5/3) | — | H |
| 5-ethyl-3-(trifluoromethyl)pyrazol-1-yl | X¹ | G-2 | J-9 (5/3) | — | H |
| 3,5-bis-(trifluoromethyl)pyrazol-1-yl | X¹ | G-2 | J-9 (5/3) | — | H |
| 1-methyl-3-(trifluoromethyl)pyrazol-5-yl | X¹ | G-2 | J-9 (5/3) | — | H |
| 1-methyl-4-(trifluoromethyl)imidazol-2-yl | X¹ | G-2 | J-9 (5/3) | — | H |
| 2,5-dichlorophenyl | X¹ | G-2 | J-11 (3/5) | — | H |
| 2-chloro-5-(trifluoromethyl)phenyl | X¹ | G-2 | J-11 (3/5) | — | H |
| 2,5-dimethylphenyl | X¹ | G-2 | J-11 (3/5) | — | H |
| 2-methyl-5-(trifluoromethyl)phenyl | X¹ | G-2 | J-11 (3/5) | — | H |
| 3,5-dimethylpyrazol-1-yl | X¹ | G-2 | J-11 (3/5) | — | H |
| 5-methyl-3-(trifluoromethyl)pyrazol-1-yl | X¹ | G-2 | J-11 (3/5) | — | H |
| 5-chloro-3-(trifluoromethyl)pyrazol-1-yl | X¹ | G-2 | J-11 (3/5) | — | H |
| 5-bromo-3-(trifluoromethyl)pyrazol-1-yl | X¹ | G-2 | J-11 (3/5) | — | H |
| 5-ethyl-3-(trifluoromethyl)pyrazol-1-yl | X¹ | G-2 | J-11 (3/5) | — | H |
| 3,5-bis-(trifluoromethyl)pyrazol-1-yl | X¹ | G-2 | J-11 (3/5) | — | H |
| 1-methyl-3-(trifluoromethyl)pyrazol-5-yl | X¹ | G-2 | J-11 (3/5) | — | H |
| 1-methyl-4-(trifluoromethyl)imidazol-2-yl | X¹ | G-2 | J-11 (3/5) | — | H |
| 2,5-dichlorophenyl | X¹ | G-2 | J-12 (3/5) | — | H |
| 2-chloro-5-(trifluoromethyl)phenyl | X¹ | G-2 | J-12 (3/5) | — | H |
| 2,5-dimethylphenyl | X¹ | G-2 | J-12 (3/5) | — | H |
| 2-methyl-5-(trifluoromethyl)phenyl | X¹ | G-2 | J-12 (3/5) | — | H |
| 3,5-dimethylpyrazol-1-yl | X¹ | G-2 | J-12 (3/5) | — | H |
| 5-methyl-3-(trifluoromethyl)pyrazol-1-yl | X¹ | G-2 | J-12 (3/5) | — | H |
| 5-chloro-3-(trifluoromethyl)pyrazol-1-yl | X¹ | G-2 | J-12 (3/5) | — | H |
| 5-bromo-3-(trifluoromethyl)pyrazol-1-yl | X¹ | G-2 | J-12 (3/5) | — | H |
| 5-ethyl-3-(trifluoromethyl)pyrazol-1-yl | X¹ | G-2 | J-12 (3/5) | — | H |
| 3,5-bis-(trifluoromethyl)pyrazol-1-yl | X¹ | G-2 | J-12 (3/5) | — | H |
| 1-methyl-3-(trifluoromethyl)pyrazol-5-yl | X¹ | G-2 | J-12 (3/5) | — | H |
| 1-methyl-4-(trifluoromethyl)imidazol-2-yl | X¹ | G-2 | J-12 (3/5) | — | H |
| 2,5-dichlorophenyl | X¹ | G-2 | J-12 (3/5) | 1-Me | H |
| 2-chloro-5-(trifluoromethyl)phenyl | X¹ | G-2 | J-12 (3/5) | 1-Me | H |
| 2,5-dimethylphenyl | X¹ | G-2 | J-12 (3/5) | 1-Me | H |
| 2-methyl-5-(trifluoromethyl)phenyl | X¹ | G-2 | J-12 (3/5) | 1-Me | H |
| 3,5-dimethylpyrazol-1-yl | X¹ | G-2 | J-12 (3/5) | 1-Me | H |
| 5-methyl-3-(trifluoromethyl)pyrazol-1-yl | X¹ | G-2 | J-12 (3/5) | 1-Me | H |
| 5-chloro-3-(trifluoromethyl)pyrazol-1-yl | X¹ | G-2 | J-12 (3/5) | 1-Me | H |
| 5-bromo-3-(trifluoromethyl)pyrazol-1-yl | X¹ | G-2 | J-12 (3/5) | 1-Me | H |
| 5-ethyl-3-(trifluoromethyl)pyrazol-1-yl | X¹ | G-2 | J-12 (3/5) | 1-Me | H |
| 3,5-bis-(trifluoromethyl)pyrazol-1-yl | X¹ | G-2 | J-12 (3/5) | 1-Me | H |
| 1-methyl-3-(trifluoromethyl)pyrazol-5-yl | X¹ | G-2 | J-12 (3/5) | 1-Me | H |
| 1-methyl-4-(trifluoromethyl)imidazol-2-yl | X¹ | G-2 | J-12 (3/5) | 1-Me | H |
| 2,5-dichlorophenyl | X¹ | G-2 | J-14 (3/5) | — | H |
| 2-chloro-5-(trifluoromethyl)phenyl | X¹ | G-2 | J-14 (3/5) | — | H |
| 2,5-dimethylphenyl | X¹ | G-2 | J-14 (3/5) | — | H |
| 2-methyl-5-(trifluoromethyl)phenyl | X¹ | G-2 | J-14 (3/5) | — | H |
| 3,5-dimethylpyrazol-1-yl | X¹ | G-2 | J-14 (3/5) | — | H |
| 5-methyl-3-(trifluoromethyl)pyrazol-1-yl | X¹ | G-2 | J-14 (3/5) | — | H |
| 5-chloro-3-(trifluoromethyl)pyrazol-1-yl | X¹ | G-2 | J-14 (3/5) | — | H |
| 5-bromo-3-(trifluoromethyl)pyrazol-1-yl | X¹ | G-2 | J-14 (3/5) | — | H |
| 5-ethyl-3-(trifluoromethyl)pyrazol-1-yl | X¹ | G-2 | J-14 (3/5) | — | H |
| 3,5-bis-(trifluoromethyl)pyrazol-1-yl | X¹ | G-2 | J-14 (3/5) | — | H |
| 1-methyl-3-(trifluoromethyl)pyrazol-5-yl | X¹ | G-2 | J-14 (3/5) | — | H |
| 1-methyl-4-(trifluoromethyl)imidazol-2-yl | X¹ | G-2 | J-14 (3/5) | — | H |
| 2,5-dichlorophenyl | X¹ | G-2 | J-15 (2/5) | — | H |
| 2-chloro-5-(trifluoromethyl)phenyl | X¹ | G-2 | J-15 (2/5) | — | H |
| 2,5-dimethylphenyl | X¹ | G-2 | J-15 (2/5) | — | H |
| 2-methyl-5-(trifluoromethyl)phenyl | X¹ | G-2 | J-15 (2/5) | — | H |
| 3,5-dimethylpyrazol-1-yl | X¹ | G-2 | J-15 (2/5) | — | H |
| 5-methyl-3-(trifluoromethyl)pyrazol-1-yl | X¹ | G-2 | J-15 (2/5) | — | H |
| 5-chloro-3-(trifluoromethyl)pyrazol-1-yl | X¹ | G-2 | J-15 (2/5) | — | H |
| 5-bromo-3-(trifluoromethyl)pyrazol-1-yl | X¹ | G-2 | J-15 (2/5) | — | H |

TABLE 4*-continued

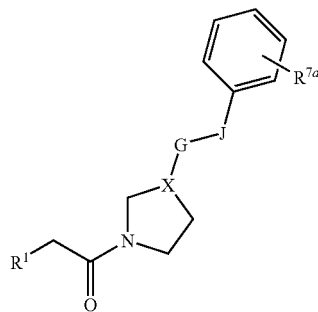

| R$^1$ | X | G | J* | (R$^5$)$_y$ | R$^{7a}$ |
|---|---|---|---|---|---|
| 5-ethyl-3-(trifluoromethyl)pyrazol-1-yl | X$^1$ | G-2 | J-15 (2/5) | — | H |
| 3,5-bis-(trifluoromethyl)pyrazol-1-yl | X$^1$ | G-2 | J-15 (2/5) | — | H |
| 1-methyl-3-(trifluoromethyl)pyrazol-5-yl | X$^1$ | G-2 | J-15 (2/5) | — | H |
| 1-methyl-4-(trifluoromethyl)imidazol-2-yl | X$^1$ | G-2 | J-15 (2/5) | — | H |
| 2,5-dichlorophenyl | X$^1$ | G-2 | J-16 (2/5) | — | H |
| 2-chloro-5-(trifluoromethyl)phenyl | X$^1$ | G-2 | J-16 (2/5) | — | H |
| 2,5-dimethylphenyl | X$^1$ | G-2 | J-16 (2/5) | — | H |
| 2-methyl-5-(trifluoromethyl)phenyl | X$^1$ | G-2 | J-16 (2/5) | — | H |
| 3,5-dimethylpyrazol-1-yl | X$^1$ | G-2 | J-16 (2/5) | — | H |
| 5-methyl-3-(trifluoromethyl)pyrazol-1-yl | X$^1$ | G-2 | J-16 (2/5) | — | H |
| 5-chloro-3-(trifluoromethyl)pyrazol-1-yl | X$^1$ | G-2 | J-16 (2/5) | — | H |
| 5-bromo-3-(trifluoromethyl)pyrazol-1-yl | X$^1$ | G-2 | J-16 (2/5) | — | H |
| 5-ethyl-3-(trifluoromethyl)pyrazol-1-yl | X$^1$ | G-2 | J-16 (2/5) | — | H |
| 3,5-bis-(trifluoromethyl)pyrazol-1-yl | X$^1$ | G-2 | J-16 (2/5) | — | H |
| 1-methyl-3-(trifluoromethyl)pyrazol-5-yl | X$^1$ | G-2 | J-16 (2/5) | — | H |
| 1-methyl-4-(trifluoromethyl)imidazol-2-yl | X$^1$ | G-2 | J-16 (2/5) | — | H |
| 2,5-dichlorophenyl | X$^1$ | G-2 | J-22 (2/4) | — | H |
| 2-chloro-5-(trifluoromethyl)phenyl | X$^1$ | G-2 | J-22 (2/4) | — | H |
| 2,5-dimethylphenyl | X$^1$ | G-2 | J-22 (2/4) | — | H |
| 2-methyl-5-(trifluoromethyl)phenyl | X$^1$ | G-2 | J-22 (2/4) | — | H |
| 3,5-dimethylpyrazol-1-yl | X$^1$ | G-2 | J-22 (2/4) | — | H |
| 5-methyl-3-(trifluoromethyl)pyrazol-1-yl | X$^1$ | G-2 | J-22 (2/4) | — | H |
| 5-chloro-3-(trifluoromethyl)pyrazol-1-yl | X$^1$ | G-2 | J-22 (2/4) | — | H |
| 5-bromo-3-(trifluoromethyl)pyrazol-1-yl | X$^1$ | G-2 | J-22 (2/4) | — | H |
| 5-ethyl-3-(trifluoromethyl)pyrazol-1-yl | X$^1$ | G-2 | J-22 (2/4) | — | H |
| 3,5-bis-(trifluoromethyl)pyrazol-1-yl | X$^1$ | G-2 | J-22 (2/4) | — | H |
| 1-methyl-3-(trifluoromethyl)pyrazol-5-yl | X$^1$ | G-2 | J-22 (2/4) | — | H |
| 1-methyl-4-(trifluoromethyl)imidazol-2-yl | X$^1$ | G-2 | J-22 (2/4) | — | H |
| 2,5-dichlorophenyl | X$^1$ | G-2 | J-24 (2/4) | — | H |
| 2-chloro-5-(trifluoromethyl)phenyl | X$^1$ | G-2 | J-24 (2/4) | — | H |
| 2,5-dimethylphenyl | X$^1$ | G-2 | J-24 (2/4) | — | H |
| 2-methyl-5-(trifluoromethyl)phenyl | X$^1$ | G-2 | J-24 (2/4) | — | H |
| 3,5-dimethylpyrazol-1-yl | X$^1$ | G-2 | J-24 (2/4) | — | H |
| 5-methyl-3-(trifluoromethyl)pyrazol-1-yl | X$^1$ | G-2 | J-24 (2/4) | — | H |
| 5-chloro-3-(trifluoromethyl)pyrazol-1-yl | X$^1$ | G-2 | J-24 (2/4) | — | H |
| 5-bromo-3-(trifluoromethyl)pyrazol-1-yl | X$^1$ | G-2 | J-24 (2/4) | — | H |
| 5-ethyl-3-(trifluoromethyl)pyrazol-1-yl | X$^1$ | G-2 | J-24 (2/4) | — | H |
| 3,5-bis-(trifluoromethyl)pyrazol-1-yl | X$^1$ | G-2 | J-24 (2/4) | — | H |
| 1-methyl-3-(trifluoromethyl)pyrazol-5-yl | X$^1$ | G-2 | J-24 (2/4) | — | H |
| 1-methyl-4-(trifluoromethyl)imidazol-2-yl | X$^1$ | G-2 | J-24 (2/4) | — | H |
| 2,5-dichlorophenyl | X$^1$ | G-2 | J-25 (2/4) | — | H |
| 2-chloro-5-(trifluoromethyl)phenyl | X$^1$ | G-2 | J-25 (2/4) | — | H |
| 2,5-dimethylphenyl | X$^1$ | G-2 | J-25 (2/4) | — | H |
| 2-methyl-5-(trifluoromethyl)phenyl | X$^1$ | G-2 | J-25 (2/4) | — | H |
| 3,5-dimethylpyrazol-1-yl | X$^1$ | G-2 | J-25 (2/4) | — | H |
| 5-methyl-3-(trifluoromethyl)pyrazol-1-yl | X$^1$ | G-2 | J-25 (2/4) | — | H |
| 5-chloro-3-(trifluoromethyl)pyrazol-1-yl | X$^1$ | G-2 | J-25 (2/4) | — | H |
| 5-bromo-3-(trifluoromethyl)pyrazol-1-yl | X$^1$ | G-2 | J-25 (2/4) | — | H |
| 5-ethyl-3-(trifluoromethyl)pyrazol-1-yl | X$^1$ | G-2 | J-25 (2/4) | — | H |
| 3,5-bis-(trifluoromethyl)pyrazol-1-yl | X$^1$ | G-2 | J-25 (2/4) | — | H |
| 1-methyl-3-(trifluoromethyl)pyrazol-5-yl | X$^1$ | G-2 | J-25 (2/4) | — | H |
| 1-methyl-4-(trifluoromethyl)imidazol-2-yl | X$^1$ | G-2 | J-25 (2/4) | — | H |
| 2,5-dichlorophenyl | X$^1$ | G-2 | J-26 (2/4) | — | H |
| 2-chloro-5-(trifluoromethyl)phenyl | X$^1$ | G-2 | J-26 (2/4) | — | H |
| 2,5-dimethylphenyl | X$^1$ | G-2 | J-26 (2/4) | — | H |
| 2-methyl-5-(trifluoromethyl)phenyl | X$^1$ | G-2 | J-26 (2/4) | — | H |
| 3,5-dimethylpyrazol-1-yl | X$^1$ | G-2 | J-26 (2/4) | — | H |
| 5-methyl-3-(trifluoromethyl)pyrazol-1-yl | X$^1$ | G-2 | J-26 (2/4) | — | H |
| 5-chloro-3-(trifluoromethyl)pyrazol-1-yl | X$^1$ | G-2 | J-26 (2/4) | — | H |
| 5-bromo-3-(trifluoromethyl)pyrazol-1-yl | X$^1$ | G-2 | J-26 (2/4) | — | H |
| 5-ethyl-3-(trifluoromethyl)pyrazol-1-yl | X$^1$ | G-2 | J-26 (2/4) | — | H |
| 3,5-bis-(trifluoromethyl)pyrazol-1-yl | X$^1$ | G-2 | J-26 (2/4) | — | H |

TABLE 4*-continued

| R¹ | X | G | J* | (R⁵)_y | R⁷ᵃ |
|---|---|---|---|---|---|
| 1-methyl-3-(trifluoromethyl)pyrazol-5-yl | X¹ | G-2 | J-26 (2/4) | — | H |
| 1-methyl-4-(trifluoromethyl)imidazol-2-yl | X¹ | G-2 | J-26 (2/4) | — | H |
| 2,5-dichlorophenyl | X¹ | G-2 | J-26 (2/4) | 1-Me | H |
| 2-chloro-5-(trifluoromethyl)phenyl | X¹ | G-2 | J-26 (2/4) | 1-Me | H |
| 2,5-dimethylphenyl | X¹ | G-2 | J-26 (2/4) | 1-Me | H |
| 2-methyl-5-(trifluoromethyl)phenyl | X¹ | G-2 | J-26 (2/4) | 1-Me | H |
| 3,5-dimethylpyrazol-1-yl | X¹ | G-2 | J-26 (2/4) | 1-Me | H |
| 5-methyl-3-(trifluoromethyl)pyrazol-1-yl | X¹ | G-2 | J-26 (2/4) | 1-Me | H |
| 5-chloro-3-(trifluoromethyl)pyrazol-1-yl | X¹ | G-2 | J-26 (2/4) | 1-Me | H |
| 5-bromo-3-(trifluoromethyl)pyrazol-1-yl | X¹ | G-2 | J-26 (2/4) | 1-Me | H |
| 5-ethyl-3-(trifluoromethyl)pyrazol-1-yl | X¹ | G-2 | J-26 (2/4) | 1-Me | H |
| 3,5-bis-(trifluoromethyl)pyrazol-1-yl | X¹ | G-2 | J-26 (2/4) | 1-Me | H |
| 1-methyl-3-(trifluoromethyl)pyrazol-5-yl | X¹ | G-2 | J-26 (2/4) | 1-Me | H |
| 1-methyl-4-(trifluoromethyl)imidazol-2-yl | X¹ | G-2 | J-26 (2/4) | 1-Me | H |
| 2,5-dichlorophenyl | X¹ | G-2 | J-26 (2/5) | 1-Me | H |
| 2-chloro-5-(trifluoromethyl)phenyl | X¹ | G-2 | J-26 (2/5) | 1-Me | H |
| 2,5-dimethylphenyl | X¹ | G-2 | J-26 (2/5) | 1-Me | H |
| 2-methyl-5-(trifluoromethyl)phenyl | X¹ | G-2 | J-26 (2/5) | 1-Me | H |
| 3,5-dimethylpyrazol-1-yl | X¹ | G-2 | J-26 (2/5) | 1-Me | H |
| 5-methyl-3-(trifluoromethyl)pyrazol-1-yl | X¹ | G-2 | J-26 (2/5) | 1-Me | H |
| 5-chloro-3-(trifluoromethyl)pyrazol-1-yl | X¹ | G-2 | J-26 (2/5) | 1-Me | H |
| 5-bromo-3-(trifluoromethyl)pyrazol-1-yl | X¹ | G-2 | J-26 (2/5) | 1-Me | H |
| 5-ethyl-3-(trifluoromethyl)pyrazol-1-yl | X¹ | G-2 | J-26 (2/5) | 1-Me | H |
| 3,5-bis-(trifluoromethyl)pyrazol-1-yl | X¹ | G-2 | J-26 (2/5) | 1-Me | H |
| 1-methyl-3-(trifluoromethyl)pyrazol-5-yl | X¹ | G-2 | J-26 (2/5) | 1-Me | H |
| 1-methyl-4-(trifluoromethyl)imidazol-2-yl | X¹ | G-2 | J-26 (2/5) | 1-Me | H |
| 2,5-dichlorophenyl | X¹ | G-2 | J-28 (3/5) | — | H |
| 2-chloro-5-(trifluoromethyl)phenyl | X¹ | G-2 | J-28 (3/5) | — | H |
| 2,5-dimethylphenyl | X¹ | G-2 | J-28 (3/5) | — | H |
| 2-methyl-5-(trifluoromethyl)phenyl | X¹ | G-2 | J-28 (3/5) | — | H |
| 3,5-dimethylpyrazol-1-yl | X¹ | G-2 | J-28 (3/5) | — | H |
| 5-methyl-3-(trifluoromethyl)pyrazol-1-yl | X¹ | G-2 | J-28 (3/5) | — | H |
| 5-chloro-3-(trifluoromethyl)pyrazol-1-yl | X¹ | G-2 | J-28 (3/5) | — | H |
| 5-bromo-3-(trifluoromethyl)pyrazol-1-yl | X¹ | G-2 | J-28 (3/5) | — | H |
| 5-ethyl-3-(trifluoromethyl)pyrazol-1-yl | X¹ | G-2 | J-28 (3/5) | — | H |
| 3,5-bis-(trifluoromethyl)pyrazol-1-yl | X¹ | G-2 | J-28 (3/5) | — | H |
| 1-methyl-3-(trifluoromethyl)pyrazol-5-yl | X¹ | G-2 | J-28 (3/5) | — | H |
| 1-methyl-4-(trifluoromethyl)imidazol-2-yl | X¹ | G-2 | J-28 (3/5) | — | H |
| 2,5-dichlorophenyl | X¹ | G-2 | J-30 (3/5) | — | H |
| 2-chloro-5-(trifluoromethyl)phenyl | X¹ | G-2 | J-30 (3/5) | — | H |
| 2,5-dimethylphenyl | X¹ | G-2 | J-30 (3/5) | — | H |
| 2-methyl-5-(trifluoromethyl)phenyl | X¹ | G-2 | J-30 (3/5) | — | H |
| 3,5-dimethylpyrazol-1-yl | X¹ | G-2 | J-30 (3/5) | — | H |
| 5-methyl-3-(trifluoromethyl)pyrazol-1-yl | X¹ | G-2 | J-30 (3/5) | — | H |
| 5-chloro-3-(trifluoromethyl)pyrazol-1-yl | X¹ | G-2 | J-30 (3/5) | — | H |
| 5-bromo-3-(trifluoromethyl)pyrazol-1-yl | X¹ | G-2 | J-30 (3/5) | — | H |
| 5-ethyl-3-(trifluoromethyl)pyrazol-1-yl | X¹ | G-2 | J-30 (3/5) | — | H |
| 3,5-bis-(trifluoromethyl)pyrazol-1-yl | X¹ | G-2 | J-30 (3/5) | — | H |
| 1-methyl-3-(trifluoromethyl)pyrazol-5-yl | X¹ | G-2 | J-30 (3/5) | — | H |
| 1-methyl-4-(trifluoromethyl)imidazol-2-yl | X¹ | G-2 | J-30 (3/5) | — | H |
| 2,5-dichlorophenyl | X¹ | G-2 | J-30 (3/5) | 1-Me | H |
| 2-chloro-5-(trifluoromethyl)phenyl | X¹ | G-2 | J-30 (3/5) | 1-Me | H |
| 2,5-dimethylphenyl | X¹ | G-2 | J-30 (3/5) | 1-Me | H |
| 2-methyl-5-(trifluoromethyl)phenyl | X¹ | G-2 | J-30 (3/5) | 1-Me | H |
| 3,5-dimethylpyrazol-1-yl | X¹ | G-2 | J-30 (3/5) | 1-Me | H |
| 5-methyl-3-(trifluoromethyl)pyrazol-1-yl | X¹ | G-2 | J-30 (3/5) | 1-Me | H |
| 5-chloro-3-(trifluoromethyl)pyrazol-1-yl | X¹ | G-2 | J-30 (3/5) | 1-Me | H |
| 5-bromo-3-(trifluoromethyl)pyrazol-1-yl | X¹ | G-2 | J-30 (3/5) | 1-Me | H |
| 5-ethyl-3-(trifluoromethyl)pyrazol-1-yl | X¹ | G-2 | J-30 (3/5) | 1-Me | H |
| 3,5-bis-(trifluoromethyl)pyrazol-1-yl | X¹ | G-2 | J-30 (3/5) | 1-Me | H |
| 1-methyl-3-(trifluoromethyl)pyrazol-5-yl | X¹ | G-2 | J-30 (3/5) | 1-Me | H |
| 1-methyl-4-(trifluoromethyl)imidazol-2-yl | X¹ | G-2 | J-30 (3/5) | 1-Me | H |

TABLE 4*-continued

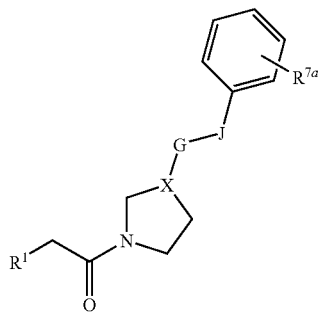

| R¹ | X | G | J* | (R⁵)ᵧ | R⁷ᵃ |
|---|---|---|---|---|---|
| 2,5-dichlorophenyl | X¹ | G-2 | J-36 (3/5) | 1-Me | H |
| 2-chloro-5-(trifluoromethyl)phenyl | X¹ | G-2 | J-36 (3/5) | 1-Me | H |
| 2,5-dimethylphenyl | X¹ | G-2 | J-36 (3/5) | 1-Me | H |
| 2-methyl-5-(trifluoromethyl)phenyl | X¹ | G-2 | J-36 (3/5) | 1-Me | H |
| 3,5-dimethylpyrazol-1-yl | X¹ | G-2 | J-36 (3/5) | 1-Me | H |
| 5-methyl-3-(trifluoromethyl)pyrazol-1-yl | X¹ | G-2 | J-36 (3/5) | 1-Me | H |
| 5-chloro-3-(trifluoromethyl)pyrazol-1-yl | X¹ | G-2 | J-36 (3/5) | 1-Me | H |
| 5-bromo-3-(trifluoromethyl)pyrazol-1-yl | X¹ | G-2 | J-36 (3/5) | 1-Me | H |
| 5-ethyl-3-(trifluoromethyl)pyrazol-1-yl | X¹ | G-2 | J-36 (3/5) | 1-Me | H |
| 3,5-bis-(trifluoromethyl)pyrazol-1-yl | X¹ | G-2 | J-36 (3/5) | 1-Me | H |
| 1-methyl-3-(trifluoromethyl)pyrazol-5-yl | X¹ | G-2 | J-36 (3/5) | 1-Me | H |
| 1-methyl-4-(trifluoromethyl)imidazol-2-yl | X¹ | G-2 | J-36 (3/5) | 1-Me | H |
| 2,5-dichlorophenyl | X¹ | G-2 | J-37 (2/5) | — | H |
| 2-chloro-5-(trifluoromethyl)phenyl | X¹ | G-2 | J-37 (2/5) | — | H |
| 2,5-dimethylphenyl | X¹ | G-2 | J-37 (2/5) | — | H |
| 2-methyl-5-(trifluoromethyl)phenyl | X¹ | G-2 | J-37 (2/5) | — | H |
| 3,5-dimethylpyrazol-1-yl | X¹ | G-2 | J-37 (2/5) | — | H |
| 5-methyl-3-(trifluoromethyl)pyrazol-1-yl | X¹ | G-2 | J-37 (2/5) | — | H |
| 5-chloro-3-(trifluoromethyl)pyrazol-1-yl | X¹ | G-2 | J-37 (2/5) | — | H |
| 5-bromo-3-(trifluoromethyl)pyrazol-1-yl | X¹ | G-2 | J-37 (2/5) | — | H |
| 5-ethyl-3-(trifluoromethyl)pyrazol-1-yl | X¹ | G-2 | J-37 (2/5) | — | H |
| 3,5-bis-(trifluoromethyl)pyrazol-1-yl | X¹ | G-2 | J-37 (2/5) | — | H |
| 1-methyl-3-(trifluoromethyl)pyrazol-5-yl | X¹ | G-2 | J-37 (2/5) | — | H |
| 1-methyl-4-(trifluoromethyl)imidazol-2-yl | X¹ | G-2 | J-37 (2/5) | — | H |
| 2,5-dichlorophenyl | X¹ | G-2 | J-38 (2/5) | — | H |
| 2-chloro-5-(trifluoromethyl)phenyl | X¹ | G-2 | J-38 (2/5) | — | H |
| 2,5-dimethylphenyl | X¹ | G-2 | J-38 (2/5) | — | H |
| 2-methyl-5-(trifluoromethyl)phenyl | X¹ | G-2 | J-38 (2/5) | — | H |
| 3,5-dimethylpyrazol-1-yl | X¹ | G-2 | J-38 (2/5) | — | H |
| 5-methyl-3-(trifluoromethyl)pyrazol-1-yl | X¹ | G-2 | J-38 (2/5) | — | H |
| 5-chloro-3-(trifluoromethyl)pyrazol-1-yl | X¹ | G-2 | J-38 (2/5) | — | H |
| 5-bromo-3-(trifluoromethyl)pyrazol-1-yl | X¹ | G-2 | J-38 (2/5) | — | H |
| 5-ethyl-3-(trifluoromethyl)pyrazol-1-yl | X¹ | G-2 | J-38 (2/5) | — | H |
| 3,5-bis-(trifluoromethyl)pyrazol-1-yl | X¹ | G-2 | J-38 (2/5) | — | H |
| 1-methyl-3-(trifluoromethyl)pyrazol-5-yl | X¹ | G-2 | J-38 (2/5) | — | H |
| 1-methyl-4-(trifluoromethyl)imidazol-2-yl | X¹ | G-2 | J-38 (2/5) | — | H |
| 2,5-dichlorophenyl | X¹ | G-2 | J-39 (3/5) | — | H |
| 2-chloro-5-(trifluoromethyl)phenyl | X¹ | G-2 | J-39 (3/5) | — | H |
| 2,5-dimethylphenyl | X¹ | G-2 | J-39 (3/5) | — | H |
| 2-methyl-5-(trifluoromethyl)phenyl | X¹ | G-2 | J-39 (3/5) | — | H |
| 3,5-dimethylpyrazol-1-yl | X¹ | G-2 | J-39 (3/5) | — | H |
| 5-methyl-3-(trifluoromethyl)pyrazol-1-yl | X¹ | G-2 | J-39 (3/5) | — | H |
| 5-chloro-3-(trifluoromethyl)pyrazol-1-yl | X¹ | G-2 | J-39 (3/5) | — | H |
| 5-bromo-3-(trifluoromethyl)pyrazol-1-yl | X¹ | G-2 | J-39 (3/5) | — | H |
| 5-ethyl-3-(trifluoromethyl)pyrazol-1-yl | X¹ | G-2 | J-39 (3/5) | — | H |
| 3,5-bis-(trifluoromethyl)pyrazol-1-yl | X¹ | G-2 | J-39 (3/5) | — | H |
| 1-methyl-3-(trifluoromethyl)pyrazol-5-yl | X¹ | G-2 | J-39 (3/5) | — | H |
| 1-methyl-4-(trifluoromethyl)imidazol-2-yl | X¹ | G-2 | J-39 (3/5) | — | H |
| 2,5-dichlorophenyl | X¹ | G-2 | J-40 (3/5) | — | H |
| 2-chloro-5-(trifluoromethyl)phenyl | X¹ | G-2 | J-40 (3/5) | — | H |
| 2,5-dimethylphenyl | X¹ | G-2 | J-40 (3/5) | — | H |
| 2-methyl-5-(trifluoromethyl)phenyl | X¹ | G-2 | J-40 (3/5) | — | H |
| 3,5-dimethylpyrazol-1-yl | X¹ | G-2 | J-40 (3/5) | — | H |
| 5-methyl-3-(trifluoromethyl)pyrazol-1-yl | X¹ | G-2 | J-40 (3/5) | — | H |
| 5-chloro-3-(trifluoromethyl)pyrazol-1-yl | X¹ | G-2 | J-40 (3/5) | — | H |
| 5-bromo-3-(trifluoromethyl)pyrazol-1-yl | X¹ | G-2 | J-40 (3/5) | — | H |
| 5-ethyl-3-(trifluoromethyl)pyrazol-1-yl | X¹ | G-2 | J-40 (3/5) | — | H |
| 3,5-bis-(trifluoromethyl)pyrazol-1-yl | X¹ | G-2 | J-40 (3/5) | — | H |
| 1-methyl-3-(trifluoromethyl)pyrazol-5-yl | X¹ | G-2 | J-40 (3/5) | — | H |
| 1-methyl-4-(trifluoromethyl)imidazol-2-yl | X¹ | G-2 | J-40 (3/5) | — | H |
| 2,5-dichlorophenyl | X¹ | G-2 | J-69 (1/3) | — | H |
| 2-chloro-5-(trifluoromethyl)phenyl | X¹ | G-2 | J-69 (1/3) | — | H |

TABLE 4*-continued

| R¹ | X | G | J* | (R⁵)ᵧ | R⁷ᵃ |
|---|---|---|---|---|---|
| 2,5-dimethylphenyl | X¹ | G-2 | J-69 (1/3) | — | H |
| 2-methyl-5-(trifluoromethyl)phenyl | X¹ | G-2 | J-69 (1/3) | — | H |
| 3,5-dimethylpyrazol-1-yl | X¹ | G-2 | J-69 (1/3) | — | H |
| 5-methyl-3-(trifluoromethyl)pyrazol-1-yl | X¹ | G-2 | J-69 (1/3) | — | H |
| 5-chloro-3-(trifluoromethyl)pyrazol-1-yl | X¹ | G-2 | J-69 (1/3) | — | H |
| 5-bromo-3-(trifluoromethyl)pyrazol-1-yl | X¹ | G-2 | J-69 (1/3) | — | H |
| 5-ethyl-3-(trifluoromethyl)pyrazol-1-yl | X¹ | G-2 | J-69 (1/3) | — | H |
| 3,5-bis-(trifluoromethyl)pyrazol-1-yl | X¹ | G-2 | J-69 (1/3) | — | H |
| 1-methyl-3-(trifluoromethyl)pyrazol-5-yl | X¹ | G-2 | J-69 (1/3) | — | H |
| 1-methyl-4-(trifluoromethyl)imidazol-2-yl | X¹ | G-2 | J-69 (1/3) | — | H |
| 2,5-dichlorophenyl | X¹ | G-2 | J-69 (1/4) | — | H |
| 2-chloro-5-(trifluoromethyl)phenyl | X¹ | G-2 | J-69 (1/4) | — | H |
| 2,5-dimethylphenyl | X¹ | G-2 | J-69 (1/4) | — | H |
| 2-methyl-5-(trifluoromethyl)phenyl | X¹ | G-2 | J-69 (1/4) | — | H |
| 3,5-dimethylpyrazol-1-yl | X¹ | G-2 | J-69 (1/4) | — | H |
| 5-methyl-3-(trifluoromethyl)pyrazol-1-yl | X¹ | G-2 | J-69 (1/4) | — | H |
| 5-chloro-3-(trifluoromethyl)pyrazol-1-yl | X¹ | G-2 | J-69 (1/4) | — | H |
| 5-bromo-3-(trifluoromethyl)pyrazol-1-yl | X¹ | G-2 | J-69 (1/4) | — | H |
| 5-ethyl-3-(trifluoromethyl)pyrazol-1-yl | X¹ | G-2 | J-69 (1/4) | — | H |
| 3,5-bis-(trifluoromethyl)pyrazol-1-yl | X¹ | G-2 | J-69 (1/4) | — | H |
| 1-methyl-3-(trifluoromethyl)pyrazol-5-yl | X¹ | G-2 | J-69 (1/4) | — | H |
| 1-methyl-4-(trifluoromethyl)imidazol-2-yl | X¹ | G-2 | J-69 (1/4) | — | H |
| 2,5-dichlorophenyl | X¹ | G-2 | J-11 (3/5) | — | 2-Me |
| 2-chloro-5-(trifluoromethyl)phenyl | X¹ | G-2 | J-11 (3/5) | — | 2-Me |
| 2,5-dimethylphenyl | X¹ | G-2 | J-11 (3/5) | — | 2-Me |
| 2-methyl-5-(trifluoromethyl)phenyl | X¹ | G-2 | J-11 (3/5) | — | 2-Me |
| 3,5-dimethylpyrazol-1-yl | X¹ | G-2 | J-11 (3/5) | — | 2-Me |
| 5-methyl-3-(trifluoromethyl)pyrazol-1-yl | X¹ | G-2 | J-11 (3/5) | — | 2-Me |
| 5-chloro-3-(trifluoromethyl)pyrazol-1-yl | X¹ | G-2 | J-11 (3/5) | — | 2-Me |
| 5-bromo-3-(trifluoromethyl)pyrazol-1-yl | X¹ | G-2 | J-11 (3/5) | — | 2-Me |
| 5-ethyl-3-(trifluoromethyl)pyrazol-1-yl | X¹ | G-2 | J-11 (3/5) | — | 2-Me |
| 3,5-bis-(trifluoromethyl)pyrazol-1-yl | X¹ | G-2 | J-11 (3/5) | — | 2-Me |
| 1-methyl-3-(trifluoromethyl)pyrazol-5-yl | X¹ | G-2 | J-11 (3/5) | — | 2-Me |
| 1-methyl-4-(trifluoromethyl)imidazol-2-yl | X¹ | G-2 | J-11 (3/5) | — | 2-Me |
| 2,5-dichlorophenyl | X¹ | G-2 | J-11 (3/5) | — | 3-Me |
| 2-chloro-5-(trifluoromethyl)phenyl | X¹ | G-2 | J-11 (3/5) | — | 3-Me |
| 2,5-dimethylphenyl | X¹ | G-2 | J-11 (3/5) | — | 3-Me |
| 2-methyl-5-(trifluoromethyl)phenyl | X¹ | G-2 | J-11 (3/5) | — | 3-Me |
| 3,5-dimethylpyrazol-1-yl | X¹ | G-2 | J-11 (3/5) | — | 3-Me |
| 5-methyl-3-(trifluoromethyl)pyrazol-1-yl | X¹ | G-2 | J-11 (3/5) | — | 3-Me |
| 5-chloro-3-(trifluoromethyl)pyrazol-1-yl | X¹ | G-2 | J-11 (3/5) | — | 3-Me |
| 5-bromo-3-(trifluoromethyl)pyrazol-1-yl | X¹ | G-2 | J-11 (3/5) | — | 3-Me |
| 5-ethyl-3-(trifluoromethyl)pyrazol-1-yl | X¹ | G-2 | J-11 (3/5) | — | 3-Me |
| 3,5-bis-(trifluoromethyl)pyrazol-1-yl | X¹ | G-2 | J-11 (3/5) | — | 3-Me |
| 1-methyl-3-(trifluoromethyl)pyrazol-5-yl | X¹ | G-2 | J-11 (3/5) | — | 3-Me |
| 1-methyl-4-(trifluoromethyl)imidazol-2-yl | X¹ | G-2 | J-11 (3/5) | — | 3-Me |
| 2,5-dichlorophenyl | X¹ | G-2 | J-11 (3/5) | — | 4-Me |
| 2-chloro-5-(trifluoromethyl)phenyl | X¹ | G-2 | J-11 (3/5) | — | 4-Me |
| 2,5-dimethylphenyl | X¹ | G-2 | J-11 (3/5) | — | 4-Me |
| 2-methyl-5-(trifluoromethyl)phenyl | X¹ | G-2 | J-11 (3/5) | — | 4-Me |
| 3,5-dimethylpyrazol-1-yl | X¹ | G-2 | J-11 (3/5) | — | 4-Me |
| 5-methyl-3-(trifluoromethyl)pyrazol-1-yl | X¹ | G-2 | J-11 (3/5) | — | 4-Me |
| 5-chloro-3-(trifluoromethyl)pyrazol-1-yl | X¹ | G-2 | J-11 (3/5) | — | 4-Me |
| 5-bromo-3-(trifluoromethyl)pyrazol-1-yl | X¹ | G-2 | J-11 (3/5) | — | 4-Me |
| 5-ethyl-3-(trifluoromethyl)pyrazol-1-yl | X¹ | G-2 | J-11 (3/5) | — | 4-Me |
| 3,5-bis-(trifluoromethyl)pyrazol-1-yl | X¹ | G-2 | J-11 (3/5) | — | 4-Me |
| 1-methyl-3-(trifluoromethyl)pyrazol-5-yl | X¹ | G-2 | J-11 (3/5) | — | 4-Me |
| 1-methyl-4-(trifluoromethyl)imidazol-2-yl | X¹ | G-2 | J-11 (3/5) | — | 4-Me |
| 2,5-dichlorophenyl | X¹ | G-2 | J-11 (3/5) | — | 2-Cl |
| 2-chloro-5-(trifluoromethyl)phenyl | X¹ | G-2 | J-11 (3/5) | — | 2-Cl |
| 2,5-dimethylphenyl | X¹ | G-2 | J-11 (3/5) | — | 2-Cl |
| 2-methyl-5-(trifluoromethyl)phenyl | X¹ | G-2 | J-11 (3/5) | — | 2-Cl |

TABLE 4*-continued

| R¹ | X | G | J* | (R⁵)_y | R⁷ᵃ |
|---|---|---|---|---|---|
| 3,5-dimethylpyrazol-1-yl | X¹ | G-2 | J-11 (3/5) | — | 2-Cl |
| 5-methyl-3-(trifluoromethyl)pyrazol-1-yl | X¹ | G-2 | J-11 (3/5) | — | 2-Cl |
| 5-chloro-3-(trifluoromethyl)pyrazol-1-yl | X¹ | G-2 | J-11 (3/5) | — | 2-Cl |
| 5-bromo-3-(trifluoromethyl)pyrazol-1-yl | X¹ | G-2 | J-11 (3/5) | — | 2-Cl |
| 5-ethyl-3-(trifluoromethyl)pyrazol-1-yl | X¹ | G-2 | J-11 (3/5) | — | 2-Cl |
| 3,5-bis-(trifluoromethyl)pyrazol-1-yl | X¹ | G-2 | J-11 (3/5) | — | 2-Cl |
| 1-methyl-3-(trifluoromethyl)pyrazol-5-yl | X¹ | G-2 | J-11 (3/5) | — | 2-Cl |
| 1-methyl-4-(trifluoromethyl)imidazol-2-yl | X¹ | G-2 | J-11 (3/5) | — | 2-Cl |
| 2,5-dichlorophenyl | X¹ | G-2 | J-11 (3/5) | — | 4-Cl |
| 2-chloro-5-(trifluoromethyl)phenyl | X¹ | G-2 | J-11 (3/5) | — | 4-Cl |
| 2,5-dimethylphenyl | X¹ | G-2 | J-11 (3/5) | — | 4-Cl |
| 2-methyl-5-(trifluoromethyl)phenyl | X¹ | G-2 | J-11 (3/5) | — | 4-Cl |
| 3,5-dimethylpyrazol-1-yl | X¹ | G-2 | J-11 (3/5) | — | 4-Cl |
| 5-methyl-3-(trifluoromethyl)pyrazol-1-yl | X¹ | G-2 | J-11 (3/5) | — | 4-Cl |
| 5-chloro-3-(trifluoromethyl)pyrazol-1-yl | X¹ | G-2 | J-11 (3/5) | — | 4-Cl |
| 5-bromo-3-(trifluoromethyl)pyrazol-1-yl | X¹ | G-2 | J-11 (3/5) | — | 4-Cl |
| 5-ethyl-3-(trifluoromethyl)pyrazol-1-yl | X¹ | G-2 | J-11 (3/5) | — | 4-Cl |
| 3,5-bis-(trifluoromethyl)pyrazol-1-yl | X¹ | G-2 | J-11 (3/5) | — | 4-Cl |
| 1-methyl-3-(trifluoromethyl)pyrazol-5-yl | X¹ | G-2 | J-11 (3/5) | — | 4-Cl |
| 1-methyl-4-(trifluoromethyl)imidazol-2-yl | X¹ | G-2 | J-11 (3/5) | — | 4-Cl |
| 2,5-dichlorophenyl | X¹ | G-2 | J-29 (3/5) | — | 2-Me |
| 2-chloro-5-(trifluoromethyl)phenyl | X¹ | G-2 | J-29 (3/5) | — | 2-Me |
| 2,5-dimethylphenyl | X¹ | G-2 | J-29 (3/5) | — | 2-Me |
| 2-methyl-5-(trifluoromethyl)phenyl | X¹ | G-2 | J-29 (3/5) | — | 2-Me |
| 3,5-dimethylpyrazol-1-yl | X¹ | G-2 | J-29 (3/5) | — | 2-Me |
| 5-methyl-3-(trifluoromethyl)pyrazol-1-yl | X¹ | G-2 | J-29 (3/5) | — | 2-Me |
| 5-chloro-3-(trifluoromethyl)pyrazol-1-yl | X¹ | G-2 | J-29 (3/5) | — | 2-Me |
| 5-bromo-3-(trifluoromethyl)pyrazol-1-yl | X¹ | G-2 | J-29 (3/5) | — | 2-Me |
| 5-ethyl-3-(trifluoromethyl)pyrazol-1-yl | X¹ | G-2 | J-29 (3/5) | — | 2-Me |
| 3,5-bis-(trifluoromethyl)pyrazol-1-yl | X¹ | G-2 | J-29 (3/5) | — | 2-Me |
| 1-methyl-3-(trifluoromethyl)pyrazol-5-yl | X¹ | G-2 | J-29 (3/5) | — | 2-Me |
| 1-methyl-4-(trifluoromethyl)imidazol-2-yl | X¹ | G-2 | J-29 (3/5) | — | 2-Me |
| 2,5-dichlorophenyl | X¹ | G-2 | J-29 (3/5) | — | 3-Me |
| 2-chloro-5-(trifluoromethyl)phenyl | X¹ | G-2 | J-29 (3/5) | — | 3-Me |
| 2,5-dimethylphenyl | X¹ | G-2 | J-29 (3/5) | — | 3-Me |
| 2-methyl-5-(trifluoromethyl)phenyl | X¹ | G-2 | J-29 (3/5) | — | 3-Me |
| 3,5-dimethylpyrazol-1-yl | X¹ | G-2 | J-29 (3/5) | — | 3-Me |
| 5-methyl-3-(trifluoromethyl)pyrazol-1-yl | X¹ | G-2 | J-29 (3/5) | — | 3-Me |
| 5-chloro-3-(trifluoromethyl)pyrazol-1-yl | X¹ | G-2 | J-29 (3/5) | — | 3-Me |
| 5-bromo-3-(trifluoromethyl)pyrazol-1-yl | X¹ | G-2 | J-29 (3/5) | — | 3-Me |
| 5-ethyl-3-(trifluoromethyl)pyrazol-1-yl | X¹ | G-2 | J-29 (3/5) | — | 3-Me |
| 3,5-bis-(trifluoromethyl)pyrazol-1-yl | X¹ | G-2 | J-29 (3/5) | — | 3-Me |
| 1-methyl-3-(trifluoromethyl)pyrazol-5-yl | X¹ | G-2 | J-29 (3/5) | — | 3-Me |
| 1-methyl-4-(trifluoromethyl)imidazol-2-yl | X¹ | G-2 | J-29 (3/5) | — | 3-Me |
| 2,5-dichlorophenyl | X¹ | G-2 | J-29 (3/5) | — | 4-Me |
| 2-chloro-5-(trifluoromethyl)phenyl | X¹ | G-2 | J-29 (3/5) | — | 4-Me |
| 2,5-dimethylphenyl | X¹ | G-2 | J-29 (3/5) | — | 4-Me |
| 2-methyl-5-(trifluoromethyl)phenyl | X¹ | G-2 | J-29 (3/5) | — | 4-Me |
| 3,5-dimethylpyrazol-1-yl | X¹ | G-2 | J-29 (3/5) | — | 4-Me |
| 5-methyl-3-(trifluoromethyl)pyrazol-1-yl | X¹ | G-2 | J-29 (3/5) | — | 4-Me |
| 5-chloro-3-(trifluoromethyl)pyrazol-1-yl | X¹ | G-2 | J-29 (3/5) | — | 4-Me |
| 5-bromo-3-(trifluoromethyl)pyrazol-1-yl | X¹ | G-2 | J-29 (3/5) | — | 4-Me |
| 5-ethyl-3-(trifluoromethyl)pyrazol-1-yl | X¹ | G-2 | J-29 (3/5) | — | 4-Me |
| 3,5-bis-(trifluoromethyl)pyrazol-1-yl | X¹ | G-2 | J-29 (3/5) | — | 4-Me |
| 1-methyl-3-(trifluoromethyl)pyrazol-5-yl | X¹ | G-2 | J-29 (3/5) | — | 4-Me |
| 1-methyl-4-(trifluoromethyl)imidazol-2-yl | X¹ | G-2 | J-29 (3/5) | — | 4-Me |
| 2,5-dichlorophenyl | X¹ | G-2 | J-29 (3/5) | — | 2-Cl |
| 2-chloro-5-(trifluoromethyl)phenyl | X¹ | G-2 | J-29 (3/5) | — | 2-Cl |
| 2,5-dimethylphenyl | X¹ | G-2 | J-29 (3/5) | — | 2-Cl |
| 2-methyl-5-(trifluoromethyl)phenyl | X¹ | G-2 | J-29 (3/5) | — | 2-Cl |
| 3,5-dimethylpyrazol-1-yl | X¹ | G-2 | J-29 (3/5) | — | 2-Cl |
| 5-methyl-3-(trifluoromethyl)pyrazol-1-yl | X¹ | G-2 | J-29 (3/5) | — | 2-Cl |

TABLE 4*-continued

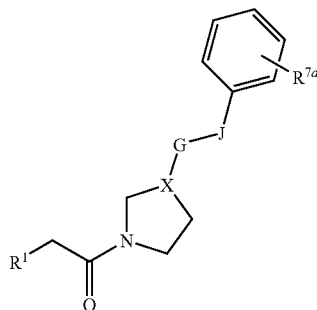

| $R^1$ | X | G | J* | $(R^5)_y$ | $R^{7a}$ |
|---|---|---|---|---|---|
| 5-chloro-3-(trifluoromethyl)pyrazol-1-yl | $X^1$ | G-2 | J-29 (3/5) | — | 2-Cl |
| 5-bromo-3-(trifluoromethyl)pyrazol-1-yl | $X^1$ | G-2 | J-29 (3/5) | — | 2-Cl |
| 5-ethyl-3-(trifluoromethyl)pyrazol-1-yl | $X^1$ | G-2 | J-29 (3/5) | — | 2-Cl |
| 3,5-bis-(trifluoromethyl)pyrazol-1-yl | $X^1$ | G-2 | J-29 (3/5) | — | 2-Cl |
| 1-methyl-3-(trifluoromethyl)pyrazol-5-yl | $X^1$ | G-2 | J-29 (3/5) | — | 2-Cl |
| 1-methyl-4-(trifluoromethyl)imidazol-2-yl | $X^1$ | G-2 | J-29 (3/5) | — | 2-Cl |
| 2,5-dichlorophenyl | $X^1$ | G-2 | J-29 (3/5) | — | 4-Cl |
| 2-chloro-5-(trifluoromethyl)phenyl | $X^1$ | G-2 | J-29 (3/5) | — | 4-Cl |
| 2,5-dimethylphenyl | $X^1$ | G-2 | J-29 (3/5) | — | 4-Cl |
| 2-methyl-5-(trifluoromethyl)phenyl | $X^1$ | G-2 | J-29 (3/5) | — | 4-Cl |
| 3,5-dimethylpyrazol-1-yl | $X^1$ | G-2 | J-29 (3/5) | — | 4-Cl |
| 5-methyl-3-(trifluoromethyl)pyrazol-1-yl | $X^1$ | G-2 | J-29 (3/5) | — | 4-Cl |
| 5-chloro-3-(trifluoromethyl)pyrazol-1-yl | $X^1$ | G-2 | J-29 (3/5) | — | 4-Cl |
| 5-bromo-3-(trifluoromethyl)pyrazol-1-yl | $X^1$ | G-2 | J-29 (3/5) | — | 4-Cl |
| 5-ethyl-3-(trifluoromethyl)pyrazol-1-yl | $X^1$ | G-2 | J-29 (3/5) | — | 4-Cl |
| 3,5-bis-(trifluoromethyl)pyrazol-1-yl | $X^1$ | G-2 | J-29 (3/5) | — | 4-Cl |
| 1-methyl-3-(trifluoromethyl)pyrazol-5-yl | $X^1$ | G-2 | J-29 (3/5) | — | 4-Cl |
| 1-methyl-4-(trifluoromethyl)imidazol-2-yl | $X^1$ | G-2 | J-29 (3/5) | — | 4-Cl |
| 2,5-dichlorophenyl | $X^1$ | G-2 | J-29 (3/5) | 5-Me | H |
| 2-chloro-5-(trifluoromethyl)phenyl | $X^1$ | G-2 | J-29 (3/5) | 5-Me | H |
| 2,5-dimethylphenyl | $X^1$ | G-2 | J-29 (3/5) | 5-Me | H |
| 2-methyl-5-(trifluoromethyl)phenyl | $X^1$ | G-2 | J-29 (3/5) | 5-Me | H |
| 3,5-dimethylpyrazol-1-yl | $X^1$ | G-2 | J-29 (3/5) | 5-Me | H |
| 5-methyl-3-(trifluoromethyl)pyrazol-1-yl | $X^1$ | G-2 | J-29 (3/5) | 5-Me | H |
| 5-chloro-3-(trifluoromethyl)pyrazol-1-yl | $X^1$ | G-2 | J-29 (3/5) | 5-Me | H |
| 5-bromo-3-(trifluoromethyl)pyrazol-1-yl | $X^1$ | G-2 | J-29 (3/5) | 5-Me | H |
| 5-ethyl-3-(trifluoromethyl)pyrazol-1-yl | $X^1$ | G-2 | J-29 (3/5) | 5-Me | H |
| 3,5-bis-(trifluoromethyl)pyrazol-1-yl | $X^1$ | G-2 | J-29 (3/5) | 5-Me | H |
| 1-methyl-3-(trifluoromethyl)pyrazol-5-yl | $X^1$ | G-2 | J-29 (3/5) | 5-Me | H |
| 1-methyl-4-(trifluoromethyl)imidazol-2-yl | $X^1$ | G-2 | J-29 (3/5) | 5-Me | H |
| 2,5-dichlorophenyl | $X^1$ | G-2 | J-29 (3/5) | 4-Me | H |
| 2-chloro-5-(trifluoromethyl)phenyl | $X^1$ | G-2 | J-29 (3/5) | 4-Me | H |
| 2,5-dimethylphenyl | $X^1$ | G-2 | J-29 (3/5) | 4-Me | H |
| 2-methyl-5-(trifluoromethyl)phenyl | $X^1$ | G-2 | J-29 (3/5) | 4-Me | H |
| 3,5-dimethylpyrazol-1-yl | $X^1$ | G-2 | J-29 (3/5) | 4-Me | H |
| 5-methyl-3-(trifluoromethyl)pyrazol-1-yl | $X^1$ | G-2 | J-29 (3/5) | 4-Me | H |
| 5-chloro-3-(trifluoromethyl)pyrazol-1-yl | $X^1$ | G-2 | J-29 (3/5) | 4-Me | H |
| 5-bromo-3-(trifluoromethyl)pyrazol-1-yl | $X^1$ | G-2 | J-29 (3/5) | 4-Me | H |
| 5-ethyl-3-(trifluoromethyl)pyrazol-1-yl | $X^1$ | G-2 | J-29 (3/5) | 4-Me | H |
| 3,5-bis-(trifluoromethyl)pyrazol-1-yl | $X^1$ | G-2 | J-29 (3/5) | 4-Me | H |
| 1-methyl-3-(trifluoromethyl)pyrazol-5-yl | $X^1$ | G-2 | J-29 (3/5) | 4-Me | H |
| 1-methyl-4-(trifluoromethyl)imidazol-2-yl | $X^1$ | G-2 | J-29 (3/5) | 4-Me | H |
| 2,5-dichlorophenyl | $X^1$ | G-2 | J-29 (3/5) | 4,4-di-Me | H |
| 2-chloro-5-(trifluoromethyl)phenyl | $X^1$ | G-2 | J-29 (3/5) | 4,4-di-Me | H |
| 2,5-dimethylphenyl | $X^1$ | G-2 | J-29 (3/5) | 4,4-di-Me | H |
| 2-methyl-5-(trifluoromethyl)phenyl | $X^1$ | G-2 | J-29 (3/5) | 4,4-di-Me | H |
| 3,5-dimethylpyrazol-1-yl | $X^1$ | G-2 | J-29 (3/5) | 4,4-di-Me | H |
| 5-methyl-3-(trifluoromethyl)pyrazol-1-yl | $X^1$ | G-2 | J-29 (3/5) | 4,4-di-Me | H |
| 5-chloro-3-(trifluoromethyl)pyrazol-1-yl | $X^1$ | G-2 | J-29 (3/5) | 4,4-di-Me | H |
| 5-bromo-3-(trifluoromethyl)pyrazol-1-yl | $X^1$ | G-2 | J-29 (3/5) | 4,4-di-Me | H |
| 5-ethyl-3-(trifluoromethyl)pyrazol-1-yl | $X^1$ | G-2 | J-29 (3/5) | 4,4-di-Me | H |
| 3,5-bis-(trifluoromethyl)pyrazol-1-yl | $X^1$ | G-2 | J-29 (3/5) | 4,4-di-Me | H |
| 1-methyl-3-(trifluoromethyl)pyrazol-5-yl | $X^1$ | G-2 | J-29 (3/5) | 4,4-di-Me | H |
| 1-methyl-4-(trifluoromethyl)imidazol-2-yl | $X^1$ | G-2 | J-29 (3/5) | 4,4-di-Me | H |
| 2,5-dichlorophenyl | $X^2$ | G-1 | J-1 (2/4) | — | H |
| 2-chloro-5-(trifluoromethyl)phenyl | $X^2$ | G-1 | J-1 (2/4) | — | H |
| 2,5-dimethylphenyl | $X^2$ | G-1 | J-1 (2/4) | — | H |
| 2-methyl-5-(trifluoromethyl)phenyl | $X^2$ | G-1 | J-1 (2/4) | — | H |
| 3,5-dimethylpyrazol-1-yl | $X^2$ | G-1 | J-1 (2/4) | — | H |
| 5-methyl-3-(trifluoromethyl)pyrazol-1-yl | $X^2$ | G-1 | J-1 (2/4) | — | H |
| 5-chloro-3-(trifluoromethyl)pyrazol-1-yl | $X^2$ | G-1 | J-1 (2/4) | — | H |
| 5-bromo-3-(trifluoromethyl)pyrazol-1-yl | $X^2$ | G-1 | J-1 (2/4) | — | H |

TABLE 4*-continued

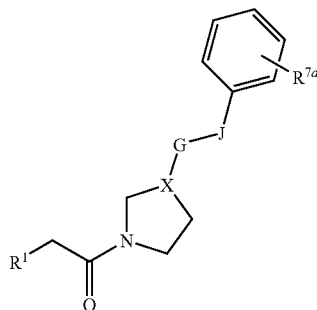

| R$^1$ | X | G | J* | (R$^5$)$_y$ | R$^{7a}$ |
|---|---|---|---|---|---|
| 5-ethyl-3-(trifluoromethyl)pyrazol-1-yl | X$^2$ | G-1 | J-1 (2/4) | — | H |
| 3,5-bis-(trifluoromethyl)pyrazol-1-yl | X$^2$ | G-1 | J-1 (2/4) | — | H |
| 1-methyl-3-(trifluoromethyl)pyrazol-5-yl | X$^2$ | G-1 | J-1 (2/4) | — | H |
| 1-methyl-4-(trifluoromethyl)imidazol-2-yl | X$^2$ | G-1 | J-1 (2/4) | — | H |
| 2,5-dichlorophenyl | X$^2$ | G-1 | J-2 (2/4) | — | H |
| 2-chloro-5-(trifluoromethyl)phenyl | X$^2$ | G-1 | J-2 (2/4) | — | H |
| 2,5-dimethylphenyl | X$^2$ | G-1 | J-2 (2/4) | — | H |
| 2-methyl-5-(trifluoromethyl)phenyl | X$^2$ | G-1 | J-2 (2/4) | — | H |
| 3,5-dimethylpyrazol-1-yl | X$^2$ | G-1 | J-2 (2/4) | — | H |
| 5-methyl-3-(trifluoromethyl)pyrazol-1-yl | X$^2$ | G-1 | J-2 (2/4) | — | H |
| 5-chloro-3-(trifluoromethyl)pyrazol-1-yl | X$^2$ | G-1 | J-2 (2/4) | — | H |
| 5-bromo-3-(trifluoromethyl)pyrazol-1-yl | X$^2$ | G-1 | J-2 (2/4) | — | H |
| 5-ethyl-3-(trifluoromethyl)pyrazol-1-yl | X$^2$ | G-1 | J-2 (2/4) | — | H |
| 3,5-bis-(trifluoromethyl)pyrazol-1-yl | X$^2$ | G-1 | J-2 (2/4) | — | H |
| 1-methyl-3-(trifluoromethyl)pyrazol-5-yl | X$^2$ | G-1 | J-2 (2/4) | — | H |
| 1-methyl-4-(trifluoromethyl)imidazol-2-yl | X$^2$ | G-1 | J-2 (2/4) | — | H |
| 2,5-dichlorophenyl | X$^2$ | G-1 | J-3 (2/4) | 1-Me | H |
| 2-chloro-5-(trifluoromethyl)phenyl | X$^2$ | G-1 | J-3 (2/4) | 1-Me | H |
| 2,5-dimethylphenyl | X$^2$ | G-1 | J-3 (2/4) | 1-Me | H |
| 2-methyl-5-(trifluoromethyl)phenyl | X$^2$ | G-1 | J-3 (2/4) | 1-Me | H |
| 3,5-dimethylpyrazol-1-yl | X$^2$ | G-1 | J-3 (2/4) | 1-Me | H |
| 5-methyl-3-(trifluoromethyl)pyrazol-1-yl | X$^2$ | G-1 | J-3 (2/4) | 1-Me | H |
| 5-chloro-3-(trifluoromethyl)pyrazol-1-yl | X$^2$ | G-1 | J-3 (2/4) | 1-Me | H |
| 5-bromo-3-(trifluoromethyl)pyrazol-1-yl | X$^2$ | G-1 | J-3 (2/4) | 1-Me | H |
| 5-ethyl-3-(trifluoromethyl)pyrazol-1-yl | X$^2$ | G-1 | J-3 (2/4) | 1-Me | H |
| 3,5-bis-(trifluoromethyl)pyrazol-1-yl | X$^2$ | G-1 | J-3 (2/4) | 1-Me | H |
| 1-methyl-3-(trifluoromethyl)pyrazol-5-yl | X$^2$ | G-1 | J-3 (2/4) | 1-Me | H |
| 1-methyl-4-(trifluoromethyl)imidazol-2-yl | X$^2$ | G-1 | J-3 (2/4) | 1-Me | H |
| 2,5-dichlorophenyl | X$^2$ | G-1 | J-4 (2/5) | — | H |
| 2-chloro-5-(trifluoromethyl)phenyl | X$^2$ | G-1 | J-4 (2/5) | — | H |
| 2,5-dimethylphenyl | X$^2$ | G-1 | J-4 (2/5) | — | H |
| 2-methyl-5-(trifluoromethyl)phenyl | X$^2$ | G-1 | J-4 (2/5) | — | H |
| 3,5-dimethylpyrazol-1-yl | X$^2$ | G-1 | J-4 (2/5) | — | H |
| 5-methyl-3-(trifluoromethyl)pyrazol-1-yl | X$^2$ | G-1 | J-4 (2/5) | — | H |
| 5-chloro-3-(trifluoromethyl)pyrazol-1-yl | X$^2$ | G-1 | J-4 (2/5) | — | H |
| 5-bromo-3-(trifluoromethyl)pyrazol-1-yl | X$^2$ | G-1 | J-4 (2/5) | — | H |
| 5-ethyl-3-(trifluoromethyl)pyrazol-1-yl | X$^2$ | G-1 | J-4 (2/5) | — | H |
| 3,5-bis-(trifluoromethyl)pyrazol-1-yl | X$^2$ | G-1 | J-4 (2/5) | — | H |
| 1-methyl-3-(trifluoromethyl)pyrazol-5-yl | X$^2$ | G-1 | J-4 (2/5) | — | H |
| 1-methyl-4-(trifluoromethyl)imidazol-2-yl | X$^2$ | G-1 | J-4 (2/5) | — | H |
| 2,5-dichlorophenyl | X$^2$ | G-1 | J-8 (5/3) | — | H |
| 2-chloro-5-(trifluoromethyl)phenyl | X$^2$ | G-1 | J-8 (5/3) | — | H |
| 2,5-dimethylphenyl | X$^2$ | G-1 | J-8 (5/3) | — | H |
| 2-methyl-5-(trifluoromethyl)phenyl | X$^2$ | G-1 | J-8 (5/3) | — | H |
| 3,5-dimethylpyrazol-1-yl | X$^2$ | G-1 | J-8 (5/3) | — | H |
| 5-methyl-3-(trifluoromethyl)pyrazol-1-yl | X$^2$ | G-1 | J-8 (5/3) | — | H |
| 5-chloro-3-(trifluoromethyl)pyrazol-1-yl | X$^2$ | G-1 | J-8 (5/3) | — | H |
| 5-bromo-3-(trifluoromethyl)pyrazol-1-yl | X$^2$ | G-1 | J-8 (5/3) | — | H |
| 5-ethyl-3-(trifluoromethyl)pyrazol-1-yl | X$^2$ | G-1 | J-8 (5/3) | — | H |
| 3,5-bis-(trifluoromethyl)pyrazol-1-yl | X$^2$ | G-1 | J-8 (5/3) | — | H |
| 1-methyl-3-(trifluoromethyl)pyrazol-5-yl | X$^2$ | G-1 | J-8 (5/3) | — | H |
| 1-methyl-4-(trifluoromethyl)imidazol-2-yl | X$^2$ | G-1 | J-8 (5/3) | — | H |
| 2,5-dichlorophenyl | X$^2$ | G-1 | J-9 (5/3) | — | H |
| 2-chloro-5-(trifluoromethyl)phenyl | X$^2$ | G-1 | J-9 (5/3) | — | H |
| 2,5-dimethylphenyl | X$^2$ | G-1 | J-9 (5/3) | — | H |
| 2-methyl-5-(trifluoromethyl)phenyl | X$^2$ | G-1 | J-9 (5/3) | — | H |
| 3,5-dimethylpyrazol-1-yl | X$^2$ | G-1 | J-9 (5/3) | — | H |
| 5-methyl-3-(trifluoromethyl)pyrazol-1-yl | X$^2$ | G-1 | J-9 (5/3) | — | H |
| 5-chloro-3-(trifluoromethyl)pyrazol-1-yl | X$^2$ | G-1 | J-9 (5/3) | — | H |
| 5-bromo-3-(trifluoromethyl)pyrazol-1-yl | X$^2$ | G-1 | J-9 (5/3) | — | H |
| 5-ethyl-3-(trifluoromethyl)pyrazol-1-yl | X$^2$ | G-1 | J-9 (5/3) | — | H |
| 3,5-bis-(trifluoromethyl)pyrazol-1-yl | X$^2$ | G-1 | J-9 (5/3) | — | H |

TABLE 4*-continued

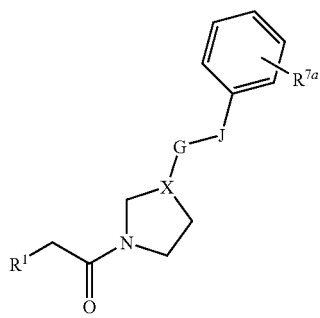

| R¹ | X | G | J* | $(R^5)_y$ | $R^{7a}$ |
|---|---|---|---|---|---|
| 1-methyl-3-(trifluoromethyl)pyrazol-5-yl | $X^2$ | G-1 | J-9 (5/3) | — | H |
| 1-methyl-4-(trifluoromethyl)imidazol-2-yl | $X^2$ | G-1 | J-9 (5/3) | — | H |
| 2,5-dichlorophenyl | $X^2$ | G-1 | J-11 (3/5) | — | H |
| 2-chloro-5-(trifluoromethyl)phenyl | $X^2$ | G-1 | J-11 (3/5) | — | H |
| 2,5-dimethylphenyl | $X^2$ | G-1 | J-11 (3/5) | — | H |
| 2-methyl-5-(trifluoromethyl)phenyl | $X^2$ | G-1 | J-11 (3/5) | — | H |
| 3,5-dimethylpyrazol-1-yl | $X^2$ | G-1 | J-11 (3/5) | — | H |
| 5-methyl-3-(trifluoromethyl)pyrazol-1-yl | $X^2$ | G-1 | J-11 (3/5) | — | H |
| 5-chloro-3-(trifluoromethyl)pyrazol-1-yl | $X^2$ | G-1 | J-11 (3/5) | — | H |
| 5-bromo-3-(trifluoromethyl)pyrazol-1-yl | $X^2$ | G-1 | J-11 (3/5) | — | H |
| 5-ethyl-3-(trifluoromethyl)pyrazol-1-yl | $X^2$ | G-1 | J-11 (3/5) | — | H |
| 3,5-bis-(trifluoromethyl)pyrazol-1-yl | $X^2$ | G-1 | J-11 (3/5) | — | H |
| 1-methyl-3-(trifluoromethyl)pyrazol-5-yl | $X^2$ | G-1 | J-11 (3/5) | — | H |
| 1-methyl-4-(trifluoromethyl)imidazol-2-yl | $X^2$ | G-1 | J-11 (3/5) | — | H |
| 2,5-dichlorophenyl | $X^2$ | G-1 | J-12 (3/5) | — | H |
| 2-chloro-5-(trifluoromethyl)phenyl | $X^2$ | G-1 | J-12 (3/5) | — | H |
| 2,5-dimethylphenyl | $X^2$ | G-1 | J-12 (3/5) | — | H |
| 2-methyl-5-(trifluoromethyl)phenyl | $X^2$ | G-1 | J-12 (3/5) | — | H |
| 3,5-dimethylpyrazol-1-yl | $X^2$ | G-1 | J-12 (3/5) | — | H |
| 5-methyl-3-(trifluoromethyl)pyrazol-1-yl | $X^2$ | G-1 | J-12 (3/5) | — | H |
| 5-chloro-3-(trifluoromethyl)pyrazol-1-yl | $X^2$ | G-1 | J-12 (3/5) | — | H |
| 5-bromo-3-(trifluoromethyl)pyrazol-1-yl | $X^2$ | G-1 | J-12 (3/5) | — | H |
| 5-ethyl-3-(trifluoromethyl)pyrazol-1-yl | $X^2$ | G-1 | J-12 (3/5) | — | H |
| 3,5-bis-(trifluoromethyl)pyrazol-1-yl | $X^2$ | G-1 | J-12 (3/5) | — | H |
| 1-methyl-3-(trifluoromethyl)pyrazol-5-yl | $X^2$ | G-1 | J-12 (3/5) | — | H |
| 1-methyl-4-(trifluoromethyl)imidazol-2-yl | $X^2$ | G-1 | J-12 (3/5) | — | H |
| 2,5-dichlorophenyl | $X^2$ | G-1 | J-12 (3/5) | 1-Me | H |
| 2-chloro-5-(trifluoromethyl)phenyl | $X^2$ | G-1 | J-12 (3/5) | 1-Me | H |
| 2,5-dimethylphenyl | $X^2$ | G-1 | J-12 (3/5) | 1-Me | H |
| 2-methyl-5-(trifluoromethyl)phenyl | $X^2$ | G-1 | J-12 (3/5) | 1-Me | H |
| 3,5-dimethylpyrazol-1-yl | $X^2$ | G-1 | J-12 (3/5) | 1-Me | H |
| 5-methyl-3-(trifluoromethyl)pyrazol-1-yl | $X^2$ | G-1 | J-12 (3/5) | 1-Me | H |
| 5-chloro-3-(trifluoromethyl)pyrazol-1-yl | $X^2$ | G-1 | J-12 (3/5) | 1-Me | H |
| 5-bromo-3-(trifluoromethyl)pyrazol-1-yl | $X^2$ | G-1 | J-12 (3/5) | 1-Me | H |
| 5-ethyl-3-(trifluoromethyl)pyrazol-1-yl | $X^2$ | G-1 | J-12 (3/5) | 1-Me | H |
| 3,5-bis-(trifluoromethyl)pyrazol-1-yl | $X^2$ | G-1 | J-12 (3/5) | 1-Me | H |
| 1-methyl-3-(trifluoromethyl)pyrazol-5-yl | $X^2$ | G-1 | J-12 (3/5) | 1-Me | H |
| 1-methyl-4-(trifluoromethyl)imidazol-2-yl | $X^2$ | G-1 | J-12 (3/5) | 1-Me | H |
| 2,5-dichlorophenyl | $X^2$ | G-1 | J-14 (3/5) | — | H |
| 2-chloro-5-(trifluoromethyl)phenyl | $X^2$ | G-1 | J-14 (3/5) | — | H |
| 2,5-dimethylphenyl | $X^2$ | G-1 | J-14 (3/5) | — | H |
| 2-methyl-5-(trifluoromethyl)phenyl | $X^2$ | G-1 | J-14 (3/5) | — | H |
| 3,5-dimethylpyrazol-1-yl | $X^2$ | G-1 | J-14 (3/5) | — | H |
| 5-methyl-3-(trifluoromethyl)pyrazol-1-yl | $X^2$ | G-1 | J-14 (3/5) | — | H |
| 5-chloro-3-(trifluoromethyl)pyrazol-1-yl | $X^2$ | G-1 | J-14 (3/5) | — | H |
| 5-bromo-3-(trifluoromethyl)pyrazol-1-yl | $X^2$ | G-1 | J-14 (3/5) | — | H |
| 5-ethyl-3-(trifluoromethyl)pyrazol-1-yl | $X^2$ | G-1 | J-14 (3/5) | — | H |
| 3,5-bis-(trifluoromethyl)pyrazol-1-yl | $X^2$ | G-1 | J-14 (3/5) | — | H |
| 1-methyl-3-(trifluoromethyl)pyrazol-5-yl | $X^2$ | G-1 | J-14 (3/5) | — | H |
| 1-methyl-4-(trifluoromethyl)imidazol-2-yl | $X^2$ | G-1 | J-14 (3/5) | — | H |
| 2,5-dichlorophenyl | $X^2$ | G-1 | J-15 (2/5) | — | H |
| 2-chloro-5-(trifluoromethyl)phenyl | $X^2$ | G-1 | J-15 (2/5) | — | H |
| 2,5-dimethylphenyl | $X^2$ | G-1 | J-15 (2/5) | — | H |
| 2-methyl-5-(trifluoromethyl)phenyl | $X^2$ | G-1 | J-15 (2/5) | — | H |
| 3,5-dimethylpyrazol-1-yl | $X^2$ | G-1 | J-15 (2/5) | — | H |
| 5-methyl-3-(trifluoromethyl)pyrazol-1-yl | $X^2$ | G-1 | J-15 (2/5) | — | H |
| 5-chloro-3-(trifluoromethyl)pyrazol-1-yl | $X^2$ | G-1 | J-15 (2/5) | — | H |
| 5-bromo-3-(trifluoromethyl)pyrazol-1-yl | $X^2$ | G-1 | J-15 (2/5) | — | H |
| 5-ethyl-3-(trifluoromethyl)pyrazol-1-yl | $X^2$ | G-1 | J-15 (2/5) | — | H |
| 3,5-bis-(trifluoromethyl)pyrazol-1-yl | $X^2$ | G-1 | J-15 (2/5) | — | H |
| 1-methyl-3-(trifluoromethyl)pyrazol-5-yl | $X^2$ | G-1 | J-15 (2/5) | — | H |
| 1-methyl-4-(trifluoromethyl)imidazol-2-yl | $X^2$ | G-1 | J-15 (2/5) | — | H |

TABLE 4*-continued

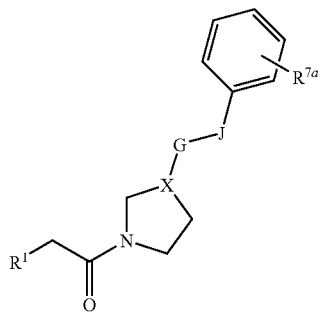

| R¹ | X | G | J* | (R⁵)ᵧ | R⁷ᵃ |
|---|---|---|---|---|---|
| 2,5-dichlorophenyl | X² | G-1 | J-16 (2/5) | — | H |
| 2-chloro-5-(trifluoromethyl)phenyl | X² | G-1 | J-16 (2/5) | — | H |
| 2,5-dimethylphenyl | X² | G-1 | J-16 (2/5) | — | H |
| 2-methyl-5-(trifluoromethyl)phenyl | X² | G-1 | J-16 (2/5) | — | H |
| 3,5-dimethylpyrazol-1-yl | X² | G-1 | J-16 (2/5) | — | H |
| 5-methyl-3-(trifluoromethyl)pyrazol-1-yl | X² | G-1 | J-16 (2/5) | — | H |
| 5-chloro-3-(trifluoromethyl)pyrazol-1-yl | X² | G-1 | J-16 (2/5) | — | H |
| 5-bromo-3-(trifluoromethyl)pyrazol-1-yl | X² | G-1 | J-16 (2/5) | — | H |
| 5-ethyl-3-(trifluoromethyl)pyrazol-1-yl | X² | G-1 | J-16 (2/5) | — | H |
| 3,5-bis-(trifluoromethyl)pyrazol-1-yl | X² | G-1 | J-16 (2/5) | — | H |
| 1-methyl-3-(trifluoromethyl)pyrazol-5-yl | X² | G-1 | J-16 (2/5) | — | H |
| 1-methyl-4-(trifluoromethyl)imidazol-2-yl | X² | G-1 | J-16 (2/5) | — | H |
| 2,5-dichlorophenyl | X² | G-1 | J-22 (2/4) | — | H |
| 2-chloro-5-(trifluoromethyl)phenyl | X² | G-1 | J-22 (2/4) | — | H |
| 2,5-dimethylphenyl | X² | G-1 | J-22 (2/4) | — | H |
| 2-methyl-5-(trifluoromethyl)phenyl | X² | G-1 | J-22 (2/4) | — | H |
| 3,5-dimethylpyrazol-1-yl | X² | G-1 | J-22 (2/4) | — | H |
| 5-methyl-3-(trifluoromethyl)pyrazol-1-yl | X² | G-1 | J-22 (2/4) | — | H |
| 5-chloro-3-(trifluoromethyl)pyrazol-1-yl | X² | G-1 | J-22 (2/4) | — | H |
| 5-bromo-3-(trifluoromethyl)pyrazol-1-yl | X² | G-1 | J-22 (2/4) | — | H |
| 5-ethyl-3-(trifluoromethyl)pyrazol-1-yl | X² | G-1 | J-22 (2/4) | — | H |
| 3,5-bis-(trifluoromethyl)pyrazol-1-yl | X² | G-1 | J-22 (2/4) | — | H |
| 1-methyl-3-(trifluoromethyl)pyrazol-5-yl | X² | G-1 | J-22 (2/4) | — | H |
| 1-methyl-4-(trifluoromethyl)imidazol-2-yl | X² | G-1 | J-22 (2/4) | — | H |
| 2,5-dichlorophenyl | X² | G-1 | J-24 (2/4) | — | H |
| 2-chloro-5-(trifluoromethyl)phenyl | X² | G-1 | J-24 (2/4) | — | H |
| 2,5-dimethylphenyl | X² | G-1 | J-24 (2/4) | — | H |
| 2-methyl-5-(trifluoromethyl)phenyl | X² | G-1 | J-24 (2/4) | — | H |
| 3,5-dimethylpyrazol-1-yl | X² | G-1 | J-24 (2/4) | — | H |
| 5-methyl-3-(trifluoromethyl)pyrazol-1-yl | X² | G-1 | J-24 (2/4) | — | H |
| 5-chloro-3-(trifluoromethyl)pyrazol-1-yl | X² | G-1 | J-24 (2/4) | — | H |
| 5-bromo-3-(trifluoromethyl)pyrazol-1-yl | X² | G-1 | J-24 (2/4) | — | H |
| 5-ethyl-3-(trifluoromethyl)pyrazol-1-yl | X² | G-1 | J-24 (2/4) | — | H |
| 3,5-bis-(trifluoromethyl)pyrazol-1-yl | X² | G-1 | J-24 (2/4) | — | H |
| 1-methyl-3-(trifluoromethyl)pyrazol-5-yl | X² | G-1 | J-24 (2/4) | — | H |
| 1-methyl-4-(trifluoromethyl)imidazol-2-yl | X² | G-1 | J-24 (2/4) | — | H |
| 2,5-dichlorophenyl | X² | G-1 | J-25 (2/4) | — | H |
| 2-chloro-5-(trifluoromethyl)phenyl | X² | G-1 | J-25 (2/4) | — | H |
| 2,5-dimethylphenyl | X² | G-1 | J-25 (2/4) | — | H |
| 2-methyl-5-(trifluoromethyl)phenyl | X² | G-1 | J-25 (2/4) | — | H |
| 3,5-dimethylpyrazol-1-yl | X² | G-1 | J-25 (2/4) | — | H |
| 5-methyl-3-(trifluoromethyl)pyrazol-1-yl | X² | G-1 | J-25 (2/4) | — | H |
| 5-chloro-3-(trifluoromethyl)pyrazol-1-yl | X² | G-1 | J-25 (2/4) | — | H |
| 5-bromo-3-(trifluoromethyl)pyrazol-1-yl | X² | G-1 | J-25 (2/4) | — | H |
| 5-ethyl-3-(trifluoromethyl)pyrazol-1-yl | X² | G-1 | J-25 (2/4) | — | H |
| 3,5-bis-(trifluoromethyl)pyrazol-1-yl | X² | G-1 | J-25 (2/4) | — | H |
| 1-methyl-3-(trifluoromethyl)pyrazol-5-yl | X² | G-1 | J-25 (2/4) | — | H |
| 1-methyl-4-(trifluoromethyl)imidazol-2-yl | X² | G-1 | J-25 (2/4) | — | H |
| 2,5-dichlorophenyl | X² | G-1 | J-26 (2/4) | — | H |
| 2-chloro-5-(trifluoromethyl)phenyl | X² | G-1 | J-26 (2/4) | — | H |
| 2,5-dimethylphenyl | X² | G-1 | J-26 (2/4) | — | H |
| 2-methyl-5-(trifluoromethyl)phenyl | X² | G-1 | J-26 (2/4) | — | H |
| 3,5-dimethylpyrazol-1-yl | X² | G-1 | J-26 (2/4) | — | H |
| 5-methyl-3-(trifluoromethyl)pyrazol-1-yl | X² | G-1 | J-26 (2/4) | — | H |
| 5-chloro-3-(trifluoromethyl)pyrazol-1-yl | X² | G-1 | J-26 (2/4) | — | H |
| 5-bromo-3-(trifluoromethyl)pyrazol-1-yl | X² | G-1 | J-26 (2/4) | — | H |
| 5-ethyl-3-(trifluoromethyl)pyrazol-1-yl | X² | G-1 | J-26 (2/4) | — | H |
| 3,5-bis-(trifluoromethyl)pyrazol-1-yl | X² | G-1 | J-26 (2/4) | — | H |
| 1-methyl-3-(trifluoromethyl)pyrazol-5-yl | X² | G-1 | J-26 (2/4) | — | H |
| 1-methyl-4-(trifluoromethyl)imidazol-2-yl | X² | G-1 | J-26 (2/4) | — | H |
| 2,5-dichlorophenyl | X² | G-1 | J-26 (2/4) | 1-Me | H |
| 2-chloro-5-(trifluoromethyl)phenyl | X² | G-1 | J-26 (2/4) | 1-Me | H |

TABLE 4*-continued

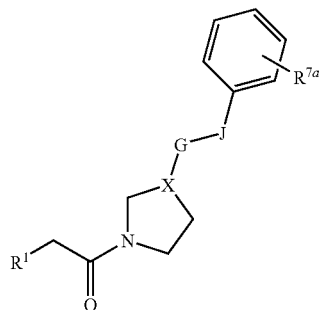

| R¹ | X | G | J* | (R⁵)_y | R⁷ᵃ |
|---|---|---|---|---|---|
| 2,5-dimethylphenyl | X² | G-1 | J-26 (2/4) | 1-Me | H |
| 2-methyl-5-(trifluoromethyl)phenyl | X² | G-1 | J-26 (2/4) | 1-Me | H |
| 3,5-dimethylpyrazol-1-yl | X² | G-1 | J-26 (2/4) | 1-Me | H |
| 5-methyl-3-(trifluoromethyl)pyrazol-1-yl | X² | G-1 | J-26 (2/4) | 1-Me | H |
| 5-chloro-3-(trifluoromethyl)pyrazol-1-yl | X² | G-1 | J-26 (2/4) | 1-Me | H |
| 5-bromo-3-(trifluoromethyl)pyrazol-1-yl | X² | G-1 | J-26 (2/4) | 1-Me | H |
| 5-ethyl-3-(trifluoromethyl)pyrazol-1-yl | X² | G-1 | J-26 (2/4) | 1-Me | H |
| 3,5-bis-(trifluoromethyl)pyrazol-1-yl | X² | G-1 | J-26 (2/4) | 1-Me | H |
| 1-methyl-3-(trifluoromethyl)pyrazol-5-yl | X² | G-1 | J-26 (2/4) | 1-Me | H |
| 1-methyl-4-(trifluoromethyl)imidazol-2-yl | X² | G-1 | J-26 (2/4) | 1-Me | H |
| 2,5-dichlorophenyl | X² | G-1 | J-26 (2/5) | 1-Me | H |
| 2-chloro-5-(trifluoromethyl)phenyl | X² | G-1 | J-26 (2/5) | 1-Me | H |
| 2,5-dimethylphenyl | X² | G-1 | J-26 (2/5) | 1-Me | H |
| 2-methyl-5-(trifluoromethyl)phenyl | X² | G-1 | J-26 (2/5) | 1-Me | H |
| 3,5-dimethylpyrazol-1-yl | X² | G-1 | J-26 (2/5) | 1-Me | H |
| 5-methyl-3-(trifluoromethyl)pyrazol-1-yl | X² | G-1 | J-26 (2/5) | 1-Me | H |
| 5-chloro-3-(trifluoromethyl)pyrazol-1-yl | X² | G-1 | J-26 (2/5) | 1-Me | H |
| 5-bromo-3-(trifluoromethyl)pyrazol-1-yl | X² | G-1 | J-26 (2/5) | 1-Me | H |
| 5-ethyl-3-(trifluoromethyl)pyrazol-1-yl | X² | G-1 | J-26 (2/5) | 1-Me | H |
| 3,5-bis-(trifluoromethyl)pyrazol-1-yl | X² | G-1 | J-26 (2/5) | 1-Me | H |
| 1-methyl-3-(trifluoromethyl)pyrazol-5-yl | X² | G-1 | J-26 (2/5) | 1-Me | H |
| 1-methyl-4-(trifluoromethyl)imidazol-2-yl | X² | G-1 | J-26 (2/5) | 1-Me | H |
| 2,5-dichlorophenyl | X² | G-1 | J-28 (3/5) | — | H |
| 2-chloro-5-(trifluoromethyl)phenyl | X² | G-1 | J-28 (3/5) | — | H |
| 2,5-dimethylphenyl | X² | G-1 | J-28 (3/5) | — | H |
| 2-methyl-5-(trifluoromethyl)phenyl | X² | G-1 | J-28 (3/5) | — | H |
| 3,5-dimethylpyrazol-1-yl | X² | G-1 | J-28 (3/5) | — | H |
| 5-methyl-3-(trifluoromethyl)pyrazol-1-yl | X² | G-1 | J-28 (3/5) | — | H |
| 5-chloro-3-(trifluoromethyl)pyrazol-1-yl | X² | G-1 | J-28 (3/5) | — | H |
| 5-bromo-3-(trifluoromethyl)pyrazol-1-yl | X² | G-1 | J-28 (3/5) | — | H |
| 5-ethyl-3-(trifluoromethyl)pyrazol-1-yl | X² | G-1 | J-28 (3/5) | — | H |
| 3,5-bis-(trifluoromethyl)pyrazol-1-yl | X² | G-1 | J-28 (3/5) | — | H |
| 1-methyl-3-(trifluoromethyl)pyrazol-5-yl | X² | G-1 | J-28 (3/5) | — | H |
| 1-methyl-4-(trifluoromethyl)imidazol-2-yl | X² | G-1 | J-28 (3/5) | — | H |
| 2,5-dichlorophenyl | X² | G-1 | J-30 (3/5) | — | H |
| 2-chloro-5-(trifluoromethyl)phenyl | X² | G-1 | J-30 (3/5) | — | H |
| 2,5-dimethylphenyl | X² | G-1 | J-30 (3/5) | — | H |
| 2-methyl-5-(trifluoromethyl)phenyl | X² | G-1 | J-30 (3/5) | — | H |
| 3,5-dimethylpyrazol-1-yl | X² | G-1 | J-30 (3/5) | — | H |
| 5-methyl-3-(trifluoromethyl)pyrazol-1-yl | X² | G-1 | J-30 (3/5) | — | H |
| 5-chloro-3-(trifluoromethyl)pyrazol-1-yl | X² | G-1 | J-30 (3/5) | — | H |
| 5-bromo-3-(trifluoromethyl)pyrazol-1-yl | X² | G-1 | J-30 (3/5) | — | H |
| 5-ethyl-3-(trifluoromethyl)pyrazol-1-yl | X² | G-1 | J-30 (3/5) | — | H |
| 3,5-bis-(trifluoromethyl)pyrazol-1-yl | X² | G-1 | J-30 (3/5) | — | H |
| 1-methyl-3-(trifluoromethyl)pyrazol-5-yl | X² | G-1 | J-30 (3/5) | — | H |
| 1-methyl-4-(trifluoromethyl)imidazol-2-yl | X² | G-1 | J-30 (3/5) | — | H |
| 2,5-dichlorophenyl | X² | G-1 | J-30 (3/5) | 1-Me | H |
| 2-chloro-5-(trifluoromethyl)phenyl | X² | G-1 | J-30 (3/5) | 1-Me | H |
| 2,5-dimethylphenyl | X² | G-1 | J-30 (3/5) | 1-Me | H |
| 2-methyl-5-(trifluoromethyl)phenyl | X² | G-1 | J-30 (3/5) | 1-Me | H |
| 3,5-dimethylpyrazol-1-yl | X² | G-1 | J-30 (3/5) | 1-Me | H |
| 5-methyl-3-(trifluoromethyl)pyrazol-1-yl | X² | G-1 | J-30 (3/5) | 1-Me | H |
| 5-chloro-3-(trifluoromethyl)pyrazol-1-yl | X² | G-1 | J-30 (3/5) | 1-Me | H |
| 5-bromo-3-(trifluoromethyl)pyrazol-1-yl | X² | G-1 | J-30 (3/5) | 1-Me | H |
| 5-ethyl-3-(trifluoromethyl)pyrazol-1-yl | X² | G-1 | J-30 (3/5) | 1-Me | H |
| 3,5-bis-(trifluoromethyl)pyrazol-1-yl | X² | G-1 | J-30 (3/5) | 1-Me | H |
| 1-methyl-3-(trifluoromethyl)pyrazol-5-yl | X² | G-1 | J-30 (3/5) | 1-Me | H |
| 1-methyl-4-(trifluoromethyl)imidazol-2-yl | X² | G-1 | J-30 (3/5) | 1-Me | H |
| 2,5-dichlorophenyl | X² | G-1 | J-36 (3/5) | 1-Me | H |
| 2-chloro-5-(trifluoromethyl)phenyl | X² | G-1 | J-36 (3/5) | 1-Me | H |
| 2,5-dimethylphenyl | X² | G-1 | J-36 (3/5) | 1-Me | H |
| 2-methyl-5-(trifluoromethyl)phenyl | X² | G-1 | J-36 (3/5) | 1-Me | H |

TABLE 4*-continued

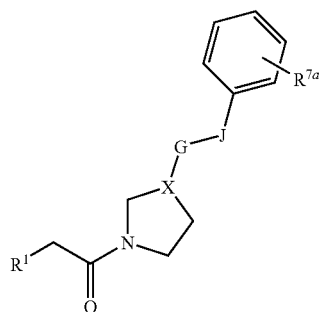

| R¹ | X | G | J* | (R⁵)_y | R⁷ᵃ |
|---|---|---|---|---|---|
| 3,5-dimethylpyrazol-1-yl | X² | G-1 | J-36 (3/5) | 1-Me | H |
| 5-methyl-3-(trifluoromethyl)pyrazol-1-yl | X² | G-1 | J-36 (3/5) | 1-Me | H |
| 5-chloro-3-(trifluoromethyl)pyrazol-1-yl | X² | G-1 | J-36 (3/5) | 1-Me | H |
| 5-bromo-3-(trifluoromethyl)pyrazol-1-yl | X² | G-1 | J-36 (3/5) | 1-Me | H |
| 5-ethyl-3-(trifluoromethyl)pyrazol-1-yl | X² | G-1 | J-36 (3/5) | 1-Me | H |
| 3,5-bis-(trifluoromethyl)pyrazol-1-yl | X² | G-1 | J-36 (3/5) | 1-Me | H |
| 1-methyl-3-(trifluoromethyl)pyrazol-5-yl | X² | G-1 | J-36 (3/5) | 1-Me | H |
| 1-methyl-4-(trifluoromethyl)imidazol-2-yl | X² | G-1 | J-36 (3/5) | 1-Me | H |
| 2,5-dichlorophenyl | X² | G-1 | J-37 (2/5) | — | H |
| 2-chloro-5-(trifluoromethyl)phenyl | X² | G-1 | J-37 (2/5) | — | H |
| 2,5-dimethylphenyl | X² | G-1 | J-37 (2/5) | — | H |
| 2-methyl-5-(trifluoromethyl)phenyl | X² | G-1 | J-37 (2/5) | — | H |
| 3,5-dimethylpyrazol-1-yl | X² | G-1 | J-37 (2/5) | — | H |
| 5-methyl-3-(trifluoromethyl)pyrazol-1-yl | X² | G-1 | J-37 (2/5) | — | H |
| 5-chloro-3-(trifluoromethyl)pyrazol-1-yl | X² | G-1 | J-37 (2/5) | — | H |
| 5-bromo-3-(trifluoromethyl)pyrazol-1-yl | X² | G-1 | J-37 (2/5) | — | H |
| 5-ethyl-3-(trifluoromethyl)pyrazol-1-yl | X² | G-1 | J-37 (2/5) | — | H |
| 3,5-bis-(trifluoromethyl)pyrazol-1-yl | X² | G-1 | J-37 (2/5) | — | H |
| 1-methyl-3-(trifluoromethyl)pyrazol-5-yl | X² | G-1 | J-37 (2/5) | — | H |
| 1-methyl-4-(trifluoromethyl)imidazol-2-yl | X² | G-1 | J-37 (2/5) | — | H |
| 2,5-dichlorophenyl | X² | G-1 | J-38 (2/5) | — | H |
| 2-chloro-5-(trifluoromethyl)phenyl | X² | G-1 | J-38 (2/5) | — | H |
| 2,5-dimethylphenyl | X² | G-1 | J-38 (2/5) | — | H |
| 2-methyl-5-(trifluoromethyl)phenyl | X² | G-1 | J-38 (2/5) | — | H |
| 3,5-dimethylpyrazol-1-yl | X² | G-1 | J-38 (2/5) | — | H |
| 5-methyl-3-(trifluoromethyl)pyrazol-1-yl | X² | G-1 | J-38 (2/5) | — | H |
| 5-chloro-3-(trifluoromethyl)pyrazol-1-yl | X² | G-1 | J-38 (2/5) | — | H |
| 5-bromo-3-(trifluoromethyl)pyrazol-1-yl | X² | G-1 | J-38 (2/5) | — | H |
| 5-ethyl-3-(trifluoromethyl)pyrazol-1-yl | X² | G-1 | J-38 (2/5) | — | H |
| 3,5-bis-(trifluoromethyl)pyrazol-1-yl | X² | G-1 | J-38 (2/5) | — | H |
| 1-methyl-3-(trifluoromethyl)pyrazol-5-yl | X² | G-1 | J-38 (2/5) | — | H |
| 1-methyl-4-(trifluoromethyl)imidazol-2-yl | X² | G-1 | J-38 (2/5) | — | H |
| 2,5-dichlorophenyl | X² | G-1 | J-39 (3/5) | — | H |
| 2-chloro-5-(trifluoromethyl)phenyl | X² | G-1 | J-39 (3/5) | — | H |
| 2,5-dimethylphenyl | X² | G-1 | J-39 (3/5) | — | H |
| 2-methyl-5-(trifluoromethyl)phenyl | X² | G-1 | J-39 (3/5) | — | H |
| 3,5-dimethylpyrazol-1-yl | X² | G-1 | J-39 (3/5) | — | H |
| 5-methyl-3-(trifluoromethyl)pyrazol-1-yl | X² | G-1 | J-39 (3/5) | — | H |
| 5-chloro-3-(trifluoromethyl)pyrazol-1-yl | X² | G-1 | J-39 (3/5) | — | H |
| 5-bromo-3-(trifluoromethyl)pyrazol-1-yl | X² | G-1 | J-39 (3/5) | — | H |
| 5-ethyl-3-(trifluoromethyl)pyrazol-1-yl | X² | G-1 | J-39 (3/5) | — | H |
| 3,5-bis-(trifluoromethyl)pyrazol-1-yl | X² | G-1 | J-39 (3/5) | — | H |
| 1-methyl-3-(trifluoromethyl)pyrazol-5-yl | X² | G-1 | J-39 (3/5) | — | H |
| 1-methyl-4-(trifluoromethyl)imidazol-2-yl | X² | G-1 | J-39 (3/5) | — | H |
| 2,5-dichlorophenyl | X² | G-1 | J-40 (3/5) | — | H |
| 2-chloro-5-(trifluoromethyl)phenyl | X² | G-1 | J-40 (3/5) | — | H |
| 2,5-dimethylphenyl | X² | G-1 | J-40 (3/5) | — | H |
| 2-methyl-5-(trifluoromethyl)phenyl | X² | G-1 | J-40 (3/5) | — | H |
| 3,5-dimethylpyrazol-1-yl | X² | G-1 | J-40 (3/5) | — | H |
| 5-methyl-3-(trifluoromethyl)pyrazol-1-yl | X² | G-1 | J-40 (3/5) | — | H |
| 5-chloro-3-(trifluoromethyl)pyrazol-1-yl | X² | G-1 | J-40 (3/5) | — | H |
| 5-bromo-3-(trifluoromethyl)pyrazol-1-yl | X² | G-1 | J-40 (3/5) | — | H |
| 5-ethyl-3-(trifluoromethyl)pyrazol-1-yl | X² | G-1 | J-40 (3/5) | — | H |
| 3,5-bis-(trifluoromethyl)pyrazol-1-yl | X² | G-1 | J-40 (3/5) | — | H |
| 1-methyl-3-(trifluoromethyl)pyrazol-5-yl | X² | G-1 | J-40 (3/5) | — | H |
| 1-methyl-4-(trifluoromethyl)imidazol-2-yl | X² | G-1 | J-40 (3/5) | — | H |
| 2,5-dichlorophenyl | X² | G-1 | J-69 (1/3) | — | H |
| 2-chloro-5-(trifluoromethyl)phenyl | X² | G-1 | J-69 (1/3) | — | H |
| 2,5-dimethylphenyl | X² | G-1 | J-69 (1/3) | — | H |
| 2-methyl-5-(trifluoromethyl)phenyl | X² | G-1 | J-69 (1/3) | — | H |
| 3,5-dimethylpyrazol-1-yl | X² | G-1 | J-69 (1/3) | — | H |
| 5-methyl-3-(trifluoromethyl)pyrazol-1-yl | X² | G-1 | J-69 (1/3) | — | H |

TABLE 4*-continued

| R¹ | X | G | J* | (R⁵)_y | R⁷ᵃ |
|---|---|---|---|---|---|
| 5-chloro-3-(trifluoromethyl)pyrazol-1-yl | X² | G-1 | J-69 (1/3) | — | H |
| 5-bromo-3-(trifluoromethyl)pyrazol-1-yl | X² | G-1 | J-69 (1/3) | — | H |
| 5-ethyl-3-(trifluoromethyl)pyrazol-1-yl | X² | G-1 | J-69 (1/3) | — | H |
| 3,5-bis-(trifluoromethyl)pyrazol-1-yl | X² | G-1 | J-69 (1/3) | — | H |
| 1-methyl-3-(trifluoromethyl)pyrazol-5-yl | X² | G-1 | J-69 (1/3) | — | H |
| 1-methyl-4-(trifluoromethyl)imidazol-2-yl | X² | G-1 | J-69 (1/3) | — | H |
| 2,5-dichlorophenyl | X² | G-1 | J-69 (1/4) | — | H |
| 2-chloro-5-(trifluoromethyl)phenyl | X² | G-1 | J-69 (1/4) | — | H |
| 2,5-dimethylphenyl | X² | G-1 | J-69 (1/4) | — | H |
| 2-methyl-5-(trifluoromethyl)phenyl | X² | G-1 | J-69 (1/4) | — | H |
| 3,5-dimethylpyrazol-1-yl | X² | G-1 | J-69 (1/4) | — | H |
| 5-methyl-3-(trifluoromethyl)pyrazol-1-yl | X² | G-1 | J-69 (1/4) | — | H |
| 5-chloro-3-(trifluoromethyl)pyrazol-1-yl | X² | G-1 | J-69 (1/4) | — | H |
| 5-bromo-3-(trifluoromethyl)pyrazol-1-yl | X² | G-1 | J-69 (1/4) | — | H |
| 5-ethyl-3-(trifluoromethyl)pyrazol-1-yl | X² | G-1 | J-69 (1/4) | — | H |
| 3,5-bis-(trifluoromethyl)pyrazol-1-yl | X² | G-1 | J-69 (1/4) | — | H |
| 1-methyl-3-(trifluoromethyl)pyrazol-5-yl | X² | G-1 | J-69 (1/4) | — | H |
| 1-methyl-4-(trifluoromethyl)imidazol-2-yl | X² | G-1 | J-69 (1/4) | — | H |
| 2,5-dichlorophenyl | X² | G-1 | J-11 (3/5) | — | 2-Me |
| 2-chloro-5-(trifluoromethyl)phenyl | X² | G-1 | J-11 (3/5) | — | 2-Me |
| 2,5-dimethylphenyl | X² | G-1 | J-11 (3/5) | — | 2-Me |
| 2-methyl-5-(wifluoromethyl)phenyl | X² | G-1 | J-11 (3/5) | — | 2-Me |
| 3,5-dimethylpyrazol-1-yl | X² | G-1 | J-11 (3/5) | — | 2-Me |
| 5-methyl-3-(trifluoromethyl)pyrazol-1-yl | X² | G-1 | J-11 (3/5) | — | 2-Me |
| 5-chloro-3-(trifluoromethyl)pyrazol-1-yl | X² | G-1 | J-11 (3/5) | — | 2-Me |
| 5-bromo-3-(trifluoromethyl)pyrazol-1-yl | X² | G-1 | J-11 (3/5) | — | 2-Me |
| 5-ethyl-3-(trifluoromethyl)pyrazol-1-yl | X² | G-1 | J-11 (3/5) | — | 2-Me |
| 3,5-bis-(trifluoromethyl)pyrazol-1-yl | X² | G-1 | J-11 (3/5) | — | 2-Me |
| 1-methyl-3-(trifluoromethyl)pyrazol-5-yl | X² | G-1 | J-11 (3/5) | — | 2-Me |
| 1-methyl-4-(trifluoromethyl)imidazol-2-yl | X² | G-1 | J-11 (3/5) | — | 2-Me |
| 2,5-dichlorophenyl | X² | G-1 | J-11 (3/5) | — | 3-Me |
| 2-chloro-5-(trifluoromethyl)phenyl | X² | G-1 | J-11 (3/5) | — | 3-Me |
| 2,5-dimethylphenyl | X² | G-1 | J-11 (3/5) | — | 3-Me |
| 2-methyl-5-(trifluoromethyl)phenyl | X² | G-1 | J-11 (3/5) | — | 3-Me |
| 3,5-dimethylpyrazol-1-yl | X² | G-1 | J-11 (3/5) | — | 3-Me |
| 5-methyl-3-(trifluoromethyl)pyrazol-1-yl | X² | G-1 | J-11 (3/5) | — | 3-Me |
| 5-chloro-3-(trifluoromethyl)pyrazol-1-yl | X² | G-1 | J-11 (3/5) | — | 3-Me |
| 5-bromo-3-(trifluoromethyl)pyrazol-1-yl | X² | G-1 | J-11 (3/5) | — | 3-Me |
| 5-ethyl-3-(trifluoromethyl)pyrazol-1-yl | X² | G-1 | J-11 (3/5) | — | 3-Me |
| 3,5-bis-(trifluoromethyl)pyrazol-1-yl | X² | G-1 | J-11 (3/5) | — | 3-Me |
| 1-methyl-3-(trifluoromethyl)pyrazol-5-yl | X² | G-1 | J-11 (3/5) | — | 3-Me |
| 1-methyl-4-(trifluoromethyl)imidazol-2-yl | X² | G-1 | J-11 (3/5) | — | 3-Me |
| 2,5-dichlorophenyl | X² | G-1 | J-11 (3/5) | — | 4-Me |
| 2-chloro-5-(trifluoromethyl)phenyl | X² | G-1 | J-11 (3/5) | — | 4-Me |
| 2,5-dimethylphenyl | X² | G-1 | J-11 (3/5) | — | 4-Me |
| 2-methyl-5-(trifluoromethyl)phenyl | X² | G-1 | J-11 (3/5) | — | 4-Me |
| 3,5-dimethylpyrazol-1-yl | X² | G-1 | J-11 (3/5) | — | 4-Me |
| 5-methyl-3-(trifluoromethyl)pyrazol-1-yl | X² | G-1 | J-11 (3/5) | — | 4-Me |
| 5-chloro-3-(trifluoromethyl)pyrazol-1-yl | X² | G-1 | J-11 (3/5) | — | 4-Me |
| 5-bromo-3-(trifluoromethyl)pyrazol-1-yl | X² | G-1 | J-11 (3/5) | — | 4-Me |
| 5-ethyl-3-(trifluoromethyl)pyrazol-1-yl | X² | G-1 | J-11 (3/5) | — | 4-Me |
| 3,5-bis-(trifluoromethyl)pyrazol-1-yl | X² | G-1 | J-11 (3/5) | — | 4-Me |
| 1-methyl-3-(trifluoromethyl)pyrazol-5-yl | X² | G-1 | J-11 (3/5) | — | 4-Me |
| 1-methyl-4-(trifluoromethyl)imidazol-2-yl | X² | G-1 | J-11 (3/5) | — | 4-Me |
| 2,5-dichlorophenyl | X² | G-1 | J-11 (3/5) | — | 2-Cl |
| 2-chloro-5-(trifluoromethyl)phenyl | X² | G-1 | J-11 (3/5) | — | 2-Cl |
| 2,5-dimethylphenyl | X² | G-1 | J-11 (3/5) | — | 2-Cl |
| 2-methyl-5-(trifluoromethyl)phenyl | X² | G-1 | J-11 (3/5) | — | 2-Cl |
| 3,5-dimethylpyrazol-1-yl | X² | G-1 | J-11 (3/5) | — | 2-Cl |
| 5-methyl-3-(trifluoromethyl)pyrazol-1-yl | X² | G-1 | J-11 (3/5) | — | 2-Cl |
| 5-chloro-3-(trifluoromethyl)pyrazol-1-yl | X² | G-1 | J-11 (3/5) | — | 2-Cl |
| 5-bromo-3-(trifluoromethyl)pyrazol-1-yl | X² | G-1 | J-11 (3/5) | — | 2-Cl |

TABLE 4*-continued

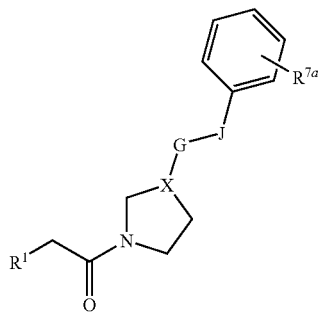

| R¹ | X | G | J* | (R⁵)_y | R⁷ᵃ |
|---|---|---|---|---|---|
| 5-ethyl-3-(trifluoromethyl)pyrazol-1-yl | X² | G-1 | J-11 (3/5) | — | 2-Cl |
| 3,5-bis-(trifluoromethyl)pyrazol-1-yl | X² | G-1 | J-11 (3/5) | — | 2-Cl |
| 1-methyl-3-(trifluoromethyl)pyrazol-5-yl | X² | G-1 | J-11 (3/5) | — | 2-Cl |
| 1-methyl-4-(trifluoromethyl)imidazol-2-yl | X² | G-1 | J-11 (3/5) | — | 2-Cl |
| 2,5-dichlorophenyl | X² | G-1 | J-11 (3/5) | — | 4-Cl |
| 2-chloro-5-(trifluoromethyl)phenyl | X² | G-1 | J-11 (3/5) | — | 4-Cl |
| 2,5-dimethylphenyl | X² | G-1 | J-11 (3/5) | — | 4-Cl |
| 2-methyl-5-(trifluoromethyl)phenyl | X² | G-1 | J-11 (3/5) | — | 4-Cl |
| 3,5-dimethylpyrazol-1-yl | X² | G-1 | J-11 (3/5) | — | 4-Cl |
| 5-methyl-3-(trifluoromethyl)pyrazol-1-yl | X² | G-1 | J-11 (3/5) | — | 4-Cl |
| 5-chloro-3-(trifluoromethyl)pyrazol-1-yl | X² | G-1 | J-11 (3/5) | — | 4-Cl |
| 5-bromo-3-(trifluoromethyl)pyrazol-1-yl | X² | G-1 | J-11 (3/5) | — | 4-Cl |
| 5-ethyl-3-(trifluoromethyl)pyrazol-1-yl | X² | G-1 | J-11 (3/5) | — | 4-Cl |
| 3,5-bis-(trifluoromethyl)pyrazol-1-yl | X² | G-1 | J-11 (3/5) | — | 4-Cl |
| 1-methyl-3-(trifluoromethyl)pyrazol-5-yl | X² | G-1 | J-11 (3/5) | — | 4-Cl |
| 1-methyl-4-(trifluoromethyl)imidazol-2-yl | X² | G-1 | J-11 (3/5) | — | 4-Cl |
| 2,5-dichlorophenyl | X² | G-1 | J-29 (3/5) | — | 2-Me |
| 2-chloro-5-(trifluoromethyl)phenyl | X² | G-1 | J-29 (3/5) | — | 2-Me |
| 2,5-dimethylphenyl | X² | G-1 | J-29 (3/5) | — | 2-Me |
| 2-methyl-5-(trifluoromethyl)phenyl | X² | G-1 | J-29 (3/5) | — | 2-Me |
| 3,5-dimethylpyrazol-1-yl | X² | G-1 | J-29 (3/5) | — | 2-Me |
| 5-methyl-3-(trifluoromethyl)pyrazol-1-yl | X² | G-1 | J-29 (3/5) | — | 2-Me |
| 5-chloro-3-(trifluoromethyl)pyrazol-1-yl | X² | G-1 | J-29 (3/5) | — | 2-Me |
| 5-bromo-3-(trifluoromethyl)pyrazol-1-yl | X² | G-1 | J-29 (3/5) | — | 2-Me |
| 5-ethyl-3-(trifluoromethyl)pyrazol-1-yl | X² | G-1 | J-29 (3/5) | — | 2-Me |
| 3,5-bis-(trifluoromethyl)pyrazol-1-yl | X² | G-1 | J-29 (3/5) | — | 2-Me |
| 1-methyl-3-(trifluoromethyl)pyrazol-5-yl | X² | G-1 | J-29 (3/5) | — | 2-Me |
| 1-methyl-4-(trifluoromethyl)imidazol-2-yl | X² | G-1 | J-29 (3/5) | — | 2-Me |
| 2,5-dichlorophenyl | X² | G-1 | J-29 (3/5) | — | 3-Me |
| 2-chloro-5-(trifluoromethyl)phenyl | X² | G-1 | J-29 (3/5) | — | 3-Me |
| 2,5-dimethylphenyl | X² | G-1 | J-29 (3/5) | — | 3-Me |
| 2-methyl-5-(trifluoromethyl)phenyl | X² | G-1 | J-29 (3/5) | — | 3-Me |
| 3,5-dimethylpyrazol-1-yl | X² | G-1 | J-29 (3/5) | — | 3-Me |
| 5-methyl-3-(trifluoromethyl)pyrazol-1-yl | X² | G-1 | J-29 (3/5) | — | 3-Me |
| 5-chloro-3-(trifluoromethyl)pyrazol-1-yl | X² | G-1 | J-29 (3/5) | — | 3-Me |
| 5-bromo-3-(trifluoromethyl)pyrazol-1-yl | X² | G-1 | J-29 (3/5) | — | 3-Me |
| 5-ethyl-3-(trifluoromethyl)pyrazol-1-yl | X² | G-1 | J-29 (3/5) | — | 3-Me |
| 3,5-bis-(trifluoromethyl)pyrazol-1-yl | X² | G-1 | J-29 (3/5) | — | 3-Me |
| 1-methyl-3-(trifluoromethyl)pyrazol-5-yl | X² | G-1 | J-29 (3/5) | — | 3-Me |
| 1-methyl-4-(trifluoromethyl)imidazol-2-yl | X² | G-1 | J-29 (3/5) | — | 3-Me |
| 2,5-dichlorophenyl | X² | G-1 | J-29 (3/5) | — | 4-Me |
| 2-chloro-5-(trifluoromethyl)phenyl | X² | G-1 | J-29 (3/5) | — | 4-Me |
| 2,5-dimethylphenyl | X² | G-1 | J-29 (3/5) | — | 4-Me |
| 2-methyl-5-(trifluoromethyl)phenyl | X² | G-1 | J-29 (3/5) | — | 4-Me |
| 3,5-dimethylpyrazol-1-yl | X² | G-1 | J-29 (3/5) | — | 4-Me |
| 5-methyl-3-(trifluoromethyl)pyrazol-1-yl | X² | G-1 | J-29 (3/5) | — | 4-Me |
| 5-chloro-3-(trifluoromethyl)pyrazol-1-yl | X² | G-1 | J-29 (3/5) | — | 4-Me |
| 5-bromo-3-(trifluoromethyl)pyrazol-1-yl | X² | G-1 | J-29 (3/5) | — | 4-Me |
| 5-ethyl-3-(trifluoromethyl)pyrazol-1-yl | X² | G-1 | J-29 (3/5) | — | 4-Me |
| 3,5-bis-(trifluoromethyl)pyrazol-1-yl | X² | G-1 | J-29 (3/5) | — | 4-Me |
| 1-methyl-3-(trifluoromethyl)pyrazol-5-yl | X² | G-1 | J-29 (3/5) | — | 4-Me |
| 1-methyl-4-(trifluoromethyl)imidazol-2-yl | X² | G-1 | J-29 (3/5) | — | 4-Me |
| 2,5-dichlorophenyl | X² | G-1 | J-29 (3/5) | — | 2-Cl |
| 2-chloro-5-(trifluoromethyl)phenyl | X² | G-1 | J-29 (3/5) | — | 2-Cl |
| 2,5-dimethylphenyl | X² | G-1 | J-29 (3/5) | — | 2-Cl |
| 2-methyl-5-(trifluoromethyl)phenyl | X² | G-1 | J-29 (3/5) | — | 2-Cl |
| 3,5-dimethylpyrazol-1-yl | X² | G-1 | J-29 (3/5) | — | 2-Cl |
| 5-methyl-3-(trifluoromethyl)pyrazol-1-yl | X² | G-1 | J-29 (3/5) | — | 2-Cl |
| 5-chloro-3-(trifluoromethyl)pyrazol-1-yl | X² | G-1 | J-29 (3/5) | — | 2-Cl |
| 5-bromo-3-(trifluoromethyl)pyrazol-1-yl | X² | G-1 | J-29 (3/5) | — | 2-Cl |
| 5-ethyl-3-(trifluoromethyl)pyrazol-1-yl | X² | G-1 | J-29 (3/5) | — | 2-Cl |
| 3,5-bis-(trifluoromethyl)pyrazol-1-yl | X² | G-1 | J-29 (3/5) | — | 2-Cl |

TABLE 4*-continued

| R¹ | X | G | J* | (R⁵)_y | R⁷ᵃ |
|---|---|---|---|---|---|
| 1-methyl-3-(trifluoromethyl)pyrazol-5-yl | X² | G-1 | J-29 (3/5) | — | 2-Cl |
| 1-methyl-4-(trifluoromethyl)imidazol-2-yl | X² | G-1 | J-29 (3/5) | — | 2-Cl |
| 2,5-dichlorophenyl | X² | G-1 | J-29 (3/5) | — | 4-Cl |
| 2-chloro-5-(trifluoromethyl)phenyl | X² | G-1 | J-29 (3/5) | — | 4-Cl |
| 2,5-dimethylphenyl | X² | G-1 | J-29 (3/5) | — | 4-Cl |
| 2-methyl-5-(trifluoromethyl)phenyl | X² | G-1 | J-29 (3/5) | — | 4-Cl |
| 3,5-dimethylpyrazol-1-yl | X² | G-1 | J-29 (3/5) | — | 4-Cl |
| 5-methyl-3-(trifluoromethyl)pyrazol-1-yl | X² | G-1 | J-29 (3/5) | — | 4-Cl |
| 5-chloro-3-(trifluoromethyl)pyrazol-1-yl | X² | G-1 | J-29 (3/5) | — | 4-Cl |
| 5-bromo-3-(trifluoromethyl)pyrazol-1-yl | X² | G-1 | J-29 (3/5) | — | 4-Cl |
| 5-ethyl-3-(trifluoromethyl)pyrazol-1-yl | X² | G-1 | J-29 (3/5) | — | 4-Cl |
| 3,5-bis-(trifluoromethyl)pyrazol-1-yl | X² | G-1 | J-29 (3/5) | — | 4-Cl |
| 1-methyl-3-(trifluoromethyl)pyrazol-5-yl | X² | G-1 | J-29 (3/5) | — | 4-Cl |
| 1-methyl-4-(trifluoromethyl)imidazol-2-yl | X² | G-1 | J-29 (3/5) | — | 4-Cl |
| 2,5-dichlorophenyl | X² | G-1 | J-29 (3/5) | 5-Me | H |
| 2-chloro-5-(trifluoromethyl)phenyl | X² | G-1 | J-29 (3/5) | 5-Me | H |
| 2,5-dimethylphenyl | X² | G-1 | J-29 (3/5) | 5-Me | H |
| 2-methyl-5-(trifluoromethyl)phenyl | X² | G-1 | J-29 (3/5) | 5-Me | H |
| 3,5-dimethylpyrazol-1-yl | X² | G-1 | J-29 (3/5) | 5-Me | H |
| 5-methyl-3-(trifluoromethyl)pyrazol-1-yl | X² | G-1 | J-29 (3/5) | 5-Me | H |
| 5-chloro-3-(trifluoromethyl)pyrazol-1-yl | X² | G-1 | J-29 (3/5) | 5-Me | H |
| 5-bromo-3-(trifluoromethyl)pyrazol-1-yl | X² | G-1 | J-29 (3/5) | 5-Me | H |
| 5-ethyl-3-(trifluoromethyl)pyrazol-1-yl | X² | G-1 | J-29 (3/5) | 5-Me | H |
| 3,5-bis-(trifluoromethyl)pyrazol-1-yl | X² | G-1 | J-29 (3/5) | 5-Me | H |
| 1-methyl-3-(trifluoromethyl)pyrazol-5-yl | X² | G-1 | J-29 (3/5) | 5-Me | H |
| 1-methyl-4-(trifluoromethyl)imidazol-2-yl | X² | G-1 | J-29 (3/5) | 5-Me | H |
| 2,5-dichlorophenyl | X² | G-1 | J-29 (3/5) | 4-Me | H |
| 2-chloro-5-(trifluoromethyl)phenyl | X² | G-1 | J-29 (3/5) | 4-Me | H |
| 2,5-dimethylphenyl | X² | G-1 | J-29 (3/5) | 4-Me | H |
| 2-methyl-5-(trifluoromethyl)phenyl | X² | G-1 | J-29 (3/5) | 4-Me | H |
| 3,5-dimethylpyrazol-1-yl | X² | G-1 | J-29 (3/5) | 4-Me | H |
| 5-methyl-3-(trifluoromethyl)pyrazol-1-yl | X² | G-1 | J-29 (3/5) | 4-Me | H |
| 5-chloro-3-(trifluoromethyl)pyrazol-1-yl | X² | G-1 | J-29 (3/5) | 4-Me | H |
| 5-bromo-3-(trifluoromethyl)pyrazol-1-yl | X² | G-1 | J-29 (3/5) | 4-Me | H |
| 5-ethyl-3-(trifluoromethyl)pyrazol-1-yl | X² | G-1 | J-29 (3/5) | 4-Me | H |
| 3,5-bis-(trifluoromethyl)pyrazol-1-yl | X² | G-1 | J-29 (3/5) | 4-Me | H |
| 1-methyl-3-(trifluoromethyl)pyrazol-5-yl | X² | G-1 | J-29 (3/5) | 4-Me | H |
| 1-methyl-4-(trifluoromethyl)imidazol-2-yl | X² | G-1 | J-29 (3/5) | 4-Me | H |
| 2,5-dichlorophenyl | X² | G-1 | J-29 (3/5) | 4,4-di-Me | H |
| 2-chloro-5-(trifluoromethyl)phenyl | X² | G-1 | J-29 (3/5) | 4,4-di-Me | H |
| 2,5-dimethylphenyl | X² | G-1 | J-29 (3/5) | 4,4-di-Me | H |
| 2-methyl-5-(trifluoromethyl)phenyl | X² | G-1 | J-29 (3/5) | 4,4-di-Me | H |
| 3,5-dimethylpyrazol-1-yl | X² | G-1 | J-29 (3/5) | 4,4-di-Me | H |
| 5-methyl-3-(trifluoromethyl)pyrazol-1-yl | X² | G-1 | J-29 (3/5) | 4,4-di-Me | H |
| 5-chloro-3-(trifluoromethyl)pyrazol-1-yl | X² | G-1 | J-29 (3/5) | 4,4-di-Me | H |
| 5-bromo-3-(trifluoromethyl)pyrazol-1-yl | X² | G-1 | J-29 (3/5) | 4,4-di-Me | H |
| 5-ethyl-3-(trifluoromethyl)pyrazol-1-yl | X² | G-1 | J-29 (3/5) | 4,4-di-Me | H |
| 3,5-bis-(trifluoromethyl)pyrazol-1-yl | X² | G-1 | J-29 (3/5) | 4,4-di-Me | H |
| 1-methyl-3-(trifluoromethyl)pyrazol-5-yl | X² | G-1 | J-29 (3/5) | 4,4-di-Me | H |
| 1-methyl-4-(trifluoromethyl)imidazol-2-yl | X² | G-1 | J-29 (3/5) | 4,4-di-Me | H |
| 2,5-dichlorophenyl | X² | G-2 | J-1 (2/4) | — | H |
| 2-chloro-5-(trifluoromethyl)phenyl | X² | G-2 | J-1 (2/4) | — | H |
| 2,5-dimethylphenyl | X² | G-2 | J-1 (2/4) | — | H |
| 2-methyl-5-(trifluoromethyl)phenyl | X² | G-2 | J-1 (2/4) | — | H |
| 3,5-dimethylpyrazol-1-yl | X² | G-2 | J-1 (2/4) | — | H |
| 5-methyl-3-(trifluoromethyl)pyrazol-1-yl | X² | G-2 | J-1 (2/4) | — | H |
| 5-chloro-3-(trifluoromethyl)pyrazol-1-yl | X² | G-2 | J-1 (2/4) | — | H |
| 5-bromo-3-(trifluoromethyl)pyrazol-1-yl | X² | G-2 | J-1 (2/4) | — | H |
| 5-ethyl-3-(trifluoromethyl)pyrazol-1-yl | X² | G-2 | J-1 (2/4) | — | H |
| 3,5-bis-(trifluoromethyl)pyrazol-1-yl | X² | G-2 | J-1 (2/4) | — | H |
| 1-methyl-3-(trifluoromethyl)pyrazol-5-yl | X² | G-2 | J-1 (2/4) | — | H |
| 1-methyl-4-(trifluoromethyl)imidazol-2-yl | X² | G-2 | J-1 (2/4) | — | H |

TABLE 4*-continued

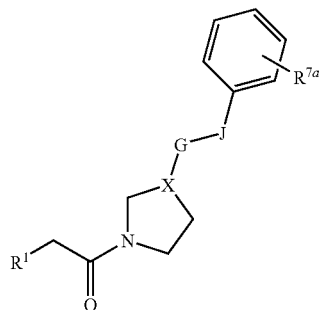

| R¹ | X | G | J* | (R⁵)ᵧ | R⁷ᵃ |
|---|---|---|---|---|---|
| 2,5-dichlorophenyl | X² | G-2 | J-2 (2/4) | — | H |
| 2-chloro-5-(trifluoromethyl)phenyl | X² | G-2 | J-2 (2/4) | — | H |
| 2,5-dimethylphenyl | X² | G-2 | J-2 (2/4) | — | H |
| 2-methyl-5-(trifluoromethyl)phenyl | X² | G-2 | J-2 (2/4) | — | H |
| 3,5-dimethylpyrazol-1-yl | X² | G-2 | J-2 (2/4) | — | H |
| 5-methyl-3-(trifluoromethyl)pyrazol-1-yl | X² | G-2 | J-2 (2/4) | — | H |
| 5-chloro-3-(trifluoromethyl)pyrazol-1-yl | X² | G-2 | J-2 (2/4) | — | H |
| 5-bromo-3-(trifluoromethyl)pyrazol-1-yl | X² | G-2 | J-2 (2/4) | — | H |
| 5-ethyl-3-(trifluoromethyl)pyrazol-1-yl | X² | G-2 | J-2 (2/4) | — | H |
| 3,5-bis-(trifluoromethyl)pyrazol-1-yl | X² | G-2 | J-2 (2/4) | — | H |
| 1-methyl-3-(trifluoromethyl)pyrazol-5-yl | X² | G-2 | J-2 (2/4) | — | H |
| 1-methyl-4-(trifluoromethyl)imidazol-2-yl | X² | G-2 | J-2 (2/4) | — | H |
| 2,5-dichlorophenyl | X² | G-2 | J-3 (2/4) | 1-Me | H |
| 2-chloro-5-(trifluoromethyl)phenyl | X² | G-2 | J-3 (2/4) | 1-Me | H |
| 2,5-dimethylphenyl | X² | G-2 | J-3 (2/4) | 1-Me | H |
| 2-methyl-5-(trifluoromethyl)phenyl | X² | G-2 | J-3 (2/4) | 1-Me | H |
| 3,5-dimethylpyrazol-1-yl | X² | G-2 | J-3 (2/4) | 1-Me | H |
| 5-methyl-3-(trifluoromethyl)pyrazol-1-yl | X² | G-2 | J-3 (2/4) | 1-Me | H |
| 5-chloro-3-(trifluoromethyl)pyrazol-1-yl | X² | G-2 | J-3 (2/4) | 1-Me | H |
| 5-bromo-3-(trifluoromethyl)pyrazol-1-yl | X² | G-2 | J-3 (2/4) | 1-Me | H |
| 5-ethyl-3-(trifluoromethyl)pyrazol-1-yl | X² | G-2 | J-3 (2/4) | 1-Me | H |
| 3,5-bis-(trifluoromethyl)pyrazol-1-yl | X² | G-2 | J-3 (2/4) | 1-Me | H |
| 1-methyl-3-(trifluoromethyl)pyrazol-5-yl | X² | G-2 | J-3 (2/4) | 1-Me | H |
| 1-methyl-4-(trifluoromethyl)imidazol-2-yl | X² | G-2 | J-3 (2/4) | 1-Me | H |
| 2,5-dichlorophenyl | X² | G-2 | J-4 (2/5) | — | H |
| 2-chloro-5-(trifluoromethyl)phenyl | X² | G-2 | J-4 (2/5) | — | H |
| 2,5-dimethylphenyl | X² | G-2 | J-4 (2/5) | — | H |
| 2-methyl-5-(wifluoromethyl)phenyl | X² | G-2 | J-4 (2/5) | — | H |
| 3,5-dimethylpyrazol-1-yl | X² | G-2 | J-4 (2/5) | — | H |
| 5-methyl-3-(trifluoromethyl)pyrazol-1-yl | X² | G-2 | J-4 (2/5) | — | H |
| 5-chloro-3-(trifluoromethyl)pyrazol-1-yl | X² | G-2 | J-4 (2/5) | — | H |
| 5-bromo-3-(trifluoromethyl)pyrazol-1-yl | X² | G-2 | J-4 (2/5) | — | H |
| 5-ethyl-3-(trifluoromethyl)pyrazol-1-yl | X² | G-2 | J-4 (2/5) | — | H |
| 3,5-bis-(trifluoromethyl)pyrazol-1-yl | X² | G-2 | J-4 (2/5) | — | H |
| 1-methyl-3-(trifluoromethyl)pyrazol-5-yl | X² | G-2 | J-4 (2/5) | — | H |
| 1-methyl-4-(trifluoromethyl)imidazol-2-yl | X² | G-2 | J-4 (2/5) | — | H |
| 2,5-dichlorophenyl | X² | G-2 | J-8 (5/3) | — | H |
| 2-chloro-5-(trifluoromethyl)phenyl | X² | G-2 | J-8 (5/3) | — | H |
| 2,5-dimethylphenyl | X² | G-2 | J-8 (5/3) | — | H |
| 2-methyl-5-(trifluoromethyl)phenyl | X² | G-2 | J-8 (5/3) | — | H |
| 3,5-dimethylpyrazol-1-yl | X² | G-2 | J-8 (5/3) | — | H |
| 5-methyl-3-(trifluoromethyl)pyrazol-1-yl | X² | G-2 | J-8 (5/3) | — | H |
| 5-chloro-3-(trifluoromethyl)pyrazol-1-yl | X² | G-2 | J-8 (5/3) | — | H |
| 5-bromo-3-(trifluoromethyl)pyrazol-1-yl | X² | G-2 | J-8 (5/3) | — | H |
| 5-ethyl-3-(trifluoromethyl)pyrazol-1-yl | X² | G-2 | J-8 (5/3) | — | H |
| 3,5-bis-(trifluoromethyl)pyrazol-1-yl | X² | G-2 | J-8 (5/3) | — | H |
| 1-methyl-3-(trifluoromethyl)pyrazol-5-yl | X² | G-2 | J-8 (5/3) | — | H |
| 1-methyl-4-(trifluoromethyl)imidazol-2-yl | X² | G-2 | J-8 (5/3) | — | H |
| 2,5-dichlorophenyl | X² | G-2 | J-9 (5/3) | — | H |
| 2-chloro-5-(trifluoromethyl)phenyl | X² | G-2 | J-9 (5/3) | — | H |
| 2,5-dimethylphenyl | X² | G-2 | J-9 (5/3) | — | H |
| 2-methyl-5-(trifluoromethyl)phenyl | X² | G-2 | J-9 (5/3) | — | H |
| 3,5-dimethylpyrazol-1-yl | X² | G-2 | J-9 (5/3) | — | H |
| 5-methyl-3-(trifluoromethyl)pyrazol-1-yl | X² | G-2 | J-9 (5/3) | — | H |
| 5-chloro-3-(trifluoromethyl)pyrazol-1-yl | X² | G-2 | J-9 (5/3) | — | H |
| 5-bromo-3-(trifluoromethyl)pyrazol-1-yl | X² | G-2 | J-9 (5/3) | — | H |
| 5-ethyl-3-(trifluoromethyl)pyrazol-1-yl | X² | G-2 | J-9 (5/3) | — | H |
| 3,5-bis-(trifluoromethyl)pyrazol-1-yl | X² | G-2 | J-9 (5/3) | — | H |
| 1-methyl-3-(trifluoromethyl)pyrazol-5-yl | X² | G-2 | J-9 (5/3) | — | H |
| 1-methyl-4-(trifluoromethyl)imidazol-2-yl | X² | G-2 | J-9 (5/3) | — | H |
| 2,5-dichlorophenyl | X² | G-2 | J-11 (3/5) | — | H |
| 2-chloro-5-(trifluoromethyl)phenyl | X² | G-2 | J-11 (3/5) | — | H |

TABLE 4*-continued

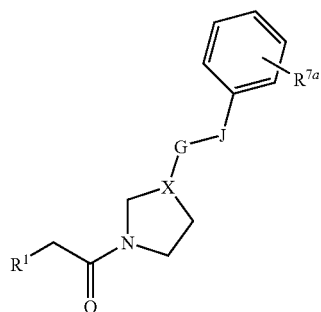

| R¹ | X | G | J* | (R⁵)_y | R⁷ᵃ |
|---|---|---|---|---|---|
| 2,5-dimethylphenyl | X² | G-2 | J-11 (3/5) | — | H |
| 2-methyl-5-(trifluoromethyl)phenyl | X² | G-2 | J-11 (3/5) | — | H |
| 3,5-dimethylpyrazol-1-yl | X² | G-2 | J-11 (3/5) | — | H |
| 5-methyl-3-(trifluoromethyl)pyrazol-1-yl | X² | G-2 | J-11 (3/5) | — | H |
| 5-chloro-3-(trifluoromethyl)pyrazol-1-yl | X² | G-2 | J-11 (3/5) | — | H |
| 5-bromo-3-(trifluoromethyl)pyrazol-1-yl | X² | G-2 | J-11 (3/5) | — | H |
| 5-ethyl-3-(trifluoromethyl)pyrazol-1-yl | X² | G-2 | J-11 (3/5) | — | H |
| 3,5-bis-(trifluoromethyl)pyrazol-1-yl | X² | G-2 | J-11 (3/5) | — | H |
| 1-methyl-3-(trifluoromethyl)pyrazol-5-yl | X² | G-2 | J-11 (3/5) | — | H |
| 1-methyl-4-(trifluoromethyl)imidazol-2-yl | X² | G-2 | J-11 (3/5) | — | H |
| 2,5-dichlorophenyl | X² | G-2 | J-12 (3/5) | — | H |
| 2-chloro-5-(trifluoromethyl)phenyl | X² | G-2 | J-12 (3/5) | — | H |
| 2,5-dimethylphenyl | X² | G-2 | J-12 (3/5) | — | H |
| 2-methyl-5-(trifluoromethyl)phenyl | X² | G-2 | J-12 (3/5) | — | H |
| 3,5-dimethylpyrazol-1-yl | X² | G-2 | J-12 (3/5) | — | H |
| 5-methyl-3-(trifluoromethyl)pyrazol-1-yl | X² | G-2 | J-12 (3/5) | — | H |
| 5-chloro-3-(trifluoromethyl)pyrazol-1-yl | X² | G-2 | J-12 (3/5) | — | H |
| 5-bromo-3-(trifluoromethyl)pyrazol-1-yl | X² | G-2 | J-12 (3/5) | — | H |
| 5-ethyl-3-(trifluoromethyl)pyrazol-1-yl | X² | G-2 | J-12 (3/5) | — | H |
| 3,5-bis-(trifluoromethyl)pyrazol-1-yl | X² | G-2 | J-12 (3/5) | — | H |
| 1-methyl-3-(trifluoromethyl)pyrazol-5-yl | X² | G-2 | J-12 (3/5) | — | H |
| 1-methyl-4-(trifluoromethyl)imidazol-2-yl | X² | G-2 | J-12 (3/5) | — | H |
| 2,5-dichlorophenyl | X² | G-2 | J-12 (3/5) | 1-Me | H |
| 2-chloro-5-(trifluoromethyl)phenyl | X² | G-2 | J-12 (3/5) | 1-Me | H |
| 2,5-dimethylphenyl | X² | G-2 | J-12 (3/5) | 1-Me | H |
| 2-methyl-5-(trifluoromethyl)phenyl | X² | G-2 | J-12 (3/5) | 1-Me | H |
| 3,5-dimethylpyrazol-1-yl | X² | G-2 | J-12 (3/5) | 1-Me | H |
| 5-methyl-3-(trifluoromethyl)pyrazol-1-yl | X² | G-2 | J-12 (3/5) | 1-Me | H |
| 5-chloro-3-(trifluoromethyl)pyrazol-1-yl | X² | G-2 | J-12 (3/5) | 1-Me | H |
| 5-bromo-3-(trifluoromethyl)pyrazol-1-yl | X² | G-2 | J-12 (3/5) | 1-Me | H |
| 5-ethyl-3-(trifluoromethyl)pyrazol-1-yl | X² | G-2 | J-12 (3/5) | 1-Me | H |
| 3,5-bis-(trifluoromethyl)pyrazol-1-yl | X² | G-2 | J-12 (3/5) | 1-Me | H |
| 1-methyl-3-(trifluoromethyl)pyrazol-5-yl | X² | G-2 | J-12 (3/5) | 1-Me | H |
| 1-methyl-4-(trifluoromethyl)imidazol-2-yl | X² | G-2 | J-12 (3/5) | 1-Me | H |
| 2,5-dichlorophenyl | X² | G-2 | J-14 (3/5) | — | H |
| 2-chloro-5-(trifluoromethyl)phenyl | X² | G-2 | J-14 (3/5) | — | H |
| 2,5-dimethylphenyl | X² | G-2 | J-14 (3/5) | — | H |
| 2-methyl-5-(trifluoromethyl)phenyl | X² | G-2 | J-14 (3/5) | — | H |
| 3,5-dimethylpyrazol-1-yl | X² | G-2 | J-14 (3/5) | — | H |
| 5-methyl-3-(trifluoromethyl)pyrazol-1-yl | X² | G-2 | J-14 (3/5) | — | H |
| 5-chloro-3-(trifluoromethyl)pyrazol-1-yl | X² | G-2 | J-14 (3/5) | — | H |
| 5-bromo-3-(trifluoromethyl)pyrazol-1-yl | X² | G-2 | J-14 (3/5) | — | H |
| 5-ethyl-3 -(trifluoromethyl)pyrazol-1-yl | X² | G-2 | J-14 (3/5) | — | H |
| 3,5-bis-(trifluoromethyl)pyrazol-1-yl | X² | G-2 | J-14 (3/5) | — | H |
| 1-methyl-3-(trifluoromethyl)pyrazol-5-yl | X² | G-2 | J-14 (3/5) | — | H |
| 1-methyl-4-(trifluoromethyl)imidazol-2-yl | X² | G-2 | J-14 (3/5) | — | H |
| 2,5-dichlorophenyl | X² | G-2 | J-15 (2/5) | — | H |
| 2-chloro-5-(trifluoromethyl)phenyl | X² | G-2 | J-15 (2/5) | — | H |
| 2,5-dimethylphenyl | X² | G-2 | J-15 (2/5) | — | H |
| 2-methyl-5-(trifluoromethyl)phenyl | X² | G-2 | J-15 (2/5) | — | H |
| 3,5-dimethylpyrazol-1-yl | X² | G-2 | J-15 (2/5) | — | H |
| 5-methyl-3-(trifluoromethyl)pyrazol-1-yl | X² | G-2 | J-15 (2/5) | — | H |
| 5-chloro-3-(trifluoromethyl)pyrazol-1-yl | X² | G-2 | J-15 (2/5) | — | H |
| 5-bromo-3-(trifluoromethyl)pyrazol-1-yl | X² | G-2 | J-15 (2/5) | — | H |
| 5-ethyl-3-(trifluoromethyl)pyrazol-1-yl | X² | G-2 | J-15 (2/5) | — | H |
| 3,5-bis-(trifluoromethyl)pyrazol-1-yl | X² | G-2 | J-15 (2/5) | — | H |
| 1-methyl-3-(trifluoromethyl)pyrazol-5-yl | X² | G-2 | J-15 (2/5) | — | H |
| 1-methyl-4-(trifluoromethyl)imidazol-2-yl | X² | G-2 | J-15 (2/5) | — | H |
| 2,5-dichlorophenyl | X² | G-2 | J-16 (2/5) | — | H |
| 2-chloro-5-(trifluoromethyl)phenyl | X² | G-2 | J-16 (2/5) | — | H |
| 2,5-dimethylphenyl | X² | G-2 | J-16 (2/5) | — | H |
| 2-methyl-5-(trifluoromethyl)phenyl | X² | G-2 | J-16 (2/5) | — | H |

TABLE 4*-continued

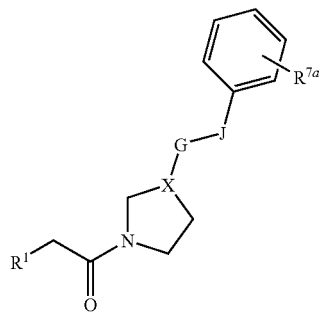

| R$^1$ | X | G | J* | (R$^5$)$_y$ | R$^{7a}$ |
|---|---|---|---|---|---|
| 3,5-dimethylpyrazol-1-yl | X$^2$ | G-2 | J-16 (2/5) | — | H |
| 5-methyl-3-(trifluoromethyl)pyrazol-1-yl | X$^2$ | G-2 | J-16 (2/5) | — | H |
| 5-chloro-3-(trifluoromethyl)pyrazol-1-yl | X$^2$ | G-2 | J-16 (2/5) | — | H |
| 5-bromo-3-(trifluoromethyl)pyrazol-1-yl | X$^2$ | G-2 | J-16 (2/5) | — | H |
| 5-ethyl-3-(trifluoromethyl)pyrazol-1-yl | X$^2$ | G-2 | J-16 (2/5) | — | H |
| 3,5-bis-(trifluoromethyl)pyrazol-1-yl | X$^2$ | G-2 | J-16 (2/5) | — | H |
| 1-methyl-3-(trifluoromethyl)pyrazol-5-yl | X$^2$ | G-2 | J-16 (2/5) | — | H |
| 1-methyl-4-(trifluoromethyl)imidazol-2-yl | X$^2$ | G-2 | J-16 (2/5) | — | H |
| 2,5-dichlorophenyl | X$^2$ | G-2 | J-22 (2/4) | — | H |
| 2-chloro-5-(trifluoromethyl)phenyl | X$^2$ | G-2 | J-22 (2/4) | — | H |
| 2,5-dimethylphenyl | X$^2$ | G-2 | J-22 (2/4) | — | H |
| 2-methyl-5-(trifluoromethyl)phenyl | X$^2$ | G-2 | J-22 (2/4) | — | H |
| 3,5-dimethylpyrazol-1-yl | X$^2$ | G-2 | J-22 (2/4) | — | H |
| 5-methyl-3-(trifluoromethyl)pyrazol-1-yl | X$^2$ | G-2 | J-22 (2/4) | — | H |
| 5-chloro-3-(trifluoromethyl)pyrazol-1-yl | X$^2$ | G-2 | J-22 (2/4) | — | H |
| 5-bromo-3-(trifluoromethyl)pyrazol-1-yl | X$^2$ | G-2 | J-22 (2/4) | — | H |
| 5-ethyl-3-(trifluoromethyl)pyrazol-1-yl | X$^2$ | G-2 | J-22 (2/4) | — | H |
| 3,5-bis-(trifluoromethyl)pyrazol-1-yl | X$^2$ | G-2 | J-22 (2/4) | — | H |
| 1-methyl-3-(trifluoromethyl)pyrazol-5-yl | X$^2$ | G-2 | J-22 (2/4) | — | H |
| 1-methyl-4-(trifluoromethyl)imidazol-2-yl | X$^2$ | G-2 | J-22 (2/4) | — | H |
| 2,5-dichlorophenyl | X$^2$ | G-2 | J-24 (2/4) | — | H |
| 2-chloro-5-(trifluoromethyl)phenyl | X$^2$ | G-2 | J-24 (2/4) | — | H |
| 2,5-dimethylphenyl | X$^2$ | G-2 | J-24 (2/4) | — | H |
| 2-methyl-5-(trifluoromethyl)phenyl | X$^2$ | G-2 | J-24 (2/4) | — | H |
| 3,5-dimethylpyrazol-1-yl | X$^2$ | G-2 | J-24 (2/4) | — | H |
| 5-methyl-3-(trifluoromethyl)pyrazol-1-yl | X$^2$ | G-2 | J-24 (2/4) | — | H |
| 5-chloro-3-(trifluoromethyl)pyrazol-1-yl | X$^2$ | G-2 | J-24 (2/4) | — | H |
| 5-bromo-3-(trifluoromethyl)pyrazol-1-yl | X$^2$ | G-2 | J-24 (2/4) | — | H |
| 5-ethyl-3-(trifluoromethyl)pyrazol-1-yl | X$^2$ | G-2 | J-24 (2/4) | — | H |
| 3,5-bis-(trifluoromethyl)pyrazol-1-yl | X$^2$ | G-2 | J-24 (2/4) | — | H |
| 1-methyl-3-(trifluoromethyl)pyrazol-5-yl | X$^2$ | G-2 | J-24 (2/4) | — | H |
| 1-methyl-4-(trifluoromethyl)imidazol-2-yl | X$^2$ | G-2 | J-24 (2/4) | — | H |
| 2,5-dichlorophenyl | X$^2$ | G-2 | J-25 (2/4) | — | H |
| 2-chloro-5-(trifluoromethyl)phenyl | X$^2$ | G-2 | J-25 (2/4) | — | H |
| 2,5-dimethylphenyl | X$^2$ | G-2 | J-25 (2/4) | — | H |
| 2-methyl-5-(trifluoromethyl)phenyl | X$^2$ | G-2 | J-25 (2/4) | — | H |
| 3,5-dimethylpyrazol-1-yl | X$^2$ | G-2 | J-25 (2/4) | — | H |
| 5-methyl-3-(trifluoromethyl)pyrazol-1-yl | X$^2$ | G-2 | J-25 (2/4) | — | H |
| 5-chloro-3-(trifluoromethyl)pyrazol-1-yl | X$^2$ | G-2 | J-25 (2/4) | — | H |
| 5-bromo-3-(trifluoromethyl)pyrazol-1-yl | X$^2$ | G-2 | J-25 (2/4) | — | H |
| 5-ethyl-3-(trifluoromethyl)pyrazol-1-yl | X$^2$ | G-2 | J-25 (2/4) | — | H |
| 3,5-bis-(trifluoromethyl)pyrazol-1-yl | X$^2$ | G-2 | J-25 (2/4) | — | H |
| 1-methyl-3-(trifluoromethyl)pyrazol-5-yl | X$^2$ | G-2 | J-25 (2/4) | — | H |
| 1-methyl-4-(trifluoromethyl)imidazol-2-yl | X$^2$ | G-2 | J-25 (2/4) | — | H |
| 2,5-dichlorophenyl | X$^2$ | G-2 | J-26 (2/4) | — | H |
| 2-chloro-5-(trifluoromethyl)phenyl | X$^2$ | G-2 | J-26 (2/4) | — | H |
| 2,5-dimethylphenyl | X$^2$ | G-2 | J-26 (2/4) | — | H |
| 2-methyl-5-(trifluoromethyl)phenyl | X$^2$ | G-2 | J-26 (2/4) | — | H |
| 3,5-dimethylpyrazol-1-yl | X$^2$ | G-2 | J-26 (2/4) | — | H |
| 5-methyl-3-(trifluoromethyl)pyrazol-1-yl | X$^2$ | G-2 | J-26 (2/4) | — | H |
| 5-chloro-3-(trifluoromethyl)pyrazol-1-yl | X$^2$ | G-2 | J-26 (2/4) | — | H |
| 5-bromo-3-(trifluoromethyl)pyrazol-1-yl | X$^2$ | G-2 | J-26 (2/4) | — | H |
| 5-ethyl-3-(trifluoromethyl)pyrazol-1-yl | X$^2$ | G-2 | J-26 (2/4) | — | H |
| 3,5-bis-(trifluoromethyl)pyrazol-1-yl | X$^2$ | G-2 | J-26 (2/4) | — | H |
| 1-methyl-3-(trifluoromethyl)pyrazol-5-yl | X$^2$ | G-2 | J-26 (2/4) | — | H |
| 1-methyl-4-(trifluoromethyl)imidazol-2-yl | X$^2$ | G-2 | J-26 (2/4) | — | H |
| 2,5-dichlorophenyl | X$^2$ | G-2 | J-26 (2/4) | 1-Me | H |
| 2-chloro-5-(trifluoromethyl)phenyl | X$^2$ | G-2 | J-26 (2/4) | 1-Me | H |
| 2,5-dimethylphenyl | X$^2$ | G-2 | J-26 (2/4) | 1-Me | H |
| 2-methyl-5-(trifluoromethyl)phenyl | X$^2$ | G-2 | J-26 (2/4) | 1-Me | H |
| 3,5-dimethylpyrazol-1-yl | X$^2$ | G-2 | J-26 (2/4) | 1-Me | H |
| 5-methyl-3-(trifluoromethyl)pyrazol-1-yl | X$^2$ | G-2 | J-26 (2/4) | 1-Me | H |

TABLE 4*-continued

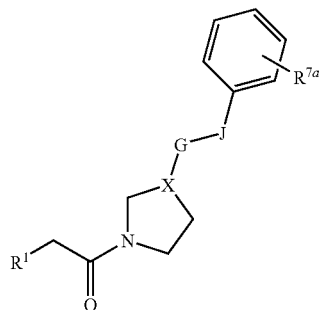

| R¹ | X | G | J* | (R⁵)ᵧ | R⁷ᵃ |
|---|---|---|---|---|---|
| 5-chloro-3-(trifluoromethyl)pyrazol-1-yl | X² | G-2 | J-26 (2/4) | 1-Me | H |
| 5-bromo-3-(trifluoromethyl)pyrazol-1-yl | X² | G-2 | J-26 (2/4) | 1-Me | H |
| 5-ethyl-3-(trifluoromethyl)pyrazol-1-yl | X² | G-2 | J-26 (2/4) | 1-Me | H |
| 3,5-bis-(trifluoromethyl)pyrazol-1-yl | X² | G-2 | J-26 (2/4) | 1-Me | H |
| 1-methyl-3-(trifluoromethyl)pyrazol-5-yl | X² | G-2 | J-26 (2/4) | 1-Me | H |
| 1-methyl-4-(trifluoromethyl)imidazol-2-yl | X² | G-2 | J-26 (2/4) | 1-Me | H |
| 2,5-dichlorophenyl | X² | G-2 | J-26 (2/5) | 1-Me | H |
| 2-chloro-5-(trifluoromethyl)phenyl | X² | G-2 | J-26 (2/5) | 1-Me | H |
| 2,5-dimethylphenyl | X² | G-2 | J-26 (2/5) | 1-Me | H |
| 2-methyl-5-(trifluoromethyl)phenyl | X² | G-2 | J-26 (2/5) | 1-Me | H |
| 3,5-dimethylpyrazol-1-yl | X² | G-2 | J-26 (2/5) | 1-Me | H |
| 5-methyl-3-(trifluoromethyl)pyrazol-1-yl | X² | G-2 | J-26 (2/5) | 1-Me | H |
| 5-chloro-3-(trifluoromethyl)pyrazol-1-yl | X² | G-2 | J-26 (2/5) | 1-Me | H |
| 5-bromo-3-(trifluoromethyl)pyrazol-1-yl | X² | G-2 | J-26 (2/5) | 1-Me | H |
| 5-ethyl-3-(trifluoromethyl)pyrazol-1-yl | X² | G-2 | J-26 (2/5) | 1-Me | H |
| 3,5-bis-(trifluoromethyl)pyrazol-1-yl | X² | G-2 | J-26 (2/5) | 1-Me | H |
| 1-methyl-3-(trifluoromethyl)pyrazol-5-yl | X² | G-2 | J-26 (2/5) | 1-Me | H |
| 1-methyl-4-(trifluoromethyl)imidazol-2-yl | X² | G-2 | J-26 (2/5) | 1-Me | H |
| 2,5-dichlorophenyl | X² | G-2 | J-28 (3/5) | — | H |
| 2-chloro-5-(trifluoromethyl)phenyl | X² | G-2 | J-28 (3/5) | — | H |
| 2,5-dimethylphenyl | X² | G-2 | J-28 (3/5) | — | H |
| 2-methyl-5-(trifluoromethyl)phenyl | X² | G-2 | J-28 (3/5) | — | H |
| 3,5-dimethylpyrazol-1-yl | X² | G-2 | J-28 (3/5) | — | H |
| 5-methyl-3-(trifluoromethyl)pyrazol-1-yl | X² | G-2 | J-28 (3/5) | — | H |
| 5-chloro-3-(trifluoromethyl)pyrazol-1-yl | X² | G-2 | J-28 (3/5) | — | H |
| 5-bromo-3-(trifluoromethyl)pyrazol-1-yl | X² | G-2 | J-28 (3/5) | — | H |
| 5-ethyl-3-(trifluoromethyl)pyrazol-1-yl | X² | G-2 | J-28 (3/5) | — | H |
| 3,5-bis-(trifluoromethyl)pyrazol-1-yl | X² | G-2 | J-28 (3/5) | — | H |
| 1-methyl-3-(trifluoromethyl)pyrazol-5-yl | X² | G-2 | J-28 (3/5) | — | H |
| 1-methyl-4-(trifluoromethyl)imidazol-2-yl | X² | G-2 | J-28 (3/5) | — | H |
| 2,5-dichlorophenyl | X² | G-2 | J-30 (3/5) | — | H |
| 2-chloro-5-(trifluoromethyl)phenyl | X² | G-2 | J-30 (3/5) | — | H |
| 2,5-dimethylphenyl | X² | G-2 | J-30 (3/5) | — | H |
| 2-methyl-5-(trifluoromethyl)phenyl | X² | G-2 | J-30 (3/5) | — | H |
| 3,5-dimethylpyrazol-1-yl | X² | G-2 | J-30 (3/5) | — | H |
| 5-methyl-3-(trifluoromethyl)pyrazol-1-yl | X² | G-2 | J-30 (3/5) | — | H |
| 5-chloro-3-(trifluoromethyl)pyrazol-1-yl | X² | G-2 | J-30 (3/5) | — | H |
| 5-bromo-3-(trifluoromethyl)pyrazol-1-yl | X² | G-2 | J-30 (3/5) | — | H |
| 5-ethyl-3-(trifluoromethyl)pyrazol-1-yl | X² | G-2 | J-30 (3/5) | — | H |
| 3,5-bis-(trifluoromethyl)pyrazol-1-yl | X² | G-2 | J-30 (3/5) | — | H |
| 1-methyl-3-(trifluoromethyl)pyrazol-5-yl | X² | G-2 | J-30 (3/5) | — | H |
| 1-methyl-4-(trifluoromethyl)imidazol-2-yl | X² | G-2 | J-30 (3/5) | — | H |
| 2,5-dichlorophenyl | X² | G-2 | J-30 (3/5) | 1-Me | H |
| 2-chloro-5-(trifluoromethyl)phenyl | X² | G-2 | J-30 (3/5) | 1-Me | H |
| 2,5-dimethylphenyl | X² | G-2 | J-30 (3/5) | 1-Me | H |
| 2-methyl-5-(trifluoromethyl)phenyl | X² | G-2 | J-30 (3/5) | 1-Me | H |
| 3,5-dimethylpyrazol-1-yl | X² | G-2 | J-30 (3/5) | 1-Me | H |
| 5-methyl-3-(trifluoromethyl)pyrazol-1-yl | X² | G-2 | J-30 (3/5) | 1-Me | H |
| 5-chloro-3-(trifluoromethyl)pyrazol-1-yl | X² | G-2 | J-30 (3/5) | 1-Me | H |
| 5-bromo-3-(trifluoromethyl)pyrazol-1-yl | X² | G-2 | J-30 (3/5) | 1-Me | H |
| 5-ethyl-3-(trifluoromethyl)pyrazol-1-yl | X² | G-2 | J-30 (3/5) | 1-Me | H |
| 3,5-bis-(trifluoromethyl)pyrazol-1-yl | X² | G-2 | J-30 (3/5) | 1-Me | H |
| 1-methyl-3-(trifluoromethyl)pyrazol-5-yl | X² | G-2 | J-30 (3/5) | 1-Me | H |
| 1-methyl-4-(trifluoromethyl)imidazol-2-yl | X² | G-2 | J-30 (3/5) | 1-Me | H |
| 2,5-dichlorophenyl | X² | G-2 | J-36 (3/5) | 1-Me | H |
| 2-chloro-5-(trifluoromethyl)phenyl | X² | G-2 | J-36 (3/5) | 1-Me | H |
| 2,5-dimethylphenyl | X² | G-2 | J-36 (3/5) | 1-Me | H |
| 2-methyl-5-(trifluoromethyl)phenyl | X² | G-2 | J-36 (3/5) | 1-Me | H |
| 3,5-dimethylpyrazol-1-yl | X² | G-2 | J-36 (3/5) | 1-Me | H |
| 5-methyl-3-(trifluoromethyl)pyrazol-1-yl | X² | G-2 | J-36 (3/5) | 1-Me | H |
| 5-chloro-3-(trifluoromethyl)pyrazol-1-yl | X² | G-2 | J-36 (3/5) | 1-Me | H |
| 5-bromo-3-(trifluoromethyl)pyrazol-1-yl | X² | G-2 | J-36 (3/5) | 1-Me | H |

TABLE 4*-continued

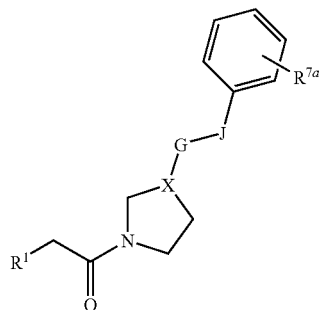

| R¹ | X | G | J* | (R⁵)ᵧ | R⁷ᵃ |
|---|---|---|---|---|---|
| 5-ethyl-3-(trifluoromethyl)pyrazol-1-yl | X² | G-2 | J-36 (3/5) | 1-Me | H |
| 3,5-bis-(trifluoromethyl)pyrazol-1-yl | X² | G-2 | J-36 (3/5) | 1-Me | H |
| 1-methyl-3-(trifluoromethyl)pyrazol-5-yl | X² | G-2 | J-36 (3/5) | 1-Me | H |
| 1-methyl-4-(trifluoromethyl)imidazol-2-yl | X² | G-2 | J-36 (3/5) | 1-Me | H |
| 2,5-dichlorophenyl | X² | G-2 | J-37 (2/5) | — | H |
| 2-chloro-5-(trifluoromethyl)phenyl | X² | G-2 | J-37 (2/5) | — | H |
| 2,5-dimethylphenyl | X² | G-2 | J-37 (2/5) | — | H |
| 2-methyl-5-(trifluoromethyl)phenyl | X² | G-2 | J-37 (2/5) | — | H |
| 3,5-dimethylpyrazol-1-yl | X² | G-2 | J-37 (2/5) | — | H |
| 5-methyl-3-(trifluoromethyl)pyrazol-1-yl | X² | G-2 | J-37 (2/5) | — | H |
| 5-chloro-3-(trifluoromethyl)pyrazol-1-yl | X² | G-2 | J-37 (2/5) | — | H |
| 5-bromo-3-(trifluoromethyl)pyrazol-1-yl | X² | G-2 | J-37 (2/5) | — | H |
| 5-ethyl-3-(trifluoromethyl)pyrazol-1-yl | X² | G-2 | J-37 (2/5) | — | H |
| 3,5-bis-(trifluoromethyl)pyrazol-1-yl | X² | G-2 | J-37 (2/5) | — | H |
| 1-methyl-3-(trifluoromethyl)pyrazol-5-yl | X² | G-2 | J-37 (2/5) | — | H |
| 1-methyl-4-(trifluoromethyl)imidazol-2-yl | X² | G-2 | J-37 (2/5) | — | H |
| 2,5-dichlorophenyl | X² | G-2 | J-38 (2/5) | — | H |
| 2-chloro-5-(trifluoromethyl)phenyl | X² | G-2 | J-38 (2/5) | — | H |
| 2,5-dimethylphenyl | X² | G-2 | J-38 (2/5) | — | H |
| 2-methyl-5-(trifluoromethyl)phenyl | X² | G-2 | J-38 (2/5) | — | H |
| 3,5-dimethylpyrazol-1-yl | X² | G-2 | J-38 (2/5) | — | H |
| 5-methyl-3-(trifluoromethyl)pyrazol-1-yl | X² | G-2 | J-38 (2/5) | — | H |
| 5-chloro-3-(trifluoromethyl)pyrazol-1-yl | X² | G-2 | J-38 (2/5) | — | H |
| 5-bromo-3-(trifluoromethyl)pyrazol-1-yl | X² | G-2 | J-38 (2/5) | — | H |
| 5-ethyl-3-(trifluoromethyl)pyrazol-1-yl | X² | G-2 | J-38 (2/5) | — | H |
| 3,5-bis-(trifluoromethyl)pyrazol-1-yl | X² | G-2 | J-38 (2/5) | — | H |
| 1-methyl-3-(trifluoromethyl)pyrazol-5-yl | X² | G-2 | J-38 (2/5) | — | H |
| 1-methyl-4-(trifluoromethyl)imidazol-2-yl | X² | G-2 | J-38 (2/5) | — | H |
| 2,5-dichlorophenyl | X² | G-2 | J-39 (3/5) | — | H |
| 2-chloro-5-(trifluoromethyl)phenyl | X² | G-2 | J-39 (3/5) | — | H |
| 2,5-dimethylphenyl | X² | G-2 | J-39 (3/5) | — | H |
| 2-methyl-5-(trifluoromethyl)phenyl | X² | G-2 | J-39 (3/5) | — | H |
| 3,5-dimethylpyrazol-1-yl | X² | G-2 | J-39 (3/5) | — | H |
| 5-methyl-3-(trifluoromethyl)pyrazol-1-yl | X² | G-2 | J-39 (3/5) | — | H |
| 5-chloro-3-(trifluoromethyl)pyrazol-1-yl | X² | G-2 | J-39 (3/5) | — | H |
| 5-bromo-3-(trifluoromethyl)pyrazol-1-yl | X² | G-2 | J-39 (3/5) | — | H |
| 5-ethyl-3-(trifluoromethyl)pyrazol-1-yl | X² | G-2 | J-39 (3/5) | — | H |
| 3,5-bis-(trifluoromethyl)pyrazol-1-yl | X² | G-2 | J-39 (3/5) | — | H |
| 1-methyl-3-(trifluoromethyl)pyrazol-5-yl | X² | G-2 | J-39 (3/5) | — | H |
| 1-methyl-4-(trifluoromethyl)imidazol-2-yl | X² | G-2 | J-39 (3/5) | — | H |
| 2,5-dichlorophenyl | X² | G-2 | J-40 (3/5) | — | H |
| 2-chloro-5-(trifluoromethyl)phenyl | X² | G-2 | J-40 (3/5) | — | H |
| 2,5-dimethylphenyl | X² | G-2 | J-40 (3/5) | — | H |
| 2-methyl-5-(trifluoromethyl)phenyl | X² | G-2 | J-40 (3/5) | — | H |
| 3,5-dimethylpyrazol-1-yl | X² | G-2 | J-40 (3/5) | — | H |
| 5-methyl-3-(trifluoromethyl)pyrazol-1-yl | X² | G-2 | J-40 (3/5) | — | H |
| 5-chloro-3-(trifluoromethyl)pyrazol-1-yl | X² | G-2 | J-40 (3/5) | — | H |
| 5-bromo-3-(trifluoromethyl)pyrazol-1-yl | X² | G-2 | J-40 (3/5) | — | H |
| 5-ethyl-3-(trifluoromethyl)pyrazol-1-yl | X² | G-2 | J-40 (3/5) | — | H |
| 3,5-bis-(trifluoromethyl)pyrazol-1-yl | X² | G-2 | J-40 (3/5) | — | H |
| 1-methyl-3-(trifluoromethyl)pyrazol-5-yl | X² | G-2 | J-40 (3/5) | — | H |
| 1-methyl-4-(trifluoromethyl)imidazol-2-yl | X² | G-2 | J-40 (3/5) | — | H |
| 2,5-dichlorophenyl | X² | G-2 | J-69 (1/3) | — | H |
| 2-chloro-5-(trifluoromethyl)phenyl | X² | G-2 | J-69 (1/3) | — | H |
| 2,5-dimethylphenyl | X² | G-2 | J-69 (1/3) | — | H |
| 2-methyl-5-(trifluoromethyl)phenyl | X² | G-2 | J-69 (1/3) | — | H |
| 3,5-dimethylpyrazol-1-yl | X² | G-2 | J-69 (1/3) | — | H |
| 5-methyl-3-(trifluoromethyl)pyrazol-1-yl | X² | G-2 | J-69 (1/3) | — | H |
| 5-chloro-3-(trifluoromethyl)pyrazol-1-yl | X² | G-2 | J-69 (1/3) | — | H |
| 5-bromo-3-(trifluoromethyl)pyrazol-1-yl | X² | G-2 | J-69 (1/3) | — | H |
| 5-ethyl-3-(trifluoromethyl)pyrazol-1-yl | X² | G-2 | J-69 (1/3) | — | H |
| 3,5-bis-(trifluoromethyl)pyrazol-1-yl | X² | G-2 | J-69 (1/3) | — | H |

TABLE 4*-continued

| R¹ | X | G | J* | (R⁵)_y | R⁷ᵃ |
|---|---|---|---|---|---|
| 1-methyl-3-(trifluoromethyl)pyrazol-5-yl | X² | G-2 | J-69 (1/3) | — | H |
| 1-methyl-4-(trifluoromethyl)imidazol-2-yl | X² | G-2 | J-69 (1/3) | — | H |
| 2,5-dichlorophenyl | X² | G-2 | J-69 (1/4) | — | H |
| 2-chloro-5-(trifluoromethyl)phenyl | X² | G-2 | J-69 (1/4) | — | H |
| 2,5-dimethylphenyl | X² | G-2 | J-69 (1/4) | — | H |
| 2-methyl-5-(trifluoromethyl)phenyl | X² | G-2 | J-69 (1/4) | — | H |
| 3,5-dimethylpyrazol-1-yl | X² | G-2 | J-69 (1/4) | — | H |
| 5-methyl-3-(trifluoromethyl)pyrazol-1-yl | X² | G-2 | J-69 (1/4) | — | H |
| 5-chloro-3-(trifluoromethyl)pyrazol-1-yl | X² | G-2 | J-69 (1/4) | — | H |
| 5-bromo-3-(trifluoromethyl)pyrazol-1-yl | X² | G-2 | J-69 (1/4) | — | H |
| 5-ethyl-3-(trifluoromethyl)pyrazol-1-yl | X² | G-2 | J-69 (1/4) | — | H |
| 3,5-bis-(trifluoromethyl)pyrazol-1-yl | X² | G-2 | J-69 (1/4) | — | H |
| 1-methyl-3-(trifluoromethyl)pyrazol-5-yl | X² | G-2 | J-69 (1/4) | — | H |
| 1-methyl-4-(trifluoromethyl)imidazol-2-yl | X² | G-2 | J-69 (1/4) | — | H |
| 2,5-dichlorophenyl | X² | G-2 | J-11 (3/5) | — | 2-Me |
| 2-chloro-5-(trifluoromethyl)phenyl | X² | G-2 | J-11 (3/5) | — | 2-Me |
| 2,5-dimethylphenyl | X² | G-2 | J-11 (3/5) | — | 2-Me |
| 2-methyl-5-(trifluoromethyl)phenyl | X² | G-2 | J-11 (3/5) | — | 2-Me |
| 3,5-dimethylpyrazol-1-yl | X² | G-2 | J-11 (3/5) | — | 2-Me |
| 5-methyl-3-(trifluoromethyl)pyrazol-1-yl | X² | G-2 | J-11 (3/5) | — | 2-Me |
| 5-chloro-3-(trifluoromethyl)pyrazol-1-yl | X² | G-2 | J-11 (3/5) | — | 2-Me |
| 5-bromo-3-(trifluoromethyl)pyrazol-1-yl | X² | G-2 | J-11 (3/5) | — | 2-Me |
| 5-ethyl-3-(trifluoromethyl)pyrazol-1-yl | X² | G-2 | J-11 (3/5) | — | 2-Me |
| 3,5-bis-(trifluoromethyl)pyrazol-1-yl | X² | G-2 | J-11 (3/5) | — | 2-Me |
| 1-methyl-3-(trifluoromethyl)pyrazol-5-yl | X² | G-2 | J-11 (3/5) | — | 2-Me |
| 1-methyl-4-(trifluoromethyl)imidazol-2-yl | X² | G-2 | J-11 (3/5) | — | 2-Me |
| 2,5-dichlorophenyl | X² | G-2 | J-11 (3/5) | — | 3-Me |
| 2-chloro-5-(trifluoromethyl)phenyl | X² | G-2 | J-11 (3/5) | — | 3-Me |
| 2,5-dimethylphenyl | X² | G-2 | J-11 (3/5) | — | 3-Me |
| 2-methyl-5-(trifluoromethyl)phenyl | X² | G-2 | J-11 (3/5) | — | 3-Me |
| 3,5-dimethylpyrazol-1-yl | X² | G-2 | J-11 (3/5) | — | 3-Me |
| 5-methyl-3-(trifluoromethyl)pyrazol-1-yl | X² | G-2 | J-11 (3/5) | — | 3-Me |
| 5-chloro-3-(trifluoromethyl)pyrazol-1-yl | X² | G-2 | J-11 (3/5) | — | 3-Me |
| 5-bromo-3-(trifluoromethyl)pyrazol-1-yl | X² | G-2 | J-11 (3/5) | — | 3-Me |
| 5-ethyl-3-(trifluoromethyl)pyrazol-1-yl | X² | G-2 | J-11 (3/5) | — | 3-Me |
| 3,5-bis-(trifluoromethyl)pyrazol-1-yl | X² | G-2 | J-11 (3/5) | — | 3-Me |
| 1-methyl-3-(trifluoromethyl)pyrazol-5-yl | X² | G-2 | J-11 (3/5) | — | 3-Me |
| 1-methyl-4-(trifluoromethyl)imidazol-2-yl | X² | G-2 | J-11 (3/5) | — | 3-Me |
| 2,5-dichlorophenyl | X² | G-2 | J-11 (3/5) | — | 4-Me |
| 2-chloro-5-(trifluoromethyl)phenyl | X² | G-2 | J-11 (3/5) | — | 4-Me |
| 2,5-dimethylphenyl | X² | G-2 | J-11 (3/5) | — | 4-Me |
| 2-methyl-5-(trifluoromethyl)phenyl | X² | G-2 | J-11 (3/5) | — | 4-Me |
| 3,5-dimethylpyrazol-1-yl | X² | G-2 | J-11 (3/5) | — | 4-Me |
| 5-methyl-3-(trifluoromethyl)pyrazol-1-yl | X² | G-2 | J-11 (3/5) | — | 4-Me |
| 5-chloro-3-(trifluoromethyl)pyrazol-1-yl | X² | G-2 | J-11 (3/5) | — | 4-Me |
| 5-bromo-3-(trifluoromethyl)pyrazol-1-yl | X² | G-2 | J-11 (3/5) | — | 4-Me |
| 5-ethyl-3-(trifluoromethyl)pyrazol-1-yl | X² | G-2 | J-11 (3/5) | — | 4-Me |
| 3,5-bis-(trifluoromethyl)pyrazol-1-yl | X² | G-2 | J-11 (3/5) | — | 4-Me |
| 1-methyl-3-(trifluoromethyl)pyrazol-5-yl | X² | G-2 | J-11 (3/5) | — | 4-Me |
| 1-methyl-4-(trifluoromethyl)imidazol-2-yl | X² | G-2 | J-11 (3/5) | — | 4-Me |
| 2,5-dichlorophenyl | X² | G-2 | J-11 (3/5) | — | 2-Cl |
| 2-chloro-5-(trifluoromethyl)phenyl | X² | G-2 | J-11 (3/5) | — | 2-Cl |
| 2,5-dimethylphenyl | X² | G-2 | J-11 (3/5) | — | 2-Cl |
| 2-methyl-5-(trifluoromethyl)phenyl | X² | G-2 | J-11 (3/5) | — | 2-Cl |
| 3,5-dimethylpyrazol-1-yl | X² | G-2 | J-11 (3/5) | — | 2-Cl |
| 5-methyl-3-(trifluoromethyl)pyrazol-1-yl | X² | G-2 | J-11 (3/5) | — | 2-Cl |
| 5-chloro-3-(trifluoromethyl)pyrazol-1-yl | X² | G-2 | J-11 (3/5) | — | 2-Cl |
| 5-bromo-3-(trifluoromethyl)pyrazol-1-yl | X² | G-2 | J-11 (3/5) | — | 2-Cl |
| 5-ethyl-3-(trifluoromethyl)pyrazol-1-yl | X² | G-2 | J-11 (3/5) | — | 2-Cl |
| 3,5-bis-(trifluoromethyl)pyrazol-1-yl | X² | G-2 | J-11 (3/5) | — | 2-Cl |
| 1-methyl-3-(trifluoromethyl)pyrazol-5-yl | X² | G-2 | J-11 (3/5) | — | 2-Cl |
| 1-methyl-4-(trifluoromethyl)imidazol-2-yl | X² | G-2 | J-11 (3/5) | — | 2-Cl |

TABLE 4*-continued

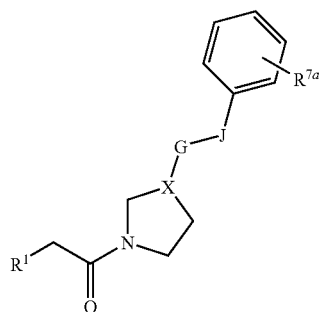

| R¹ | X | G | J* | (R⁵)_y | R⁷ᵃ |
|---|---|---|---|---|---|
| 2,5-dichlorophenyl | X² | G-2 | J-11 (3/5) | — | 4-Cl |
| 2-chloro-5-(trifluoromethyl)phenyl | X² | G-2 | J-11 (3/5) | — | 4-Cl |
| 2,5-dimethylphenyl | X² | G-2 | J-11 (3/5) | — | 4-Cl |
| 2-methyl-5-(trifluoromethyl)phenyl | X² | G-2 | J-11 (3/5) | — | 4-Cl |
| 3,5-dimethylpyrazol-1-yl | X² | G-2 | J-11 (3/5) | — | 4-Cl |
| 5-methyl-3-(trifluoromethyl)pyrazol-1-yl | X² | G-2 | J-11 (3/5) | — | 4-Cl |
| 5-chloro-3-(trifluoromethyl)pyrazol-1-yl | X² | G-2 | J-11 (3/5) | — | 4-Cl |
| 5-bromo-3-(trifluoromethyl)pyrazol-1-yl | X² | G-2 | J-11 (3/5) | — | 4-Cl |
| 5-ethyl-3-(trifluoromethyl)pyrazol-1-yl | X² | G-2 | J-11 (3/5) | — | 4-Cl |
| 3,5-bis-(trifluoromethyl)pyrazol-1-yl | X² | G-2 | J-11 (3/5) | — | 4-Cl |
| 1-methyl-3-(trifluoromethyl)pyrazol-5-yl | X² | G-2 | J-11 (3/5) | — | 4-Cl |
| 1-methyl-4-(trifluoromethyl)imidazol-2-yl | X² | G-2 | J-11 (3/5) | — | 4-Cl |
| 2,5-dichlorophenyl | X² | G-2 | J-29 (3/5) | — | 2-Me |
| 2-chloro-5-(trifluoromethyl)phenyl | X² | G-2 | J-29 (3/5) | — | 2-Me |
| 2,5-dimethylphenyl | X² | G-2 | J-29 (3/5) | — | 2-Me |
| 2-methyl-5-(trifluoromethyl)phenyl | X² | G-2 | J-29 (3/5) | — | 2-Me |
| 3,5-dimethylpyrazol-1-yl | X² | G-2 | J-29 (3/5) | — | 2-Me |
| 5-methyl-3-(trifluoromethyl)pyrazol-1-yl | X² | G-2 | J-29 (3/5) | — | 2-Me |
| 5-chloro-3-(trifluoromethyl)pyrazol-1-yl | X² | G-2 | J-29 (3/5) | — | 2-Me |
| 5-bromo-3-(trifluoromethyl)pyrazol-1-yl | X² | G-2 | J-29 (3/5) | — | 2-Me |
| 5-ethyl-3-(trifluoromethyl)pyrazol-1-yl | X² | G-2 | J-29 (3/5) | — | 2-Me |
| 3,5-bis-(trifluoromethyl)pyrazol-1-yl | X² | G-2 | J-29 (3/5) | — | 2-Me |
| 1-methyl-3-(trifluoromethyl)pyrazol-5-yl | X² | G-2 | J-29 (3/5) | — | 2-Me |
| 1-methyl-4-(trifluoromethyl)imidazol-2-yl | X² | G-2 | J-29 (3/5) | — | 2-Me |
| 2,5-dichlorophenyl | X² | G-2 | J-29 (3/5) | — | 3-Me |
| 2-chloro-5-(trifluoromethyl)phenyl | X² | G-2 | J-29 (3/5) | — | 3-Me |
| 2,5-dimethylphenyl | X² | G-2 | J-29 (3/5) | — | 3-Me |
| 2-methyl-5-(trifluoromethyl)phenyl | X² | G-2 | J-29 (3/5) | — | 3-Me |
| 3,5-dimethylpyrazol-1-yl | X² | G-2 | J-29 (3/5) | — | 3-Me |
| 5-methyl-3-(trifluoromethyl)pyrazol-1-yl | X² | G-2 | J-29 (3/5) | — | 3-Me |
| 5-chloro-3-(trifluoromethyl)pyrazol-1-yl | X² | G-2 | J-29 (3/5) | — | 3-Me |
| 5-bromo-3-(trifluoromethyl)pyrazol-1-yl | X² | G-2 | J-29 (3/5) | — | 3-Me |
| 5-ethyl-3-(trifluoromethyl)pyrazol-1-yl | X² | G-2 | J-29 (3/5) | — | 3-Me |
| 3,5-bis-(trifluoromethyl)pyrazol-1-yl | X² | G-2 | J-29 (3/5) | — | 3-Me |
| 1-methyl-3-(trifluoromethyl)pyrazol-5-yl | X² | G-2 | J-29 (3/5) | — | 3-Me |
| 1-methyl-4-(trifluoromethyl)imidazol-2-yl | X² | G-2 | J-29 (3/5) | — | 3-Me |
| 2,5-dichlorophenyl | X² | G-2 | J-29 (3/5) | — | 4-Me |
| 2-chloro-5-(trifluoromethyl)phenyl | X² | G-2 | J-29 (3/5) | — | 4-Me |
| 2,5-dimethylphenyl | X² | G-2 | J-29 (3/5) | — | 4-Me |
| 2-methyl-5-(trifluoromethyl)phenyl | X² | G-2 | J-29 (3/5) | — | 4-Me |
| 3,5-dimethylpyrazol-1-yl | X² | G-2 | J-29 (3/5) | — | 4-Me |
| 5-methyl-3-(trifluoromethyl)pyrazol-1-yl | X² | G-2 | J-29 (3/5) | — | 4-Me |
| 5-chloro-3-(trifluoromethyl)pyrazol-1-yl | X² | G-2 | J-29 (3/5) | — | 4-Me |
| 5-bromo-3-(trifluoromethyl)pyrazol-1-yl | X² | G-2 | J-29 (3/5) | — | 4-Me |
| 5-ethyl-3-(trifluoromethyl)pyrazol-1-yl | X² | G-2 | J-29 (3/5) | — | 4-Me |
| 3,5-bis-(trifluoromethyl)pyrazol-1-yl | X² | G-2 | J-29 (3/5) | — | 4-Me |
| 1-methyl-3-(trifluoromethyl)pyrazol-5-yl | X² | G-2 | J-29 (3/5) | — | 4-Me |
| 1-methyl-4-(trifluoromethyl)imidazol-2-yl | X² | G-2 | J-29 (3/5) | — | 4-Me |
| 2,5-dichlorophenyl | X² | G-2 | J-29 (3/5) | — | 2-Cl |
| 2-chloro-5-(trifluoromethyl)phenyl | X² | G-2 | J-29 (3/5) | — | 2-Cl |
| 2,5-dimethylphenyl | X² | G-2 | J-29 (3/5) | — | 2-Cl |
| 2-methyl-5-(trifluoromethyl)phenyl | X² | G-2 | J-29 (3/5) | — | 2-Cl |
| 3,5-dimethylpyrazol-1-yl | X² | G-2 | J-29 (3/5) | — | 2-Cl |
| 5-methyl-3-(trifluoromethyl)pyrazol-1-yl | X² | G-2 | J-29 (3/5) | — | 2-Cl |
| 5-chloro-3-(trifluoromethyl)pyrazol-1-yl | X² | G-2 | J-29 (3/5) | — | 2-Cl |
| 5-bromo-3-(trifluoromethyl)pyrazol-1-yl | X² | G-2 | J-29 (3/5) | — | 2-Cl |
| 5-ethyl-3-(trifluoromethyl)pyrazol-1-yl | X² | G-2 | J-29 (3/5) | — | 2-Cl |
| 3,5-bis-(trifluoromethyl)pyrazol-1-yl | X² | G-2 | J-29 (3/5) | — | 2-Cl |
| 1-methyl-3-(trifluoromethyl)pyrazol-5-yl | X² | G-2 | J-29 (3/5) | — | 2-Cl |
| 1-methyl-4-(trifluoromethyl)imidazol-2-yl | X² | G-2 | J-29 (3/5) | — | 2-Cl |
| 2,5-dichlorophenyl | X² | G-2 | J-29 (3/5) | — | 4-Cl |
| 2-chloro-5-(trifluoromethyl)phenyl | X² | G-2 | J-29 (3/5) | — | 4-Cl |

TABLE 4*-continued

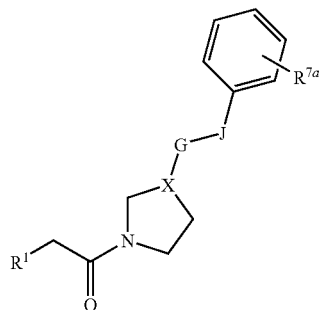

| R¹ | X | G | J* | (R⁵)_y | R⁷ᵃ |
|---|---|---|---|---|---|
| 2,5-dimethylphenyl | X² | G-2 | J-29 (3/5) | — | 4-Cl |
| 2-methyl-5-(trifluoromethyl)phenyl | X² | G-2 | J-29 (3/5) | — | 4-Cl |
| 3,5-dimethylpyrazol-1-yl | X² | G-2 | J-29 (3/5) | — | 4-Cl |
| 5-methyl-3-(trifluoromethyl)pyrazol-1-yl | X² | G-2 | J-29 (3/5) | — | 4-Cl |
| 5-chloro-3-(trifluoromethyl)pyrazol-1-yl | X² | G-2 | J-29 (3/5) | — | 4-Cl |
| 5-bromo-3-(trifluoromethyl)pyrazol-1-yl | X² | G-2 | J-29 (3/5) | — | 4-Cl |
| 5-ethyl-3-(trifluoromethyl)pyrazol-1-yl | X² | G-2 | J-29 (3/5) | — | 4-Cl |
| 3,5-bis-(trifluoromethyl)pyrazol-1-yl | X² | G-2 | J-29 (3/5) | — | 4-Cl |
| 1-methyl-3-(trifluoromethyl)pyrazol-5-yl | X² | G-2 | J-29 (3/5) | — | 4-Cl |
| 1-methyl-4-(trifluoromethyl)imidazol-2-yl | X² | G-2 | J-29 (3/5) | — | 4-Cl |
| 2,5-dichlorophenyl | X² | G-2 | J-29 (3/5) | 5-Me | H |
| 2-chloro-5-(trifluoromethyl)phenyl | X² | G-2 | J-29 (3/5) | 5-Me | H |
| 2,5-dimethylphenyl | X² | G-2 | J-29 (3/5) | 5-Me | H |
| 2-methyl-5-(trifluoromethyl)phenyl | X² | G-2 | J-29 (3/5) | 5-Me | H |
| 3,5-dimethylpyrazol-1-yl | X² | G-2 | J-29 (3/5) | 5-Me | H |
| 5-methyl-3-(trifluoromethyl)pyrazol-1-yl | X² | G-2 | J-29 (3/5) | 5-Me | H |
| 5-chloro-3-(trifluoromethyl)pyrazol-1-yl | X² | G-2 | J-29 (3/5) | 5-Me | H |
| 5-bromo-3-(trifluoromethyl)pyrazol-1-yl | X² | G-2 | J-29 (3/5) | 5-Me | H |
| 5-ethyl-3-(trifluoromethyl)pyrazol-1-yl | X² | G-2 | J-29 (3/5) | 5-Me | H |
| 3,5-bis-(trifluoromethyl)pyrazol-1-yl | X² | G-2 | J-29 (3/5) | 5-Me | H |
| 1-methyl-3-(trifluoromethyl)pyrazol-5-yl | X² | G-2 | J-29 (3/5) | 5-Me | H |
| 1-methyl-4-(trifluoromethyl)imidazol-2-yl | X² | G-2 | J-29 (3/5) | 5-Me | H |
| 2,5-dichlorophenyl | X² | G-2 | J-29 (3/5) | 4-Me | H |
| 2-chloro-5-(trifluoromethyl)phenyl | X² | G-2 | J-29 (3/5) | 4-Me | H |
| 2,5-dimethylphenyl | X² | G-2 | J-29 (3/5) | 4-Me | H |
| 2-methyl-5-(trifluoromethyl)phenyl | X² | G-2 | J-29 (3/5) | 4-Me | H |
| 3,5-dimethylpyrazol-1-yl | X² | G-2 | J-29 (3/5) | 4-Me | H |
| 5-methyl-3-(trifluoromethyl)pyrazol-1-yl | X² | G-2 | J-29 (3/5) | 4-Me | H |
| 5-chloro-3-(trifluoromethyl)pyrazol-1-yl | X² | G-2 | J-29 (3/5) | 4-Me | H |
| 5-bromo-3-(trifluoromethyl)pyrazol-1-yl | X² | G-2 | J-29 (3/5) | 4-Me | H |
| 5-ethyl-3-(trifluoromethyl)pyrazol-1-yl | X² | G-2 | J-29 (3/5) | 4-Me | H |
| 3,5-bis-(trifluoromethyl)pyrazol-1-yl | X² | G-2 | J-29 (3/5) | 4-Me | H |
| 1-methyl-3-(trifluoromethyl)pyrazol-5-yl | X² | G-2 | J-29 (3/5) | 4-Me | H |
| 1-methyl-4-(trifluoromethyl)imidazol-2-yl | X² | G-2 | J-29 (3/5) | 4-Me | H |
| 2,5-dichlorophenyl | X² | G-2 | J-29 (3/5) | 4,4-di-Me | H |
| 2-chloro-5-(trifluoromethyl)phenyl | X² | G-2 | J-29 (3/5) | 4,4-di-Me | H |
| 2,5-dimethylphenyl | X² | G-2 | J-29 (3/5) | 4,4-di-Me | H |
| 2-methyl-5-(trifluoromethyl)phenyl | X² | G-2 | J-29 (3/5) | 4,4-di-Me | H |
| 3,5-dimethylpyrazol-1-yl | X² | G-2 | J-29 (3/5) | 4,4-di-Me | H |
| 5-methyl-3-(trifluoromethyl)pyrazol-1-yl | X² | G-2 | J-29 (3/5) | 4,4-di-Me | H |
| 5-chloro-3-(trifluoromethyl)pyrazol-1-yl | X² | G-2 | J-29 (3/5) | 4,4-di-Me | H |
| 5-bromo-3-(trifluoromethyl)pyrazol-1-yl | X² | G-2 | J-29 (3/5) | 4,4-di-Me | H |
| 5-ethyl-3-(trifluoromethyl)pyrazol-1-yl | X² | G-2 | J-29 (3/5) | 4,4-di-Me | H |
| 3,5-bis-(trifluoromethyl)pyrazol-1-yl | X² | G-2 | J-29 (3/5) | 4,4-di-Me | H |
| 1-methyl-3-(trifluoromethyl)pyrazol-5-yl | X² | G-2 | J-29 (3/5) | 4,4-di-Me | H |
| 1-methyl-4-(trifluoromethyl)imidazol-2-yl | X² | G-2 | J-29 (3/5) | 4,4-di-Me | H |

*The definitions of G and J in the compounds of this table are as defined in Exhibits 2 and 3 in the above Embodiments. The (R⁵)_y column refers the substituents (R⁵)_x shown on J groups in Exhibit 3 other than the phenyl ring substituted by R⁷ᵃ shown in the structure heading this table. R⁷ᵃ may be selected from H (to indicate no substitution on the phenyl ring) as well as the substituents defined for R⁷. A dash "—" in the (R⁵)_y column indicates no substitution on J besides the phenyl ring substituted by R⁷ᵃ.
**R³ᵃ substituent in G is H.
***Numbers in parentheses refer to the attachment points of ring J to ring G and the phenyl ring. The first number is the ring position on J where ring G is attached; the second number is the ring position on J where the phenyl ring is attached.

As disclosed in Scheme 2 above, compounds of Formula 3 are useful intermediates for the preparation of compounds of Formula 1a wherein W is O (i.e. such as the compounds of Formula 1a disclosed in Table 4). The present invention includes but is not limited to the following exemplary species of the compounds Formula 3: Table 4ᵃ wherein n in the structure of Formula 3 is 0, Z¹ is a direct bond, and X, G and J are as defined in Table 4. Thus, the compounds disclosed in Table 4ᵃ include the compounds disclosed in Table 4 wherein R¹CH₂C(O) in the structure above Table 4 is replaced with H. For example, Table 4ᵃ specifically discloses, 4-[4-[5-(2-chlorophenyl)-3-isoxazolyl]-2-thiazolyl]piperidine, 4-[4-[4,5

-dihydro-5-(2-methylphenyl)-3-isoxazolyl]-2-oxazolyl]piperidine, 1-[4-[4,5-dihydro-5-(2-methylphenyl)-3-isoxazolyl]-2-thiazolyl]piperazine and 1-[4-[5-(2-chlorophenyl)-4,5-dihydro-3-isoxazolyl]-2-oxazolyl]piperazine.

TABLE 5*

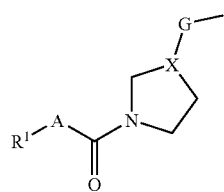

| J | J | J | J | J | J |
|---|---|---|---|---|---|
| $R^1$ is 2,5-dichlorophenyl; A is $CH_2$; X is $X^1$; G is G-1**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| $R^1$ is 2,5-dichlorophenyl; A is $CH_2$; X is $X^2$; G is G-1**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| $R^1$ is 2,5-dichlorophenyl; A is $CH_2$; X is $X^1$; G is G-2**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| $R^1$ is 2,5-dichlorophenyl; A is $CH_2$; X is $X^2$; G is G-2**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| $R^1$ is 2-chloro-5-(trifluoromethyl)phenyl; A is $CH_2$; X is $X^1$; G is G-1**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

TABLE 5*-continued

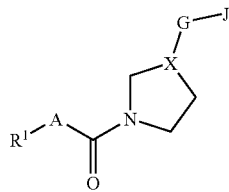

| J | J | J | J | J | J |
|---|---|---|---|---|---|
| $R^1$ is 2-chloro-5-(trifluoromethyl)phenyl; A is $CH_2$; X is $X^2$; G is G-1**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| $R^1$ is 2-chloro-5-(trifluoromethyl)phenyl; A is $CH_2$; X is $X^1$; G is G-2**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| $R^1$ is 2-chloro-5-(trifluoromethyl)phenyl; A is $CH_2$; X is $X^2$; G is G-2**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| $R^1$ is 2,5-dimethylphenyl; A is $CH_2$; X is $X^1$; G is G-1**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| $R^1$ is 2,5-dimethylphenyl; A is $CH_2$; X is $X^2$; G is G-1**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| $R^1$ is 2,5-dimethylphenyl; A is $CH_2$; X is $X^1$; G is G-2**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |

TABLE 5*-continued

[Structure: G-J attached to X in a 5-membered ring with N, where N is bonded to C(=O)-A-R¹]

| J | J | J | J | J | J |
|---|---|---|---|---|---|
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2,5-dimethylphenyl; A is CH₂; X is X²; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2-methyl-5-(trifluoromethyl)phenyl; A is CH₂; X is X¹; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2-methyl-5-(trifluoromethyl)phenyl; A is CH₂; X is X²; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2-methyl-5-(trifluoromethyl)phenyl; A is CH₂; X is X¹; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2-methyl-5-(trifluoromethyl)phenyl; A is CH₂; X is X²; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |

TABLE 5*-continued

[Structure: G-J attached to X in a 5-membered ring with N, where N is bonded to C(=O)-A-R¹]

| J | J | J | J | J | J |
|---|---|---|---|---|---|
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dimethylpyrazol-1-yl; A is CH₂; X is X¹; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dimethylpyrazol-1-yl; A is CH₂; X is X²; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dimethylpyrazol-1-yl; A is CH₂; X is X¹; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dimethylpyrazol-1-yl; A is CH₂; X is X²; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dichloropyrazol-1-yl; A is CH₂; X is X¹; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dichloropyrazol-1-yl; A is CH₂; X is X²; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |

TABLE 5*-continued

[Structure: R¹–A–C(=O)–N in pyrrolidine ring with X and G–J substituent]

| J | J | J | J | J | J |
|---|---|---|---|---|---|
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-56 |
| J-29-7  | J-29-17 | J-29-27 | J-29-37 | J-29-47 | J-29-57 |
| J-29-8  | J-29-18 | J-29-28 | J-29-38 | J-29-48 | J-29-58 |
| J-29-9  | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dichloropyrazol-1-yl; A is CH₂; X is X¹; G is G-2**.

| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-56 |
| J-29-7  | J-29-17 | J-29-27 | J-29-37 | J-29-47 | J-29-57 |
| J-29-8  | J-29-18 | J-29-28 | J-29-38 | J-29-48 | J-29-58 |
| J-29-9  | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dichloropyrazol-1-yl; A is CH₂; X is X²; G is G-2**.

| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-56 |
| J-29-7  | J-29-17 | J-29-27 | J-29-37 | J-29-47 | J-29-57 |
| J-29-8  | J-29-18 | J-29-28 | J-29-38 | J-29-48 | J-29-58 |
| J-29-9  | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dibromopyrazol-1-yl; A is CH₂; X is X¹; G is G-1**.

| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-56 |
| J-29-7  | J-29-17 | J-29-27 | J-29-37 | J-29-47 | J-29-57 |
| J-29-8  | J-29-18 | J-29-28 | J-29-38 | J-29-48 | J-29-58 |
| J-29-9  | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dibromopyrazol-1-yl; A is CH₂; X is X²; G is G-1**.

| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-56 |
| J-29-7  | J-29-17 | J-29-27 | J-29-37 | J-29-47 | J-29-57 |
| J-29-8  | J-29-18 | J-29-28 | J-29-38 | J-29-48 | J-29-58 |
| J-29-9  | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dibromopyrazol-1-yl; A is CH₂; X is X¹; G is G-2**.

| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-56 |
| J-29-7  | J-29-17 | J-29-27 | J-29-37 | J-29-47 | J-29-57 |
| J-29-8  | J-29-18 | J-29-28 | J-29-38 | J-29-48 | J-29-58 |
| J-29-9  | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dibromopyrazol-1-yl; A is CH₂; X is X²; G is G-2**.

| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-56 |
| J-29-7  | J-29-17 | J-29-27 | J-29-37 | J-29-47 | J-29-57 |
| J-29-8  | J-29-18 | J-29-28 | J-29-38 | J-29-48 | J-29-58 |
| J-29-9  | J-29-19 | J-29-29 | J-29-39 | J-29-49 | J-29-59 |
| J-29-10 | J-29-20 | J-29-30 | J-29-40 | J-29-50 | J-29-60 |

R¹ is 5-methyl-3-(trifluoromethyl)pyrazol-1-yl;
A is CH₂; X is X¹; G is G-1**.

| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-56 |
| J-29-7  | J-29-17 | J-29-27 | J-29-37 | J-29-47 | J-29-57 |
| J-29-8  | J-29-18 | J-29-28 | J-29-38 | J-29-48 | J-29-58 |
| J-29-9  | J-29-19 | J-29-29 | J-29-39 | J-29-49 | J-29-59 |
| J-29-10 | J-29-20 | J-29-30 | J-29-40 | J-29-50 | J-29-60 |

R¹ is 5-methyl-3-(trifluoromethyl)pyrazol-1-yl;
A is CH₂; X is X²; G is G-1**.

| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-56 |
| J-29-7  | J-29-17 | J-29-27 | J-29-37 | J-29-47 | J-29-57 |
| J-29-8  | J-29-18 | J-29-28 | J-29-38 | J-29-48 | J-29-58 |
| J-29-9  | J-29-19 | J-29-29 | J-29-39 | J-29-49 | J-29-59 |
| J-29-10 | J-29-20 | J-29-30 | J-29-40 | J-29-50 | J-29-60 |

R¹ is 5-methyl-3-(trifluoromethyl)pyrazol-1-yl;
A is CH₂; X is X¹; G is G-2**.

| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-56 |
| J-29-7  | J-29-17 | J-29-27 | J-29-37 | J-29-47 | J-29-57 |
| J-29-8  | J-29-18 | J-29-28 | J-29-38 | J-29-48 | J-29-58 |
| J-29-9  | J-29-19 | J-29-29 | J-29-39 | J-29-49 | J-29-59 |
| J-29-10 | J-29-20 | J-29-30 | J-29-40 | J-29-50 | J-29-60 |

R¹ is 5-methyl-3-(trifluoromethyl)pyrazol-1-yl;
A is CH₂; X is X²; G is G-2**.

| J-29-1  | J-29-11 | J-29-21 | J-29-31 | J-29-41 | J-29-51 |
| J-29-2  | J-29-12 | J-29-22 | J-29-32 | J-29-42 | J-29-52 |
| J-29-3  | J-29-13 | J-29-23 | J-29-33 | J-29-43 | J-29-53 |
| J-29-4  | J-29-14 | J-29-24 | J-29-34 | J-29-44 | J-29-54 |
| J-29-5  | J-29-15 | J-29-25 | J-29-35 | J-29-45 | J-29-55 |
| J-29-6  | J-29-16 | J-29-26 | J-29-36 | J-29-46 | J-29-56 |
| J-29-7  | J-29-17 | J-29-27 | J-29-37 | J-29-47 | J-29-57 |
| J-29-8  | J-29-18 | J-29-28 | J-29-38 | J-29-48 | J-29-58 |
| J-29-9  | J-29-19 | J-29-29 | J-29-39 | J-29-49 | J-29-59 |
| J-29-10 | J-29-20 | J-29-30 | J-29-40 | J-29-50 | J-29-60 |

TABLE 5*-continued $R^1$ is 5-chloro-3-(trifluoromethyl)pyrazol-1-yl;
A is CH$_2$; X is X$^1$; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-chloro-3-(trifluoromethyl)pyrazol-1-yl;
A is CH$_2$; X is X$^2$; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-chloro-3-(trifluoromethyl)pyrazol-1-yl;
A is CH$_2$; X is X$^1$; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-chloro-3-(trifluoromethyl)pyrazol-1-yl;
A is CH$_2$; X is X$^2$; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-bromo-3-(trifluoromethyl)pyrazol-1-yl;
A is CH$_2$; X is X$^1$; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

TABLE 5*-continued $R^1$ is 5-bromo-3-(trifluoromethyl)pyrazol-1-yl;
A is CH$_2$; X is X$^2$; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-bromo-3-(trifluoromethyl)pyrazol-1-yl;
A is CH$_2$; X is X$^1$; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-bromo-3-(trifluoromethyl)pyrazol-1-yl;
A is CH$_2$; X is X$^2$; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-ethyl-3-(trifluoromethyl)pyrazol-1-yl;
A is CH$_2$; X is X$^1$; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-ethyl-3-(trifluoromethyl)pyrazol-1-yl;
A is CH$_2$; X is X$^2$; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

TABLE 5*-continued $$\text{R}^1\text{-A-C(=O)-N} \diagup \text{X-G-J (pyrrolidine-like ring)}$$

| J | J | J | J | J | J |
|---|---|---|---|---|---|
| R¹ is 5-ethyl-3-(trifluoromethyl)pyrazol-1-yl; A is CH₂; X is X¹; G is G-2**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| R¹ is 5-ethyl-3-(trifluoromethyl)pyrazol-1-yl; A is CH₂; X is X²; G is G-2**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| R¹ is 3,5-bis-(trifluoromethyl)pyrazol-1-yl; A is CH₂; X is X¹; G is G-1**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| R¹ is 3,5-bis-(trifluoromethyl)pyrazol-1-yl; A is CH₂; X is X²; G is G-1**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| R¹ is 3,5-bis-(trifluoromethyl)pyrazol-1-yl; A is CH₂; X is X¹; G is G-2**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| R¹ is 3,5-bis-(trifluoromethyl)pyrazol-1-yl; A is CH₂; X is X²; G is G-2**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| R¹ is 3-methyl-5-(trifluoromethyl)pyrazol-1-yl; A is CH₂; X is X¹; G is G-1**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| R¹ is 3-methyl-5-(trifluoromethyl)pyrazol-1-yl; A is CH₂; X is X²; G is G-1**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| R¹ is 3-methyl-5-(trifluoromethyl)pyrazol-1-yl; A is CH₂; X is X¹; G is G-2**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |
| R¹ is 3-methyl-5-(trifluoromethyl)pyrazol-1-yl; A is CH₂; X is X²; G is G-2**. | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

TABLE 5*-continued

![structure: R1-A-C(=O)-N in a ring with X, G-J substituent]

| J | J | J | J | J | J |
|---|---|---|---|---|---|

R¹ is 3-chloro-5-(trifluoromethyl)pyrazol-1-yl;
A is CH$_2$; X is X$^1$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-chloro-5-(trifluoromethyl)pyrazol-1-yl;
A is CH$_2$; X is X$^2$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-chloro-5-(trifluoromethyl)pyrazol-1-yl;
A is CH$_2$; X is X$^1$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-chloro-5-(trifluoromethyl)pyrazol-1-yl;
A is CH$_2$; X is X$^2$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-bromo-5-(trifluoromethyl)pyrazol-1-yl;
A is CH$_2$; X is X$^1$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-bromo-5-(trifluoromethyl)pyrazol-1-yl;
A is CH$_2$; X is X$^2$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-bromo-5-(trifluoromethyl)pyrazol-1-yl;
A is CH$_2$; X is X$^1$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-bromo-5-(trifluoromethyl)pyrazol-1-yl;
A is CH$_2$; X is X$^2$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 5-methoxy-3-(trifluoromethyl)pyrazol-1-yl;
A is CH$_2$; X is X$^1$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 5-methoxy-3-(trifluoromethyl)pyrazol-1-yl;
A is CH$_2$; X is X$^2$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

TABLE 5*-continued

[Structure: R¹–A–C(=O)–N in a ring with X, where ring bears G–J substituent]

| J | J | J | J | J | J |
|---|---|---|---|---|---|

R¹ is 5-methoxy-3-(trifluoromethyl)pyrazol-1-yl;
A is CH₂; X is X¹; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 5-methoxy-3-(trifluoromethyl)pyrazol-1-yl;
A is CH₂; X is X²; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 5-difluoromethoxy-3-(trifluoromethyl)pyrazol-1-yl;
A is CH₂; X is X¹; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 5-difluoromethoxy-3-(trifluoromethyl)pyrazol-1-yl;
A is CH₂; X is X²; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 5-difluoromethoxy-3-(trifluoromethyl)pyrazol-1-yl;
A is CH₂; X is X¹; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 5-difluoromethoxy-3-(trifluoromethyl)pyrazol-1-yl;
A is CH₂; X is X²; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dichlorotriazol-1-yl; A is CH₂; X is X¹; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dichlorotriazol-1-yl; A is CH₂; X is X²; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dichlorotriazol-1-yl; A is CH₂; X is X¹; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dichlorotriazol-1-yl; A is CH₂; X is X²; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dibromotriazol-1-yl; A is CH₂; X is X¹; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |

TABLE 5*-continued

| J | J | J | J | J | J |
|---|---|---|---|---|---|
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dibromotriazol-1-yl; A is CH₂; X is X²; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dibromotriazol-1-yl; A is CH₂; X is X¹; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3,5-dibromotriazol-1-yl; A is CH₂; X is X²; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-methyl-5-chlorotriazol-1-yl; A is CH₂; X is X¹; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-methyl-5-chlorotriazol-1-yl; A is CH₂; X is X²; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-methyl-5-chlorotriazol-1-yl; A is CH₂; X is X¹; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-methyl-5-chlorotriazol-1-yl; A is CH₂; X is X²; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-methyl-5-bromotriazol-1-yl; A is CH₂; X is X¹; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-methyl-5-bromotriazol-1-yl; A is CH₂; X is X²; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-methyl-5-bromotriazol-1-yl; A is CH₂; X is X¹; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-methyl-5-bromotriazol-1-yl; A is CH₂; X is X²; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |

TABLE 5*-continued

[Structure: pyrrolidine ring with X, G—J substituent, and R¹—A—C(=O)— on N]

| J | J | J | J | J | J |
|---|---|---|---|---|---|
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-trifluoromethyl-5-chlorotriazol-1-yl; A is CH₂; X is X¹; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-trifluoromethyl-5-chlorotriazol-1-yl; A is CH₂; X is X²; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-trifluoromethyl-5-chlorotriazol-1-yl; A is CH₂; X is X¹; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-trifluoromethyl-5-chlorotriazol-1-yl; A is CH₂; X is X²; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-trifluoromethyl-5-bromotriazol-1-yl; A is CH₂; X is X¹; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-trifluoromethyl-5-bromotriazol-1-yl; A is CH₂; X is X¹; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 3-trifluoromethyl-5-bromotriazol-1-yl; A is CH₂; X is X²; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2,5-dimethylphenyl; A is NH; X is X¹; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2,5-dimethylphenyl; A is NH; X is X²; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

TABLE 5*-continued

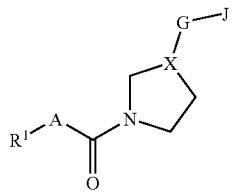

| J | J | J | J | J | J |
|---|---|---|---|---|---|
| \multicolumn{6}{c}{$R^1$ is 2,5-dimethylphenyl; A is NH; X is $X^1$; G is G-2**.} |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2,5-dimethylphenyl; A is NH; X is $X^2$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2,5-dichlorophenyl; A is NH; X is $X^1$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2,5-dichlorophenyl; A is NH; X is $X^2$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2,5-dichlorophenyl; A is NH; X is $X^1$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2,5-dichlorophenyl; A is NH; X is $X^2$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |

TABLE 5*-continued

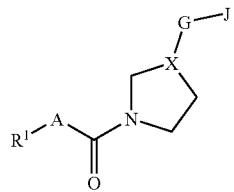

| J | J | J | J | J | J |
|---|---|---|---|---|---|
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2-methyl-5-chlorophenyl; A is NH; X is $X^1$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2-methyl-5-chlorophenyl; A is NH; X is $X^2$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2-methyl-5-chlorophenyl; A is NH; X is $X^1$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2-methyl-5-chlorophenyl; A is NH; X is $X^2$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2-methyl-5-bromophenyl; A is NH; X is $X^1$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2-methyl-5-bromophenyl; A is NH; X is $X^2$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |

TABLE 5*-continued

[Structure: pyrrolidine ring with G—J substituent on X position, and R¹—A—C(=O)— on N position]

R¹ is 2-methyl-5-bromophenyl; A is NH; X is X¹; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2-methyl-5-bromophenyl; A is NH; X is X²; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2-chloro-5-methylphenyl; A is NH; X is X¹; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2-chloro-5-methylphenyl; A is NH; X is X²; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2-chloro-5-methylphenyl; A is NH; X is X¹; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2-chloro-5-methylphenyl; A is NH; X is X²; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2-bromo-5-methylphenyl; A is NH; X is X¹; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2-bromo-5-methylphenyl; A is NH; X is X²; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2-bromo-5-methylphenyl; A is NH; X is X¹; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2-bromo-5-methylphenyl; A is NH; X is X²; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 5-methyl-3-(trifluoromethyl)pyrazol-1-yl; A is NH; X is X¹; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |

TABLE 5*-continued

![Structure: R1-A-C(=O)-N in pyrrolidine ring with X bearing G-J substituent]

| J | J | J | J | J | J |
|---|---|---|---|---|---|
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-methyl-3-(trifluoromethyl)pyrazol-1-yl; A is NH; X is $X^2$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-methyl-3-(trifluoromethyl)pyrazol-1-yl; A is NH; X is $X^1$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-methyl-3-(trifluoromethyl)pyrazol-1-yl; A is NH; X is $X^2$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 3,5-dimethylpyrazol-1-yl; A is NH; X is $X^1$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 3,5-dimethylpyrazol-1-yl; A is NH; X is $X^2$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 3,5-dimethylpyrazol-1-yl; A is NH; X is $X^1$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 3,5-dimethylpyrazol-1-yl; A is NH; X is $X^2$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2,5-dimethylphenyl; A is CHOH; X is $X^1$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2,5-dimethylphenyl; A is CHOH; X is $X^2$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2,5-dimethylphenyl; A is CHOH; X is $X^1$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 2,5-dimethylphenyl; A is CHOH; X is $X^2$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |

TABLE 5*-continued

[Structure: R¹–A–C(=O)–N-pyrrolidine ring with X, substituted by G–J]

| J | J | J | J | J | J |
|---|---|---|---|---|---|
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2,5-dichlorophenyl; A is CHOH; X is $X^1$; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2,5-dichlorophenyl; A is CHOH; X is $X^2$; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2,5-dichlorophenyl; A is CHOH; X is $X^1$; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2,5-dichlorophenyl; A is CHOH; X is $X^2$; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2,5-dimethylphenyl; A is CHOMe; X is $X^1$; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2,5-dimethylphenyl; A is CHOMe; X is $X^2$; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2,5-dimethylphenyl; A is CHOMe; X is $X^1$; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2,5-dimethylphenyl; A is CHOMe; X is $X^2$; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2,5-dichlorophenyl; A is CHOMe; X is $X^1$; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2,5-dichlorophenyl; A is CHOMe; X is $X^2$; G is G-1**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

R¹ is 2,5-dichlorophenyl; A is CHOMe; X is $X^1$; G is G-2**.

| J | J | J | J | J | J |
|---|---|---|---|---|---|
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

TABLE 5*-continued

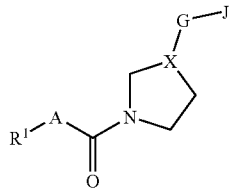

| J | J | J | J | J | J |
|---|---|---|---|---|---|
| \multicolumn{6}{c}{$R^1$ is 2,5-dichlorophenyl; A is CHOMe; X is $X^2$; G is G-2**.} | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-methyl-3-(trifluoromethyl)pyrazol-1-yl;
A is CHOH; X is $X^1$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-methyl-3-(trifluoromethyl)pyrazol-1-yl;
A is CHOH; X is $X^2$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-methyl-3-(trifluoromethyl)pyrazol-1-yl;
A is CHOH; X is $X^1$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-methyl-3-(trifluoromethyl)pyrazol-1-yl;
A is CHOH; X is $X^2$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

TABLE 5*-continued

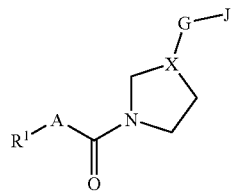

| J | J | J | J | J | J |
|---|---|---|---|---|---|
| \multicolumn{6}{c}{$R^1$ is 5-methyl-3-(trifluoromethyl)pyrazol-1-yl; A is CHOMe; X is $X^1$; G is G-1**.} | | | | | |
| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-methyl-3-(trifluoromethyl)pyrazol-1-yl;
A is CHOMe; X is $X^2$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-methyl-3-(trifluoromethyl)pyrazol-1-yl;
A is CHOMe; X is $X^2$; G is G-1**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

$R^1$ is 5-methyl-3-(trifluoromethyl)pyrazol-1-yl;
A is CHOMe; X is $X^2$; G is G-2**.

| J-29-1 | J-29-11 | J-29-21 | J-29-31 | J-29-41 | J-29-51 |
| J-29-2 | J-29-12 | J-29-22 | J-29-32 | J-29-42 | J-29-52 |
| J-29-3 | J-29-13 | J-29-23 | J-29-33 | J-29-43 | J-29-53 |
| J-29-4 | J-29-14 | J-29-24 | J-29-34 | J-29-44 | J-29-54 |
| J-29-5 | J-29-15 | J-29-25 | J-29-35 | J-29-45 | J-29-55 |
| J-29-6 | J-29-16 | J-29-26 | J-29-36 | J-29-46 | J-29-56 |
| J-29-7 | J-29-17 | J-29-27 | J-29-37 | J-29-47 | J-29-57 |
| J-29-8 | J-29-18 | J-29-28 | J-29-38 | J-29-48 | J-29-58 |
| J-29-9 | J-29-19 | J-29-29 | J-29-39 | J-29-49 | J-29-59 |
| J-29-10 | J-29-20 | J-29-30 | J-29-40 | J-29-50 | J-29-60 |

*The definitions of J and G in the compounds of this table are as defined in Exhibits 2 and A in the above Embodiments. As shown in Exhibit A, J can be selected from J-29-1 through J-29-60 (i.e. particular examples of J-29). As many J-29-1 to J-29-60 groups include a chiral center, these J groups are illustrated in a particular enantiomeric configuration, which in some instances may provide the greatest fungicidal activity. One skilled in the art immediately recognizes the antipode (i.e. opposite enantiomer) for each of the compounds listed, and furthermore understands that the enantiomers can be present as pure enantiomers or in mixtures enriched in one enantiomer or in racemic mixtures.

**$R^{3a}$ substituent in G-1 and G-2 is H.

The invention includes but is not limited to the following exemplary species of Formula 1A compounds.

TABLE 6A

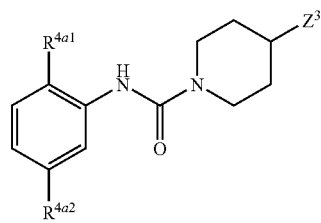

| $R^{4a1}$ | $R^{4a2}$ | $Z^3$ |
|---|---|---|
| Me | Me | CN |
| Me | Et | CN |
| Me | Cl | CN |
| Me | Br | CN |
| Me | I | CN |
| Me | $CF_2H$ | CN |
| Me | $CF_3$ | CN |
| Me | $CF_3CH_2$ | CN |
| Me | $CF_3CF_2$ | CN |
| Me | $CCl_3$ | CN |
| Me | MeO | CN |
| Et | Me | CN |
| Et | Et | CN |
| Et | Cl | CN |
| Et | Br | CN |
| Et | I | CN |
| Et | $CF_2H$ | CN |
| Et | $CF_3$ | CN |
| Et | $CF_3CH_2$ | CN |
| Et | $CF_3CF_2$ | CN |
| Et | $CCl_3$ | CN |
| Et | MeO | CN |
| Cl | Me | CN |
| Cl | Et | CN |
| Cl | Cl | CN |
| Cl | Br | CN |
| Cl | I | CN |
| Cl | $CF_2H$ | CN |
| Cl | $CF_3$ | CN |
| Cl | $CF_3CH_2$ | CN |
| Cl | $CF_3CF_2$ | CN |
| Cl | $CCl_3$ | CN |
| Cl | MeO | CN |
| Br | Me | CN |
| Br | Et | CN |
| Br | Cl | CN |
| Br | Br | CN |
| Br | I | CN |
| Br | $CF_2H$ | CN |
| Br | $CF_3$ | CN |
| Br | $CF_3CH_2$ | CN |
| Br | $CF_3CF_2$ | CN |
| Br | $CCl_3$ | CN |
| Br | MeO | CN |
| I | Me | CN |
| I | Et | CN |
| I | Cl | CN |
| I | Br | CN |
| I | I | CN |
| I | $CF_2H$ | CN |
| I | $CF_3$ | CN |
| I | $CF_3CF_2$ | CN |
| I | $CF_3CF_2$ | CN |
| I | $CCl_3$ | CN |
| I | MeO | CN |
| $CF_2H$ | Me | CN |
| $CF_2H$ | Et | CN |
| $CF_2H$ | Cl | CN |
| $CF_2H$ | Br | CN |
| $CF_2H$ | I | CN |
| $CF_2H$ | $CF_2H$ | CN |
| $CF_2H$ | $CF_3$ | CN |
| $CF_2H$ | $CF_3CH_2$ | CN |
| $CF_2H$ | $CF_3CF_2$ | CN |
| $CF_2H$ | $CCl_3$ | CN |
| $CF_2H$ | MeO | CN |
| $CF_3$ | Me | CN |
| $CF_3$ | Et | CN |
| $CF_3$ | Cl | CN |
| $CF_3$ | Br | CN |
| $CF_3$ | I | CN |
| $CF_3$ | $CF_2H$ | CN |
| $CF_3$ | $CF_3$ | CN |
| $CF_3$ | $CF_3CH_2$ | CN |
| $CF_3$ | $CF_3CF_2$ | CN |
| $CF_3$ | $CCl_3$ | CN |
| $CF_3$ | MeO | CN |
| $CF_3CH_2$ | Me | CN |
| $CF_3CH_2$ | Et | CN |
| $CF_3CH_2$ | Cl | CN |
| $CF_3CH_2$ | Br | CN |
| $CF_3CH_2$ | I | CN |
| $CF_3CH_2$ | $CF_2H$ | CN |
| $CF_3CH_2$ | $CF_3$ | CN |
| $CF_3CH_2$ | $CF_3CH_2$ | CN |
| $CF_3CH_2$ | $CF_3CF_2$ | CN |
| $CF_3CH_2$ | $CCl_3$ | CN |
| $CF_3CH_2$ | MeO | CN |
| $CF_3CF_2$ | Me | CN |
| $CF_3CF_2$ | Et | CN |
| $CF_3CF_2$ | Cl | CN |
| $CF_3CF_2$ | Br | CN |
| $CF_3CF_2$ | I | CN |
| $CF_3CF_2$ | $CF_2H$ | CN |
| $CF_3CF_2$ | $CF_3$ | CN |
| $CF_3CF_2$ | $CF_3CH_2$ | CN |
| $CF_3CF_2$ | $CF_3CF_2$ | CN |
| $CF_3CF_2$ | $CCl_3$ | CN |
| $CF_3CF_2$ | MeO | CN |
| $CCl_3$ | Me | CN |
| $CCl_3$ | Et | CN |
| $CCl_3$ | Cl | CN |
| $CCl_3$ | Br | CN |
| $CCl_3$ | I | CN |
| $CCl_3$ | $CF_2H$ | CN |
| $CCl_3$ | $CF_3$ | CN |
| $CCl_3$ | $CF_3CH_2$ | CN |
| $CCl_3$ | $CF_3CF_2$ | CN |
| $CCl_3$ | $CCl_3$ | CN |
| $CCl_3$ | MeO | CN |
| MeO | Me | CN |
| MeO | Et | CN |
| MeO | Cl | CN |
| MeO | Br | CN |
| MeO | I | CN |
| MeO | $CF_2H$ | CN |
| MeO | $CF_3$ | CN |
| MeO | $CF_3CH_2$ | CN |
| MeO | $CF_3CF_2$ | CN |
| MeO | $CCl_3$ | CN |
| MeO | MeO | CN |
| $OCF_2H$ | Me | CN |
| $OCF_2H$ | Et | CN |
| $OCF_2H$ | Cl | CN |
| $OCF_2H$ | Br | CN |
| $OCF_2H$ | I | CN |
| $OCF_2H$ | $CF_2H$ | CN |
| $OCF_2H$ | $CF_3$ | CN |
| $OCF_2H$ | $CF_3CH_2$ | CN |
| $OCF_2H$ | $CF_3CF_2$ | CN |

TABLE 6A-continued

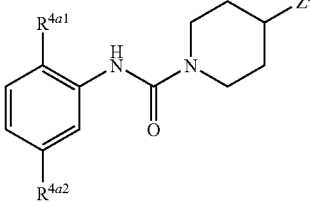

| $R^{4a1}$ | $R^{4a2}$ | $Z^3$ |
|---|---|---|
| $OCF_2H$ | $CCl_3$ | CN |
| $OCF_2H$ | MeO | CN |
| Me | Me | $C(=S)NH_2$ |
| Me | Et | $C(=S)NH_2$ |
| Me | Cl | $C(=S)NH_2$ |
| Me | Br | $C(=S)NH_2$ |
| Me | I | $C(=S)NH_2$ |
| Me | $CF_2H$ | $C(=S)NH_2$ |
| Me | $CF_3$ | $C(=S)NH_2$ |
| Me | $CF_3CH_2$ | $C(=S)NH_2$ |
| Me | $CF_3CF_2$ | $C(=S)NH_2$ |
| Me | $CCl_3$ | $C(=S)NH_2$ |
| Me | MeO | $C(=S)NH_2$ |
| Et | Me | $C(=S)NH_2$ |
| Et | Et | $C(=S)NH_2$ |
| Et | Cl | $C(=S)NH_2$ |
| Et | Br | $C(=S)NH_2$ |
| Et | I | $C(=S)NH_2$ |
| Et | $CF_2H$ | $C(=S)NH_2$ |
| Et | $CF_3$ | $C(=S)NH_2$ |
| Et | $CF_3CH_2$ | $C(=S)NH_2$ |
| Et | $CF_3CF_2$ | $C(=S)NH_2$ |
| Et | $CCl_3$ | $C(=S)NH_2$ |
| Et | MeO | $C(=S)NH_2$ |
| Cl | Me | $C(=S)NH_2$ |
| Cl | Et | $C(=S)NH_2$ |
| Cl | Cl | $C(=S)NH_2$ |
| Cl | Br | $C(=S)NH_2$ |
| Cl | I | $C(=S)NH_2$ |
| Cl | $CF_2H$ | $C(=S)NH_2$ |
| Cl | $CF_3$ | $C(=S)NH_2$ |
| Cl | $CF_3CH_2$ | $C(=S)NH_2$ |
| Cl | $CF_3CF_2$ | $C(=S)NH_2$ |
| Cl | $CCl_3$ | $C(=S)NH_2$ |
| Cl | MeO | $C(=S)NH_2$ |
| Br | Me | $C(=S)NH_2$ |
| Br | Et | $C(=S)NH_2$ |
| Br | Cl | $C(=S)NH_2$ |
| Br | Br | $C(=S)NH_2$ |
| Br | I | $C(=S)NH_2$ |
| Br | $CF_2H$ | $C(=S)NH_2$ |
| Br | $CF_3$ | $C(=S)NH_2$ |
| Br | $CF_3CH_2$ | $C(=S)NH_2$ |
| Br | $CF_3CF_2$ | $C(=S)NH_2$ |
| Br | $CCl_3$ | $C(=S)NH_2$ |
| Br | MeO | $C(=S)NH_2$ |
| I | Me | $C(=S)NH_2$ |
| I | Et | $C(=S)NH_2$ |
| I | Cl | $C(=S)NH_2$ |
| I | Br | $C(=S)NH_2$ |
| I | I | $C(=S)NH_2$ |
| I | $CF_2H$ | $C(=S)NH_2$ |
| I | $CF_3$ | $C(=S)NH_2$ |
| I | $CF_3CH_2$ | $C(=S)NH_2$ |
| I | $CF_3CF_2$ | $C(=S)NH_2$ |
| I | $CCl_3$ | $C(=S)NH_2$ |
| I | MeO | $C(=S)NH_2$ |
| $CF_2H$ | Me | $C(=S)NH_2$ |
| $CF_2H$ | Et | $C(=S)NH_2$ |
| $CF_2H$ | Cl | $C(=S)NH_2$ |
| $CF_2H$ | Br | $C(=S)NH_2$ |
| $CF_2H$ | I | $C(=S)NH_2$ |
| $CF_2H$ | $CF_2H$ | $C(=S)NH_2$ |
| $CF_2H$ | $CF_3$ | $C(=S)NH_2$ |
| $CF_2H$ | $CF_3CH_2$ | $C(=S)NH_2$ |
| $CF_2H$ | $CF_3CF_2$ | $C(=S)NH_2$ |
| $CF_2H$ | $CCl_3$ | $C(=S)NH_2$ |
| $CF_2H$ | MeO | $C(=S)NH_2$ |
| $CF_3$ | Me | $C(=S)NH_2$ |
| $CF_3$ | Et | $C(=S)NH_2$ |
| $CF_3$ | Cl | $C(=S)NH_2$ |
| $CF_3$ | Br | $C(=S)NH_2$ |
| $CF_3$ | I | $C(=S)NH_2$ |
| $CF_3$ | $CF_2H$ | $C(=S)NH_2$ |
| $CF_3$ | $CF_3$ | $C(=S)NH_2$ |
| $CF_3$ | $CF_3CH_2$ | $C(=S)NH_2$ |
| $CF_3$ | $CF_3CF_2$ | $C(=S)NH_2$ |
| $CF_3$ | $CCl_3$ | $C(=S)NH_2$ |
| $CF_3$ | MeO | $C(=S)NH_2$ |
| $CF_3CH_2$ | Me | $C(=S)NH_2$ |
| $CF_3CH_2$ | Et | $C(=S)NH_2$ |
| $CF_3CH_2$ | Cl | $C(=S)NH_2$ |
| $CF_3CH_2$ | Br | $C(=S)NH_2$ |
| $CF_3CH_2$ | I | $C(=S)NH_2$ |
| $CF_3CH_2$ | $CF_2H$ | $C(=S)NH_2$ |
| $CF_3CH_2$ | $CF_3$ | $C(=S)NH_2$ |
| $CF_3CH_2$ | $CF_3CH_2$ | $C(=S)NH_2$ |
| $CF_3CH_2$ | $CF_3CF_2$ | $C(=S)NH_2$ |
| $CF_3CH_2$ | $CCl_3$ | $C(=S)NH_2$ |
| $CF_3CH_2$ | MeO | $C(=S)NH_2$ |
| $CF_3CF_2$ | Me | $C(=S)NH_2$ |
| $CF_3CF_2$ | Et | $C(=S)NH_2$ |
| $CF_3CF_2$ | Cl | $C(=S)NH_2$ |
| $CF_3CF_2$ | Br | $C(=S)NH_2$ |
| $CF_3CF_2$ | I | $C(=S)NH_2$ |
| $CF_3CF_2$ | $CF_2H$ | $C(=S)NH_2$ |
| $CF_3CF_2$ | $CF_3$ | $C(=S)NH_2$ |
| $CF_3CF_2$ | $CF_3CH_2$ | $C(=S)NH_2$ |
| $CF_3CF_2$ | $CF_3CF_2$ | $C(=S)NH_2$ |
| $CF_3CF_2$ | $CCl_3$ | $C(=S)NH_2$ |
| $CF_3CF_2$ | MeO | $C(=S)NH_2$ |
| $CCl_3$ | Me | $C(=S)NH_2$ |
| $CCl_3$ | Et | $C(=S)NH_2$ |
| $CCl_3$ | Cl | $C(=S)NH_2$ |
| $CCl_3$ | Br | $C(=S)NH_2$ |
| $CCl_3$ | I | $C(=S)NH_2$ |
| $CCl_3$ | $CF_2H$ | $C(=S)NH_2$ |
| $CCl_3$ | $CF_3$ | $C(=S)NH_2$ |
| $CCl_3$ | $CF_3CH_2$ | $C(=S)NH_2$ |
| $CCl_3$ | $CF_3CF_2$ | $C(=S)NH_2$ |
| $CCl_3$ | $CCl_3$ | $C(=S)NH_2$ |
| $CCl_3$ | MeO | $C(=S)NH_2$ |
| MeO | Me | $C(=S)NH_2$ |
| MeO | Et | $C(=S)NH_2$ |
| MeO | Cl | $C(=S)NH_2$ |
| MeO | Br | $C(=S)NH_2$ |
| MeO | I | $C(=S)NH_2$ |
| MeO | $CF_2H$ | $C(=S)NH_2$ |
| MeO | $CF_3$ | $C(=S)NH_2$ |
| MeO | $CF_3CH_2$ | $C(=S)NH_2$ |
| MeO | $CF_3CF_2$ | $C(=S)NH_2$ |
| MeO | $CCl_3$ | $C(=S)NH_2$ |
| MeO | MeO | $C(=S)NH_2$ |
| $OCF_2H$ | Me | $C(=S)NH_2$ |
| $OCF_2H$ | Et | $C(=S)NH_2$ |
| $OCF_2H$ | Cl | $C(=S)NH_2$ |
| $OCF_2H$ | Br | $C(=S)NH_2$ |
| $OCF_2H$ | I | $C(=S)NH_2$ |
| $OCF_2H$ | $CF_2H$ | $C(=S)NH_2$ |
| $OCF_2H$ | $CF_3$ | $C(=S)NH_2$ |
| $OCF_2H$ | $CF_3CH_2$ | $C(=S)NH_2$ |
| $OCF_2H$ | $CF_3CF_2$ | $C(=S)NH_2$ |

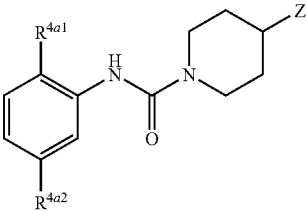

TABLE 6A-continued

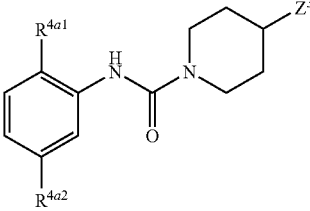

| $R^{4a1}$ | $R^{4a2}$ | $Z^3$ |
|---|---|---|
| OCF$_2$H | CCl$_3$ | C(=S)NH$_2$ |
| OCF$_2$H | MeO | C(=S)NH$_2$ |

The present disclosure includes Table 6A$^a$ wherein the piperidinyl moiety in the structure above Table 6A is replaced with piperazinyl, and $R^{4a1}$, $R^{4a2}$ and $Z^3$ are as listed in Table 6A. For example, Table 6A$^a$ specifically discloses 4-(aminothioxomehtyl)-N-(2,5-dimethylphenyl)-1-piperazinecarboxamide, 4-(aminothioxomethyl)-N-(2,5-diclorophenyl)-1-piperazinecarboxamine and 4-(aminothioxomethyl)-N-(2-chloro-5-(trifluoromethyl)phenyl)-1-piperazinecarboxamine.

TABLE 6B

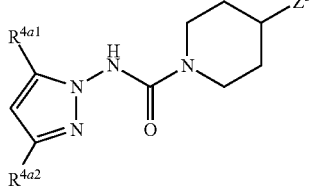

| $R^{4a1}$ | $R^{4a2}$ | $Z^3$ |
|---|---|---|
| Me | Me | CN |
| Me | CF$_3$ | CN |
| CF$_3$ | CF$_3$ | CN |
| Cl | Me | CN |
| Cl | CF$_3$ | CN |
| Br | Me | CN |
| Br | CF$_3$ | CN |
| Cl | Cl | CN |
| Br | Br | CN |
| Me | Me | C(=S)NH$_2$ |
| Me | CF$_3$ | C(=S)NH$_2$ |
| CF$_3$ | CF$_3$ | C(=S)NH$_2$ |
| Cl | Me | C(=S)NH$_2$ |
| Cl | CF$_3$ | C(=S)NH$_2$ |
| Br | Me | C(=S)NH$_2$ |
| Br | CF$_3$ | C(=S)NH$_2$ |
| Cl | Cl | C(=S)NH$_2$ |
| Br | Br | C(=S)NH$_2$ |

The present disclosure includes Table 6B$^a$ wherein the piperidinyl moiety in the structure above Table 6B is replaced with piperazinyl, and $R^{4a1}$, $R^{4a2}$ and $Z^3$ are as listed in Table 6B. For example, Table 6B$^a$ specifically discloses 4-(aminothioxomehtyl)-N-[5-methyl-3-(trifluoromethyl)-1H-pyrazol-1-yl]-1-piperazinecarboxamide and 4-(aminothioxomethyl)-N-(3,5-dimethyl-1H-pyrazol-1-yl)-1-piperazinecarboxamide.

TABLE 6C

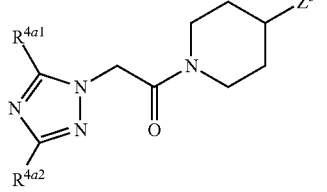

| $R^{4a1}$ | $R^{4a2}$ | $Z^3$ |
|---|---|---|
| Me | Me | CN |
| Me | CF$_3$ | CN |
| CF$_3$ | CF$_3$ | CN |
| Cl | Me | CN |
| Cl | CF$_3$ | CN |
| Br | Me | CN |
| Br | CF$_3$ | CN |
| Cl | Cl | CN |
| Br | Br | CN |
| Me | Me | C(=S)NH$_2$ |
| Me | CF$_3$ | C(=S)NH$_2$ |
| CF$_3$ | CF$_3$ | C(=S)NH$_2$ |
| Cl | Me | C(=S)NH$_2$ |
| Cl | CF$_3$ | C(=S)NH$_2$ |
| Br | Me | C(=S)NH$_2$ |
| Br | CF$_3$ | C(=S)NH$_2$ |
| Cl | Cl | C(=S)NH$_2$ |
| Br | Br | C(=S)NH$_2$ |

The present disclosure includes Table 6C$^a$ wherein the piperidinyl moiety in the structure above Table 6C is replaced with piperazinyl, and $R^{4a1}$, $R^{4a2}$ and $Z^3$ are as listed in Table 6C. For example, Table 6C$^a$ specifically discloses 4-[2-(3,5-dichloro-1H-1,2,4-triazol-1-yl)acetyl]-1-piperazinecarbothioamide and 4-[2-(3,5-dibromo-1H-1,2,4-triazol-1-yl)acetyl]-1-piperazinecarbothioamide.

TABLE 6D

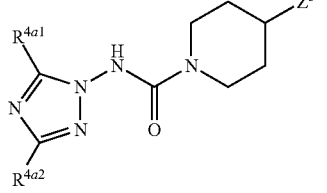

| $R^{4a1}$ | $R^{4a2}$ | $Z^3$ |
|---|---|---|
| Me | Me | CN |
| Me | CF$_3$ | CN |
| CF$_3$ | CF$_3$ | CN |
| Cl | Me | CN |
| Cl | CF$_3$ | CN |
| Br | Me | CN |
| Br | CF$_3$ | CN |
| Cl | Cl | CN |
| Br | Br | CN |
| Me | Me | C(=S)NH$_2$ |
| Me | CF$_3$ | C(=S)NH$_2$ |
| CF$_3$ | CF$_3$ | C(=S)NH$_2$ |
| Cl | Me | C(=S)NH$_2$ |
| Cl | CF$_3$ | C(=S)NH$_2$ |
| Br | Me | C(=S)NH$_2$ |
| Br | CF$_3$ | C(=S)NH$_2$ |
| Cl | Cl | C(=S)NH$_2$ |
| Br | Br | C(=S)NH$_2$ |

The present disclosure includes Table 6D$^a$ wherein the piperidinyl moiety in the structure above Table 6D is replaced with piperazinyl, and $R^{4a1}$, $R^{4a2}$ and $Z^3$ are as listed in Table 6D. For example, Table 6D$^a$ specifically discloses 4-(aminothioxomethyl)-N-(3,5-dichloro-1H-1,2,4-triazole-1-yl)-1-piperazinecarboxamide and 4-(amino)-N-(3,5-dibromo-1H-1,2,4-triazol-1-yl)-1-piperazinecarboxamide.

TABLE 6E

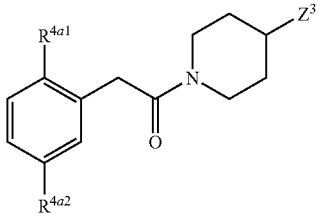

| R$^{4a1}$ | R$^{4a2}$ | Z$^3$ |
|---|---|---|
| Me | Me | CN |
| Me | Et | CN |
| Me | Cl | CN |
| Me | Br | CN |
| Me | I | CN |
| Me | CF$_2$H | CN |
| Me | CF$_3$ | CN |
| Me | CF$_3$CH$_2$ | CN |
| Me | CF$_3$CF$_2$ | CN |
| Me | CCl$_3$ | CN |
| Me | MeO | CN |
| Et | Me | CN |
| Et | Et | CN |
| Et | Cl | CN |
| Et | Br | CN |
| Et | I | CN |
| Et | CF$_2$H | CN |
| Et | CF$_3$ | CN |
| Et | CF$_3$CH$_2$ | CN |
| Et | CF$_3$CF$_2$ | CN |
| Et | CCl$_3$ | CN |
| Et | MeO | CN |
| Cl | Me | CN |
| Cl | Et | CN |
| Cl | Cl | CN |
| Cl | Br | CN |
| Cl | I | CN |
| Cl | CF$_2$H | CN |
| Cl | CF$_3$ | CN |
| Cl | CF$_3$CH$_2$ | CN |
| Cl | CF$_3$CF$_2$ | CN |
| Cl | CCl$_3$ | CN |
| Cl | MeO | CN |
| Br | Me | CN |
| Br | Et | CN |
| Br | Cl | CN |
| Br | Br | CN |
| Br | I | CN |
| Br | CF$_2$H | CN |
| Br | CF$_3$ | CN |
| Br | CF$_3$CH$_2$ | CN |
| Br | CF$_3$CF$_2$ | CN |
| Br | CCl$_3$ | CN |
| Br | MeO | CN |
| I | Me | CN |
| I | Et | CN |
| I | Cl | CN |
| I | Br | CN |
| I | I | CN |
| I | CF$_2$H | CN |
| I | CF$_3$ | CN |
| I | CF$_3$CH$_2$ | CN |
| I | CF$_3$CF$_2$ | CN |
| I | CCl$_3$ | CN |
| I | MeO | CN |
| CF$_2$H | Me | CN |
| CF$_2$H | Et | CN |
| CF$_2$H | Cl | CN |
| CF$_2$H | Br | CN |
| CF$_2$H | I | CN |
| CF$_2$H | CF$_2$H | CN |
| CF$_2$H | CF$_3$ | CN |

TABLE 6E-continued

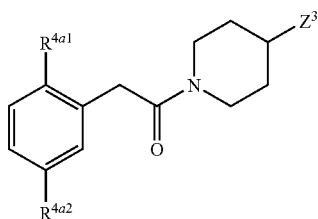

| R$^{4a1}$ | R$^{4a2}$ | Z$^3$ |
|---|---|---|
| CF$_2$H | CF$_3$CH$_2$ | CN |
| CF$_2$H | CF$_3$CF$_2$ | CN |
| CF$_2$H | CCl$_3$ | CN |
| CF$_2$H | MeO | CN |
| CF$_3$ | Me | CN |
| CF$_3$ | Et | CN |
| CF$_3$ | Cl | CN |
| CF$_3$ | Br | CN |
| CF$_3$ | I | CN |
| CF$_3$ | CF$_2$H | CN |
| CF$_3$ | CF$_3$ | CN |
| CF$_3$ | CF$_3$CH$_2$ | CN |
| CF$_3$ | CF$_3$CF$_2$ | CN |
| CF$_3$ | CCl$_3$ | CN |
| CF$_3$ | MeO | CN |
| CF$_3$CH$_2$ | Me | CN |
| CF$_3$CH$_2$ | Et | CN |
| CF$_3$CH$_2$ | Cl | CN |
| CF$_3$CH$_2$ | Br | CN |
| CF$_3$CH$_2$ | I | CN |
| CF$_3$CH$_2$ | CF$_2$H | CN |
| CF$_3$CH$_2$ | CF$_3$ | CN |
| CF$_3$CH$_2$ | CF$_3$CH$_2$ | CN |
| CF$_3$CH$_2$ | CF$_3$CF$_2$ | CN |
| CF$_3$CH$_2$ | CCl$_3$ | CN |
| CF$_3$CH$_2$ | MeO | CN |
| CF$_3$CF$_2$ | Me | CN |
| CF$_3$CF$_2$ | Et | CN |
| CF$_3$CF$_2$ | Cl | CN |
| CF$_3$CF$_2$ | Br | CN |
| CF$_3$CF$_2$ | I | CN |
| CF$_3$CF$_2$ | CF$_2$H | CN |
| CF$_3$CF$_2$ | CF$_3$ | CN |
| CF$_3$CF$_2$ | CF$_3$CH$_2$ | CN |
| CF$_3$CF$_2$ | CF$_3$CF$_2$ | CN |
| CF$_3$CF$_2$ | CCl$_3$ | CN |
| CF$_3$CF$_2$ | MeO | CN |
| CCl$_3$ | Me | CN |
| CCl$_3$ | Et | CN |
| CCl$_3$ | Cl | CN |
| CCl$_3$ | Br | CN |
| CCl$_3$ | I | CN |
| CCl$_3$ | CF$_2$H | CN |
| CCl$_3$ | CF$_3$ | CN |
| CCl$_3$ | CF$_3$CH$_2$ | CN |
| CCl$_3$ | CF$_3$CF$_2$ | CN |
| CCl$_3$ | CCl$_3$ | CN |
| CCl$_3$ | MeO | CN |
| MeO | Me | CN |
| MeO | Et | CN |
| MeO | Cl | CN |
| MeO | Br | CN |
| MeO | I | CN |
| MeO | CF$_2$H | CN |
| MeO | CF$_3$ | CN |
| MeO | CF$_3$CH$_2$ | CN |
| MeO | CF$_3$CF$_2$ | CN |
| MeO | CCl$_3$ | CN |
| MeO | MeO | CN |
| OCF$_2$H | Me | CN |
| OCF$_2$H | Et | CN |
| OCF$_2$H | Cl | CN |
| OCF$_2$H | Br | CN |
| OCF$_2$H | I | CN |
| OCF$_2$H | CF$_2$H | CN |
| OCF$_2$H | CF$_3$ | CN |

TABLE 6E-continued

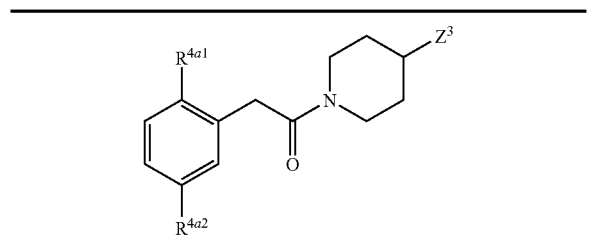

| $R^{4a1}$ | $R^{4a2}$ | $Z^3$ |
|---|---|---|
| OCF$_2$H | CF$_3$CH$_2$ | CN |
| OCF$_2$H | CF$_3$CF$_2$ | CN |
| OCF$_2$H | CCl$_3$ | CN |
| OCF$_2$H | MeO | CN |
| Me | Me | C(=S)NH$_2$ |
| Me | Et | C(=S)NH$_2$ |
| Me | Cl | C(=S)NH$_2$ |
| Me | Br | C(=S)NH$_2$ |
| Me | I | C(=S)NH$_2$ |
| Me | CF$_2$H | C(=S)NH$_2$ |
| Me | CF$_3$ | C(=S)NH$_2$ |
| Me | CF$_3$CH$_2$ | C(=S)NH$_2$ |
| Me | CF$_3$CF$_2$ | C(=S)NH$_2$ |
| Me | CCl$_3$ | C(=S)NH$_2$ |
| Me | MeO | C(=S)NH$_2$ |
| Et | Me | C(=S)NH$_2$ |
| Et | Et | C(=S)NH$_2$ |
| Et | Cl | C(=S)NH$_2$ |
| Et | Br | C(=S)NH$_2$ |
| Et | I | C(=S)NH$_2$ |
| Et | CF$_2$H | C(=S)NH$_2$ |
| Et | CF$_3$ | C(=S)NH$_2$ |
| Et | CF$_3$CH$_2$ | C(=S)NH$_2$ |
| Et | CF$_3$CF$_2$ | C(=S)NH$_2$ |
| Et | CCl$_3$ | C(=S)NH$_2$ |
| Et | MeO | C(=S)NH$_2$ |
| Cl | Me | C(=S)NH$_2$ |
| Cl | Et | C(=S)NH$_2$ |
| Cl | Cl | C(=S)NH$_2$ |
| Cl | Br | C(=S)NH$_2$ |
| Cl | I | C(=S)NH$_2$ |
| Cl | CF$_2$H | C(=S)NH$_2$ |
| Cl | CF$_3$ | C(=S)NH$_2$ |
| Cl | CF$_3$CH$_2$ | C(=S)NH$_2$ |
| Cl | CF$_3$CF$_2$ | C(=S)NH$_2$ |
| Cl | CCl$_3$ | C(=S)NH$_2$ |
| Cl | MeO | C(=S)NH$_2$ |
| Br | Me | C(=S)NH$_2$ |
| Br | Et | C(=S)NH$_2$ |
| Br | Cl | C(=S)NH$_2$ |
| Br | Br | C(=S)NH$_2$ |
| Br | I | C(=S)NH$_2$ |
| Br | CF$_2$H | C(=S)NH$_2$ |
| Br | CF$_3$ | C(=S)NH$_2$ |
| Br | CF$_3$CH$_2$ | C(=S)NH$_2$ |
| Br | CF$_3$CF$_2$ | C(=S)NH$_2$ |
| Br | CCl$_3$ | C(=S)NH$_2$ |
| Br | MeO | C(=S)NH$_2$ |
| I | Me | C(=S)NH$_2$ |
| I | Et | C(=S)NH$_2$ |
| I | Cl | C(=S)NH$_2$ |
| I | Br | C(=S)NH$_2$ |
| I | I | C(=S)NH$_2$ |
| I | CF$_2$H | C(=S)NH$_2$ |
| I | CF$_3$ | C(=S)NH$_2$ |
| I | CF$_3$CH$_2$ | C(=S)NH$_2$ |
| I | CF$_3$CF$_2$ | C(=S)NH$_2$ |
| I | CCl$_3$ | C(=S)NH$_2$ |
| I | MeO | C(=S)NH$_2$ |
| CF$_2$H | Me | C(=S)NH$_2$ |
| CF$_2$H | Et | C(=S)NH$_2$ |
| CF$_2$H | Cl | C(=S)NH$_2$ |
| CF$_2$H | Br | C(=S)NH$_2$ |
| CF$_2$H | I | C(=S)NH$_2$ |
| CF$_2$H | CF$_2$H | C(=S)NH$_2$ |
| CF$_2$H | CF$_3$ | C(=S)NH$_2$ |

TABLE 6E-continued

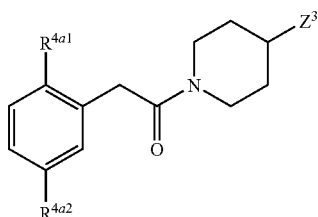

| $R^{4a1}$ | $R^{4a2}$ | $Z^3$ |
|---|---|---|
| CF$_2$H | CF$_3$CH$_2$ | C(=S)NH$_2$ |
| CF$_2$H | CF$_3$CF$_2$ | C(=S)NH$_2$ |
| CF$_2$H | CCl$_3$ | C(=S)NH$_2$ |
| CF$_2$H | MeO | C(=S)NH$_2$ |
| CF$_3$ | Me | C(=S)NH$_2$ |
| CF$_3$ | Et | C(=S)NH$_2$ |
| CF$_3$ | Cl | C(=S)NH$_2$ |
| CF$_3$ | Br | C(=S)NH$_2$ |
| CF$_3$ | I | C(=S)NH$_2$ |
| CF$_3$ | CF$_2$H | C(=S)NH$_2$ |
| CF$_3$ | CF$_3$ | C(=S)NH$_2$ |
| CF$_3$ | CF$_3$CH$_2$ | C(=S)NH$_2$ |
| CF$_3$ | CF$_3$CF$_2$ | C(=S)NH$_2$ |
| CF$_3$ | CCl$_3$ | C(=S)NH$_2$ |
| CF$_3$ | MeO | C(=S)NH$_2$ |
| CF$_3$CH$_2$ | Me | C(=S)NH$_2$ |
| CF$_3$CH$_2$ | Et | C(=S)NH$_2$ |
| CF$_3$CH$_2$ | Cl | C(=S)NH$_2$ |
| CF$_3$CH$_2$ | Br | C(=S)NH$_2$ |
| CF$_3$CH$_2$ | I | C(=S)NH$_2$ |
| CF$_3$CH$_2$ | CF$_2$H | C(=S)NH$_2$ |
| CF$_3$CH$_2$ | CF$_3$ | C(=S)NH$_2$ |
| CF$_3$CH$_2$ | CF$_3$CH$_2$ | C(=S)NH$_2$ |
| CF$_3$CH$_2$ | CF$_3$CF$_2$ | C(=S)NH$_2$ |
| CF$_3$CH$_2$ | CCl$_3$ | C(=S)NH$_2$ |
| CF$_3$CH$_2$ | MeO | C(=S)NH$_2$ |
| CF$_3$CF$_2$ | Me | C(=S)NH$_2$ |
| CF$_3$CF$_2$ | Et | C(=S)NH$_2$ |
| CF$_3$CF$_2$ | Cl | C(=S)NH$_2$ |
| CF$_3$CF$_2$ | Br | C(=S)NH$_2$ |
| CF$_3$CF$_2$ | I | C(=S)NH$_2$ |
| CF$_3$CF$_2$ | CF$_2$H | C(=S)NH$_2$ |
| CF$_3$CF$_2$ | CF$_3$ | C(=S)NH$_2$ |
| CF$_3$CF$_2$ | CF$_3$CH$_2$ | C(=S)NH$_2$ |
| CF$_3$CF$_2$ | CF$_3$CF$_2$ | C(=S)NH$_2$ |
| CF$_3$CF$_2$ | CCl$_3$ | C(=S)NH$_2$ |
| CF$_3$CF$_2$ | MeO | C(=S)NH$_2$ |
| CCl$_3$ | Me | C(=S)NH$_2$ |
| CCl$_3$ | Et | C(=S)NH$_2$ |
| CCl$_3$ | Cl | C(=S)NH$_2$ |
| CCl$_3$ | Br | C(=S)NH$_2$ |
| CCl$_3$ | I | C(=S)NH$_2$ |
| CCl$_3$ | CF$_2$H | C(=S)NH$_2$ |
| CCl$_3$ | CF$_3$ | C(=S)NH$_2$ |
| CCl$_3$ | CF$_3$CH$_2$ | C(=S)NH$_2$ |
| CCl$_3$ | CF$_3$CF$_2$ | C(=S)NH$_2$ |
| CCl$_3$ | CCl$_3$ | C(=S)NH$_2$ |
| CCl$_3$ | MeO | C(=S)NH$_2$ |
| MeO | Me | C(=S)NH$_2$ |
| MeO | Et | C(=S)NH$_2$ |
| MeO | Cl | C(=S)NH$_2$ |
| MeO | Br | C(=S)NH$_2$ |
| MeO | I | C(=S)NH$_2$ |
| MeO | CF$_2$H | C(=S)NH$_2$ |
| MeO | CF$_3$ | C(=S)NH$_2$ |
| MeO | CF$_3$CH$_2$ | C(=S)NH$_2$ |
| MeO | CF$_3$CF$_2$ | C(=S)NH$_2$ |
| MeO | CCl$_3$ | C(=S)NH$_2$ |
| MeO | MeO | C(=S)NH$_2$ |
| OCF$_2$H | Me | C(=S)NH$_2$ |
| OCF$_2$H | Et | C(=S)NH$_2$ |
| OCF$_2$H | Cl | C(=S)NH$_2$ |
| OCF$_2$H | Br | C(=S)NH$_2$ |
| OCF$_2$H | I | C(=S)NH$_2$ |
| OCF$_2$H | CF$_2$H | C(=S)NH$_2$ |
| OCF$_2$H | CF$_3$ | C(=S)NH$_2$ |

TABLE 6E-continued

Structure: 2,5-disubstituted phenyl-CH2-C(=O)-N(piperidine-4-Z³), with R^4a1 at position 2 and R^4a2 at position 5.

| R^4a1 | R^4a2 | Z³ |
|---|---|---|
| OCF₂H | CF₃CH₂ | C(=S)NH₂ |
| OCF₂H | CF₃CF₂ | C(=S)NH₂ |
| OCF₂H | CCl₃ | C(=S)NH₂ |
| OCF₂H | MeO | C(=S)NH₂ |

The present disclosure includes Table 6E^a wherein the piperidinyl moiety in the structure above Table 6E is replaced with piperazinyl, and R^4a1, R^4a2 and Z³ are as listed in Table 6E. For example, Table 6E^a specifically discloses 4-[2-(2,5-dimethylphenyl)acetyl]-1-piperazinecarbothioamide, 4-[2-(2,5-diclorophenyl)acetyl]-1-piperazinecarbothioamide and 4-[2-[2-chloro-5-(trifluoromethyl)phenyl]acetyl]-1-piperazinecarbothioamide.

TABLE 6F

Structure: 2,5-disubstituted phenyl-CH(R¹⁵)-C(=O)-N(piperidine-4-Z³), R¹⁵ is OH.

| R^4a1 | R^4a2 | Z³ |
|---|---|---|
| Me | Me | CN |
| Me | Et | CN |
| Me | Cl | CN |
| Me | Br | CN |
| Me | I | CN |
| Me | CF₂H | CN |
| Me | CF₃ | CN |
| Me | CF₃CH₂ | CN |
| Me | CF₃CF₂ | CN |
| Me | CCl₃ | CN |
| Me | MeO | CN |
| Et | Me | CN |
| Et | Et | CN |
| Et | Cl | CN |
| Et | Br | CN |
| Et | I | CN |
| Et | CF₂H | CN |
| Et | CF₃ | CN |
| Et | CF₃CH₂ | CN |
| Et | CF₃CF₂ | CN |
| Et | CCl₃ | CN |
| Et | MeO | CN |
| Cl | Me | CN |
| Cl | Et | CN |
| Cl | Cl | CN |
| Cl | Br | CN |
| Cl | I | CN |
| Cl | CF₂H | CN |
| Cl | CF₃ | CN |
| Cl | CF₃CH₂ | CN |
| Cl | CF₃CF₂ | CN |
| Cl | CCl₃ | CN |

TABLE 6F-continued

Structure: 2,5-disubstituted phenyl-CH(R¹⁵)-C(=O)-N(piperidine-4-Z³), R¹⁵ is OH.

| R^4a1 | R^4a2 | Z³ |
|---|---|---|
| Cl | MeO | CN |
| Br | Me | CN |
| Br | Et | CN |
| Br | Cl | CN |
| Br | Br | CN |
| Br | I | CN |
| Br | CF₂H | CN |
| Br | CF₃ | CN |
| Br | CF₃CH₂ | CN |
| Br | CF₃CF₂ | CN |
| Br | CCl₃ | CN |
| Br | MeO | CN |
| I | Me | CN |
| I | Et | CN |
| I | Cl | CN |
| I | Br | CN |
| I | I | CN |
| I | CF₂H | CN |
| I | CF₃ | CN |
| I | CF₃CH₂ | CN |
| I | CF₃CF₂ | CN |
| I | CCl₃ | CN |
| I | MeO | CN |
| CF₂H | Me | CN |
| CF₂H | Et | CN |
| CF₂H | Cl | CN |
| CF₂H | Br | CN |
| CF₂H | I | CN |
| CF₂H | CF₂H | CN |
| CF₂H | CF₃ | CN |
| CF₂H | CF₃CH₂ | CN |
| CF₂H | CF₃CF₂ | CN |
| CF₂H | CCl₃ | CN |
| CF₂H | MeO | CN |
| CF₃ | Me | CN |
| CF₃ | Et | CN |
| CF₃ | Cl | CN |
| CF₃ | Br | CN |
| CF₃ | I | CN |
| CF₃ | CF₂H | CN |
| CF₃ | CF₃ | CN |
| CF₃ | CF₃CH₂ | CN |
| CF₃ | CF₃CF₂ | CN |
| CF₃ | CCl₃ | CN |
| CF₃ | MeO | CN |
| CF₃CH₂ | Me | CN |
| CF₃CH₂ | Et | CN |
| CF₃CH₂ | Cl | CN |
| CF₃CH₂ | Br | CN |
| CF₃CH₂ | I | CN |
| CF₃CH₂ | CF₂H | CN |
| CF₃CH₂ | CF₃ | CN |
| CF₃CH₂ | CF₃CH₂ | CN |
| CF₃CH₂ | CF₃CF₂ | CN |
| CF₃CH₂ | CCl₃ | CN |
| CF₃CH₂ | MeO | CN |
| CF₃CF₂ | Me | CN |
| CF₃CF₂ | Et | CN |
| CF₃CF₂ | Cl | CN |
| CF₃CF₂ | Br | CN |
| CF₃CF₂ | I | CN |
| CF₃CF₂ | CF₂H | CN |
| CF₃CF₂ | CF₃ | CN |
| CF₃CF₂ | CF₃CH₂ | CN |

TABLE 6F-continued

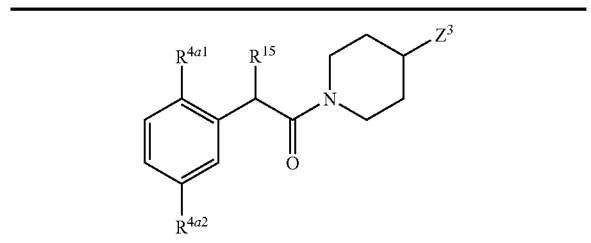

R$^{15}$ is OH

| R$^{4a1}$ | R$^{4a2}$ | Z$^3$ |
|---|---|---|
| CF$_3$CF$_2$ | CF$_3$CF$_2$ | CN |
| CF$_3$CF$_2$ | CCl$_3$ | CN |
| CF$_3$CF$_2$ | MeO | CN |
| CCl$_3$ | Me | CN |
| CCl$_3$ | Et | CN |
| CCl$_3$ | Cl | CN |
| CCl$_3$ | Br | CN |
| CCl$_3$ | I | CN |
| CCl$_3$ | CF$_2$H | CN |
| CCl$_3$ | CF$_3$ | CN |
| CCl$_3$ | CF$_3$CH$_2$ | CN |
| CCl$_3$ | CF$_3$CF$_2$ | CN |
| CCl$_3$ | CCl$_3$ | CN |
| CCl$_3$ | MeO | CN |
| MeO | Me | CN |
| MeO | Et | CN |
| MeO | Cl | CN |
| MeO | Br | CN |
| MeO | I | CN |
| MeO | CF$_2$H | CN |
| MeO | CF$_3$ | CN |
| MeO | CF$_3$CH$_2$ | CN |
| MeO | CF$_3$CF$_2$ | CN |
| MeO | CCl$_3$ | CN |
| MeO | MeO | CN |
| OCF$_2$H | Me | CN |
| OCF$_2$H | Et | CN |
| OCF$_2$H | Cl | CN |
| OCF$_2$H | Br | CN |
| OCF$_2$H | I | CN |
| OCF$_2$H | CF$_2$H | CN |
| OCF$_2$H | CF$_3$ | CN |
| OCF$_2$H | CF$_3$CH$_2$ | CN |
| OCF$_2$H | CF$_3$CF$_2$ | CN |
| OCF$_2$H | CCl$_3$ | CN |
| OCF$_2$H | MeO | CN |
| Me | Me | C(=S)NH$_2$ |
| Me | Et | C(=S)NH$_2$ |
| Me | Cl | C(=S)NH$_2$ |
| Me | Br | C(=S)NH$_2$ |
| Me | I | C(=S)NH$_2$ |
| Me | CF$_2$H | C(=S)NH$_2$ |
| Me | CF$_3$ | C(=S)NH$_2$ |
| Me | CF$_3$CH$_2$ | C(=S)NH$_2$ |
| Me | CF$_3$CF$_2$ | C(=S)NH$_2$ |
| Me | CCl$_3$ | C(=S)NH$_2$ |
| Me | MeO | C(=S)NH$_2$ |
| Et | Me | C(=S)NH$_2$ |
| Et | Et | C(=S)NH$_2$ |
| Et | Cl | C(=S)NH$_2$ |
| Et | Br | C(=S)NH$_2$ |
| Et | I | C(=S)NH$_2$ |
| Et | CF$_2$H | C(=S)NH$_2$ |
| Et | CF$_3$ | C(=S)NH$_2$ |
| Et | CF$_3$CH$_2$ | C(=S)NH$_2$ |
| Et | CF$_3$CF$_2$ | C(=S)NH$_2$ |
| Et | CCl$_3$ | C(=S)NH$_2$ |
| Et | MeO | C(=S)NH$_2$ |
| Cl | Me | C(=S)NH$_2$ |
| Cl | Et | C(=S)NH$_2$ |
| Cl | Cl | C(=S)NH$_2$ |
| Cl | Br | C(=S)NH$_2$ |
| Cl | I | C(=S)NH$_2$ |
| Cl | CF$_2$H | C(=S)NH$_2$ |

TABLE 6F-continued

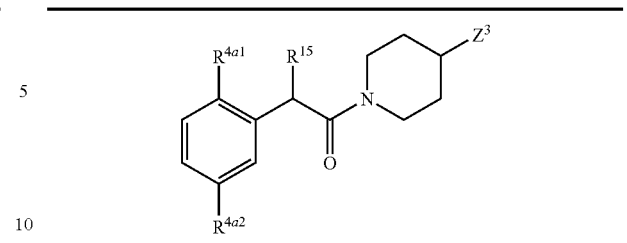

R$^{15}$ is OH

| R$^{4a1}$ | R$^{4a2}$ | Z$^3$ |
|---|---|---|
| Cl | CF$_3$ | C(=S)NH$_2$ |
| Cl | CF$_3$CH$_2$ | C(=S)NH$_2$ |
| Cl | CF$_3$CF$_2$ | C(=S)NH$_2$ |
| Cl | CCl$_3$ | C(=S)NH$_2$ |
| Cl | MeO | C(=S)NH$_2$ |
| Br | Me | C(=S)NH$_2$ |
| Br | Et | C(=S)NH$_2$ |
| Br | Cl | C(=S)NH$_2$ |
| Br | Br | C(=S)NH$_2$ |
| Br | I | C(=S)NH$_2$ |
| Br | CF$_2$H | C(=S)NH$_2$ |
| Br | CF$_3$ | C(=S)NH$_2$ |
| Br | CF$_3$CH$_2$ | C(=S)NH$_2$ |
| Br | CF$_3$CF$_2$ | C(=S)NH$_2$ |
| Br | CCl$_3$ | C(=S)NH$_2$ |
| Br | MeO | C(=S)NH$_2$ |
| I | Me | C(=S)NH$_2$ |
| I | Et | C(=S)NH$_2$ |
| I | Cl | C(=S)NH$_2$ |
| I | Br | C(=S)NH$_2$ |
| I | I | C(=S)NH$_2$ |
| I | CF$_2$H | C(=S)NH$_2$ |
| I | CF$_3$ | C(=S)NH$_2$ |
| I | CF$_3$CH$_2$ | C(=S)NH$_2$ |
| I | CF$_3$CF$_2$ | C(=S)NH$_2$ |
| I | CCl$_3$ | C(=S)NH$_2$ |
| I | MeO | C(=S)NH$_2$ |
| CF$_2$H | Me | C(=S)NH$_2$ |
| CF$_2$H | Et | C(=S)NH$_2$ |
| CF$_2$H | Cl | C(=S)NH$_2$ |
| CF$_2$H | Br | C(=S)NH$_2$ |
| CF$_2$H | I | C(=S)NH$_2$ |
| CF$_2$H | CF$_2$H | C(=S)NH$_2$ |
| CF$_2$H | CF$_3$ | C(=S)NH$_2$ |
| CF$_2$H | CF$_3$CH$_2$ | C(=S)NH$_2$ |
| CF$_2$H | CF$_3$CF$_2$ | C(=S)NH$_2$ |
| CF$_2$H | CCl$_3$ | C(=S)NH$_2$ |
| CF$_2$H | MeO | C(=S)NH$_2$ |
| CF$_3$ | Me | C(=S)NH$_2$ |
| CF$_3$ | Et | C(=S)NH$_2$ |
| CF$_3$ | Cl | C(=S)NH$_2$ |
| CF$_3$ | Br | C(=S)NH$_2$ |
| CF$_3$ | I | C(=S)NH$_2$ |
| CF$_3$ | CF$_2$H | C(=S)NH$_2$ |
| CF$_3$ | CF$_3$ | C(=S)NH$_2$ |
| CF$_3$ | CF$_3$CH$_2$ | C(=S)NH$_2$ |
| CF$_3$ | CF$_3$CF$_2$ | C(=S)NH$_2$ |
| CF$_3$ | CCl$_3$ | C(=S)NH$_2$ |
| CF$_3$ | MeO | C(=S)NH$_2$ |
| CF$_3$CH$_2$ | Me | C(=S)NH$_2$ |
| CF$_3$CH$_2$ | Et | C(=S)NH$_2$ |
| CF$_3$CH$_2$ | Cl | C(=S)NH$_2$ |
| CF$_3$CH$_2$ | Br | C(=S)NH$_2$ |
| CF$_3$CH$_2$ | I | C(=S)NH$_2$ |
| CF$_3$CH$_2$ | CF$_2$H | C(=S)NH$_2$ |
| CF$_3$CH$_2$ | CF$_3$ | C(=S)NH$_2$ |
| CF$_3$CH$_2$ | CF$_3$CH$_2$ | C(=S)NH$_2$ |
| CF$_3$CH$_2$ | CF$_3$CF$_2$ | C(=S)NH$_2$ |
| CF$_3$CH$_2$ | CCl$_3$ | C(=S)NH$_2$ |
| CF$_3$CH$_2$ | MeO | C(=S)NH$_2$ |
| CF$_3$CF$_2$ | Me | C(=S)NH$_2$ |
| CF$_3$CF$_2$ | Et | C(=S)NH$_2$ |
| CF$_3$CF$_2$ | Cl | C(=S)NH$_2$ |
| CF$_3$CF$_2$ | Br | C(=S)NH$_2$ |

TABLE 6F-continued

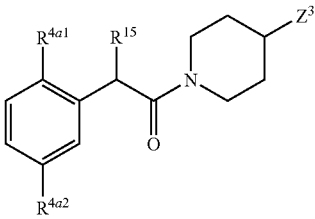

$R^{15}$ is OH

| $R^{4a1}$ | $R^{4a2}$ | $Z^3$ |
|---|---|---|
| $CF_3CF_2$ | I | $C(=S)NH_2$ |
| $CF_3CF_2$ | $CF_2H$ | $C(=S)NH_2$ |
| $CF_3CF_2$ | $CF_3$ | $C(=S)NH_2$ |
| $CF_3CF_2$ | $CF_3CH_2$ | $C(=S)NH_2$ |
| $CF_3CF_2$ | $CF_3CF_2$ | $C(=S)NH_2$ |
| $CF_3CF_2$ | $CCl_3$ | $C(=S)NH_2$ |
| $CF_3CF_2$ | MeO | $C(=S)NH_2$ |
| $CCl_3$ | Me | $C(=S)NH_2$ |
| $CCl_3$ | Et | $C(=S)NH_2$ |
| $CCl_3$ | Cl | $C(=S)NH_2$ |
| $CCl_3$ | Br | $C(=S)NH_2$ |
| $CCl_3$ | I | $C(=S)NH_2$ |
| $CCl_3$ | $CF_2H$ | $C(=S)NH_2$ |
| $CCl_3$ | $CF_3$ | $C(=S)NH_2$ |
| $CCl_3$ | $CF_3CH_2$ | $C(=S)NH_2$ |
| $CCl_3$ | $CF_3CF_2$ | $C(=S)NH_2$ |
| $CCl_3$ | $CCl_3$ | $C(=S)NH_2$ |
| $CCl_3$ | MeO | $C(=S)NH_2$ |
| MeO | Me | $C(=S)NH_2$ |
| MeO | Et | $C(=S)NH_2$ |
| MeO | Cl | $C(=S)NH_2$ |
| MeO | Br | $C(=S)NH_2$ |
| MeO | I | $C(=S)NH_2$ |
| MeO | $CF_2H$ | $C(=S)NH_2$ |
| MeO | $CF_3$ | $C(=S)NH_2$ |
| MeO | $CF_3CH_2$ | $C(=S)NH_2$ |
| MeO | $CF_3CF_2$ | $C(=S)NH_2$ |
| MeO | $CCl_3$ | $C(=S)NH_2$ |
| MeO | MeO | $C(=S)NH_2$ |
| $OCF_2H$ | Me | $C(=S)NH_2$ |
| $OCF_2H$ | Et | $C(=S)NH_2$ |
| $OCF_2H$ | Cl | $C(=S)NH_2$ |
| $OCF_2H$ | Br | $C(=S)NH_2$ |
| $OCF_2H$ | I | $C(=S)NH_2$ |
| $OCF_2H$ | $CF_2H$ | $C(=S)NH_2$ |
| $OCF_2H$ | $CF_3$ | $C(=S)NH_2$ |
| $OCF_2H$ | $CF_3CH_2$ | $C(=S)NH_2$ |
| $OCF_2H$ | $CF_3CF_2$ | $C(=S)NH_2$ |
| $OCF_2H$ | $CCl_3$ | $C(=S)NH_2$ |
| $OCF_2H$ | MeO | $C(=S)NH_2$ |

$R^{15}$ is OH

The present disclosure includes Table $6F^a$ wherein $R^{15}$ in the structure above Table 6F is OMe, and $R^{4a1}$, $R^{4a2}$ and $Z^3$ are as listed in Table 6F. For example, Table $6F^a$ specifically discloses 1-[2-(2,5-dimethylphenyl)-2-methoxyacetyl]-4-piperdinecarbothioamide, 1-[2-(2,5-dichlorophenyl)-2-methoxyacetyl]-4-piperdinecarbothioamide and 1-[2-[2-chloro-5-(trifluoromethyl)phenyl]-2-methoxyacetyl]-4-piperdinecarbothioamide.

Also, the present disclosure includes Table $6F^b$ wherein $R^{15}$ in the structure above Table 6F is $CH_3C(=O)-$, and $R^{4a1}$, $R^{4a2}$ and $Z^3$ are as listed in Table 6F. For example, Table $6F^b$ specifically discloses 1-[2-(acetyloxy)-2-(2,5-dimethylphenyl)acetyl]-4-piperdine-carbothioamide, 1-[2-acetyloxy)-2-(2,5-dichlorophenyl)acetyl]-4-piperidinecarbothioamide and 1-[2-(acetyloxy)-2-[2-chloro-5-(trifluoromethyl)phenyl]acetyl]-4-piperidinecarbothioamide.

The present disclosure includes Table $6F^c$ wherein the piperidinyl moiety in the structure above Table 6F is replaced with piperazinyl, and $R^{4a1}$, $R^{4a2}$ and $Z^3$ are as listed in Table 6F. For example, Table $6F^c$ specifically discloses 4-[2-(2,5-dimethylphenyl)-2-hydroxyacetyl]-1-piperazinecarbothioamide, 4-[2-(2,5-dichlorophenyl)-2-hydroxyacetyl]-1-piperazinecarbothioamide and 4-[2-[2-chloro-5-(trifluoromethyl)phenyl]-2-hydroxyacetyl]-1-piperazinecarbothioamide.

The invention includes but is not limited to the following exemplary species of Formula 1B compounds.

TABLE 7*

M—C(=O)—$J^1$

| M | $J^1$ |
|---|---|
| $CH_3$ | J-29-1 |
| $CH_2Cl$ | J-29-1 |
| $CH_2Br$ | J-29-1 |
| $CH_2I$ | J-29-1 |
| OH | J-29-1 |
| OMe | J-29-1 |
| OEt | J-29-1 |
| OPr | J-29-1 |
| O—i-Pr | J-29-1 |
| O—n-Bu | J-29-1 |
| O—t-Bu | J-29-1 |
| $NMe_2$ | J-29-1 |
| $NEt_2$ | J-29-1 |
| $N(n-Pr)_2$ | J-29-1 |
| 1-piperdinyl | J-29-1 |
| 1-pyrrolidinyl | J-29-1 |
| 4-morpholinyl | J-29-1 |
| $CH_3$ | J-29-2 |
| $CH_2Cl$ | J-29-2 |
| $CH_2Br$ | J-29-2 |
| $CH_2I$ | J-29-2 |
| OH | J-29-2 |
| OMe | J-29-2 |
| OEt | J-29-2 |
| OPr | J-29-2 |
| O—i-Pr | J-29-2 |
| O—n-Bu | J-29-2 |
| O—t-Bu | J-29-2 |
| $NMe_2$ | J-29-2 |
| $NEt_2$ | J-29-2 |
| $N(n-Pr)_2$ | J-29-2 |
| 1-piperdinyl | J-29-2 |
| 1-pyrrolidinyl | J-29-2 |
| 4-morpholinyl | J-29-2 |
| $CH_3$ | J-29-3 |
| $CH_2Cl$ | J-29-3 |
| $CH_2Br$ | J-29-3 |
| $CH_2I$ | J-29-3 |
| OH | J-29-3 |
| OMe | J-29-3 |
| OEt | J-29-3 |
| OPr | J-29-3 |
| O—i-Pr | J-29-3 |
| O—n-Bu | J-29-3 |
| O—t-Bu | J-29-3 |
| $NMe_2$ | J-29-3 |
| $NEt_2$ | J-29-3 |
| $N(n-Pr)_2$ | J-29-3 |
| 1-piperdinyl | J-29-3 |
| 1-pyrrolidinyl | J-29-3 |
| 4-morpholinyl | J-29-3 |
| $CH_3$ | J-29-4 |
| $CH_2Cl$ | J-29-4 |
| $CH_2Br$ | J-29-4 |
| $CH_2I$ | J-29-4 |
| OH | J-29-4 |
| OMe | J-29-4 |
| OEt | J-29-4 |
| OPr | J-29-4 |
| O—i-Pr | J-29-4 |
| O—n-Bu | J-29-4 |

TABLE 7*-continued $$\underset{O}{M-C-J^1}$$

| M | J¹ |
|---|---|
| O—t-Bu | J-29-4 |
| NMe₂ | J-29-4 |
| NEt₂ | J-29-4 |
| N(n-Pr)₂ | J-29-4 |
| 1-piperdinyl | J-29-4 |
| 1-pyrrolidinyl | J-29-4 |
| 4-morpholinyl | J-29-4 |
| CH₃ | J-29-5 |
| CH₂Cl | J-29-5 |
| CH₂Br | J-29-5 |
| CH₂I | J-29-5 |
| OH | J-29-5 |
| OMe | J-29-5 |
| OEt | J-29-5 |
| OPr | J-29-5 |
| O—i-Pr | J-29-5 |
| O—n-Bu | J-29-5 |
| O—t-Bu | J-29-5 |
| NMe₂ | J-29-5 |
| NEt₂ | J-29-5 |
| N(n-Pr)₂ | J-29-5 |
| 1-piperdinyl | J-29-5 |
| 1-pyrrolidinyl | J-29-5 |
| 4-morpholinyl | J-29-5 |
| CH₃ | J-29-6 |
| CH₂Cl | J-29-6 |
| CH₂Br | J-29-6 |
| CH₂I | J-29-6 |
| OH | J-29-6 |
| OMe | J-29-6 |
| OEt | J-29-6 |
| OPr | J-29-6 |
| O—i-Pr | J-29-6 |
| O—n-Bu | J-29-6 |
| O—t-Bu | J-29-6 |
| NMe₂ | J-29-6 |
| NEt₂ | J-29-6 |
| N(n-Pr)₂ | J-29-6 |
| 1-piperdinyl | J-29-6 |
| 1-pyrrolidinyl | J-29-6 |
| 4-morpholinyl | J-29-6 |
| CH₃ | J-29-7 |
| CH₂Cl | J-29-7 |
| CH₂Br | J-29-7 |
| CH₂I | J-29-7 |
| OH | J-29-7 |
| OMe | J-29-7 |
| OEt | J-29-7 |
| OPr | J-29-7 |
| O—i-Pr | J-29-7 |
| O—n-Bu | J-29-7 |
| O—t-Bu | J-29-7 |
| NMe₂ | J-29-7 |
| NEt₂ | J-29-7 |
| N(n-Pr)₂ | J-29-7 |
| 1-piperdinyl | J-29-7 |
| 1-pyrrolidinyl | J-29-7 |
| 4-morpholinyl | J-29-7 |
| CH₃ | J-29-8 |
| CH₂Cl | J-29-8 |
| CH₂Br | J-29-8 |
| CH₂I | J-29-8 |
| OH | J-29-8 |
| OMe | J-29-8 |
| OEt | J-29-8 |
| OPr | J-29-8 |
| O—i-Pr | J-29-8 |
| O—n-Bu | J-29-8 |
| O—t-Bu | J-29-8 |
| NMe₂ | J-29-8 |
| NEt₂ | J-29-8 |
| N(n-Pr)₂ | J-29-8 |
| 1-piperdinyl | J-29-8 |
| 1-pyrrolidinyl | J-29-8 |
| 4-morpholinyl | J-29-8 |
| CH₃ | J-29-9 |
| CH₂Cl | J-29-9 |
| CH₂Br | J-29-9 |
| CH₂I | J-29-9 |
| OH | J-29-9 |
| OMe | J-29-9 |
| OEt | J-29-9 |
| OPr | J-29-9 |
| O—i-Pr | J-29-9 |
| O—n-Bu | J-29-9 |
| O—t-Bu | J-29-9 |
| NMe₂ | J-29-9 |
| NEt₂ | J-29-9 |
| N(n-Pr)₂ | J-29-9 |
| 1-piperdinyl | J-29-9 |
| 1-pyrrolidinyl | J-29-9 |
| 4-morpholinyl | J-29-9 |
| CH₃ | J-29-10 |
| CH₂Cl | J-29-10 |
| CH₂Br | J-29-10 |
| CH₂I | J-29-10 |
| OH | J-29-10 |
| OMe | J-29-10 |
| OEt | J-29-10 |
| OPr | J-29-10 |
| O—i-Pr | J-29-10 |
| O—n-Bu | J-29-10 |
| O—t-Bu | J-29-10 |
| NMe₂ | J-29-10 |
| NEt₂ | J-29-10 |
| N(n-Pr)₂ | J-29-10 |
| 1-piperdinyl | J-29-10 |
| 1-pyrrolidinyl | J-29-10 |
| 4-morpholinyl | J-29-10 |
| CH₃ | J-29-11 |
| CH₂Cl | J-29-11 |
| CH₂Br | J-29-11 |
| CH₂I | J-29-11 |
| OH | J-29-11 |
| OMe | J-29-11 |
| OEt | J-29-11 |
| OPr | J-29-11 |
| O—i-Pr | J-29-11 |
| O—n-Bu | J-29-11 |
| O—t-Bu | J-29-11 |
| NMe₂ | J-29-11 |
| NEt₂ | J-29-11 |
| N(n-Pr)₂ | J-29-11 |
| 1-piperdinyl | J-29-11 |
| 1-pyrrolidinyl | J-29-11 |
| 4-morpholinyl | J-29-11 |
| CH₃ | J-29-12 |
| CH₂Cl | J-29-12 |
| CH₂Br | J-29-12 |
| CH₂I | J-29-12 |
| OH | J-29-12 |
| OMe | J-29-12 |
| OEt | J-29-12 |
| OPr | J-29-12 |
| O—i-Pr | J-29-12 |
| O—n-Bu | J-29-12 |
| O—t-Bu | J-29-12 |
| NMe₂ | J-29-12 |
| NEt₂ | J-29-12 |
| N(n-Pr)₂ | J-29-12 |
| 1-piperdinyl | J-29-12 |
| 1-pyrrolidinyl | J-29-12 |
| 4-morpholinyl | J-29-12 |
| CH₃ | J-29-13 |
| CH₂Cl | J-29-13 |
| CH₂Br | J-29-13 |

TABLE 7*-continued

| M | J¹ |
|---|---|
| CH₂I | J-29-13 |
| OH | J-29-13 |
| OMe | J-29-13 |
| OEt | J-29-13 |
| OPr | J-29-13 |
| O—i-Pr | J-29-13 |
| O—n-Bu | J-29-13 |
| O—t-Bu | J-29-13 |
| NMe₂ | J-29-13 |
| NEt₂ | J-29-13 |
| N(n-Pr)₂ | J-29-13 |
| 1-piperdinyl | J-29-13 |
| 1-pyrrolidinyl | J-29-13 |
| 4-morpholinyl | J-29-13 |
| CH₃ | J-29-14 |
| CH₂Cl | J-29-14 |
| CH₂Br | J-29-14 |
| CH₂I | J-29-14 |
| OH | J-29-14 |
| OMe | J-29-14 |
| OEt | J-29-14 |
| OPr | J-29-14 |
| O—i-Pr | J-29-14 |
| O—n-Bu | J-29-14 |
| O—t-Bu | J-29-14 |
| NMe₂ | J-29-14 |
| NEt₂ | J-29-14 |
| N(n-Pr)₂ | J-29-14 |
| 1-piperdinyl | J-29-14 |
| 1-pyrrolidinyl | J-29-14 |
| 4-morpholinyl | J-29-14 |
| CH₃ | J-29-15 |
| CH₂Cl | J-29-15 |
| CH₂Br | J-29-15 |
| CH₂I | J-29-15 |
| OH | J-29-15 |
| OMe | J-29-15 |
| OEt | J-29-15 |
| OPr | J-29-15 |
| O—i-Pr | J-29-15 |
| O—n-Bu | J-29-15 |
| O—t-Bu | J-29-15 |
| NMe₂ | J-29-15 |
| NEt₂ | J-29-15 |
| N(n-Pr)₂ | J-29-15 |
| 1-piperdinyl | J-29-15 |
| 1-pyrrolidinyl | J-29-15 |
| 4-morpholinyl | J-29-15 |
| CH₃ | J-29-16 |
| CH₂Cl | J-29-16 |
| CH₂Br | J-29-16 |
| CH₂I | J-29-16 |
| OH | J-29-16 |
| OMe | J-29-16 |
| OEt | J-29-16 |
| OPr | J-29-16 |
| O—i-Pr | J-29-16 |
| O—n-Bu | J-29-16 |
| O—t-Bu | J-29-16 |
| NMe₂ | J-29-16 |
| NEt₂ | J-29-16 |
| N(n-Pr)₂ | J-29-16 |
| 1-piperdinyl | J-29-16 |
| 1-pyrrolidinyl | J-29-16 |
| 4-morpholinyl | J-29-16 |
| CH₃ | J-29-17 |
| CH₂Cl | J-29-17 |
| CH₂Br | J-29-17 |
| CH₂I | J-29-17 |
| OH | J-29-17 |
| OMe | J-29-17 |
| OEt | J-29-17 |
| OPr | J-29-17 |
| O—i-Pr | J-29-17 |
| O—n-Bu | J-29-17 |
| O—t-Bu | J-29-17 |
| NMe₂ | J-29-17 |
| NEt₂ | J-29-17 |
| N(n-Pr)₂ | J-29-17 |
| 1-piperdinyl | J-29-17 |
| 1-pyrrolidinyl | J-29-17 |
| 4-morpholinyl | J-29-17 |
| CH₃ | J-29-18 |
| CH₂Cl | J-29-18 |
| CH₂Br | J-29-18 |
| CH₂I | J-29-18 |
| OH | J-29-18 |
| OMe | J-29-18 |
| OEt | J-29-18 |
| OPr | J-29-18 |
| O—i-Pr | J-29-18 |
| O—n-Bu | J-29-18 |
| O—t-Bu | J-29-18 |
| NMe₂ | J-29-18 |
| NEt₂ | J-29-18 |
| N(n-Pr)₂ | J-29-18 |
| 1-piperdinyl | J-29-18 |
| 1-pyrrolidinyl | J-29-18 |
| 4-morpholinyl | J-29-18 |
| CH₃ | J-29-19 |
| CH₂Cl | J-29-19 |
| CH₂Br | J-29-19 |
| CH₂I | J-29-19 |
| OH | J-29-19 |
| OMe | J-29-19 |
| OEt | J-29-19 |
| OPr | J-29-19 |
| O—i-Pr | J-29-19 |
| O—n-Bu | J-29-19 |
| O—t-Bu | J-29-19 |
| NMe₂ | J-29-19 |
| NEt₂ | J-29-19 |
| N(n-Pr)₂ | J-29-19 |
| 1-piperdinyl | J-29-19 |
| 1-pyrrolidinyl | J-29-19 |
| 4-morpholinyl | J-29-19 |
| CH₃ | J-29-20 |
| CH₂Cl | J-29-20 |
| CH₂Br | J-29-20 |
| CH₂I | J-29-20 |
| OH | J-29-20 |
| OMe | J-29-20 |
| OEt | J-29-20 |
| OPr | J-29-20 |
| O—i-Pr | J-29-20 |
| O—n-Bu | J-29-20 |
| O—t-Bu | J-29-20 |
| NMe₂ | J-29-20 |
| NEt₂ | J-29-20 |
| N(n-Pr)₂ | J-29-20 |
| 1-piperdinyl | J-29-20 |
| 1-pyrrolidinyl | J-29-20 |
| 4-morpholinyl | J-29-20 |
| CH₃ | J-29-21 |
| CH₂Cl | J-29-21 |
| CH₂Br | J-29-21 |
| CH₂I | J-29-21 |
| OH | J-29-21 |
| OMe | J-29-21 |
| OEt | J-29-21 |
| OPr | J-29-21 |
| O—i-Pr | J-29-21 |
| O—n-Bu | J-29-21 |
| O—t-Bu | J-29-21 |
| NMe₂ | J-29-21 |
| NEt₂ | J-29-21 |

TABLE 7*-continued

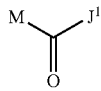

| M | J¹ |
|---|---|
| N(n-Pr)₂ | J-29-21 |
| 1-piperdinyl | J-29-21 |
| 1-pyrrolidinyl | J-29-21 |
| 4-morpholinyl | J-29-21 |
| CH₃ | J-29-22 |
| CH₂Cl | J-29-22 |
| CH₂Br | J-29-22 |
| CH₂I | J-29-22 |
| OH | J-29-22 |
| OMe | J-29-22 |
| OEt | J-29-22 |
| OPr | J-29-22 |
| O—i-Pr | J-29-22 |
| O—n-Bu | J-29-22 |
| O—t-Bu | J-29-22 |
| NMe₂ | J-29-22 |
| NEt₂ | J-29-22 |
| N(n-Pr)₂ | J-29-22 |
| 1-piperdinyl | J-29-22 |
| 1-pyrrolidinyl | J-29-22 |
| 4-morpholinyl | J-29-22 |
| CH₃ | J-29-23 |
| CH₂Cl | J-29-23 |
| CH₂Br | J-29-23 |
| CH₂I | J-29-23 |
| OH | J-29-23 |
| OMe | J-29-23 |
| OEt | J-29-23 |
| OPr | J-29-23 |
| O—i-Pr | J-29-23 |
| O—n-Bu | J-29-23 |
| O—t-Bu | J-29-23 |
| NMe₂ | J-29-23 |
| NEt₂ | J-29-23 |
| N(n-Pr)₂ | J-29-23 |
| 1-piperdinyl | J-29-23 |
| 1-pyrrolidinyl | J-29-23 |
| 4-morpholinyl | J-29-23 |
| CH₃ | J-29-24 |
| CH₂Cl | J-29-24 |
| CH₂Br | J-29-24 |
| CH₂I | J-29-24 |
| OH | J-29-24 |
| OMe | J-29-24 |
| OEt | J-29-24 |
| OPr | J-29-24 |
| O—i-Pr | J-29-24 |
| O—n-Bu | J-29-24 |
| O—t-Bu | J-29-24 |
| NMe₂ | J-29-24 |
| NEt₂ | J-29-24 |
| N(n-Pr)₂ | J-29-24 |
| 1-piperdinyl | J-29-24 |
| 1-pyrrolidinyl | J-29-24 |
| 4-morpholinyl | J-29-24 |
| CH₃ | J-29-25 |
| CH₂Cl | J-29-25 |
| CH₂Br | J-29-25 |
| CH₂I | J-29-25 |
| OH | J-29-25 |
| OMe | J-29-25 |
| OEt | J-29-25 |
| OPr | J-29-25 |
| O—i-Pr | J-29-25 |
| O—n-Bu | J-29-25 |
| O—t-Bu | J-29-25 |
| NMe₂ | J-29-25 |
| NEt₂ | J-29-25 |
| N(n-Pr)₂ | J-29-25 |
| 1-piperdinyl | J-29-25 |
| 1-pyrrolidinyl | J-29-25 |
| 4-morpholinyl | J-29-25 |
| CH₃ | J-29-26 |
| CH₂Cl | J-29-26 |
| CH₂Br | J-29-26 |
| CH₂I | J-29-26 |
| OH | J-29-26 |
| OMe | J-29-26 |
| OEt | J-29-26 |
| OPr | J-29-26 |
| O—i-Pr | J-29-26 |
| O—n-Bu | J-29-26 |
| O—t-Bu | J-29-26 |
| NMe₂ | J-29-26 |
| NEt₂ | J-29-26 |
| N(n-Pr)₂ | J-29-26 |
| 1-piperdinyl | J-29-26 |
| 1-pyrrolidinyl | J-29-26 |
| 4-morpholinyl | J-29-26 |
| CH₃ | J-29-27 |
| CH₂Cl | J-29-27 |
| CH₂Br | J-29-27 |
| CH₂I | J-29-27 |
| OH | J-29-27 |
| OMe | J-29-27 |
| OEt | J-29-27 |
| OPr | J-29-27 |
| O—i-Pr | J-29-27 |
| O—n-Bu | J-29-27 |
| O—t-Bu | J-29-27 |
| NMe₂ | J-29-27 |
| NEt₂ | J-29-27 |
| N(n-Pr)₂ | J-29-27 |
| 1-piperdinyl | J-29-27 |
| 1-pyrrolidinyl | J-29-27 |
| 4-morpholinyl | J-29-27 |
| CH₃ | J-29-28 |
| CH₂Cl | J-29-28 |
| CH₂Br | J-29-28 |
| CH₂I | J-29-28 |
| OH | J-29-28 |
| OMe | J-29-28 |
| OEt | J-29-28 |
| OPr | J-29-28 |
| O—i-Pr | J-29-28 |
| O—n-Bu | J-29-28 |
| O—t-Bu | J-29-28 |
| NMe₂ | J-29-28 |
| NEt₂ | J-29-28 |
| N(n-Pr)₂ | J-29-28 |
| 1-piperdinyl | J-29-28 |
| 1-pyrrolidinyl | J-29-28 |
| 4-morpholinyl | J-29-28 |
| CH₃ | J-29-29 |
| CH₂Cl | J-29-29 |
| CH₂Br | J-29-29 |
| CH₂I | J-29-29 |
| OH | J-29-29 |
| OMe | J-29-29 |
| OEt | J-29-29 |
| OPr | J-29-29 |
| O—i-Pr | J-29-29 |
| O—n-Bu | J-29-29 |
| O—t-Bu | J-29-29 |
| NMe₂ | J-29-29 |
| NEt₂ | J-29-29 |
| N(n-Pr)₂ | J-29-29 |
| 1-piperdinyl | J-29-29 |
| 1-pyrrolidinyl | J-29-29 |
| 4-morpholinyl | J-29-29 |
| CH₃ | J-29-30 |
| CH₂Cl | J-29-30 |
| CH₂Br | J-29-30 |
| CH₂I | J-29-30 |
| OH | J-29-30 |
| OMe | J-29-30 |

TABLE 7*-continued

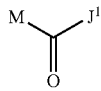

| M | J¹ |
|---|---|
| OEt | J-29-30 |
| OPr | J-29-30 |
| O—i-Pr | J-29-30 |
| O—n-Bu | J-29-30 |
| O—t-Bu | J-29-30 |
| NMe₂ | J-29-30 |
| NEt₂ | J-29-30 |
| N(n-Pr)₂ | J-29-30 |
| 1-piperdinyl | J-29-30 |
| 1-pyrrolidinyl | J-29-30 |
| 4-morpholinyl | J-29-30 |
| CH₃ | J-29-31 |
| CH₂Cl | J-29-31 |
| CH₂Br | J-29-31 |
| CH₂I | J-29-31 |
| OH | J-29-31 |
| OMe | J-29-31 |
| OEt | J-29-31 |
| OPr | J-29-31 |
| O—i-Pr | J-29-31 |
| O—n-Bu | J-29-31 |
| O—t-Bu | J-29-31 |
| NMe₂ | J-29-31 |
| NEt₂ | J-29-31 |
| N(n-Pr)₂ | J-29-31 |
| 1-piperdinyl | J-29-31 |
| 1-pyrrolidinyl | J-29-31 |
| 4-morpholinyl | J-29-31 |
| CH₃ | J-29-32 |
| CH₂Cl | J-29-32 |
| CH₂Br | J-29-32 |
| CH₂I | J-29-32 |
| OH | J-29-32 |
| OMe | J-29-32 |
| OEt | J-29-32 |
| OPr | J-29-32 |
| O—i-Pr | J-29-32 |
| O—n-Bu | J-29-32 |
| O—t-Bu | J-29-32 |
| NMe₂ | J-29-32 |
| NEt₂ | J-29-32 |
| N(n-Pr)₂ | J-29-32 |
| 1-piperdinyl | J-29-32 |
| 1-pyrrolidinyl | J-29-32 |
| 4-morpholinyl | J-29-32 |
| CH₃ | J-29-33 |
| CH₂Cl | J-29-33 |
| CH₂Br | J-29-33 |
| CH₂I | J-29-33 |
| OH | J-29-33 |
| OMe | J-29-33 |
| OEt | J-29-33 |
| OPr | J-29-33 |
| O—i-Pr | J-29-33 |
| O—n-Bu | J-29-33 |
| O—t-Bu | J-29-33 |
| NMe₂ | J-29-33 |
| NEt₂ | J-29-33 |
| N(n-Pr)₂ | J-29-33 |
| 1-piperdinyl | J-29-33 |
| 1-pyrrolidinyl | J-29-33 |
| 4-morpholinyl | J-29-33 |
| CH₃ | J-29-34 |
| CH₂Cl | J-29-34 |
| CH₂Br | J-29-34 |
| CH₂I | J-29-34 |
| OH | J-29-34 |
| OMe | J-29-34 |
| OEt | J-29-34 |
| OPr | J-29-34 |
| O—i-Pr | J-29-34 |
| O—n-Bu | J-29-34 |
| O—t-Bu | J-29-34 |

TABLE 7*-continued

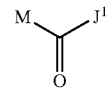

| M | J¹ |
|---|---|
| NMe₂ | J-29-34 |
| NEt₂ | J-29-34 |
| N(n-Pr)₂ | J-29-34 |
| 1-piperdinyl | J-29-34 |
| 1-pyrrolidinyl | J-29-34 |
| 4-morpholinyl | J-29-34 |
| CH₃ | J-29-35 |
| CH₂Cl | J-29-35 |
| CH₂Br | J-29-35 |
| CH₂I | J-29-35 |
| OH | J-29-35 |
| OMe | J-29-35 |
| OEt | J-29-35 |
| OPr | J-29-35 |
| O—i-Pr | J-29-35 |
| O—n-Bu | J-29-35 |
| O—t-Bu | J-29-35 |
| NMe₂ | J-29-35 |
| NEt₂ | J-29-35 |
| N(n-Pr)₂ | J-29-35 |
| 1-piperdinyl | J-29-35 |
| 1-pyrrolidinyl | J-29-35 |
| 4-morpholinyl | J-29-35 |
| CH₃ | J-29-36 |
| CH₂Cl | J-29-36 |
| CH₂Br | J-29-36 |
| CH₂I | J-29-36 |
| OH | J-29-36 |
| OMe | J-29-36 |
| OEt | J-29-36 |
| OPr | J-29-36 |
| O—i-Pr | J-29-36 |
| O—n-Bu | J-29-36 |
| O—t-Bu | J-29-36 |
| NMe₂ | J-29-36 |
| NEt₂ | J-29-36 |
| N(n-Pr)₂ | J-29-36 |
| 1-piperdinyl | J-29-36 |
| 1-pyrrolidinyl | J-29-36 |
| 4-morpholinyl | J-29-36 |
| CH₃ | J-29-37 |
| CH₂Cl | J-29-37 |
| CH₂Br | J-29-37 |
| CH₂I | J-29-37 |
| OH | J-29-37 |
| OMe | J-29-37 |
| OEt | J-29-37 |
| OPr | J-29-37 |
| O—i-Pr | J-29-37 |
| O—n-Bu | J-29-37 |
| O—t-Bu | J-29-37 |
| NMe₂ | J-29-37 |
| NEt₂ | J-29-37 |
| N(n-Pr)₂ | J-29-37 |
| 1-piperdinyl | J-29-37 |
| 1-pyrrolidinyl | J-29-37 |
| 4-morpholinyl | J-29-37 |
| CH₃ | J-29-38 |
| CH₂Cl | J-29-38 |
| CH₂Br | J-29-38 |
| CH₂I | J-29-38 |
| OH | J-29-38 |
| OMe | J-29-38 |
| OEt | J-29-38 |
| OPr | J-29-38 |
| O—i-Pr | J-29-38 |
| O—n-Bu | J-29-38 |
| O—t-Bu | J-29-38 |
| NMe₂ | J-29-38 |
| NEt₂ | J-29-38 |
| N(n-Pr)₂ | J-29-38 |
| 1-piperdinyl | J-29-38 |
| 1-pyrrolidinyl | J-29-38 |

TABLE 7*-continued

| M | J¹ |
|---|---|
| 4-morpholinyl | J-29-38 |
| CH₃ | J-29-39 |
| CH₂Cl | J-29-39 |
| CH₂Br | J-29-39 |
| CH₂I | J-29-39 |
| OH | J-29-39 |
| OMe | J-29-39 |
| OEt | J-29-39 |
| OPr | J-29-39 |
| O—i-Pr | J-29-39 |
| O—n-Bu | J-29-39 |
| O—t-Bu | J-29-39 |
| NMe₂ | J-29-39 |
| NEt₂ | J-29-39 |
| N(n-Pr)₂ | J-29-39 |
| 1-piperdinyl | J-29-39 |
| 1-pyrrolidinyl | J-29-39 |
| 4-morpholinyl | J-29-39 |
| CH₃ | J-29-40 |
| CH₂Cl | J-29-40 |
| CH₂Br | J-29-40 |
| CH₂I | J-29-40 |
| OH | J-29-40 |
| OMe | J-29-40 |
| OEt | J-29-40 |
| OPr | J-29-40 |
| O—i-Pr | J-29-40 |
| O—n-Bu | J-29-40 |
| O—t-Bu | J-29-40 |
| NMe₂ | J-29-40 |
| NEt₂ | J-29-40 |
| N(n-Pr)₂ | J-29-40 |
| 1-piperdinyl | J-29-40 |
| 1-pyrrolidinyl | J-29-40 |
| 4-morpholinyl | J-29-40 |
| CH₃ | J-29-41 |
| CH₂Cl | J-29-41 |
| CH₂Br | J-29-41 |
| CH₂I | J-29-41 |
| OH | J-29-41 |
| OMe | J-29-41 |
| OEt | J-29-41 |
| OPr | J-29-41 |
| O—i-Pr | J-29-41 |
| O—n-Bu | J-29-41 |
| O—t-Bu | J-29-41 |
| NMe₂ | J-29-41 |
| NEt₂ | J-29-41 |
| N(n-Pr)₂ | J-29-41 |
| 1-piperdinyl | J-29-41 |
| 1-pyrrolidinyl | J-29-41 |
| 4-morpholinyl | J-29-41 |
| CH₃ | J-29-42 |
| CH₂Cl | J-29-42 |
| CH₂Br | J-29-42 |
| CH₂I | J-29-42 |
| OH | J-29-42 |
| OMe | J-29-42 |
| OEt | J-29-42 |
| OPr | J-29-42 |
| O—i-Pr | J-29-42 |
| O—n-Bu | J-29-42 |
| O—t-Bu | J-29-42 |
| NMe₂ | J-29-42 |
| NEt₂ | J-29-42 |
| N(n-Pr)₂ | J-29-42 |
| 1-piperdinyl | J-29-42 |
| 1-pyrrolidinyl | J-29-42 |
| 4-morpholinyl | J-29-42 |
| CH₃ | J-29-43 |
| CH₂Cl | J-29-43 |
| CH₂Br | J-29-43 |
| CH₂I | J-29-43 |

TABLE 7*-continued

| M | J¹ |
|---|---|
| OH | J-29-43 |
| OMe | J-29-43 |
| OEt | J-29-43 |
| OPr | J-29-43 |
| O—i-Pr | J-29-43 |
| O—n-Bu | J-29-43 |
| O—t-Bu | J-29-43 |
| NMe₂ | J-29-43 |
| NEt₂ | J-29-43 |
| N(n-Pr)₂ | J-29-43 |
| 1-piperdinyl | J-29-43 |
| 1-pyrrolidinyl | J-29-43 |
| 4-morpholinyl | J-29-43 |
| CH₃ | J-29-44 |
| CH₂Cl | J-29-44 |
| CH₂Br | J-29-44 |
| CH₂I | J-29-44 |
| OH | J-29-44 |
| OMe | J-29-44 |
| OEt | J-29-44 |
| OPr | J-29-44 |
| O—i-Pr | J-29-44 |
| O—n-Bu | J-29-44 |
| O—t-Bu | J-29-44 |
| NMe₂ | J-29-44 |
| NEt₂ | J-29-44 |
| N(n-Pr)₂ | J-29-44 |
| 1-piperdinyl | J-29-44 |
| 1-pyrrolidinyl | J-29-44 |
| 4-morpholinyl | J-29-44 |
| CH₃ | J-29-45 |
| CH₂Cl | J-29-45 |
| CH₂Br | J-29-45 |
| CH₂I | J-29-45 |
| OH | J-29-45 |
| OMe | J-29-45 |
| OEt | J-29-45 |
| OPr | J-29-45 |
| O—i-Pr | J-29-45 |
| O—n-Bu | J-29-45 |
| O—t-Bu | J-29-45 |
| NMe₂ | J-29-45 |
| NEt₂ | J-29-45 |
| N(n-Pr)₂ | J-29-45 |
| 1-piperdinyl | J-29-45 |
| 1-pyrrolidinyl | J-29-45 |
| 4-morpholinyl | J-29-45 |
| CH₃ | J-29-46 |
| CH₂Cl | J-29-46 |
| CH₂Br | J-29-46 |
| CH₂I | J-29-46 |
| OH | J-29-46 |
| OMe | J-29-46 |
| OEt | J-29-46 |
| OPr | J-29-46 |
| O—i-Pr | J-29-46 |
| O—n-Bu | J-29-46 |
| O—t-Bu | J-29-46 |
| NMe₂ | J-29-46 |
| NEt₂ | J-29-46 |
| N(n-Pr)₂ | J-29-46 |
| 1-piperdinyl | J-29-46 |
| 1-pyrrolidinyl | J-29-46 |
| 4-morpholinyl | J-29-46 |
| CH₃ | J-29-47 |
| CH₂Cl | J-29-47 |
| CH₂Br | J-29-47 |
| CH₂I | J-29-47 |
| OH | J-29-47 |
| OMe | J-29-47 |
| OEt | J-29-47 |
| OPr | J-29-47 |
| O—i-Pr | J-29-47 |

TABLE 7*-continued

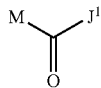

| M | J¹ |
|---|---|
| O—n-Bu | J-29-47 |
| O—t-Bu | J-29-47 |
| NMe₂ | J-29-47 |
| NEt₂ | J-29-47 |
| N(n-Pr)₂ | J-29-47 |
| 1-piperdinyl | J-29-47 |
| 1-pyrrolidinyl | J-29-47 |
| 4-morpholinyl | J-29-47 |
| CH₃ | J-29-48 |
| CH₂Cl | J-29-48 |
| CH₂Br | J-29-48 |
| CH₂I | J-29-48 |
| OH | J-29-48 |
| OMe | J-29-48 |
| OEt | J-29-48 |
| OPr | J-29-48 |
| O—i-Pr | J-29-48 |
| O—n-Bu | J-29-48 |
| O—t-Bu | J-29-48 |
| NMe₂ | J-29-48 |
| NEt₂ | J-29-48 |
| N(n-Pr)₂ | J-29-48 |
| 1-piperdinyl | J-29-48 |
| 1-pyrrolidinyl | J-29-48 |
| 4-morpholinyl | J-29-48 |
| CH₃ | J-29-49 |
| CH₂Cl | J-29-49 |
| CH₂Br | J-29-49 |
| CH₂I | J-29-49 |
| OH | J-29-49 |
| OMe | J-29-49 |
| OEt | J-29-49 |
| OPr | J-29-49 |
| O—i-Pr | J-29-49 |
| O—n-Bu | J-29-49 |
| O—t-Bu | J-29-49 |
| NMe₂ | J-29-49 |
| NEt₂ | J-29-49 |
| N(n-Pr)₂ | J-29-49 |
| 1-piperdinyl | J-29-49 |
| 1-pyrrolidinyl | J-29-49 |
| 4-morpholinyl | J-29-49 |
| CH₃ | J-29-50 |
| CH₂Cl | J-29-50 |
| CH₂Br | J-29-50 |
| CH₂I | J-29-50 |
| OH | J-29-50 |
| OMe | J-29-50 |
| OEt | J-29-50 |
| OPr | J-29-50 |
| O—i-Pr | J-29-50 |
| O—n-Bu | J-29-50 |
| O—t-Bu | J-29-50 |
| NMe₂ | J-29-50 |
| NEt₂ | J-29-50 |
| N(n-Pr)₂ | J-29-50 |
| 1-piperdinyl | J-29-50 |
| 1-pyrrolidinyl | J-29-50 |
| 4-morpholinyl | J-29-50 |
| CH₃ | J-29-51 |
| CH₂Cl | J-29-51 |
| CH₂Br | J-29-51 |
| CH₂I | J-29-51 |
| OH | J-29-51 |
| OMe | J-29-51 |
| OEt | J-29-51 |
| OPr | J-29-51 |
| O—i-Pr | J-29-51 |
| O—n-Bu | J-29-51 |
| O—t-Bu | J-29-51 |
| NMe₂ | J-29-51 |
| NEt₂ | J-29-51 |
| N(n-Pr)₂ | J-29-51 |

TABLE 7*-continued

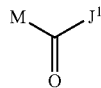

| M | J¹ |
|---|---|
| 1-piperdinyl | J-29-51 |
| 1-pyrrolidinyl | J-29-51 |
| 4-morpholinyl | J-29-51 |
| CH₃ | J-29-52 |
| CH₂Cl | J-29-52 |
| CH₂Br | J-29-52 |
| CH₂I | J-29-52 |
| OH | J-29-52 |
| OMe | J-29-52 |
| OEt | J-29-52 |
| OPr | J-29-52 |
| O—i-Pr | J-29-52 |
| O—n-Bu | J-29-52 |
| O—t-Bu | J-29-52 |
| NMe₂ | J-29-52 |
| NEt₂ | J-29-52 |
| N(n-Pr)₂ | J-29-52 |
| 1-piperdinyl | J-29-52 |
| 1-pyrrolidinyl | J-29-52 |
| 4-morpholinyl | J-29-52 |
| CH₃ | J-29-53 |
| CH₂Cl | J-29-53 |
| CH₂Br | J-29-53 |
| CH₂I | J-29-53 |
| OH | J-29-53 |
| OMe | J-29-53 |
| OEt | J-29-53 |
| OPr | J-29-53 |
| O—i-Pr | J-29-53 |
| O—n-Bu | J-29-53 |
| O—t-Bu | J-29-53 |
| NMe₂ | J-29-53 |
| NEt₂ | J-29-53 |
| N(n-Pr)₂ | J-29-53 |
| 1-piperdinyl | J-29-53 |
| 1-pyrrolidinyl | J-29-53 |
| 4-morpholinyl | J-29-53 |
| CH₃ | J-29-54 |
| CH₂Cl | J-29-54 |
| CH₂Br | J-29-54 |
| CH₂I | J-29-54 |
| OH | J-29-54 |
| OMe | J-29-54 |
| OEt | J-29-54 |
| OPr | J-29-54 |
| O—i-Pr | J-29-54 |
| O—n-Bu | J-29-54 |
| O—t-Bu | J-29-54 |
| NMe₂ | J-29-54 |
| NEt₂ | J-29-54 |
| N(n-Pr)₂ | J-29-54 |
| 1-piperdinyl | J-29-54 |
| 1-pyrrolidinyl | J-29-54 |
| 4-morpholinyl | J-29-54 |
| CH₃ | J-29-55 |
| CH₂Cl | J-29-55 |
| CH₂Br | J-29-55 |
| CH₂I | J-29-55 |
| OH | J-29-55 |
| OMe | J-29-55 |
| OEt | J-29-55 |
| OPr | J-29-55 |
| O—i-Pr | J-29-55 |
| O—n-Bu | J-29-55 |
| O—t-Bu | J-29-55 |
| NMe₂ | J-29-55 |
| NEt₂ | J-29-55 |
| N(n-Pr)₂ | J-29-55 |
| 1-piperdinyl | J-29-55 |
| 1-pyrrolidinyl | J-29-55 |
| 4-morpholinyl | J-29-55 |
| CH₃ | J-29-56 |
| CH₂Cl | J-29-56 |

TABLE 7*-continued

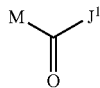

| M | J¹ |
|---|---|
| CH₂Br | J-29-56 |
| CH₂I | J-29-56 |
| OH | J-29-56 |
| OMe | J-29-56 |
| OEt | J-29-56 |
| OPr | J-29-56 |
| O—i-Pr | J-29-56 |
| O—n-Bu | J-29-56 |
| O—t-Bu | J-29-56 |
| NMe₂ | J-29-56 |
| NEt₂ | J-29-56 |
| N(n-Pr)₂ | J-29-56 |
| 1-piperdinyl | J-29-56 |
| 1-pyrrolidinyl | J-29-56 |
| 4-morpholinyl | J-29-56 |
| CH₃ | J-29-57 |
| CH₂Cl | J-29-57 |
| CH₂Br | J-29-57 |
| CH₂I | J-29-57 |
| OH | J-29-57 |
| OMe | J-29-57 |
| OEt | J-29-57 |
| OPr | J-29-57 |
| O—i-Pr | J-29-57 |
| O—n-Bu | J-29-57 |
| O—t-Bu | J-29-57 |
| NMe₂ | J-29-57 |
| NEt₂ | J-29-57 |
| N(n-Pr)₂ | J-29-57 |
| 1-piperdinyl | J-29-57 |
| 1-pyrrolidinyl | J-29-57 |
| 4-morpholinyl | J-29-57 |
| CH₃ | J-29-58 |
| CH₂Cl | J-29-58 |
| CH₂Br | J-29-58 |
| CH₂I | J-29-58 |
| OH | J-29-58 |
| OMe | J-29-58 |
| OEt | J-29-58 |
| OPr | J-29-58 |
| O—i-Pr | J-29-58 |
| O—n-Bu | J-29-58 |
| O—t-Bu | J-29-58 |
| NMe₂ | J-29-58 |
| NEt₂ | J-29-58 |
| N(n-Pr)₂ | J-29-58 |
| 1-piperdinyl | J-29-58 |
| 1-pyrrolidinyl | J-29-58 |
| 4-morpholinyl | J-29-58 |
| CH₃ | J-29-59 |
| CH₂Cl | J-29-59 |
| CH₂Br | J-29-59 |
| CH₂I | J-29-59 |
| OH | J-29-59 |
| OMe | J-29-59 |
| OEt | J-29-59 |
| OPr | J-29-59 |
| O—i-Pr | J-29-59 |
| O—n-Bu | J-29-59 |
| O—t-Bu | J-29-59 |
| NMe₂ | J-29-59 |
| NEt₂ | J-29-59 |
| N(n-Pr)₂ | J-29-59 |
| 1-piperdinyl | J-29-59 |
| 1-pyrrolidinyl | J-29-59 |
| 4-morpholinyl | J-29-59 |
| CH₃ | J-29-60 |
| CH₃ | J-29-60 |
| CH₂Cl | J-29-60 |
| CH₂Br | J-29-60 |
| CH₂I | J-29-60 |
| OH | J-29-60 |
| OMe | J-29-60 |

TABLE 7*-continued

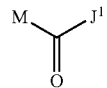

| M | J¹ |
|---|---|
| OEt | J-29-60 |
| OPr | J-29-60 |
| O—i-Pr | J-29-60 |
| O—n-Bu | J-29-60 |
| O—t-Bu | J-29-60 |
| NMe₂ | J-29-60 |
| NEt₂ | J-29-60 |
| N(n-Pr)₂ | J-29-60 |
| 1-piperdinyl | J-29-60 |
| 1-pyrrolidinyl | J-29-60 |
| 4-morpholinyl | J-29-60 |

*The definition of J¹ in the compounds of this table are as defined in Exhibit A in the above Embodiments. As shown in Exhibit A, J can be selected from J-29-1 through J-29-60 (i.e. particular examples of J-29). As many J-29-1 to J-29-60 groups include a chiral center, these J groups are illustrated in a particular enantiomeric configuration. One skilled in the art immediately recognizes the antipode (i.e. opposite enantiomer) for each of the compounds listed, and furthermore understands that the enantiomers can be present as pure enantiomers or in mixtures enriched in one enantiomer or in racemic mixtures.

Formulation/Utility

A mixture or compound of this invention will generally be used to provide fungicidal active ingredients in compositions, i.e. formulations, with at least one additional component selected from the group consisting of surfactants, solid diluents and liquid diluents, which serve as a carrier. The formulation or composition ingredients are selected to be consistent with the physical properties of the active ingredients, mode of application and environmental factors such as soil type, moisture and temperature.

The mixtures of component (a) (i.e. at least one compound of Formula 1, N-oxides or salts thereof) with component (b) (e.g., selected from (b1) to (b46) and salts thereof as described above) and/or one or more other biologically active compound or agent (i.e. insecticides, other fungicides, nematocides, acaricides, herbicides and other biological agents) can be formulated in a number of ways, including:

(i) component (a), component (b) and/or one or more other biologically active compound or agent can be formulated separately and applied separately or applied simultaneously in an appropriate weight ratio, e.g., as a tank mix; or (ii) component (a), component (b) and/or one or more other biologically active compound or agent can be formulated together in the proper weight ratio.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated").

Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compounds of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

EXAMPLE A

| High Strength Concentrate | |
|---|---|
| Compound 3 | 50.0% |
| folpet | 48.5% |
| silica aerogel | 0.5% |
| synthetic amorphous fine silica | 1.0% |

EXAMPLE B

| Wettable Powder | |
|---|---|
| Compound 3 | 50.0% |
| copper hydroxide | 15.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

EXAMPLE C

Granule

| | |
|---|---|
| Compound 149 | 8.0% |
| fluopicolide | 2.0% |
| attapulgite granules (low volatile matter, 0.71/0.30 mm; U.S.S. No. 25-50 sieves) | 90.0% |

EXAMPLE D

Extruded Pellet

| | |
|---|---|
| Compound 2 | 13.0% |
| cymoxanil | 12.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

EXAMPLE E

Emulsifiable Concentrate

| | |
|---|---|
| Compound 3 | 5.0% |
| azoxystrobin | 5.0% |
| polyoxyethylene sorbitol hexoleate | 20.0% |
| $C_6$-$C_{10}$ fatty acid methyl ester | 70.0% |

EXAMPLE F

Microemulsion

| | |
|---|---|
| Compound 391 | 4.0% |
| pyraclostrobin | 1.0% |
| polyvinylpyrrolidone-vinyl acetate copolymer | 30.0% |
| alkylpolyglycoside | 30.0% |
| glyceryl monooleate | 15.0% |
| water | 20.0% |

EXAMPLE G

Seed Treatment

| | |
|---|---|
| Compound 114 | 10.00% |
| fosetyl-aluminum | 10.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Examples of component (b) fungicides include acibenzolar-S-methyl, aldimorph, amisulbrom, anilazine, azaconazole, azoxystrobin, benalaxyl, benalaxyl-M, benodanil, benomyl, benthiavalicarb, benthiavalicarb-isopropyl, bethoxazin, binapacryl, biphenyl, bitertanol, bixafen, blasticidin-S, Bordeaux mixture (tribasic copper sulfate), boscalid, bromuconazole, bupirimate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole, diniconazole-M, dinocap, dithianon, dodemorph, dodine, edifenphos, enestroburin, epoxiconazole, ethaboxam, etridiazole, famoxadone, fenamidone, fenarimol, fenbuconazole, fenfuram, fenhexamid, fenoxanil, fenpiclonil, fenpropidin, fenpropimorph, fentin acetate, fentin chloride, fentin hydroxide, ferbam, ferimzone, fluazinam, fludioxonil, flumetover, flumorph, fluopicolide, fluopyram, fluoroimide, fluoxastrobin, fluquinconazole, flusilazole, flusulfamide, flutolanil, flutriafol, folpet, fosetyl-aluminum, fuberidazole, furalaxyl, furametpyr, hexaconazole, hymexazol, guazatine, imazalil, imibenconazole, iminoctadine, iodocarb, ipconazole, iprobenfos, iprodione, iprovalicarb, isoprothiolane, isopyrazam, isotianil, kasugamycin, kresoxim-methyl, mancozeb, mandipropamid, maneb, mepronil, meptyldinocap, metalaxyl, metalaxyl-M, metconazole, methasulfocarb, metiram, metominostrobin, mepanipyrim, metrafenone, myclobutanil, naftifine, neoasozin (ferric methanearsonate), nuarimol, octhilinone, ofurace, orysastrobin, oxadixyl, oxolinic acid, oxpoconazole, oxycarboxin, oxytetracycline, penconazole, pencycuron, penthiopyrad, pefurazoate, phosphorous acid and salts, phthalide, picobenzamid, picoxystrobin, piperalin, polyoxin, probenazole, prochloraz, procymidone, propamocarb, propamocarb-hydrochloride, propiconazole, propineb, proquinazid, prothioconazole, pyraclostrobin, pryazophos, pyribencarb, pyrifenox, pyrimethanil, pyrolnitrine, pyroquilon, quinomethionate, quinoxyfen, quintozene, silthiofam, simeconazole, spiroxamine, streptomycin, sulfur, tebuconazole, tecloftalam, tecnazene, terbinafine, tetraconazole, thiabendazole, thifluzamide, thiophanate, thiophanate-methyl, thiram, tiadinil, tolclofos-methyl, tolylfluanid, triadimefon, triadimenol, triazoxide, tricyclazole, tridemorph, triflumizole, tricyclazole, trifloxystrobin, triforine, triticonazole, uniconazole, validamycin, valiphenal, vinclozolin, zineb, ziram, zoxamide, 5-chloro-6-(2,4,6-trifluorophenyl)-7-(4-methylpiperidin-1-yl)[1,2,4]triazolo[1,5-α]pyrimidine (BAS600), N-[2-(1,3-dimethylbutyl)phenyl]-5-fluoro-1,3-dimethyl-1H-pyrazol-4-carboxamide, N-[2-[4-[[3-(4-chlorophenyl)-2-propyn-1-yl]oxy]-3-methoxyphenyl]ethyl]-3-methyl-2-[(methylsulfonyl)amino]butanamide, N-[2-[4-[[3-(4-chlorophenyl)-2-propyn-1-yl]oxy]-3-methoxyphenyl] ethyl]-3-methyl-2-[ethylsulfonyl)amino]butanamide, 2-butoxy-6-iodo-3-propyl-4H-1-benzopyran-4-one, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl]carbamate, N-[[(cyclopropylmethoxy)amino][6-(difluoromethoxy)-2,3-difluorophenyl]methylene]benzeneacetamide, α-(methoxyimino)-N-methyl-2-[[[1-[3-(trifluoromethyl)phenyl]ethoxy]imino]methyl]benzeneacetamide, N'-[4-[4-chloro-3-(trifluoromethyl)phenoxy]-2,5-dimethylphenyl]-N-ethyl-N-methylmethanimidamide, 2-[[2-fluoro-5-(trifluoromethyl)phenyl]thio]-2-[3-(2-methoxyphenyl)-2-thiazolidinylidene]acetonitrile (flutianil), N-[2-(1S,2R)-[1,1'-bicyclopropyl]-2- ylphenyl]-3-(difluoromethyl)-1-methyl-1H-pyrazole-4-carboxamide, N-(4-chloro-2-nitrophenyl)-N-ethyl-4-methylbenzenesulfonamide, 2-[[[[3-(2,6-dichlorophenyl)-1-methyl-2-propen-1-ylidene]amino]oxy]methyl]-α-(methoxyimino)-N-methylbenzeneacetamide, 1-[(2-propenylthio)carbonyl]-2-(1-methylethyl)-4-(2-methylphenyl)-5-amino-1H-pyrazol-3-one and 5-ethyl-6-octyl-[1,2,4]triazolo[1,5-a]pyrimidin-7-ylamine.

Specifically preferred mixtures (compound numbers refer to compounds in Index Table A) are selected from the group: compound 3 and acibenzolar-S-methyl, compound 3 and aldimorph, compound 3 and amisulbrom, compound 3 and anilazine, compound 3 and azaconazole, compound 3 and azoxystrobin, compound 3 and benalaxyl, compound 3 and benalaxyl-M, compound 3 and benodanil, compound 3 and benomyl, compound 3 and benthiavalicarb, compound 3 and benthiavalicarb-isopropyl, compound 3 and bethoxazin, compound 3 and binapacryl, compound 3 and biphenyl, compound 3 and bitertanol, compound 3 and bixafen, compound 3 and blasticidin-S, compound 3 and Bordeaux mixture (tribasic copper sulfate), compound 3 and boscalid, compound 3 and bromuconazole, compound 3 and bupirimate, compound 3 and carboxin, compound 3 and carpropamid, compound 3 and captafol, compound 3 and captan, compound 3 and carbendazim, compound 3 and chloroneb, compound 3 and chlorothalonil, compound 3 and chlozolinate, compound 3 and clotrimazole, compound 3 and copper oxychloride, compound 3 and copper salts such as copper sulfate and copper hydroxide, compound 3 and cyazofamid, compound 3 and cyflufenamid, compound 3 and cymoxanil, compound 3 and cyproconazole, compound 3 and cyprodinil, compound 3 and dichlofluanid, compound 3 and diclocymet, compound 3 and diclomezine, compound 3 and dicloran, compound 3 and diethofencarb, compound 3 and difenoconazole, compound 3 and diflumetorim, compound 3 and dimethirimol, compound 3 and dimethomorph, compound 3 and dimoxystrobin, compound 3 and diniconazole, compound 3 and diniconazole-M, compound 3 and dinocap, compound 3 and dithianon, compound 3 and dodemorph, compound 3 and dodine, compound 3 and edifenphos, compound 3 and enestroburin, compound 3 and epoxiconazole, compound 3 and ethaboxam, compound 3 and etridiazole, compound 3 and famoxadone, compound 3 and fenamidone, compound 3 and fenarimol, compound 3 and fenbuconazole, compound 3 and fenfuram, compound 3 and fenhexamid, compound 3 and fenoxanil, compound 3 and fenpiclonil, compound 3 and fenpropidin, compound 3 and fenpropimorph, compound 3 and fentin acetate, compound 3 and fentin chloride, compound 3 and fentin hydroxide, compound 3 and ferbam, compound 3 and ferimzone, compound 3 and fluazinam, compound 3 and fludioxonil, compound 3 and flumetover, compound 3 and flumorph, compound 3 and fluopicolide, compound 3 and fluopyram, compound 3 and fluoroimide, compound 3 and fluoxastrobin, compound 3 and fluquinconazole, compound 3 and flusilazole, compound 3 and flusulfamide, compound 3 and flutolanil, compound 3 and flutriafol, compound 3 and folpet, compound 3 and fosetyl-aluminum, compound 3 and fuberidazole, compound 3 and furalaxyl, compound 3 and furametpyr, compound 3 and hexaconazole, compound 3 and hymexazol, compound 3 and guazatine, compound 3 and imazalil, compound 3 and imibenconazole, compound 3 and iminoctadine, compound 3 and iodocarb, compound 3 and ipconazole, compound 3 and iprobenfos, compound 3 and iprodione, compound 3 and iprovalicarb, compound 3 and isoprothiolane, compound 3 and isopyrazam, compound 3 and isotianil, compound 3 and kasugamycin, compound 3 and kresoxim-methyl, compound 3 and mancozeb, compound 3 and mandipropamid, compound 3 and maneb, compound 3 and mepronil, compound 3 and meptyldinocap, compound 3 and metalaxyl, compound 3 and metalaxyl-M, compound 3 and metconazole, compound 3 and methasulfocarb, compound 3 and metiram, compound 3 and metominostrobin, compound 3 and mepanipyrim, compound 3 and metrafenone, compound 3 and myclobutanil, compound 3 and naftifine, compound 3 and neo-asozin (ferric methanearsonate), compound 3 and nuarimol, compound 3 and octhilinone, compound 3 and ofurace, compound 3 and orysastrobin, compound 3 and oxadixyl, compound 3 and oxolinic acid, compound 3 and oxpoconazole, compound 3 and oxycarboxin, compound 3 and oxytetracycline, compound 3 and penconazole, compound 3 and pencycuron, compound 3 and penthiopyrad, compound 3 and pefurazoate, compound 3 and phosphorous acid and salts, compound 3 and phthalide, compound 3 and picobenzamid, compound 3 and picoxystrobin, compound 3 and piperalin, compound 3 and polyoxin, compound 3 and probenazole, compound 3 and prochloraz, compound 3 and procymidone, compound 3 and propamocarb, compound 3 and propamocarb-hydrochloride, compound 3 and propiconazole, compound 3 and propineb, compound 3 and proquinazid, compound 3 and prothioconazole, compound 3 and pyraclostrobin, compound 3 and pryazophos, compound 3 and pyribencarb, compound 3 and pyrifenox, compound 3 and pyrimethanil, compound 3 and pyrolnitrine, compound 3 and pyroquilon, compound 3 and quinomethionate, compound 3 and quinoxyfen, compound 3 and quintozene, compound 3 and silthiofam, compound 3 and simeconazole, compound 3 and spiroxamine, compound 3 and streptomycin, compound 3 and sulfur, compound 3 and tebuconazole, compound 3 and tecloftalam, compound 3 and tecnazene, compound 3 and terbinafine, compound 3 and tetraconazole, compound 3 and thiabendazole, compound 3 and thifluzamide, compound 3 and thiophanate, compound 3 and thiophanate-methyl, compound 3 and thiram, compound 3 and tiadinil, compound 3 and tolclofos-methyl, compound 3 and tolylfluanid, compound 3 and triadimefon, compound 3 and triadimenol, compound 3 and triazoxide, compound 3 and tricyclazole, compound 3 and tridemorph, compound 3 and triflumizole, compound 3 and tricyclazole, compound 3 and trifloxystrobin, compound 3 and triforine, compound 3 and triticonazole, compound 3 and uniconazole, compound 3 and validamycin, compound 3 and valiphenal, compound 3 and vinclozolin, compound 3 and zineb, compound 3 and ziram, compound 3 and zoxamide, compound 3 and 5-chloro-6-(2,4,6-trifluorophenyl)-7-(4-methylpiperidin-1-yl)[1,2,4]triazolo[1,5-α]pyrimidine (BAS600), compound 3 and N-[2-(1,3-dimethylbutyl)phenyl]-5-fluoro-1,3-dimethyl-1H-pyrazol-4-carboxamide, compound 3 and N-[2-[4-[[3-(4-chlorophenyl)-2-propyn-1-yl]oxy]-3-methoxyphenyl]ethyl]-3-methyl-2-[(methylsulfonyl)amino]butanamide, compound 3 and N-[2-[4-[[3-(4-chlorophenyl)-2-propyn-1-yl]oxy]-3-methoxyphenyl]ethyl]-3-methyl-2-[ethylsulfonyl)amino]butanamide, compound 3 and 2-butoxy-6-iodo-3-propyl-4H-1-benzopyran-4-one, compound 3 and 3-[5-(4-chlorophenyl)-2,3-dimethyl-3-isoxazolidinyl]pyridine, compound 3 and 4-fluorophenyl N-[1-[[[1-(4-cyanophenyl)ethyl]sulfonyl]methyl]propyl]carbamate, compound 3 and N-[[(cyclopropylmethoxy)amino][6-(difluoromethoxy)-2,3-difluorophenyl]methylene]benzeneacetamide, compound 3 and α-(methoxyimino)-N-methyl-2-[[[1-[3-(trifluoromethyl)phenyl]ethoxy]imino]methyl]benzeneacetamide, compound 3 and N'-[4-[4-chloro-3-(trifluoromethyl)phenoxy]-2,5-dimethylphenyl]-N-ethyl-N-methylmethanimidamide, compound 3 and 2-[[2-fluoro-5-(trifluoromethyl)phenyl]thio]-2-[3-(2-methoxyphenyl)-2-thiazolidinylidene]acetonitrile, compound 3 and N-[2-(1S,2R)-[1,1'-bicyclopropyl]-2-ylphenyl]-3-(difluoromethyl)-1-methyl-1H-pyrazole-4-carboxamide, and compound 3 and N-(4-chloro-2-nitrophenyl)-N-ethyl-4-methylbenzenesulfonamide, compound 22 and acibenzolar-S-methyl, compound 22 and aldimorph, compound 22 and amisulbrom, compound 22 and anilazine, compound 22 and azaconazole, compound 22 and azoxystrobin, compound 22 and benalaxyl, compound 22 and benalaxyl-M, compound 22 and benodanil, compound 22 and benomyl, compound 22 and benthiavalicarb, compound 22 and benthiavalicarb-isopropyl, compound 22 and bethoxazin, compound 22 and binapacryl, compound 22 and biphenyl, compound 22 and bitertanol, compound 22 and bixafen, compound 22 and blasticidin-S, compound 22 and Bordeaux mixture (tribasic copper sulfate), compound 22 and boscalid, compound 22 and bromuconazole, compound 22 and bupirimate, compound 22 and carboxin, compound 22 and carpropamid, compound 22 and captafol, compound 22 and captan, compound 22 and carbendazim, compound 22 and chloroneb, compound 22 and chlorothalonil, compound 22 and chlozolinate, compound 22 and clotrimazole, compound 22 and copper oxychloride, compound 22 and copper salts such as copper sulfate and copper hydroxide, compound 22 and cyazofamid, compound 22 and cyflufenamid, compound 22 and cymoxanil, compound 22 and cyproconazole, compound 22 and cyprodinil, compound 22 and dichlofluanid, compound 22 and diclocymet, compound 22 and diclomezine, compound 22 and dicloran, compound 22 and diethofencarb, compound 22 and difenoconazole, compound 22 and diflumetorim, compound 22 and dimethirimol, compound 22 and dimethomorph, compound 22 and dimoxystrobin, compound 22 and diniconazole, compound 22 and diniconazole-M, compound 22 and dinocap, compound 22 and dithianon, compound 22 and dodemorph, compound 22 and dodine, compound 22 and edifenphos, compound 22 and enestroburin, compound 22 and epoxiconazole, compound 22 and ethaboxam, compound 22 and etridiazole, compound 22 and famoxadone, compound 22 and fenamidone, compound 22 and fenarimol, compound 22 and fenbuconazole, compound 22 and fenfuram, compound 22 and fenhexamid, compound 22 and fenoxanil, compound 22 and fenpiclonil, compound 22 and fenpropidin, compound 22 and fenpropimorph, compound 22 and fentin acetate, compound 22 and fentin chloride, compound 22 and fentin hydroxide, compound 22 and ferbam, compound 22 and ferimzone, compound 22 and fluazinam, compound 22 and fludioxonil, compound 22 and flumetover, compound 22 and flumorph, compound 22 and fluopicolide, compound 22 and fluopyram, compound 22 and fluoroimide, compound 22 and fluoxastrobin, compound 22 and fluquinconazole, compound 22 and flusilazole, compound 22 and flusulfamide, compound 22 and flutolanil, compound 22 and flutriafol, compound 22 and folpet, compound 22 and fosetyl-aluminum, compound 22 and fuberidazole, compound 22 and furalaxyl, compound 22 and furametpyr, compound 22 and hexaconazole, compound 22 and hymexazol, compound 22 and guazatine, compound 22 and imazalil, compound 22 and imibenconazole, compound 22 and iminoctadine, compound 22 and iodocarb, compound 22 and ipconazole, compound 22 and iprobenfos, compound 22 and iprodione, compound 22 and iprovalicarb, compound 22 and isoprothiolane, compound 22 and isopyrazam, compound 22 and isotianil, compound 22 and kasugamycin, compound 22 and kresoxim-methyl, compound 22 and mancozeb, compound 22 and mandipropamid, compound 22 and maneb, compound 22 and mepronil, compound 22 and meptyldinocap, compound 22 and metalaxyl, compound 22 and metalaxyl-M, compound 22 and metconazole, compound 22 and methasulfocarb, compound 22 and metiram, compound 22 and metominostrobin, compound 22 and mepanipyrim, compound 22 and metrafenone, compound 22 and myclobutanil, compound 22 and naftifine, compound 22 and neo-asozin (ferric methanearsonate), compound 22 and nuarimol, compound 22 and octhilinone, compound 22 and ofurace, compound 22 and orysastrobin, compound 22 and oxadixyl, compound 22 and oxolinic acid, compound 22 and oxpoconazole, compound 22 and oxycarboxin, compound 22 and oxytetracycline, compound 22 and penconazole, compound 22 and pencycuron, compound 22 and penthiopyrad, compound 22 and pefurazoate, compound 22 and phosphorous acid and salts, compound 22 and phthalide, compound 22 and picobenzamid, compound 22 and picoxystrobin, compound 22 and piperalin, compound 22 and polyoxin, compound 22 and probenazole, compound 22 and prochloraz, compound 22 and procymidone, compound 22 and propamocarb, compound 22 and propamocarb-hydrochloride, compound 22 and propiconazole, compound 22 and propineb, compound 22 and proquinazid, compound 22 and prothioconazole, compound 22 and pyraclostrobin, compound 22 and pryazophos, compound 22 and pyribencarb, compound 22 and pyrifenox, compound 22 and pyrimethanil, compound 22 and pyrolnitrine, compound 22 and pyroquilon, compound 22 and quinomethionate, compound 22 and quinoxyfen, compound 22 and quintozene, compound 22 and silthiofam, compound 22 and simeconazole, compound 22 and spiroxamine, compound 22 and streptomycin, compound 22 and sulfur, compound 22 and tebuconazole, compound 22 and tecloftalam, compound 22 and tecnazene, compound 22 and terbinafine, compound 22 and tetraconazole, compound 22 and thiabendazole, compound 22 and thifluzamide, compound 22 and thiophanate, compound 22 and thiophanate-methyl, compound 22 and thiram, compound 22 and tiadinil, compound 22 and tolclofos-methyl, compound 22 and tolylfluanid, compound 22 and triadimefon, compound 22 and triadimenol, compound 22 and triazoxide, compound 22 and tricyclazole, compound 22 and tridemorph, compound 22 and triflumizole, compound 22 and tricyclazole, compound 22 and trifloxystrobin, compound 22 and triforine, compound 22 and triticonazole, compound 22 and uniconazole, compound 22 and validamycin, compound 22 and valiphenal, compound 22 and vinclozolin, compound 22 and zineb, compound 22 and ziram, compound 22 and zoxamide, compound 22 and 5-chloro-6-(2,4,6-trifluorophenyl)-7-(4-methylpiperidin-1-yl)[1,2,4]triazolo[1,5-α]pyrimidine (BAS600), compound 22 and N-[2-(1,3-dimethylbutyl)phenyl]-5-fluoro-1,3-dimethyl-1H-pyrazol-4-carboxamide, compound 22 and N-[2-[4-[[3-(4-chlorophenyl)-2-propyn-1-yl]oxy]-3-methoxyphenyl]ethyl]-3-methyl-2-[(methylsulfonyl)amino]butanamide, compound 22 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 22 and 2-butoxy-6-iodo-3-propyl-4H-1-benzopyran-4-one, compound 22 and 3-[5-(4-chlorophenyl)-2,3-dimethyl-3-isoxazolidinyl]pyridine , compound 22 and 4-fluorophenyl N-[1-[[[1-(4-cyanophenyl)ethyl]sulfonyl]methyl]propyl]carbamate, compound 22 and N-[[(cyclopropylmethoxy)amino][6-(difluoromethoxy)-2,3-difluorophenyl]methylene]benzeneacetamide, compound 22 and α-(methoxyimino)-N-methyl-2-[[[1-[3-(trifluoromethyl)phenyl]ethoxy]imino]methyl]benzeneacetamide, compound 22 and N'-[4-[4-chloro-3-(trifluoromethyl)phenoxy]-2,5-dimethylphenyl]-N-ethyl-N-methylmethanimidamide, compound 22 and 2-[[2-fluoro-5-(trifluoromethyl)phenyl]thio]-2-[3-(2-methoxyphenyl)-2-thiazolidinylidene]acetonitrile, compound 22 and N-[2-(1S,2R)-[1,1'-bicyclopropyl]-2-ylphenyl]-3-(difluoromethyl)-1-methyl-1H-pyrazole-4- carboxamide, and compound 22 and N-(4-chloro-2-nitrophenyl)-N-ethyl-4-methylbenzenesulfonamide, compound 37 and acibenzolar-S-methyl, compound 37 and aldimorph, compound 37 and amisulbrom, compound 37 and anilazine, compound 37 and azaconazole, compound 37 and azoxystrobin, compound 37 and benalaxyl, compound 37 and benalaxyl-M, compound 37 and benodanil, compound 37 and benomyl, compound 37 and benthiavalicarb, compound 37 and benthiavalicarb-isopropyl, compound 37 and bethoxazin, compound 37 and binapacryl, compound 37 and biphenyl, compound 37 and bitertanol, compound 37 and bixafen, compound 37 and blasticidin-S, compound 37 and Bordeaux mixture (tribasic copper sulfate), compound 37 and boscalid, compound 37 and bromuconazole, compound 37 and bupirimate, compound 37 and carboxin, compound 37 and carpropamid, compound 37 and captafol, compound 37 and captan, compound 37 and carbendazim, compound 37 and chloroneb, compound 37 and chlorothalonil, compound 37 and chlozolinate, compound 37 and clotrimazole, compound 37 and copper oxychloride, compound 37 and copper salts such as copper sulfate and copper hydroxide, compound 37 and cyazofamid, compound 37 and cyflufenamid, compound 37 and cymoxanil, compound 37 and cyproconazole, compound 37 and cyprodinil, compound 37 and dichlofluanid, compound 37 and diclocymet, compound 37 and diclomezine, compound 37 and dicloran, compound 37 and diethofencarb, compound 37 and difenoconazole, compound 37 and diflumetorim, compound 37 and dimethirimol, compound 37 and dimethomorph, compound 37 and dimoxystrobin, compound 37 and diniconazole, compound 37 and diniconazole-M, compound 37 and dinocap, compound 37 and dithianon, compound 37 and dodemorph, compound 37 and dodine, compound 37 and edifenphos, compound 37 and enestroburin, compound 37 and epoxiconazole, compound 37 and ethaboxam, compound 37 and etridiazole, compound 37 and famoxadone, compound 37 and fenamidone, compound 37 and fenarimol, compound 37 and fenbuconazole, compound 37 and fenfuram, compound 37 and fenhexamid, compound 37 and fenoxanil, compound 37 and fenpiclonil, compound 37 and fenpropidin, compound 37 and fenpropimorph, compound 37 and fentin acetate, compound 37 and fentin chloride, compound 37 and fentin hydroxide, compound 37 and ferbam, compound 37 and ferimzone, compound 37 and fluazinam, compound 37 and fludioxonil, compound 37 and flumetover, compound 37 and flumorph, compound 37 and fluopicolide, compound 37 and fluopyram, compound 37 and fluoroimide, compound 37 and fluoxastrobin, compound 37 and fluquinconazole, compound 37 and flusilazole, compound 37 and flusulfamide, compound 37 and flutolanil, compound 37 and flutriafol, compound 37 and folpet, compound 37 and fosetyl-aluminum, compound 37 and fuberidazole, compound 37 and furalaxyl, compound 37 and furametpyr, compound 37 and hexaconazole, compound 37 and hymexazol, compound 37 and guazatine, compound 37 and imazalil, compound 37 and imibenconazole, compound 37 and iminoctadine, compound 37 and iodocarb, compound 37 and ipconazole, compound 37 and iprobenfos, compound 37 and iprodione, compound 37 and iprovalicarb, compound 37 and isoprothiolane, compound 37 and isopyrazam, compound 37 and isotianil, compound 37 and kasugamycin, compound 37 and kresoxim-methyl, compound 37 and mancozeb, compound 37 and mandipropamid, compound 37 and maneb, compound 37 and mepronil, compound 37 and meptyldinocap, compound 37 and metalaxyl, compound 37 and metalaxyl-M, compound 37 and metconazole, compound 37 and methasulfocarb, compound 37 and metiram, compound 37 and metominostrobin, compound 37 and mepanipyrim, compound 37 and metrafenone, compound 37 and myclobutanil, compound 37 and naftifine, compound 37 and neo-asozin (ferric methanearsonate), compound 37 and nuarimol, compound 37 and octhilinone, compound 37 and ofurace, compound 37 and orysastrobin, compound 37 and oxadixyl, compound 37 and oxolinic acid, compound 37 and oxpoconazole, compound 37 and oxycarboxin, compound 37 and oxytetracycline, compound 37 and penconazole, compound 37 and pencycuron, compound 37 and penthiopyrad, compound 37 and pefurazoate, compound 37 and phosphorous acid and salts, compound 37 and phthalide, compound 37 and picobenzamid, compound 37 and picoxystrobin, compound 37 and piperalin, compound 37 and polyoxin, compound 37 and probenazole, compound 37 and prochloraz, compound 37 and procymidone, compound 37 and propamocarb, compound 37 and propamocarb-hydrochloride, compound 37 and propiconazole, compound 37 and propineb, compound 37 and proquinazid, compound 37 and prothioconazole, compound 37 and pyraclostrobin, compound 37 and pryazophos, compound 37 and pyribencarb, compound 37 and pyrifenox, compound 37 and pyrimethanil, compound 37 and pyrolnitrine, compound 37 and pyroquilon, compound 37 and quinomethionate, compound 37 and quinoxyfen, compound 37 and quintozene, compound 37 and silthiofam, compound 37 and simeconazole, compound 37 and spiroxamine, compound 37 and streptomycin, compound 37 and sulfur, compound 37 and tebuconazole, compound 37 and tecloftalam, compound 37 and tecnazene, compound 37 and terbinafine, compound 37 and tetraconazole, compound 37 and thiabendazole, compound 37 and thifluzamide, compound 37 and thiophanate, compound 37 and thiophanate-methyl, compound 37 and thiram, compound 37 and tiadinil, compound 37 and tolclofos-methyl, compound 37 and tolylfluanid, compound 37 and triadimefon, compound 37 and triadimenol, compound 37 and triazoxide, compound 37 and tricyclazole, compound 37 and tridemorph, compound 37 and triflumizole, compound 37 and tricyclazole, compound 37 and trifloxystrobin, compound 37 and triforine, compound 37 and triticonazole, compound 37 and uniconazole, compound 37 and validamycin, compound 37 and valiphenal, compound 37 and vinclozolin, compound 37 and zineb, compound 37 and ziram, compound 37 and zoxamide, compound 37 and 5-chloro-6-(2,4,6-trifluorophenyl)-7-(4-methylpiperidin-1-yl)[1,2,4]triazolo[1,5-α]pyrimidine (BAS600), compound 37 and N-[2-(1,3-dimethylbutyl)phenyl]-5-fluoro-1,3-dimethyl-1H-pyrazol-4-carboxamide, compound 37 and N-[2-[[3-(4-chlorophenyl)-2-propyn-1-yl]oxy]-3-methoxyphenyl]ethyl]-3-methyl-2-[(methylsulfonyl)amino]butanamide, compound 37 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 37 and 2-butoxy-6-iodo-3-propyl-4H-1-benzopyran-4-one, compound 37 and 3-[5-(4-chlorophenyl)-2,3-dimethyl-3-isoxazolidinyl]pyridine , compound 37 and 4-fluorophenyl N-[1-[[[1-(4-cyanophenyl) ethyl]sulfonyl]methyl]propyl]carbamate, compound 37 and N-[[(cyclopropylmethoxy)amino][6-(difluoromethoxy)-2,3-difluorophenyl]methylene]benzeneacetamide, compound 37 and α-(methoxyimino)-N-methyl-2-[[[1-[3-(trifluoromethyl)phenyl]ethoxy]imino]methyl]benzeneacetamide, compound 37 and N'-[4-[4-chloro-3-(trifluoromethyl)phenoxy]-2,5-dimethylphenyl]-N-ethyl-N-methylmethanimidamide, compound 37 and 2-[[2-fluoro-5-(trifluoromethyl)phenyl]thio]-2-[3-(2-methoxyphenyl)-2-thiazolidinylidene]acetonitrile, compound 37 and N-[2-(1S,2R)-[1,1'-bicyclopropyl]-2-ylphenyl]-3-(difluoromethyl)-1-methyl-1H-pyrazole-4-carboxamide, and compound 37 and N-(4-chloro-2-nitrophenyl)-N-ethyl-4-methylbenzenesulfonamide, compound 44 and acibenzolar-S-methyl, compound 44 and aldimorph, compound 44 and amisulbrom, compound 44 and anilazine, compound 44 and azaconazole, compound 44 and azoxystrobin, compound 44 and benalaxyl, compound 44 and benalaxyl-M, compound 44 and benodanil, compound 44 and benomyl, compound 44 and benthiavalicarb, compound 44 and benthiavalicarb-isopropyl, compound 44 and bethoxazin, compound 44 and binapacryl, compound 44 and biphenyl, compound 44 and bitertanol, compound 44 and bixafen, compound 44 and blasticidin-S, compound 44 and Bordeaux mixture (tribasic copper sulfate), compound 44 and boscalid, compound 44 and bromuconazole, compound 44 and bupirimate, compound 44 and carboxin, compound 44 and carpropamid, compound 44 and captafol, compound 44 and captan, compound 44 and carbendazim, compound 44 and chloroneb, compound 44 and chlorothalonil, compound 44 and chlozolinate, compound 44 and clotrimazole, compound 44 and copper oxychloride, compound 44 and copper salts such as copper sulfate and copper hydroxide, compound 44 and cyazofamid, compound 44 and cyflufenamid, compound 44 and cymoxanil, compound 44 and cyproconazole, compound 44 and cyprodinil, compound 44 and dichlofluanid, compound 44 and diclocymet, compound 44 and diclomezine, compound 44 and dicloran, compound 44 and diethofencarb, compound 44 and difenoconazole, compound 44 and diflumetorim, compound 44 and dimethirimol, compound 44 and dimethomorph, compound 44 and dimoxystrobin, compound 44 and diniconazole, compound 44 and diniconazole-M, compound 44 and dinocap, compound 44 and dithianon, compound 44 and dodemorph, compound 44 and dodine, compound 44 and edifenphos, compound 44 and enestroburin, compound 44 and epoxiconazole, compound 44 and ethaboxam, compound 44 and etridiazole, compound 44 and famoxadone, compound 44 and fenamidone, compound 44 and fenarimol, compound 44 and fenbuconazole, compound 44 and fenfuram, compound 44 and fenhexamid, compound 44 and fenoxanil, compound 44 and fenpiclonil, compound 44 and fenpropidin, compound 44 and fenpropimorph, compound 44 and fentin acetate, compound 44 and fentin chloride, compound 44 and fentin hydroxide, compound 44 and ferbam, compound 44 and ferimzone, compound 44 and fluazinam, compound 44 and fludioxonil, compound 44 and flumetover, compound 44 and flumorph, compound 44 and fluopicolide, compound 44 and fluopyram, compound 44 and fluoroimide, compound 44 and fluoxastrobin, compound 44 and fluquinconazole, compound 44 and flusilazole, compound 44 and flusulfamide, compound 44 and flutolanil, compound 44 and flutriafol, compound 44 and folpet, compound 44 and fosetyl-aluminum, compound 44 and fuberidazole, compound 44 and furalaxyl, compound 44 and furametpyr, compound 44 and hexaconazole, compound 44 and hymexazol, compound 44 and guazatine, compound 44 and imazalil, compound 44 and imibenconazole, compound 44 and iminoctadine, compound 44 and iodocarb, compound 44 and ipconazole, compound 44 and iprobenfos, compound 44 and iprodione, compound 44 and iprovalicarb, compound 44 and isoprothiolane, compound 44 and isopyrazam, compound 44 and isotianil, compound 44 and kasugamycin, compound 44 and kresoxim-methyl, compound 44 and mancozeb, compound 44 and mandipropamid, compound 44 and maneb, compound 44 and mepronil, compound 44 and meptyldinocap, compound 44 and metalaxyl, compound 44 and metalaxyl-M, compound 44 and metconazole, compound 44 and methasulfocarb, compound 44 and metiram, compound 44 and metominostrobin, compound 44 and mepanipyrim, compound 44 and metrafenone, compound 44 and myclobutanil, compound 44 and naftifine, compound 44 and neo-asozin (ferric methanearsonate), compound 44 and nuarimol, compound 44 and octhilinone, compound 44 and ofurace, compound 44 and orysastrobin, compound 44 and oxadixyl, compound 44 and oxolinic acid, compound 44 and oxpoconazole, compound 44 and oxycarboxin, compound 44 and oxytetracycline, compound 44 and penconazole, compound 44 and pencycuron, compound 44 and penthiopyrad, compound 44 and pefurazoate, compound 44 and phosphorous acid and salts, compound 44 and phthalide, compound 44 and picobenzamid, compound 44 and picoxystrobin, compound 44 and piperalin, compound 44 and polyoxin, compound 44 and probenazole, compound 44 and prochloraz, compound 44 and procymidone, compound 44 and propamocarb, compound 44 and propamocarb-hydrochloride, compound 44 and propiconazole, compound 44 and propineb, compound 44 and proquinazid, compound 44 and prothioconazole, compound 44 and pyraclostrobin, compound 44 and pryazophos, compound 44 and pyribencarb, compound 44 and pyrifenox, compound 44 and pyrimethanil, compound 44 and pyrolnitrine, compound 44 and pyroquilon, compound 44 and quinomethionate, compound 44 and quinoxyfen, compound 44 and quintozene, compound 44 and silthiofam, compound 44 and simeconazole, compound 44 and spiroxamine, compound 44 and streptomycin, compound 44 and sulfur, compound 44 and tebuconazole, compound 44 and tecloftalam, compound 44 and tecnazene, compound 44 and terbinafine, compound 44 and tetraconazole, compound 44 and thiabendazole, compound 44 and thifluzamide, compound 44 and thiophanate, compound 44 and thiophanate-methyl, compound 44 and thiram, compound 44 and tiadinil, compound 44 and tolclofos-methyl, compound 44 and tolylfluanid, compound 44 and triadimefon, compound 44 and triadimenol, compound 44 and triazoxide, compound 44 and tricyclazole, compound 44 and tridemorph, compound 44 and triflumizole, compound 44 and tricyclazole, compound 44 and trifloxystrobin, compound 44 and triforine, compound 44 and triticonazole, compound 44 and uniconazole, compound 44 and validamycin, compound 44 and valiphenal, compound 44 and vinclozolin, compound 44 and zineb, compound 44 and ziram, compound 44 and zoxamide, compound 44 and 5-chloro-6-(2,4,6-trifluorophenyl)-7-(4-methylpiperidin-1-yl)[1,2,4]triazolo[1,5-α]pyrimidine (BAS600), compound 44 and N-[2-(1,3-dimethylbutyl)phenyl]-5-fluoro-1,3-dimethyl-1H-pyrazol-4-carboxamide, compound 44 and N-[2-[4-[[3-(4-chlorophenyl)-2-propyn-1-yl]oxy]-3-methoxyphenyl]ethyl]-3-methyl-2-[(methylsulfonyl)amino]butanamide, compound 44 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 44 and 2-butoxy-6-iodo-3-propyl-4H-1-benzopyran-4-one, compound 44 and 3-[5-(4-chlorophenyl)-2,3-dimethyl-3-isoxazolidinyl]pyridine, compound 44 and 4-fluorophenyl N-[1-[[[1-(4-cyanophenyl)ethyl]sulfonyl]methyl]propyl]carbamate, compound 44 and N-[[(cyclopropylmethoxy)amino][6-(difluoromethoxy)-2,3-difluorophenyl]methylene]benzeneacetamide, compound 44 and α-(methoxyimino)-N-methyl-2-[[[1-[3-(trifluoromethyl)phenyl]ethoxy]imino]methyl]benzeneacetamide, compound 44 and N'-[4-[4-chloro-3-(trifluoromethyl)phenoxy]-2,5-dimethylphenyl]-N-ethyl-N-methylmethanimidamide, compound 44 and 2-[[2-fluoro-5-(trifluoromethyl)phenyl]thio]-2-[3-(2-methoxyphenyl)-2-thiazolidinylidene]acetonitrile, compound 44 and N-[2-(1S,2R)-[1,1'-bicyclopropyl]-2-ylphenyl]-3-(difluoromethyl)-1-methyl-1H-pyrazole-4-carboxamide, and compound 44 and N-(4-chloro-2-nitrophenyl)-N-ethyl-4-methylbenzenesulfonamide, compound 79 and acibenzolar-S-methyl, compound 79 and aldimorph, compound 79 and amisulbrom, compound 79 and anilazine, compound 79 and azaconazole, compound 79 and azoxystrobin, compound 79 and benalaxyl, compound 79 and benalaxyl-M, compound 79 and benodanil, compound 79 and benomyl, compound 79 and benthiavalicarb, compound 79 and benthiavalicarb-isopropyl, compound 79 and bethoxazin, compound 79 and binapacryl, compound 79 and biphenyl, compound 79 and bitertanol, compound 79 and bixafen, compound 79 and blasticidin-S, compound 79 and Bordeaux mixture (tribasic copper sulfate), compound 79 and boscalid, compound 79 and bromuconazole, compound 79 and bupirimate, compound 79 and carboxin, compound 79 and carpropamid, compound 79 and captafol, compound 79 and captan, compound 79 and carbendazim, compound 79 and chloroneb, compound 79 and chlorothalonil, compound 79 and chlozolinate, compound 79 and clotrimazole, compound 79 and copper oxychloride, compound 79 and copper salts such as copper sulfate and copper hydroxide, compound 79 and cyazofamid, compound 79 and cyflufenamid, compound 79 and cymoxanil, compound 79 and cyproconazole, compound 79 and cyprodinil, compound 79 and dichlofluanid, compound 79 and diclocymet, compound 79 and diclomezine, compound 79 and dicloran, compound 79 and diethofencarb, compound 79 and difenoconazole, compound 79 and diflumetorim, compound 79 and dimethirimol, compound 79 and dimethomorph, compound 79 and dimoxystrobin, compound 79 and diniconazole, compound 79 and diniconazole-M, compound 79 and dinocap, compound 79 and dithianon, compound 79 and dodemorph, compound 79 and dodine, compound 79 and edifenphos, compound 79 and enestroburin, compound 79 and epoxiconazole, compound 79 and ethaboxam, compound 79 and etridiazole, compound 79 and famoxadone, compound 79 and fenamidone, compound 79 and fenarimol, compound 79 and fenbuconazole, compound 79 and fenfuram, compound 79 and fenhexamid, compound 79 and fenoxanil, compound 79 and fenpiclonil, compound 79 and fenpropidin, compound 79 and fenpropimorph, compound 79 and fentin acetate, compound 79 and fentin chloride, compound 79 and fentin hydroxide, compound 79 and ferbam, compound 79 and ferimzone, compound 79 and fluazinam, compound 79 and fludioxonil, compound 79 and flumetover, compound 79 and flumorph, compound 79 and fluopicolide, compound 79 and fluopyram, compound 79 and fluoroimide, compound 79 and fluoxastrobin, compound 79 and fluquinconazole, compound 79 and flusilazole, compound 79 and flusulfamide, compound 79 and flutolanil, compound 79 and flutriafol, compound 79 and folpet, compound 79 and fosetyl-aluminum, compound 79 and fuberidazole, compound 79 and furalaxyl, compound 79 and furametpyr, compound 79 and hexaconazole, compound 79 and hymexazol, compound 79 and guazatine, compound 79 and imazalil, compound 79 and imibenconazole, compound 79 and iminoctadine, compound 79 and iodocarb, compound 79 and ipconazole, compound 79 and iprobenfos, compound 79 and iprodione, compound 79 and iprovalicarb, compound 79 and isoprothiolane, compound 79 and isopyrazam, compound 79 and isotianil, compound 79 and kasugamycin, compound 79 and kresoxim-methyl, compound 79 and mancozeb, compound 79 and mandipropamid, compound 79 and maneb, compound 79 and mepronil, compound 79 and meptyldinocap, compound 79 and metalaxyl, compound 79 and metalaxyl-M, compound 79 and metconazole, compound 79 and methasulfocarb, compound 79 and metiram, compound 79 and metominostrobin, compound 79 and mepanipyrim, compound 79 and metrafenone, compound 79 and myclobutanil, compound 79 and naftifine, compound 79 and neo-asozin (ferric methanearsonate), compound 79 and nuarimol, compound 79 and octhilinone, compound 79 and ofurace, compound 79 and orysastrobin, compound 79 and oxadixyl, compound 79 and oxolinic acid, compound 79 and oxpoconazole, compound 79 and oxycarboxin, compound 79 and oxytetracycline, compound 79 and penconazole, compound 79 and pencycuron, compound 79 and penthiopyrad, compound 79 and pefurazoate, compound 79 and phosphorous acid and salts, compound 79 and phthalide, compound 79 and picobenzamid, compound 79 and picoxystrobin, compound 79 and piperalin, compound 79 and polyoxin, compound 79 and probenazole, compound 79 and prochloraz, compound 79 and procymidone, compound 79 and propamocarb, compound 79 and propamocarb-hydrochloride, compound 79 and propiconazole, compound 79 and propineb, compound 79 and proquinazid, compound 79 and prothioconazole, compound 79 and pyraclostrobin, compound 79 and pryazophos, compound 79 and pyribencarb, compound 79 and pyrifenox, compound 79 and pyrimethanil, compound 79 and pyrolnitrine, compound 79 and pyroquilon, compound 79 and quinomethionate, compound 79 and quinoxyfen, compound 79 and quintozene, compound 79 and silthiofam, compound 79 and simeconazole, compound 79 and spiroxamine, compound 79 and streptomycin, compound 79 and sulfur, compound 79 and tebuconazole, compound 79 and tecloftalam, compound 79 and tecnazene, compound 79 and terbinafine, compound 79 and tetraconazole, compound 79 and thiabendazole, compound 79 and thifluzamide, compound 79 and thiophanate, compound 79 and thiophanate-methyl, compound 79 and thiram, compound 79 and tiadinil, compound 79 and tolclofos-methyl, compound 79 and tolylfluanid, compound 79 and triadimefon, compound 79 and triadimenol, compound 79 and triazoxide, compound 79 and tricyclazole, compound 79 and tridemorph, compound 79 and triflumizole, compound 79 and tricyclazole, compound 79 and trifloxystrobin, compound 79 and triforine, compound 79 and triticonazole, compound 79 and uniconazole, compound 79 and validamycin, compound 79 and valiphenal, compound 79 and vinclozolin, compound 79 and zineb, compound 79 and ziram, compound 79 and zoxamide, compound 79 and 5-chloro-6-(2,4,6-trifluorophenyl)-7-(4-methylpiperidin-1-yl)[1,2,4]triazolo[1,5-α]pyrimidine (BAS600), compound 79 and N-[2-(1,3-dimethylbutyl)phenyl]-5-fluoro-1,3-dimethyl-1H-pyrazol-4-carboxamide, compound 79 and N-[2-[4-[[3-(4-chlorophenyl)-2-propyn-1-yl]oxy]-3-methoxyphenyl]ethyl]-3-methyl-2-[(methylsulfonyl)amino]butanamide, compound 79 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 79 and 2-butoxy-6-iodo-3-propyl-4H-1-benzopyran-4-one, compound 79 and 3-[5-(4-chlorophenyl)-2,3-dimethyl-3-isoxazolidinyl]pyridine, compound 79 and 4-fluorophenyl N-[1-[[[1-(4-cyanophenyl)ethyl]sulfonyl]methyl]propyl]carbamate, compound 79 and N-[[(cyclopropylmethoxy)amino][6-(difluoromethoxy)-2,3-difluorophenyl]methylene]benzeneacetamide, compound 79 and α-(methoxyimino)-N-methyl-2-[[[1-[3-(trifluoromethyl)phenyl]ethoxy]imino]methyl]benzeneacetamide, compound 79 and N'-[4-[4-chloro-3-(trifluoromethyl)phenoxy]-2,5-dimethylphenyl]-N-ethyl-N-methylmethanimidamide, compound 79 and 2-[[2-fluoro-5-(trifluoromethyl)phenyl]thio]-2-[3-(2-methoxyphenyl)-2-thiazolidinylidene]acetonitrile, compound 79 and N-[2-(1S,2R)-[1,1'-bicyclopropyl]-2-ylphenyl]-3-(difluoromethyl)-1-methyl-1H-pyrazole-4-carboxamide, and compound 79 and N-(4-chloro-2-nitrophenyl)-N-ethyl-4-methylbenzenesulfonamide, compound 114 and acibenzolar-S-methyl, compound 114 and aldimorph, compound 114 and amisulbrom, compound 114 and anilazine, compound 114 and azaconazole, compound 114 and azoxystrobin, compound 114 and benalaxyl, compound 114 and benalaxyl-M, compound 114 and benodanil, compound 114 and benomyl, compound 114 and benthiavalicarb, compound 114 and benthiavalicarb-isopropyl, compound 114 and bethoxazin, compound 114 and binapacryl, compound 114 and biphenyl, compound 114 and bitertanol, compound 114 and bixafen, compound 114 and blasticidin-S, compound 114 and Bordeaux mixture (tribasic copper sulfate), compound 114 and boscalid, compound 114 and bromuconazole, compound 114 and bupirimate, compound 114 and carboxin, compound 114 and carpropamid, compound 114 and captafol, compound 114 and captan, compound 114 and carbendazim, compound 114 and chloroneb, compound 114 and chlorothalonil, compound 114 and chlozolinate, compound 114 and clotrimazole, compound 114 and copper oxychloride, compound 114 and copper salts such as copper sulfate and copper hydroxide, compound 114 and cyazofamid, compound 114 and cyflufenamid, compound 114 and cymoxanil, compound 114 and cyproconazole, compound 114 and cyprodinil, compound 114 and dichlofluanid, compound 114 and diclocymet, compound 114 and diclomezine, compound 114 and dicloran, compound 114 and diethofencarb, compound 114 and difenoconazole, compound 114 and diflumetorim, compound 114 and dimethirimol, compound 114 and dimethomorph, compound 114 and dimoxystrobin, compound 114 and diniconazole, compound 114 and diniconazole-M, compound 114 and dinocap, compound 114 and dithianon, compound 114 and dodemorph, compound 114 and dodine, compound 114 and edifenphos, compound 114 and enestroburin, compound 114 and epoxiconazole, compound 114 and ethaboxam, compound 114 and etridiazole, compound 114 and famoxadone, compound 114 and fenamidone, compound 114 and fenarimol, compound 114 and fenbuconazole, compound 114 and fenfuram, compound 114 and fenhexamid, compound 114 and fenoxanil, compound 114 and fenpiclonil, compound 114 and fenpropidin, compound 114 and fenpropimorph, compound 114 and fentin acetate, compound 114 and fentin chloride, compound 114 and fentin hydroxide, compound 114 and ferbam, compound 114 and ferimzone, compound 114 and fluazinam, compound 114 and fludioxonil, compound 114 and flumetover, compound 114 and flumorph, compound 114 and fluopicolide, compound 114 and fluopyram, compound 114 and fluoroimide, compound 114 and fluoxastrobin, compound 114 and fluquinconazole, compound 114 and flusilazole, compound 114 and flusulfamide, compound 114 and flutolanil, compound 114 and flutriafol, compound 114 and folpet, compound 114 and fosetyl-aluminum, compound 114 and fuberidazole, compound 114 and furalaxyl, compound 114 and furametpyr, compound 114 and hexaconazole, compound 114 and hymexazol, compound 114 and guazatine, compound 114 and imazalil, compound 114 and imibenconazole, compound 114 and iminoctadine, compound 114 and iodocarb, compound 114 and ipconazole, compound 114 and iprobenfos, compound 114 and iprodione, compound 114 and iprovalicarb, compound 114 and isoprothiolane, compound 114 and isopyrazam, compound 114 and isotianil, compound 114 and kasugamycin, compound 114 and kresoxim-methyl, compound 114 and mancozeb, compound 114 and mandipropamid, compound 114 and maneb, compound 114 and mepronil, compound 114 and meptyldinocap, compound 114 and metalaxyl, compound 114 and metalaxyl-M, compound 114 and metconazole, compound 114 and methasulfocarb, compound 114 and metiram, compound 114 and metominostrobin, compound 114 and mepanipyrim, compound 114 and metrafenone, compound 114 and myclobutanil, compound 114 and naftifine, compound 114 and neo-asozin (ferric methanearsonate), compound 114 and nuarimol, compound 114 and octhilinone, compound 114 and ofurace, compound 114 and orysastrobin, compound 114 and oxadixyl, compound 114 and oxolinic acid, compound 114 and oxpoconazole, compound 114 and oxycarboxin, compound 114 and oxytetracycline, compound 114 and penconazole, compound 114 and pencycuron, compound 114 and penthiopyrad, compound 114 and pefurazoate, compound 114 and phosphorous acid and salts, compound 114 and phthalide, compound 114 and picobenzamid, compound 114 and picoxystrobin, compound 114 and piperalin, compound 114 and polyoxin, compound 114 and probenazole, compound 114 and prochloraz, compound 114 and procymidone, compound 114 and propamocarb, compound 114 and propamocarb-hydrochloride, compound 114 and propiconazole, compound 114 and propineb, compound 114 and proquinazid, compound 114 and prothioconazole, compound 114 and pyraclostrobin, compound 114 and pryazophos, compound 114 and pyribencarb, compound 114 and pyrifenox, compound 114 and pyrimethanil, compound 114 and pyrolnitrine, compound 114 and pyroquilon, compound 114 and quinomethionate, compound 114 and quinoxyfen, compound 114 and quintozene, compound 114 and silthiofam, compound 114 and simeconazole, compound 114 and spiroxamine, compound 114 and streptomycin, compound 114 and sulfur, compound 114 and tebuconazole, compound 114 and tecloftalam, compound 114 and tecnazene, compound 114 and terbinafine, compound 114 and tetraconazole, compound 114 and thiabendazole, compound 114 and thifluzamide, compound 114 and thiophanate, compound 114 and thiophanate-methyl, compound 114 and thiram, compound 114 and tiadinil, compound 114 and tolclofos-methyl, compound 114 and tolylfluanid, compound 114 and triadimefon, compound 114 and triadimenol, compound 114 and triazoxide, compound 114 and tricyclazole, compound 114 and tridemorph, compound 114 and triflumizole, compound 114 and tricyclazole, compound 114 and trifloxystrobin, compound 114 and triforine, compound 114 and triticonazole, compound 114 and uniconazole, compound 114 and validamycin, compound 114 and valiphenal, compound 114 and vinclozolin, compound 114 and zineb, compound 114 and ziram, compound 114 and zoxamide, compound 114 and 5-chloro-6-(2,4,6-trifluorophenyl)-7-(4-methylpiperidin-1-yl)[1,2,4]triazolo[1,5-α]pyrimidine (BAS600), compound 114 and N-[2-(1,3-dimethylbutyl)phenyl]-5-fluoro-1,3-dimethyl-1H-pyrazol-4-carboxamide, compound 114 and N-[2-[4-[[3-(4-chlorophenyl)-2-propyn-1-yl]oxy]-3-methoxyphenyl]ethyl]-3-methyl-2-[(methylsulfonyl)amino]butanamide, compound 114 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 114 and 2-butoxy-6-iodo-3-propyl-4H-1-benzopyran-4-one, compound 114 and 3-[5-(4-chlorophenyl)-2,3-dimethyl-3-isoxazolidinyl]pyridine, compound 114 and 4-fluorophenyl N-[1-[[[1-(4-cyanophenyl)ethyl]sulfonyl]methyl]propyl]carbamate, compound 114 and N-[[(cyclopropylmethoxy)amino][6-(difluoromethoxy)-2,3-difluorophenyl]methylene]benzeneacetamide, compound 114 and α-(methoxyimino)-N-methyl-2-[[[1-[3-(trifluoromethyl)phenyl]ethoxy]imino]methyl]benzeneacetamide, compound 114 and N'-[4-[4-chloro-3-(trifluoromethyl)phenoxy]-2,5-dimethylphenyl]-N-ethyl-N-methylmethanimidamide, compound 114 and 2-[[2-fluoro-5-(trifluoromethyl)phenyl]thio]-2-[3-(2-methoxyphenyl)-2-thiazolidinylidene]acetonitrile, compound 114 and N-[2-(1S,2R)-[1,1'-bicyclopropyl]-2-ylphenyl]-3-(difluoromethyl)-1-methyl-1H-pyrazole-4-carboxamide, and compound 114 and N-(4-chloro-2-nitrophenyl)-N-ethyl-4-methylbenzenesulfonamide, compound 129 and acibenzolar-S-methyl, compound 129 and aldimorph, compound 129 and amisulbrom, compound 129 and anilazine, compound 129 and azaconazole, compound 129 and azoxystrobin, compound 129 and benalaxyl, compound 129 and benalaxyl-M, compound 129 and benodanil, compound 129 and benomyl, compound 129 and benthiavalicarb, compound 129 and benthiavalicarb-isopropyl, compound 129 and bethoxazin, compound 129 and binapacryl, compound 129 and biphenyl, compound 129 and bitertanol, compound 129 and bixafen, compound 129 and blasticidin-S, compound 129 and Bordeaux mixture (tribasic copper sulfate), compound 129 and boscalid, compound 129 and bromuconazole, compound 129 and bupirimate, compound 129 and carboxin, compound 129 and carpropamid, compound 129 and captafol, compound 129 and captan, compound 129 and carbendazim, compound 129 and chloroneb, compound 129 and chlorothalonil, compound 129 and chlozolinate, compound 129 and clotrimazole, compound 129 and copper oxychloride, compound 129 and copper salts such as copper sulfate and copper hydroxide, compound 129 and cyazofamid, compound 129 and cyflufenamid, compound 129 and cymoxanil, compound 129 and cyproconazole, compound 129 and cyprodinil, compound 129 and dichlofluanid, compound 129 and diclocymet, compound 129 and diclomezine, compound 129 and dicloran, compound 129 and diethofencarb, compound 129 and difenoconazole, compound 129 and diflumetorim, compound 129 and dimethirimol, compound 129 and dimethomorph, compound 129 and dimoxystrobin, compound 129 and diniconazole, compound 129 and diniconazole-M, compound 129 and dinocap, compound 129 and dithianon, compound 129 and dodemorph, compound 129 and dodine, compound 129 and edifenphos, compound 129 and enestroburin, compound 129 and epoxiconazole, compound 129 and ethaboxam, compound 129 and etridiazole, compound 129 and famoxadone, compound 129 and fenamidone, compound 129 and fenarimol, compound 129 and fenbuconazole, compound 129 and fenfuram, compound 129 and fenhexamid, compound 129 and fenoxanil, compound 129 and fenpiclonil, compound 129 and fenpropidin, compound 129 and fenpropimorph, compound 129 and fentin acetate, compound 129 and fentin chloride, compound 129 and fentin hydroxide, compound 129 and ferbam, compound 129 and ferimzone, compound 129 and fluazinam, compound 129 and fludioxonil, compound 129 and flumetover, compound 129 and flumorph, compound 129 and fluopicolide, compound 129 and fluopyram, compound 129 and fluoroimide, compound 129 and fluoxastrobin, compound 129 and fluquinconazole, compound 129 and flusilazole, compound 129 and flusulfamide, compound 129 and flutolanil, compound 129 and flutriafol, compound 129 and folpet, compound 129 and fosetyl-aluminum, compound 129 and fuberidazole, compound 129 and furalaxyl, compound 129 and furametpyr, compound 129 and hexaconazole, compound 129 and hymexazol, compound 129 and guazatine, compound 129 and imazalil, compound 129 and imibenconazole, compound 129 and iminoctadine, compound 129 and iodocarb, compound 129 and ipconazole, compound 129 and iprobenfos, compound 129 and iprodione, compound 129 and iprovalicarb, compound 129 and isoprothiolane, compound 129 and isopyrazam, compound 129 and isotianil, compound 129 and kasugamycin, compound 129 and kresoxim-methyl, compound 129 and mancozeb, compound 129 and mandipropamid, compound 129 and maneb, compound 129 and mepronil, compound 129 and meptyldinocap, compound 129 and metalaxyl, compound 129 and metalaxyl-M, compound 129 and metconazole, compound 129 and methasulfocarb, compound 129 and metiram, compound 129 and metominostrobin, compound 129 and mepanipyrim, compound 129 and metrafenone, compound 129 and myclobutanil, compound 129 and naftifine, compound 129 and neo-asozin (ferric methanearsonate), compound 129 and nuarimol, compound 129 and octhilinone, compound 129 and ofurace, compound 129 and orysastrobin, compound 129 and oxadixyl, compound 129 and oxolinic acid, compound 129 and oxpoconazole, compound 129 and oxycarboxin, compound 129 and oxytetracycline, compound 129 and penconazole, compound 129 and pencycuron, compound 129 and penthiopyrad, compound 129 and pefurazoate, compound 129 and phosphorous acid and salts, compound 129 and phthalide, compound 129 and picobenzamid, compound 129 and picoxystrobin, compound 129 and piperalin, compound 129 and polyoxin, compound 129 and probenazole, compound 129 and prochloraz, compound 129 and procymidone, compound 129 and propamocarb, compound 129 and propamocarb-hydrochloride, compound 129 and propiconazole, compound 129 and propineb, compound 129 and proquinazid, compound 129 and prothioconazole, compound 129 and pyraclostrobin, compound 129 and pryazophos, compound 129 and pyribencarb, compound 129 and pyrifenox, compound 129 and pyrimethanil, compound 129 and pyrolnitrine, compound 129 and pyroquilon, compound 129 and quinomethionate, compound 129 and quinoxyfen, compound 129 and quintozene, compound 129 and silthiofam, compound 129 and simeconazole, compound 129 and spiroxamine, compound 129 and streptomycin, compound 129 and sulfur, compound 129 and tebuconazole, compound 129 and tecloftalam, compound 129 and tecnazene, compound 129 and terbinafine, compound 129 and tetraconazole, compound 129 and thiabendazole, compound 129 and thifluzamide, compound 129 and thiophanate, compound 129 and thiophanate-methyl, compound 129 and thiram, compound 129 and tiadinil, compound 129 and tolclofos-methyl, compound 129 and tolylfluanid, compound 129 and triadimefon, compound 129 and triadimenol, compound 129 and triazoxide, compound 129 and tricyclazole, compound 129 and tridemorph, compound 129 and triflumizole, compound 129 and tricyclazole, compound 129 and trifloxystrobin, compound 129 and triforine, compound 129 and triticonazole, compound 129 and uniconazole, compound 129 and validamycin, compound 129 and valiphenal, compound 129 and vinclozolin, compound 129 and zineb, compound 129 and ziram, compound 129 and zoxamide, compound 129 and 5-chloro-6-(2,4,6-trifluorophenyl)-7-(4-methylpiperidin-1-yl)[1,2,4]triazolo[1,5-α] pyrimidine (BAS600), compound 129 and N-[2-(1,3-dimethylbutyl)phenyl]-5-fluoro-1,3-dimethyl-1H-pyrazol-4-carboxamide, compound 129 and N-[2-[4-[[3-(4-chlorophenyl)-2-propyn-1-yl]oxy]-3-methoxyphenyl] ethyl]-3-methyl-2-[(methylsulfonyl)amino]butanamide, compound 129 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 129 and 2-butoxy-6-iodo-3-propyl-4H-1-benzopyran-4-one, compound 129 and 3-[5-(4-chlorophenyl)-2,3-dimethyl-3-isoxazolidinyl]pyridine, compound 129 and 4-fluorophenyl N-[1-[[[1-(4-cyanophenyl)ethyl]sulfonyl]methyl]propyl]carbamate, compound 129 and N-[[(cyclopropylmethoxy)amino][6-(difluoromethoxy)-2,3-difluorophenyl]methylene]benzeneacetamide, compound 129 and α-(methoxyimino)-N-methyl-2-[[[1-[3-(trifluoromethyl)phenyl]ethoxy]imino]methyl] benzeneacetamide, compound 129 and N'-[4-[4-chloro-3-(trifluoromethyl)phenoxy]-2,5-dimethylphenyl]-N-ethyl-N-methylmethanimidamide, compound 129 and 2-[[2-fluoro-5-(trifluoromethyl)phenyl]thio]-2-[3-(2-methoxyphenyl)-2-thiazolidinylidene]acetonitrile, compound 129 and N-[2-(1S,2R)-[1,1'-bicyclopropyl]-2-ylphenyl]-3-(difluoromethyl)-1- methyl-1H-pyrazole-4-carboxamide, and compound 129 and N-(4-chloro-2-nitrophenyl)-N-ethyl-4-methylbenzenesulfonamide, compound 178 and acibenzolar-S-methyl, compound 178 and aldimorph, compound 178 and amisulbrom, compound 178 and anilazine, compound 178 and azaconazole, compound 178 and azoxystrobin, compound 178 and benalaxyl, compound 178 and benalaxyl-M, compound 178 and benodanil, compound 178 and benomyl, compound 178 and benthiavalicarb, compound 178 and benthiavalicarb-isopropyl, compound 178 and bethoxazin, compound 178 and binapacryl, compound 178 and biphenyl, compound 178 and bitertanol, compound 178 and bixafen, compound 178 and blasticidin-S, compound 178 and Bordeaux mixture (tribasic copper sulfate), compound 178 and boscalid, compound 178 and bromuconazole, compound 178 and bupirimate, compound 178 and carboxin, compound 178 and carpropamid, compound 178 and captafol, compound 178 and captan, compound 178 and carbendazim, compound 178 and chloroneb, compound 178 and chlorothalonil, compound 178 and chlozolinate, compound 178 and clotrimazole, compound 178 and copper oxychloride, compound 178 and copper salts such as copper sulfate and copper hydroxide, compound 178 and cyazofamid, compound 178 and cyflufenamid, compound 178 and cymoxanil, compound 178 and cyproconazole, compound 178 and cyprodinil, compound 178 and dichlofluanid, compound 178 and diclocymet, compound 178 and diclomezine, compound 178 and dicloran, compound 178 and diethofencarb, compound 178 and difenoconazole, compound 178 and diflumetorim, compound 178 and dimethirimol, compound 178 and dimethomorph, compound 178 and dimoxystrobin, compound 178 and diniconazole, compound 178 and diniconazole-M, compound 178 and dinocap, compound 178 and dithianon, compound 178 and dodemorph, compound 178 and dodine, compound 178 and edifenphos, compound 178 and enestroburin, compound 178 and epoxiconazole, compound 178 and ethaboxam, compound 178 and etridiazole, compound 178 and famoxadone, compound 178 and fenamidone, compound 178 and fenarimol, compound 178 and fenbuconazole, compound 178 and fenfuram, compound 178 and fenhexamid, compound 178 and fenoxanil, compound 178 and fenpiclonil, compound 178 and fenpropidin, compound 178 and fenpropimorph, compound 178 and fentin acetate, compound 178 and fentin chloride, compound 178 and fentin hydroxide, compound 178 and ferbam, compound 178 and ferimzone, compound 178 and fluazinam, compound 178 and fludioxonil, compound 178 and flumetover, compound 178 and flumorph, compound 178 and fluopicolide, compound 178 and fluopyram, compound 178 and fluoroimide, compound 178 and fluoxastrobin, compound 178 and fluquinconazole, compound 178 and flusilazole, compound 178 and flusulfamide, compound 178 and flutolanil, compound 178 and flutriafol, compound 178 and folpet, compound 178 and fosetyl-aluminum, compound 178 and fuberidazole, compound 178 and furalaxyl, compound 178 and furametpyr, compound 178 and hexaconazole, compound 178 and hymexazol, compound 178 and guazatine, compound 178 and imazalil, compound 178 and imibenconazole, compound 178 and iminoctadine, compound 178 and iodocarb, compound 178 and ipconazole, compound 178 and iprobenfos, compound 178 and iprodione, compound 178 and iprovalicarb, compound 178 and isoprothiolane, compound 178 and isopyrazam, compound 178 and isotianil, compound 178 and kasugamycin, compound 178 and kresoxim-methyl, compound 178 and mancozeb, compound 178 and mandipropamid, compound 178 and maneb, compound 178 and mepronil, compound 178 and meptyldinocap, compound 178 and metalaxyl, compound 178 and metalaxyl-M, compound 178 and metconazole, compound 178 and methasulfocarb, compound 178 and metiram, compound 178 and metominostrobin, compound 178 and mepanipyrim, compound 178 and metrafenone, compound 178 and myclobutanil, compound 178 and naftifine, compound 178 and neo-asozin (ferric methanearsonate), compound 178 and nuarimol, compound 178 and octhilinone, compound 178 and ofurace, compound 178 and orysastrobin, compound 178 and oxadixyl, compound 178 and oxolinic acid, compound 178 and oxpoconazole, compound 178 and oxycarboxin, compound 178 and oxytetracycline, compound 178 and penconazole, compound 178 and pencycuron, compound 178 and penthiopyrad, compound 178 and pefurazoate, compound 178 and phosphorous acid and salts, compound 178 and phthalide, compound 178 and picobenzamid, compound 178 and picoxystrobin, compound 178 and piperalin, compound 178 and polyoxin, compound 178 and probenazole, compound 178 and prochloraz, compound 178 and procymidone, compound 178 and propamocarb, compound 178 and propamocarb-hydrochloride, compound 178 and propiconazole, compound 178 and propineb, compound 178 and proquinazid, compound 178 and prothioconazole, compound 178 and pyraclostrobin, compound 178 and pryazophos, compound 178 and pyribencarb, compound 178 and pyrifenox, compound 178 and pyrimethanil, compound 178 and pyrolnitrine, compound 178 and pyroquilon, compound 178 and quinomethionate, compound 178 and quinoxyfen, compound 178 and quintozene, compound 178 and silthiofam, compound 178 and simeconazole, compound 178 and spiroxamine, compound 178 and streptomycin, compound 178 and sulfur, compound 178 and tebuconazole, compound 178 and tecloftalam, compound 178 and tecnazene, compound 178 and terbinafine, compound 178 and tetraconazole, compound 178 and thiabendazole, compound 178 and thifluzamide, compound 178 and thiophanate, compound 178 and thiophanate-methyl, compound 178 and thiram, compound 178 and tiadinil, compound 178 and tolclofos-methyl, compound 178 and tolylfluanid, compound 178 and triadimefon, compound 178 and triadimenol, compound 178 and triazoxide, compound 178 and tricyclazole, compound 178 and tridemorph, compound 178 and triflumizole, compound 178 and tricyclazole, compound 178 and trifloxystrobin, compound 178 and triforine, compound 178 and triticonazole, compound 178 and uniconazole, compound 178 and validamycin, compound 178 and valiphenal, compound 178 and vinclozolin, compound 178 and zineb, compound 178 and ziram, compound 178 and zoxamide, compound 178 and 5-chloro-6-(2,4,6-trifluorophenyl)-7-(4-methylpiperidin-1-yl)[1,2,4]triazolo[1,5α]pyrimidine (BAS600), compound 178 and N-[2-(1,3-dimethylbutyl)phenyl]-5-fluoro-1,3-dimethyl-1H-pyrazol-4-carboxamide, compound 178 and N-[2-[4-[[3-(4-chlorophenyl)-2-propyn-1-yl]oxy]-3-methoxyphenyl]ethyl]-3-methyl-2-[(methylsulfonyl)amino]butanamide, compound 178 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 178 and 2-butoxy-6-iodo-3-propyl-4H-1-benzopyran-4-one, compound 178 and 345-(4-chlorophenyl)-2,3-dimethyl-3-isoxazolidinyl]pyridine, compound 178 and 4-fluorophenyl N-[1-[[[1-(4-cyanophenyl)ethyl]sulfonyl]methyl]propyl]carbamate, compound 178 and N-[[(cyclopropylmethoxy)amino][6-(difluoromethoxy)-2,3-difluorophenyl]methylene]benzeneacetamide, compound 178 and α-(methoxyimino)-N-methyl-2-[[[1-[3-(trifluoromethyl)phenyl]ethoxy]imino]methyl]
benzeneacetamide, compound 178 and N'-[4-[4-chloro-3-(trifluoromethyl)phenoxy]-2,5-dimethylphenyl]-N-ethyl-N-methylmethanimidamide, compound 178 and 2-[[2-fluoro-5-

(trifluoromethyl)phenyl]thio]-2-[3-(2-methoxyphenyl)-2-thiazolidinylidene]acetonitrile, compound 178 and N-[2-(1S,2R)-[1,1'-bicyclopropyl]-2-ylphenyl]-3-(difluoromethyl)-1-methyl-1H-pyrazole-4-carboxamide, and compound 178 and N-(4-chloro-2-nitrophenyl)-N-ethyl-4-methylbenzenesulfonamide, compound 214 and acibenzolar-S-methyl, compound 214 and aldimorph, compound 214 and amisulbrom, compound 214 and anilazine, compound 214 and azaconazole, compound 214 and azoxystrobin, compound 214 and benalaxyl, compound 214 and benalaxyl-M, compound 214 and benodanil, compound 214 and benomyl, compound 214 and benthiavalicarb, compound 214 and benthiavalicarb-isopropyl, compound 214 and bethoxazin, compound 214 and binapacryl, compound 214 and biphenyl, compound 214 and bitertanol, compound 214 and bixafen, compound 214 and blasticidin-S, compound 214 and Bordeaux mixture (tribasic copper sulfate), compound 214 and boscalid, compound 214 and bromuconazole, compound 214 and bupirimate, compound 214 and carboxin, compound 214 and carpropamid, compound 214 and captafol, compound 214 and captan, compound 214 and carbendazim, compound 214 and chloroneb, compound 214 and chlorothalonil, compound 214 and chlozolinate, compound 214 and clotrimazole, compound 214 and copper oxychloride, compound 214 and copper salts such as copper sulfate and copper hydroxide, compound 214 and cyazofamid, compound 214 and cyflufenamid, compound 214 and cymoxanil, compound 214 and cyproconazole, compound 214 and cyprodinil, compound 214 and dichlofluanid, compound 214 and diclocymet, compound 214 and diclomezine, compound 214 and dicloran, compound 214 and diethofencarb, compound 214 and difenoconazole, compound 214 and diflumetorim, compound 214 and dimethirimol, compound 214 and dimethomorph, compound 214 and dimoxystrobin, compound 214 and diniconazole, compound 214 and diniconazole-M, compound 214 and dinocap, compound 214 and dithianon, compound 214 and dodemorph, compound 214 and dodine, compound 214 and edifenphos, compound 214 and enestroburin, compound 214 and epoxiconazole, compound 214 and ethaboxam, compound 214 and etridiazole, compound 214 and famoxadone, compound 214 and fenamidone, compound 214 and fenarimol, compound 214 and fenbuconazole, compound 214 and fenfuram, compound 214 and fenhexamid, compound 214 and fenoxanil, compound 214 and fenpiclonil, compound 214 and fenpropidin, compound 214 and fenpropimorph, compound 214 and fentin acetate, compound 214 and fentin chloride, compound 214 and fentin hydroxide, compound 214 and ferbam, compound 214 and ferimzone, compound 214 and fluazinam, compound 214 and fludioxonil, compound 214 and flumetover, compound 214 and flumorph, compound 214 and fluopicolide, compound 214 and fluopyram, compound 214 and fluoroimide, compound 214 and fluoxastrobin, compound 214 and fluquinconazole, compound 214 and flusilazole, compound 214 and flusulfamide, compound 214 and flutolanil, compound 214 and flutriafol, compound 214 and folpet, compound 214 and fosetyl-aluminum, compound 214 and fuberidazole, compound 214 and furalaxyl, compound 214 and furametpyr, compound 214 and hexaconazole, compound 214 and hymexazol, compound 214 and guazatine, compound 214 and imazalil, compound 214 and imibenconazole, compound 214 and iminoctadine, compound 214 and iodocarb, compound 214 and ipconazole, compound 214 and iprobenfos, compound 214 and iprodione, compound 214 and iprovalicarb, compound 214 and isoprothiolane, compound 214 and isopyrazam, compound 214 and isotianil, compound 214 and kasugamycin, compound 214 and kresoxim-methyl, compound 214 and mancozeb, compound 214 and mandipropamid, compound 214 and maneb, compound 214 and mepronil, compound 214 and meptyldinocap, compound 214 and metalaxyl, compound 214 and metalaxyl-M, compound 214 and metconazole, compound 214 and methasulfocarb, compound 214 and metiram, compound 214 and metominostrobin, compound 214 and mepanipyrim, compound 214 and metrafenone, compound 214 and myclobutanil, compound 214 and naftifine, compound 214 and neo-asozin (ferric methanearsonate), compound 214 and nuarimol, compound 214 and octhilinone, compound 214 and ofurace, compound 214 and orysastrobin, compound 214 and oxadixyl, compound 214 and oxolinic acid, compound 214 and oxpoconazole, compound 214 and oxycarboxin, compound 214 and oxytetracycline, compound 214 and penconazole, compound 214 and pencycuron, compound 214 and penthiopyrad, compound 214 and pefurazoate, compound 214 and phosphorous acid and salts, compound 214 and phthalide, compound 214 and picobenzamid, compound 214 and picoxystrobin, compound 214 and piperalin, compound 214 and polyoxin, compound 214 and probenazole, compound 214 and prochloraz, compound 214 and procymidone, compound 214 and propamocarb, compound 214 and propamocarb-hydrochloride, compound 214 and propiconazole, compound 214 and propineb, compound 214 and proquinazid, compound 214 and prothioconazole, compound 214 and pyraclostrobin, compound 214 and pryazophos, compound 214 and pyribencarb, compound 214 and pyrifenox, compound 214 and pyrimethanil, compound 214 and pyrolnitrine, compound 214 and pyroquilon, compound 214 and quinomethionate, compound 214 and quinoxyfen, compound 214 and quintozene, compound 214 and silthiofam, compound 214 and simeconazole, compound 214 and spiroxamine, compound 214 and streptomycin, compound 214 and sulfur, compound 214 and tebuconazole, compound 214 and tecloftalam, compound 214 and tecnazene, compound 214 and terbinafine, compound 214 and tetraconazole, compound 214 and thiabendazole, compound 214 and thifluzamide, compound 214 and thiophanate, compound 214 and thiophanate-methyl, compound 214 and thiram, compound 214 and tiadinil, compound 214 and tolclofos-methyl, compound 214 and tolylfluanid, compound 214 and triadimefon, compound 214 and triadimenol, compound 214 and triazoxide, compound 214 and tricyclazole, compound 214 and tridemorph, compound 214 and triflumizole, compound 214 and tricyclazole, compound 214 and trifloxystrobin, compound 214 and triforine, compound 214 and triticonazole, compound 214 and uniconazole, compound 214 and validamycin, compound 214 and valiphenal, compound 214 and vinclozolin, compound 214 and zineb, compound 214 and ziram, compound 214 and zoxamide, compound 214 and 5-chloro-6-(2,4,6-trifluorophenyl)-7-(4-methylpiperidin-1-yl)[1,2,4]triazolo[1,5-α]pyrimidine (BAS600), compound 214 and N-[2-(1,3-dimethylbutyl)phenyl]-5-fluoro-1,3-dimethyl-1H-pyrazol-4-carboxamide, compound 214 and N-[2-[4-[[3-(4-chlorophenyl)-2-propyn-1-yl]oxy]-3-methoxyphenyl]ethyl]-3-methyl-2-[(methylsulfonyl)amino]butanamide, compound 214 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 214 and 2-butoxy-6-iodo-3-propyl-4H-1-benzopyran-4-one, compound 214 and 345-(4-chlorophenyl)-2,3-dimethyl-3-isoxazolidinyl]pyridine, compound 214 and 4-fluorophenyl N-[1-[[[1-(4-cyanophenyl)ethyl]sulfonyl]methyl]propyl]carbamate, compound 214 and N-[[(cyclopropylmethoxy)amino][6-(difluoromethoxy)-2,3-difluorophenyl]methylene]benzeneacetamide, compound 214 and α-(methoxyimino)-N-methyl-2-[[[1-[3-(trifluoromethyl)phenyl]ethoxy]imino]methyl]

benzeneacetamide, compound 214 and N'-[4-[4-chloro-3-(trifluoromethyl)phenoxy]-2,5-dimethylphenyl]-N-ethyl-N-methylmethanimidamide, compound 214 and 2-[[2-fluoro-5-(trifluoromethyl)phenyl]thio]-2-[3-(2-methoxyphenyl)-2-thiazolidinylidene]acetonitrile compound 214 and N-[2-(1S,2R)-[1,1'-bicyclopropyl]-2-ylphenyl]-3-(difluoromethyl)-1-methyl-1H-pyrazole-4-carboxamide, and compound 214 and N-(4-chloro-2-nitrophenyl)-N-ethyl-4-methylbenzenesulfonamide, compound 220 and acibenzolar-S-methyl, compound 220 and aldimorph, compound 220 and amisulbrom, compound 220 and anilazine, compound 220 and azaconazole, compound 220 and azoxystrobin, compound 220 and benalaxyl, compound 220 and benalaxyl-M, compound 220 and benodanil, compound 220 and benomyl, compound 220 and benthiavalicarb, compound 220 and benthiavalicarb-isopropyl, compound 220 and bethoxazin, compound 220 and binapacryl, compound 220 and biphenyl, compound 220 and bitertanol, compound 220 and bixafen, compound 220 and blasticidin-S, compound 220 and Bordeaux mixture (tribasic copper sulfate), compound 220 and boscalid, compound 220 and bromuconazole, compound 220 and bupirimate, compound 220 and carboxin, compound 220 and carpropamid, compound 220 and captafol, compound 220 and captan, compound 220 and carbendazim, compound 220 and chloroneb, compound 220 and chlorothalonil, compound 220 and chlozolinate, compound 220 and clotrimazole, compound 220 and copper oxychloride, compound 220 and copper salts such as copper sulfate and copper hydroxide, compound 220 and cyazofamid, compound 220 and cyflufenamid, compound 220 and cymoxanil, compound 220 and cyproconazole, compound 220 and cyprodinil, compound 220 and dichlofluanid, compound 220 and diclocymet, compound 220 and diclomezine, compound 220 and dicloran, compound 220 and diethofencarb, compound 220 and difenoconazole, compound 220 and diflumetorim, compound 220 and dimethirimol, compound 220 and dimethomorph, compound 220 and dimoxystrobin, compound 220 and diniconazole, compound 220 and diniconazole-M, compound 220 and dinocap, compound 220 and dithianon, compound 220 and dodemorph, compound 220 and dodine, compound 220 and edifenphos, compound 220 and enestroburin, compound 220 and epoxiconazole, compound 220 and ethaboxam, compound 220 and etridiazole, compound 220 and famoxadone, compound 220 and fenamidone, compound 220 and fenarimol, compound 220 and fenbuconazole, compound 220 and fenfuram, compound 220 and fenhexamid, compound 220 and fenoxanil, compound 220 and fenpiclonil, compound 220 and fenpropidin, compound 220 and fenpropimorph, compound 220 and fentin acetate, compound 220 and fentin chloride, compound 220 and fentin hydroxide, compound 220 and ferbam, compound 220 and ferimzone, compound 220 and fluazinam, compound 220 and fludioxonil, compound 220 and flumetover, compound 220 and flumorph, compound 220 and fluopicolide, compound 220 and fluopyram, compound 220 and fluoroimide, compound 220 and fluoxastrobin, compound 220 and fluquinconazole, compound 220 and flusilazole, compound 220 and flusulfamide, compound 220 and flutolanil, compound 220 and flutriafol, compound 220 and folpet, compound 220 and fosetyl-aluminum, compound 220 and fuberidazole, compound 220 and furalaxyl, compound 220 and furametpyr, compound 220 and hexaconazole, compound 220 and hymexazol, compound 220 and guazatine, compound 220 and imazalil, compound 220 and imibenconazole, compound 220 and iminoctadine, compound 220 and iodocarb, compound 220 and ipconazole, compound 220 and iprobenfos, compound 220 and iprodione, compound 220 and iprovalicarb, compound 220 and isoprothiolane, compound 220 and isopyrazam, compound 220 and isotianil, compound 220 and kasugamycin, compound 220 and kresoxim-methyl, compound 220 and mancozeb, compound 220 and mandipropamid, compound 220 and maneb, compound 220 and mepronil, compound 220 and meptyldinocap, compound 220 and metalaxyl, compound 220 and metalaxyl-M, compound 220 and metconazole, compound 220 and methasulfocarb, compound 220 and metiram, compound 220 and metominostrobin, compound 220 and mepanipyrim, compound 220 and metrafenone, compound 220 and myclobutanil, compound 220 and naftifine, compound 220 and neo-asozin (ferric methanearsonate), compound 220 and nuarimol, compound 220 and octhilinone, compound 220 and ofurace, compound 220 and orysastrobin, compound 220 and oxadixyl, compound 220 and oxolinic acid, compound 220 and oxpoconazole, compound 220 and oxycarboxin, compound 220 and oxytetracycline, compound 220 and penconazole, compound 220 and pencycuron, compound 220 and penthiopyrad, compound 220 and pefurazoate, compound 220 and phosphorous acid and salts, compound 220 and phthalide, compound 220 and picobenzamid, compound 220 and picoxystrobin, compound 220 and piperalin, compound 220 and polyoxin, compound 220 and probenazole, compound 220 and prochloraz, compound 220 and procymidone, compound 220 and propamocarb, compound 220 and propamocarb-hydrochloride, compound 220 and propiconazole, compound 220 and propineb, compound 220 and proquinazid, compound 220 and prothioconazole, compound 220 and pyraclostrobin, compound 220 and pryazophos, compound 220 and pyribencarb, compound 220 and pyrifenox, compound 220 and pyrimethanil, compound 220 and pyrolnitrine, compound 220 and pyroquilon, compound 220 and quinomethionate, compound 220 and quinoxyfen, compound 220 and quintozene, compound 220 and silthiofam, compound 220 and simeconazole, compound 220 and spiroxamine, compound 220 and streptomycin, compound 220 and sulfur, compound 220 and tebuconazole, compound 220 and tecloftalam, compound 220 and tecnazene, compound 220 and terbinafine, compound 220 and tetraconazole, compound 220 and thiabendazole, compound 220 and thifluzamide, compound 220 and thiophanate, compound 220 and thiophanate-methyl, compound 220 and thiram, compound 220 and tiadinil, compound 220 and tolclofos-methyl, compound 220 and tolylfluanid, compound 220 and triadimefon, compound 220 and triadimenol, compound 220 and triazoxide, compound 220 and tricyclazole, compound 220 and tridemorph, compound 220 and triflumizole, compound 220 and tricyclazole, compound 220 and trifloxystrobin, compound 220 and triforine, compound 220 and triticonazole, compound 220 and uniconazole, compound 220 and validamycin, compound 220 and valiphenal, compound 220 and vinclozolin, compound 220 and zineb, compound 220 and ziram, compound 220 and zoxamide, compound 220 and 5-chloro-6-(2,4,6-trifluorophenyl)-7-(4-methylpiperidin-1-yl)[1,2,4]triazolo[1,5-α]pyrimidine (BAS600), compound 220 and N-[2-(1,3-dimethylbutyl)phenyl]-5-fluoro-1,3-dimethyl-1H-pyrazol-4-carboxamide, compound 220 and N-[2-[4-[[3-(4-chlorophenyl)-2-propyn-1-yl]oxy]-3-methoxyphenyl]ethyl]-3-methyl-2-[(methylsulfonyl)amino]butanamide, compound 220 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 220 and 2-butoxy-6-iodo-3-propyl-4H-1-benzopyran-4-one, compound 220 and 3-[5-(4-chlorophenyl)-2,3-dimethyl-3-isoxazolidinyl]pyridine, compound 220 and 4-fluorophenyl N-[1-[[[1-(4-cyanophenyl)ethyl]sulfonyl]methyl]propyl]carbamate, compound 220 and N-[[(cyclopropylmethoxy)amino][6-(difluoromethoxy)-

2,3-difluorophenyl]methylene]benzeneacetamide, compound 220 and α-(methoxyimino)-N-methyl-2-[[[1-[3-(trifluoromethyl)phenyl]ethoxy]imino]methyl]benzeneacetamide, compound 220 and N'-[4-[4-chloro-3-(trifluoromethyl)phenoxy]-2,5-dimethylphenyl]-N-ethyl-N-methylmethanimidamide, compound 220 and 2-[[2-fluoro-5-(trifluoromethyl)phenyl]thio]-2-[3-(2-methoxyphenyl)-2-thiazolidinylidene]acetonitrile, compound 220 and N-[2-(1S,2R)-[1,1'-bicyclopropyl]-2-ylphenyl]-3-(difluoromethyl)-1-methyl-1H-pyrazole-4-carboxamide, and compound 220 and N-(4-chloro-2-nitrophenyl)-N-ethyl-4-methylbenzenesulfonamide, compound 225 and acibenzolar-S-methyl, compound 225 and aldimorph, compound 225 and amisulbrom, compound 225 and anilazine, compound 225 and azaconazole, compound 225 and azoxystrobin, compound 225 and benalaxyl, compound 225 and benalaxyl-M, compound 225 and benodanil, compound 225 and benomyl, compound 225 and benthiavalicarb, compound 225 and benthiavalicarb-isopropyl, compound 225 and bethoxazin, compound 225 and binapacryl, compound 225 and biphenyl, compound 225 and bitertanol, compound 225 and bixafen, compound 225 and blasticidin-S, compound 225 and Bordeaux mixture (tribasic copper sulfate), compound 225 and boscalid, compound 225 and bromuconazole, compound 225 and bupirimate, compound 225 and carboxin, compound 225 and carpropamid, compound 225 and captafol, compound 225 and captan, compound 225 and carbendazim, compound 225 and chloroneb, compound 225 and chlorothalonil, compound 225 and chlozolinate, compound 225 and clotrimazole, compound 225 and copper oxychloride, compound 225 and copper salts such as copper sulfate and copper hydroxide, compound 225 and cyazofamid, compound 225 and cyflufenamid, compound 225 and cymoxanil, compound 225 and cyproconazole, compound 225 and cyprodinil, compound 225 and dichlofluanid, compound 225 and diclocymet, compound 225 and diclomezine, compound 225 and dicloran, compound 225 and diethofencarb, compound 225 and difenoconazole, compound 225 and diflumetorim, compound 225 and dimethirimol, compound 225 and dimethomorph, compound 225 and dimoxystrobin, compound 225 and diniconazole, compound 225 and diniconazole-M, compound 225 and dinocap, compound 225 and dithianon, compound 225 and dodemorph, compound 225 and dodine, compound 225 and edifenphos, compound 225 and enestroburin, compound 225 and epoxiconazole, compound 225 and ethaboxam, compound 225 and etridiazole, compound 225 and famoxadone, compound 225 and fenamidone, compound 225 and fenarimol, compound 225 and fenbuconazole, compound 225 and fenfuram, compound 225 and fenhexamid, compound 225 and fenoxanil, compound 225 and fenpiclonil, compound 225 and fenpropidin, compound 225 and fenpropimorph, compound 225 and fentin acetate, compound 225 and fentin chloride, compound 225 and fentin hydroxide, compound 225 and ferbam, compound 225 and ferimzone, compound 225 and fluazinam, compound 225 and fludioxonil, compound 225 and flumetover, compound 225 and flumorph, compound 225 and fluopicolide, compound 225 and fluopyram, compound 225 and fluoroimide, compound 225 and fluoxastrobin, compound 225 and fluquinconazole, compound 225 and flusilazole, compound 225 and flusulfamide, compound 225 and flutolanil, compound 225 and flutriafol, compound 225 and folpet, compound 225 and fosetyl-aluminum, compound 225 and fuberidazole, compound 225 and furalaxyl, compound 225 and furametpyr, compound 225 and hexaconazole, compound 225 and hymexazol, compound 225 and guazatine, compound 225 and imazalil, compound 225 and imibenconazole, compound 225 and iminoctadine, compound 225 and iodocarb, compound 225 and ipconazole, compound 225 and iprobenfos, compound 225 and iprodione, compound 225 and iprovalicarb, compound 225 and isoprothiolane, compound 225 and isopyrazam, compound 225 and isotianil, compound 225 and kasugamycin, compound 225 and kresoxim-methyl, compound 225 and mancozeb, compound 225 and mandipropamid, compound 225 and maneb, compound 225 and mepronil, compound 225 and meptyldinocap, compound 225 and metalaxyl, compound 225 and metalaxyl-M, compound 225 and metconazole, compound 225 and methasulfocarb, compound 225 and metiram, compound 225 and metominostrobin, compound 225 and mepanipyrim, compound 225 and metrafenone, compound 225 and myclobutanil, compound 225 and naftifine, compound 225 and neo-asozin (ferric methanearsonate), compound 225 and nuarimol, compound 225 and octhilinone, compound 225 and ofurace, compound 225 and orysastrobin, compound 225 and oxadixyl, compound 225 and oxolinic acid, compound 225 and oxpoconazole, compound 225 and oxycarboxin, compound 225 and oxytetracycline, compound 225 and penconazole, compound 225 and pencycuron, compound 225 and penthiopyrad, compound 225 and pefurazoate, compound 225 and phosphorous acid and salts, compound 225 and phthalide, compound 225 and picobenzamid, compound 225 and picoxystrobin, compound 225 and piperalin, compound 225 and polyoxin, compound 225 and probenazole, compound 225 and prochloraz, compound 225 and procymidone, compound 225 and propamocarb, compound 225 and propamocarb-hydrochloride, compound 225 and propiconazole, compound 225 and propineb, compound 225 and proquinazid, compound 225 and prothioconazole, compound 225 and pyraclostrobin, compound 225 and pryazophos, compound 225 and pyribencarb, compound 225 and pyrifenox, compound 225 and pyrimethanil, compound 225 and pyrolnitrine, compound 225 and pyroquilon, compound 225 and quinomethionate, compound 225 and quinoxyfen, compound 225 and quintozene, compound 225 and silthiofam, compound 225 and simeconazole, compound 225 and spiroxamine, compound 225 and streptomycin, compound 225 and sulfur, compound 225 and tebuconazole, compound 225 and tecloftalam, compound 225 and tecnazene, compound 225 and terbinafine, compound 225 and tetraconazole, compound 225 and thiabendazole, compound 225 and thifluzamide, compound 225 and thiophanate, compound 225 and thiophanate-methyl, compound 225 and thiram, compound 225 and tiadinil, compound 225 and tolclofos-methyl, compound 225 and tolylfluanid, compound 225 and triadimefon, compound 225 and triadimenol, compound 225 and triazoxide, compound 225 and tricyclazole, compound 225 and tridemorph, compound 225 and triflumizole, compound 225 and tricyclazole, compound 225 and trifloxystrobin, compound 225 and triforine, compound 225 and triticonazole, compound 225 and uniconazole, compound 225 and validamycin, compound 225 and valiphenal, compound 225 and vinclozolin, compound 225 and zineb, compound 225 and ziram, compound 225 and zoxamide, compound 225 and 5-chloro-6-(2,4,6-trifluorophenyl)-7-(4-methylpiperidin-1-yl)[1,2,4]triazolo[1,5-α]pyrimidine (BAS600), compound 225 and N-[2-(1,3-dimethylbutyl)phenyl]-5-fluoro-1,3-dimethyl-1H-pyrazol-4-carboxamide, compound 225 and N-[2-[4-[[3-(4-chlorophenyl)-2-propyn-1-yl]oxy]-3-methoxyphenyl]ethyl]-3-methyl-2-[(methylsulfonyl)amino]butanamide, compound 225 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 225 and 2-butoxy-6-iodo-3-propyl-4H-1-benzopyran-4-one, compound 225 and 3-[5-(4-chlorophenyl)-2,3-dimethyl-3-isoxazolidinyl]pyridine, compound 225 and 4-fluorophenyl N-[1-[[[1-(4-cyanophenyl)ethyl]sulfonyl]methyl]propyl]carbamate, compound 225 and N-[[(cyclopropylmethoxy)amino][6-(difluoromethoxy)-2,3-difluorophenyl]methylene]benzeneacetamide, compound 225 and α-(methoxyimino)-N-methyl-2-[[[1-[3-(trifluoromethyl)phenyl]ethoxy]imino]methyl] benzeneacetamide, compound 225 and N'-[4-[4-chloro-3-(trifluoromethyl)phenoxy]-2,5-dimethylphenyl]-N-ethyl-N-methylmethanimidamide, compound 225 and 2-[[2-fluoro-5-(trifluoromethyl)phenyl]thio]-2-[3-(2-methoxyphenyl)-2-thiazolidinylidene]acetonitrile, compound 225 and N-[2-(1S,2R)-[1,1'-bicyclopropyl]-2-ylphenyl]-3-(difluoromethyl)-1-methyl-1H-pyrazole-4-carboxamide, and compound 225 and N-(4-chloro-2-nitrophenyl)-N-ethyl-4-methylbenzenesulfonamide, compound 265 and acibenzolar-S-methyl, compound 265 and aldimorph, compound 265 and amisulbrom, compound 265 and anilazine, compound 265 and azaconazole, compound 265 and azoxystrobin, compound 265 and benalaxyl, compound 265 and benalaxyl-M, compound 265 and benodanil, compound 265 and benomyl, compound 265 and benthiavalicarb, compound 265 and benthiavalicarb-isopropyl, compound 265 and bethoxazin, compound 265 and binapacryl, compound 265 and biphenyl, compound 265 and bitertanol, compound 265 and bixafen, compound 265 and blasticidin-S, compound 265 and Bordeaux mixture (tribasic copper sulfate), compound 265 and boscalid, compound 265 and bromuconazole, compound 265 and bupirimate, compound 265 and carboxin, compound 265 and carpropamid, compound 265 and captafol, compound 265 and captan, compound 265 and carbendazim, compound 265 and chloroneb, compound 265 and chlorothalonil, compound 265 and chlozolinate, compound 265 and clotrimazole, compound 265 and copper oxychloride, compound 265 and copper salts such as copper sulfate and copper hydroxide, compound 265 and cyazofamid, compound 265 and cyflufenamid, compound 265 and cymoxanil, compound 265 and cyproconazole, compound 265 and cyprodinil, compound 265 and dichlofluanid, compound 265 and diclocymet, compound 265 and diclomezine, compound 265 and dicloran, compound 265 and diethofencarb, compound 265 and difenoconazole, compound 265 and diflumetorim, compound 265 and dimethirimol, compound 265 and dimethomorph, compound 265 and dimoxystrobin, compound 265 and diniconazole, compound 265 and diniconazole-M, compound 265 and dinocap, compound 265 and dithianon, compound 265 and dodemorph, compound 265 and dodine, compound 265 and edifenphos, compound 265 and enestroburin, compound 265 and epoxiconazole, compound 265 and ethaboxam, compound 265 and etridiazole, compound 265 and famoxadone, compound 265 and fenamidone, compound 265 and fenarimol, compound 265 and fenbuconazole, compound 265 and fenfuram, compound 265 and fenhexamid, compound 265 and fenoxanil, compound 265 and fenpiclonil, compound 265 and fenpropidin, compound 265 and fenpropimorph, compound 265 and fentin acetate, compound 265 and fentin chloride, compound 265 and fentin hydroxide, compound 265 and ferbam, compound 265 and ferimzone, compound 265 and fluazinam, compound 265 and fludioxonil, compound 265 and flumetover, compound 265 and flumorph, compound 265 and fluopicolide, compound 265 and fluopyram, compound 265 and fluoroimide, compound 265 and fluoxastrobin, compound 265 and fluquinconazole, compound 265 and flusilazole, compound 265 and flusulfamide, compound 265 and flutolanil, compound 265 and flutriafol, compound 265 and folpet, compound 265 and fosetyl-aluminum, compound 265 and fuberidazole, compound 265 and furalaxyl, compound 265 and furametpyr, compound 265 and hexaconazole, compound 265 and hymexazol, compound 265 and guazatine, compound 265 and imazalil, compound 265 and imibenconazole, compound 265 and iminoctadine, compound 265 and iodocarb, compound 265 and ipconazole, compound 265 and iprobenfos, compound 265 and iprodione, compound 265 and iprovalicarb, compound 265 and isoprothiolane, compound 265 and isopyrazam, compound 265 and isotianil, compound 265 and kasugamycin, compound 265 and kresoxim-methyl, compound 265 and mancozeb, compound 265 and mandipropamid, compound 265 and maneb, compound 265 and mepronil, compound 265 and meptyldinocap, compound 265 and metalaxyl, compound 265 and metalaxyl-M, compound 265 and metconazole, compound 265 and methasulfocarb, compound 265 and metiram, compound 265 and metominostrobin, compound 265 and mepanipyrim, compound 265 and metrafenone, compound 265 and myclobutanil, compound 265 and naftifine, compound 265 and neo-asozin (ferric methanearsonate), compound 265 and nuarimol, compound 265 and octhilinone, compound 265 and ofurace, compound 265 and orysastrobin, compound 265 and oxadixyl, compound 265 and oxolinic acid, compound 265 and oxpoconazole, compound 265 and oxycarboxin, compound 265 and oxytetracycline, compound 265 and penconazole, compound 265 and pencycuron, compound 265 and penthiopyrad, compound 265 and pefurazoate, compound 265 and phosphorous acid and salts, compound 265 and phthalide, compound 265 and picobenzamid, compound 265 and picoxystrobin, compound 265 and piperalin, compound 265 and polyoxin, compound 265 and probenazole, compound 265 and prochloraz, compound 265 and procymidone, compound 265 and propamocarb, compound 265 and propamocarb-hydrochloride, compound 265 and propiconazole, compound 265 and propineb, compound 265 and proquinazid, compound 265 and prothioconazole, compound 265 and pyraclostrobin, compound 265 and pryazophos, compound 265 and pyribencarb, compound 265 and pyrifenox, compound 265 and pyrimethanil, compound 265 and pyrolnitrine, compound 265 and pyroquilon, compound 265 and quinomethionate, compound 265 and quinoxyfen, compound 265 and quintozene, compound 265 and silthiofam, compound 265 and simeconazole, compound 265 and spiroxamine, compound 265 and streptomycin, compound 265 and sulfur, compound 265 and tebuconazole, compound 265 and tecloftalam, compound 265 and tecnazene, compound 265 and terbinafine, compound 265 and tetraconazole, compound 265 and thiabendazole, compound 265 and thifluzamide, compound 265 and thiophanate, compound 265 and thiophanate-methyl, compound 265 and thiram, compound 265 and tiadinil, compound 265 and tolclofos-methyl, compound 265 and tolylfluanid, compound 265 and triadimefon, compound 265 and triadimenol, compound 265 and triazoxide, compound 265 and tricyclazole, compound 265 and tridemorph, compound 265 and triflumizole, compound 265 and tricyclazole, compound 265 and trifloxystrobin, compound 265 and triforine, compound 265 and triticonazole, compound 265 and uniconazole, compound 265 and validamycin, compound 265 and valiphenal, compound 265 and vinclozolin, compound 265 and zineb, compound 265 and ziram, compound 265 and zoxamide, compound 265 and 5-chloro-6-(2,4,6-trifluorophenyl)-7-(4-methylpiperidin-1-yl)[1,2,4]triazolo[1,5-α]pyrimidine (BAS600), compound 265 and N-[2-(1,3-dimethylbutyl)phenyl]-5-fluoro-1,3-dimethyl-1H-pyrazol-4-carboxamide, compound 265 and N-[2-[4-[[3-(4-chlorophenyl)-2-propyn-1-yl]oxy]-3-methoxyphenyl]ethyl]-3-methyl-2-[(methylsulfonyl)amino]butanamide, compound 265 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 265 and 2-butoxy-6-iodo-3-propyl-4H-1-benzopyran-4-one, compound 265 and 3-[5-(4-chlorophenyl)-2,3-dimethyl-3-isoxazolidinyl]pyridine, compound 265 and 4-fluorophenyl N-[1-[[[1-(4-cyanophenyl)ethyl]sulfonyl]methyl]propyl]carbamate, compound 265 and N-[[(cyclopropylmethoxy)amino][6-(difluoromethoxy)-2,3-difluorophenyl]methylene]benzeneacetamide, compound 265 and α-(methoxyimino)-N-methyl-2-[[[1-[3-(trifluoromethyl)phenyl]ethoxy]imino]methyl]benzeneacetamide, compound 265 and N'-[4-[4-chloro-3-(trifluoromethyl)phenoxy]-2,5-dimethylphenyl]-N-ethyl-N-methylmethanimidamide, compound 265 and 2-[[2-fluoro-5-(trifluoromethyl)phenyl]thio]-2-[3-(2-methoxyphenyl)-2-thiazolidinylidene]acetonitrile, compound 265 and N-[2-(1S,2R)-[1,1'-bicyclopropyl]-2-ylphenyl]-3-(difluoromethyl)-1-methyl-1H-pyrazole-4-carboxamide, and compound 265 and N-(4-chloro-2-nitrophenyl)-N-ethyl-4-methylbenzenesulfonamide, compound 292 and acibenzolar-S-methyl, compound 292 and aldimorph, compound 292 and amisulbrom, compound 292 and anilazine, compound 292 and azaconazole, compound 292 and azoxystrobin, compound 292 and benalaxyl, compound 292 and benalaxyl-M, compound 292 and benodanil, compound 292 and benomyl, compound 292 and benthiavalicarb, compound 292 and benthiavalicarb-isopropyl, compound 292 and bethoxazin, compound 292 and binapacryl, compound 292 and biphenyl, compound 292 and bitertanol, compound 292 and bixafen, compound 292 and blasticidin-S, compound 292 and Bordeaux mixture (tribasic copper sulfate), compound 292 and boscalid, compound 292 and bromuconazole, compound 292 and bupirimate, compound 292 and carboxin, compound 292 and carpropamid, compound 292 and captafol, compound 292 and captan, compound 292 and carbendazim, compound 292 and chloroneb, compound 292 and chlorothalonil, compound 292 and chlozolinate, compound 292 and clotrimazole, compound 292 and copper oxychloride, compound 292 and copper salts such as copper sulfate and copper hydroxide, compound 292 and cyazofamid, compound 292 and cyflufenamid, compound 292 and cymoxanil, compound 292 and cyproconazole, compound 292 and cyprodinil, compound 292 and dichlofluanid, compound 292 and diclocymet, compound 292 and diclomezine, compound 292 and dicloran, compound 292 and diethofencarb, compound 292 and difenoconazole, compound 292 and diflumetorim, compound 292 and dimethirimol, compound 292 and dimethomorph, compound 292 and dimoxystrobin, compound 292 and diniconazole, compound 292 and diniconazole-M, compound 292 and dinocap, compound 292 and dithianon, compound 292 and dodemorph, compound 292 and dodine, compound 292 and edifenphos, compound 292 and enestroburin, compound 292 and epoxiconazole, compound 292 and ethaboxam, compound 292 and etridiazole, compound 292 and famoxadone, compound 292 and fenamidone, compound 292 and fenarimol, compound 292 and fenbuconazole, compound 292 and fenfuram, compound 292 and fenhexamid, compound 292 and fenoxanil, compound 292 and fenpiclonil, compound 292 and fenpropidin, compound 292 and fenpropimorph, compound 292 and fentin acetate, compound 292 and fentin chloride, compound 292 and fentin hydroxide, compound 292 and ferbam, compound 292 and ferimzone, compound 292 and fluazinam, compound 292 and fludioxonil, compound 292 and flumetover, compound 292 and flumorph, compound 292 and fluopicolide, compound 292 and fluopyram, compound 292 and fluoroimide, compound 292 and fluoxastrobin, compound 292 and fluquinconazole, compound 292 and flusilazole, compound 292 and flusulfamide, compound 292 and flutolanil, compound 292 and flutriafol, compound 292 and folpet, compound 292 and fosetyl-aluminum, compound 292 and fuberidazole, compound 292 and furalaxyl, compound 292 and furametpyr, compound 292 and hexaconazole, compound 292 and hymexazol, compound 292 and guazatine, compound 292 and imazalil, compound 292 and imibenconazole, compound 292 and iminoctadine, compound 292 and iodocarb, compound 292 and ipconazole, compound 292 and iprobenfos, compound 292 and iprodione, compound 292 and iprovalicarb, compound 292 and isoprothiolane, compound 292 and isopyrazam, compound 292 and isotianil, compound 292 and kasugamycin, compound 292 and kresoxim-methyl, compound 292 and mancozeb, compound 292 and mandipropamid, compound 292 and maneb, compound 292 and mepronil, compound 292 and meptyldinocap, compound 292 and metalaxyl, compound 292 and metalaxyl-M, compound 292 and metconazole, compound 292 and methasulfocarb, compound 292 and metiram, compound 292 and metominostrobin, compound 292 and mepanipyrim, compound 292 and metrafenone, compound 292 and myclobutanil, compound 292 and naftifine, compound 292 and neo-asozin (ferric methanearsonate), compound 292 and nuarimol, compound 292 and octhilinone, compound 292 and ofurace, compound 292 and orysastrobin, compound 292 and oxadixyl, compound 292 and oxolinic acid, compound 292 and oxpoconazole, compound 292 and oxycarboxin, compound 292 and oxytetracycline, compound 292 and penconazole, compound 292 and pencycuron, compound 292 and penthiopyrad, compound 292 and pefurazoate, compound 292 and phosphorous acid and salts, compound 292 and phthalide, compound 292 and picobenzamid, compound 292 and picoxystrobin, compound 292 and piperalin, compound 292 and polyoxin, compound 292 and probenazole, compound 292 and prochloraz, compound 292 and procymidone, compound 292 and propamocarb, compound 292 and propamocarb-hydrochloride, compound 292 and propiconazole, compound 292 and propineb, compound 292 and proquinazid, compound 292 and prothioconazole, compound 292 and pyraclostrobin, compound 292 and pryazophos, compound 292 and pyribencarb, compound 292 and pyrifenox, compound 292 and pyrimethanil, compound 292 and pyrolnitrine, compound 292 and pyroquilon, compound 292 and quinomethionate, compound 292 and quinoxyfen, compound 292 and quintozene, compound 292 and silthiofam, compound 292 and simeconazole, compound 292 and spiroxamine, compound 292 and streptomycin, compound 292 and sulfur, compound 292 and tebuconazole, compound 292 and tecloftalam, compound 292 and tecnazene, compound 292 and terbinafine, compound 292 and tetraconazole, compound 292 and thiabendazole, compound 292 and thifluzamide, compound 292 and thiophanate, compound 292 and thiophanate-methyl, compound 292 and thiram, compound 292 and tiadinil, compound 292 and tolclofos-methyl, compound 292 and tolylfluanid, compound 292 and triadimefon, compound 292 and triadimenol, compound 292 and triazoxide, compound 292 and tricyclazole, compound 292 and tridemorph, compound 292 and triflumizole, compound 292 and tricyclazole, compound 292 and trifloxystrobin, compound 292 and triforine, compound 292 and triticonazole, compound 292 and uniconazole, compound 292 and validamycin, compound 292 and valiphenal, compound 292 and vinclozolin, compound 292 and zineb, compound 292 and ziram, compound 292 and zoxamide, compound 292 and 5-chloro-6-(2,4,6-trifluorophenyl)-7-(4-methylpiperidin-1-yl)[1,2,4]triazolo[1,5-c]pyrimidine (BAS600), compound 292 and N-[2-(1,3-dimethylbutyl)phenyl]-5-fluoro-1,3-dimethyl-1H-pyrazol-4-carboxamide, compound 292 and N-[2-[4-[[3-(4-chlorophenyl)-2-propyn-1-yl]oxy]-3-methoxyphenyl]

ethyl]-3-methyl-2-[(methylsulfonyl)amino]butanamide, compound 292 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 292 and 2-butoxy-6-iodo-3-propyl-4H-1-benzopyran-4-one, compound 292 and 3-[5-(4-chlorophenyl)-2,3-dimethyl-3-isoxazolidinyl]pyridine, compound 292 and 4-fluorophenyl N-[1-[[[1-(4-cyanophenyl)ethyl]sulfonyl]methyl]propyl]carbamate, compound 292 and N-[[(cyclopropylmethoxy)amino][6-(difluoromethoxy)-2,3-difluorophenyl]methylene]benzeneacetamide, compound 292 and α-(methoxyimino)-N-methyl-2-[[[1-[3-(trifluoromethyl)phenyl]ethoxy]imino]methyl]benzeneacetamide, compound 292 and N'-[4-[4-chloro-3-(trifluoromethyl)phenoxy]-2,5-dimethylphenyl]-N-ethyl-N-methylmethanimidamide, compound 292 and 2-[[2-fluoro-5-(trifluoromethyl)phenyl]thio]-2-[3-(2-methoxyphenyl)-2-thiazolidinylidene]acetonitrile, compound 292 and N-[2-(1S,2R)-[1,1'-bicyclopropyl]-2-ylphenyl]-3-(difluoromethyl)-1-methyl-1H-pyrazole-4-carboxamide, and compound 292 and N-(4-chloro-2-nitrophenyl)-N-ethyl-4-methylbenzenesulfonamide, compound 342 and acibenzolar-S-methyl, compound 342 and aldimorph, compound 342 and amisulbrom, compound 342 and anilazine, compound 342 and azaconazole, compound 342 and azoxystrobin, compound 342 and benalaxyl, compound 342 and benalaxyl-M, compound 342 and benodanil, compound 342 and benomyl, compound 342 and benthiavalicarb, compound 342 and benthiavalicarb-isopropyl, compound 342 and bethoxazin, compound 342 and binapacryl, compound 342 and biphenyl, compound 342 and bitertanol, compound 342 and bixafen, compound 342 and blasticidin-S, compound 342 and Bordeaux mixture (tribasic copper sulfate), compound 342 and boscalid, compound 342 and bromuconazole, compound 342 and bupirimate, compound 342 and carboxin, compound 342 and carpropamid, compound 342 and captafol, compound 342 and captan, compound 342 and carbendazim, compound 342 and chloroneb, compound 342 and chlorothalonil, compound 342 and chlozolinate, compound 342 and clotrimazole, compound 342 and copper oxychloride, compound 342 and copper salts such as copper sulfate and copper hydroxide, compound 342 and cyazofamid, compound 342 and cyflufenamid, compound 342 and cymoxanil, compound 342 and cyproconazole, compound 342 and cyprodinil, compound 342 and dichlofluanid, compound 342 and diclocymet, compound 342 and diclomezine, compound 342 and dicloran, compound 342 and diethofencarb, compound 342 and difenoconazole, compound 342 and diflumetorim, compound 342 and dimethirimol, compound 342 and dimethomorph, compound 342 and dimoxystrobin, compound 342 and diniconazole, compound 342 and diniconazole-M, compound 342 and dinocap, compound 342 and dithianon, compound 342 and dodemorph, compound 342 and dodine, compound 342 and edifenphos, compound 342 and enestroburin, compound 342 and epoxiconazole, compound 342 and ethaboxam, compound 342 and etridiazole, compound 342 and famoxadone, compound 342 and fenamidone, compound 342 and fenarimol, compound 342 and fenbuconazole, compound 342 and fenfuram, compound 342 and fenhexamid, compound 342 and fenoxanil, compound 342 and fenpiclonil, compound 342 and fenpropidin, compound 342 and fenpropimorph, compound 342 and fentin acetate, compound 342 and fentin chloride, compound 342 and fentin hydroxide, compound 342 and ferbam, compound 342 and ferimzone, compound 342 and fluazinam, compound 342 and fludioxonil, compound 342 and flumetover, compound 342 and flumorph, compound 342 and fluopicolide, compound 342 and fluopyram, compound 342 and fluoroimide, compound 342 and fluoxastrobin, compound 342 and fluquinconazole, compound 342 and flusilazole, compound 342 and flusulfamide, compound 342 and flutolanil, compound 342 and flutriafol, compound 342 and folpet, compound 342 and fosetyl-aluminum, compound 342 and fuberidazole, compound 342 and furalaxyl, compound 342 and furametpyr, compound 342 and hexaconazole, compound 342 and hymexazol, compound 342 and guazatine, compound 342 and imazalil, compound 342 and imibenconazole, compound 342 and iminoctadine, compound 342 and iodocarb, compound 342 and ipconazole, compound 342 and iprobenfos, compound 342 and iprodione, compound 342 and iprovalicarb, compound 342 and isoprothiolane, compound 342 and isopyrazam, compound 342 and isotianil, compound 342 and kasugamycin, compound 342 and kresoxim-methyl, compound 342 and mancozeb, compound 342 and mandipropamid, compound 342 and maneb, compound 342 and mepronil, compound 342 and meptyldinocap, compound 342 and metalaxyl, compound 342 and metalaxyl-M, compound 342 and metconazole, compound 342 and methasulfocarb, compound 342 and metiram, compound 342 and metominostrobin, compound 342 and mepanipyrim, compound 342 and metrafenone, compound 342 and myclobutanil, compound 342 and naftifine, compound 342 and neo-asozin (ferric methanearsonate), compound 342 and nuarimol, compound 342 and octhilinone, compound 342 and ofurace, compound 342 and orysastrobin, compound 342 and oxadixyl, compound 342 and oxolinic acid, compound 342 and oxpoconazole, compound 342 and oxycarboxin, compound 342 and oxytetracycline, compound 342 and penconazole, compound 342 and pencycuron, compound 342 and penthiopyrad, compound 342 and pefurazoate, compound 342 and phosphorous acid and salts, compound 342 and phthalide, compound 342 and picobenzamid, compound 342 and picoxystrobin, compound 342 and piperalin, compound 342 and polyoxin, compound 342 and probenazole, compound 342 and prochloraz, compound 342 and procymidone, compound 342 and propamocarb, compound 342 and propamocarb-hydrochloride, compound 342 and propiconazole, compound 342 and propineb, compound 342 and proquinazid, compound 342 and prothioconazole, compound 342 and pyraclostrobin, compound 342 and pryazophos, compound 342 and pyribencarb, compound 342 and pyrifenox, compound 342 and pyrimethanil, compound 342 and pyrolnitrine, compound 342 and pyroquilon, compound 342 and quinomethionate, compound 342 and quinoxyfen, compound 342 and quintozene, compound 342 and silthiofam, compound 342 and simeconazole, compound 342 and spiroxamine, compound 342 and streptomycin, compound 342 and sulfur, compound 342 and tebuconazole, compound 342 and tecloftalam, compound 342 and tecnazene, compound 342 and terbinafine, compound 342 and tetraconazole, compound 342 and thiabendazole, compound 342 and thifluzamide, compound 342 and thiophanate, compound 342 and thiophanate-methyl, compound 342 and thiram, compound 342 and tiadinil, compound 342 and tolclofos-methyl, compound 342 and tolylfluanid, compound 342 and triadimefon, compound 342 and triadimenol, compound 342 and triazoxide, compound 342 and tricyclazole, compound 342 and tridemorph, compound 342 and triflumizole, compound 342 and tricyclazole, compound 342 and trifloxystrobin, compound 342 and triforine, compound 342 and triticonazole, compound 342 and uniconazole, compound 342 and validamycin, compound 342 and valiphenal, compound 342 and vinclozolin, compound 342 and zineb, compound 342 and ziram, compound 342 and zoxamide, compound 342 and 5-chloro-6-bixafen, compound 391 and blasticidin-S, compound 391 and Bordeaux mixture (tribasic copper(2,4,6-trifluorophenyl)-7-(4-methylpiperidin-1-yl)[1,2,4]triazolo[1,5-α]pyrimidine (BAS600), compound 342 and N-[2-(1,3-dimethylbutyl)phenyl]-5-fluoro-1,3-dimethyl-1H-pyrazol-4-carboxamide, compound 342 and N-[2-[4-[[3-(4-chlorophenyl)-2-propyn-1-yl]oxy]-3-methoxyphenyl]ethyl]-3-methyl-2-[(methylsulfonyl)amino]butanamide, compound 342 and N-[2-[4-[[3-(4-chlorophenyl)-2-propyn-1-yl]oxy]-3-methoxyphenyl] ethyl]-3-methyl-2-[(ethylsulfonyl)amino]butanamide, compound 342 and 2-butoxy-6-iodo-3-propyl-4H-1-benzopyran-4-one, compound 342 and 3-[5-(4-chlorophenyl)-2,3-dimethyl-3-isoxazolidinyl]pyridine, compound 342 and 4-fluorophenyl N-[1-[[[1-(4-cyanophenyl)ethyl]sulfonyl]methyl]propyl]carbamate, compound 342 and N-[[(cyclopropylmethoxy)amino][6-(difluoromethoxy)-2,3-difluorophenyl]methylene]benzeneacetamide, compound 342 and α-(methoxyimino)-N-methyl-2-[[[1-[3-(trifluoromethyl)phenyl]ethoxy]imino]methyl]benzeneacetamide, compound 342 and N'-[4-[4-chloro-3-(trifluoromethyl)phenoxy]-2,5-dimethylphenyl]-N-ethyl-N-methylmethanimidamide, compound 342 and 2-[[2-fluoro-5-(trifluoromethyl)phenyl]thio]-2-[3-(2-methoxyphenyl)-2-thiazolidinylidene]acetonitrile, compound 342 and N-[2-(1S,2R)-[1,1'-bicyclopropyl]-2-ylphenyl]-3-(difluoromethyl)-1-methyl-1H-pyrazole-4-carboxamide, and compound 342 and N-(4-chloro-2-nitrophenyl)-N-ethyl-4-methylbenzenesulfonamide, compound 391 and acibenzolar-S-methyl, compound 391 and aldimorph, compound 391 and amisulbrom, compound 391 and anilazine, compound 391 and azaconazole, compound 391 and azoxystrobin, compound 391 and benalaxyl, compound 391 and benalaxyl-M, compound 391 and benodanil, compound 391 and benomyl, compound 391 and benthiavalicarb, compound 391 and benthiavalicarb-isopropyl, compound 391 and bethoxazin, compound 391 and binapacryl, compound 391 and biphenyl, compound 391 and bitertanol, compound 391 and sulfate), compound 391 and boscalid, compound 391 and bromuconazole, compound 391 and bupirimate, compound 391 and carboxin, compound 391 and carpropamid, compound 391 and captafol, compound 391 and captan, compound 391 and carbendazim, compound 391 and chloroneb, compound 391 and chlorothalonil, compound 391 and chlozolinate, compound 391 and clotrimazole, compound 391 and copper oxychloride, compound 391 and copper salts such as copper sulfate and copper hydroxide, compound 391 and cyazofamid, compound 391 and cyflufenamid, compound 391 and cymoxanil, compound 391 and cyproconazole, compound 391 and cyprodinil, compound 391 and dichlofluanid, compound 391 and diclocymet, compound 391 and diclomezine, compound 391 and dicloran, compound 391 and diethofencarb, compound 391 and difenoconazole, compound 391 and diflumetorim, compound 391 and dimethirimol, compound 391 and dimethomorph, compound 391 and dimoxystrobin, compound 391 and diniconazole, compound 391 and diniconazole-M, compound 391 and dinocap, compound 391 and dithianon, compound 391 and dodemorph, compound 391 and dodine, compound 391 and edifenphos, compound 391 and enestroburin, compound 391 and epoxiconazole, compound 391 and ethaboxam, compound 391 and etridiazole, compound 391 and famoxadone, compound 391 and fenamidone, compound 391 and fenarimol, compound 391 and fenbuconazole, compound 391 and fenfuram, compound 391 and fenhexamid, compound 391 and fenoxanil, compound 391 and fenpiclonil, compound 391 and fenpropidin, compound 391 and fenpropimorph, compound 391 and fentin acetate, compound 391 and fentin chloride, compound 391 and fentin hydroxide, compound 391 and ferbam, compound 391 and ferimzone, compound 391 and fluazinam, compound 391 and fludioxonil, compound 391 and flumetover, compound 391 and flumorph, compound 391 and fluopicolide, compound 391 and fluopyram, compound 391 and fluoroimide, compound 391 and fluoxastrobin, compound 391 and fluquinconazole, compound 391 and flusilazole, compound 391 and flusulfamide, compound 391 and flutolanil, compound 391 and flutriafol, compound 391 and folpet, compound 391 and fosetyl-aluminum, compound 391 and fuberidazole, compound 391 and furalaxyl, compound 391 and furametpyr, compound 391 and hexaconazole, compound 391 and hymexazol, compound 391 and guazatine, compound 391 and imazalil, compound 391 and imibenconazole, compound 391 and iminoctadine, compound 391 and iodocarb, compound 391 and ipconazole, compound 391 and iprobenfos, compound 391 and iprodione, compound 391 and iprovalicarb, compound 391 and isoprothiolane, compound 391 and isopyrazam, compound 391 and isotianil, compound 391 and kasugamycin, compound 391 and kresoxim-methyl, compound 391 and mancozeb, compound 391 and mandipropamid, compound 391 and maneb, compound 391 and mepronil, compound 391 and meptyldinocap, compound 391 and metalaxyl, compound 391 and metalaxyl-M, compound 391 and metconazole, compound 391 and methasulfocarb, compound 391 and metiram, compound 391 and metominostrobin, compound 391 and mepanipyrim, compound 391 and metrafenone, compound 391 and myclobutanil, compound 391 and naftifine, compound 391 and neo-asozin (ferric methanearsonate), compound 391 and nuarimol, compound 391 and octhilinone, compound 391 and ofurace, compound 391 and orysastrobin, compound 391 and oxadixyl, compound 391 and oxolinic acid, compound 391 and oxpoconazole, compound 391 and oxycarboxin, compound 391 and oxytetracycline, compound 391 and penconazole, compound 391 and pencycuron, compound 391 and penthiopyrad, compound 391 and pefurazoate, compound 391 and phosphorous acid and salts, compound 391 and phthalide, compound 391 and picobenzamid, compound 391 and picoxystrobin, compound 391 and piperalin, compound 391 and polyoxin, compound 391 and probenazole, compound 391 and prochloraz, compound 391 and procymidone, compound 391 and propamocarb, compound 391 and propamocarb-hydrochloride, compound 391 and propiconazole, compound 391 and propineb, compound 391 and proquinazid, compound 391 and prothioconazole, compound 391 and pyraclostrobin, compound 391 and pryazophos, compound 391 and pyribencarb, compound 391 and pyrifenox, compound 391 and pyrimethanil, compound 391 and pyrolnitrine, compound 391 and pyroquilon, compound 391 and quinomethionate, compound 391 and quinoxyfen, compound 391 and quintozene, compound 391 and silthiofam, compound 391 and simeconazole, compound 391 and spiroxamine, compound 391 and streptomycin, compound 391 and sulfur, compound 391 and tebuconazole, compound 391 and tecloftalam, compound 391 and tecnazene, compound 391 and terbinafine, compound 391 and tetraconazole, compound 391 and thiabendazole, compound 391 and thifluzamide, compound 391 and thiophanate, compound 391 and thiophanate-methyl, compound 391 and thiram, compound 391 and tiadinil, compound 391 and tolclofos-methyl, compound 391 and tolylfluanid, compound 391 and triadimefon, compound 391 and triadimenol, compound 391 and triazoxide, compound 391 and tricyclazole, compound 391 and tridemorph, compound 391 and triflumizole, compound 391 and tricyclazole, compound 391 and trifloxystrobin, compound 391 and triforine, compound 391 and triticonazole, compound 391 and uniconazole, compound 391 and validamycin, compound 391 and valiphenal, compound 391 and vinclozolin, compound 391 and zineb, compound 391 and ziram, compound 391 and zoxamide, compound 391 and 5-chloro-6-(2,4,6-trifluorophenyl)-7-(4-methylpiperidin-1-yl)[1,2,4]triazolo[1,5-c]pyrimidine (BAS600), compound 391 and N-[2-(1,3-dimethylbutyl)phenyl]-5-fluoro-1,3-dimethyl-1H-pyrazol-4-carboxamide, compound 391 and N-[2-[4-[[3-(4-chlorophenyl)-2-propyn-1-yl]oxy]-3-methoxyphenyl]ethyl]-3-methyl-2-[(methylsulfonyl)amino]butanamide, compound 391 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 391 and 2-butoxy-6-iodo-3-propyl-4H-1-benzopyran-4-one, compound 391 and 3-[5-(4-chlorophenyl)-2,3-dimethyl-3-isoxazolidinyl]pyridine, compound 391 and 4-fluorophenyl N-[1-[[[1-(4-cyanophenyl)ethyl]sulfonyl]methyl]propyl]carbamate, compound 391 and N-[[(cyclopropylmethoxy)amino][6-(difluoromethoxy)-2,3-difluorophenyl]methylene]benzeneacetamide, compound 391 and α-(methoxyimino)-N-methyl-2-[[[1-[3-(trifluoromethyl)phenyl]ethoxy]imino]methyl]benzeneacetamide, compound 391 and N'-[4-[4-chloro-3-(trifluoromethyl)phenoxy]-2,5-dimethylphenyl]-N-ethyl-N-methylmethanimidamide, compound 391 and 2-[[2-fluoro-5-(trifluoromethyl)phenyl]thio]-2-[3-(2-methoxyphenyl)-2-thiazolidinylidene]acetonitrile, compound 391 and N-[2-(1S,2R)-[1,1'-bicyclopropyl]-2-ylphenyl]-3-(difluoromethyl)-1-methyl-1H-pyrazole-4-carboxamide, and compound 391 and N-(4-chloro-2-nitrophenyl)-N-ethyl-4-methylbenzenesulfonamide, compound 425 and acibenzolar-S-methyl, compound 425 and aldimorph, compound 425 and amisulbrom, compound 425 and anilazine, compound 425 and azaconazole, compound 425 and azoxystrobin, compound 425 and benalaxyl, compound 425 and benalaxyl-M, compound 425 and benodanil, compound 425 and benomyl, compound 425 and benthiavalicarb, compound 425 and benthiavalicarb-isopropyl, compound 425 and bethoxazin, compound 425 and binapacryl, compound 425 and biphenyl, compound 425 and bitertanol, compound 425 and bixafen, compound 425 and blasticidin-S, compound 425 and Bordeaux mixture (tribasic copper sulfate), compound 425 and boscalid, compound 425 and bromuconazole, compound 425 and bupirimate, compound 425 and carboxin, compound 425 and carpropamid, compound 425 and captafol, compound 425 and captan, compound 425 and carbendazim, compound 425 and chloroneb, compound 425 and chlorothalonil, compound 425 and chlozolinate, compound 425 and clotrimazole, compound 425 and copper oxychloride, compound 425 and copper salts such as copper sulfate and copper hydroxide, compound 425 and cyazofamid, compound 425 and cyflufenamid, compound 425 and cymoxanil, compound 425 and cyproconazole, compound 425 and cyprodinil, compound 425 and dichlofluanid, compound 425 and diclocymet, compound 425 and diclomezine, compound 425 and dicloran, compound 425 and diethofencarb, compound 425 and difenoconazole, compound 425 and diflumetorim, compound 425 and dimethirimol, compound 425 and dimethomorph, compound 425 and dimoxystrobin, compound 425 and diniconazole, compound 425 and diniconazole-M, compound 425 and dinocap, compound 425 and dithianon, compound 425 and dodemorph, compound 425 and dodine, compound 425 and edifenphos, compound 425 and enestroburin, compound 425 and epoxiconazole, compound 425 and ethaboxam, compound 425 and etridiazole, compound 425 and famoxadone, compound 425 and fenamidone, compound 425 and fenarimol, compound 425 and fenbuconazole, compound 425 and fenfuram, compound 425 and fenhexamid, compound 425 and fenoxanil, compound 425 and fenpiclonil, compound 425 and fenpropidin, compound 425 and fenpropimorph, compound 425 and fentin acetate, compound 425 and fentin chloride, compound 425 and fentin hydroxide, compound 425 and ferbam, compound 425 and ferimzone, compound 425 and fluazinam, compound 425 and fludioxonil, compound 425 and flumetover, compound 425 and flumorph, compound 425 and fluopicolide, compound 425 and fluopyram, compound 425 and fluoroimide, compound 425 and fluoxastrobin, compound 425 and fluquinconazole, compound 425 and flusilazole, compound 425 and flusulfamide, compound 425 and flutolanil, compound 425 and flutriafol, compound 425 and folpet, compound 425 and fosetyl-aluminum, compound 425 and fuberidazole, compound 425 and furalaxyl, compound 425 and furametpyr, compound 425 and hexaconazole, compound 425 and hymexazol, compound 425 and guazatine, compound 425 and imazalil, compound 425 and imibenconazole, compound 425 and iminoctadine, compound 425 and iodocarb, compound 425 and ipconazole, compound 425 and iprobenfos, compound 425 and iprodione, compound 425 and iprovalicarb, compound 425 and isoprothiolane, compound 425 and isopyrazam, compound 425 and isotianil, compound 425 and kasugamycin, compound 425 and kresoxim-methyl, compound 425 and mancozeb, compound 425 and mandipropamid, compound 425 and maneb, compound 425 and mepronil, compound 425 and meptyldinocap, compound 425 and metalaxyl, compound 425 and metalaxyl-M, compound 425 and metconazole, compound 425 and methasulfocarb, compound 425 and metiram, compound 425 and metominostrobin, compound 425 and mepanipyrim, compound 425 and metrafenone, compound 425 and myclobutanil, compound 425 and naftifine, compound 425 and neo-asozin (ferric methanearsonate), compound 425 and nuarimol, compound 425 and octhilinone, compound 425 and ofurace, compound 425 and orysastrobin, compound 425 and oxadixyl, compound 425 and oxolinic acid, compound 425 and oxpoconazole, compound 425 and oxycarboxin, compound 425 and oxytetracycline, compound 425 and penconazole, compound 425 and pencycuron, compound 425 and penthiopyrad, compound 425 and pefurazoate, compound 425 and phosphorous acid and salts, compound 425 and phthalide, compound 425 and picobenzamid, compound 425 and picoxystrobin, compound 425 and piperalin, compound 425 and polyoxin, compound 425 and probenazole, compound 425 and prochloraz, compound 425 and procymidone, compound 425 and propamocarb, compound 425 and propamocarb-hydrochloride, compound 425 and propiconazole, compound 425 and propineb, compound 425 and proquinazid, compound 425 and prothioconazole, compound 425 and pyraclostrobin, compound 425 and pryazophos, compound 425 and pyribencarb, compound 425 and pyrifenox, compound 425 and pyrimethanil, compound 425 and pyrolnitrine, compound 425 and pyroquilon, compound 425 and quinomethionate, compound 425 and quinoxyfen, compound 425 and quintozene, compound 425 and silthiofam, compound 425 and simeconazole, compound 425 and spiroxamine, compound 425 and streptomycin, compound 425 and sulfur, compound 425 and tebuconazole, compound 425 and tecloftalam, compound 425 and tecnazene, compound 425 and terbinafine, compound 425 and tetraconazole, compound 425 and thiabendazole, compound 425 and thifluzamide, compound 425 and thiophanate, compound 425 and thiophanate-methyl, compound 425 and thiram, compound 425 and tiadinil, compound 425 and tolclofos-methyl, compound 425 and tolylfluanid, compound 425 and triadimefon, compound 425 and triadimenol, compound 425 and triazoxide, compound 425 and tricyclazole, compound 425 and tridemorph, compound 425 and triflumizole, compound 425 and tricyclazole, compound 425 and trifloxystrobin, compound 425 and triforine, compound 425 and triticonazole, compound 425 and uniconazole, compound 425 and validamycin, compound 425 and valiphenal, compound 425 and vinclozolin, compound 425 and zineb, compound 425 and ziram, compound 425 and zoxamide, compound 425 and 5-chloro-6-(2,4,6-trifluorophenyl)-7-(4-methylpiperidin-1-yl)[1,2,4]triazolo[1,5-α]pyrimidine (BAS600), compound 425 and N-[2-(1,3-dimethylbutyl)phenyl]-5-fluoro-1,3-dimethyl-1H-pyrazol-4-carboxamide, compound 425 and N-[2-[4-[[3-(4-chlorophenyl)-2-propyn-1-yl]oxy]-3-methoxyphenyl]ethyl]-3-methyl-2-[(methylsulfonyl)amino]butanamide, compound 425 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 425 and 2-butoxy-6-iodo-3-propyl-4H-1-benzopyran-4-one, compound 425 and 3-[5-(4-chlorophenyl)-2,3-dimethyl-3-isoxazolidinyl]pyridine, compound 425 and 4-fluorophenyl N-[1-[[[1-(4-cyanophenyl)ethyl]sulfonyl]methyl]propyl]carbamate, compound 425 and N-[[(cyclopropylmethoxy)amino][6-(difluoromethoxy)-2,3-difluorophenyl]methylene]benzeneacetamide, compound 425 and α-(methoxyimino)-N-methyl-2-[[[1-[3-(trifluoromethyl)phenyl]ethoxy]imino]methyl]benzeneacetamide, compound 425 and N'-[4-[4-chloro-3-(trifluoromethyl)phenoxy]-2,5-dimethylphenyl]-N-ethyl-N-methylmethanimidamide, compound 425 and 2-[[2-fluoro-5-(trifluoromethyl)phenyl]thio]-2-[3-(2-methoxyphenyl)-2-thiazolidinylidene]acetonitrile compound 425 and N-[2-(1S,2R)-[1,1'-bicyclopropyl]-2-ylphenyl]-3-(difluoromethyl)-1-methyl-1H-pyrazole-4-carboxamide, and compound 425 and N-(4-chloro-2-nitrophenyl)-N-ethyl-4-methylbenzenesulfonamide, compound 455 and acibenzolar-S-methyl, compound 455 and aldimorph, compound 455 and amisulbrom, compound 455 and anilazine, compound 455 and azaconazole, compound 455 and azoxystrobin, compound 455 and benalaxyl, compound 455 and benalaxyl-M, compound 455 and benodanil, compound 455 and benomyl, compound 455 and benthiavalicarb, compound 455 and benthiavalicarb-isopropyl, compound 455 and bethoxazin, compound 455 and binapacryl, compound 455 and biphenyl, compound 455 and bitertanol, compound 455 and bixafen, compound 455 and blasticidin-S, compound 455 and Bordeaux mixture (tribasic copper sulfate), compound 455 and boscalid, compound 455 and bromuconazole, compound 455 and bupirimate, compound 455 and carboxin, compound 455 and carpropamid, compound 455 and captafol, compound 455 and captan, compound 455 and carbendazim, compound 455 and chloroneb, compound 455 and chlorothalonil, compound 455 and chlozolinate, compound 455 and clotrimazole, compound 455 and copper oxychloride, compound 455 and copper salts such as copper sulfate and copper hydroxide, compound 455 and cyazofamid, compound 455 and cyflufenamid, compound 455 and cymoxanil, compound 455 and cyproconazole, compound 455 and cyprodinil, compound 455 and dichlofluanid, compound 455 and diclocymet, compound 455 and diclomezine, compound 455 and dicloran, compound 455 and diethofencarb, compound 455 and difenoconazole, compound 455 and diflumetorim, compound 455 and dimethirimol, compound 455 and dimethomorph, compound 455 and dimoxystrobin, compound 455 and diniconazole, compound 455 and diniconazole-M, compound 455 and dinocap, compound 455 and dithianon, compound 455 and dodemorph, compound 455 and dodine, compound 455 and edifenphos, compound 455 and enestroburin, compound 455 and epoxiconazole, compound 455 and ethaboxam, compound 455 and etridiazole, compound 455 and famoxadone, compound 455 and fenamidone, compound 455 and fenarimol, compound 455 and fenbuconazole, compound 455 and fenfuram, compound 455 and fenhexamid, compound 455 and fenoxanil, compound 455 and fenpiclonil, compound 455 and fenpropidin, compound 455 and fenpropimorph, compound 455 and fentin acetate, compound 455 and fentin chloride, compound 455 and fentin hydroxide, compound 455 and ferbam, compound 455 and ferimzone, compound 455 and fluazinam, compound 455 and fludioxonil, compound 455 and flumetover, compound 455 and flumorph, compound 455 and fluopicolide, compound 455 and fluopyram, compound 455 and fluoroimide, compound 455 and fluoxastrobin, compound 455 and fluquinconazole, compound 455 and flusilazole, compound 455 and flusulfamide, compound 455 and flutolanil, compound 455 and flutriafol, compound 455 and folpet, compound 455 and fosetyl-aluminum, compound 455 and fuberidazole, compound 455 and furalaxyl, compound 455 and furametpyr, compound 455 and hexaconazole, compound 455 and hymexazol, compound 455 and guazatine, compound 455 and imazalil, compound 455 and imibenconazole, compound 455 and iminoctadine, compound 455 and iodocarb, compound 455 and ipconazole, compound 455 and iprobenfos, compound 455 and iprodione, compound 455 and iprovalicarb, compound 455 and isoprothiolane, compound 455 and isopyrazam, compound 455 and isotianil, compound 455 and kasugamycin, compound 455 and kresoxim-methyl, compound 455 and mancozeb, compound 455 and mandipropamid, compound 455 and maneb, compound 455 and mepronil, compound 455 and meptyldinocap, compound 455 and metalaxyl, compound 455 and metalaxyl-M, compound 455 and metconazole, compound 455 and methasulfocarb, compound 455 and metiram, compound 455 and metominostrobin, compound 455 and mepanipyrim, compound 455 and metrafenone, compound 455 and myclobutanil, compound 455 and naftifine, compound 455 and neo-asozin (ferric methanearsonate), compound 455 and nuarimol, compound 455 and octhilinone, compound 455 and ofurace, compound 455 and orysastrobin, compound 455 and oxadixyl, compound 455 and oxolinic acid, compound 455 and oxpoconazole, compound 455 and oxycarboxin, compound 455 and oxytetracycline, compound 455 and penconazole, compound 455 and pencycuron, compound 455 and penthiopyrad, compound 455 and pefurazoate, compound 455 and phosphorous acid and salts, compound 455 and phthalide, compound 455 and picobenzamid, compound 455 and picoxystrobin, compound 455 and piperalin, compound 455 and polyoxin, compound 455 and probenazole, compound 455 and prochloraz, compound 455 and procymidone, compound 455 and propamocarb, compound 455 and propamocarb-hydrochloride, compound 455 and propiconazole, compound 455 and propineb, compound 455 and proquinazid, compound 455 and prothioconazole, compound 455 and pyraclostrobin, compound 455 and pryazophos, compound 455 and pyribencarb, compound 455 and pyrifenox, compound 455 and pyrimethanil, compound 455 and pyrolnitrine, compound 455 and pyroquilon, compound 455 and quinomethionate, compound 455 and quinoxyfen, compound 455 and quintozene, compound 455 and silthiofam, compound 455 and simeconazole, compound 455 and spiroxamine, compound 455 and streptomycin, compound 455 and sulfur, compound 455 and tebuconazole, compound 455 and tecloftalam, compound 455 and tecnazene, compound 455 and terbinafine, compound 455 and tetraconazole, compound 455 and thiabendazole, compound 455 and thifluzamide, compound 455 and thiophanate, compound 455 and thiophanate-methyl, compound 455 and thiram, compound 455 and tiadinil, compound 455 and tolclofos-methyl, compound 455 and tolylfluanid, compound 455 and triadimefon, compound 455 and triadimenol, compound 455 and triazoxide, compound 455 and tricyclazole, compound 455 and tridemorph, compound 455 and triflumizole, compound 455 and tricyclazole, compound 455 and trifloxystrobin, compound 455 and triforine, compound 455 and triticonazole, compound 455 and uniconazole, compound 455 and validamycin, compound 455 and valiphenal, compound 455 and vinclozolin, compound 455 and zineb, compound 455 and ziram, compound 455 and zoxamide, compound 455 and 5-chloro-6-(2,4,6-trifluorophenyl)-7-(4-methylpiperidin-1-yl)[1,2,4]triazolo[1,5-α]pyrimidine(BAS600), compound 455 and N-[2-(1,3-dimethylbutyl)phenyl]-5-fluoro-1,3-dimethyl-1H-pyrazol-4-carboxamide, compound 455 and N-[2-[4-[[3-(4-chlorophenyl)-2-propyn-1-yl]oxy]-3-methoxyphenyl]ethyl]-3-methyl-2-[(methylsulfonyl)amino]butanamide, compound 455 and N-[2-[4-[[3-(4-chlorophenyl)-2-propyn-1-yl]oxy]-3-methoxyphenyl]ethyl]-3-methyl-2-[(ethylsulfonyl)amino]butanamide, compound 455 and 2-butoxy-6-iodo-3-propyl-4H-1-benzopyran-4-one, compound 455 and 3-[5-(4-chlorophenyl)-2,3-dimethyl-3-isoxazolidinyl]pyridine, compound 455 and 4-fluorophenyl N-[1-[[[1-(4-cyanophenyl)ethyl]sulfonyl]methyl]propyl]carbamate, compound 455 and N-[[(cyclopropylmethoxy)amino][6-(difluoromethoxy)-2,3-difluorophenyl]methylene]henzeneacetamide, compound 455 and α-(methoxyimino)-N-methyl-2-[[[1-[3-(trifluoromethyl)phenyl]ethoxy]imino]methyl]benzeneacetamide, compound 455 and N'-[4-[4-chloro-3-(trifluoromethyl)phenoxy]-2,5-dimethylphenyl]-N-ethyl-N-methylmethanimidamide, compound 455 and 2-[[2-fluoro-5-(trifluoromethyl)phenyl]thio]-2-[3-(2-methoxyphenyl)-2-thiazolidinylidene]acetonitrile, compound 455 and N-[2-(1S,2R)-[1,1'-bicyclopropyl]-2-ylphenyl]-3-(difluoromethyl)-1-methyl-1H-pyrazole-4-carboxamide, and compound 455 and N-(4-chloro-2-nitrophenyl)-N-ethyl-4-methylbenzenesulfonamide.

Component (a) compounds of this invention and/or combinations thereof with component (b) compounds and/or one or more other biologically active compound or agent can be applied to plants genetically transformed to express proteins toxic to invertebrate pests (such as *Bacillus thuringiensis* delta-endotoxins). The effect of the exogenously applied invertebrate pest control compounds of this invention may be synergistic with the expressed toxin proteins.

General references for these agricultural protectants (i.e. insecticides, fungicides, nematocides, acaricides, herbicides and biological agents) include *The Pesticide Manual, 13th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

Table A1 lists specific combinations of a component (b) compound with component (a) illustrative of the mixtures, compositions and methods of the present invention. The first column of Table A1 lists the specific component (b) compound (e.g., "Acibenzolar-S-methyl" in the first line). The second, third and fourth columns of Table A1 lists ranges of weight ratios for rates at which the component (b) compound is typically applied relative to component (a) (e.g., "22:1 to 1:60" of acibenzolar-S-methyl relative to component (a) by weight). Thus, for example, the first line of Table A1 specifically discloses the combination of acibenzolar-S-methyl with component (a) is typically applied in a weight ratio between 22:1 to 1:60. The remaining lines of Table A1 are to be construed similarly.

TABLE A1

| Component (b) | Typical Weight Ratio | More Typical Weight Ratio | Most Typical Weight Ratio |
| --- | --- | --- | --- |
| acibenzolar-S-methyl | 22:1 to 1:60 | 7:1 to 1:20 | 4:1 to 1:3 |
| aldimorph | 300:1 to 1:1 | 100:1 to 3:1 | 60:1 to 8:1 |
| amisulbrom | 60:1 to 1:6 | 20:1 to 1:2 | 12:1 to 2:1 |
| anilazine | 900:1 to 4:1 | 300:1 to 10:1 | 180:1 to 27:1 |
| azaconazole | 75:1 to 1:6 | 25:1 to 1:2 | 18:1 to 2:1 |
| azoxystrobin | 90:1 to 1:4 | 30:1 to 1:2 | 24:1 to 3:1 |
| benalaxyl | 45:1 to 1:6 | 15:1 to 1:2 | 12:1 to 2:1 |
| benalaxyl-M | 45:1 to 1:12 | 15:1 to 1:4 | 9:1 to 1:1 |
| benodanil | 180:1 to 1:2 | 60:1 to 2:1 | 36:1 to 4:1 |
| benomyl | 450:1 to 1:2 | 150:1 to 3:1 | 90:1 to 10:1 |
| benthiavalicarb | 22:1 to 1:12 | 7:1 to 1:4 | 4:1 to 1:2 |
| benthiavalicarb-isopropyl | 22:1 to 1:12 | 7:1 to 1:4 | 4:1 to 1:2 |
| bethoxazin | 1500:1 to 1:12 | 500:1 to 1:4 | 120:1 to 14:1 |
| binapacryl | 1500:1 to 1:12 | 500:1 to 1:4 | 120:1 to 14:1 |
| biphenyl | 1500:1 to 1:12 | 500:1 to 1:4 | 120:1 to 14:1 |
| bitertanol | 150:1 to 1:2 | 50:1 to 2:1 | 30:1 to 6:1 |
| bixafen | 120:1 to 1:3 | 40:1 to 1:1 | 18:1 to 3:1 |
| blasticidin-S | 30:1 to 1:30 | 10:1 to 1:10 | 1:1 to 1:4 |
| Bordeaux mixture (tribasic copper sulfate) | 4500:1 to 4:1 | 1500:1 to 10:1 | 360:1 to 40:1 |
| boscalid | 180:1 to 1:2 | 60:1 to 2:1 | 36:1 to 4:1 |
| bromuconazole | 150:1 to 1:3 | 50:1 to 1:1 | 24:1 to 3:1 |
| bupirimate | 30:1 to 1:30 | 10:1 to 1:10 | 2:1 to 1:4 |
| captafol | 900:1 to 1:2 | 300:1 to 3:1 | 120:1 to 14:1 |
| captan | 900:1 to 1:2 | 300:1 to 3:1 | 120:1 to 14:1 |
| carbendazim | 450:1 to 1:2 | 150:1 to 3:1 | 90:1 to 10:1 |
| carboxin | 180:1 to 1:2 | 60:1 to 2:1 | 36:1 to 4:1 |
| carpropamid | 150:1 to 1:3 | 50:1 to 1:1 | 24:1 to 3:1 |
| chloroneb | 3000:1 to 4:1 | 1000:1 to 10:1 | 800:1 to 107:1 |
| chlorothalonil | 900:1 to 1:2 | 300:1 to 3:1 | 120:1 to 14:1 |
| chlozolinate | 450:1 to 2:1 | 150:1 to 5:1 | 90:1 to 14:1 |
| clotrimazole | 150:1 to 1:3 | 50:1 to 1:1 | 24:1 to 3:1 |
| copper oxychloride | 2250:1 to 4:1 | 750:1 to 10:1 | 480:1 to 54:1 |
| copper salts such as copper sulfate and copper hydroxide | 1200:1 to 1:2 | 400:1 to 2:1 | 60:1 to 7:1 |
| cyazofamid | 45:1 to 1:6 | 15:1 to 1:2 | 9:1 to 2:1 |
| cyflufenamid | 15:1 to 1:30 | 5:1 to 1:10 | 3:1 to 1:3 |

TABLE A1-continued

| Component (b) | Typical Weight Ratio | More Typical Weight Ratio | Most Typical Weight Ratio |
|---|---|---|---|
| cymoxanil | 60:1 to 1:6 | 20:1 to 1:2 | 14:1 to 2:1 |
| cyproconazole | 45:1 to 1:6 | 15:1 to 1:2 | 9:1 to 2:1 |
| cyprodinil | 225:1 to 1:3 | 75:1 to 1:1 | 36:1 to 4:1 |
| dichlofluanid | 1500:1 to 1:12 | 500:1 to 1:4 | 120:1 to 14:1 |
| diclocymet | 1500:1 to 1:12 | 500:1 to 1:4 | 120:1 to 14:1 |
| diclomezine | 150:1 to 1:3 | 50:1 to 1:1 | 30:1 to 4:1 |
| dicloran | 1500:1 to 1:12 | 500:1 to 1:4 | 120:1 to 14:1 |
| diethofencarb | 225:1 to 1:3 | 75:1 to 1:1 | 60:1 to 7:1 |
| difenoconazole | 45:1 to 1:12 | 15:1 to 1:4 | 6:1 to 1:2 |
| diflumetorim | 1500:1 to 1:12 | 500:1 to 1:4 | 120:1 to 14:1 |
| dimethirimol | 30:1 to 1:30 | 10:1 to 1:10 | 2:1 to 1:4 |
| dimethomorph | 90:1 to 1:2 | 30:1 to 2:1 | 24:1 to 4:1 |
| dimoxystrobin | 90:1 to 1:6 | 30:1 to 1:2 | 18:1 to 2:1 |
| diniconazole | 30:1 to 1:12 | 10:1 to 1:4 | 8:1 to 1:1 |
| diniconazole M | 30:1 to 1:30 | 10:1 to 1:10 | 6:1 to 1:2 |
| dinocap | 75:1 to 1:3 | 25:1 to 1:1 | 18:1 to 3:1 |
| dithianon | 150:1 to 1:2 | 50:1 to 3:1 | 40:1 to 7:1 |
| dodemorph | 300:1 to 1:1 | 100:1 to 3:1 | 60:1 to 8:1 |
| dodine | 300:1 to 2:1 | 100:1 to 5:1 | 80:1 to 14:1 |
| edifenphos | 300:1 to 1:3 | 100:1 to 1:1 | 30:1 to 4:1 |
| enestroburin | 90:1 to 1:6 | 30:1 to 1:2 | 18:1 to 2:1 |
| epoxiconazole | 37:1 to 1:12 | 12:1 to 1:4 | 10:1 to 2:1 |
| ethaboxam | 75:1 to 1:3 | 25:1 to 1:1 | 18:1 to 3:1 |
| etridiazole | 300:1 to 1:3 | 100:1 to 1:1 | 60:1 to 7:1 |
| famoxadone | 90:1 to 1:6 | 30:1 to 1:2 | 18:1 to 2:1 |
| fenamidone | 60:1 to 1:6 | 20:1 to 1:2 | 16:1 to 2:1 |
| fenarimol | 30:1 to 1:30 | 10:1 to 1:10 | 3:1 to 1:3 |
| fenbuconazole | 30:1 to 1:10 | 10:1 to 1:4 | 6:1 to 1:2 |
| fenfuram | 180:1 to 1:2 | 60:1 to 2:1 | 36:1 to 4:1 |
| fenhexamid | 300:1 to 2:1 | 100:1 to 5:1 | 80:1 to 14:1 |
| fenoxanil | 1500:1 to 1:12 | 500:1 to 1:4 | 120:1 to 14:1 |
| fenpiclonil | 750:1 to 1:3 | 250:1 to 1:1 | 120:1 to 14:1 |
| fenpropidin | 300:1 to 1:1 | 100:1 to 3:1 | 60:1 to 8:1 |
| fenpropimorph | 300:1 to 1:1 | 100:1 to 3:1 | 60:1 to 8:1 |
| fentin acetate | 150:1 to 1:3 | 50:1 to 1:1 | 24:1 to 3:1 |
| fentin chloride | 150:1 to 1:3 | 50:1 to 1:1 | 24:1 to 3:1 |
| fentin hydroxide | 150:1 to 1:3 | 50:1 to 1:1 | 24:1 to 3:1 |
| ferbam | 3000:1 to 2:1 | 1000:1 to 5:1 | 240:1 to 27:1 |
| ferimzone | 300:1 to 1:2 | 100:1 to 2:1 | 60:1 to 7:1 |
| fluazinam | 225:1 to 1:2 | 75:1 to 2:1 | 30:1 to 6:1 |
| fludioxonil | 75:1 to 1:4 | 25:1 to 1:2 | 18:1 to 2:1 |
| flumetover | 90:1 to 1:2 | 30:1 to 2:1 | 24:1 to 4:1 |
| flumorph | 90:1 to 1:6 | 30:1 to 1:2 | 24:1 to 3:1 |
| fluopicolide | 37:1 to 1:6 | 12:1 to 1:2 | 9:1 to 2:1 |
| fluopyram | 150:1 to 1:30 | 50:1 to 1:10 | 24:1 to 3:1 |
| fluoromide | 1500:1 to 4:1 | 500:1 to 10:1 | 300:1 to 34:1 |
| fluoxastrobin | 45:1 to 1:6 | 15:1 to 1:2 | 12:1 to 2:1 |
| fluquinconazole | 45:1 to 1:4 | 15:1 to 1:2 | 12:1 to 2:1 |
| flusilazole | 150:1 to 1:3 | 50:1 to 1:1 | 24:1 to 3:1 |
| flusulfamide | 900:1 to 2:1 | 300:1 to 5:1 | 120:1 to 14:1 |
| flutianil | 75:1 to 1:12 | 25:1 to 1:4 | 12:1 to 2:1 |
| flutolanil | 180:1 to 1:2 | 60:1 to 2:1 | 36:1 to 4:1 |
| flutriafol | 45:1 to 1:4 | 15:1 to 1:2 | 12:1 to 2:1 |
| folpet | 900:1 to 1:2 | 300:1 to 3:1 | 120:1 to 14:1 |
| fosetyl-aluminum | 2250:1 to 5:1 | 750:1 to 15:1 | 240:1 to 40:1 |
| fuberidazole | 450:1 to 1:2 | 150:1 to 3:1 | 90:1 to 10:1 |
| furalaxyl | 150:1 to 1:15 | 50:1 to 1:5 | 12:1 to 2:1 |
| furametpyr | 1500:1 to 1:12 | 500:1 to 1:4 | 120:1 to 14:1 |
| guazatine | 1500:1 to 1:12 | 500:1 to 1:4 | 120:1 to 14:1 |
| hexaconazole | 150:1 to 1:12 | 50:1 to 1:4 | 15:1 to 2:1 |
| hymexazol | 2250:1 to 4:1 | 750:1 to 10:1 | 600:1 to 67:1 |
| imazalil | 75:1 to 1:6 | 25:1 to 1:2 | 15:1 to 2:1 |
| imibenconazole | 150:1 to 1:12 | 50:1 to 1:4 | 15:1 to 2:1 |
| iodocarb | 1500:1 to 1:12 | 500:1 to 1:4 | 120:1 to 14:1 |
| ipconazole | 150:1 to 1:12 | 50:1 to 1:4 | 15:1 to 2:1 |
| iprobenfos | 1500:1 to 1:12 | 500:1 to 1:4 | 120:1 to 14:1 |
| iprodione | 1200:1 to 2:1 | 400:1 to 5:1 | 120:1 to 14:1 |
| iprovalicarb | 90:1 to 1:3 | 30:1 to 1:1 | 18:1 to 3:1 |
| isoprothiolane | 1500:1 to 4:1 | 500:1 to 10:1 | 360:1 to 40:1 |
| isopyrazam | 120:1 to 1:3 | 40:1 to 1:1 | 18:1 to 3:1 |
| isotianil | 120:1 to 1:3 | 40:1 to 1:1 | 18:1 to 3:1 |
| kasugamycin | 75:1 to 1:30 | 25:1 to 1:10 | 3:1 to 1:3 |
| kresoxim-methyl | 75:1 to 1:6 | 25:1 to 1:2 | 18:1 to 2:1 |
| mancozeb | 1800:1 to 2:1 | 600:1 to 4:1 | 180:1 to 20:1 |
| mandipropamid | 60:1 to 1:6 | 20:1 to 1:2 | 16:1 to 2:1 |
| maneb | 1800:1 to 2:1 | 600:1 to 4:1 | 180:1 to 20:1 |
| mepanipyrim | 180:1 to 1:1 | 60:1 to 3:1 | 48:1 to 8:1 |

TABLE A1-continued

| Component (b) | Typical Weight Ratio | More Typical Weight Ratio | Most Typical Weight Ratio |
|---|---|---|---|
| mepronil | 75:1 to 1:12 | 25:1 to 1:4 | 12:1 to 2:1 |
| meptyldinocap | 75:1 to 1:3 | 25:1 to 1:1 | 18:1 to 3:1 |
| metalaxyl | 150:1 to 1:15 | 50:1 to 1:5 | 12:1 to 2:1 |
| metalaxyl-M | 150:1 to 1:15 | 50:1 to 1:5 | 12:1 to 2:1 |
| metconazole | 30:1 to 1:6 | 10:1 to 1:2 | 8:1 to 2:1 |
| methasulfocarb | 1500:1 to 1:12 | 500:1 to 1:4 | 120:1 to 14:1 |
| metiram | 1500:1 to 1:12 | 500:1 to 1:4 | 120:1 to 14:1 |
| metominostrobin | 90:1 to 1:4 | 30:1 to 1:2 | 24:1 to 3:1 |
| metrafenone | 60:1 to 1:4 | 20:1 to 1:2 | 16:1 to 2:1 |
| myclobutanil | 52:1 to 1:9 | 17:1 to 1:3 | 9:1 to 1:1 |
| naftifine | 1500:1 to 1:12 | 500:1 to 1:4 | 120:1 to 14:1 |
| neo-asozin (ferric methanearsonate) | 1500:1 to 1:12 | 500:1 to 1:4 | 120:1 to 14:1 |
| nuarimol | 150:1 to 1:3 | 50:1 to 1:1 | 24:1 to 3:1 |
| octhilinone | 1500:1 to 1:12 | 500:1 to 1:4 | 120:1 to 14:1 |
| ofurace | 150:1 to 1:15 | 50:1 to 1:5 | 12:1 to 2:1 |
| orysastrobin | 90:1 to 1:4 | 30:1 to 1:2 | 24:1 to 3:1 |
| oxadixyl | 150:1 to 1:15 | 50:1 to 1:5 | 12:1 to 2:1 |
| oxolinic acid | 300:1 to 1:3 | 100:1 to 1:1 | 60:1 to 7:1 |
| oxpoconazole | 150:1 to 1:12 | 50:1 to 1:4 | 15:1 to 2:1 |
| oxycarboxin | 180:1 to 1:2 | 60:1 to 2:1 | 36:1 to 4:1 |
| oxytetracycline | 150:1 to 1:3 | 50:1 to 1:1 | 30:1 to 4:1 |
| pefurazoate | 1500:1 to 1:12 | 500:1 to 1:4 | 120:1 to 14:1 |
| penconazole | 15:1 to 1:15 | 5:1 to 1:5 | 3:1 to 1:2 |
| pencycuron | 1500:1 to 2:1 | 500:1 to 5:1 | 90:1 to 14:1 |
| penthiopyrad | 120:1 to 1:3 | 40:1 to 1:1 | 18:1 to 3:1 |
| phosphorous acid and salts | 1500:1 to 1:12 | 500:1 to 1:4 | 120:1 to 14:1 |
| phthalide | 1500:1 to 1:12 | 500:1 to 1:4 | 120:1 to 14:1 |
| picoxystrobin | 75:1 to 1:6 | 25:1 to 1:2 | 15:1 to 2:1 |
| piperalin | 150:1 to 1:3 | 50:1 to 1:1 | 24:1 to 3:1 |
| polyoxin | 150:1 to 1:3 | 50:1 to 1:1 | 30:1 to 4:1 |
| probenazole | 150:1 to 1:3 | 50:1 to 1:1 | 24:1 to 3:1 |
| prochloraz | 225:1 to 1:2 | 75:1 to 3:1 | 60:1 to 7:1 |
| procymidone | 450:1 to 1:1 | 150:1 to 3:1 | 90:1 to 10:1 |
| propamocarb | 300:1 to 2:1 | 100:1 to 5:1 | 80:1 to 14:1 |
| propamocarb-hydrochloride | 300:1 to 2:1 | 100:1 to 5:1 | 80:1 to 14:1 |
| propiconazole | 45:1 to 1:6 | 15:1 to 1:2 | 12:1 to 2:1 |
| propineb | 450:1 to 2:1 | 150:1 to 5:1 | 90:1 to 14:1 |
| proquinazid | 30:1 to 1:12 | 10:1 to 1:4 | 6:1 to 1:2 |
| prothioconazole | 60:1 to 1:6 | 20:1 to 1:2 | 15:1 to 2:1 |
| pyraclostrobin | 90:1 to 1:6 | 30:1 to 1:2 | 18:1 to 2:1 |
| pyrazophos | 1500:1 to 1:12 | 500:1 to 1:4 | 120:1 to 14:1 |
| pyribencarb | 150:1 to 1:2 | 50:1 to 2:1 | 36:1 to 4:1 |
| pyrifenox | 150:1 to 1:3 | 50:1 to 1:1 | 24:1 to 3:1 |
| pyrimethanil | 300:1 to 1:2 | 100:1 to 2:1 | 30:1 to 4:1 |
| pyroquilon | 150:1 to 1:3 | 50:1 to 1:1 | 24:1 to 3:1 |
| pyrrolnitrin | 1500:1 to 1:12 | 500:1 to 1:4 | 120:1 to 14:1 |
| quinmethionate | 1500:1 to 1:12 | 500:1 to 1:4 | 120:1 to 14:1 |
| quinoxyfen | 45:1 to 1:6 | 15:1 to 1:2 | 9:1 to 2:1 |
| quintozene | 1500:1 to 1:12 | 500:1 to 1:4 | 120:1 to 14:1 |
| silthiofam | 75:1 to 1:6 | 25:1 to 1:2 | 18:1 to 2:1 |
| simeconazole | 150:1 to 1:12 | 50:1 to 1:4 | 15:1 to 2:1 |
| spiroxamine | 225:1 to 1:2 | 75:1 to 3:1 | 45:1 to 7:1 |
| streptomycin | 150:1 to 1:3 | 50:1 to 1:1 | 30:1 to 4:1 |
| sulfur | 3000:1 to 9:1 | 1000:1 to 25:1 | 600:1 to 67:1 |
| tebuconazole | 75:1 to 1:6 | 25:1 to 1:2 | 15:1 to 2:1 |
| tecloftalam | 1500:1 to 1:12 | 500:1 to 1:4 | 120:1 to 14:1 |
| tecnazene | 1500:1 to 1:12 | 500:1 to 1:4 | 120:1 to 14:1 |
| terbinafine | 1500:1 to 1:12 | 500:1 to 1:4 | 120:1 to 14:1 |
| tetraconazole | 150:1 to 1:12 | 50:1 to 1:4 | 15:1 to 2:1 |
| thiabendazole | 450:1 to 1:2 | 150:1 to 3:1 | 90:1 to 10:1 |
| thifluzamide | 150:1 to 1:3 | 50:1 to 1:1 | 24:1 to 3:1 |
| thiophanate | 450:1 to 2:1 | 150:1 to 4:1 | 90:1 to 11:1 |
| thiophanate-methyl | 450:1 to 2:1 | 150:1 to 4:1 | 90:1 to 11:1 |
| thiram | 1500:1 to 2:1 | 500:1 to 5:1 | 300:1 to 34:1 |
| tiadinil | 120:1 to 1:3 | 40:1 to 1:1 | 18:1 to 3:1 |
| tolclofos-methyl | 1500:1 to 2:1 | 500:1 to 5:1 | 300:1 to 34:1 |
| tolylfluanid | 1500:1 to 1:12 | 500:1 to 1:4 | 120:1 to 14:1 |
| triadimefon | 150:1 to 1:12 | 50:1 to 1:4 | 15:1 to 2:1 |
| triadimenol | 150:1 to 1:12 | 50:1 to 1:4 | 15:1 to 2:1 |
| triazoxide | 1500:1 to 1:12 | 500:1 to 1:4 | 120:1 to 14:1 |
| tricyclazole | 150:1 to 1:3 | 50:1 to 1:1 | 24:1 to 3:1 |
| tridemorph | 300:1 to 1:1 | 100:1 to 3:1 | 60:1 to 8:1 |
| trifloxystrobin | 60:1 to 1:6 | 20:1 to 1:2 | 16:1 to 2:1 |
| triflumizole | 150:1 to 1:3 | 50:1 to 1:1 | 24:1 to 3:1 |
| triforine | 150:1 to 1:3 | 50:1 to 1:1 | 24:1 to 3:1 |
| trimorphamide | 450:1 to 1:3 | 150:1 to 1:1 | 60:1 to 7:1 |

TABLE A1-continued

| Component (b) | Typical Weight Ratio | More Typical Weight Ratio | Most Typical Weight Ratio |
|---|---|---|---|
| triticonazole | 150:1 to 1:12 | 50:1 to 1:4 | 15:1 to 2:1 |
| uniconazole | 150:1 to 1:12 | 50:1 to 1:4 | 15:1 to 2:1 |
| validamycin | 1500:1 to 1:12 | 500:1 to 1:4 | 24:1 to 3:1 |
| valiphenal | 60:1 to 1:6 | 20:1 to 1:2 | 16:1 to 2:1 |
| vinclozolin | 1200:1 to 2:1 | 400:1 to 5:1 | 120:1 to 14:1 |
| zineb | 1500:1 to 2:1 | 500:1 to 5:1 | 300:1 to 34:1 |
| ziram | 1500:1 to 2:1 | 500:1 to 5:1 | 300:1 to 34:1 |
| zoxamide | 60:1 to 1:6 | 20:1 to 1:2 | 16:1 to 2:1 |
| 5-chloro-6-(2,4,6-trifluorophenyl)-7-(4-methylpiperidin-1-yl)[1,2,4]triazolo[1,5-a]pyrimidine | 150:1 to 1:12 | 50:1 to 1:4 | 12:1 to 2:1 |
| N-[2-(1,3-dimethylbutyl)phenyl]-5-fluoro-1,3-dimethyl-1H-pyrazol-4-carboxamide | 120:1 to 1:3 | 40:1 to 1:1 | 18:1 to 3:1 |
| N-[2-[4-[[3-(4-chlorophenyl)-2-propyn-1-yl]oxy]-3-methoxyphenyl]ethyl]-3-methyl-2-[(methylsulfonyl)amino]butanamide | 60:1 to 1:6 | 20:1 to 1:2 | 16:1 to 2:1 |
| N-[2-[4-[[3-(4-chlorophenyl)-2-propyn-1-yl]oxy]-3-methoxyphenyl]ethyl]-3-methyl-2-[(ethylsulfonyl)amino]butanamide | 60:1 to 1:6 | 20:1 to 1:2 | 16:1 to 2:1 |
| 2-butoxy-6-iodo-3-propyl-4H-1-benzopyran-4-one | 30:1 to 1:12 | 10:1 to 1:4 | 6:1 to 1:2 |
| 3-[5-(4-chlorophenyl)-2,3-dimethyl-3-isoxazolidinyl]pyridine | 150:1 to 1:3 | 50:1 to 1:1 | 24:1 to 3:1 |
| 4-fluorophenyl N-[1-[[[1-(4-cyano-phenyl)ethyl]sulfonyl]methyl]propyl]carbamate | 60:1 to 1:6 | 20:1 to 1:2 | 16:1 to 2:1 |
| N-[[(cyclopropylmethoxy)amino][6-(difluoromethoxy)-2,3-difluorophenyl]methylene]benzeneacetamide | 15:1 to 1:30 | 5:1 to 1:10 | 3:1 to 1:3 |
| α-[methoxyimino]-N-methyl-2-[[[1-[3-(trifluoromethyl)phenyl]ethoxy]imino]methyl]benzeneacetamide | 90:1 to 1:6 | 30:1 to 1:2 | 24:1 to 3:1 |
| N'-[4-[4-chloro-3-(trifluoromethyl)phenoxy]-2,5-dimethylphenyl]-N-ethyl-N-methylmethanimidamide | 150:1 to 1:6 | 50:1 to 1:2 | 24:1 to 3:1 |
| N-[2-(1S,2R-[1,1'-bicyclopropyl]-2-ylphenyl]-3-(difluoromethyl)-1-methyl-1H-pyrazole-4-carboxamide | 120:1 to1:3 | 40:1 to 1:1 | 18:1 to 3:1 |
| N-(4-chloro-2-nitrophenyl)-N-ethyl-4-methylbenzenesulfonamide | 150:1 to 1:6 | 50:1 to 1:2 | 24:1 to 3:1 |
| 2-[[[3-(2,6-dichlorophenyl)-1-methyl-2-propen-1-ylidene]amino]oxy]methyl]-α-(methoxyimino)-N-methylbenzeneacetamide | 90:1 to 1:6 | 30:1 to 1:2 | 18:1 to 2:1 |
| 2-[[[3-(2,6-dichlorophenyl)-1-methyl-2-propen-1-ylidene]amino]oxy]methyl]-α-(methoxyimino)-N-methylbenzeneacetamide | 150:1 to 1:3 | 50:1 to 1:1 | 36:1 to 4:1 |

Of note is a composition of the present invention which comprises in addition to a component (a) compound at least one additional biologically active compound or agent including at least one insecticide. For embodiments where one or more of these insecticides are used, the weight ratio of these insecticides (in total) to the component (a) compounds is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of invertebrate pests controlled beyond the spectrum controlled by the component (a) compounds alone.

Of note is a composition of the present invention which comprises in addition to a component (a) compound at least one additional biologically active compound or agent selected from the group consisting of abamectin, acephate, acetamiprid, acetoprole, aldicarb, amidoflumet, amitraz, avermectin, azadirachtin, azinphos-methyl, bifenthrin, bifenazate, bistrifluron, buprofezin, carbofuran, cartap, chinomethionat, chlorfenapyr, chlorfluazuron, chlorantraniliprole, 3-bromo-1-(3-chloro-2-pyridinyl)-N-[4-cyano-2-methyl-6-[[(1-methylethyl)amino]carbonyl]phenyl]-1H-pyrazole-5-carboxamide, 3-bromo-1-(3-chloro-2-pyridinyl)-N-[4-cyano-2-methyl-6-[(methylamino)carbonyl]phenyl]-1H-pyrazole-5-carboxamide, 3-chloro-1-(3-chloro-2-pyridinyl)-N-[4-cyano-2-methyl-6-[(methylamino)carbonyl]phenyl]-1H-pyrazole-5-carboxamide, 3-chloro-1-(3-chloro-2-pyridinyl)-N-[4-cyano-2-methyl-6-[[(1-methylethyl)amino]carbonyl]phenyl]-1H-pyrazole-5-carboxamide, chlorpyrifos, chlorpyrifos-methyl, chlorobenzilate, chromafenozide, clothianidin, cyflumetofen, cyfluthrin, beta-cyfluthrin, cyhalothrin, gamma-cyhalothrin, lambda-cyhalothrin, cyhexatin, cypermethrin, cyromazine, deltamethrin, diafenthiuron, diazinon, dicofol, dieldrin, dienochlor, diflubenzuron, dimefluthrin, dimethoate, dinotefuran, diofenolan, emamectin, endosulfan, esfenvalerate, ethiprole, etoxazole, fenamiphos, fenazaquin, fenbutatin oxide, fenothiocarb, fenoxycarb, fenpropathrin, fenpyroximate, fenvalerate, fipronil, flonicamid, flubendiamide, flucythrinate, tau-fluvalinate, flufenerim, flufenoxuron, fonophos, halofenozide, hexaflumuron, hexythiazox, hydramethylnon, imicyafos, imidacloprid, indoxacarb, isofenphos, lufenuron, malathion, metaflumizone, metaldehyde, methamidophos, methidathion, methomyl, methoprene, methoxychlor, methoxyfenozide, metofluthrin, monocrotophos, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spiridiclofen, spiromesifen, spirotetramat, sulprofos, tebufenozide, tebufenpyrad, teflubenzuron, tefluthrin, terbufos, tetrachlorvinphos, thiacloprid, thiamethoxam, thiodicarb, thiosultap-sodium, tolfenpyrad, tralomethrin, triazamate, trichlorfon, triflumuron, *Bacillus thuringiensis* subsp. *aizawai*, *Bacillus thuringiensis* subsp. *kurstaki*, nucleopolyhedro viruses, encapsulated delta-endotoxins of *Bacillus thuringiensis*, baculoviruses, entomopathogenic bacteria, entomopathogenic viruses and entomopathogenic fungi.

In certain instances, combinations of a compound of Formula 1 with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Table A2 lists specific combinations of invertebrate pest control agents with a component (a) compound illustrative of mixtures and compositions comprising these active ingredients and methods using them according to the present invention. The first column of Table A2 lists the specific invertebrate pest control agents (e.g., "Abamectin" in the first line). The second column of Table A2 lists the mode of action (if known) or chemical class of the invertebrate pest control agents. The third column of Table A2 lists embodiment(s) of ranges of weight ratios for rates at which the invertebrate pest control agent is typically applied relative to a component (a) compound (e.g., "50:1 to 1:50" of abamectin relative to a compound of Formula 1 by weight). Thus, for example, the first line of Table A2 specifically discloses the combination of a component (a) compound with abamectin is typically applied in a weight ratio between 50:1 to 1:50. The remaining lines of Table A2 are to be construed similarly.

TABLE A2

| Invertebrate Pest Control Agent | Mode of Action or Chemical Class | Typical Weight Ratio |
| --- | --- | --- |
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |
| Endosulfan | cyclodiene insecticides | 200:1 to 1:100 |
| Esfenvalerate | sodium channel modulators | 100:1 to 1:400 |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone | | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| Oxamyl | cholinesterase inhibitors | 200:1 to 1:200 |
| Pymetrozine | | 200:1 to 1:100 |
| Pyrethrin | sodium channel modulators | 100:1 to 1:10 |
| Pyridaben | mitochondrial electron transport inhibitors | 200:1 to 1:100 |

TABLE A2-continued

| Invertebrate Pest Control Agent | Mode of Action or Chemical Class | Typical Weight Ratio |
|---|---|---|
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium | | 150:1 to 1:100 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

One embodiment of invertebrate pest control agents (e.g., insecticides and acaricides) for mixing with compounds of component (a) include sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-regulated chloride channel blockers such as endosulfan, ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; ecdysone agonists such as azadirachtin, methoxyfenozide and tebufenozide; ryanodine receptor ligands such as ryanodine, anthranilic diamides such as chlorantraniliprole (see U.S. Pat. No. 6,747,047, PCT Publications WO 2003/015518 and WO 2004/067528), flubendiamide (see U.S. Pat. No. 6,603,044), 3-bromo-1-(3-chloro-2-pyridinyl)-N-[4-cyano-2-methyl-6-[[(1-methylethyl)amino]carbonyl]phenyl]-1H-pyrazole-5-carboxamide, 3-bromo-1-(3-chloro-2-pyridinyl)-N-[4-cyano-2-methyl-6-[(methylamino)carbonyl]phenyl]-1H-pyrazole-5-carboxamide, 3-chloro-1-(3-chloro-2-pyridinyl)-N-[4-cyano-2-methyl-6-[(methylamino)carbonyl]phenyl]-1H-pyrazole-5-carboxamide and 3-chloro-1-(3-chloro-2-pyridinyl)-N-[4-cyano-2-methyl-6-[[(1-methylethyl)amino]carbonyl]phenyl]-1H-pyrazole-5-carboxamide; nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin; cyflumetofen; fenothiocarb; flonicamid; metaflumizone; pyrafluprole; pyridalyl; pyriprole; pymetrozine; spirotetramat; and thiosultap-sodium. One embodiment of biological agents for mixing with compounds of component (a) include nucleopolyhedro virus such as HzNPV and AfNPV; *Bacillus thuringiensis* and encapsulated delta-endotoxins of *Bacillus thuringiensis* such as Cellcap, MPV and MPVII; as well as naturally occurring and genetically modified viral insecticides including members of the family Baculoviridae as well as entomophagous fungi. Of note is a composition comprising component (a) and at least one additional biologically active compound or agent selected from the Invertebrate Pest Control Agents listed in Table A2 above.

Compositions of component (a) with component (b) can be further mixed with one or more other biologically active compounds or agents including insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a fungicidally effective amount of a mixture of component (a) with component (b) and a biologically effective amount of at least one additional biologically active compound or agent and can further comprise at least one of a surfactant, a solid diluent or a liquid diluent. The other biologically active compounds or agents can also be separately formulated in compositions comprising at least one of a surfactant, solid or liquid diluent. For compositions of the present invention, one or more other biologically active compounds or agents can be formulated together with one or both of components (a) and (b) to form a premix, or one or more other biologically active compounds or agents can be formulated separately from components (a) and (b) and the formulations combined together before application (e.g., in a spray tank) or, alternatively, applied in succession.

Examples of such biologically active compounds or agents with which compositions of component (a) with component (b) can be formulated are: insecticides such as abamectin, acephate, acetamiprid, acetoprole, aldicarb, amidoflumet, amitraz, avermectin, azadirachtin, azinphos-methyl, bifenthrin, bifenazate, bistrifluron, buprofezin, carbofuran, cartap, chinomethionat, chlorfenapyr, chlorfluazuron, chlorantraniliprole, 3-bromo-1-(3-chloro-2-pyridinyl)-N-[4-cyano-2-methyl-6-[[(1-methylethyl)amino]carbonyl]phenyl]-1H-pyrazole-5-carboxamide, 3-bromo-1-(3-chloro-2-pyridinyl)-N-[4-cyano-2-methyl-6-[(methylamino)carbonyl]phenyl]-1H-pyrazole-5-carboxamide, 3-chloro-1-(3-chloro-2-pyridinyl)-N-[4-cyano-2-methyl-6-[(methylamino)carbonyl]phenyl]-1H-pyrazole-5- carboxamide, 3-chloro-1-(3-chloro-2-pyridinyl)-N-[4-cyano-2-methyl-6-[[(1-methylethyl)amino]carbonyl]phenyl]-1H-pyrazole-5-carboxamide, chlorpyrifos, chlorpyrifos-methyl, chlorobenzilate, chromafenozide, clothianidin, cyflumetofen, cyfluthrin, beta-cyfluthrin, cyhalothrin, gamma-cyhalothrin, lambda-cyhalothrin, cyhexatin, cypermethrin, cyromazine, deltamethrin, diafenthiuron, diazinon, dicofol, dieldrin, dienochlor, diflubenzuron, dimefluthrin, dimethoate, dinotefuran, diofenolan, emamectin, endosulfan, esfenvalerate, ethiprole, etoxazole, fenamiphos, fenazaquin, fenbutatin oxide, fenothiocarb, fenoxycarb, fenpropathrin, fenpyroximate, fenvalerate, flpronil, flonicamid, flubendiamide, flucythrinate, tau-fluvalinate, flufenerim, flufenoxuron, fonophos, halofenozide, hexaflumuron, hexythiazox, hydramethylnon, imicyafos, imidacloprid, indoxacarb, isofenphos, lufenuron, malathion, metaflumizone, metaldehyde, methamidophos, methidathion, methomyl, methoprene, methoxychlor, methoxyfenozide, metofluthrin, monocrotophos, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spiridiclofen, spiromesifen, spirotetramat, sulprofos, tebufenozide, tebufenpyrad, teflubenzuron, tefluthrin, terbufos, tetrachlorvinphos, thiacloprid, thiamethoxam, thiodicarb, thiosultap-sodium, tolfenpyrad, tralomethrin, triazamate, trichlorfon, triflumuron; nematocides such as aldicarb, imicyafos, oxamyl and fenamiphos; bactericides such as streptomycin; acaricides such as amitraz, chinomethionat, chlorobenzilate, cyenopyrafen, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Mixtures of this invention and compositions thereof can be applied to plants genetically transformed to express proteins toxic to invertebrate pests (such as *Bacillus thuringiensis* delta-endotoxins). The effect of the exogenously applied fungicidal mixtures of this invention may be synergistic with the expressed toxin proteins.

General references for agricultural protectants (i.e. insecticides, fungicides, nematocides, acaricides, herbicides and biological agents) include *The Pesticide Manual*, 13th Edition, C. D. S. Tomlin, Ed., British Crop Protection Council, Farnham, Surrey, U.K., 2003 and *The BioPesticide Manual*, 2nd Edition, L. G. Copping, Ed., British Crop Protection Council, Farnham, Surrey, U.K., 2001.

For embodiments where one or more of these various mixing partners are used, the weight ratio of these various mixing partners (in total) to the mixture of component (a) with component (b) is typically between about 1:100 and about 3000:1. Of note are weight ratios between about 1:30 and about 300:1 (for example ratios between about 1:1 and about 30:1). It will be evident that including these additional components may expand the spectrum of diseases controlled beyond the spectrum controlled by a mixture of component (a) with component (b).

Of note is a composition embodiment wherein granules of a solid composition comprising a compound of Formula 1 is mixed with granules of a solid composition comprising component (b). These mixtures can be further mixed with granules comprising additional agricultural protectants. Alternatively, two or more agricultural protectants (e.g., a component (a) (Formula 1) compound, a component (b) compound, an agricultural protectant other than component (a) or (b)) can be combined in the solid composition of one set of granules, which is then mixed with one or more sets of granules of solid compositions comprising one or more additional agricultural protectants. These granule mixtures can be in accordance with the general granule mixture disclosure of PCT Patent Publication WO 94/24861 or more preferably the homogeneous granule mixture teaching of U.S. Pat. No. 6,022,552.

The compositions of this invention are useful as plant disease control agents. The present invention therefore further comprises a method for controlling plant diseases caused by fungal plant pathogens comprising applying to the plant or portion thereof to be protected, or to the plant seed or vegetative propagation unit to be protected, an effective amount of a mixture of the invention or a fungicidal composition comprising said mixture.

Plant disease control is ordinarily accomplished by applying an effective amount of a mixture of this invention, typically as a formulated composition, either pre- or post-infection, to the portion of the plant to be protected such as the roots, stems, foliage, fruit, seeds, tubers or bulbs, or to the media (soil or sand) in which the plants to be protected are growing. The mixtures can also be applied to seeds to protect the seeds and seedlings developing from the seeds. The mixtures can also be applied through irrigation water to treat plants.

Rates of application for these mixtures and compositions of this invention can be influenced by many factors of the environment and should be determined under actual use conditions. Foliage can normally be protected when treated at a rate of from less than about 1 g/ha to about 5,000 g/ha of active ingredients. Seed and seedlings can normally be protected when seed is treated at a rate of from about 0.1 to about 10 g per kilogram of seed; and vegetative propagation units (e.g., cuttings and tubers) can normally be protected when propagation unit is treated at a rate of from about 0.1 to about 10 g per kilogram of propagation unit.

The mixtures and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, foliar pathogens of crops including: cereal grain crops such as wheat, barley, oats, rye, triticale, rice, maize, sorghum and millet; vine crops such as table and wine grapes; field crops such as oilseed rape (canola), sunflower; sugar beets, sugar cane, soybean, peanuts (groundnut), tobacco, alfafa, clover, lespedeza, trefoil and vetch; pome fruits such as apple, pear, crabapple, loquat, mayhaw and quince; stone fruits such as peaches, cherries, plums, apricots, nectarines and almonds; citrus fruits such as lemons, limes, oranges, grapefruit, mandarin (tangerines) and kumquat; root and tuber vegetables and field crops (and their foliage) such as artichoke, garden and sugar beet, carrot, cassava, ginger, ginseng, horseradish, parsnip, potato, radish, rutabaga, sweet potato, turnip and yam; bulb vegetables such as garlic, leek, onion and shallot; leafy vegetables such as arugula (roquette), celery, celery, cress, endive (escarole), fennel, head and leaf lettuce, parsley, radicchio (red chicory), rhubarb, spinach and Swiss chard; brassica (cole) leafy vegetables such as broccoli, broccoli raab (rapini), Brussels sprouts, cabbage, bok Choy, cauliflower, collards, kale, kohlrabi, mustard and greens; legume vegetables (succulent or dried) such as lupin, bean (*Phaseolus* spp.) (including field bean, kidney bean, lima bean, navy bean, pinto bean, runner bean, snap bean, tepary bean and wax bean), bean (*Vigna* spp.) (including adzuki bean, asparagus bean, blackeyed pea, catjang, Chinese longbean, cowpea, crowder pea, moth bean, mung bean, rice bean, southern pea, urd bean and yardlong bean), broad bean (fava), chickpea (garbanzo), guar, jackbean, lablab bean, lentil and pea (*Pisum* spp.) (including dwarf pea, edible-podded pea, English pea, field pea, garden pea, green pea, snowpea, sugar snap pea, pigeon pea and soybean); fruiting vegetables such as eggplant, groundcherry (*Physalis* spp.), pepino and pepper (including bell pepper, chili pepper, cooking pepper, pimento, sweet pepper; tomatillo and tomato); cucurbit vegetables such as Chayote (fruit), Chinese waxgourd (Chinese preserving melon), citron melon, cucumber, gherkin, edible gourd (including hyotan, cucuzza, hechima, and Chinese okra), *Momordica* spp. (including balsam apple, balsam pear, bittermelon and Chinese cucumber), muskmelon (including cantaloupe and pumpkin), summer and winter squash (including butternut squash, calabaza, hubbard squash, acorn squash, spaghetti squash) and watermelon; berries such as blackberry (including bingleberry, boysenberry, dewberry, lowberry, marionberry, olallieberry and youngberry), blueberry, cranberry, currant, elderberry, gooseberry, huckleberry, loganberry, raspberry and strawberry; tree nuts such as almond, beech nut, Brazil nut, butternut, cashew, chestnut, chinquapin, filbert (hazelnut), hickory nut, macadamia nut, pecan and walnut; tropical fruits and other crops such as bananas, plantains, mangos, coconuts, papaya, guava, avocado, lichee, agave, coffee, cacao, sugar cane, oil palm, sesame, rubber and spices; fiber crops such as cotton, flax and hemp; turfgrasses (including warm- and cool-season turfgrasses) such as bentgrass, Kentucky bluegrass, St. Augustine grass, tall fescue and Bermuda grass.

These pathogens include: Oomycetes, including *Phytophthora* diseases such as *Phytophthora infestans*, *Phytophthora megasperma*, *Phytophthora parasitica*, *Phytophthora cinnamomi* and *Phytophthora capsici*, *Pythium* diseases such as *Pythium aphanidermatum*, and diseases in the Peronosporaceae family such as *Plasmopara viticola*, *Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae*, *Guignardia* diseases such as *Guignardia bidwelli*, *Venturia* diseases such as *Venturia inaequalis*, *Septoria* diseases such as *Septoria nodorum* and *Septoria tritici*, powdery mildew diseases such as *Erysiphe* spp. (including *Erysiphe graminis* and *Erysiphe polygoni*), *Uncinula necatur*, *Sphaerotheca fuligena* and *Podosphaera leucotricha*, *Pseudocercosporella herpotrichoides*, *Botrytis* diseases such as *Botrytis cinerea*, *Monilinia fructicola*, *Sclerotinia* diseases such as *Sclerotinia sclerotiorum*, *Magnaporthe grisea*, *Phomopsis viticola*, *Helminthosporium* diseases such as *Helminthosporium tritici repentis*, *Pyrenophora teres*, anthracnose diseases such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondite*, *Puccinia striiformis*, *Puccinia hordei*, *Puccinia graminis* and *Puccinia arachidis*), *Hemileia vastatrix* and *Phakopsora pachyrhizi*; other pathogens including *Rhizoctonia* spp. (such as *Rhizoctonia solani* and *Rhizoctonia oryzae*); *Fusarium* diseases such as *Fusarium roseum*, *Fusarium graminearum* and *Fusarium oxysporum*; *Verticillium dahliae*; *Sclerotium rolfsii*; *Rynchosporium secalis*; *Cercosporidium personatum*, *Cercospora arachidicola* and *Cercospora beticola*; *Rutstroemia floccosum* (also known as *Sclerontina homoeocarpa*); and other genera and species closely related to these pathogens. In addition to their fungicidal activity, the compositions or combinations also have activity against bacteria such as *Erwinia amylovora*, *Xanthomonas campestris*, *Pseudomonas syringae*, and other related species.

Mixtures of fungicides may provide significantly better disease control than could be predicted based on the activity of the individual components. This synergism has been described as "the cooperative action of two components of a mixture, such that the total effect is greater or more prolonged than the sum of the effects of the two (or more) taken independently" (see Tames, P. M. L., Neth. J. *Plant Pathology*, (1964), 70, 73-80).

Compositions are provided in accordance with this invention that comprise proportions of component (a) and component (b) that are especially useful for controlling particular fungal diseases. These compositions are considered especially useful for controlling Oomycetes (such as *Phytophthora infestans*, *Phytophthora megasperma*, *Phytophthora parasitica*, *Phytophthora cinnamomi*, *Phytophthora capsici*, *Pythium aphanidermatum*, *Plasmopara viticola*, *Peronospora tabacina*, *Peronospora parasitica*, *Pseudoperonospora cubensis* and *Bremia lactucae*).

The following Tests demonstrate the control efficacy of mixtures of this invention on specific pathogens. The disease control afforded by the mixtures is not limited, however, to the pathogenic fungi species exemplified. See Index Table A for compound descriptions of Formula 1. The following abbreviations are used in the Index Table which follows: t means tertiary, s means secondary, Ph means phenyl. The stereocenters are labeled as R (rectus) and S (sinister) based on Cahn-Ingold-Prelog system. The abbreviation "Ex." stands for "Example" and is followed by a number indicating in which example the compound is prepared. Index Table A lists the molecular weight of the highest isotopic abundance parent ion (M+1) formed by addition of H$^+$ (molecular weight of 1) to the molecule, observed by mass spectrometry using atmospheric pressure chemical ionization (AP$^+$). Chiral separation of Compound 1 into Compounds 3 and 4 was accomplished using a preparative CHIRALPAK® AD-RH column (Chiral Technologies, Inc., West Chester, Pa, U.S.A.) containing silica gel coated with amylose-tris(3,5-dimethylphenyl carbamate) and eluted with a water-methanol gradient. Specific rotation ([α]$_D$) was measured in ethanol solution at 25° C. using a 100-mm path cell.

INDEX TABLE A
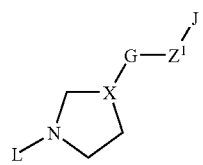
G is as defined in Exhibit 2; $R^{3a}$ and $R^{11a}$ in G are each H. L groups are defined as illustrated below.
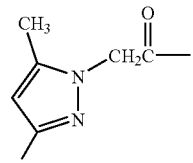
L-1
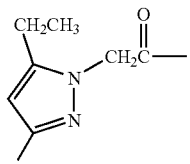
L-2
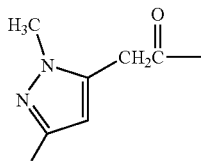
L-3
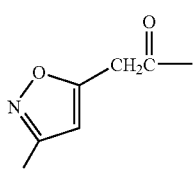
L-4
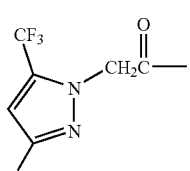
L-5
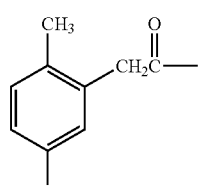
L-6
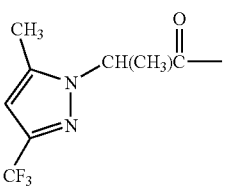
L-7
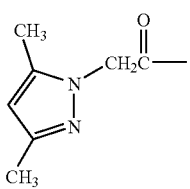
L-8
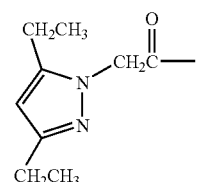
L-9
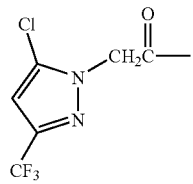
L-10
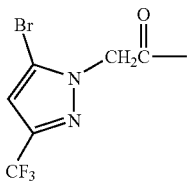
L-11
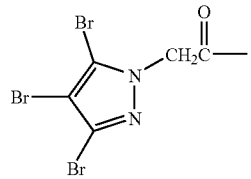
L-12
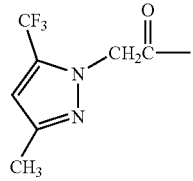
L-13
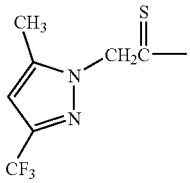
L-14
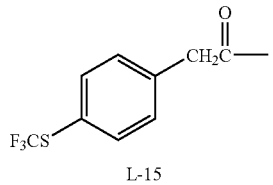
L-15
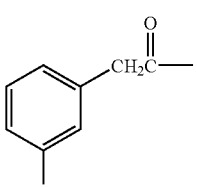
L-16
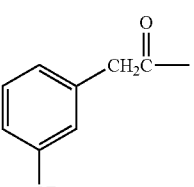
L-17
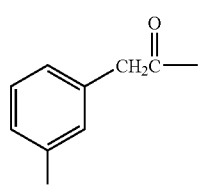
L-18

INDEX TABLE A-continued
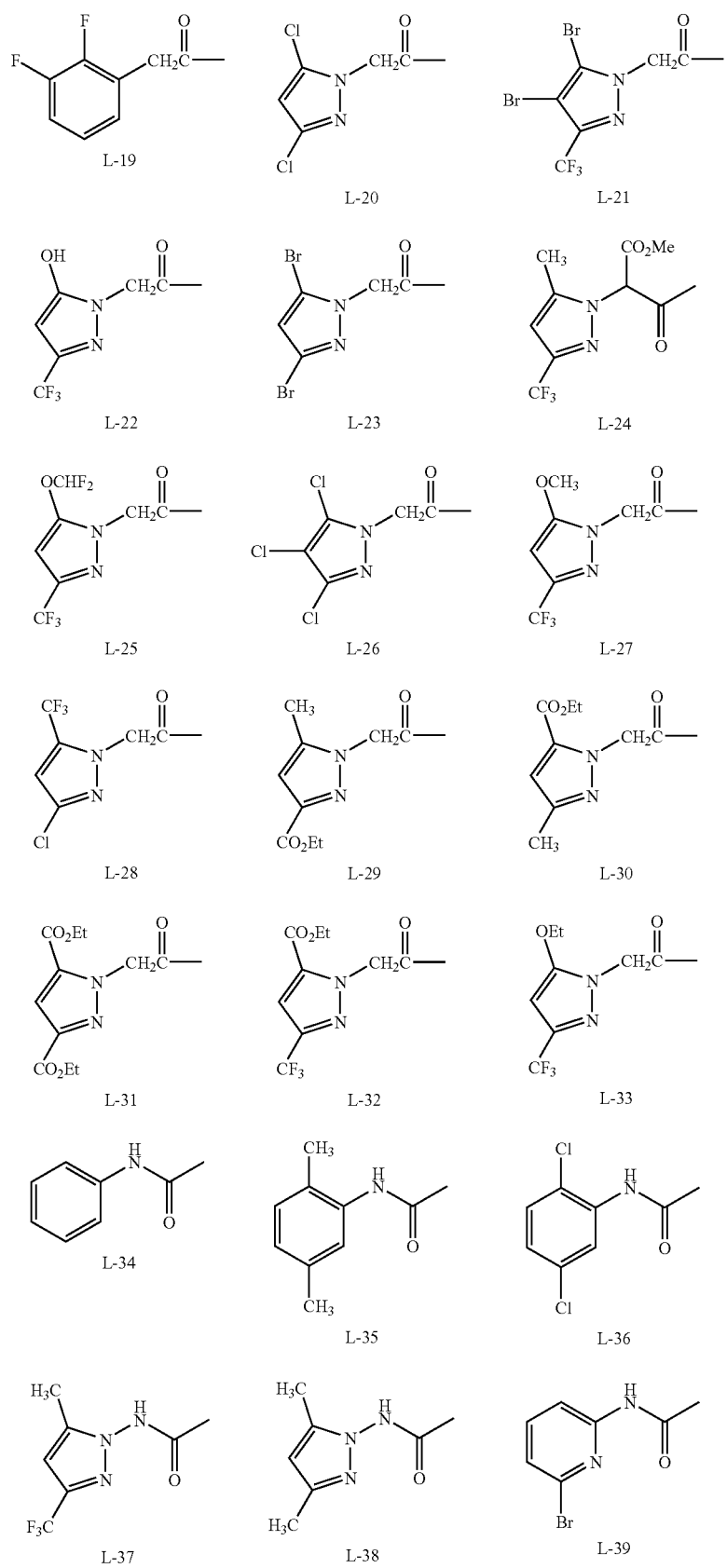

INDEX TABLE A-continued
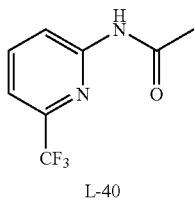 L-40
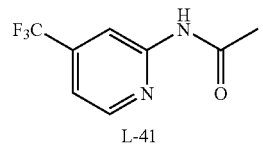 L-41
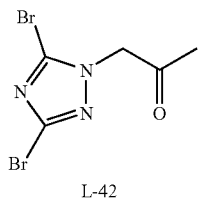 L-42
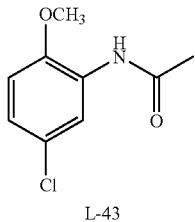 L-43
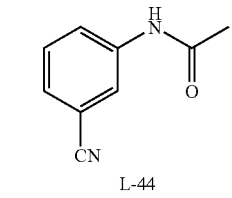 L-44
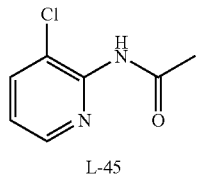 L-45
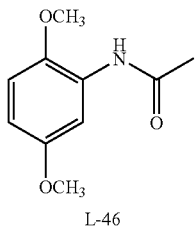 L-46
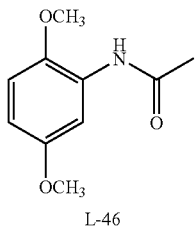 L-47
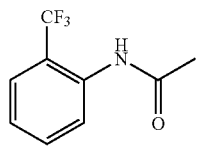 L-48
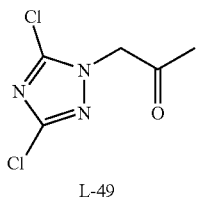 L-49
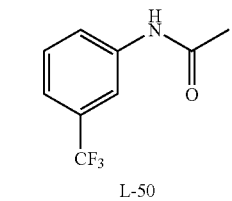 L-50
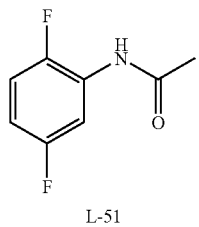 L-51
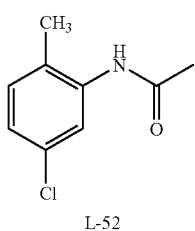 L-52
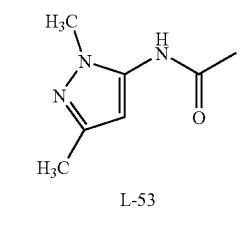 L-53
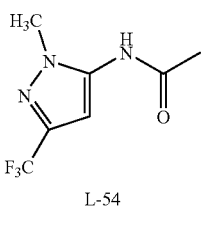 L-54
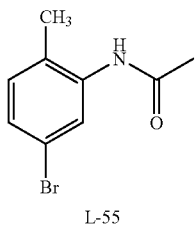 L-55
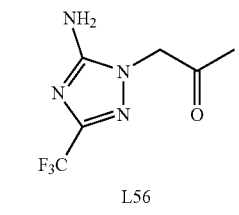 L56
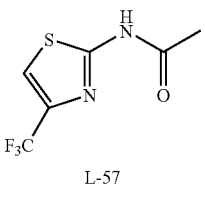 L-57
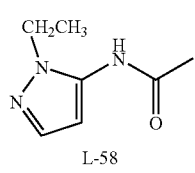 L-58
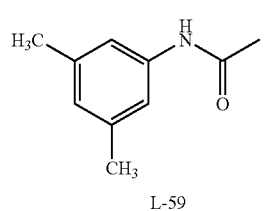 L-59
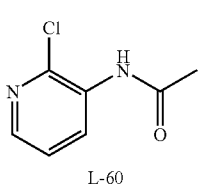 L-60

INDEX TABLE A-continued
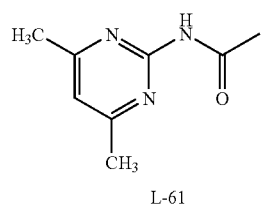
L-61
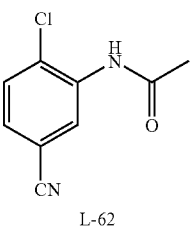
L-62
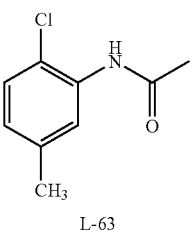
L-63
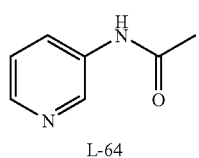
L-64
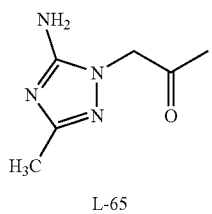
L-65
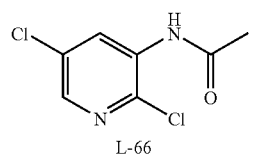
L-66
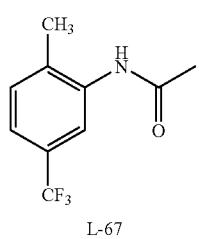
L-67
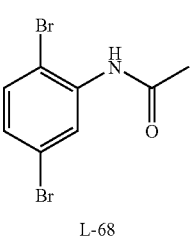
L-68
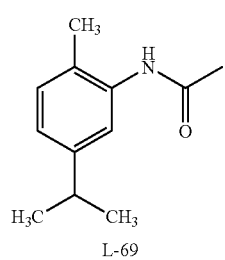
L-69
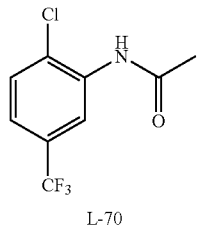
L-70
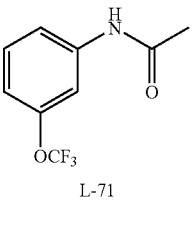
L-71
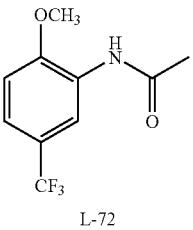 [SMILES: COc1ccc(C(F)(F)F)cc1NC(C)=O]
L-72
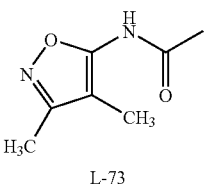
L-73
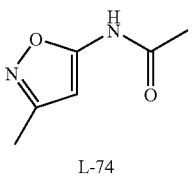
L-74
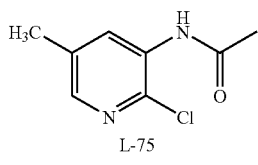
L-75
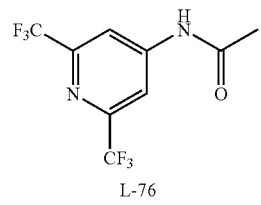 [SMILES: CC(=O)Nc1cc(C(F)(F)F)nc(C(F)(F)F)c1]
L-76
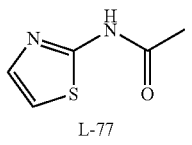
L-77
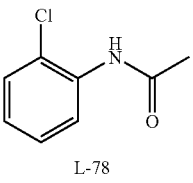
L-78
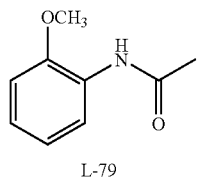
L-79
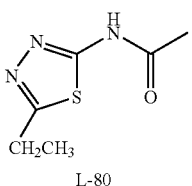
L-80
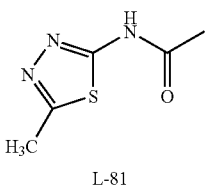
L-81

INDEX TABLE A-continued

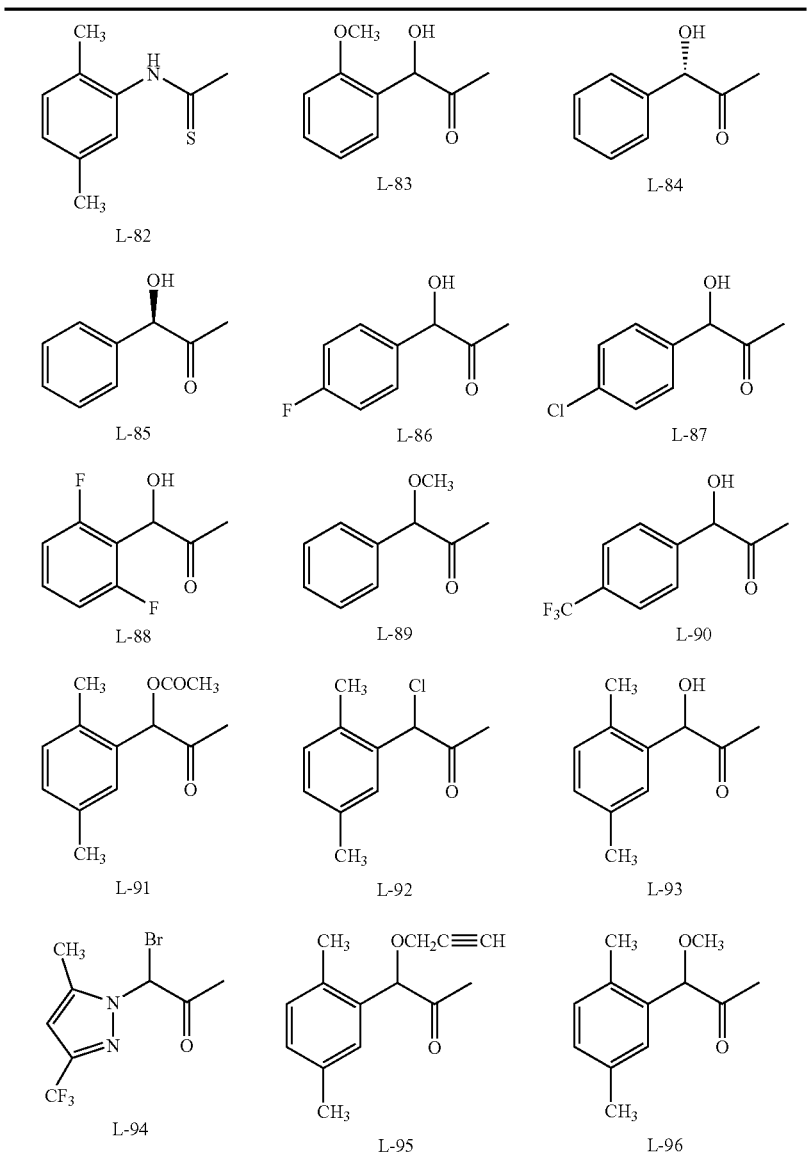

| Cmpd. | L | X | G | Z¹—J | AP⁺ (M + 1) |
|---|---|---|---|---|---|
| 1 (Ex. 1) | L-1 | X¹ | G-1 | 4,5-dihydro-5-phenyl-3-isoxazolyl | 504 |
| 2 (Ex. 2) | L-1 | X¹ | G-1 | 5-phenyl-3-isoxazolyl | 502 |
| 3 (Ex. 12) | L-1 | X¹ | G-1 | 4,5-dihydro-5-phenyl-3-isoxazolyl [Note 1] | 504 |
| 4 | L-1 | X¹ | G-1 | 4,5-dihydro-5-phenyl-3-isoxazolyl [Note 2] | 504 |
| 5 | L-1 | X¹ | G-1 | 5,6-dihydro-6-phenyl-4H-1,2-oxazin-3-yl | 518 |
| 6 (Ex. 4) | L-1 | X¹ | G-1 | 4,5-dihydro-3-phenyl-5-isoxazolyl | 504 |
| 7 (Ex. 3) | L-1 | X¹ | G-1 | (5S)-4,5-dihydro-1-methyl-5-phenyl-1H-imidazol-2-yl | 517 |
| 8 (Ex. 5) | L-1 | X¹ | G-1 | 5-(2-chlorophenyl)-4,5-dihydro-3-isoxazolyl | 538 |
| 9 | L-1 | X¹ | G-1 | 5-(4-chlorophenyl)-4,5-dihydro-3-isoxazolyl | 538 |
| 10 | L-1 | X¹ | G-1 | 4,5-dihydro-5-(4-methylphenyl)-3-isoxazolyl | 518 |
| 11 | L-1 | X¹ | G-1 | (4R**,5R**)-4,5-dihydro-4-methyl-5-phenyl-3-isoxazolyl | 518 |
| 12 | L-1 | X¹ | G-27 | 3-phenyl-1H-pyrazol-1-yl | 483 |
| 13 | L-1 | X¹ | G-1 | 4-phenyl-2-oxazolidinyl | 506 |
| 14 | L-1 | X¹ | G-1 | 3-acetyl-4-phenyl-2-oxazolidinyl | 548 |
| 15 | L-1 | X¹ | G-1 | 4,5-dihydro-5-methyl-5-phenyl-3-isoxazolyl | 518 |

INDEX TABLE A-continued

| | | | | | |
|---|---|---|---|---|---|
| 16 (Ex. 8) | L-1 | X$^1$ | G-1 | 3a,4,5,9b-tetrahydronaphth[2,1-d]isoxazol-3-yl | 530 |
| 17 (Ex. 8) | L-1 | X$^1$ | G-1 | 5-(3-chlorophenyl)-4,5-dihydro-3-isoxazolyl | 538 |
| 18 | L-1 | X$^1$ | G-1 | 4,5-dihydro-5-(4-methoxyphenyl)-3-isoxazolyl | 534 |
| 19 (Ex. 8) | L-2 | X$^1$ | G-1 | 4,5-dihydro-5-phenyl-3-isoxazolyl | 518 |
| 20 (Ex. 1) | L-3 | X$^1$ | G-1 | 4,5-dihydro-5-phenyl-3-isoxazolyl | 504 |
| 21 | L-4 | X$^1$ | G-1 | 4,5-dihydro-5-phenyl-3-isoxazolyl | 491 |
| 22 | L-5 | X$^1$ | G-1 | 4,5-dihydro-5-phenyl-3-isoxazolyl | 558 |
| 23 (Ex. 1) | L-6 | X$^1$ | G-1 | 4,5-dihydro-5-phenyl-3-isoxazolyl | 460 |
| 24 | L-1 | X$^1$ | G-1 | 4,5-dihydro-5-(phenylmethyl)-3-isoxazolyl | 518 |
| 25 | L-1 | X$^1$ | G-1 | (4R**,5S**)-4,5-dihydro-4-methyl-5-phenyl-3-isoxazolyl | 518 |
| 26 | L-1 | X$^1$ | G-1 | 4-biphenyl | 511 |
| 27 | L-1 | X$^1$ | G-1 | 4,5-dihydro-5-(3-methylbutyl)-3-isoxazolyl | 498 |
| 28 | L-1 | X$^1$ | G-1 | 4,5-dihydro-5-(2,2-dimethylpropyl)-3-isoxazolyl | 498 |
| 29 | L-1 | X$^1$ | G-1 | 5,6-dihydro-6-methyl-6-phenyl-4H-1,2-oxazin-3-yl | 532 |
| 30 | L-1 | X$^1$ | G-1 | 3-phenyl-5-isoxazolyl | 502 |
| 31 | L-1 | X$^1$ | G-1 | 4,5-dihydro-4-phenyl-2-oxazolyl | 504 |
| 32 | L-1 | X$^1$ | G-1 | 4,5-dihydro-1-(phenylmethyl)-1H-imidazol-2-yl | 517 |
| 33 | L-1 | X$^1$ | G-27 | 3-biphenyl | 494 |
| 34 | L-1 | X$^1$ | G-27 | 6-phenyl-2-pyridyl | 495 |
| 35 | L-1 | X$^1$ | G-1 | 4,5-dihydro-5-phenyl-5-(trifluoromethyl)-3-isoxazolyl | 572 |
| 36 | L-1 | X$^1$ | G-1 | 5-[3-(trifluoromethyl)phenyl]-3-isoxazolyl | 570 |
| 37 (Ex. 8) | L-1 | X$^1$ | G-1 | *[spiro tetrahydronaphthalene-isoxazoline structure]* | 544 |
| 38 | L-1 | X$^1$ | G-1 | 5-(4-biphenyl)-3-isoxazolyl | 578 |
| 39 | L-1 | X$^1$ | G-1 | 4,5-dihydro-5-(3,5-dichlorophenyl)-5-(trifluoromethyl)-3-isoxazolyl | 640 |
| 40 | L-1 | X$^1$ | G-1 | 5-phenyl-1,3,4-oxadiazol-2-yl | 503 |
| 41 | L-1 | X$^1$ | G-1 | 4,5-dihydro-5-phenyl-2-oxazolyl | 504 |
| 42 | L-1 | X$^1$ | G-1 | 5-phenyl-2-oxazolyl | 502 |
| 43 | L-1 | X$^1$ | G-1 | 2-benzothiazolyl | 492 |
| 44 (Ex.8) | L-1 | X$^1$ | G-1 | *[spiro indane-isoxazoline structure]* | 530 |
| 45 | L-1 | X$^1$ | G-1 | *[N-methyl succinimide fused isoxazoline structure]* | 511 |
| 46 | L-1 | X$^1$ | G-1 | (4R)-4,5-dihydro-4-phenyl-2-oxazolyl | 504 |
| 47 | L-1 | X$^1$ | G-1 | (5S)-4,5-dihydro-5-phenyl-2-oxazolyl | 504 |
| 48 | L-1 | X$^1$ | G-1 | 5,6-dihydro-6-phenyl-4H-1,3-oxazin-2-yl | 518 |
| 49 | L-1 | X$^1$ | G-1 | (4S)-4,5-dihydro-4-phenyl-2-oxazolyl | 504 |
| 50 | L-1 | X$^1$ | G-1 | (5R)-4,5-dihydro-5-phenyl-2-oxazolyl | 504 |

INDEX TABLE A-continued

| | | | | | |
|---|---|---|---|---|---|
| 51 | L-1 | X¹ | G-1 | 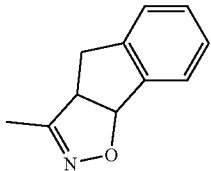 | 516 |
| 52 | L-1 | X¹ | G-1 | 2-benzoxazolyl | 475 |
| 53 | L-1 | X¹ | G-1 | 5,6-dihydro-5-phenyl-4H-1,3-oxazin-2-yl | 518 |
| 54 | L-1 | X¹ | G-1 | 5,6-dihydro-4-phenyl-4H-1,3-oxazin-2-yl | 518 |
| 55 | L-1 | X¹ | G-1 | 4,5-dihydro-5-(methoxycarbonyl)-3-isoxazolyl | 486 |
| 56 | L-1 | X¹ | G-1 | 4,5-dihydro-5-(1,1-dimethylethyl)-3-isoxazolyl | 484 |
| 57 | L-1 | X¹ | G-1 | 4,5-dihydro-5-(2-bromoethyl)-3-isoxazolyl | 534 |
| 58 | L-1 | X¹ | G-1 | 2-benzimidazolyl | 475 |
| 59 | L-1 | X¹ | G-1 | 5-(2-fluorophenyl)-3-isoxazolyl | 520 |
| 60 | L-1 | X¹ | G-1 | 5-(2-trifluoromethylphenyl)-3-isoxazolyl | 570 |
| 61 | L-1 | X¹ | G-1 | 2-naphthalenyl | 485 |
| 62 | L-1 | X¹ | G-1 | phenyl | 435 |
| 63 | L-7 | X¹ | G-1 | 4,5-dihydro-5-phenyl-3-isoxazolyl | 518 |
| 64 | L-1 | X¹ | G-1 | 5-(2,4-difluorophenyl)-3-isoxazolyl | 538 |
| 65 | L-1 | X¹ | G-1 | 1-phenyl-2-pyrrolidon-4-yl | 518 |
| 66 | L-1 | X¹ | G-1 | 4,5-dihydro-5-cyano-3-isoxazolyl | 453 |
| 67 | L-1 | X¹ | G-1 | 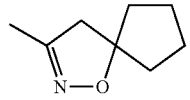 | 482 |
| 68 | L-1 | X¹ | G-1 | 3-phenyl-1,2,4-oxadiazol-5-yl | 503 |
| 69 | L-15 | X¹ | G-1 | 4,5-dihydro-5-phenyl-3-isoxazolyl | 532 |
| 70 | L-16 | X¹ | G-1 | 4,5-dihydro-5-phenyl-3-isoxazolyl | 478 |
| 71 | L-17 | X¹ | G-1 | 4,5-dihydro-5-phenyl-3-isoxazolyl | 500 |
| 72 | L-1 | X¹ | G-1 | 4-phenoxyphenyl | 527 |
| 73 | L-1 | X¹ | G-1 | 1-naphthalenyl | 485 |
| 74 | L-1 | X¹ | G-1 | 3-biphenyl | 511 |
| 75 | L-1 | X¹ | G-1 | 3-phenoxyphenyl | 527 |
| 76 | L-1 | X¹ | G-1 | 1-phenylpyrazol-3-yl | 501 |
| 77 | L-1 | X¹ | G-1 | 1-(4-methylphenyl)-1,2,3-triazol-4-yl | 516 |
| 78 | L-1 | X¹ | G-1 | 1-phenylpyrazol-5-yl | 501 |
| 79 | L-1 | X¹ | G-1 | 4,5-dihydro-5-(2-fluorophenyl)-3-isoxazolyl | 522 |
| 80 | L-17 | X¹ | G-1 | 4,5-dihydro-5-(2-fluorophenyl)-3-isoxazolyl | 518 |
| 81 | L-1 | X¹ | G-1 | 5,6-dihydro-5-phenyl-6-methoxy-4H-1,2-oxazin-3-yl | 548 |
| 82 | L-1 | X¹ | G-1 | 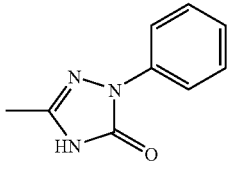 | 518 |
| 83 | L-1 | X¹ | G-1 | 5-phenyl-2-furanyl | 501 |
| 84 | L-1 | X¹ | G-1 | 2-phenyl-4-thiazoyl | 518 |
| 85 | L-1 | X¹ | G-1 | 5-phenyl-2-thienyl | 517 |
| 86 | L-1 | X¹ | G-1 | 3-(2,4-dichlorophenyl)-5-isoxazoyl | 570 |
| 87 | L-1 | X¹ | G-1 | 3-(3,4-dichlorophenyl)-5-isoxazoyl | 570 |
| 88 | L-1 | X¹ | G-1 | 4,5-dihydro-5-(naphthalen-2-yl)-3-isoxazolyl | 554 |
| 89 | L-18 | X¹ | G-1 | 4,5-dihydro-5-phenyl-3-isoxazolyl | 462 |
| 90 | L-19 | X¹ | G-1 | 4,5-dihydro-5-phenyl-3-isoxazolyl | 468 |
| 91 | L-1 | X¹ | G-1 | 4,5-dihydro-5-(4-t-butylphenyl)-3-isoxazolyl | 560 |
| 92 | L-1 | X¹ | G-1 | (5R)-4,5-dihydro-5-phenyl-1H-imidazol-2-yl | 503 |
| 93 | L-8 | X¹ | G-1 | 4,5-dihydro-5-phenyl-3-isoxazolyl | 450 |
| 94 | L-9 | X¹ | G-1 | 4,5-dihydro-5-phenyl-3-isoxazolyl | 478 |
| 95 | L-1 | X¹ | G-1 | 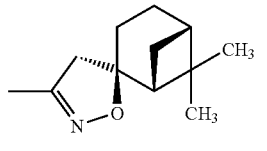 | 536 |
| 96 | L-1 | X¹ | G-1 | 4,5-dihydro-5-(4-fluorophenyl)-3-isoxazolyl | 522 |
| 97 | L-1 | X¹ | G-1 | 4,5-dihydro-5-(4-trifluoromethylphenyl)-3-isoxazolyl | 572 |
| 98 | L-1 | X¹ | G-1 | 4,5-dihydro-5-(2-pyridyl)-3-isoxazolyl | 505 |

INDEX TABLE A-continued

| | | | | | |
|---|---|---|---|---|---|
| (Ex. 9) | | | | | |
| 99 | L-1 | $X^1$ | G-1 | 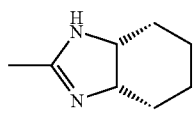 | 481 |
| 100 | L-1 | $X^1$ | G-1 | 4,5-dihydro-5-isopropyl-5-phenyl-3-isoxazolyl | 546 |
| 101 | L-1 | $X^1$ | G-1 | 4,5-dihydro-5-propyl-5-phenyl-3-isoxazolyl | 546 |
| 102 (Ex. 1) | L-1 | $X^1$ | G-1 | 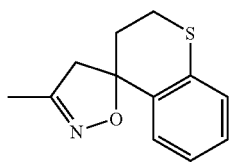 | 562 |
| 103 | L-1 | $X^1$ | G-1 | 4,5-dihydro-5-cyclopropyl-5-phenyl-3-isoxazolyl | 544 |
| 104 | L-1 | $X^1$ | G-1 | 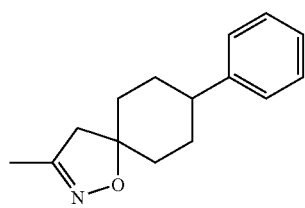 | 572 |
| 105 | L-1 | $X^1$ | G-1 | 4,5-dihydro-5-ethyl-5-phenyl-3-isoxazolyl | 532 |
| 106 | L-1 | $X^1$ | G-1 | 4,5-dihydro-5-(4-biphenyl)-3-isoxazolyl | 580 |
| 107 (Ex. 10) | L-10 | $X^1$ | G-1 | 4,5-dihydro-5-phenyl-3-isoxazolyl | 524 |
| 108 | L-1 | $X^1$ | G-1 | (4R,5R)-4,5-dihydro-4,5-diphenyl-1H-imidazol-2-yl | 579 |
| 109 | L-1 | $X^1$ | G-1 | 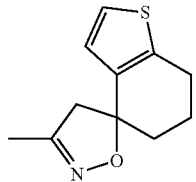 | 550 |
| 110 | L-1 | $X^1$ | G-1 | 4,5-dihydro-5-(4-hydroxyphenyl)-3-isoxazolyl | 520 |
| 111 | L-1 | $X^1$ | G-1 | 4,5-dihydro-5-(2-pyrazinyl)-3-isoxazolyl | 506 |
| 112 | L-1 | $X^1$ | G-1 | 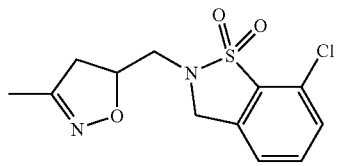 | 643 |
| 113 | L-1 | $X^1$ | G-1 | 4,5-dihydro-5-(4-acetoxyphenyl)-3-isoxazolyl | 562 |
| 114 | L-1 | $X^1$ | G-1 | 4,5-dihydro-5-(2-trifluoromethylphenyl)-3-isoxazolyl | 572 |
| 115 | L-1 | $X^1$ | G-1 | 4,5-dihydro-5-(3-trifluoromethylphenyl)-3-isoxazolyl | 572 |
| 116 | L-1 | $X^1$ | G-1 | 4,5-dihydro-5-(methoxycarbonylmethyl)-3-isoxazolyl | 500 |
| 117 | L-1 | $X^1$ | G-1 | 4,5-dihydro-5-(phenylsulfonyl)-3-isoxazolyl | 568 |
| 118 | L-1 | $X^1$ | G-1 | (5R)-4,5-dihydro-1-methyl-5-phenyl-1H-imidazol-2-yl | 517 |
| 119 | L-1 | $X^1$ | G-1 | (4S,5R)-4,5-dihydro-4,5-diphenyl-1H-imidazol-2-yl | 579 |
| 120 | L-1 | $X^1$ | G-1 | 4-chlorophenyl | 469 |
| 121 | L-1 | $X^1$ | G-1 | 2-chlorophenyl | 469 |
| 122 | L-1 | $X^1$ | G-1 | 4-(trifluoromethyl)phenyl | 503 |
| 123 | L-1 | $X^1$ | G-1 | 3-chlorophenyl | 469 |
| 124 | L-1 | $X^1$ | G-1 | 3-pyridyl | 436 |
| 125 | L-1 | $X^1$ | G-1 | 4,5-dihydro-5-(3,4-dihydroxyphenyl)-3-isoxazolyl | 536 |
| 126 (Ex. 11) | L-11 | $X^1$ | G-1 | 4,5-dihydro-5-phenyl-3-isoxazolyl | 568 |
| 127 | L-12 | $X^1$ | G-1 | 4,5-dihydro-5-phenyl-3-isoxazolyl | 658 |
| 128 | L-13 | $X^1$ | G-1 | 4,5-dihydro-5-phenyl-3-isoxazolyl | 504 |

INDEX TABLE A-continued (Ex. 1)

| | | | | | | |
|---|---|---|---|---|---|---|
| 129 | L-1 | X¹ | G-1 | 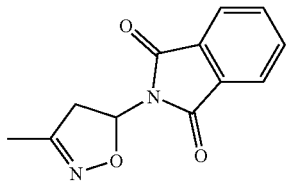 [SMILES: CC1=NOC(N2C(=O)c3ccccc3C2=O)C1] | | 573 |
| 130 (Ex. 6) | L-14 | X¹ | G-1 | 4,5-dihydro-5-phenyl-3-isoxazolyl | | 520 |
| 131 | L-1 | X¹ | G-1 | 4,5-dihydro-5-(2-methoxyphenyl)-3-isoxazolyl | | 534 |
| 132 | L-1 | X¹ | G-1 | 4,5-dihydro-5-methyl-5-(2,5-dichloro-3-thienyl)-3-isoxazolyl | | 592 |
| 133 | L-1 | X¹ | G-1 | 4,5-dihydro-5-(2,5-dimethylphenyl)-3-isoxazolyl | | 532 |
| 134 | L-1 | X¹ | G-1 | 4,5-dihydro-5-(4-methoxycarbonylphenyl)-3 isoxazolyl | | 562 |
| 135 | L-1 | X¹ | G-1 | 4,5-dihydro-5-(2,6-dichlorophenyl)-3-isoxazolyl | | 572 |
| 136 | L-1 | X¹ | G-1 | 4,5-dihydro-5-(2,4-dimethylphenyl)-3-isoxazolyl | | 532 |
| 137 (Ex. 1) | L-1 | X¹ | G-1 | 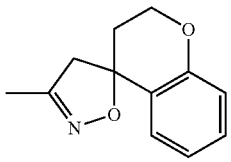 | | 546 |
| 138 | L-1 | X¹ | G-1 | 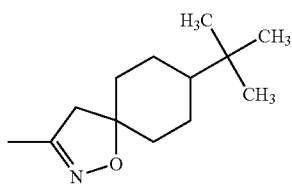 | | 552 |
| 139 | L-1 | X¹ | G-1 | 4,5-dihydro-5,5-diphenyl-3-isoxazolyl | | 580 |
| 140 | L-1 | X¹ | G-1 | 4,5-dihydro-5-(2-methoxyphenyl)-5-methyl-3-isoxazolyl | | 548 |
| 141 | L-1 | X¹ | G-1 | 4,5-dihydro-5-(methoxymethyl)-5-phenyl-3-isoxazolyl | | 548 |
| 142 | L-1 | X¹ | G-1 | 4,5-dihydro-5-(methylthiomethyl)-5-phenyl-3-isoxazolyl | | 564 |
| 143 | L-1 | X¹ | G-1 | 4,5-dihydro-5-(methylsulfonylmethyl)-5-phenyl-3-isoxazolyl | | 596 |
| 144 | L-1 | X¹ | G-1 | 4,5-dihydro-5-(methylsulfinylmethyl)-5-phenyl-3-isoxazolyl | | 580 |
| 145 | L-1 | X¹ | G-1 | 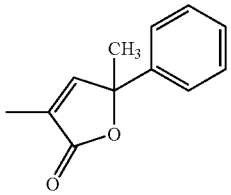 | | 531 |
| 146 | L-1 | X¹ | G-1 | 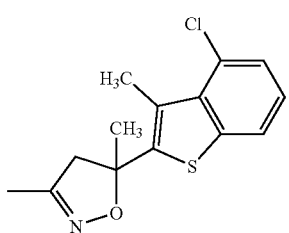 [SMILES: CC1=NOC(C)(c2sc3cccc(Cl)c3c2C)C1] | | 622 |

INDEX TABLE A-continued

| | | | | | |
|---|---|---|---|---|---|
| 147 | L-1 | X¹ | G-1 | 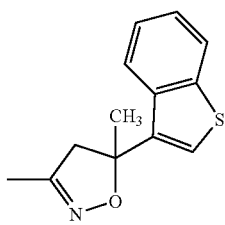 [SMILES: CC1=NOC(C)(c2csc3ccccc23)C1] | 574 |
| 148 | L-1 | X¹ | G-1 | 4,5-dihydro-5-(3-thienyl)-3-isoxazolyl | 510 |
| 149 | L-1 | X¹ | G-1 | 3-methylphenyl | 449 |
| 150 | L-1 | X¹ | G-1 | 4-methoxyphenyl | 465 |
| 151 | L-1 | X¹ | G-1 | 4-methylphenyl | 449 |
| 152 | L-1 | X¹ | G-1 | 3-methoxyphenyl | 465 |
| 153 | L-1 | X¹ | G-1 | 2-methoxyphenyl | 465 |
| 154 (Ex. 7) | L-1 | X² | G-1 | 4,5-dihydro-5-phenyl-3-isoxazolyl | 505 |
| 155 | L-1 | X¹ | G-1 | 4,5-dihydro-5-(2,4,6-trimethoxyphenyl)-3-isoxazolyl | 594 |
| 156 | L-1 | X¹ | G-1 | 4,5-dihydro-5-acetoxymethyl-5-phenyl-3-isoxazolyl | 576 |
| 157 | L-1 | X¹ | G-1 | 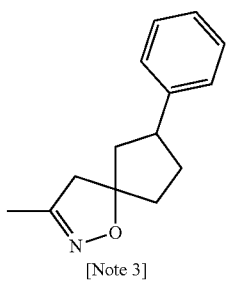 [Note 3] | 558 |
| 158 | L-1 | X¹ | G-1 | 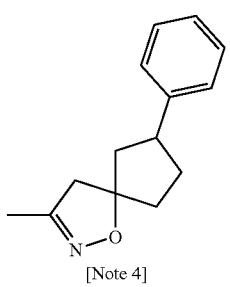 [Note 4] | 558 |
| 159 | L-1 | X¹ | G-1 | 4,5-dihydro-5-hydroxymethyl-5-phenyl-3-isoxazolyl | 534 |
| 160 | L-1 | X¹ | G-1 | 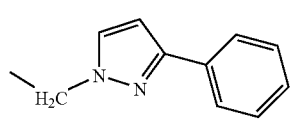 | 515 |
| 161 | L-1 | X¹ | G-1 | 4,5-dihydro-5-(2-methylphenyl)-3-isoxazolyl | 518 |
| 162 | L-1 | X¹ | G-1 | 4,5-dihydro-5-thien-2-yl-3-isoxazolyl | 510 |
| 163 | L-8 | X¹ | G-1 | 4,5-dihydro-5-methyl-5-phenyl-3-isoxazolyl | 464 |
| 164 | L-8 | X¹ | G-1 | 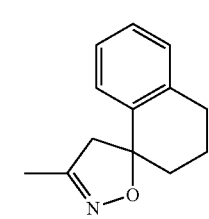 | 490 |

INDEX TABLE A-continued
| 165 | L-8 | X¹ | G-1 | 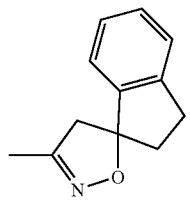 | 476 |
| --- | --- | --- | --- | --- | --- |
| 166 | L-20 | X¹ | G-1 | 4,5-dihydro-5-phenyl-3-isoxazolyl | 490 |
| 167 | L-21 | X¹ | G-1 | 4,5-dihydro-5-phenyl-3-isoxazolyl | 647 |
| 168 | L-23 | X¹ | G-1 | 4,5-dihydro-5-phenyl-3-isoxazolyl | 579 |
| 169 | L-1 | X¹ | G-1 | 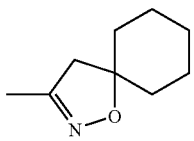 | 496 |
| 170 | L-1 | X¹ | G-1 | 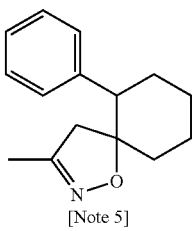 [Note 5] | 572 |
| 171 | L-1 | X¹ | G-1 | 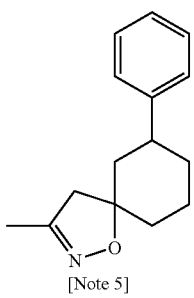 [Note 5] | 572 |
| 172 | L-24 | X¹ | G-1 | 4,5-dihydro-5-phenyl-3-isoxazolyl | 562 |
| 173 | L-1 | X¹ | G-1 | 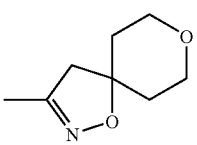 | 498 |
| 174 | L-1 | X¹ | G-1 | 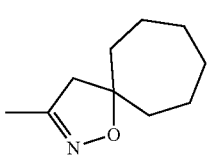 | 510 |
| 175 | L-1 | X¹ | G-1 | 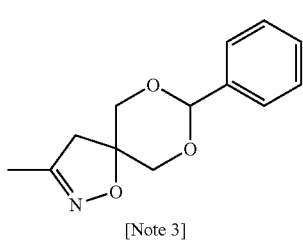 [Note 3] | 576 |

INDEX TABLE A-continued
| 176 | L-1 | X¹ | G-1 | 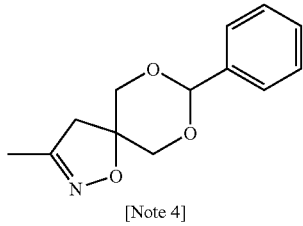 [Note 4] | 576 |
| --- | --- | --- | --- | --- | --- |
| 177 | L-1 | X¹ | G-1 | 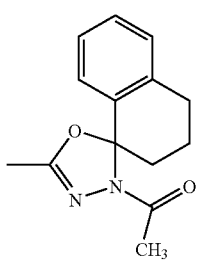 | 587 |
| 178 | L-1 | X¹ | G-1 | 4,5-dihydro-5-(2,6-dimethylphenyl)-3-isoxazolyl | 532 |
| 179 | L-1 | X¹ | G-1 | 4,5-dihydro-5-(2,4,6-trimethylphenyl)-3-isoxazolyl | 546 |
| 180 | L-1 | X¹ | G-1 | 4,5-dihydro-5-pyridin-4-yl-3-isoxazolyl | 505 |
| 181 | L-1 | X¹ | G-1 | 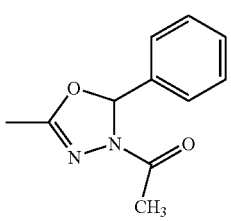 | 547 |
| 182 | L-1 | X¹ | G-1 | 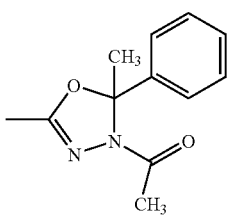 [SMILES: CC(=O)N1N=C(C)OC1(C)c1ccccc1] | 561 |
| 183 | L-1 | X¹ | G-1 | 4,5-dihydro-5-phenyl-1H-pyrazol-3-yl | 503 |
| 184 | L-1 | X¹ | G-1 | 4,5-dihydro-5-phenyl-(1-methyl-1H-pyrazol-3-yl) | 517 |
| 185 | L-1 | X¹ | G-1 | 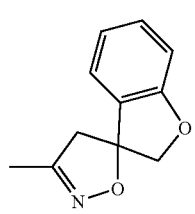 | 532 |
| 186 | L-1 | X¹ | G-1 | 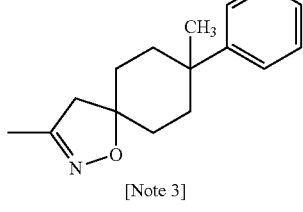 [Note 3] | 586 |

INDEX TABLE A-continued
| 187 | L-1 | X¹ | G-1 | 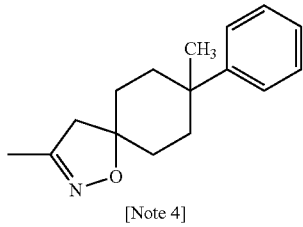 [Note 4] | 586 |
| --- | --- | --- | --- | --- | --- |
| 188 | L-1 | X¹ | G-1 | 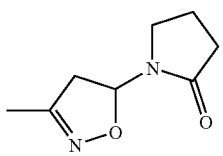 | 511 |
| 189 | L-1 | X¹ | G-1 | 4,5-dihydro-5-(2-bromophenyl)-3-isoxazolyl | 582 |
| 190 | L-26 | X¹ | G-1 | 4,5-dihydro-5-phenyl-3-isoxazolyl | 524 |
| 191 | L-1 | X¹ | G-1 | 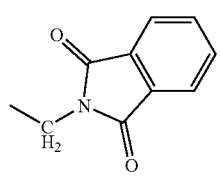 | 518 |
| 192 | L-1 | X¹ | G-1 | 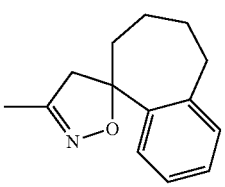 [SMILES: CC1=NOC2(CCCCc3ccccc32)C1] | 558 |
| 193 | L-1 | X¹ | G-1 | 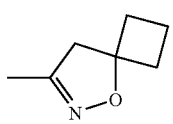 | 468 |
| 194 | L-1 | X¹ | G-1 | 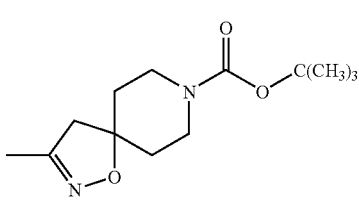 [SMILES: CC1=NOC2(CCN(C(=O)OC(C)(C)C)CC2)C1] | 597 |
| 95 | L-1 | X¹ | G-1 | 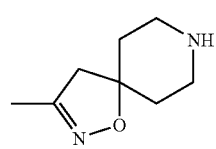 | 497 |
| 196 | L-1 | X¹ | G-1 | 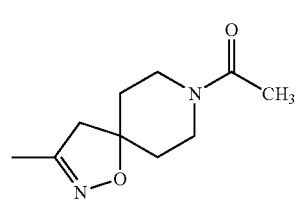 | 539 |
| 197 | L-1 | X¹ | G-1 | 4,5-dihydro-5-phenyl-(1-acetyl-1H-pyrazol-3-yl) | 545 |
| 198 | L-28 | X¹ | G-1 | 4,5-dihydro-5-phenyl-3-isoxazolyl | 524 |

INDEX TABLE A-continued
| 199 | L-1 | X¹ | G-1 | 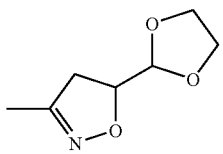 | 500 |
| 200 | L-1 | X¹ | G-1 | 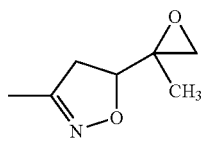 | 484 |
| 201 | L-1 | X¹ | G-1 | 4,5-dihydro-5-(4-methylthiazol-5-yl)-3-isoxazolyl | 525 |
| 202 | L-1 | X¹ | G-1 | 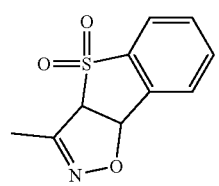 | 566 |
| 203 | L-1 | X¹ | G-1 | 3-isoxazolyl | 425 |
| 204 | L-1 | X¹ | G-1 | 4,5-dihydro-5-phenoxy-3-isoxazolyl | 520 |
| 205 | L-1 | X¹ | G-1 | 4,5-dihydro-5-methyl-5-(2-methylphenyl)-3-isoxazolyl | 532 |
| 206 | L-1 | X¹ | G-1 | 4,5-dihydro-5-(2,6-dimethoxyphenyl)-3-isoxazolyl | 564 |
| 207 | L-1 | X¹ | G-1 | 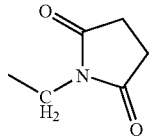 | 469 |
| 208 | L-1 | X¹ | G-1 | 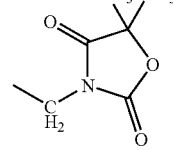 | 500 |
| 209 | L-1 | X¹ | G-1 | 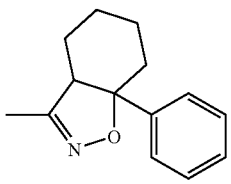 [SMILES: CC1=NOC2(c3ccccc3)CCCCC12] | 558 |
| 210 | L-1 | X¹ | G-1 | 5-(2-hydroxycarbonylphenyl)-3-isoxazolyl | 546 |
| 211 | L-1 | X¹ | G-1 | 4,5-dihydro-5-(1,1-dimethylethoxy)-3-isoxazolyl | 500 |
| 212 | L-1 | X¹ | G-1 | 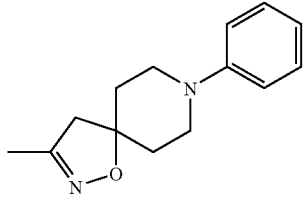 [SMILES: CC1=NOC2(CCN(c3ccccc3)CC2)C1] | 573 |
| 213 | L-1 | X¹ | G-1 | 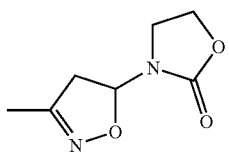 | 513 |

INDEX TABLE A-continued
| | | | | | |
|---|---|---|---|---|---|
| 214 | L-1 | X¹ | G-1 | 4,5-dihydro-5-(2,6-difluorophenyl)-3-isoxazolyl [Note 22], [Note 23] and [Note 24] | 540 |
| 215 | L-1 | X¹ | G-1 | 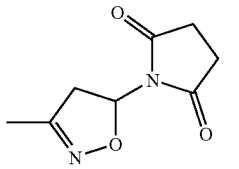 | 525 |
| 216 | L-1 | X¹ | G-1 | 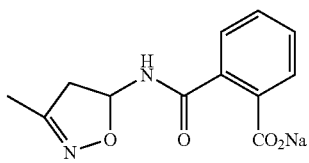 | 613 |
| 217 (Ex. 13) | L-1 | X³ | G-1 | 4,5-dihydro-5-phenyl-3-isoxazolyl | 502 |
| 218 | L-1 | X¹ | G-1 | 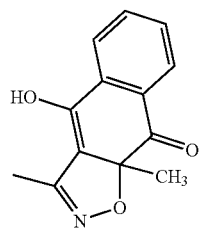 [SMILES: CC1=NOC2(C)C(=O)c3ccccc3C(O)=C12] | 572 |
| 219 | L-1 | X¹ | G-1 | 4,5-dihydro-5-(1-methylbenzimidazol-2-yl)-3-isoxazolyl | 558 |
| 220 | L-1 | X¹ | G-1 | 4,5-dihydro-5-(2-cyanophenyl)-3-isoxazolyl | 529 |
| 221 | L-1 | X¹ | G-1 | 4,5-dihydro-5-2-methoxycarbonylphenyl)-3-isoxazolyl | 562 |
| 222 | L-1 | X¹ | G-1 | 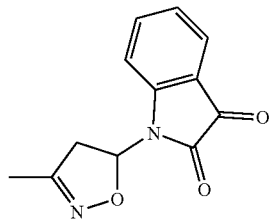 [SMILES: CC1=NOC(N2C(=O)C(=O)c3ccccc32)C1] | 573 |
| 223 | L-1 | X¹ | G-1 | 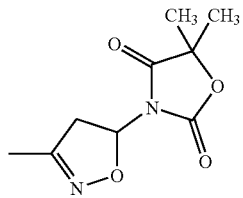 | 555 |
| 224 | L-1 | X¹ | G-1 | 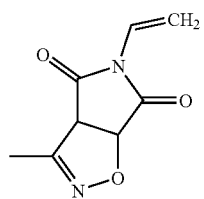 | 523 |
| 225 | L-1 | X¹ | G-1 | 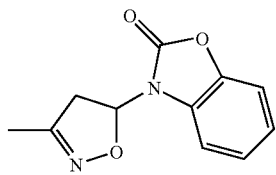 [SMILES: CC1=NOC(n2c(=O)oc3ccccc32)C1] | 561 |

INDEX TABLE A-continued
| 226 | L-1 | X¹ | G-1 | 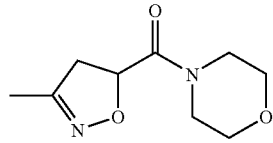 | 541 |
| 227 | L-1 | X¹ | G-1 | 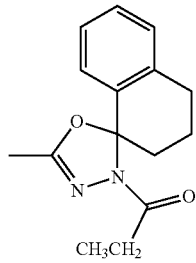 | 601 |
| 228 | L-1 | X¹ | G-1 | 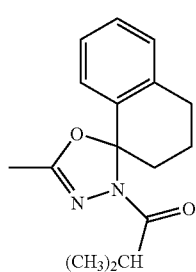 | 615 |
| 229 | L-5 | X¹ | G-1 | 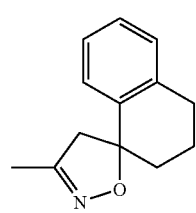 | 598 |
| 230 | L-10 | X¹ | G-1 | 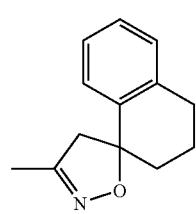 | 564 |
| 231 | L-5 | X¹ | G-1 | 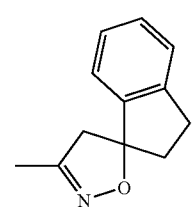 | 584 |
| 232 | L-10 | X¹ | G-1 | 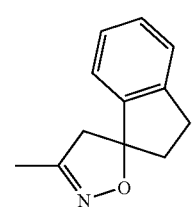 | 550 |

INDEX TABLE A-continued

| | | | | | |
|---|---|---|---|---|---|
| 233 | L-1 | X¹ | G-1 | (1-(3-methyl-4,5-dihydroisoxazol-5-yl)indolin-2-one) | 559 |
| 234 | L-1 | X¹ | G-1 | (1-methyl-3-(3-methyl-4,5-dihydroisoxazol-5-yl)imidazolidine-2,4-dione) | 540 |
| 235 | L-1 | X¹ | G-1 | (1,5,5-trimethyl-3-(3-methyl-4,5-dihydroisoxazol-5-yl)imidazolidine-2,4-dione) | 568 |
| 236 | L-1 | X¹ | G-1 | (2-(3-methyl-4,5-dihydroisoxazol-5-yl)benzo[d]isothiazol-3(2H)-one 1,1-dioxide) | 609 |
| 237 | L-29 | X¹ | G-1 | 4,5-dihydro-5-phenyl-3-isoxazolyl | 508 |
| 238 | L-30 | X¹ | G-1 | 4,5-dihydro-5-phenyl-3-isoxazolyl | 508 |
| 239 | L-31 | X¹ | G-1 | 4,5-dihydro-5-phenyl-3-isoxazolyl | 566 |
| 240 | L-32 | X¹ | G-1 | 4,5-dihydro-5-phenyl-3-isoxazolyl | 562 |
| 241 | L-33 | X¹ | G-1 | 4,5-dihydro-5-phenyl-3-isoxazolyl | 534 |
| 242 | L-1 | X¹ | G-1 | (3-methyl-5-phenyloxazolidin-2-one) | 520 |
| 243 | L-1 | X¹ | G-1 | (1-(3-methyl-4,5-dihydroisoxazol-5-yl)piperidine-2,6-dione) | 539 |
| 244 | L-1 | X¹ | G-1 | (4-isopropyl-2-(3-methyl-4,5-dihydroisoxazol-5-yl)-1,2,4-oxadiazolidine-3,5-dione) | 570 |
| 245 | L-1 | X¹ | G-1 | 4-fluorophenyl | 453 |
| 246 | L-1 | X¹ | G-1 | 4-t-butylphenyl | 491 |
| 247 | L-1 | X¹ | G-1 | 4-cyanophenyl | 460 |
| 248 | L-1 | X¹ | G-1 | 4-nitrophenyl | 480 |
| 249 | L-1 | X¹ | G-1 | 4-bromophenyl | 513 |
| 250 | L-1 | X¹ | G-1 | 4-iodophenyl | 561 |

INDEX TABLE A-continued

| | | | | | |
|---|---|---|---|---|---|
| 251 | L-1 | X¹ | G-1 | 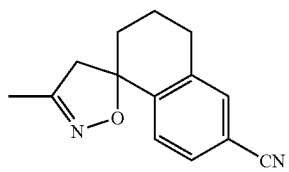 [SMILES: CC1=NOC2(CCCc3cc(C#N)ccc32)C1] | 569 |
| 252 | L-1 | X¹ | G-1 | 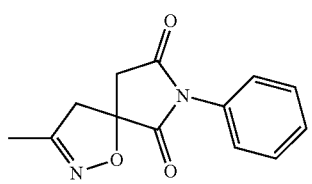 [SMILES: CC1=NOC2(CC(=O)N(c3ccccc3)C2=O)C1] | 587 |
| 253 | L-1 | X¹ | G-1 | 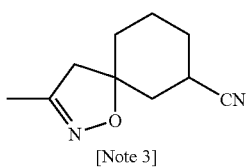 [Note 3] | 521 |
| 254 | L-1 | X¹ | G-1 | 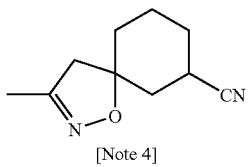 [Note 4] | 521 |
| 255 | L-1 | X¹ | G-1 | 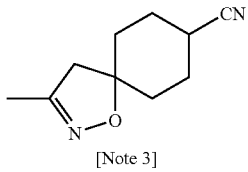 [Note 3] | 521 |
| 256 | L-1 | X¹ | G-1 | 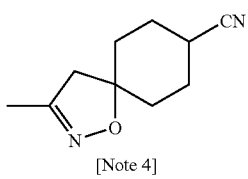 [Note 4] | 521 |
| 257 | L-22 | X¹ | G-1 | 4,5-dihydro-5-phenyl-3-isoxazolyl | 506 |
| 258 | L-25 | X¹ | G-1 | 4,5-dihydro-5-phenyl-3-isoxazolyl | 556 |
| 259 | L-27 | X¹ | G-1 | 4,5-dihydro-5-phenyl-3-isoxazolyl | 520 |
| 260 | L-5 | X¹ | G-1 | 4,5-dihydro-5-methyl-5-phenyl-3-isoxazolyl | 572 |
| 261 | L-10 | X¹ | G-1 | 4,5-dihydro-5-methyl-5-phenyl-3-isoxazolyl | 538 |
| 262 | L-1 | X¹ | G-1 | 4,5-dihydro-5-(2-aminosulfonylbenzyl)-3-isoxazolyl | 597 |
| 263 | L-1 | X¹ | G-1 | 4,5-dihydro-5-(2-acetoxyphenyl)-3-isoxazolyl | 562 |
| 264 | L-1 | X¹ | G-1 | 4,5-dihydro-5-(N-methyl-N-phenylcarbonylamino)-3-isoxazolyl | 561 |
| 265 | L-1 | X¹ | G-1 | 4,5-dihydro-5-cyano-5-phenyl-3-isoxazolyl | 529 |
| 266 | L-8 | X¹ | G-1 | 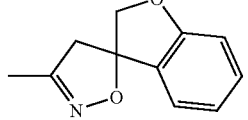 | 478 |
| 267 | L-1 | X¹ | G-1 | 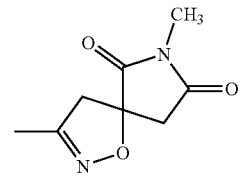 | 525 |

INDEX TABLE A-continued
| | | | | | |
|---|---|---|---|---|---|
| 268 | L-1 | X¹ | G-1 | 4-ethylphenyl | 463 |
| 269 | L-1 | X¹ | G-1 | 4-(trifluoromethoxy)phenyl | 519 |
| 270 | L-1 | X¹ | G-1 | 4-(methoxycarbonyl)phenyl | 493 |
| 271 | L-1 | X¹ | G-1 | 4-propylphenyl | 477 |
| 272 | L-1 | X¹ | G-1 | 4-methylthiophenyl | 481 |
| 273 | L-1 | X¹ | G-1 | 4-isopropylphenyl | 477 |
| 274 | L-1 | X¹ | G-1 | 4-isobutylphenyl | 491 |
| 275 | L-1 | X¹ | G-1 | 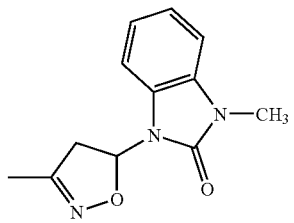 | 574 |
| 276 | L-5 | X¹ | G-1 | 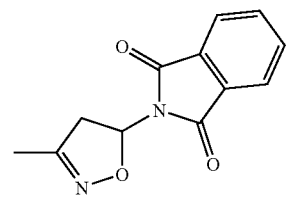 [SMILES: CC1=NOC(N2C(=O)c3ccccc3C2=O)C1] | 627 |
| 277 | L-8 | X¹ | G-1 | 4,5-dihydro-5-(2,4,6-trimethoxyphenyl)-3-isoxazolyl | 540 |
| 278 | L-1 | X¹ | G-1 | 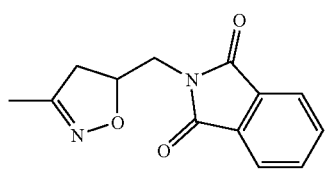 [SMILES: CC1=NOC(CN2C(=O)c3ccccc3C2=O)C1] | 587 |
| 279 | L-1 | X¹ | G-1 | 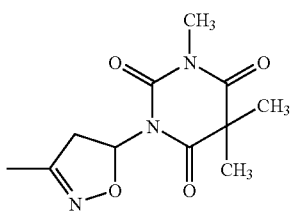 | 596 |
| 280 | L-1 | X¹ | G-1 | 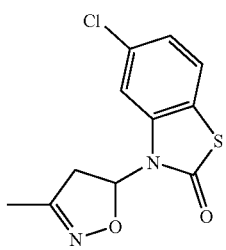 [SMILES: CC1=NOC(n2c(=O)sc3ccc(Cl)cc32)C1] | 611 |
| 281 | L-1 | X¹ | G-1 | 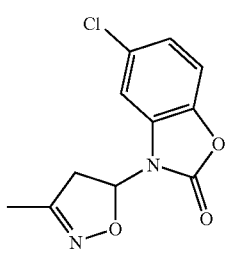 [SMILES: CC1=NOC(n2c(=O)oc3ccc(Cl)cc32)C1] | 595 |

INDEX TABLE A-continued
| 282 | L-1 | X¹ | G-1 | 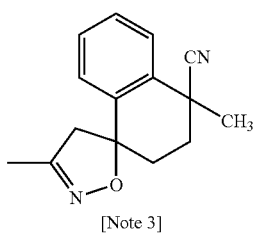 [Note 3] | 583 |
| --- | --- | --- | --- | --- | --- |
| 283 | L-1 | X¹ | G-1 | 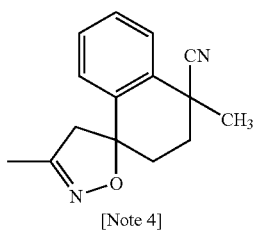 [Note 4] | 583 |
| 284 | L-8 | X¹ | G-1 | 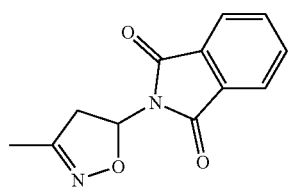 [SMILES: CC1=NOC(N2C(=O)c3ccccc3C2=O)C1] | 519 |
| 285 | L-1 | X¹ | G-1 | 4,5-dihydro-5-(N-phenyl-N-acetylamino)-3-isoxazolyl | 561 |
| 286 | L-1 | X¹ | G-1 | 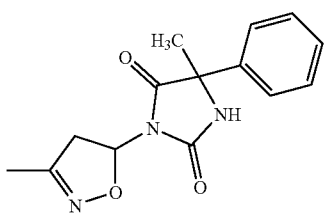 [SMILES: CC1=NOC(N2C(=O)NC(C)(c3ccccc3)C2=O)C1] | 616 |
| 287 | L-1 | X¹ | G-1 | 4,5-dihydro-5-acetoxy-3-isoxazolyl | 486 |
| 288 | L-8 | X¹ | G-1 | 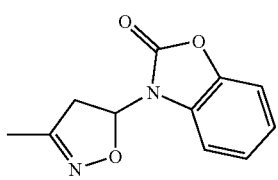 [SMILES: CC1=NOC(n2c(=O)oc3ccccc32)C1] | 507 |
| 289 | L-5 | X¹ | G-1 | 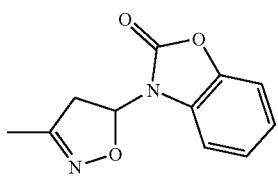 [SMILES: CC1=NOC(n2c(=O)oc3ccccc32)C1] | 615 |
| 290 | L-1 | X¹ | G-1 | 4-(dimethylamino)phenyl | 478 |
| 291 | L-34 | X¹ | G-1 | 4,5-dihydro-5-phenyl-3-isoxazolyl | 433 |
| 292 | L-35 | X¹ | G-1 | 4,5-dihydro-5-phenyl-3-isoxazolyl | 461 |
| 293 | L-36 | X¹ | G-1 | 4,5-dihydro-5-phenyl-3-isoxazolyl | 500 |
| 294 | L-1 | X¹ | G-1 | 4-methylsulfonylphenyl | 513 |
| 295 | L-1 | X¹ | G-1 | 4-ethoxyphenyl | 479 |

INDEX TABLE A-continued
| 296 | L-1 | X¹ | G-1 | 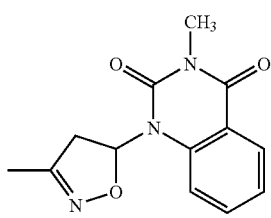 [SMILES: CC1=NOC(n2c(=O)n(C)c(=O)c3ccccc32)C1] | 602 |
| --- | --- | --- | --- | --- | --- |
| 297 | L-1 | X¹ | G-1 | 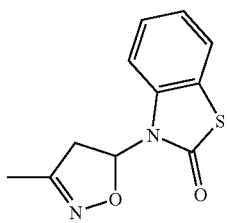 [SMILES: CC1=NOC(n2c(=O)sc3ccccc32)C1] | 577 |
| 298 | L-1 | X¹ | G-1 | 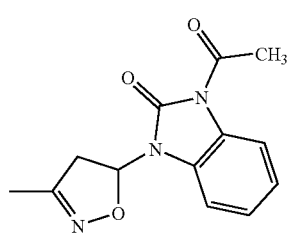 [SMILES: CC(=O)n1c(=O)n(C2CC(C)=NO2)c2ccccc21] | 602 |
| 299 | L-1 | X¹ | G-1 | 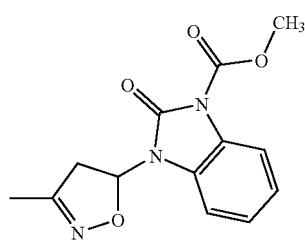 | 618 |
| 300 | L-37 | X¹ | G-1 | 4,5-dihydro-5-phenyl-3-isoxazolyl | 505 |
| 301 | L-38 | X¹ | G-1 | 4,5-dihydro-5-phenyl-3-isoxazolyl | 451 |
| 302 | L-1 | X¹ | G-1 | 3-hydroxyphenyl | 451 |
| 303 | L-1 | X¹ | G-1 | 4-(2-methylpropyl)phenyl [Note 6] | 505 |
| 304 | L-1 | X¹ | G-1 | 3,4-dihydroxyphenyl | 467 |
| 305 | L-1 | X¹ | G-1 | 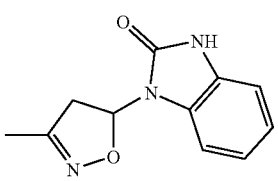 | 560 |
| 306 | L-1 | X¹ | G-1 | 3,4-dimethoxyphenyl | 495 |
| 307 | L-1 | X¹ | G-1 | 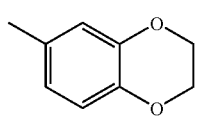 | 493 |
| 308 | L-1 | X¹ | G-1 | 3-allyloxyphenyl | 491 |
| 309 | L-1 | X¹ | G-1 | 3-propargyloxyphenyl | 489 |
| 310 | L-1 | X¹ | G-1 | 3-benzyloxyphenyl | 541 |

INDEX TABLE A-continued

| 311 | L-1 | X¹ | G-1 | [structure: methyl-oxadiazoline spiro-cyclohexane with N-acetyl group] | 539 |
| --- | --- | --- | --- | --- | --- |
| 312 | L-1 | X¹ | G-1 | 3-(2-phenylethoxy)-phenyl | 555 |
| 313 | L-1 | X¹ | G-1 | [structure: 2-(3-methylphenyl)isoindoline-1,3-dione] | 581 |
| 314 | L-1 | X¹ | G-1 | 3-butoxyphenyl | 507 |
| 315 | L-1 | X¹ | G-1 | 3-propoxyphenyl | 493 |
| 316 | L-1 | X¹ | G-1 | 4,5-dihydro-4,5-diphenyl-3-isoxazolyl | 580 |
| 317 | L-1 | X¹ | G-1 | 3-(2-methylpropoxy)-phenyl | 507 |
| 318 | L-1 | X¹ | G-1 | [structure: 6-methyl-2H-benzo[b][1,4]oxazin-3(4H)-one] | 506 |
| 319 | L-39 | X¹ | G-1 | 4,5-dihydro-5-phenyl-3-isoxazolyl | 511 |
| 320 | L-40 | X¹ | G-1 | 4,5-dihydro-5-phenyl-3-isoxazolyl | 502 |
| 321 | L-41 | X¹ | G-1 | 4,5-dihydro-5-phenyl-3-isoxazolyl | 502 |
| 322 | L-1 | X¹ | G-1 | 5-(N-phenyl-N-isopropylcarbonylamino)-3-isoxazolyl | 587 |
| 323 | L-1 | X¹ | G-1 | 4,5-dihydro-5-(2-nitrophenyl)-3-isoxazolyl | 549 |
| 324 | L-42 | X¹ | G-1 | 4,5-dihydro-5-phenyl-3-isoxazolyl | 580 |
| 326 | L-43 | X¹ | G-1 | 4,5-dihydro-5-phenyl-3-isoxazolyl | 497 |
| 327 | L-44 | X¹ | G-1 | 4,5-dihydro-5-phenyl-3-isoxazolyl | 458 |
| 328 | L-45 | X¹ | G-1 | 4,5-dihydro-5-phenyl-3-isoxazolyl | 468 |
| 329 | L-46 | X¹ | G-1 | 4,5-dihydro-5-phenyl-3-isoxazolyl | 493 |
| 330 | L-47 | X¹ | G-1 | 4,5-dihydro-5-phenyl-3-isoxazolyl | 447 |
| 331 | L-48 | X¹ | G-1 | 4,5-dihydro-5-phenyl-3-isoxazolyl | 501 |
| 332 | L-49 | X¹ | G-1 | 4,5-dihydro-5-phenyl-3-isoxazolyl | 491 |
| 333 | L-50 | X¹ | G-1 | 4,5-dihydro-5-phenyl-3-isoxazolyl | 501 |
| 334 | L-51 | X¹ | G-1 | 4,5-dihydro-5-phenyl-3-isoxazolyl | 469 |
| 335 | L-5 | X¹ | G-1 | 4,5-dihydro-5-(2-cyanophenyl)-3-isoxazolyl | 583 |
| 336 | L-5 | X¹ | G-1 | 4,5-dihydro-5-(2,6-difluorophenyl)-3-isoxazolyl | 594 |
| 337 | L-1 | X¹ | G-1 | [structure: 3-methyl-4,5-dihydroisoxazole linked to 1-methoxy-benzimidazol-2(3H)-one] | 590 |
| 338 | L-8 | X¹ | G-1 | 4,5-dihydro-5-(2-cyanophenyl)-3-isoxazolyl | 475 |
| 339 | L-52 | X¹ | G-1 | 4,5-dihydro-5-phenyl-3-isoxazolyl | 481 |
| 340 | L-1 | X¹ | G-1 | 4,5-dihydro-5-(2,6-difluorophenyl)-3-isoxazolyl [Note 7] | 540 |
| 341 | L-1 | X¹ | G-1 | 4,5-dihydro-5-(2,6-difluorophenyl)-3-isoxazolyl [Note 8] | 540 |
| 342 | L-8 | X¹ | G-1 | 4,5-dihydro-5-(2,6-difluorophenyl)-3-isoxazolyl | 486 |
| 343 (Ex. 14) | L-35 | X¹ | G-1 | (5R)-4,5-dihydro-5-phenyl-3-isoxazolyl | 461 |
| 344 | L-1 | X¹ | G-1 | [structure: 2-methylquinoline] | 486 |
| 345 | L-53 | X¹ | G-1 | 4,5-dihydro-5-phenyl-3-isoxazolyl | 451 |
| 346 | L-1 | X¹ | G-1 | 4-propoxyphenyl | 493 |
| 347 | L-1 | X¹ | G-1 | 4-isopropoxyphenyl | 493 |
| 348 | L-1 | X¹ | G-1 | 4,5-dihydro-5-(2-trifluoromethylphenyl)-3-isoxazolyl [Note 9] | 572 |

INDEX TABLE A-continued

| | | | | | |
|---|---|---|---|---|---|
| 349 | L-1 | X¹ | G-1 | 4,5-dihydro-5-(2-trifluoromethylphenyl)-3-isoxazolyl [Note 10] | 572 |
| 350 | L-35 | X¹ | G-1 | 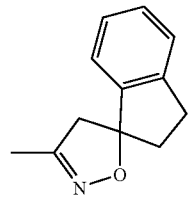 | 487 |
| 351 | L-35 | X¹ | G-1 | 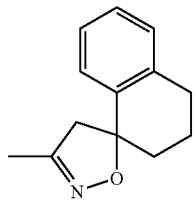 | 501 |
| 352 | L-35 | X¹ | G-1 | 4,5-dihydro-5-methyl-5-phenyl-3-isoxazolyl | 475 |
| 353 | L-5 | X¹ | G-1 | (4R)-4,5-dihydro-5-phenyl-3-isoxazolyl | 558 |
| 354 | L-1 | X¹ | G-1 | 4,5-dihydro-5-(2-carboxyphenyl)-3-isoxazolyl | 548 |
| 355 | L-54 | X¹ | G-1 | 4,5-dihydro-5-phenyl-3-isoxazolyl | 505 |
| 356 | L-1 | X¹ | G-1 | 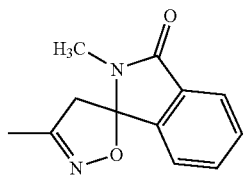 [SMILES: CC1=NOC2(C1)c1ccccc1C(=O)N2C] | 559 |
| 357 | L-55 | X¹ | G-1 | 4,5-dihydro-5-phenyl-3-isoxazolyl | 525 |
| 358 | L-56 | X¹ | G-1 | 4,5-dihydro-5-phenyl-3-isoxazolyl | 506 |
| 359 | L-57 | X¹ | G-1 | 4,5-dihydro-5-phenyl-3-isoxazolyl | 508 |
| 360 | L-1 | X¹ | G-1 | 4-propargyloxyphenyl | 489 |
| 361 | L-1 | X¹ | G-1 | 4-isobutoxyphenyl | 507 |
| 362 | L-1 | X¹ | G-1 | 4-butoxyphenyl | 507 |
| 363 | L-1 | X¹ | G-1 | 4-allyloxyphenyl | 491 |
| 364 | L-58 | X¹ | G-1 | 4,5-dihydro-5-phenyl-3-isoxazolyl | 451 |
| 365 | L-59 | X¹ | G-1 | 4,5-dihydro-5-phenyl-3-isoxazolyl | 461 |
| 366 | L-60 | X¹ | G-1 | 4,5-dihydro-5-phenyl-3-isoxazolyl | 468 |
| 367 | L-61 | X¹ | G-1 | 4,5-dihydro-5-phenyl-3-isoxazolyl | 463 |
| 368 | L-1 | X¹ | G-1 | 4,5-dihydro-5-(1-imidazolyl)-3-isoxazolyl | 494 |
| 369 | L-1 | X¹ | G-1 | 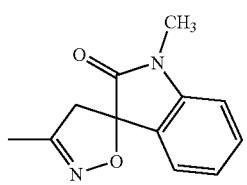 [SMILES: CC1=NOC2(C1)C(=O)N(C)c1ccccc12] | 559 |
| 370 | L-1 | X¹ | G-1 | 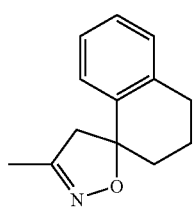 [Note 11] | 544 |

INDEX TABLE A-continued

| 371 | L-1 | X¹ | G-1 | 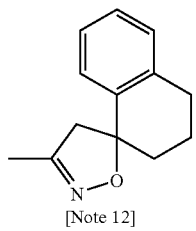 [Note 12] | 544 |
|---|---|---|---|---|---|
| 372 | L-1 | X¹ | G-1 | 4,5-dihydro-5-methyl-5-phenyl-3-isoxazolyl [Note 13] | 518 |
| 373 | L-1 | X¹ | G-1 | 4,5-dihydro-5-methyl-5-phenyl-3-isoxazolyl [Note 14] | 518 |
| 374 | L-62 | X¹ | G-1 | 4,5-dihydro-5-phenyl-3-isoxazolyl | 492 |
| 375 | L-63 | X¹ | G-1 | 4,5-dihydro-5-phenyl-3-isoxazolyl | 480 |
| 376 | L-64 | X¹ | G-1 | 4,5-dihydro-5-phenyl-3-isoxazolyl | 434 |
| 377 | L-65 | X¹ | G-1 | 4,5-dihydro-5-phenyl-3-isoxazolyl | 452 |
| 378 | L-66 | X¹ | G-1 | 4,5-dihydro-5-phenyl-3-isoxazolyl | 502 |
| 379 | L-67 | X¹ | G-1 | 4,5-dihydro-5-phenyl-3-isoxazolyl | 515 |
| 380 | L-68 | X¹ | G-1 | 4,5-dihydro-5-phenyl-3-isoxazolyl | 589 |
| 381 | L-69 | X¹ | G-1 | 4,5-dihydro-5-phenyl-3-isoxazolyl | 489 |
| 382 | L-1 | X¹ | G-1 | 4,5-dihydro-5-(3-iodophenyl)-3-isoxazolyl | 630 |
| 383 | L-1 | X¹ | G-1 | 4,5-dihydro-5-[1-(1,2,4-triazolyl)]-3-isoxazolyl | 495 |
| 384 | L-70 | X¹ | G-1 | 4,5-dihydro-5-phenyl-3-isoxazolyl | 535 |
| 385 | L-71 | X¹ | G-1 | 4,5-dihydro-5-phenyl-3-isoxazolyl | 517 |
| 386 | L-72 | X¹ | G-1 | 4,5-dihydro-5-phenyl-3-isoxazolyl | 531 |
| 387 | L-73 | X¹ | G-1 | 4,5-dihydro-5-phenyl-3-isoxazolyl | 452 |
| 388 | L-74 | X¹ | G-1 | 4,5-dihydro-5-phenyl-3-isoxazolyl | 438 |
| 389 | L-75 | X¹ | G-1 | 4,5-dihydro-5-phenyl-3-isoxazolyl | 481 |
| 390 | L-76 | X¹ | G-1 | 4,5-dihydro-5-phenyl-3-isoxazolyl | 570 |
| 391 | L-35 | X¹ | G-1 | 4,5-dihydro-5-(2,6-difluorophenyl)-3-isoxazolyl | 497 |
| 392 | L-1 | X¹ | G-1 | 4-cyclopropylmethoxyphenyl | 505 |
| 393 | L-1 | X¹ | G-1 | 4-cyclopentoxyphenyl | 519 |
| 394 | L-1 | X¹ | G-1 | 4-cyclohexoxyphenyl | 533 |
| 395 | L-77 | X¹ | G-1 | 4,5-dihydro-5-phenyl-3-isoxazolyl | 440 |
| 396 | L-1 | X¹ | G-1 | 4-hydroxyphenyl | 451 |
| 397 | L-35 | X¹ | G-1 | 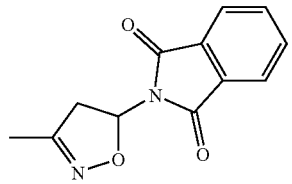 [SMILES: CC1=NOC(N2C(=O)c3ccccc3C2=O)C1] | 530 |
| 398 | L-35 | X¹ | G-1 | 4,5-dihydro-5-(2-cyanophenyl)-3-isoxazolyl | 486 |
| 399 | L-49 | X¹ | G-1 | 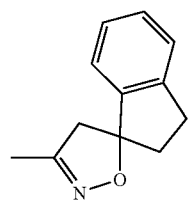 | 517 |
| 400 | L-49 | X¹ | G-1 | 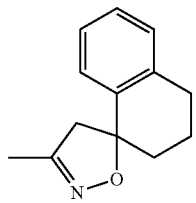 | 531 |
| 401 | L-42 | X¹ | G-1 | 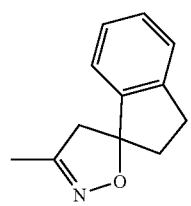 | 605 |

INDEX TABLE A-continued

| 402 | L-42 | X¹ | G-1 | (structure: spiro tetrahydronaphthalene methyl isoxazoline) | 619 |

| 403 | L-1 | X¹ | G-1 | (structure: N-(3-methyl-4,5-dihydroisoxazol-5-yl)phthalimide) [Note 15] | 573 |

| 404 | L-1 | X¹ | G-1 | (structure: N-(3-methyl-4,5-dihydroisoxazol-5-yl)phthalimide) [Note 16] | 573 |

| 405 | L-1 | X¹ | G-1 | 4,5-dihydro-5-(4-iodophenyl)-3-isoxazolyl | 630 |
| 406 | L-1 | X¹ | G-1 | 4,5-dihydro-5-(1-methyl-2-imidazolyl)-3-isoxazolyl | 508 |
| 407 | L-78 | X¹ | G-1 | 4,5-dihydro-5-phenyl-3-isoxazolyl | 467 |
| 408 | L-79 | X¹ | G-1 | 4,5-dihydro-5-phenyl-3-isoxazolyl | 463 |
| 409 (Ex. 15) | L-42 | X¹ | G-1 | 4,5-dihydro-5-(2,6-difluorophenyl)-3-isoxazolyl | 615 |
| 410 (Ex. 16) | L-49 | X¹ | G-1 | 4,5-dihydro-5-(2,6-difluorophenyl)-3-isoxazolyl | 527 |
| 411 | L-80 | X¹ | G-1 | 4,5-dihydro-5-phenyl-3-isoxazolyl | 469 |
| 412 | L-81 | X¹ | G-1 | 4,5-dihydro-5-phenyl-3-isoxazolyl | 455 |
| 413 | L-35 | X¹ | G-1 | 4,5-dihydro-5-(2,6-difluorophenyl)-3-isoxazolyl [Note 17] | 497 |
| 414 | L-35 | X¹ | G-1 | 4,5-dihydro-5-(2,6-difluorophenyl)-3-isoxazolyl [Note 18] | 497 |
| 415 | L-82 | X¹ | G-1 | 4,5-dihydro-5-phenyl-3-isoxazolyl | 477 |
| 416 | L-1 | X¹ | G-1 | 4-benzyloxyphenyl | 541 |

| 417 | L-1 | X¹ | G-1 | (structure: 2-(2,6-difluorophenyl)-3-acetyl-5-methyl-2,3-dihydro-1,3,4-oxadiazole) | 583 |

| 418 | L-35 | X¹ | G-1 | 4,5-dihydro-5-(2-fluorophenyl)-3-isoxazolyl | 479 |

| 419 | L-35 | X¹ | G-1 | (structure: 3-(3-methyl-4,5-dihydroisoxazol-5-yl)benzothiazol-2(3H)-one) | 534 |

| 420 | L-35 | X¹ | G-1 | 4,5-dihydro-5-(2-methylphenyl)-3-isoxazolyl | 475 |
| 421 | L-35 | X² | G-1 | 4,5-dihydro-5-phenyl-3-isoxazolyl | 462 |

| 422 | L-35 | X¹ | G-1 | (structure: 3-(3-methyl-4,5-dihydroisoxazol-5-yl)benzoxazol-2(3H)-one) | 518 |

INDEX TABLE A-continued

| | | | | | |
|---|---|---|---|---|---|
| 423 | L-35 | $X^1$ | G-1 | 4,5-dihydro-5-(2,6-dimethylphenyl)-3-isoxazolyl | 489 |
| 424 | L-35 | $X^1$ | G-1 | 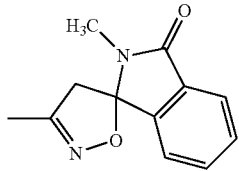 [SMILES: CC1=NOC2(C1)c1ccccc1C(=O)N2C] | 516 |
| 425 | L-6 | $X^1$ | G-1 | 4,5-dihydro-5-(2,6-difluorophenyl)-3-isoxazolyl | 496 |
| 426 | L-35 | $X^1$ | G-1 | 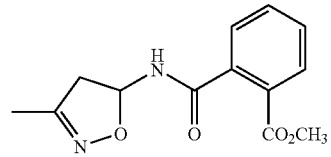 [SMILES: COC(=O)c1ccccc1C(=O)NC1CC(C)=NO1] | 562 |
| 428 | L-6 | $X^1$ | G-1 | 4,5-dihydro-5-(2,6-difluorophenyl)-3-isoxazolyl | 496 |
| 430 | L-35 | $X^1$ | G-1 | 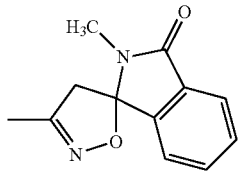 [SMILES: CC1=NOC2(C1)c1ccccc1C(=O)N2C] | 515 |
| 431 | L-1 | $X^1$ | G-1 | 4,5-dihydro-5-(2-iodophenyl)-3-isoxazolyl | 629 |
| 432 | L-6 | $X^1$ | G-1 | 4,5-dihydro-5-(2,6-difluorophenyl)-3-isoxazolyl [Note 19] | 496 |
| 433 | L-1 | $X^1$ | G-3 | 4,5-dihydro-5-phenyl-3-isoxazolyl | 486 |
| 434 | L-6 | $X^1$ | G-1 | 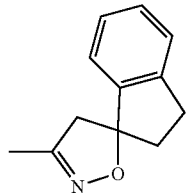 | 486 |
| 435 | L-6 | $X^1$ | G-1 | 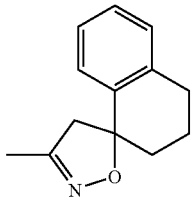 | 500 |
| 436 | L-82 | $X^1$ | G-1 | 4,5-dihydro-5-(2,6-difluorophenyl)-3-isoxazolyl | 513 |
| 437 | L-35 | $X^1$ | G-3 | 4,5-dihydro-5-phenyl-3-isoxazolyl | 444 |
| 438 | L-1 | $X^1$ | G-1 | 4,5-dihydro-5-(2-fluorophenyl)-3-isoxazolyl[Note 20] | 521 |
| 439 | L-1 | $X^1$ | G-1 | 4,5-dihydro-5-(2-fluorophenyl)-3-isoxazolyl[Note 21] | 521 |
| 440 | L1 | $X^1$ | G-3 | 4,5-dihydro-5-(2,6-difluorophenyl)-3-isoxazolyl | 523 |
| 441 | L-1 | $X^1$ | G-20 | 4,5-dihydro-5-(2,6-difluorophenyl)-3-isoxazolyl | 525 |
| 442 | L-83 | $X^1$ | G-1 | 4,5-dihydro-5-(2,6-difluorophenyl)-3-isoxazolyl | 514 |
| 443 | L-84 | $X^1$ | G-1 | 4,5-dihydro-5-(2,6-difluorophenyl)-3-isoxazolyl | 484 |
| 444 | L-86 | $X^1$ | G-1 | 4,5-dihydro-5-(2,6-difluorophenyl)-3-isoxazolyl | 502 |
| 445 | L-87 | $X^1$ | G-1 | 4,5-dihydro-5-(2,6-difluorophenyl)-3-isoxazolyl | 518 |
| 446 | L-88 | $X^1$ | G-1 | 4,5-dihydro-5-(2,6-difluorophenyl)-3-isoxazolyl | 520 |
| 447 | L-85 | $X^1$ | G-1 | 4,5-dihydro-5-(2,6-difluorophenyl)-3-isoxazolyl | 484 |
| 448 | L-89 | $X^1$ | G-1 | 4,5-dihydro-5-(2,6-difluorophenyl)-3-isoxazolyl | 498 |
| 449 | L-90 | $X^1$ | G-1 | 4,5-dihydro-5-(2,6-difluorophenyl)-3-isoxazolyl | 552 |
| 450 | L-91 | $X^1$ | G-1 | 4,5-dihydro-5-(2,6-difluorophenyl)-3-isoxazolyl | 553 |
| 451 | L-6 | $X^1$ | G-2 | 4,5-dihydro-5-(2,6-difluorophenyl)-3-isoxazolyl | 480 |
| 452 | L-35 | $X^1$ | G-2 | 4,5-dihydro-5-(2,6-difluorophenyl)-3-isoxazolyl | 481 |
| 453 | L-1 | $X^1$ | G-2 | 4,5-dihydro-5-(2,6-difluorophenyl)-3-isoxazolyl | 524 |
| 454 | L-92 | $X^1$ | G-2 | 4,5-dihydro-5-(2-fluorophenyl)-3-isoxazolyl | 511 |
| 455 | L-93 | $X^1$ | G-1 | 4,5-dihydro-5-(2,6-difluorophenyl)-3-isoxazolyl | 511 |
| 456 | L-92 | $X^1$ | G-1 | 4,5-dihydro-5-(2,6-difluorophenyl)-3-isoxazolyl | 529 |

INDEX TABLE A-continued

| | | | | | |
|---|---|---|---|---|---|
| 457 | L-35 | $X^1$ | G-2 | 4,5-dihydro-5-(2-fluorophenyl)-3-isoxazolyl | 463 |
| 458 | L-1 | $X^1$ | G-2 | 4,5-dihydro-5-(2-fluorophenyl)-3-isoxazolyl | 506 |
| 459 | L-6 | $X^1$ | G-2 | 4,5-dihydro-5-(2-fluorophenyl)-3-isoxazolyl | 462 |
| 460 | L-1 | $X^1$ | G-2 | (structure) | 528 |
| 461 | L-35 | $X^1$ | G-2 | (structure) | 485 |
| 462 | L-6 | $X^1$ | G-2 | (structure) | 484 |
| 463 | L-94 | $X^1$ | G-1 | 4,5-dihydro-5-(2-fluorophenyl)-3-isoxazolyl | 618 |
| 464 | L-95 | $X^1$ | G-1 | 4,5-dihydro-5-(2-fluorophenyl)-3-isoxazolyl | 550 |
| 465 | L-1 | $X^1$ | G-1 | 4,5-dihydro-5-(2,6-difluorophenyl)-3-isoxazolyl | 540 |
| 466 | L-1 | $X^1$ | G-1 | 5-(2,6-difluorophenyl)-3-isoxazolyl | 538 |
| 467 | L-96 | $X^1$ | G-1 | 4,5-dihydro-5-(2,6-difluorophenyl)-3-isoxazolyl | 526 |

[Note 1]: Faster eluting enantiomer from the CHIRALPAK ® AD-RH [Amylose tris (3,5-dimethylphenylcarbamate) coated on 5 μm silica-gel] column using methanol in water as eluant, specific rotation = −98.8°. Analysis using analytical CHIRALPAK ® AD-RH column indicated about 100% optical purity.

[Note 2]: Slower eluting enantiomer from the CHIRALPAK ® AD-RH reverse phase column using methanol in water as eluant, specific rotation = +88°. Analysis using analytical CHIRALPAK ® AD-RH column indicated about 93% optical purity.

[Note 3]: Diastereomer A.

[Note 4]: Diastereomer B.

[Note 5]: Mixture of isomers.

[Note 6]: G-1 substituted with a methyl group in the 5 position.

[Note 7]: Faster eluting enantiomer from the CHIRACEL ® OJ-RH column using 1:1 acetonitrile:methanol in water as eluant. specific rotation = −219°. Analysis using analytical CHIRACEL ® OJ-RH column indicated about 100% optical purity.

[Note 8]: Slower eluting enantiomer from the CHIRACEL ® OJ-RH column using 1:1 acetonitrile:methanol in water as eluant. specific rotation = +201°. Analysis using analytical CHIRACEL ® OJ-RH column indicated about 95% optical purity.

[Note 9]: Faster eluting enantiomer from the CHIRACEL ® OJ-RH column using 1:1 acetonitrile:methanol in water as eluant. Analysis using analytical CHIRACEL ® OJ-RH column indicated about 95% optical purity.

[Note 10]: Slower eluting enantiomer from the CHIRACEL ® OJ-RH column using 1:1 acetonitrile:methanol in water as eluant. Analysis using analytical CHIRACEL ® OJ-RH column indicated about 100% optical purity.

[Note 11]: Faster eluting enantiomer from the CHIRACEL ® OJ-RH column using 1:1 acetonitrile:methanol in water as eluant. Analysis using analytical CHIRACEL ® OJ-RH column indicated about 92% optical purity. specific rotation = −83°.

[Note 12]: Slower eluting enantiomer from the CHIRACEL ® OJ-RH column using 1:1 acetonitrile:methanol in water as eluant. Analysis using analytical CHIRACEL ® OJ-RH column indicated about 99% optical purity. specific rotation = +129°.

[Note 13]: Faster eluting enantiomer from the CHIRALPAK ® AD ® column using 3:7 hexane:IPA as eluant. Analysis using analytical CHIRALPAK ® AD ® column indicated about 99% optical purity. specific rotation = −36°.

[Note 14]: Slower eluting enantiomer from the CHIRALPAK ® AD ® column using 3:7 hexane:IPA as eluant. Analysis using analytical CHIRALPAK ® AD ® column indicated about 99% optical purity. specific rotation = +33°.

[Note 15]: Faster eluting enantiomer from the CHIRACEL ® OJ-RH column using 1:1 acetonitrile:methanol in water as eluant. Analysis using analytical CHIRACEL ® OJ-RH column indicated about 99% optical purity.

[Note 16]: Slower eluting enantiomer from the CHIRACEL ® OJ-RH column using 1:1 acetonitrile:methanol in water as eluant. Analysis using analytical CHIRACEL ® OJ-RH column indicated about 100% optical purity.

[Note 17]: Faster eluting enantiomer from the CHIRACEL ® OJ-RH column using 1:1 acetonitrile:methanol in water as eluant. Analysis using analytical CHIRACEL ® OJ-RH column indicated about 99% optical purity.

[Note 18]: Slower eluting enantiomer from the CHIRACEL ® OJ-RH column using 1:1 acetonitrile:methanol in water as eluant. Analysis using analytical CHIRACEL ® OJ-RH column indicated about 100% optical purity.

[Note 19]: HBr salt.

[Note 20]: Faster eluting enantiomer from the CHIRACEL ® OJ-RH column using 1:1 acetonitrile:methanol in water as eluant. Analysis using analytical CHIRACEL ® OJ-RH column indicated about 94% optical purity.

[Note 21]: Slower eluting enantiomer from the CHIRACEL ® OJ-RH column using 1:1 acetonitrile:methanol in water as eluant. Analysis using analytical CHIRACEL ® OJ-RH column indicated about 99% optical purity.

[Note 22]: The m.p. of compound 214 was 125-128° C. when the compound was prepared by the method of Example 12, Step F, with the exception that methanol was used in place of ethanol as the reaction solvent and upon dilution of the reaction mixture with water compound 214 parcipated from the reaction mixture, was collected and allowed to dry.

[Note 23]: The m.p. of compound 214 was 130-135° C. when the compound was prepared prepared according to the procedures disclosed herein and then recystallized from method.

[Note 24]: One skilled in the art recognizes that "4,5-dihydro-5-(2,6-difluorophenyl)-3-isoxazolyl" is equivalent to "5-(2,6-difluorophenyl)-4,5-dihydro-3-isoxazoly".

BIOLOGICAL EXAMPLES OF THE INVENTION

General protocol for preparing test compositions for Tests A-B: 5-chloro-6-(2,4,6-trifluorophenyl)-7-(4-methylpiperidin-1-yl)[1,2,4]triazolo[1,5-a]pyrimidine (BAS600), fenamidone, fluopicolide, penthiopyrad and quinoxyfen were obtained as unformulated, technical-grade materials. Azoxystrobin, benthiovalicarb, boscalid, chlorothalonil, copper hydroxide, cyazofamid, cymoxanil, dimethomorph, ethaboxam, famoxadone, fluazinam, folpet, fosetyl-aluminum, iprovalicarb, kresoxim-methyl, mancozeb, mandipropamid, mefenoxam, propamocarb, proquinazid, pyraclostrobin and trifloxystrobin were obtained as formulated products marketed under the trademarks Amistar®, Benthiovalicard®, Endura®, Bravo®, Weatherstik®, Kocide®, Ranman®, Curzate®, Acrobat®, Guardian®, Famoxate®, Shirlan®, Phaltan®, Aliette®, Melody®, kresoxim-methyl®, Manzate®, Revus®, Ridomil Gold®, Previcur®, Talius®, Headline® and Flint®, respectively. Compound 1 and compound 214 were each formulated as an oil dispersion containing a mixture of POE (polyoxyethylene) 40 sorbitol hexaoleate, POE 20 sorbitan trioleate, and alkyl-peg resin surfactants in a liquid carrier consisting of a distilled C18 fatty acid methyl ester. Unformulated materials were first dissolved in acetone and then suspended at the desired concentration (in ppm) in acetone and purified water (50/50 mix by volume) containing 250 ppm of the surfactant Trem® 014 (polyhydric alcohol esters). Formulated materials were dispersed in sufficient water to give the desired concentration, and neither organic solvent nor surfactant was added to the suspension. The resulting test mixtures were then used in Tests A-B. Spraying a 200 ppm test mixture to the point of run-off on the test plants was the equivalent of a rate of 500 g/ha. The tests were replicated three times and the results reported as the mean average of the three replicates.

The presence of a synergistic effect between two active ingredients was established with the aid of the Colby equation (see Colby, S. R. "Calculating Synergistic and Antagonistic Responses of Herbicide Combinations", *Weeds*, (1967), 15, 20-22):

$$p = A + B - \left[\frac{A \times B}{100}\right].$$

Using the method of Colby, the presence of a synergistic interaction between two active ingredients is established by first calculating the predicted activity, p, of the mixture based on activities of the two components applied alone. If p is lower than the experimentally established effect, synergism has occurred. In the equation above, A is the fungicidal activity in percentage control of one component applied alone at rate x. The B term is the fungicidal activity in percentage control of the second component applied at rate y. The equation estimates p, the expected fungicidal activity of the mixture of A at rate x with B at rate y if their effects are strictly additive and no interaction has occurred.

Test A

The test mixture was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 4 days, after which time disease ratings were made.

Test B

The test mixture was sprayed to the point of run-off on cucumber seedlings. The following day the seedlings were inoculated with a spore suspension of *Pseudoperonospora cubensis* (the causal agent of cucumber downy mildew) and incubated in saturated atmosphere at 20° C. for 24 h, and moved to a growth chamber at 20° C. for 6 days, after which time disease ratings were made.

Results for Tests A to B are given in Tables A-P. Each table corresponds to a set of evaluations performed together at the same time. In each table, a rating of 100 indicates 100% disease control and a rating of 0 indicates no disease control (relative to the controls). Columns labeled "Obsd" indicate the average of results observed from three replications. Columns labeled "Exp" indicate the expected value for each treatment mixture using the Colby equation.

TABLE A

Observed and Expected Effects of Compound 1 Alone and Mixtures with Boscalid, Mancozeb, Proquinazid, Cymoxanil and Penthiopyrad in Controlling Tomato Late Blight and Cucumber Downy Mildew

| Application Rate (ppm) of Compound 1 | Component (b) | Application Rate (ppm) of Component (b) | TLB Obsd | TLB Exp | CDM Obsd | CDM Exp |
|---|---|---|---|---|---|---|
| 0 | — | 0 | 17 | — | 47 | — |
| 0.05 | — | 0 | 34 | — | 88 | — |
| 0.1 | — | 0 | 78 | — | 95 | — |
| 0.15 | — | 0 | 97 | — | 100 | — |
| 0.2 | — | 0 | 94 | — | 100 | — |
| 1 | — | 0 | 100 | — | 100 | — |
| 0 | boscalid | 0.4 | 9 | — | 47 | — |
| 0 | boscalid | 2 | 17 | — | 47 | — |
| 0 | boscalid | 10 | 17 | — | 47 | — |
| 0 | boscalid | 40 | 17 | — | 47 | — |
| 0 | boscalid | 200 | 9 | — | 47 | — |
| 0.1 | boscalid | 0.4 | 83 | 80 | 91 | 98 |
| 0.1 | boscalid | 2 | 82 | 82 | 98 | 98 |
| 0.1 | boscalid | 10 | 76 | 82 | 95 | 98 |
| 0.1 | boscalid | 40 | 70 | 82 | 93 | 98 |
| 0.1 | boscalid | 200 | 88 | 80 | 95 | 98 |
| 0.15 | boscalid | 0.4 | 97 | 97 | 99 | 100 |
| 0.15 | boscalid | 2 | 93 | 98 | 97 | 100 |
| 0.15 | boscalid | 10 | 100 | 98 | 100 | 100 |
| 0.15 | boscalid | 40 | 98 | 98 | 100 | 100 |
| 0.15 | boscalid | 200 | 93 | 97 | 99 | 100 |
| 0 | mancozeb | 0.4 | 0 | — | 77 | — |
| 0 | mancozeb | 2 | 9 | — | 64 | — |
| 0 | mancozeb | 10 | 9 | — | 91 | — |
| 0 | mancozeb | 40 | 89 | — | 100 | — |
| 0 | mancozeb | 200 | 100 | — | 100 | — |
| 0.1 | mancozeb | 0.4 | 80 | 78 | 99 | 99 |
| 0.1 | mancozeb | 2 | 85 | 80 | 99 | 98 |
| 0.1 | mancozeb | 10 | 88 | 80 | 99 | 100 |
| 0.1 | mancozeb | 40 | 99 | 98 | 100 | 100 |
| 0.1 | mancozeb | 200 | 100 | 100 | 100 | 100 |
| 0.15 | mancozeb | 0.4 | 88 | 97 | 100 | 100 |
| 0.15 | mancozeb | 2 | 87 | 97 | 100 | 100 |
| 0.15 | mancozeb | 10 | 100 | 97 | 100 | 100 |
| 0.15 | mancozeb | 40 | 100 | 100 | 100 | 100 |
| 0.15 | mancozeb | 200 | 100 | 100 | 100 | 100 |
| 0 | proquinazid | 0.4 | 0 | — | 47 | — |
| 0 | proquinazid | 2 | 0 | — | 47 | — |
| 0 | proquinazid | 10 | 0 | — | 47 | — |
| 0 | proquinazid | 40 | 24 | — | 47 | — |
| 0 | proquinazid | 200 | 0 | — | 47 | — |
| 0.1 | proquinazid | 0.4 | 99 | 78 | 90 | 98 |

TABLE A-continued

Observed and Expected Effects of Compound 1 Alone and Mixtures with Boscalid, Mancozeb, Proquinazid, Cymoxanil and Penthiopyrad in Controlling Tomato Late Blight and Cucumber Downy Mildew

| Application Rate (ppm) of Compound 1 | Component (b) | Application Rate (ppm) of Component (b) | TLB Obsd | TLB Exp | CDM Obsd | CDM Exp |
|---|---|---|---|---|---|---|
| 0.1 | proquinazid | 2 | 95 | 78 | 88 | 98 |
| 0.1 | proquinazid | 10 | 85 | 78 | 94 | 98 |
| 0.1 | proquinazid | 40 | 93 | 83 | 99 | 98 |
| 0.1 | proquinazid | 200 | 100 | 78 | 100 | 98 |
| 0.15 | proquinazid | 0.4 | 99 | 97 | 99 | 100 |
| 0.15 | proquinazid | 2 | 96 | 97 | 100 | 100 |
| 0.15 | proquinazid | 10 | 99 | 97 | 100 | 100 |
| 0.15 | proquinazid | 40 | 100 | 98 | 100 | 100 |
| 0.15 | proquinazid | 200 | 99 | 97 | 100 | 100 |
| 0 | cymoxanil | 0.4 | 9 | — | 47 | — |
| 0 | cymoxanil | 2 | 76 | — | 47 | — |
| 0 | cymoxanil | 10 | 100 | — | 47 | — |
| 0 | cymoxanil | 40 | 100 | — | 47 | — |
| 0 | cymoxanil | 200 | 100 | — | 47 | — |
| 0.1 | cymoxanil | 0.4 | 82 | 80 | 94 | 98 |
| 0.1 | cymoxanil | 2 | 98 | 95 | 93 | 98 |
| 0.1 | cymoxanil | 10 | 100 | 100 | 91 | 98 |
| 0.1 | cymoxanil | 40 | 100 | 100 | 91 | 98 |
| 0.1 | cymoxanil | 200 | 100 | 100 | 99 | 98 |
| 0.15 | cymoxanil | 0.4 | 91 | 97 | 99 | 100 |
| 0.15 | cymoxanil | 2 | 100 | 99 | 100 | 100 |
| 0.15 | cymoxanil | 10 | 100 | 100 | 93 | 100 |
| 0.15 | cymoxanil | 40 | 100 | 100 | 97 | 100 |
| 0.15 | cymoxanil | 200 | 100 | 100 | 100 | 100 |
| 0 | penthiopyrad | 0.4 | 0 | — | 47 | — |
| 0 | penthiopyrad | 2 | 0 | — | 47 | — |
| 0 | penthiopyrad | 10 | 9 | — | 47 | — |
| 0 | penthiopyrad | 40 | 17 | — | 47 | — |
| 0 | penthiopyrad | 200 | 17 | — | 47 | — |
| 0.1 | penthiopyrad | 0.4 | 100 | 78 | 99 | 98 |
| 0.1 | penthiopyrad | 2 | 98 | 78 | 97 | 98 |
| 0.1 | penthiopyrad | 10 | 98 | 80 | 95 | 98 |
| 0.1 | penthiopyrad | 40 | 98 | 82 | 93 | 98 |
| 0.1 | penthiopyrad | 200 | 84 | 82 | 100 | 98 |
| 0.15 | penthiopyrad | 0.4 | 100 | 97 | 98 | 100 |
| 0.15 | penthiopyrad | 2 | 100 | 97 | 100 | 100 |
| 0.15 | penthiopyrad | 10 | 100 | 97 | 100 | 100 |
| 0.15 | penthiopyrad | 40 | 100 | 98 | 100 | 100 |
| 0.15 | penthiopyrad | 200 | 93 | 98 | 100 | 100 |

TABLE B

Observed and Expected Effects of Compound 1 Alone and Mixtures with Benthiovalicarb, Dimethomorph, Azoxystrobin, Iprovalicarb and Fluopicolide in Controlling Tomato Late Blight and Cucumber Downy Mildew

| Application Rate (ppm) of Compound 1 | Component (b) | Application Rate (ppm) of Component (b) | TLB Obsd | TLB Exp | CDM Obsd | CDM Exp |
|---|---|---|---|---|---|---|
| 0 | — | 0 | 0 | — | 76 | — |
| 0.05 | — | 0 | 26 | — | 64 | — |
| 0.1 | — | 0 | 53 | — | 86 | — |
| 0.15 | — | 0 | 59 | — | 85 | — |
| 0.2 | — | 0 | 56 | — | 92 | — |
| 1 | — | 0 | 100 | — | 100 | — |
| 0 | — | 0.08 | 9 | — | 72 | — |
| 0 | benthiovalicarb | 0.4 | 53 | — | 90 | — |
| 0 | benthiovalicarb | 2 | 100 | — | 100 | — |
| 0 | benthiovalicarb | 10 | 100 | — | 100 | — |
| 0 | benthiovalicarb | 40 | 100 | — | 100 | — |
| 0.1 | benthiovalicarb | 0.08 | 58 | 57 | 91 | 96 |
| 0.1 | benthiovalicarb | 0.4 | 89 | 78 | 97 | 99 |
| 0.1 | benthiovalicarb | 2 | 100 | 100 | 100 | 100 |
| 0.1 | benthiovalicarb | 10 | 100 | 100 | 100 | 100 |
| 0.1 | benthiovalicarb | 40 | 100 | 100 | 100 | 100 |
| 0.15 | benthiovalicarb | 0.08 | 50 | 62 | 82 | 96 |
| 0.15 | benthiovalicarb | 0.4 | 99 | 80 | 100 | 99 |
| 0.15 | benthiovalicarb | 2 | 100 | 100 | 100 | 100 |
| 0.15 | benthiovalicarb | 10 | 100 | 100 | 100 | 100 |
| 0.15 | benthiovalicarb | 40 | 100 | 100 | 100 | 100 |
| 0 | dimethomorph | 0.08 | 9 | — | 47 | — |
| 0 | dimethomorph | 0.4 | 9 | — | 57 | — |
| 0 | dimethomorph | 2 | 47 | — | 70 | — |
| 0 | dimethomorph | 10 | 86 | — | 100 | — |
| 0 | dimethomorph | 40 | 99 | — | 100 | — |
| 0.1 | dimethomorph | 0.08 | 53 | 57 | 68 | 93 |
| 0.1 | dimethomorph | 0.4 | 46 | 57 | 68 | 94 |
| 0.1 | dimethomorph | 2 | 66 | 75 | 83 | 96 |
| 0.1 | dimethomorph | 10 | 85 | 93 | 100 | 100 |
| 0.1 | dimethomorph | 40 | 88 | 99 | 100 | 100 |
| 0.15 | dimethomorph | 0.08 | 68 | 62 | 77 | 92 |
| 0.15 | dimethomorph | 0.4 | 46 | 62 | 92 | 94 |
| 0.15 | dimethomorph | 2 | 40 | 78 | 95 | 96 |
| 0.15 | dimethomorph | 10 | 92 | 94 | 100 | 100 |
| 0.15 | dimethomorph | 40 | 92 | 100 | 100 | 100 |
| 0 | azoxystrobin | 0.08 | 0 | — | 64 | — |

TABLE B-continued

Observed and Expected Effects of Compound 1 Alone and Mixtures with Benthiovalicarb, Dimethomorph, Azoxystrobin, Iprovalicarb and Fluopicolide in Controlling Tomato Late Blight and Cucumber Downy Mildew

| Application Rate (ppm) of Compound 1 | Component (b) | Application Rate (ppm) of Component (b) | TLB Obsd | TLB Exp | CDM Obsd | CDM Exp |
|---|---|---|---|---|---|---|
| 0 | azoxystrobin | 0.4 | 16 | — | 80 | — |
| 0 | azoxystrobin | 2 | 26 | — | 100 | — |
| 0 | azoxystrobin | 10 | 58 | — | 100 | — |
| 0 | azoxystrobin | 40 | 99 | — | 100 | — |
| 0.1 | azoxystrobin | 0.08 | 17 | 53 | 79 | 95 |
| 0.1 | azoxystrobin | 0.4 | 37 | 60 | 85 | 97 |
| 0.1 | azoxystrobin | 2 | 64 | 65 | 100 | 100 |
| 0.1 | azoxystrobin | 10 | 70 | 80 | 100 | 100 |
| 0.1 | azoxystrobin | 40 | 79 | 99 | 100 | 100 |
| 0.15 | azoxystrobin | 0.08 | 46 | 59 | 82 | 95 |
| 0.15 | azoxystrobin | 0.4 | 39 | 65 | 94 | 97 |
| 0.15 | azoxystrobin | 2 | 87 | 69 | 100 | 100 |
| 0.15 | azoxystrobin | 10 | 87 | 83 | 100 | 100 |
| 0.15 | azoxystrobin | 40 | 98 | 100 | 100 | 100 |
| 0 | iprovalicarb | 0.08 | 0 | — | 47 | — |
| 0 | iprovalicarb | 0.4 | 9 | — | 57 | — |
| 0 | iprovalicarb | 2 | 39 | — | 77 | — |
| 0 | iprovalicarb | 10 | 99 | — | 100 | — |
| 0 | iprovalicarb | 40 | 100 | — | 100 | — |
| 0.1 | iprovalicarb | 0.08 | 30 | 53 | 68 | 93 |
| 0.1 | iprovalicarb | 0.4 | 24 | 57 | 80 | 94 |
| 0.1 | iprovalicarb | 2 | 71 | 71 | 80 | 97 |
| 0.1 | iprovalicarb | 10 | 100 | 99 | 99 | 100 |
| 0.1 | iprovalicarb | 40 | 100 | 100 | 100 | 100 |
| 0.15 | iprovalicarb | 0.08 | 51 | 59 | 83 | 92 |
| 0.15 | iprovalicarb | 0.4 | 53 | 62 | 90 | 94 |
| 0.15 | iprovalicarb | 2 | 53 | 75 | 71 | 97 |
| 0.15 | iprovalicarb | 10 | 96 | 100 | 100 | 100 |
| 0.15 | iprovalicarb | 40 | 100 | 100 | 100 | 100 |
| 0 | fluopicolide | 0.08 | 26 | — | 47 | — |
| 0 | fluopicolide | 0.4 | 9 | — | 47 | — |
| 0 | fluopicolide | 2 | 59 | — | 94 | — |
| 0 | fluopicolide | 10 | 100 | — | 100 | — |
| 0 | fluopicolide | 40 | 100 | — | 100 | — |
| 0.1 | fluopicolide | 0.08 | 26 | 65 | 53 | 93 |
| 0.1 | fluopicolide | 0.4 | 87 | 57 | 82 | 93 |
| 0.1 | fluopicolide | 2 | 94 | 80 | 95 | 99 |
| 0.1 | fluopicolide | 10 | 100 | 100 | 100 | 100 |
| 0.1 | fluopicolide | 40 | 100 | 100 | 100 | 100 |
| 0.15 | fluopicolide | 0.08 | 46 | 69 | 47 | 92 |
| 0.15 | fluopicolide | 0.4 | 92 | 62 | 72 | 92 |
| 0.15 | fluopicolide | 2 | 88 | 83 | 100 | 99 |
| 0.15 | fluopicolide | 10 | 100 | 100 | 100 | 100 |
| 0.15 | fluopicolide | 40 | 100 | 100 | 100 | 100 |

TABLE C

Observed and Expected Effects of Compound 1 Alone and Mixtures with Famoxadone, Fluazinam, Kresoxim-Methyl, Trifloxystrobin and Folpet in Controlling Tomato Late Blight and Cucumber Downy Mildew

| Application Rate (ppm) of Compound 1 | Component (b) | Application Rate (ppm) of Component (b) | TLB Obsd | TLB Exp | CDM Obsd | CDM Exp |
|---|---|---|---|---|---|---|
| 0 | — | 0 | 0 | — | 57 | — |
| 0.05 | — | 0 | 17 | — | 77 | — |
| 0.1 | — | 0 | 17 | — | 86 | — |
| 0.15 | — | 0 | 57 | — | 95 | — |
| 0.2 | — | 0 | 51 | — | 100 | — |
| 1 | — | 0 | 99 | — | 100 | — |
| 0 | famoxadone | 0.4 | 17 | — | 47 | — |
| 0 | famoxadone | 2 | 26 | — | 63 | — |
| 0 | famoxadone | 10 | 67 | — | 95 | — |
| 0 | famoxadone | 40 | 53 | — | 100 | — |
| 0 | famoxadone | 200 | 66 | — | 100 | — |
| 0.1 | famoxadone | 0.4 | 26 | 64 | 88 | 97 |
| 0.1 | famoxadone | 2 | 40 | 68 | 93 | 98 |
| 0.1 | famoxadone | 10 | 45 | 86 | 99 | 100 |

TABLE C-continued

Observed and Expected Effects of Compound 1 Alone and Mixtures with Famoxadone, Fluazinam, Kresoxim-Methyl, Trifloxystrobin and Folpet in Controlling Tomato Late Blight and Cucumber Downy Mildew

| Application Rate (ppm) of Compound 1 | Component (b) | Application Rate (ppm) of Component (b) | TLB Obsd | TLB Exp | CDM Obsd | CDM Exp |
|---|---|---|---|---|---|---|
| 0.1 | famoxadone | 40 | 72 | 79 | 100 | 100 |
| 0.1 | famoxadone | 200 | 99 | 85 | 100 | 100 |
| 0.15 | famoxadone | 0.4 | 24 | 59 | 91 | 100 |
| 0.15 | famoxadone | 2 | 53 | 64 | 99 | 100 |
| 0.15 | famoxadone | 10 | 90 | 84 | 100 | 100 |
| 0.15 | famoxadone | 40 | 75 | 77 | 100 | 100 |
| 0.15 | famoxadone | 200 | 84 | 83 | 100 | 100 |
| 0 | fluazinam | 0.4 | 17 | — | 57 | — |
| 0 | fluazinam | 2 | 40 | — | 60 | — |
| 0 | fluazinam | 10 | 80 | — | 91 | — |
| 0 | fluazinam | 40 | 98 | — | 100 | — |
| 0 | fluazinam | 200 | 100 | — | 100 | — |
| 0.1 | fluazinam | 0.4 | 68 | 64 | 82 | 98 |
| 0.1 | fluazinam | 2 | 85 | 74 | 87 | 98 |
| 0.1 | fluazinam | 10 | 100 | 91 | 100 | 100 |
| 0.1 | fluazinam | 40 | 100 | 99 | 100 | 100 |
| 0.1 | fluazinam | 200 | 100 | 100 | 100 | 100 |
| 0.15 | fluazinam | 0.4 | 50 | 59 | 93 | 100 |
| 0.15 | fluazinam | 2 | 97 | 71 | 99 | 100 |
| 0.15 | fluazinam | 10 | 100 | 90 | 100 | 100 |
| 0.15 | fluazinam | 40 | 100 | 99 | 100 | 100 |
| 0.15 | fluazinam | 200 | 100 | 100 | 100 | 100 |
| 0 | kresoxim-methyl | 0.4 | 9 | — | 47 | — |
| 0 | kresoxim-methyl | 2 | 33 | — | 47 | — |
| 0 | kresoxim-methyl | 10 | 80 | — | 53 | — |
| 0 | kresoxim-methyl | 40 | 99 | — | 57 | — |
| 0 | kresoxim-methyl | 200 | 99 | — | 100 | — |
| 0.1 | kresoxim-methyl | 0.4 | 16 | 61 | 80 | 97 |
| 0.1 | kresoxim-methyl | 2 | 57 | 71 | 83 | 97 |
| 0.1 | kresoxim-methyl | 10 | 83 | 91 | 91 | 98 |
| 0.1 | kresoxim-methyl | 40 | 100 | 100 | 95 | 98 |
| 0.1 | kresoxim-methyl | 200 | 100 | 100 | 100 | 100 |
| 0.15 | kresoxim-methyl | 0.4 | 33 | 55 | 73 | 100 |
| 0.15 | kresoxim-methyl | 2 | 33 | 67 | 84 | 100 |
| 0.15 | kresoxim-methyl | 10 | 95 | 90 | 95 | 100 |
| 0.15 | kresoxim-methyl | 40 | 100 | 99 | 99 | 100 |
| 0.15 | kresoxim-methyl | 200 | 98 | 99 | 100 | 100 |
| 0 | trifloxystrobin | 0.4 | 0 | — | 47 | — |
| 0 | trifloxystrobin | 2 | 40 | — | 47 | — |
| 0 | trifloxystrobin | 10 | 26 | — | 58 | — |
| 0 | trifloxystrobin | 40 | 45 | — | 94 | — |
| 0 | trifloxystrobin | 200 | 53 | — | 100 | — |
| 0.1 | trifloxystrobin | 0.4 | 17 | 57 | 47 | 97 |
| 0.1 | trifloxystrobin | 2 | 17 | 74 | 47 | 97 |
| 0.1 | trifloxystrobin | 10 | 53 | 68 | 91 | 98 |
| 0.1 | trifloxystrobin | 40 | 58 | 76 | 100 | 100 |
| 0.1 | trifloxystrobin | 200 | 70 | 80 | 100 | 100 |
| 0.15 | trifloxystrobin | 0.4 | 33 | 51 | 96 | 100 |
| 0.15 | trifloxystrobin | 2 | 40 | 71 | 95 | 100 |
| 0.15 | trifloxystrobin | 10 | 24 | 64 | 94 | 100 |
| 0.15 | trifloxystrobin | 40 | 86 | 73 | 100 | 100 |
| 0.15 | trifloxystrobin | 200 | 67 | 77 | 100 | 100 |
| 0 | folpet | 0.4 | 0 | — | 47 | — |
| 0 | folpet | 2 | 9 | — | 47 | — |
| 0 | folpet | 10 | 9 | — | 47 | — |
| 0 | folpet | 40 | 24 | — | 92 | — |
| 0 | folpet | 200 | 75 | — | 95 | — |
| 0.1 | folpet | 0.4 | 16 | 57 | 76 | 97 |
| 0.1 | folpet | 2 | 9 | 61 | 60 | 97 |
| 0.1 | folpet | 10 | 9 | 61 | 89 | 97 |
| 0.1 | folpet | 40 | 26 | 67 | 95 | 100 |
| 0.1 | folpet | 200 | 79 | 89 | 100 | 100 |
| 0.15 | folpet | 0.4 | 33 | 51 | 88 | 100 |
| 0.15 | folpet | 2 | 9 | 55 | 93 | 100 |
| 0.15 | folpet | 10 | 24 | 55 | 99 | 100 |
| 0.15 | folpet | 40 | 31 | 63 | 100 | 100 |
| 0.15 | folpet | 200 | 73 | 88 | 100 | 100 |

TABLE D

Observed and Expected Effects of Compound 1 Alone and Mixtures with Pyraclostrobin, Copper Hydroxide, Fosetyl-Aluminum, Propamocarb and 5-chloro-6-(2,4,6-trifluorophenyl)-7-(4-methylpiperidin-1-yl)[1,2,4]triazolo[1,5-a]pyrimidine (BAS600) in Controlling Tomato Late Blight and Cucumber Downy Mildew

| Application Rate (ppm) of Compound 1 | Component (b) | Application Rate (ppm) of Component (b) | TLB Obsd | TLB Exp | CDM Obsd | CDM Exp |
|---|---|---|---|---|---|---|
| 0 | — | 0 | 19 | — | 47 | — |
| 0.05 | — | 0 | 32 | — | 64 | — |
| 0.1 | — | 0 | 52 | — | 77 | — |
| 0.15 | — | 0 | 90 | — | 86 | — |
| 0.2 | — | 0 | 67 | — | 93 | — |
| 1 | — | 0 | 100 | — | 100 | — |
| 0 | pyraclostrobin | 0.08 | 26 | — | 47 | — |
| 0 | pyraclostrobin | 0.4 | 40 | — | 47 | — |
| 0 | pyraclostrobin | 2 | 78 | — | 98 | — |
| 0 | pyraclostrobin | 10 | 85 | — | 100 | — |
| 0 | pyraclostrobin | 40 | 95 | — | 100 | — |
| 0.1 | pyraclostrobin | 0.08 | 62 | 65 | 80 | 88 |
| 0.1 | pyraclostrobin | 0.4 | 78 | 71 | 89 | 88 |
| 0.1 | pyraclostrobin | 2 | 92 | 89 | 93 | 99 |
| 0.1 | pyraclostrobin | 10 | 91 | 93 | 100 | 100 |
| 0.1 | pyraclostrobin | 40 | 95 | 97 | 100 | 100 |
| 0.15 | pyraclostrobin | 0.08 | 94 | 93 | 96 | 93 |
| 0.15 | pyraclostrobin | 0.4 | 93 | 94 | 93 | 93 |
| 0.15 | pyraclostrobin | 2 | 97 | 98 | 100 | 100 |
| 0.15 | pyraclostrobin | 10 | 95 | 99 | 100 | 100 |
| 0.15 | pyraclostrobin | 40 | 99 | 99 | 100 | 100 |
| 0 | copper hydroxide | 2 | 32 | — | 53 | — |
| 0 | copper hydroxide | 10 | 48 | — | 63 | — |
| 0 | copper hydroxide | 40 | 40 | — | 85 | — |
| 0 | copper hydroxide | 200 | 70 | — | 85 | — |
| 0 | copper hydroxide | 500 | 91 | — | 88 | — |
| 0.1 | copper hydroxide | 2 | 81 | 68 | 47 | 89 |
| 0.1 | copper hydroxide | 10 | 70 | 75 | 57 | 91 |
| 0.1 | copper hydroxide | 40 | 59 | 71 | 83 | 97 |
| 0.1 | copper hydroxide | 200 | 62 | 86 | 87 | 97 |
| 0.1 | copper hydroxide | 500 | 90 | 96 | 95 | 97 |
| 0.15 | copper hydroxide | 2 | 32 | 93 | 57 | 93 |
| 0.15 | copper hydroxide | 10 | 92 | 95 | 83 | 95 |
| 0.15 | copper hydroxide | 40 | 91 | 94 | 96 | 98 |
| 0.15 | copper hydroxide | 200 | 79 | 97 | 100 | 98 |
| 0.15 | copper hydroxide | 500 | 79 | 99 | 100 | 98 |
| 0 | fosetyl-aluminum | 10 | 0 | — | 47 | — |
| 0 | fosetyl-aluminum | 40 | 20 | — | 47 | — |
| 0 | fosetyl-aluminum | 200 | 65 | — | 47 | — |
| 0 | fosetyl-aluminum | 1000 | 97 | — | 98 | — |
| 0 | fosetyl-aluminum | 2000 | 100 | — | 100 | — |
| 0.1 | fosetyl-aluminum | 10 | 45 | 52 | 89 | 88 |
| 0.1 | fosetyl-aluminum | 40 | 83 | 62 | 83 | 88 |
| 0.1 | fosetyl-aluminum | 200 | 93 | 83 | 87 | 88 |
| 0.1 | fosetyl-aluminum | 1000 | 100 | 99 | 100 | 99 |
| 0.1 | fosetyl-aluminum | 2000 | 100 | 100 | 100 | 100 |
| 0.15 | fosetyl-aluminum | 10 | 90 | 90 | 95 | 93 |
| 0.15 | fosetyl-aluminum | 40 | 88 | 92 | 94 | 93 |
| 0.15 | fosetyl-aluminum | 200 | 96 | 97 | 99 | 93 |
| 0.15 | fosetyl-aluminum | 1000 | 100 | 100 | 99 | 100 |
| 0.15 | fosetyl-aluminum | 2000 | 100 | 100 | 100 | 100 |
| 0 | propamocarb | 10 | 6 | — | 47 | — |
| 0 | propamocarb | 40 | 6 | — | 47 | — |
| 0 | propamocarb | 200 | 19 | — | 58 | — |
| 0 | propamocarb | 1000 | 57 | — | 76 | — |
| 0 | propamocarb | 5000 | 77 | — | 98 | — |
| 0.1 | propamocarb | 10 | 76 | 55 | 47 | 88 |
| 0.1 | propamocarb | 40 | 51 | 55 | 88 | 88 |
| 0.1 | propamocarb | 200 | 68 | 61 | 97 | 90 |
| 0.1 | propamocarb | 1000 | 100 | 79 | 100 | 94 |
| 0.1 | propamocarb | 5000 | 95 | 89 | 100 | 99 |
| 0.15 | propamocarb | 10 | 100 | 91 | 90 | 93 |
| 0.15 | propamocarb | 40 | 91 | 91 | 95 | 93 |
| 0.15 | propamocarb | 200 | 89 | 92 | 99 | 94 |
| 0.15 | propamocarb | 1000 | 100 | 96 | 100 | 97 |
| 0.15 | propamocarb | 5000 | 100 | 98 | 99 | 100 |
| 0 | BAS600 | 2 | 26 | — | 47 | — |
| 0 | BAS600 | 10 | 6 | — | 99 | — |
| 0 | BAS600 | 40 | 56 | — | 100 | — |
| 0 | BAS600 | 200 | 20 | — | 100 | — |
| 0 | BAS600 | 500 | 12 | — | 100 | — |

TABLE D-continued

Observed and Expected Effects of Compound 1 Alone and Mixtures with Pyraclostrobin, Copper Hydroxide, Fosetyl-Aluminum, Propamocarb and 5-chloro-6-(2,4,6-trifluorophenyl)-7-(4-methylpiperidin-1-yl)[1,2,4]triazolo[1,5-a]pyrimidine (BAS600) in Controlling Tomato Late Blight and Cucumber Downy Mildew

| Application Rate (ppm) of Compound 1 | Component (b) | Application Rate (ppm) of Component (b) | TLB Obsd | TLB Exp | CDM Obsd | CDM Exp |
|---|---|---|---|---|---|---|
| 0.1 | BAS600 | 2 | 78 | 65 | 57 | 88 |
| 0.1 | BAS600 | 10 | 100 | 55 | 93 | 100 |
| 0.1 | BAS600 | 40 | 82 | 79 | 100 | 100 |
| 0.1 | BAS600 | 200 | 69 | 62 | 100 | 100 |
| 0.1 | BAS600 | 500 | 79 | 58 | 100 | 100 |
| 0.15 | BAS600 | 2 | 100 | 93 | 57 | 93 |
| 0.15 | BAS600 | 10 | 87 | 91 | 94 | 100 |
| 0.15 | BAS600 | 40 | 78 | 96 | 100 | 100 |
| 0.15 | BAS600 | 200 | 92 | 92 | 100 | 100 |
| 0.15 | BAS600 | 500 | 98 | 91 | 100 | 100 |

TABLE E

Observed and Expected Effects of Compound 1 Alone and Mixtures with Chlorothalonil, Mandipropamid and Quinoxyfen in Controlling Tomato Late Blight

| Application Rate (ppm) of Compound 1 | Component (b) | Application Rate (ppm) of Component (b) | TLB Obsd | TLB Exp |
|---|---|---|---|---|
| 0 | — | 0 | 9 | — |
| 0.05 | — | 0 | 33 | — |
| 0.1 | — | 0 | 75 | — |
| 0.15 | — | 0 | 92 | — |
| 0.2 | — | 0 | 90 | — |
| 1 | — | 0 | 100 | — |
| 0 | chlorothalonil | 0.016 | 31 | — |
| 0 | chlorothalonil | 0.08 | 0 | — |
| 0 | chlorothalonil | 0.4 | 73 | — |
| 0 | chlorothalonil | 2 | 100 | — |
| 0 | chlorothalonil | 10 | 100 | — |
| 0.1 | chlorothalonil | 0.016 | 51 | 83 |
| 0.1 | chlorothalonil | 0.08 | 58 | 75 |
| 0.1 | chlorothalonil | 0.4 | 75 | 93 |
| 0.1 | chlorothalonil | 2 | 100 | 100 |
| 0.1 | chlorothalonil | 10 | 100 | 100 |
| 0.15 | chlorothalonil | 0.016 | 68 | 94 |
| 0.15 | chlorothalonil | 0.08 | 24 | 92 |
| 0.15 | chlorothalonil | 0.4 | 95 | 98 |
| 0.15 | chlorothalonil | 2 | 95 | 100 |
| 0.15 | chlorothalonil | 10 | 100 | 100 |
| 0 | mandipropamid | 0.016 | 26 | — |
| 0 | mandipropamid | 0.08 | 33 | — |
| 0 | mandipropamid | 0.4 | 88 | — |
| 0 | mandipropamid | 2 | 100 | — |
| 0 | mandipropamid | 10 | 100 | — |
| 0.1 | mandipropamid | 0.016 | 40 | 82 |
| 0.1 | mandipropamid | 0.08 | 38 | 83 |
| 0.1 | mandipropamid | 0.4 | 83 | 97 |
| 0.1 | mandipropamid | 2 | 100 | 100 |
| 0.1 | mandipropamid | 10 | 100 | 100 |
| 0.15 | mandipropamid | 0.016 | 83 | 94 |
| 0.15 | mandipropamid | 0.08 | 95 | 95 |
| 0.15 | mandipropamid | 0.4 | 97 | 99 |
| 0.15 | mandipropamid | 2 | 100 | 100 |
| 0.15 | mandipropamid | 10 | 100 | 100 |
| 0 | quinoxyfen | 0.016 | 9 | — |
| 0 | quinoxyfen | 0.08 | 24 | — |
| 0 | quinoxyfen | 0.4 | 26 | — |
| 0 | quinoxyfen | 2 | 9 | — |
| 0 | quinoxyfen | 10 | 9 | — |
| 0.1 | quinoxyfen | 0.016 | 57 | 78 |
| 0.1 | quinoxyfen | 0.08 | 94 | 81 |
| 0.1 | quinoxyfen | 0.4 | 92 | 82 |
| 0.1 | quinoxyfen | 2 | 84 | 78 |
| 0.1 | quinoxyfen | 10 | 97 | 78 |
| 0.15 | quinoxyfen | 0.016 | 96 | 93 |
| 0.15 | quinoxyfen | 0.08 | 95 | 94 |
| 0.15 | quinoxyfen | 0.4 | 100 | 94 |
| 0.15 | quinoxyfen | 2 | 100 | 93 |
| 0.15 | quinoxyfen | 10 | 96 | 93 |

TABLE F

Observed and Expected Effects of Compound 1 Alone and Mixtures with Chlorothalonil, Mandipropamid and Quinoxyfen in Controlling Cucumber Downy Mildew

| Application Rate (ppm) of Compound 1 | Component (b) | Application Rate (ppm) of Component (b) | CDM Obsd | CDM Exp |
|---|---|---|---|---|
| 0 | — | 0 | 26 | — |
| 0.025 | — | 0 | 40 | — |
| 0.05 | — | 0 | 68 | — |
| 0.075 | — | 0 | 39 | — |
| 0.1 | — | 0 | 47 | — |
| 0.125 | — | 0 | 58 | — |
| 0 | chlorothalonil | 0.016 | 47 | — |
| 0 | chlorothalonil | 0.08 | 33 | — |
| 0 | chlorothalonil | 0.4 | 47 | — |
| 0 | chlorothalonil | 2 | 99 | — |
| 0 | chlorothalonil | 10 | 100 | — |
| 0.025 | chlorothalonil | 0.016 | 40 | 64 |
| 0.025 | chlorothalonil | 0.08 | 33 | 60 |
| 0.025 | chlorothalonil | 0.4 | 33 | 68 |
| 0.025 | chlorothalonil | 2 | 100 | 99 |
| 0.025 | chlorothalonil | 10 | 100 | 100 |
| 0.05 | chlorothalonil | 0.016 | 64 | 81 |
| 0.05 | chlorothalonil | 0.08 | 68 | 79 |
| 0.05 | chlorothalonil | 0.4 | 86 | 83 |
| 0.05 | chlorothalonil | 2 | 99 | 100 |
| 0.05 | chlorothalonil | 10 | 100 | 100 |
| 0 | mandipropamid | 0.016 | 33 | — |
| 0 | mandipropamid | 0.08 | 97 | — |
| 0 | mandipropamid | 0.4 | 100 | — |
| 0 | mandipropamid | 2 | 100 | — |
| 0 | mandipropamid | 10 | 100 | — |
| 0.025 | mandipropamid | 0.016 | 58 | 60 |

TABLE F-continued

Observed and Expected Effects of Compound 1 Alone and Mixtures with Chlorothalonil, Mandipropamid and Quinoxyfen in Controlling Cucumber Downy Mildew

| Application Rate (ppm) of Compound 1 | Component (b) | Application Rate (ppm) of Component (b) | CDM Obsd | CDM Exp |
|---|---|---|---|---|
| 0.025 | mandipropamid | 0.08 | 100 | 98 |
| 0.025 | mandipropamid | 0.4 | 100 | 100 |
| 0.025 | mandipropamid | 2 | 100 | 100 |
| 0.025 | mandipropamid | 10 | 100 | 100 |
| 0.05 | mandipropamid | 0.016 | 83 | 79 |
| 0.05 | mandipropamid | 0.08 | 100 | 99 |
| 0.05 | mandipropamid | 0.4 | 100 | 100 |
| 0.05 | mandipropamid | 2 | 100 | 100 |
| 0.05 | mandipropamid | 10 | 100 | 100 |
| 0 | quinoxyfen | 0.016 | 26 | — |
| 0 | quinoxyfen | 0.08 | 26 | — |
| 0 | quinoxyfen | 0.4 | 26 | — |
| 0 | quinoxyfen | 2 | 26 | — |
| 0 | quinoxyfen | 10 | 26 | — |
| 0.025 | quinoxyfen | 0.016 | 47 | 56 |
| 0.025 | quinoxyfen | 0.08 | 47 | 56 |
| 0.025 | quinoxyfen | 0.4 | 33 | 56 |
| 0.025 | quinoxyfen | 2 | 26 | 56 |
| 0.025 | quinoxyfen | 10 | 26 | 56 |
| 0.05 | quinoxyfen | 0.016 | 53 | 76 |
| 0.05 | quinoxyfen | 0.08 | 47 | 76 |
| 0.05 | quinoxyfen | 0.4 | 53 | 76 |
| 0.05 | quinoxyfen | 2 | 26 | 76 |
| 0.05 | quinoxyfen | 10 | 26 | 76 |

TABLE G

Observed and Expected Effects of Compound 1 Alone and Mixtures with Boscalid, Mancozeb, Proquinazid, Cymoxanil and Penthiopyrad in Controlling Cucumber Downy Mildew

| Application Rate (ppm) of Compound 1 | Component (b) | Application Rate (ppm) of Component (b) | CDM Obsd | CDM Exp |
|---|---|---|---|---|
| 0 | — | 0 | 26 | — |
| 0.025 | — | 0 | 26 | — |
| 0.05 | — | 0 | 26 | — |
| 0.075 | — | 0 | 47 | — |
| 0.1 | — | 0 | 47 | — |
| 0.125 | — | 0 | 68 | — |
| 0 | boscalid | 0.4 | 47 | — |
| 0 | boscalid | 2 | 47 | — |
| 0 | boscalid | 10 | 26 | — |
| 0 | boscalid | 40 | 26 | — |
| 0 | boscalid | 200 | 26 | — |
| 0.025 | boscalid | 0.4 | 33 | 61 |
| 0.025 | boscalid | 2 | 26 | 61 |
| 0.025 | boscalid | 10 | 47 | 45 |
| 0.025 | boscalid | 40 | 47 | 45 |
| 0.025 | boscalid | 200 | 47 | 45 |
| 0.05 | boscalid | 0.4 | 33 | 61 |
| 0.05 | boscalid | 2 | 64 | 61 |
| 0.05 | boscalid | 10 | 64 | 45 |
| 0.05 | boscalid | 40 | 72 | 45 |
| 0.05 | boscalid | 200 | 50 | 45 |
| 0 | mancozeb | 0.4 | 39 | — |
| 0 | mancozeb | 2 | 26 | — |
| 0 | mancozeb | 10 | 26 | — |
| 0 | mancozeb | 40 | 94 | — |
| 0 | mancozeb | 200 | 100 | — |
| 0.025 | mancozeb | 0.4 | 26 | 55 |
| 0.025 | mancozeb | 2 | 33 | 45 |
| 0.025 | mancozeb | 10 | 26 | 45 |
| 0.025 | mancozeb | 40 | 96 | 96 |
| 0.025 | mancozeb | 200 | 100 | 100 |
| 0.05 | mancozeb | 0.4 | 63 | 55 |

TABLE G-continued

Observed and Expected Effects of Compound 1 Alone and Mixtures with Boscalid, Mancozeb, Proquinazid, Cymoxanil and Penthiopyrad in Controlling Cucumber Downy Mildew

| Application Rate (ppm) of Compound 1 | Component (b) | Application Rate (ppm) of Component (b) | CDM Obsd | CDM Exp |
|---|---|---|---|---|
| 0.05 | mancozeb | 2 | 94 | 45 |
| 0.05 | mancozeb | 10 | 97 | 45 |
| 0.05 | mancozeb | 40 | 100 | 96 |
| 0.05 | mancozeb | 200 | 100 | 100 |
| 0 | proquinazid | 0.4 | 26 | — |
| 0 | proquinazid | 2 | 26 | — |
| 0 | proquinazid | 10 | 26 | — |
| 0 | proquinazid | 40 | 26 | — |
| 0 | proquinazid | 200 | 26 | — |
| 0.025 | proquinazid | 0.4 | 83 | 45 |
| 0.025 | proquinazid | 2 | 57 | 45 |
| 0.025 | proquinazid | 10 | 47 | 45 |
| 0.025 | proquinazid | 40 | 57 | 45 |
| 0.025 | proquinazid | 200 | 77 | 45 |
| 0.05 | proquinazid | 0.4 | 60 | 45 |
| 0.05 | proquinazid | 2 | 57 | 45 |
| 0.05 | proquinazid | 10 | 43 | 45 |
| 0.05 | proquinazid | 40 | 39 | 45 |
| 0.05 | proquinazid | 200 | 68 | 45 |
| 0 | cymoxanil | 0.4 | 26 | — |
| 0 | cymoxanil | 2 | 26 | — |
| 0 | cymoxanil | 10 | 26 | — |
| 0 | cymoxanil | 40 | 26 | — |
| 0 | cymoxanil | 200 | 26 | — |
| 0.025 | cymoxanil | 0.4 | 26 | 45 |
| 0.025 | cymoxanil | 2 | 33 | 45 |
| 0.025 | cymoxanil | 10 | 33 | 45 |
| 0.025 | cymoxanil | 40 | 26 | 45 |
| 0.025 | cymoxanil | 200 | 26 | 45 |
| 0.05 | cymoxanil | 0.4 | 26 | 45 |
| 0.05 | cymoxanil | 2 | 39 | 45 |
| 0.05 | cymoxanil | 10 | 33 | 45 |
| 0.05 | cymoxanil | 40 | 73 | 45 |
| 0.05 | cymoxanil | 200 | 86 | 45 |
| 0 | penthiopyrad | 0.4 | 43 | — |
| 0 | penthiopyrad | 2 | 33 | — |
| 0 | penthiopyrad | 10 | 26 | — |
| 0 | penthiopyrad | 40 | 26 | — |
| 0 | penthiopyrad | 200 | 47 | — |
| 0.025 | penthiopyrad | 0.4 | 87 | 58 |
| 0.025 | penthiopyrad | 2 | 26 | 50 |
| 0.025 | penthiopyrad | 10 | 63 | 45 |
| 0.025 | penthiopyrad | 40 | 46 | 45 |
| 0.025 | penthiopyrad | 200 | 47 | 61 |
| 0.05 | penthiopyrad | 0.4 | 33 | 58 |
| 0.05 | penthiopyrad | 2 | 33 | 50 |
| 0.05 | penthiopyrad | 10 | 47 | 45 |
| 0.05 | penthiopyrad | 40 | 47 | 45 |
| 0.05 | penthiopyrad | 200 | 63 | 61 |

TABLE H

Observed and Expected Effects of Compound 1 Alone and Mixtures with Benthiovalicarb, Dimethomorph, Azoxystrobin, Iprovalicarb and Fluopicolide in Controlling Cucumber Downy Mildew

| Application Rate (ppm) of Compound 1 | Component (b) | Application Rate (ppm) of Component (b) | CDM Obsd | CDM Exp |
|---|---|---|---|---|
| 0 | — | 0 | 33 | — |
| 0.025 | — | 0 | 33 | — |
| 0.05 | — | 0 | 40 | — |
| 0.075 | — | 0 | 40 | — |
| 0.1 | — | 0 | 76 | — |
| 0.125 | — | 0 | 81 | — |

TABLE H-continued

Observed and Expected Effects of Compound 1 Alone and Mixtures with Benthiovalicarb, Dimethomorph, Azoxystrobin, Iprovalicarb and Fluopicolide in Controlling Cucumber Downy Mildew

| Application Rate (ppm) of Compound 1 | Component (b) | Application Rate (ppm) of Component (b) | CDM Obsd | Exp |
|---|---|---|---|---|
| 0 | benthiovalicarb | 0.08 | 33 | — |
| 0 | benthiovalicarb | 0.4 | 86 | — |
| 0 | benthiovalicarb | 2 | 100 | — |
| 0 | benthiovalicarb | 10 | 100 | — |
| 0 | benthiovalicarb | 40 | 100 | — |
| 0.025 | benthiovalicarb | 0.08 | 26 | 55 |
| 0.025 | benthiovalicarb | 0.4 | 76 | 91 |
| 0.025 | benthiovalicarb | 2 | 100 | 100 |
| 0.025 | benthiovalicarb | 10 | 100 | 100 |
| 0.025 | benthiovalicarb | 40 | 100 | 100 |
| 0.05 | benthiovalicarb | 0.08 | 39 | 60 |
| 0.05 | benthiovalicarb | 0.4 | 73 | 92 |
| 0.05 | benthiovalicarb | 2 | 100 | 100 |
| 0.05 | benthiovalicarb | 10 | 100 | 100 |
| 0.05 | benthiovalicarb | 40 | 100 | 100 |
| 0 | dimethomorph | 0.08 | 26 | — |
| 0 | dimethomorph | 0.4 | 26 | — |
| 0 | dimethomorph | 2 | 83 | — |
| 0 | dimethomorph | 10 | 100 | — |
| 0 | dimethomorph | 40 | 100 | — |
| 0.025 | dimethomorph | 0.08 | 26 | 50 |
| 0.025 | dimethomorph | 0.4 | 26 | 50 |
| 0.025 | dimethomorph | 2 | 53 | 89 |
| 0.025 | dimethomorph | 10 | 100 | 100 |
| 0.025 | dimethomorph | 40 | 100 | 100 |
| 0.05 | dimethomorph | 0.08 | 33 | 56 |
| 0.05 | dimethomorph | 0.4 | 91 | 56 |
| 0.05 | dimethomorph | 2 | 96 | 90 |
| 0.05 | dimethomorph | 10 | 100 | 100 |
| 0.05 | dimethomorph | 40 | 100 | 100 |
| 0 | azoxystrobin | 0.08 | 26 | — |
| 0 | azoxystrobin | 0.4 | 40 | — |
| 0 | azoxystrobin | 2 | 100 | — |
| 0 | azoxystrobin | 10 | 100 | — |
| 0 | azoxystrobin | 40 | 100 | — |
| 0.025 | azoxystrobin | 0.08 | 59 | 50 |
| 0.025 | azoxystrobin | 0.4 | 63 | 60 |
| 0.025 | azoxystrobin | 2 | 100 | 100 |
| 0.025 | azoxystrobin | 10 | 100 | 100 |
| 0.025 | azoxystrobin | 40 | 100 | 100 |
| 0.05 | azoxystrobin | 0.08 | 47 | 56 |
| 0.05 | azoxystrobin | 0.4 | 33 | 64 |
| 0.05 | azoxystrobin | 2 | 100 | 100 |
| 0.05 | azoxystrobin | 10 | 100 | 100 |
| 0.05 | azoxystrobin | 40 | 100 | 100 |
| 0 | iprovalicarb | 0.08 | 26 | — |
| 0 | iprovalicarb | 0.4 | 26 | — |
| 0 | iprovalicarb | 2 | 26 | — |
| 0 | iprovalicarb | 10 | 88 | — |
| 0 | iprovalicarb | 40 | 100 | — |
| 0.025 | iprovalicarb | 0.08 | 26 | 50 |
| 0.025 | iprovalicarb | 0.4 | 26 | 50 |
| 0.025 | iprovalicarb | 2 | 33 | 50 |
| 0.025 | iprovalicarb | 10 | 92 | 92 |
| 0.025 | iprovalicarb | 40 | 100 | 100 |
| 0.05 | iprovalicarb | 0.08 | 39 | 56 |
| 0.05 | iprovalicarb | 0.4 | 33 | 56 |
| 0.05 | iprovalicarb | 2 | 33 | 56 |
| 0.05 | iprovalicarb | 10 | 100 | 93 |
| 0.05 | iprovalicarb | 40 | 100 | 100 |
| 0 | fluopicolide | 0.08 | 33 | — |
| 0 | fluopicolide | 0.4 | 79 | — |
| 0 | fluopicolide | 2 | 96 | — |
| 0 | fluopicolide | 10 | 100 | — |
| 0 | fluopicolide | 40 | 100 | — |
| 0.025 | fluopicolide | 0.08 | 59 | 55 |
| 0.025 | fluopicolide | 0.4 | 57 | 86 |
| 0.025 | fluopicolide | 2 | 95 | 98 |
| 0.025 | fluopicolide | 10 | 100 | 100 |
| 0.025 | fluopicolide | 40 | 100 | 100 |
| 0.05 | fluopicolide | 0.08 | 50 | 60 |
| 0.05 | fluopicolide | 0.4 | 47 | 87 |
| 0.05 | fluopicolide | 2 | 93 | 98 |
| 0.05 | fluopicolide | 10 | 100 | 100 |
| 0.05 | fluopicolide | 40 | 100 | 100 |

TABLE I

Observed and Expected Effects of Compound 1 Alone and Mixtures with Famoxadone, Fluazinam, Kresoxim-Methyl, Trifloxystrobin and Folpet in Controlling Cucumber Downy Mildew

| Application Rate (ppm) of Compound 1 | Component (b) | Application Rate (ppm) of Component (b) | CDM Obsd | Exp |
|---|---|---|---|---|
| 0 | — | 0 | 47 | — |
| 0.025 | — | 0 | 47 | — |
| 0.05 | — | 0 | 47 | — |
| 0.075 | — | 0 | 47 | — |
| 0.1 | — | 0 | 57 | — |
| 0.125 | — | 0 | 57 | — |
| 0 | famoxadone | 0.4 | 47 | — |
| 0 | famoxadone | 2 | 58 | — |
| 0 | famoxadone | 10 | 87 | — |
| 0 | famoxadone | 40 | 100 | — |
| 0 | famoxadone | 200 | 100 | — |
| 0.025 | famoxadone | 0.4 | 47 | 72 |
| 0.025 | famoxadone | 2 | 63 | 78 |
| 0.025 | famoxadone | 10 | 93 | 93 |
| 0.025 | famoxadone | 40 | 99 | 100 |
| 0.025 | famoxadone | 200 | 100 | 100 |
| 0.05 | famoxadone | 0.4 | 47 | 72 |
| 0.05 | famoxadone | 2 | 47 | 80 |
| 0.05 | famoxadone | 10 | 99 | 96 |
| 0.05 | famoxadone | 40 | 100 | 99 |
| 0.05 | famoxadone | 200 | 100 | 100 |
| 0 | fluazinam | 0.4 | 47 | — |
| 0 | fluazinam | 2 | 57 | — |
| 0 | fluazinam | 10 | 92 | — |
| 0 | fluazinam | 40 | 100 | — |
| 0 | fluazinam | 200 | 100 | — |
| 0.025 | fluazinam | 0.4 | 47 | 72 |
| 0.025 | fluazinam | 2 | 57 | 77 |
| 0.025 | fluazinam | 10 | 98 | 96 |
| 0.025 | fluazinam | 40 | 99 | 100 |
| 0.025 | fluazinam | 200 | 100 | 100 |
| 0.05 | fluazinam | 0.4 | 47 | 72 |
| 0.05 | fluazinam | 2 | 70 | 77 |
| 0.05 | fluazinam | 10 | 95 | 99 |
| 0.05 | fluazinam | 40 | 98 | 99 |
| 0.05 | fluazinam | 200 | 100 | 100 |
| 0 | kresoxim-methyl | 0.4 | 47 | — |
| 0 | kresoxim-methyl | 2 | 47 | — |
| 0 | kresoxim-methyl | 10 | 47 | — |
| 0 | kresoxim-methyl | 40 | 99 | — |
| 0 | kresoxim-methyl | 200 | 100 | — |
| 0.025 | kresoxim-methyl | 0.4 | 47 | 72 |
| 0.025 | kresoxim-methyl | 2 | 47 | 72 |
| 0.025 | kresoxim-methyl | 10 | 72 | 72 |
| 0.025 | kresoxim-methyl | 40 | 76 | 99 |
| 0.025 | kresoxim-methyl | 200 | 100 | 100 |
| 0.05 | kresoxim-methyl | 0.4 | 47 | 72 |
| 0.05 | kresoxim-methyl | 2 | 47 | 72 |
| 0.05 | kresoxim-methyl | 10 | 57 | 85 |

TABLE I-continued

Observed and Expected Effects of Compound 1 Alone and Mixtures with Famoxadone, Fluazinam, Kresoxim-Methyl, Trifloxystrobin and Folpet in Controlling Cucumber Downy Mildew

| Application Rate (ppm) of Compound 1 | Component (b) | Application Rate (ppm) of Component (b) | CDM Obsd | Exp |
|---|---|---|---|---|
| 0.05 | kresoxim-methyl | 40 | 98 | 87 |
| 0.05 | kresoxim-methyl | 200 | 100 | 100 |
| 0 | trifloxystrobin | 0.4 | 47 | — |
| 0 | trifloxystrobin | 2 | 47 | — |
| 0 | trifloxystrobin | 10 | 57 | — |
| 0 | trifloxystrobin | 40 | 93 | — |
| 0 | trifloxystrobin | 200 | 100 | — |
| 0.025 | trifloxystrobin | 0.4 | 47 | 72 |
| 0.025 | trifloxystrobin | 2 | 47 | 72 |
| 0.025 | trifloxystrobin | 10 | 80 | 77 |
| 0.025 | trifloxystrobin | 40 | 97 | 96 |
| 0.025 | trifloxystrobin | 200 | 100 | 100 |
| 0.05 | trifloxystrobin | 0.4 | 47 | 72 |
| 0.05 | trifloxystrobin | 2 | 47 | 72 |
| 0.05 | trifloxystrobin | 10 | 84 | 89 |
| 0.05 | trifloxystrobin | 40 | 94 | 99 |
| 0.05 | trifloxystrobin | 200 | 100 | 100 |
| 0 | folpet | 0.4 | 47 | — |
| 0 | folpet | 2 | 47 | — |
| 0 | folpet | 10 | 47 | — |
| 0 | folpet | 40 | 47 | — |
| 0 | folpet | 200 | 88 | — |
| 0.025 | folpet | 0.4 | 47 | 72 |
| 0.025 | folpet | 2 | 47 | 72 |
| 0.025 | folpet | 10 | 47 | 72 |
| 0.025 | folpet | 40 | 53 | 72 |
| 0.025 | folpet | 200 | 95 | 93 |
| 0.05 | folpet | 0.4 | 47 | 72 |
| 0.05 | folpet | 2 | 47 | 72 |
| 0.05 | folpet | 10 | 47 | 72 |
| 0.05 | folpet | 40 | 75 | 75 |
| 0.05 | folpet | 200 | 88 | 97 |

TABLE J

Observed and Expected Effects of Compound 1 Alone and Mixtures with Pyraclostrobin, Copper Hydroxide, Fosetyl-Aluminum and Propamocarb in Controlling Cucumber Downy Mildew

| Application Rate (ppm) of Compound 1 | Component (b) | Application Rate (ppm) of Component (b) | CDM Obsd | Exp |
|---|---|---|---|---|
| 0 | — | 0 | 47 | — |
| 0.025 | — | 0 | 47 | — |
| 0.05 | — | 0 | 47 | — |
| 0.075 | — | 0 | 47 | — |
| 0.1 | — | 0 | 47 | — |
| 0.125 | — | 0 | 47 | — |
| 0 | pyraclostrobin | 0.08 | 47 | — |
| 0 | pyraclostrobin | 0.4 | 47 | — |
| 0 | pyraclostrobin | 2 | 57 | — |
| 0 | pyraclostrobin | 10 | 100 | — |
| 0 | pyraclostrobin | 40 | 100 | — |
| 0.025 | pyraclostrobin | 0.08 | 47 | 72 |
| 0.025 | pyraclostrobin | 0.4 | 47 | 72 |
| 0.025 | pyraclostrobin | 2 | 67 | 77 |
| 0.025 | pyraclostrobin | 10 | 100 | 100 |
| 0.025 | pyraclostrobin | 40 | 100 | 100 |
| 0.05 | pyraclostrobin | 0.08 | 47 | 72 |
| 0.05 | pyraclostrobin | 0.4 | 47 | 72 |
| 0.05 | pyraclostrobin | 2 | 70 | 77 |
| 0.05 | pyraclostrobin | 40 | 100 | 100 |
| 0 | copper hydroxide | 2 | 47 | — |
| 0 | copper hydroxide | 10 | 47 | — |

TABLE J-continued

Observed and Expected Effects of Compound 1 Alone and Mixtures with Pyraclostrobin, Copper Hydroxide, Fosetyl-Aluminum and Propamocarb in Controlling Cucumber Downy Mildew

| Application Rate (ppm) of Compound 1 | Component (b) | Application Rate (ppm) of Component (b) | CDM Obsd | Exp |
|---|---|---|---|---|
| 0 | copper hydroxide | 40 | 47 | — |
| 0 | copper hydroxide | 200 | 85 | — |
| 0 | copper hydroxide | 500 | 93 | — |
| 0.025 | copper hydroxide | 2 | 67 | 72 |
| 0.025 | copper hydroxide | 10 | 64 | 72 |
| 0.025 | copper hydroxide | 40 | 98 | 72 |
| 0.025 | copper hydroxide | 200 | 88 | 92 |
| 0.025 | copper hydroxide | 500 | 99 | 96 |
| 0.05 | copper hydroxide | 2 | 67 | 72 |
| 0.05 | copper hydroxide | 10 | 90 | 72 |
| 0.05 | copper hydroxide | 40 | 96 | 72 |
| 0.05 | copper hydroxide | 200 | 99 | 92 |
| 0.05 | copper hydroxide | 500 | 100 | 96 |
| 0 | fosetyl-aluminum | 10 | 47 | — |
| 0 | fosetyl-aluminum | 40 | 47 | — |
| 0 | fosetyl-aluminum | 200 | 63 | — |
| 0 | fosetyl-aluminum | 1000 | 98 | — |
| 0 | fosetyl-aluminum | 2000 | 100 | — |
| 0.025 | fosetyl-aluminum | 10 | 47 | 72 |
| 0.025 | fosetyl-aluminum | 40 | 47 | 72 |
| 0.025 | fosetyl-aluminum | 200 | 57 | 80 |
| 0.025 | fosetyl-aluminum | 1000 | 100 | 99 |
| 0.025 | fosetyl-aluminum | 2000 | 100 | 100 |
| 0.05 | fosetyl-aluminum | 10 | 47 | 72 |
| 0.05 | fosetyl-aluminum | 40 | 47 | 72 |
| 0.05 | fosetyl-aluminum | 200 | 83 | 80 |
| 0.05 | fosetyl-aluminum | 1000 | 100 | 99 |
| 0.05 | fosetyl-aluminum | 2000 | 100 | 100 |
| 0 | propamocarb | 10 | 47 | — |
| 0 | propamocarb | 40 | 47 | — |
| 0 | propamocarb | 200 | 94 | — |
| 0 | propamocarb | 1000 | 100 | — |
| 0 | propamocarb | 5000 | 100 | — |
| 0.025 | propamocarb | 10 | 47 | 72 |
| 0.025 | propamocarb | 40 | 47 | 72 |
| 0.025 | propamocarb | 200 | 95 | 97 |
| 0.025 | propamocarb | 1000 | 100 | 100 |
| 0.025 | propamocarb | 5000 | 100 | 100 |
| 0.05 | propamocarb | 10 | 47 | 72 |
| 0.05 | propamocarb | 40 | 47 | 72 |
| 0.05 | propamocarb | 200 | 47 | 97 |
| 0.05 | propamocarb | 1000 | 100 | 100 |
| 0.05 | propamocarb | 5000 | 100 | 100 |

TABLE K

Observed and Expected Effects of Compound 1 Alone and Mixtures with Cyazofamid, Mefenoxam, Valiphenol, Ethaboxam and Fenamidone in Controlling Cucumber Downy Mildew

| Application Rate (ppm) of Compound 1 | Component (b) | Application Rate (ppm) of Component (b) | CDM Obsd | Exp |
|---|---|---|---|---|
| 0 | — | 0 | 83 | — |
| 0.025 | — | 0 | 76 | — |
| 0.05 | — | 0 | 92 | — |
| 0.075 | — | 0 | 89 | — |
| 0.1 | — | 0 | 98 | — |
| 0.125 | — | 0 | 99 | — |
| 0 | cyazofamid | 0.016 | 47 | — |
| 0 | cyazofamid | 0.08 | 100 | — |
| 0 | cyazofamid | 0.4 | 100 | — |
| 0 | cyazofamid | 2 | 100 | — |
| 0 | cyazofamid | 10 | 100 | — |
| 0.025 | cyazofamid | 0.016 | 67 | 87 |

TABLE K-continued

Observed and Expected Effects of Compound 1 Alone and Mixtures with Cyazofamid, Mefenoxam, Valiphenol, Ethaboxam and Fenamidone in Controlling Cucumber Downy Mildew

| Application Rate (ppm) of Compound 1 | Component (b) | Application Rate (ppm) of Component (b) | CDM Obsd | CDM Exp |
|---|---|---|---|---|
| 0.025 | cyazofamid | 0.08 | 100 | 100 |
| 0.025 | cyazofamid | 0.4 | 100 | 100 |
| 0.025 | cyazofamid | 2 | 100 | 100 |
| 0.025 | cyazofamid | 10 | 100 | 100 |
| 0.05 | cyazofamid | 0.016 | 81 | 96 |
| 0.05 | cyazofamid | 0.08 | 100 | 100 |
| 0.05 | cyazofamid | 0.4 | 100 | 100 |
| 0.05 | cyazofamid | 2 | 100 | 100 |
| 0.05 | cyazofamid | 10 | 100 | 100 |
| 0 | mefenoxam | 0.016 | 66 | — |
| 0 | mefenoxam | 0.08 | 73 | — |
| 0 | mefenoxam | 0.4 | 95 | — |
| 0 | mefenoxam | 2 | 100 | — |
| 0 | mefenoxam | 10 | 100 | — |
| 0.025 | mefenoxam | 0.016 | 80 | 92 |
| 0.025 | mefenoxam | 0.08 | 70 | 93 |
| 0.025 | mefenoxam | 0.4 | 94 | 99 |
| 0.025 | mefenoxam | 2 | 100 | 100 |
| 0.025 | mefenoxam | 10 | 100 | 100 |
| 0.05 | mefenoxam | 0.016 | 80 | 97 |
| 0.05 | mefenoxam | 0.08 | 97 | 98 |
| 0.05 | mefenoxam | 0.4 | 99 | 100 |
| 0.05 | mefenoxam | 2 | 100 | 100 |
| 0.05 | mefenoxam | 10 | 100 | 100 |
| 0 | valiphenal | 0.016 | 65 | — |
| 0 | valiphenal | 0.08 | 47 | — |
| 0 | valiphenal | 0.4 | 47 | — |
| 0 | valiphenal | 2 | 47 | — |
| 0 | valiphenal | 10 | 57 | — |
| 0.025 | valiphenal | 0.016 | 47 | 91 |
| 0.025 | valiphenal | 0.08 | 47 | 87 |
| 0.025 | valiphenal | 0.4 | 57 | 87 |
| 0.025 | valiphenal | 2 | 47 | 87 |
| 0.025 | valiphenal | 10 | 47 | 89 |
| 0.05 | valiphenal | 0.016 | 47 | 97 |
| 0.05 | valiphenal | 0.08 | 57 | 96 |
| 0.05 | valiphenal | 0.4 | 72 | 96 |
| 0.05 | valiphenal | 2 | 70 | 96 |
| 0.05 | valiphenal | 10 | 47 | 97 |
| 0 | ethaboxam | 0.016 | 47 | — |
| 0 | ethaboxam | 0.08 | 47 | — |
| 0 | ethaboxam | 0.4 | 47 | — |
| 0 | ethaboxam | 2 | 82 | — |
| 0 | ethaboxam | 10 | 100 | — |
| 0.025 | ethaboxam | 0.016 | 65 | 87 |
| 0.025 | ethaboxam | 0.08 | 47 | 87 |
| 0.025 | ethaboxam | 0.4 | 60 | 87 |
| 0.025 | ethaboxam | 2 | 92 | 96 |
| 0.025 | ethaboxam | 10 | 100 | 100 |
| 0.05 | ethaboxam | 0.016 | 75 | 96 |
| 0.05 | ethaboxam | 0.08 | 47 | 96 |
| 0.05 | ethaboxam | 0.4 | 67 | 96 |
| 0.05 | ethaboxam | 2 | 95 | 99 |
| 0.05 | ethaboxam | 10 | 100 | 100 |
| 0 | fenamidone | 0.08 | 65 | — |
| 0 | fenamidone | 0.4 | 47 | — |
| 0 | fenamidone | 2 | 82 | — |
| 0 | fenamidone | 10 | 100 | — |
| 0 | fenamidone | 40 | 100 | — |
| 0.025 | fenamidone | 0.08 | 65 | 91 |
| 0.025 | fenamidone | 0.4 | 57 | 87 |
| 0.025 | fenamidone | 2 | 82 | 96 |
| 0.025 | fenamidone | 10 | 99 | 100 |
| 0.025 | fenamidone | 40 | 100 | 100 |
| 0.05 | fenamidone | 0.08 | 75 | 97 |
| 0.05 | fenamidone | 0.4 | 47 | 96 |
| 0.05 | fenamidone | 2 | 82 | 99 |
| 0.05 | fenamidone | 10 | 95 | 100 |
| 0.05 | fenamidone | 40 | 100 | 100 |

TABLE L

Observed and Expected Effects of Compound 1 Alone and Mixtures with 5-chloro-6-(2,4,6-trifluorophenyl)-7-(4-methylpiperidin-yl)[1,2,4]triazolo[1,5-a]pyrimidine (BAS600) in Controlling Cucumber Downy Mildew

| Application Rate (ppm) of Compound 1 | Component (b) | Application Rate (ppm) of Component (b) | CDM Obsd | CDM Exp |
|---|---|---|---|---|
| 0 | — | 0 | 51 | — |
| 0.025 | — | 0 | 51 | — |
| 0.05 | — | 0 | 51 | — |
| 0.075 | — | 0 | 51 | — |
| 0.1 | — | 0 | 98 | — |
| 0.125 | — | 0 | 81 | — |
| 0 | BAS600 | 2 | 0 | — |
| 0 | BAS600 | 10 | 72 | — |
| 0 | BAS600 | 40 | 100 | — |
| 0 | BAS600 | 200 | 100 | — |
| 0.025 | BAS600 | 2 | 23 | 51 |
| 0.025 | BAS600 | 10 | 84 | 86 |
| 0.025 | BAS600 | 40 | 100 | 100 |
| 0.025 | BAS600 | 200 | 100 | 100 |
| 0.05 | BAS600 | 2 | 44 | 51 |
| 0.05 | BAS600 | 10 | 77 | 86 |
| 0.05 | BAS600 | 40 | 100 | 100 |
| 0.05 | BAS600 | 200 | 100 | 100 |

TABLE M

Observed and Expected Effects of Compound 214 Alone and Mixtures with Azoxystrobin, Benthiavalicarb, Chlorothalonil, Copper hydroxide, Fosetyl-aluminum, Iprovalicarb and Pyraclostrobin in Controlling Tomato Late Blight and Cucumber Downy Mildew

| Application Rate (ppm) of Compound 214 | Component (b) | Application Rate (ppm) of Component (b) | TLB Obsd | TLB Exp | CDM Obsd | CDM Exp |
|---|---|---|---|---|---|---|
| 0 | — | 0 | 0 | — | 0 | — |
| 0.00001 | — | 0 | 0 | — | 0 | — |
| 0.0001 | — | 0 | 7 | — | 0 | — |
| 0.001 | — | 0 | 44 | — | 16 | — |
| 0.01 | — | 0 | 98 | — | 83 | — |
| 0.1 | — | 0 | 100 | — | 100 | — |

TABLE M-continued

Observed and Expected Effects of Compound 214 Alone and Mixtures with Azoxystrobin, Benthiavalicarb, Chlorothalonil, Copper hydroxide, Fosetyl-aluminum, Iprovalicarb and Pyraclostrobin in Controlling Tomato Late Blight and Cucumber Downy Mildew

| Application Rate (ppm) of Compound 214 | Component (b) | Application Rate (ppm) of Component (b) | TLB Obsd | TLB Exp | CDM Obsd | CDM Exp |
|---|---|---|---|---|---|---|
| 0 | — | 0.08 | 7 | — | 0 | — |
| 0 | azoxystrobin | 0.4 | 29 | — | 0 | — |
| 0 | azoxystrobin | 2 | 56 | — | 70 | — |
| 0 | azoxystrobin | 10 | 90 | — | 100 | — |
| 0 | azoxystrobin | 40 | 100 | — | 100 | — |
| 0.001 | azoxystrobin | 0.08 | 21 | 48 | 8 | 16 |
| 0.001 | azoxystrobin | 0.4 | 22 | 60 | 17 | 16 |
| 0.001 | azoxystrobin | 2 | 53 | 75 | 85 | 74 |
| 0.001 | azoxystrobin | 10 | 100 | 94 | 100 | 100 |
| 0.001 | azoxystrobin | 40 | 100 | 100 | 100 | 100 |
| 0.01 | azoxystrobin | 0.08 | 69 | 99 | 75 | 83 |
| 0.01 | azoxystrobin | 0.4 | 94 | 99 | 64 | 83 |
| 0.01 | azoxystrobin | 2 | 100 | 99 | 98 | 95 |
| 0.01 | azoxystrobin | 10 | 100 | 100 | 100 | 100 |
| 0.01 | azoxystrobin | 40 | 100 | 100 | 100 | 100 |
| 0 | benthiavalicarb | 0.08 | 21 | — | 0 | — |
| 0 | benthiavalicarb | 0.4 | 82 | — | 75 | — |
| 0 | benthiavalicarb | 2 | 100 | — | 100 | — |
| 0 | benthiavalicarb | 10 | 100 | — | 100 | — |
| 0 | benthiavalicarb | 40 | 100 | — | 100 | — |
| 0.001 | benthiavalicarb | 0.08 | 29 | 56 | 0 | 16 |
| 0.001 | benthiavalicarb | 0.4 | 100 | 90 | 81 | 79 |
| 0.001 | benthiavalicarb | 2 | 100 | 100 | 100 | 100 |
| 0.001 | benthiavalicarb | 10 | 100 | 100 | 100 | 100 |
| 0.001 | benthiavalicarb | 40 | 100 | 100 | 100 | 100 |
| 0.01 | benthiavalicarb | 0.08 | 95 | 99 | 73 | 83 |
| 0.01 | benthiavalicarb | 0.4 | 100 | 100 | 99 | 96 |
| 0.01 | benthiavalicarb | 2 | 100 | 100 | 100 | 100 |
| 0.01 | benthiavalicarb | 10 | 100 | 100 | 100 | 100 |
| 0.01 | benthiavalicarb | 40 | 100 | 100 | 100 | 100 |
| 0 | chlorothalonil | 0.08 | 14 | — | 0 | — |
| 0 | chlorothalonil | 0.4 | 14 | — | 0 | — |
| 0 | chlorothalonil | 2 | 21 | — | 0 | — |
| 0 | chlorothalonil | 10 | 100 | — | 70 | — |
| 0 | chlorothalonil | 40 | 100 | — | 71 | — |
| 0.001 | chlorothalonil | 0.08 | 36 | 52 | 0 | 16 |
| 0.001 | chlorothalonil | 0.4 | 28 | 52 | 0 | 16 |
| 0.001 | chlorothalonil | 2 | 36 | 56 | 0 | 16 |
| 0.001 | chlorothalonil | 10 | 92 | 100 | 62 | 74 |
| 0.001 | chlorothalonil | 40 | 100 | 100 | 95 | 75 |
| 0.01 | chlorothalonil | 0.08 | 82 | 99 | 75 | 83 |
| 0.01 | chlorothalonil | 0.4 | 70 | 99 | 79 | 83 |
| 0.01 | chlorothalonil | 2 | 86 | 99 | 72 | 83 |
| 0.01 | chlorothalonil | 10 | 100 | 100 | 75 | 95 |
| 0.01 | chlorothalonil | 40 | 100 | 100 | 99 | 95 |
| 0 | copper hydroxide | 2 | 22 | — | 0 | — |
| 0 | copper hydroxide | 10 | 36 | — | 0 | — |
| 0 | copper hydroxide | 40 | 50 | — | 0 | — |
| 0 | copper hydroxide | 200 | 71 | — | 29 | — |
| 0 | copper hydroxide | 500 | 77 | — | 37 | — |
| 0.001 | copper hydroxide | 2 | 56 | 56 | 0 | 16 |
| 0.001 | copper hydroxide | 10 | 61 | 64 | 0 | 16 |
| 0.001 | copper hydroxide | 40 | 84 | 72 | 26 | 16 |
| 0.001 | copper hydroxide | 200 | 71 | 83 | 52 | 40 |
| 0.001 | copper hydroxide | 500 | 82 | 87 | 64 | 47 |
| 0.01 | copper hydroxide | 2 | 88 | 99 | 47 | 83 |
| 0.01 | copper hydroxide | 10 | 80 | 99 | 47 | 83 |
| 0.01 | copper hydroxide | 40 | 74 | 99 | 47 | 83 |
| 0.01 | copper hydroxide | 200 | 71 | 100 | 47 | 88 |
| 0.01 | copper hydroxide | 500 | 85 | 100 | 47 | 89 |
| 0 | fosetyl-aluminum | 10 | 0 | — | 0 | — |
| 0 | fosetyl-aluminum | 40 | 0 | — | 0 | — |
| 0 | fosetyl-aluminum | 200 | 50 | — | 0 | — |
| 0 | fosetyl-aluminum | 1000 | 99 | — | 68 | — |
| 0 | fosetyl-aluminum | 2000 | 100 | — | 73 | — |
| 0.001 | fosetyl-aluminum | 10 | 29 | 44 | 47 | 16 |
| 0.001 | fosetyl-aluminum | 40 | 58 | 44 | 0 | 16 |
| 0.001 | fosetyl-aluminum | 200 | 90 | 72 | 33 | 16 |
| 0.001 | fosetyl-aluminum | 1000 | 99 | 100 | | |
| 0.001 | fosetyl-aluminum | 2000 | 100 | 100 | 67 | 78 |
| 0.01 | fosetyl-aluminum | 10 | 92 | 98 | 52 | 83 |
| 0.01 | fosetyl-aluminum | 40 | 99 | 98 | 75 | 83 |

TABLE M-continued

Observed and Expected Effects of Compound 214 Alone and Mixtures with Azoxystrobin, Benthiavalicarb, Chlorothalonil, Copper hydroxide, Fosetyl-aluminum, Iprovalicarb and Pyraclostrobin in Controlling Tomato Late Blight and Cucumber Downy Mildew

| Application Rate (ppm) of Compound 214 | Component (b) | Application Rate (ppm) of Component (b) | TLB Obsd | TLB Exp | CDM Obsd | CDM Exp |
|---|---|---|---|---|---|---|
| 0.01 | fosetyl-aluminum | 200 | 100 | 99 | 90 | 83 |
| 0.01 | fosetyl-aluminum | 1000 | 100 | 100 | 100 | 94 |
| 0.01 | fosetyl-aluminum | 2000 | 100 | 100 | 100 | 95 |
| 0 | iprovalicarb | 0.08 | 0 | — | 0 | — |
| 0 | iprovalicarb | 0.4 | 21 | — | 0 | — |
| 0 | iprovalicarb | 2 | 74 | — | 0 | — |
| 0 | iprovalicarb | 10 | 98 | — | 99 | — |
| 0 | iprovalicarb | 40 | 100 | — | 100 | — |
| 0.001 | iprovalicarb | 0.08 | 36 | 44 | 0 | 16 |
| 0.001 | iprovalicarb | 0.4 | 54 | 56 | 0 | 16 |
| 0.001 | iprovalicarb | 2 | 79 | 85 | 0 | 16 |
| 0.001 | iprovalicarb | 10 | 100 | 99 | 100 | 99 |
| 0.001 | iprovalicarb | 40 | 100 | 100 | 100 | 100 |
| 0.01 | iprovalicarb | 0.08 | 82 | 98 | 71 | 83 |
| 0.01 | iprovalicarb | 0.4 | 79 | 99 | 64 | 83 |
| 0.01 | iprovalicarb | 2 | 99 | 100 | 58 | 83 |
| 0.01 | iprovalicarb | 10 | 100 | 100 | 100 | 100 |
| 0.01 | iprovalicarb | 40 | 100 | 100 | 100 | 100 |
| 0 | pyraclostrobin | 0.08 | 15 | — | 0 | — |
| 0 | pyraclostrobin | 0.4 | 35 | — | 0 | — |
| 0 | pyraclostrobin | 2 | 63 | — | 68 | — |
| 0 | pyraclostrobin | 10 | 90 | — | 100 | — |
| 0 | pyraclostrobin | 40 | 94 | — | 100 | — |
| 0.001 | pyraclostrobin | 0.08 | 42 | 52 | 0 | 16 |
| 0.001 | pyraclostrobin | 0.4 | 79 | 63 | 40 | 16 |
| 0.001 | pyraclostrobin | 2 | 65 | 79 | 62 | 73 |
| 0.001 | pyraclostrobin | 10 | 82 | 94 | 100 | 100 |
| 0.001 | pyraclostrobin | 40 | 95 | 96 | 100 | 100 |
| 0.01 | pyraclostrobin | 0.08 | 94 | 99 | 60 | 83 |
| 0.01 | pyraclostrobin | 0.4 | 94 | 99 | 60 | 83 |
| 0.01 | pyraclostrobin | 2 | 95 | 99 | 95 | 95 |
| 0.01 | pyraclostrobin | 10 | 99 | 100 | 100 | 100 |
| 0.01 | pyraclostrobin | 40 | 92 | 100 | 100 | 100 |

TABLE N

Observed and Expected Effects of Compound 214 Alone and Mixtures with Cymoxanil, Dimethomorph, Fluazinam, Folpet, Mancozeb, Mandipropamid and Propamocarb in Controlling Tomato Late Blight and Cucumber Downy Mildew

| Application Rate (ppm) of Compound 214 | Component (b) | Application Rate (ppm) of Component (b) | TLB Obsd | TLB Exp | CDM Obsd | CDM Exp |
|---|---|---|---|---|---|---|
| 0 | — | 0 | 30 | — | 15 | — |
| 0.00001 | — | 0 | 8 | — | 23 | — |
| 0.0001 | — | 0 | 38 | — | 31 | — |
| 0.001 | — | 0 | 56 | — | 21 | — |
| 0.01 | — | 0 | 99 | — | 73 | — |
| 0.1 | — | 0 | 100 | — | 100 | — |
| 0 | cymoxanil | 0.04 | 44 | — | 15 | — |
| 0 | cymoxanil | 2 | 46 | — | 0 | — |
| 0 | cymoxanil | 10 | 100 | — | 0 | — |
| 0 | cymoxanil | 40 | 100 | — | 0 | — |
| 0 | cymoxanil | 200 | 100 | — | 21 | — |
| 0.001 | cymoxanil | 0.04 | 67 | 75 | 0 | 33 |
| 0.001 | cymoxanil | 2 | 72 | 76 | 15 | 21 |
| 0.001 | cymoxanil | 10 | 100 | 100 | 0 | 21 |
| 0.001 | cymoxanil | 40 | 100 | 100 | 15 | 21 |
| 0.001 | cymoxanil | 200 | 100 | 100 | 0 | 38 |
| 0.01 | cymoxanil | 0.04 | 96 | 99 | 89 | 77 |
| 0.01 | cymoxanil | 2 | 96 | 99 | 83 | 73 |
| 0.01 | cymoxanil | 10 | 100 | 100 | 65 | 73 |
| 0.01 | cymoxanil | 40 | 100 | 100 | 85 | 73 |
| 0.01 | cymoxanil | 200 | 100 | 100 | 79 | 78 |
| 0 | dimethomorph | 0.08 | 31 | — | 52 | — |
| 0 | dimethomorph | 0.4 | 62 | — | 54 | — |
| 0 | dimethomorph | 2 | 95 | — | 88 | — |
| 0 | dimethomorph | 10 | 88 | — | 100 | — |

TABLE N-continued

Observed and Expected Effects of Compound 214 Alone and Mixtures with Cymoxanil, Dimethomorph, Fluazinam, Folpet, Mancozeb, Mandipropamid and Propamocarb in Controlling Tomato Late Blight and Cucumber Downy Mildew

| Application Rate (ppm) of Compound 214 | Component (b) | Application Rate (ppm) of Component (b) | TLB Obsd | TLB Exp | CDM Obsd | CDM Exp |
|---|---|---|---|---|---|---|
| 0 | dimethomorph | 40 | 100 | — | 100 | — |
| 0.001 | dimethomorph | 0.08 | 62 | 70 | 16 | 62 |
| 0.001 | dimethomorph | 0.4 | 62 | 83 | 0 | 64 |
| 0.001 | dimethomorph | 2 | 88 | 98 | 80 | 91 |
| 0.001 | dimethomorph | 10 | 78 | 95 | 100 | 100 |
| 0.001 | dimethomorph | 40 | 97 | 100 | 100 | 100 |
| 0.01 | dimethomorph | 0.08 | 94 | 99 | 39 | 87 |
| 0.01 | dimethomorph | 0.4 | 89 | 99 | 70 | 87 |
| 0.01 | dimethomorph | 2 | 94 | 100 | 94 | 97 |
| 0.01 | dimethomorph | 10 | 88 | 100 | 100 | 100 |
| 0.01 | dimethomorph | 40 | 99 | 100 | 100 | 100 |
| 0 | fluazinam | 0.04 | 23 | — | 56 | — |
| 0 | fluazinam | 2 | 71 | — | 89 | — |
| 0 | fluazinam | 10 | 99 | — | 98 | — |
| 0 | fluazinam | 40 | 99 | — | 100 | — |
| 0 | fluazinam | 200 | 100 | — | 100 | — |
| 0.001 | fluazinam | 0.04 | 75 | 66 | 8 | 65 |
| 0.001 | fluazinam | 2 | 90 | 87 | 75 | 92 |
| 0.001 | fluazinam | 10 | 97 | 100 | 100 | 98 |
| 0.001 | fluazinam | 40 | 100 | 99 | 100 | 100 |
| 0.001 | fluazinam | 200 | 100 | 100 | 99 | 100 |
| 0.01 | fluazinam | 0.04 | 95 | 99 | 75 | 88 |
| 0.01 | fluazinam | 2 | 97 | 100 | 90 | 97 |
| 0.01 | fluazinam | 10 | 100 | 100 | 100 | 99 |
| 0.01 | fluazinam | 40 | 100 | 100 | 100 | 100 |
| 0.01 | fluazinam | 200 | 100 | 100 | 100 | 100 |
| 0 | folpet | 0.04 | 0 | — | 0 | — |
| 0 | folpet | 2 | 8 | — | 0 | — |
| 0 | folpet | 10 | 31 | — | 44 | — |
| 0 | folpet | 40 | 46 | — | 74 | — |
| 0 | folpet | 200 | 93 | — | 87 | — |
| 0.001 | folpet | 0.04 | 16 | 56 | 0 | 21 |
| 0.001 | folpet | 2 | 23 | 59 | 0 | 21 |
| 0.001 | folpet | 10 | 44 | 70 | 65 | 56 |
| 0.001 | folpet | 40 | 51 | 76 | 87 | 79 |
| 0.001 | folpet | 200 | 87 | 97 | 86 | 90 |
| 0.01 | folpet | 0.04 | 85 | 99 | 31 | 73 |
| 0.01 | folpet | 2 | 86 | 99 | 75 | 73 |
| 0.01 | folpet | 10 | 75 | 99 | 86 | 85 |
| 0.01 | folpet | 40 | 65 | 99 | 89 | 93 |
| 0.01 | folpet | 200 | 95 | 100 | 99 | 97 |
| 0 | mancozeb | 0.04 | 23 | — | 0 | — |
| 0 | mancozeb | 2 | 24 | — | 0 | — |
| 0 | mancozeb | 10 | 66 | — | 36 | — |
| 0 | mancozeb | 40 | 100 | — | 92 | — |
| 0 | mancozeb | 200 | 100 | — | 100 | — |
| 0.001 | mancozeb | 0.04 | 31 | 66 | 69 | 21 |
| 0.001 | mancozeb | 2 | 60 | 66 | 49 | 21 |
| 0.001 | mancozeb | 10 | 77 | 85 | 49 | 50 |
| 0.001 | mancozeb | 40 | 100 | 100 | 95 | 93 |
| 0.001 | mancozeb | 200 | 100 | 100 | 100 | 100 |
| 0.01 | mancozeb | 0.04 | 92 | 99 | 93 | 73 |
| 0.01 | mancozeb | 2 | 100 | 99 | 86 | 73 |
| 0.01 | mancozeb | 10 | 98 | 99 | 88 | 82 |
| 0.01 | mancozeb | 40 | 99 | 100 | 99 | 98 |
| 0.01 | mancozeb | 200 | 100 | 100 | 95 | 100 |
| 0 | mandipropamid | 0.08 | 80 | — | 86 | — |
| 0 | mandipropamid | 0.4 | 97 | — | 100 | — |
| 0 | mandipropamid | 2 | 99 | — | 100 | — |
| 0 | mandipropamid | 10 | 100 | — | 100 | — |
| 0 | mandipropamid | 40 | 100 | — | 100 | — |
| 0.001 | mandipropamid | 0.08 | 96 | 91 | 79 | 89 |
| 0.001 | mandipropamid | 0.4 | 93 | 99 | 100 | 100 |
| 0.001 | mandipropamid | 2 | 95 | 99 | 100 | 100 |
| 0.001 | mandipropamid | 10 | 98 | 100 | 100 | 100 |
| 0.001 | mandipropamid | 40 | 100 | 100 | 100 | 100 |
| 0.01 | mandipropamid | 0.08 | 98 | 100 | 97 | 96 |
| 0.01 | mandipropamid | 0.4 | 95 | 100 | 100 | 100 |
| 0.01 | mandipropamid | 2 | 100 | 100 | 100 | 100 |
| 0.01 | mandipropamid | 10 | 100 | 100 | 100 | 100 |
| 0.01 | mandipropamid | 40 | 100 | 100 | 100 | 100 |
| 0 | propamocarb | 10 | 0 | — | 46 | — |

TABLE N-continued

Observed and Expected Effects of Compound 214 Alone and Mixtures with Cymoxanil, Dimethomorph, Fluazinam, Folpet, Mancozeb, Mandipropamid and Propamocarb in Controlling Tomato Late Blight and Cucumber Downy Mildew

| Application Rate (ppm) of Compound 214 | Component (b) | Application Rate (ppm) of Component (b) | TLB Obsd | TLB Exp | CDM Obsd | CDM Exp |
|---|---|---|---|---|---|---|
| 0 | propamocarb | 40 | 0 | — | 31 | — |
| 0 | propamocarb | 200 | 0 | — | 86 | — |
| 0 | propamocarb | 1000 | 38 | — | 99 | — |
| 0 | propamocarb | 5000 | 92 | — | 100 | — |
| 0.001 | propamocarb | 10 | 38 | 56 | 72 | 57 |
| 0.001 | propamocarb | 40 | 51 | 56 | 76 | 45 |
| 0.001 | propamocarb | 200 | 56 | 56 | 88 | 89 |
| 0.001 | propamocarb | 1000 | 92 | 73 | 100 | 99 |
| 0.001 | propamocarb | 5000 | 98 | 96 | 100 | 100 |
| 0.01 | propamocarb | 10 | 97 | 99 | 93 | 85 |
| 0.01 | propamocarb | 40 | 95 | 99 | 93 | 81 |
| 0.01 | propamocarb | 200 | 97 | 99 | 100 | 96 |
| 0.01 | propamocarb | 1000 | 99 | 99 | 99 | 100 |
| 0.01 | propamocarb | 5000 | 100 | 100 | 100 | 100 |

TABLE O

Observed and Expected Effects of Compound 214 Alone and Mixtures with Mefenoxan, Ethanboxam, Fluopicolide, Fenamidone, Penthiopyrad, Quinoxyfen and BAS600 in Controlling Tomato Late Blight and Cucumber Downy Mildew

| Application Rate (ppm) of Compound 214 | Component (b) | Application Rate (ppm) of Component (b) | TLB Obsd | TLB Exp | CDM Obsd | CDM Exp |
|---|---|---|---|---|---|---|
| 0 | — | 0 | 0 | — | 0 | — |
| 0.00001 | — | 0 | 22 | — | 0 | — |
| 0.0001 | — | 0 | 7 | — | 0 | — |
| 0.001 | — | 0 | 22 | — | 24 | — |
| 0.01 | — | 0 | 98 | — | 88 | — |
| 0.1 | — | 0 | 100 | — | 100 | — |
| 0 | mefenoxam | 0.016 | 0 | — | 0 | — |
| 0 | mefenoxam | 0.08 | 22 | — | 56 | — |
| 0 | mefenoxam | 0.4 | 48 | — | 97 | — |
| 0 | mefenoxam | 2 | 100 | — | 100 | — |
| 0 | mefenoxam | 10 | 100 | — | 100 | — |
| 0.001 | mefenoxam | 0.016 | 63 | 22 | 0 | 24 |
| 0.001 | mefenoxam | 0.08 | 77 | 40 | 77 | 66 |
| 0.001 | mefenoxam | 0.4 | 95 | 59 | 97 | 98 |
| 0.001 | mefenoxam | 2 | 100 | 100 | 100 | 100 |
| 0.001 | mefenoxam | 10 | 100 | 100 | 100 | 100 |
| 0.01 | mefenoxam | 0.016 | 95 | 98 | 80 | 88 |
| 0.01 | mefenoxam | 0.08 | 100 | 99 | 90 | 95 |
| 0.01 | mefenoxam | 0.4 | 100 | 99 | 100 | 100 |
| 0.01 | mefenoxam | 2 | 100 | 100 | 100 | 100 |
| 0.01 | mefenoxam | 10 | 100 | 100 | 100 | 100 |
| 0 | ethaboxam | 0.016 | 22 | — | 0 | — |
| 0 | ethaboxam | 0.08 | 15 | — | 0 | — |
| 0 | ethaboxam | 0.4 | 95 | — | 41 | — |
| 0 | ethaboxam | 2 | 87 | — | 100 | — |
| 0 | ethaboxam | 10 | 100 | — | 100 | — |
| 0.001 | ethaboxam | 0.016 | 22 | 40 | 0 | 24 |
| 0.001 | ethaboxam | 0.08 | 33 | 34 | 0 | 24 |
| 0.001 | ethaboxam | 0.4 | 67 | 96 | 0 | 56 |
| 0.001 | ethaboxam | 2 | 91 | 90 | 100 | 100 |
| 0.001 | ethaboxam | 10 | 96 | 100 | 100 | 100 |
| 0.01 | ethaboxam | 0.016 | 84 | 99 | 58 | 88 |
| 0.01 | ethaboxam | 0.08 | 99 | 99 | 53 | 88 |
| 0.01 | ethaboxam | 0.4 | 100 | 100 | 66 | 93 |
| 0.01 | ethaboxam | 2 | 100 | 100 | 100 | 100 |
| 0.01 | ethaboxam | 10 | 100 | 100 | 100 | 100 |
| 0 | fluopicolide | 0.08 | 7 | — | 0 | — |
| 0 | fluopicolide | 0.4 | 0 | — | 0 | — |
| 0 | fluopicolide | 2 | 90 | — | 83 | — |
| 0 | fluopicolide | 10 | 100 | — | 100 | — |
| 0 | fluopicolide | 40 | 100 | — | 100 | — |
| 0.001 | fluopicolide | 0.08 | 22 | 28 | 9 | 24 |
| 0.001 | fluopicolide | 0.4 | 69 | 22 | 33 | 24 |
| 0.001 | fluopicolide | 2 | 85 | 92 | 87 | 87 |

TABLE O-continued

Observed and Expected Effects of Compound 214 Alone and Mixtures with Mefenoxan, Ethanboxam, Fluopicolide, Fenamidone, Penthiopyrad, Quinoxyfen and BAS600 in Controlling Tomato Late Blight and Cucumber Downy Mildew

| Application Rate (ppm) of Compound 214 | Component (b) | Application Rate (ppm) of Component (b) | TLB | | CDM | |
|---|---|---|---|---|---|---|
| | | | Obsd | Exp | Obsd | Exp |
| 0.001 | fluopicolide | 10 | 100 | 100 | 100 | 100 |
| 0.001 | fluopicolide | 40 | 100 | 100 | 100 | 100 |
| 0.01 | fluopicolide | 0.08 | 99 | 99 | 79 | 88 |
| 0.01 | fluopicolide | 0.4 | 100 | 98 | 71 | 88 |
| 0.01 | fluopicolide | 2 | 100 | 100 | 95 | 98 |
| 0.01 | fluopicolide | 10 | 100 | 100 | 100 | 100 |
| 0.01 | fluopicolide | 40 | 100 | 100 | 100 | 100 |
| 0 | fenamidone | 0.08 | 22 | — | 0 | — |
| 0 | fenamidone | 0.4 | 30 | — | 0 | — |
| 0 | fenamidone | 2 | 99 | — | 85 | — |
| 0 | fenamidone | 10 | 100 | — | 100 | — |
| 0 | fenamidone | 40 | 100 | — | 100 | — |
| 0.001 | fenamidone | 0.08 | 30 | 40 | 0 | 24 |
| 0.001 | fenamidone | 0.4 | 74 | 45 | 0 | 24 |
| 0.001 | fenamidone | 2 | 92 | 99 | 91 | 89 |
| 0.001 | fenamidone | 10 | 100 | 100 | 100 | 100 |
| 0.001 | fenamidone | 40 | 100 | 100 | 100 | 100 |
| 0.01 | fenamidone | 0.08 | 99 | 99 | 80 | 88 |
| 0.01 | fenamidone | 0.4 | 94 | 99 | 76 | 88 |
| 0.01 | fenamidone | 2 | 100 | 100 | 97 | 98 |
| 0.01 | fenamidone | 10 | 100 | 100 | 100 | 100 |
| 0.01 | fenamidone | 40 | 100 | 100 | 100 | 100 |
| 0 | penthiopyrad | 0.4 | 0 | — | 0 | — |
| 0 | penthiopyrad | 2 | 22 | — | 0 | — |
| 0 | penthiopyrad | 10 | 7 | — | 0 | — |
| 0 | penthiopyrad | 40 | 15 | — | 0 | — |
| 0 | penthiopyrad | 200 | 7 | — | 16 | — |
| 0.001 | penthiopyrad | 0.4 | 65 | 22 | 16 | 24 |
| 0.001 | penthiopyrad | 2 | 22 | 40 | 0 | 24 |
| 0.001 | penthiopyrad | 10 | 61 | 28 | 0 | 24 |
| 0.001 | penthiopyrad | 40 | 70 | 34 | 0 | 24 |
| 0.001 | penthiopyrad | 200 | 48 | 28 | 40 | 36 |
| 0.01 | penthiopyrad | 0.4 | 100 | 98 | 66 | 88 |
| 0.01 | penthiopyrad | 2 | 100 | 99 | 63 | 88 |
| 0.01 | penthiopyrad | 10 | 99 | 99 | 68 | 88 |
| 0.01 | penthiopyrad | 40 | 100 | 99 | 63 | 88 |
| 0.01 | penthiopyrad | 200 | 98 | 99 | 94 | 90 |
| 0 | quinoxyfen | 0.4 | 0 | — | 0 | — |
| 0 | quinoxyfen | 2 | 7 | — | 0 | — |
| 0 | quinoxyfen | 10 | 7 | — | 0 | — |
| 0 | quinoxyfen | 40 | 0 | — | 0 | — |
| 0 | quinoxyfen | 200 | 0 | — | 0 | — |
| 0.001 | quinoxyfen | 0.4 | 7 | 22 | 0 | 24 |
| 0.001 | quinoxyfen | 2 | 49 | 28 | 0 | 24 |
| 0.001 | quinoxyfen | 10 | 68 | 28 | 0 | 24 |
| 0.001 | quinoxyfen | 40 | 76 | 22 | 0 | 24 |
| 0.001 | quinoxyfen | 200 | 53 | 22 | 0 | 24 |
| 0.01 | quinoxyfen | 0.4 | 99 | 98 | 47 | 88 |
| 0.01 | quinoxyfen | 2 | 100 | 99 | 47 | 88 |
| 0.01 | quinoxyfen | 10 | 93 | 99 | 17 | 88 |
| 0.01 | quinoxyfen | 40 | 100 | 98 | 16 | 88 |
| 0.01 | quinoxyfen | 200 | 100 | 98 | 0 | 88 |
| 0 | BAS600 | 2 | 7 | — | 0 | — |
| 0 | BAS600 | 10 | 0 | — | 99 | — |
| 0 | BAS600 | 40 | 15 | — | 100 | — |
| 0 | BAS600 | 200 | 30 | — | 100 | — |
| 0 | BAS600 | 500 | 15 | — | 100 | — |
| 0.001 | BAS600 | 2 | 30 | 28 | 0 | 24 |
| 0.001 | BAS600 | 10 | 36 | 22 | 65 | 99 |
| 0.001 | BAS600 | 40 | 30 | 34 | 98 | 100 |
| 0.001 | BAS600 | 200 | 36 | 45 | 100 | 100 |
| 0.001 | BAS600 | 500 | 22 | 34 | 100 | 100 |
| 0.01 | BAS600 | 2 | 100 | 99 | 70 | 88 |
| 0.01 | BAS600 | 10 | 83 | 98 | 100 | 100 |
| 0.01 | BAS600 | 40 | 69 | 99 | 100 | 100 |
| 0.01 | BAS600 | 200 | 74 | 99 | 100 | 100 |
| 0.01 | BAS600 | 500 | 80 | 99 | 100 | 100 |

TABLE P

Observed and Expected Effects of Compound 214 Alone and Mixtures with Cyazofamid, Valiphenal, Boscalid, Famoxadone, Kresoxim-methyl, Trifloxystrobin and proquinazid in Controlling Tomato Late Blight and Cucumber Downy Mildew

| Application Rate (ppm) of Compound 214 | Component (b) | Application Rate (ppm) of Component (b) | TLB Obsd | TLB Exp | CDM Obsd | CDM Exp |
|---|---|---|---|---|---|---|
| 0 | — | 0 | 24 | — | 37 | — |
| 0.00001 | — | 0 | 8 | — | 31 | — |
| 0.0001 | — | 0 | 17 | — | 16 | — |
| 0.001 | — | 0 | 39 | — | 63 | — |
| 0.01 | — | 0 | 94 | — | 68 | — |
| 0.1 | — | 0 | 100 | — | 100 | — |
| 0 | cyazofamid | 0.016 | 25 | — | 43 | — |
| 0 | cyazofamid | 0.08 | 52 | — | 57 | — |
| 0 | cyazofamid | 0.4 | 58 | — | 100 | — |
| 0 | cyazofamid | 2 | 100 | — | 100 | — |
| 0 | cyazofamid | 10 | 100 | — | 100 | — |
| 0.001 | cyazofamid | 0.016 | 8 | 54 | 72 | 78 |
| 0.001 | cyazofamid | 0.08 | 38 | 71 | 82 | 84 |
| 0.001 | cyazofamid | 0.4 | 84 | 74 | 100 | 100 |
| 0.001 | cyazofamid | 2 | 95 | 100 | 100 | 100 |
| 0.001 | cyazofamid | 10 | 100 | 100 | 100 | 100 |
| 0.01 | cyazofamid | 0.016 | 94 | 95 | 90 | 82 |
| 0.01 | cyazofamid | 0.08 | 95 | 100 | 98 | 100 |
| 0.01 | cyazofamid | 0.4 | 96 | 100 | 99 | 100 |
| 0.01 | cyazofamid | 2 | 100 | 100 | 100 | 100 |
| 0.01 | cyazofamid | 10 | 100 | 100 | 100 | 100 |
| 0 | valiphenal | 0.016 | 8 | — | 31 | — |
| 0 | valiphenal | 0.08 | 8 | — | 16 | — |
| 0 | valiphenal | 0.4 | 8 | — | 16 | — |
| 0 | valiphenal | 2 | 32 | — | 53 | — |
| 0 | valiphenal | 10 | 99 | — | 100 | — |
| 0.001 | valiphenal | 0.016 | 17 | 44 | 67 | 74 |
| 0.001 | valiphenal | 0.08 | 24 | 44 | 64 | 68 |
| 0.001 | valiphenal | 0.4 | 32 | 44 | 68 | 68 |
| 0.001 | valiphenal | 2 | 72 | 59 | 78 | 82 |
| 0.001 | valiphenal | 10 | 99 | 99 | 95 | 100 |
| 0.01 | valiphenal | 0.016 | 81 | 94 | 92 | 78 |
| 0.01 | valiphenal | 0.08 | 72 | 100 | 95 | 100 |
| 0.01 | valiphenal | 0.4 | 75 | 100 | 94 | 100 |
| 0.01 | valiphenal | 2 | 93 | 100 | 90 | 100 |
| 0.01 | valiphenal | 10 | 99 | 100 | 99 | 100 |
| 0 | boscalid | 0.04 | 25 | — | 68 | — |
| 0 | boscalid | 2 | 0 | — | 0 | — |
| 0 | boscalid | 10 | 0 | — | 0 | — |
| 0 | boscalid | 40 | 17 | — | 0 | — |
| 0 | boscalid | 200 | 32 | — | 0 | — |
| 0.001 | boscalid | 0.04 | 8 | 54 | 31 | 88 |
| 0.001 | boscalid | 2 | 21 | 39 | 16 | 63 |
| 0.001 | boscalid | 10 | 25 | 39 | 21 | 63 |
| 0.001 | boscalid | 40 | 17 | 49 | 0 | 63 |
| 0.001 | boscalid | 200 | 25 | 59 | 0 | 63 |
| 0.01 | boscalid | 0.04 | 63 | 95 | 93 | 90 |
| 0.01 | boscalid | 2 | 62 | 100 | 91 | 100 |
| 0.01 | boscalid | 10 | 68 | 100 | 76 | 100 |
| 0.01 | boscalid | 40 | 70 | 100 | 73 | 100 |
| 0.01 | boscalid | 200 | 71 | 100 | 0 | 100 |
| 0 | famoxadone | 0.04 | 100 | — | 100 | — |
| 0 | famoxadone | 2 | 32 | — | 21 | — |
| 0 | famoxadone | 10 | 93 | — | 72 | — |
| 0 | famoxadone | 40 | 98 | — | 100 | — |
| 0 | famoxadone | 200 | 100 | — | 100 | — |
| 0.001 | famoxadone | 0.04 | 65 | 100 | 0 | 100 |
| 0.001 | famoxadone | 2 | 90 | 59 | 47 | 71 |
| 0.001 | famoxadone | 10 | 84 | 96 | 60 | 90 |
| 0.001 | famoxadone | 40 | 100 | 99 | 100 | 100 |
| 0.001 | famoxadone | 200 | 100 | 100 | 100 | 100 |
| 0.01 | famoxadone | 0.04 | 83 | 100 | 95 | 100 |
| 0.01 | famoxadone | 2 | 81 | 100 | 95 | 100 |
| 0.01 | famoxadone | 10 | 95 | 100 | 96 | 100 |
| 0.01 | famoxadone | 40 | 100 | 100 | 100 | 100 |
| 0.01 | famoxadone | 200 | 100 | 100 | 100 | 100 |
| 0 | kresoxim-methyl | 0.04 | 8 | — | 9 | — |
| 0 | kresoxim-methyl | 2 | 32 | — | 9 | — |
| 0 | kresoxim-methyl | 10 | 86 | — | 30 | — |
| 0 | kresoxim-methyl | 40 | 96 | — | 37 | — |
| 0 | kresoxim-methyl | 200 | 100 | — | 100 | — |
| 0.001 | kresoxim-methyl | 0.04 | 17 | 44 | 31 | 66 |

TABLE P-continued

Observed and Expected Effects of Compound 214 Alone and Mixtures with Cyazofamid,
Valiphenal, Boscalid, Famoxadone, Kresoxim-methyl, Trifloxystrobin and proquinazid in
Controlling Tomato Late Blight and Cucumber Downy Mildew

| Application Rate (ppm) of Compound 214 | Component (b) | Application Rate (ppm) of Component (b) | TLB Obsd | TLB Exp | CDM Obsd | CDM Exp |
|---|---|---|---|---|---|---|
| 0.001 | kresoxim-methyl | 2 | 39 | 59 | 16 | 66 |
| 0.001 | kresoxim-methyl | 10 | 85 | 92 | 75 | 74 |
| 0.001 | kresoxim-methyl | 40 | 99 | 98 | 93 | 76 |
| 0.001 | kresoxim-methyl | 200 | 100 | 100 | 100 | 100 |
| 0.01 | kresoxim-methyl | 0.04 | 90 | 94 | 90 | 71 |
| 0.01 | kresoxim-methyl | 2 | 87 | 100 | 92 | 100 |
| 0.01 | kresoxim-methyl | 10 | 94 | 100 | 95 | 100 |
| 0.01 | kresoxim-methyl | 40 | 99 | 100 | 100 | 100 |
| 0.01 | kresoxim-methyl | 200 | 100 | 100 | 100 | 100 |
| 0 | trifloxystrobin | 0.04 | 0 | — | 0 | — |
| 0 | trifloxystrobin | 2 | 0 | — | 0 | — |
| 0 | trifloxystrobin | 10 | 72 | — | 16 | — |
| 0 | trifloxystrobin | 40 | 38 | — | 89 | — |
| 0 | trifloxystrobin | 200 | 25 | — | 100 | — |
| 0.001 | trifloxystrobin | 0.04 | 38 | 39 | 63 | 63 |
| 0.001 | trifloxystrobin | 2 | 38 | 39 | 39 | 63 |
| 0.001 | trifloxystrobin | 10 | 39 | 83 | 68 | 68 |
| 0.001 | trifloxystrobin | 40 | 25 | 62 | 83 | 96 |
| 0.001 | trifloxystrobin | 200 | 52 | 54 | 100 | 100 |
| 0.01 | trifloxystrobin | 0.04 | 62 | 94 | 89 | 68 |
| 0.01 | trifloxystrobin | 2 | 87 | 100 | 85 | 100 |
| 0.01 | trifloxystrobin | 10 | 62 | 100 | 83 | 100 |
| 0.01 | trifloxystrobin | 40 | 82 | 100 | 93 | 100 |
| 0.01 | trifloxystrobin | 200 | 87 | 100 | 98 | 100 |
| 0 | proquinazid | 0.04 | 17 | — | 0 | — |
| 0 | proquinazid | 2 | 0 | — | 0 | — |
| 0 | proquinazid | 10 | 8 | — | 0 | — |
| 0 | proquinazid | 40 | 8 | — | 0 | — |
| 0 | proquinazid | 200 | 17 | — | 0 | — |
| 0.001 | proquinazid | 0.04 | 55 | 49 | 0 | 63 |
| 0.001 | proquinazid | 2 | 17 | 39 | 0 | 63 |
| 0.001 | proquinazid | 10 | 8 | 44 | 0 | 63 |
| 0.001 | proquinazid | 40 | 25 | 44 | 31 | 63 |
| 0.001 | proquinazid | 200 | 25 | 49 | 9 | 63 |
| 0.01 | proquinazid | 0.04 | 77 | 95 | 24 | 68 |
| 0.01 | proquinazid | 2 | 81 | 100 | 37 | 100 |
| 0.01 | proquinazid | 10 | 96 | 100 | 47 | 100 |
| 0.01 | proquinazid | 40 | 82 | 100 | 58 | 100 |
| 0.01 | proquinazid | 200 | 96 | 100 | 72 | 100 |

Tables A-P show compositions of the present invention comprising mixtures of a representative Formula 1 compound with a variety of component (b) compounds demonstrating synergistic control of tomato late blight and cucumber downy mildew. As control cannot exceed 100%, the increase above expected fungicidal activity can be greatest when the separate active ingredient components alone are at application rates providing considerably less than 100% control. Synergy may not be evident at low application rates where the individual active ingredient components alone have little activity. However, in some instances high activity was observed for combinations wherein individual active ingredients alone at the same application rates had essentially no activity. As demonstrated above, this invention provides advantageous method of combating tomato late blight (*Phytophthora infestans*) and cucumber downy mildew (*Pseudoperonospora cubensis*) diseases.

What is claimed is:

1. A fungicidal composition comprising:
   (a) at least one compound selected from the compounds of Formula 1, N-oxides, and salts thereof,

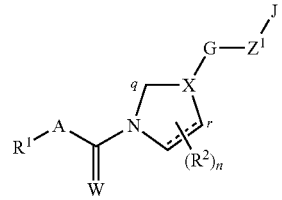

1 wherein

R$^1$ is

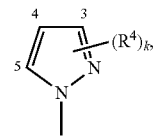

U-1

-continued

U-2: [thiophene with methyl and $(R^4)_k$]

U-3: [furan with methyl and $(R^4)_k$]

U-11: [pyrazole with methyl and $(R^4)_k$]

U-13: [imidazole with methyl and $(R^4)_k$]

U-20: [triazole with N-methyl and $(R^4)_k$]

U-22: [furan with methyl and $(R^4)_k$]

U-23: [thiophene with methyl and $(R^4)_k$]

U-36: [N-methyl imidazole with $(R^4)_k$]

U-37: [pyridine with methyl and $(R^4)_k$]

U-38: [pyridine with methyl and $(R^4)_k$]

U-39: [pyridine with methyl and $(R^4)_k$] or

U-50: [phenyl with methyl and $(R^4)_k$, positions 2,3,4,5]

each $R^{4a}$ is independently $C_1$-$C_2$ alkyl, $C_1$-$C_2$ haloalkyl, halogen, $C_1$-$C_2$ alkoxy or $C_1$-$C_2$ haloalkoxy;

each $R^{4b}$ is independently $C_1$-$C_2$ alkyl or $C_1$-$C_2$ haloalkyl;

A is $CH_2$ or NH;

W is O;

X is a radical selected from $X^1$: [saturated fragment with labels t, u, v] and $X^3$: [alkene fragment with labels t, u, v];

wherein the bond of $X^1$ or $X^3$, which is identified with "t" is connected to the carbon atom identified with "q" of Formula 1, the bond which is identified with "u" is connected to the carbon atom identified with "r" of Formula 1, and the bond which is identified with "v" is connected to G;

each $R^2$ is independently methyl, methoxy, cyano or hydroxy;

G is

G-1: [thiazole with $R^{3a}$ at 5, methyl at 2, positions 2,4,5]

G-2: [oxazole with $R^{3a}$ at 5, methyl at 2, positions 2,4,5]

G-7: [thiadiazole with methyl]

G-8: [oxadiazole with methyl]

G-14: [oxazole with $R^{3a}$ and methyl]

G-15: [thiazole with $R^{3a}$ and methyl]

G-23: [isoxazole with methyl and $R^{3a}$]

G-24: [isothiazole with methyl and $R^{3a}$]

-continued
G-26 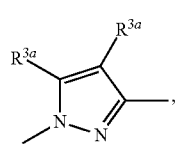
G-27 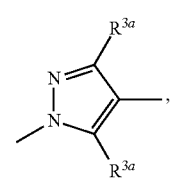
G-36 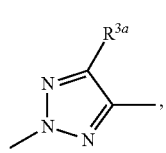
G-37 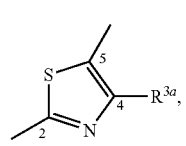
G-38 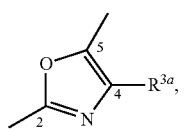
G-49 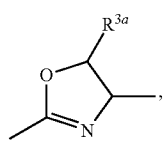
G-50 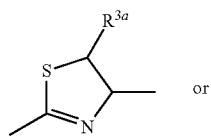 or
G-55 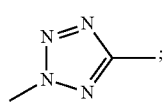
wherein the bond projecting to the left is bonded to X, and the bond projecting to the right is bonded to $Z^1$; each $R^{3a}$ is independently selected from H or $R^3$;
each $R^3$ is independently methyl or halogen;
J is
J-1 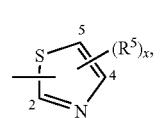
J-2 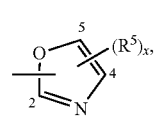
-continued
J-3 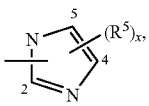
J-4 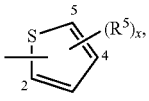
J-5 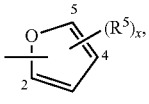
J-7 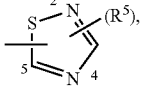
J-8 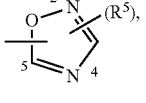
J-9 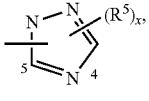
J-10 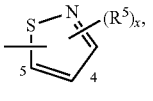
J-11 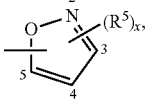
J-12 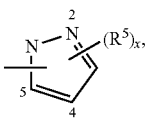
J-14 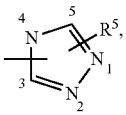
J-15 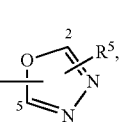
J-16

-continued

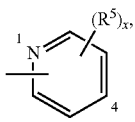 J-20

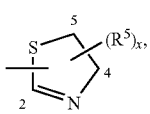 J-24

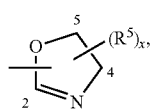 J-25

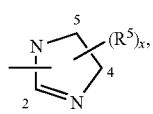 J-26

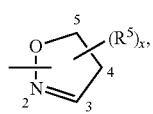 J-29

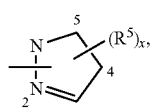 J-30

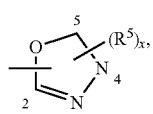 J-37

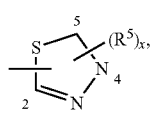 J-38

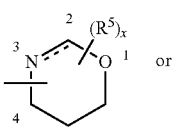 J-45

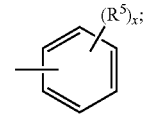 J-69

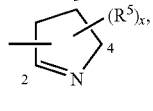 J-27 wherein the bond shown projecting to the left is bonded to $Z^1$ each $R^5$ is independently H, cyano, $C_1$-$C_6$ alkyl, $C_1$-$C_6$ haloalkyl, $C_3$-$C_8$ cycloalkyl, $C_3$-$C_8$ halocycloalkyl, $C_2$-$C_6$ alkoxalkyl, $C_1$-$C_6$ alkoxy, $C_1$-$C_6$ haloalkoxy, $C_3$-$C_8$ cycloalkoxy, $C_2$-$C_6$ alkenyloxy, $C_2$-$C_6$ haloalkenyloxy, $C_2$-$C_6$ alkynyloxy, $C_2$-$C_6$ alkoxyaloxy, $C_2$-$C_6$ alkylcarbonloxy, $C_2$-$C_6$ haloalkylcarbonyloxy, $C_1$-$C_6$ alkylthio, $C_1$-$C_6$ haloakylthio, $C_3$-$C_{10}$ trialkylsilyl, —$NR^{25}R^{26}$ or $Z^2Q$;

each $R^{25}$ is independently H, $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

each $R^{26}$ is independently $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl, $C_2$-$C_6$ haloalkoxycarbonyl or —$Z^4Q$;

Q is one of Q-1 through Q-102

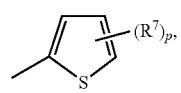 Q-1

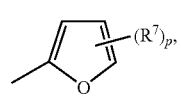 Q-2

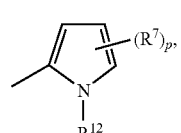 Q-3

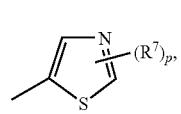 Q-4

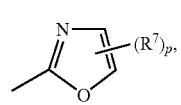 Q-5

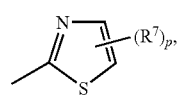 Q-6

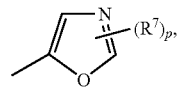 Q-7

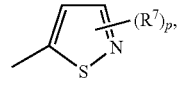 Q-8

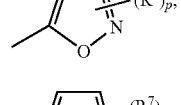 Q-9

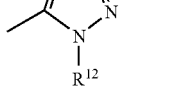 Q-10

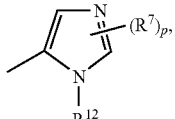 Q-11

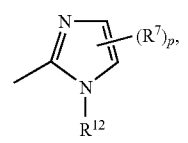 Q-12
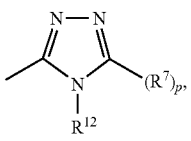 Q-13
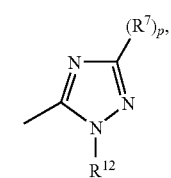 Q-14
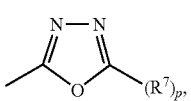 Q-15
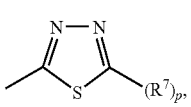 Q-16
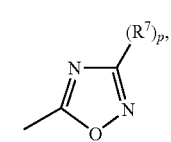 Q-17
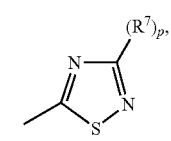 Q-18
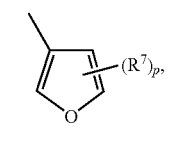 Q-19
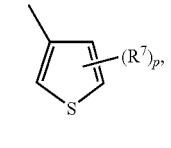 Q-20
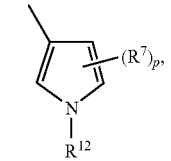 Q-21
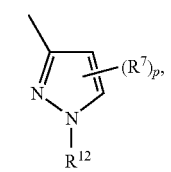 Q-22
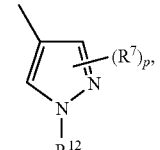 Q-23
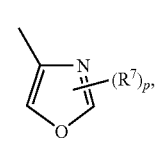 Q-24
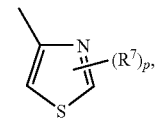 Q-25
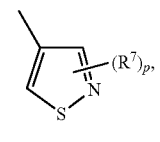 Q-26
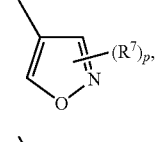 Q-27
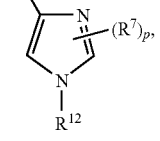 Q-28
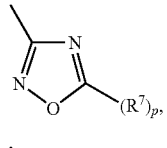 Q-29
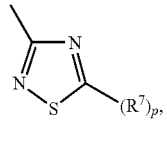 Q-30
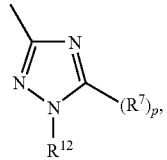 Q-31
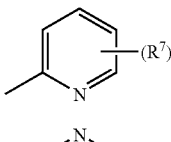 Q-32
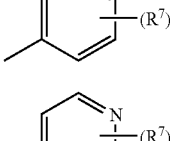 Q-33
Q-34

-continued
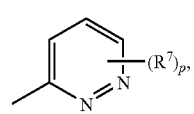 Q-35
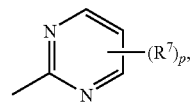 Q-36
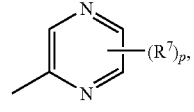 Q-37
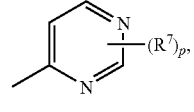 Q-38
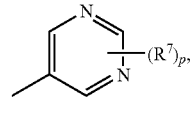 Q-39
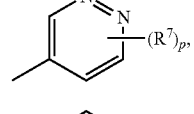 Q-40
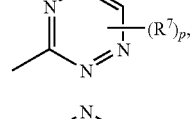 Q-41
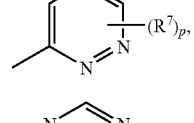 Q-42
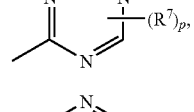 Q-43
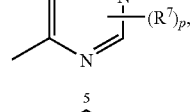 Q-44
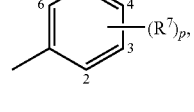 Q-45
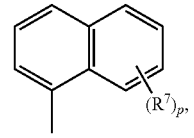 Q-46
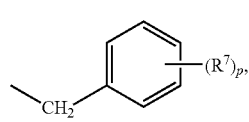 Q-47
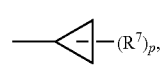 Q-48
-continued
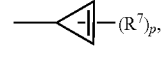 Q-49
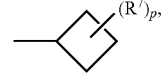 Q-50
 Q-51
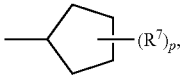 Q-52
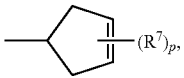 Q-53
 Q-54
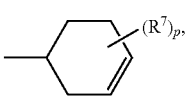 Q-55
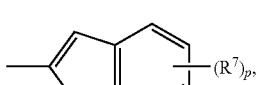 Q-56
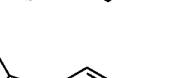 Q-57
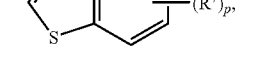 Q-58
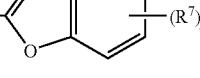 Q-59
 Q-60
 Q-61

-continued

| Q-81 | Q-92 |
| Q-82 | Q-93 |
| Q-83 | Q-94 |
| Q-84 | Q-95 |
| Q-85 | Q-96 |
| Q-86 | Q-97 |
| Q-87 | Q-98 |
| Q-88 | Q-99 |
| Q-89 | Q-100 |
| Q-90 | Q-101 or |
| Q-91 | Q-102 | each $R^7$ is independently halogen, cyano, $C_1$-$C_3$ alkyl, $C_1$-$C_3$ haloalkyl, hydroxy, $C_1$-$C_2$ alkoxy or $C_1$-$C_2$ haloalkoxy; or each $R^{12}$ is independently H, $C_1$-$C_3$ alkyl, $C_1$-$C_3$ alkylcarbonyl, $C_1$-$C_3$ alkoxycarbonyl or $C_1$-$C_3$ alkoxy;

$Z^1$ is a direct bond;

$Z^2$ is a direct bond or $NR^{21}$;

each $Z^4$ is C(=O);

each $R^{21}$ is independently H, $C_1$-$C_6$ alkyl, $C_1$-$C_6$ haloalkyl, $C_3$-$C_8$ cycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

k is 1 or 2;

x is an integer from 0 to 5;

p is 0, 1, 2, or 3; and n is 0, and (b) at least one additional fungicidal compound;

provided that:

(i) when $R^4$ is attached to a carbon ring member, said $R^4$ is selected from $R^{4a}$; and (ii) when $R^4$ is attached to a nitrogen ring member, said. $R^4$ is selected from $R^{4b}$.

2. The composition of claim 1 wherein component (a) is a compound of Formula 1 or a salt thereof, wherein A is $CH_2$;

G is selected from G-1, G-2, G-15, G-26, G-27, G-36, G-37 and G-38; and G is unsubstituted;

J is selected from J-4, J-5, J-8, J-11, J-15, J-16, J-20, J-29, J-30, J-37, J-38, and J-69;

Q is selected from Q-1, Q-45, Q-63, Q-64, Q-65, Q-68, Q-69, Q-70, Q-71, Q-72, Q-73, Q-76, Q-78, Q-79, Q-84, Q-85, Q-98, Q-99, Q-100, Q-101 and Q-102;

X is $X^1$ and the ring comprising X is saturated;

$R^1$ is U-1 or U-50;

each $R^{4a}$ is independently $C_1$-$C_2$ alkyl, trifluoromethyl, Cl, Br, I or methoxy;

each $R^{4b}$ is independently $C_1$-$C_2$ alkyl or trifluoromethyl; and each $R^5$ is independently H, cyano, $C_1$-$C_6$ alkyl, $C_1$-$C_6$ haloalkyl, $C_1$-$C_6$ alkoxy, $C_1$-$C_6$ haloalkoxy, —$NR^{25}R^{26}$ or $Z^2$Q.

3. The composition of claim 2 wherein component (a) is a compound of Formula 1 or a salt thereof, wherein G is selected from G-1, G-2, G-15, G-26 and G-36;

J is selected from J-4, J-5, J-11, J-20, J-29, J-37, J-38, and J-69; and

Q is selected from Q-45, Q-63, Q-64, Q-65, Q-68, Q-69, Q-70, Q-71, Q-72 and Q-85.

4. The composition of claim 1 wherein component (a) is selected from the group consisting of 4-[4-[(5R)-4,5-dihydro-5-phenyl-3-isoxazolyl]-2-thiazolyl]-1-[[5-methyl-3-(trifluoromethyl)-1H-pyrazol-1-yl]acetyl]piperidine and its enantiomer, 1-[[5-methyl-3-(trifluoromethyl)-1H-pyrazol-1-yl]acetyl]-4-[4-(5-phenyl-3-isoxazolyl)-2-thiazolyl]piperidine, 1-[4-[4-[(5R)-4,5-dihydro-5-methyl-5-phenyl-3-isoxazolyl]-2-thiazolyl]-1-piperidinyl]-2-[5-methyl-3-(trifluoromethyl)-1H-pyrazol-1-yl]ethanone and its enantiomer, 2-[5-methyl-3-(trifluoromethyl)-1H-pyrazol-1-yl]-1-[4-[4-[(3aS,9bR), 3a,4,5,9b-tetrahydronaphth[2,1-d]isoxazol-3-yl]-2-thiazolyl]-1-piperidinyl]ethanone and its enantiomer, 1-[4-[4-[(5R)-4,5-dihydro-5-phenyl-3-isoxazolyl]-2-thiazolyl]-1-piperidinyl]-2-[5-ethyl-3-(trifluoromethyl)-1H-pyrazol-1-yl]ethanone and its enantiomer, 2-[3,5-bis(trifluoromethyl)-1H-pyrazol-1-yl]-1-[4-[4-[(5R)-4,5-dihydro-5-phenyl-3-isoxazolyl]-2-thiazolyl]-1-piperidinyl]ethanone and its enantiomer, 1-[4-[4-[(5R)-3',4'-dihydrospiro[isoxazole-5(4H),1',(2'H)-naphthalen]-3-yl]-2-thiazolyl]-1-piperidinyl]-2-[5-methyl-3-(trifluoromethyl)-1H-pyrazol-1-yl]ethanone and its enantiomer, 1-[4-[4-[(5R)-2,3-dihydrospiro[1H-indene-1,5'(4'H)-isoxazol]-3'-yl]-2-thiazolyl]-1-piperidinyl]-2-[5-methyl-3-(trifluoromethyl)-1H-pyrazol-1-yl]ethanone and its enantiomer, 2-[5-chloro-3-(trifluoromethyl)-1H-pyrazol-1-yl]-1-[4-[4-[(5R)-4,5-dihydro-5-phenyl-3-isoxazoly]-2-thiazolyl]-1-piperidinyl]ethanone and its enantiomer, 2-[(5R)-4,5-dihydro-3-[2-[1-[2-[5-methyl-3-(trifluoromethyl)-1H-pyrazol-1-yl]acetyl]-4-piperidinyl]-4-thiazolyl-5-isoxazolyl]-1H-isoindole-1,3(2H)-dione and its enantiomer, 2-[5-chloro-3-(trifluoromethyl)-1H-pyrazol-1-yl]-1-[4-[4-[(1R)-2,3-dihydrospiro[1H-indene-1,5'(4'H)-isoxazol]-3'-yl]-2-thiazolyl]-1-piperidinyl]ethanone and its enantiomer, 2-[5-chloro-3-(trifluoromethyl)-1H-pyrazol-1-yl]-1-[4-[4-[(1'R)-3',4'-dihydrospiro[isoxazole-5(4H),1'(2H)-naphthalen]-3-yl]-2-thiazolyl]-1-piperidinyl]ethanone and its enantiomer, 2-[5-methyl-3-(trifluoromethyl)-1H-pyrazol-1-yl]-1-[4-[4-(3R)-spiro[benzofuran-3(2H),5'(4'H)-isoxazol]-3'-yl-2-thiazolyl]-1-piperidinyl]ethanone and its enantiomer, 1-[4-[4-[(1R)-2,3-dihydrospiro[1H-indene-1,5'(4'H)-isoxazol]-3'-yl]-2-thiazolyl]-1-piperidinyl-2-(3,5-dimethyl-1H-pyrazol-1-yl)ethatione and its enantiomer, 2-[3,5-bis(trifluoromethyl)-1H-pyrazol-1-yl]-1-[4-[4-[(1'R)-3',4'-dihydrospiro[isoxazole-5(4H),1'(2H)-naphthalen]-3-yl]-2-thiazolyl]-1-piperidinyl]ethatione and its enantiomer, 2-[3,5-bis(trifluoromethyl)-1H-pyrazol-1-yl]-1-[4-[4-[(1R)-2,3-dihydrospiro[1H-indene-1,5'(4'H)-isoxazol]-3'-yl]-2-thiazolyl]-1-piperidinyl]ethanone and its enantiomer, 1-[4-[4-[(5R)-5-(2,6-dichlorophenyl)-4,5-dihydro-3-isoxazolyl]-2-thiazolyl]-1-piperidinyl]-2-[5-methyl-3-(trifluoromethyl)-1H-pyrazol-1-yl]ethanone and its enantiomer, 1-[4-[4-[(5R)-4,5-dihydro-5-(2-fluorophenyl)-3-isoxazolyl]-2-thiazolyl]-1-piperidinyl]-2-[5-methyl-3-(trifluoromethyl)-1H-pyrazol-1-yl]etharione and its enantiomer, 1-[4-[4-[(5R)-4,5-dihydro-5-(2-methylphenyl)-3-isoxazolyl]-2-thiazolyl]-1-piperidinyl]-2-[5-methyl-3-(trifluoromethyl)-1H-pyrazol-1-yl]ethanone and its enantiomer, 1-[4-[4-[(5R)-4,5-dihydro-5-(2,6-dimethylphenyl)-3-isoxazolyl]-2-thiazolyl]-1-piperidinyl]-2-[5-methyl-3-(trifluoromethyl)-1H-pyrazol-1-yl]ethanone and its enantiomer, 1-[4-[4-[(5R)-4,5-dihydro-5-(2,4,6-trimethylphenyl)-3-isoxazolyl]-2-thiazolyl]-1-piperidinyl]-2-[5-methyl-3-(trifluoromethyl)-1H-pyrazol-1-yl]ethanone and its enantiomer, 1-[4-[4-[(1'R)-3',4'-dihydrospiro[isoxazole-5(4H),1'(2')-naphthalen]-3-yl]-2-thiazolyl]-1-piperidinyl]-2-(3,5-dimethyl-1H-pyrazol-1-yl)ethanone and its enantiomer, 1-[4-[4-[(5R)-4,5-dihydro-5-(2,4,6-trimethoxyphenyl)-3-isoxazolyl]-2-thiazoly]-1-piperidinyl]-2-[5-methyl-3-(trifluoromethyl)-1H-pyrazol-1-yl]ethanone and its enantiomer, 3-[(5R)-4,5-dihydro-3-2-[1-[2-[5-methyl-3-(trifluoromethyl)-1H-pyrazol-1-yl]acetyl]-4-piperidinyl]-4-thiazolyl]-5-isoxazoly]-2(3H)-benzoxazolone and its enantiomer, 1-[4-[4-[(5R)-5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone and its enantiomer, 2-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]benzonitrile and its enantiomer, 2-[5-chloro-3-(trifluoromethyl)-1H-pyrazol-1-yl]-1-[4-[4-[(5R)-4,5-dihydro-5-methyl-5-phenyl-3-isoxazolyl]-2-thiazolyl]-1-piperidinyl]ethanone and its enantiomer, 2-[3,5-bis(trifluoromethyl)-1H-pyrazol-1-yl]-1-[4-[4-[(5R)-4,5-dihydro-5-methyl-5-phenyl-3-isoxazolyl]-2-thiazolyl]-1-piperidinyl]ethanone and its enantiomer, 1-[4-[4-[(5R)-5-(2-ehlorophenyl)-4,5-dihydro-3-isoxazolyl]-2-thiazoly]-1-piperidinyl]-2-[5-methyl-3-(triluoromethyl)-1H-pyrazol-1-yl]ethanone and its enantiomer, 1-[4-[4-[(5R)-4,5-dihydro-5-phenyl-3-isoxazolyl]-2-thiazoly]-1-piperidinyl]-2-[3-methyl-5-(tritluoromethyl)-1H-pyrazol-1-yl]ethanone and its enantiomer, 1-[4-[4-[(4S)-2,3-dihydrospiro[4H-1-benzopyran-4,5'(4'H)-isoxazol]-3'-yl)-2-thiazolyl]-1-piperidinyl]-2-[5-methyl-3-(trifluoromethyl)-1H-pyrazol-1-yl]ethanone and its enantiomer, (5R)-4,5-dihydro-3-[2-[1-[2-[5-methyl-3-(trifluoromethyl)-1H-pyrazol-1-yl]acetyl]-4-piperidinyl]-4-thiazolyl]-5-phenyl-5-isoxazolecarbonitrile and its enantiomer, 1-[4-[4-[(5R)-4,5-dihydro-5-phenyl-3-isoxazolyl]-2-thiazolyl]-1-piperidinyl]-2-[5-methyl-3-(trifluoromethyl)-1H-pyrazol-1-yl]ethanone and its enantiomer, 1-[(5R)-4,5-dihydro-3-[2-[1-[2-[5-methyl-3-(triflnoromethyl)-1H-pyrazol-1-yl]acetyl]-4-piperidinyl]-4-thiazolyl]-5-isoxazolyl]-1,3-dihydro-3-methyl-2H-benzimidazol-2-one and its enantiomer, N-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-N-phenylacetamide and its enantiomer, 4-[4-[(5R)-4,5-dihydro-5-phenyl-3-isoxazolyl]-2-thiazoly]-N-(2,5-dimethylphenyl)-1-piperidineearboxamide and its enantiomer, 3-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-2(3H)-benzothiazolone and its enantiomer, 1-acetyl-3-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-1,3-dihydro-2H-benzimidazol-2-one and its enantiomer, 4-[4-[(5R)-4,5-dihydro-5-phenyl-3-isoxazolyl]-2-thiazolyl]-N-[5-methyl-3-(trifluoromethyl)-1H-pyrazolyl-1-yl]-1-piperidinecarboxamide and its enantiomer, and 1-[4-[4-[(5R)-5-(2-bromophenyl)-4,5-dihydro-3-isoxazolyl]-2-thiazolyl]-1-piperidinyl]-2-[5-methyl-3-(trifluoromethyl)-1H-pyrazol-1-yl]ethanone and its enantiomer.

5. The composition of claim 1 wherein component (a) is 4-[4-[(5R)-4,5-dihydro-5-phenyl-3-isoxazolyl]-2-thiazolyl]-1-[[5-methyl-3-(trifluoromethyl)-1H-pyrazol-1-yl]acetyl]piperidine, its enantiomer or a mixture thereof.

6. The composition of claim 1 wherein component (a) is 1-[4-[4-[(5R)-5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, its enantiomer or a mixture thereof.

7. The composition of claim 1 wherein component (b) includes at least one compound selected from the group consisting of
   (b1) methyl benzimidazole carbamate fungicides;
   (b2) dicarboximide fungicides;
   (b3) demethylation inhibitor fungicides;
   (b4) phenylamide fungicides;
   (b5) amine/morpholine fungicides;
   (b6) phospholipid biosynthesis inhibitor fungicides;
   (b7) carboxamide fungicides;
   (b8) hydroxy(2-amino-)pyrimidine fungicides;
   (b9) anilinopyrimidine fungicides;
   (b10) N-phenyl carbamate fungicides;
   (b11) quinone outside inhibitor fungicides;
   (b12) phenylpyrrole fungicides;
   (b13) quinoline fungicides;
   (b14) lipid peroxidation inhibitor fungicides;
   (b15) melanin biosynthesis inhibitors-reductase fungicides;
   (b16) melanin biosynthesis inhibitors-dehydratase fungicides;
   (b17) hydroxyanilide fungicides;
   (b18) squalene-epoxidase inhibitor fungicides;
   (b19) polyoxin fungicides;
   (b20) phenylurea fungicides;
   (b21) quinone inside inhibitor fungicides;
   (b22) benzamide fungicides;
   (b23) enopyranuronic acid antibiotic fungicides;
   (b24) hexopyranosyl antibiotic fungicides;
   (b25) glucopyranosyl antibiotic: protein synthesis fungicides;
   (b26) glucopyranosyl antibiotic: trehalase and inositol biosynthesis fungicides;
   (b27) cyanoacetamideoxime fungicides;
   (b28) carbamate fungicides;
   (b29) oxidative phosphorylation uncoupling fungicides;
   (b30) organo tin fungicides;
   (b31) carboxylic acid fungicides;
   (b32) heteroaromatic fungicides;
   (b33) phosphonate fungicides;
   (b34) phthalamic acid fungicides;
   (b35) benzotriazine fungicides;
   (b36) benzene-sulfonamide fungicides;
   (b37) pyridazinone fungicides;
   (b38) thiophene-carboxamide fungicides;
   (b39) pyrimidinamide fungicides;
   (b40) carboxylic acid amide fungicides;
   (b41) tetracycline antibiotic fungicides;
   (b42) thioearbamate fungicides;
   (b43) benzamide fungicides;
   (b44) host plant defense induction fungicides;
   (b45) multi-site contact activity fungicides; and
   (b46) fungicides other than fungicides of component (a) and components (b1) through (b45).

8. The composition of claim 1 further comprising at least one additional component selected from the group consisting of a surfactant, a solid diluent and a liquid diluent.

9. The composition of claim 1 wherein weight ratio of component (a) to component (b) is from about 125:1 to about 1:125.

10. The composition of claim 1 wherein component (a) is selected from the group consisting of
- 4-[4-[(5R)-5-(2,6-difluorophenyl)-4,5-dihydro-3-isoxazolyl]-2-thiazoly]-N-(2,5-dimethylphenyl)-1-piperidinecarboxamide and its enantiomer,
- 2-(3,5-dimethyl-1H-pyrazol-1-yl)-1-[4-[4-[(5R)-5-(2,6-difluorophenyl)-4,5-dihydro-3-isoxazoly]-2-thiazoly]-1-piperidinyl]ethanone and its enantiomer,
- 2-(2,5-dimethylphenyl)-1-[4-[4-[(5R)-5-(2,6-difluorophenyl)-4,5-dihydro-3-isoxazolyl]-2-thiazolyl]-1-piperidinyl]ehanone and its enantiomer, and
- 1-[4-[4-[(5R)-4,5-dihydro-5-[2-(trifluoromethyl)phenyl]-3-isoxazolyl]-2-thiazolyl]-1-piperidinyl]-2-[5-methyl-3-(trifluoromethyl)-1H-pyrazol-1-yl]ethanone and its enantiomer.

11. The composition of claim 1 wherein component (a) is selected from the group consisting of
- 2-[3,5-bis(trifluorornethyl)-1H-pyrazol-1-yl]-1-[4-[4-[(5R)-4,5-dihydro-5-phenyl-3-isoxazolyl]-2-thiazolyl]-1-piperidinyl]ethanone and its enantiomer,
- 1-[4-[4-[(5R)-3',4'-dihydrospiro[isoxazole-5(4H),1',(2'H)-naphthalen]-3-yl]-2-thiazolyl]-1-piperidinyl]-2-[5-methyl-3-(trifluoromethyl)-1H-pyrazol-1-yl]ethanone and its enantiomer,
- 1-[4-[4-[(5R)-2,3-dihydrospiro[1H-indene-1,5'(4'H)-isoxazol]-3'-yl]-2-thiazolyl]-1-piperidinyl]-2-[5-methyl-3-(trifluoromethyl)-1H-pyrazol-1-yl]ethanone and its enantiomer,
- 2-[(5R)-4,5-dihydro-3-[2-[1-[2-[5-methyl-3-(trifluoromethyl)-1H-pyrazol-1-yl]acetyl]-4-piperidinyl]-4-thiazolyl-5-isoxazolyl]-1H-isoindole-1,3(2H)-dione and its enantiomer,
- 1-[4-[4-[(5R)-4,5-dihydro-5-(2-fluorophenyl)-3-isoxazolyl]-2-thiazoly]-1-piperidinyl]-2-[5-methyl-3-(trifluoromethyl)-1H-pyrazol-1-yl]ethanone and its enantiomer,
- 1-[4-[4-[(5R)-5-(2,6-dimethylphenyl)-4,5-dihydro-3-isoxazolyl]-2-thiazolyl]-1-piperidinyl]-2-[5-methyl-3-(trifluoromethyl)-1H-pyrazol-1-yl]ethanone and its enantiomer,
- 3-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]-2(3H)-benzoxazolone and its enantiomer,
- 1-[4-[4-[(5R)-5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone and its enantiomer,
- 2-[(5R)-4,5-dihydro-3-[2-[1-[2-[5-methyl-3-(trifluoromethyl)-1H-pyrazol-1-yl]acetyl]-4-piperidinyl]-4-thiazolyl]-5-isoxazolyl]benzonitrile and its enantiomer,
- (5R)-4,5-dihydro-3-[2-[1-[2-[5-methyl-3-(trifluoromethyl)-1H-pyrazol-1-yl]acetyl]-4-piperidinyl]-4-thiazoly]-5-phenyl-5-isoxazolecarbonitrile and its enantiomer,
- 1-[4-[4-[(5R)-4,5-dihydro-5-phenyl-3-isoxazolyl]-2-thiazolyl]-1-piperidinyl]-2-[5-methyl-3-(trifluoromethyl)-1H-pyrazol-1-yl]ethanone and its enantiomer,
- 4-[4-[(5R)-4,5-dihydro-5-phenyl-3-isoxazolyl]-2-thiazolyl]-N-(2,5-dimethylphenyl)-1-piperidinecarboxamide and its enantiomer,
- 1-[4-[4-[(5R)-4,5-dihydro-5-[2-(trifluoromethyl)phenyl]-3-isoxazolyl]-2-thiazolyl]-1-piperidinyl]-2-[5-methyl-3-(trifluoromethyl)-1H-pyrazol-1-yl]ethanone and its enantiomer,
- 1-[4-[4-[(5R)-5-(2,6-difluorophenyl)-4,5-dihydro-3-isoxazolyl]-2-thiazolyl]-1-piperidinyl]-2-(3,5-dimethyl-1H-pyrazol-1-yl]ethanone and its enantiomer,
- [4-[4-[(5R)-5-(2,6-difluorophenyl)-4,5-dihydro-3-isoxazolyl]-2-thiazolyl]-N-(2,5-dimethylphenyl)-1-piperidinecarboxamide and its enantiomer,
- 1-[4-[4-[(5R)-5-(2,6-difluorophenyl)-4,5-dihydro-3-isoxazolyl]-2-thiazolyl]-1-piperidinyl]-2-(2,5-dimethylphenyl)ethanone and its enantiomer and
- 1-[4-[4-[(5R)-5-(2,6-difluorophenyl)-4,5-dihydro-3-isoxazolyl]-2-thiazolyl]-1-piperidinyl]-2-(2,5-dimethylphenyl)-2-hydroxy-ethanone and its enantiomer.

12. The composition of claim 1 wherein component (b) includes at least one compound selected from acibenzolar-S-methyl, aldimorph, amisulbrom, anilazine, azaconazole, azoxystrobin, benalaxyl, benalaxyl-M, benodanil, benomyl, benthiavalicarb, benthiavalicarb-isopropyl, bethoxazin, binapacryl, biphenyl, bitertanol, bixafen, blasticidin-S, Bordeaux mixture (tribasic copper sulfate), boscalid, brornuconazole, bupirimate, captafol, captan, carbendazim, carboxin, carpropamid, chloroneb, chlorothalonil, chlozolinate, clotrimazole, copper oxychloride, copper salts such as copper sulfate and copper hydroxide, cyazofamid, cyflufenamid, cymoxanil, cyproconazole, cyprodinil, dichlolluanid, diclocyrnet, diclomezine, dicloran, diethofencarb, difenoconazole, diflumetorim, dimethirimol, dimethomorph, dimoxystrobin, diniconazole, diniconazole M, dinocap, dithianon, dodemorph, dodine, edifenphos, enestroburin, epoxiconazole, ethaboxam, etridiazole, famoxadone, fenamidone, fenarimol, fenbuconazole, fenfuram, fenhexamid, fenoxanil, feripiclonil, fenpropidin, fenpropimorph, fentin acetate, fentin chloride, fentin hydroxide, ferbam, ferimzone, fluazinam, fludioxonil, flumetover, flumorph, fluopicolide, fluopyram, fluoromide, fluoxastrobin, fluquinconazole, flusilazole, flusulfamide, flutianil, flutolanil, flutriafol, folpet, fosetyl-aluminum, fuberidazole, furalaxyl, furametpyr, guazatine, hexaconazole, hymexazol, imazalil, imibenconazole, iodocarb, ipconazole, iprobenfos, iprodione, iprovalicarb, isoprothiolane, isopyrazam, isotianil, kasugamycin, kresoxim-methyl, mancozeb, mandipropamid, maneb, mefenoxam, mepanipyrim, mepronil, meptyldinocap, metalaxyl, metalaxyl-M, metconazole, methasulfocarb, metiram, metominostrobin, metrafenone, myclobutanil, naftifine, neoasozin (ferric methanearsonate), nuarimol, octhilinone, ofurace, orysastrobin, oxadixyl, oxolinic acid, oxpoconazole, oxycarboxin, oxytetracycline, pefurazoate, penconazole, pencycuron, penthiopyrad, phosphorous acid and salts, phthalide, picoxystrobin, piperalin, polyoxin, probenazole, prochloraz, procymidone, propamocarb, propamocarb-hydrochloride, propiconazole, propineb, proquinazid, prothioconazole, pyraclostrobin, pyrazophos, pyribencarb, pyrifenox, pyrimethanil, pyroquilon, pyrrolnitrin, quinmethionate, quinoxyfen, quintozene, silthiofam, simeconazole, spiroxamine, streptomycin, sulfur, tebuconazole, tecloftalam, tecnazene, terbinafine, tetraconazole, thiabendazole, thifluzamide, thiophanate, thiophanate-methyl, thiram, tiadinil, tolclofos-methyl, tolylfluanid, triadimefon, triadimenol, triazoxide, tricyclazole, tridemorph, trifloxystrohin, triflumizole, triforine, trimorphamide, triticonazole, uniconazole, validamycin, valiphenal, vinclozolin, zineb, ziram, zoxamide, 5-chloro-6-(2,4,6-trifluorophenyl)-7-(4-methylpiperidin-1-yl)[1,2,4]triazolo[1,5-a]pyrimidine, N-[2-(1,3-dimethylbutyl)phenyl]-5-fluoro-1,3-dirnethyl-1H-pyrazol-4-carboxamide, N-[2-4-[[3-(4-chlorophenyl)-2-propyn-1-yl]oxy]-3-methoxyphenyl]ethyl]-3-methyl-2-[(methylsulfonyl)amino]butanarnide, N-[2-[4-[[3-(4-chlorophenyl)-2-propyn-1-yl]oxy]-3-methoxyphenyl]ethyl]-3-methyl-2-[(ethylsulfonyl)aminol]butanamide, 2-butoxy-6-iodo-3-propyl-4H-1-benzopyran-4-one, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl]carbamate, N-[[(cyclopropylmethoxy)amino][6-(difluoromethoxy)-2,3-difluorophenyl]methylene]benzeneacetamide, α-[methoxyimino]-N-methyl-2-[[[1-[3-(trifluoromethyl)phenyl]ethoxy]imino]methyl]benzeneacetamide, N-[4-[4-chloro-3-(trifluoromethyl)phenoxy]-2,5-dimethylphenyl]-N-ethyl-N-methylmethanimidamide, N-[2-(1S,2R)-[1,1'-bicyclopropyl]-2-ylphenyl]-3-(difluoromethyl)-1-methyl-1H-pyrazole-4-carboxamide and N-(4-chloro-2-nitrophenyl)-N-ethyl-4-methylbenzenesulfonamide.

13. The composition of claim 1 wherein component (b) includes at least one compound selected from azoxystrobin, benthiavalicarb, boscalid, chlorothalonil, copper hydroxide, cyazofamid, cymoxanil, dimethomorph, ethaboxam, famoxadone, fenamidone, fluazinam, fluopicolide, folpet, fosetyl-aluminum, iprovalicarb, kresoxim-methyl, mancozeb, mandipropamid, mefenoxarn, penthiopyrad, propamocarb, proquinazid, pyraclostrobin, quinoxyfen, trifloxystrobin, valiphenal and 5-chloro-6-(2,4,6-trifluorophenyl)-7-(4-methylpiperidin-1-yl)[1,2,4]triazolo[1,5-a]pyrimidine.

14. A method for controlling a plant disease caused by a fungal plant pathogen comprising applying to the plant or portion thereof, or to the plant seed, a fungicidally effective amount of the composition of claim 1.

* * * * *